US009409987B2

(12) United States Patent
Toporik et al.

(10) Patent No.: US 9,409,987 B2
(45) Date of Patent: Aug. 9, 2016

(54) POLYPEPTIDES AND POLYNUCLEOTIDES, AND USES THEREOF FOR TREATMENT OF IMMUNE RELATED DISORDERS AND CANCER

(75) Inventors: Amir Toporik, Holon (IL); Amit Novik, Binyamina (IL); Ronen Shemesh, Modiin (IL)

(73) Assignee: COMPUGEN LTD, Holon (IL)

( * ) Notice: Subject to any disclaimer, the term of this patent is extended or adjusted under 35 U.S.C. 154(b) by 0 days.

(21) Appl. No.: 14/111,767

(22) PCT Filed: Apr. 16, 2012

(86) PCT No.: PCT/IB2012/051868
§ 371 (c)(1),
(2), (4) Date: Oct. 15, 2013

(87) PCT Pub. No.: WO2012/140627
PCT Pub. Date: Oct. 18, 2012

(65) Prior Publication Data
US 2014/0044641 A1 Feb. 13, 2014

Related U.S. Application Data

(60) Provisional application No. 61/475,682, filed on Apr. 15, 2011, provisional application No. 61/532,575, filed on Sep. 9, 2011, provisional application No. 61/581,194, filed on Dec. 29, 2011.

(51) Int. Cl.
| | | |
|---|---|---|
| C07K 16/28 | (2006.01) | |
| A61K 39/395 | (2006.01) | |
| A61K 39/00 | (2006.01) | |
| A61K 39/39 | (2006.01) | |
| C07K 14/705 | (2006.01) | |
| C07K 16/18 | (2006.01) | |
| G01N 33/53 | (2006.01) | |

(52) U.S. Cl.
CPC ............ *C07K 16/28* (2013.01); *A61K 39/001* (2013.01); *A61K 39/0008* (2013.01); *A61K 39/0011* (2013.01); *A61K 39/39* (2013.01); *A61K 39/3955* (2013.01); *C07K 14/70503* (2013.01); *C07K 16/18* (2013.01); *G01N 33/53* (2013.01); *C07K 2319/00* (2013.01); *C07K 2319/30* (2013.01); *C07K 2319/43* (2013.01); *C12N 2760/10022* (2013.01); *C12N 2760/16121* (2013.01); *C12N 2770/32031* (2013.01)

(58) Field of Classification Search
None
See application file for complete search history.

(56) References Cited

U.S. PATENT DOCUMENTS

| | | | |
|---|---|---|---|
| 6,479,238 B1 | 11/2002 | Blumenfeld et al. | |
| 7,919,091 B2* | 4/2011 | Bihain et al. ............... | 424/139.1 |
| 2005/0202526 A1 | 9/2005 | Baker et al. | |
| 2007/0041963 A1 | 2/2007 | Rosen | |
| 2007/0054268 A1 | 3/2007 | Sutherland | |
| 2007/0105133 A1 | 5/2007 | Clarke et al. | |
| 2007/0154889 A1 | 7/2007 | Wang | |
| 2007/0184444 A1 | 8/2007 | Abbas | |
| 2009/0017473 A1 | 1/2009 | Frantz | |
| 2009/0117566 A1 | 5/2009 | Frantz | |
| 2009/0222387 A1 | 9/2009 | Gehrmann | |
| 2011/0245090 A1 | 10/2011 | Abbas | |
| 2013/0165332 A1 | 6/2013 | Abbas | |

FOREIGN PATENT DOCUMENTS

| | | | |
|---|---|---|---|
| WO | 9907737 | A2 | 2/1999 |
| WO | 9958642 | A3 | 11/1999 |
| WO | 0047772 | A2 | 8/2000 |
| WO | 0121647 | A2 | 3/2001 |
| WO | 03083074 | A9 | 10/2003 |
| WO | 03087300 | A3 | 10/2003 |
| WO | 2004046342 | A3 | 6/2004 |
| WO | 2010105298 | A1 | 9/2010 |
| WO | 2012140627 | A1 | 10/2012 |

OTHER PUBLICATIONS

Sequence alignment, 2015, 1 page.*
Garcia et al., 2007, Clin. Cancer Res. 13: 6351-6358.*
Rodrigues et al., Current Topics in Medicinal Chemistry, 2013, 13, 2551-2561.*
Jacobs et al., Anticancer Research 34: 2689-2700 (2014).*
Barber et al., Nature. 2006;439:682-7.
Bhadra et al., Proc Natl Acad Sci. 2011;108(22):9196-201.
Crawford et al., Curr Opin Immunol. 2009;21:179-186.
Diepolder and Obst, Expert Rev Vaccines. Mar. 2010;9(3):243-7.
Duncan and Miller PLoS One. 2011;6:e18548.
Duttagupta et al, Crit Rev Immunol. 2009;29(6):469-86.
Finnefrock et al., J Immunol 2009;182;980-987.
Golden-Mason et al., J Virol. 2009;83:9122-30.

(Continued)

*Primary Examiner* — Ilia Ouspenski
(74) *Attorney, Agent, or Firm* — Graeser Associates International Inc; Dvorah Graeser

(57) ABSTRACT

This invention relates to LY6G6F, VSIG10, TMEM25 and LSR proteins, which are suitable targets for immunotherapy, treatment of cancer, infectious disorders, and/or immune related disorders, and drug development. This invention further relates to soluble LY6G6F, VSIG10, TMEM25 and LSR molecules, extracellular domains of LY6G6F, VSIG10, TMEM25 and LSR and conjugates, which are suitable drugs for immunotherapy, treatment of cancer, infectious disorders, and/or immune related disorders. This invention further relates to antibodies and antigen binding fragments and conjugates containing same, and/or alternative scaffolds, specific for LY6G6F, VSIG10, TMEM25 or LSR molecules, which are suitable drugs for immunotherapy, treatment of cancer, infectious disorders, and/or immune related disorders.

12 Claims, 116 Drawing Sheets

(56) References Cited

OTHER PUBLICATIONS

Greenwald, et al. (2005) The B7 Family Revisited. Ann. Rev. Immunol. 23:515-48.
Ha et al, Immunol Rev. Jun. 2008; 223:317-33.
Hofmeyer et al., J Biomed Biotechnol. vol. 2011, Art. ID 451694.
Huang et al., PNAS 2009: 106; 6303-6308).
Kaufmann et al., J Immunol 2009;182:5891-5897.
Moorman et al, Vaccine. Apr. 12, 2011;29(17):3169-76.
Rivas et al., J Immunol. 2009 ;183:4284-91.
Sadum, et al. (2007) Immune Signatures of Murine and Human Cancers Reveal Unique Mechanisms of Tumor Escape and New Targets for Cancer Immunotherapy. Clin. Canc. Res. 13(13): 4016-4025).
Sharpe et al., Nat Immunol 2007;8:239-245.
Song et al, J Immunother. Apr. 2011;34(3):297-306.
Velu et al., Nature 2009;458:206-210.
Wang (2006) Immune Suppression by Tumor Specific CD4+ Regulatory T cells in Cancer. Semin. Cancer. Biol. 16:73-79.
Watts (2005) TNF/TNFR Family Members in Co-stimulation of T Cell Responses Ann. Rev. Immunol. 23:23-68.
Wong et al 2010, Curr Opin Immunol. 22:723-731.
Phares et al, Target Dependent B7-H1 Regulation Contributes to Clearance of CNS Infection and Dampens Morbidity, J Immunol. May 1, 2009; 182(9): 5430-5438.
Doolan P, et al., TMEM25, REPS2 and Meis 1: favourable prognostic and predictive biomarkers for breast cancer; Tumour Biol. 2009, 30(4):200-9 (abstract only).
Herbsleb M. et al., "Increased Cell Motilitu and Invasion Knockdown if Lipolysis Stimulated Lipoprotein Receptor (LSR) in SW780 bladder cancer cells" BMC Medical Genomics, Jul. 2008, vol. 1.
IPRP for PCT/IB2012/051868 mailed Oct. 24, 2013.
ISR and written opinion for PCT/IB2012/051868 mailed Sep. 24, 2012.
ISR and written opinion for PCT/IL2013/050527 mailed Oct. 13, 2013.
Database UniProt, Lin et al. "Mouse lipolysis-stimulated lipoprotein receptor", 2001, Accession No. Q99KG5.
Rikke Leth-Laren et al. "Functional Heterogeneity within the CD44 high human Breast Cancer Stem Cell-Like Compartment Reveals a Gene Signature Predictive of Distant Metastasis", 2012, Mol Med, 18(1).
Office action for related CN201280028877 mailed Dec. 9, 2014 (Translated).
Garcia, Jose M., et al. "Prognostic value of LISCH7 mRNA in plasma and tumor of colon cancer patients." Clinical Cancer Research 13.21 (2007): 6351-6358.

* cited by examiner

LYG6F- SEQ ID NO:1

MAVLFLLLFLCGTPQAADNMQAIYVALGEAVELPCPSPPTLHGDEHLSWFCSPAAGSFTTLVAQVQVGRPAPDPGKPGRESRLRLLGNYSLWLEGSKEEDAGRYWCAVLGQHHNYQNWRVYDVLVLKGSQLSARAADGSPCNVLLCSVVPSRRMDSVTWQEGKGPVRGRVQSFWGSEAALLLVCPGEGLSEPRSRRPRIIRCLMTHNKGVSFSLAASIDASPALCAPSTGWDMP<u>WILMLLLTMGQGVVILALSIVLW</u>RQRVRGAPGRDASIPQFKPEIQVYENIHLARLGPPAHKPR

SP - aa 1-16: MAVLFLLLFLCGTPQA

TM - aa 235-257: <u>WILMLLLTMGQGVVILALSIVLW</u>

LYG6F ECD (without SP) – aa 17-234 (SEQ ID NO:2):

ADNMQAIYVALGEAVELPCPSPPTLHGDEHLSWFCSPAAGSFTTLVAQVQVGRPAPDPGKPGRESRLRLL
GNYSLWLEGSKEEDAGRYWCAVLGQHHNYQNWRVYDVLVLKGSQLSARAADGSPCNVLLCSVVPSRRMDS
VTWQEGKGPVRGRVQSFWGSEAALLLVCPGEGLSEPRSRRPRIIRCLMTHNKGVSFSLAASIDASPALCA
PSTGWDMP

NA encoding LYG6F ECD (SEQ ID NO:33):

GCAGACAACATGCAGGCCATCTATGTGGCCTTGGGGGAGGCAGTAGAGCTGCCCATGTCCCTCACCACCTA
CTCTACATGGGGACGAACACCTGTCATGGTTCTGCAGCCCTGCAGCAGGCTCCTTCACCACCCTGGTAGC
CCAAGTCCAAGTGGGCAGGCCAGCCCCAGACCCTGGAAAACCAGGAAGGGAATCCAGGCTCAGACTGCTG
GGGAACTATTCTTTGTGGTTGGAGGGATCCAAAGAGGAAGATGCCGGGCGGTACTGGTGCGCTGTGCTAG
GTCAGCACCACAACTACCAGAACTGGAGGGTGTACGACGTCTTGGTGCTCAAAGGATCCCAGTTATCTGC
AAGGGCTGCAGATGGATCCCCCTGCAATGTCCTCCTGTGCTCTGTGGTCCCCAGCAGACGCATGGACTCT
GTGACCTGGCAGGAAGGGAAGGGTCCCGTGAGGGGCCGTGTTCAGTCCTTCTGGGGCAGTGAGGCTGCCC
TGCTCTTGGTCTGTCCTGGGGAGGGGCTTTCTGAGCCCAGGAGCCGAAGACCAAGAATCATCCGCTGCCT
CATGACTCACAACAAGGGGTCAGCTTTAGCCTGGCAGCCTCCATCGATGCTTCTCCTGCCCTCTGTGCC
CCTTCCACGGGCTGGGACATGCCT

FIG. 1A

VSIG10 - SEQ ID NO:3

MAAGGSAPEPRVLVCLGALLAGWVAVGLEAVVIGEVHENVTLHCGNISGLRGQVTWYRNNSEPVFLLSSN
SSLRPAEPRFSLVDATSLHIESLSLGDEGIYTCQEILNVTQWFQVWLQVASGPYQIEVHIVATGTLPNGT
LYAARGSQVDFSCNSSSRPPPVVEWWFQALNSSSESFGHNLTVNFFSLLLISPNLQGNYTCLALNQLSKR
HRKVTTELLVYYPPPSAPQCWAQMASGSFMLQLTCRWDGGYPDPDFLWIEEPGGVIVGKSKLGVEMLSES
QLSDGKKFKCVTSHIVGPESGASCMVQIRGPSLLSEPMKTCFTGGNVTLTCQVSGAYPPAKILWLRNLTQ
PEVIIQPSSRHLITQDGQNSTLTIHNCSQDLDEGYYICRADSPVGVREMEIWLSVKEPLNIGG**IVGTIVS
LLLLGLAIISGLLL**HYSPVFCWKVGNTSRGQNMDDVMVLVDSEEEEEEEEEEEEDAAVGEQEGAREREEL
PKEIPKQDHIHRVTALVNGNIEQMGNGFQDLQDDSSEEQSDIVQEEDRPV

SP - aa 1-30: MAAGGSAPEPRVLVCLGALLAGWVAVGLEA

TM - aa 414-434: IVGTIVSLLLLGLAIISGLLL

VSIG10 ECD (without SP) – aa 31-413 (SEQ ID NO:4):

VVIGEVHENVTLHCGNISGLRGQVTWYRNNSEPVFLLSSNSSLRPAEPRFSLVDATSLHIESLSLGDEGI
YTCQEILNVTQWFQVWLQVASGPYQIEVHIVATGTLPNGTLYAARGSQVDFSCNSSSRPPPVVEWWFQAL
NSSSESFGHNLTVNFFSLLLISPNLQGNYTCLALNQLSKRHRKVTTELLVYYPPPSAPQCWAQMASGSFM
LQLTCRWDGGYPDPDFLWIEEPGGVIVGKSKLGVEMLSESQLSDGKKFKCVTSHIVGPESGASCMVQIRG
PSLLSEPMKTCFTGGNVTLTCQVSGAYPPAKILWLRNLTQPEVIIQPSSRHLITQDGQNSTLTIHNCSQD
LDEGYYICRADSPVGVREMEIWLSVKEPLNIGG

NA encoding VSIG10 ECD (SEQ ID NO:34):

GTTGTCATTGGAGAAGTTCATGAGAATGTTACTCTGCACTGTGGCAACATCTCGGGACTGAGGGGCCAGG
TGACCTGGTACCGGAACAACTCGGAGCCTGTCTTCCTTCTCTCGTCCAACTCTAGCCTCCGGCCAGCTGA
GCCTCGCTTCTCTCTAGTGGATGCCACCTCCCTGCACATTGAATCGCTGAGCCTGGGAGATGAGGGAATC
TACACCTGCCAGGAGATCCTGAATGTGACTCAGTGGTTCCAAGTGTGGCTGCAGGTGGCCAGCGGCCCCT
ATCAGATTGAGGTCCACATCGTGGCCACCGGCACACTCCCCAACGGCACCCTCTATGCAGCCAGGGGCTC
CCAGGTGGACTTCAGCTGCAACAGCAGCTCCAGGCCACCACCCGTGGTTGAATGGTGGTTCCAGGCCCTG
AATTCCAGCAGCGAGTCCTTTGGCCACAACCTGACAGTCAACTTTTTCTCACTGTTACTGATATCGCCAA
ACCTCCAAGGGAACTACACCTGTTTAGCCTTGAATCAGCTCAGCAAGAGACATCGAAAGGTGACCACCGA
GCTCCTGGTCTACTATCCCCCTCCATCAGCTCCCCAGTGCTGGGCACAGATGGCATCAGGATCGTTCATG
TTGCAGCTTACCTGTCGCTGGGATGGGGATACCCTGACCCTGACTTCCTGTGGATAGAAGAGCCAGGAG
GTGTAATCGTGGGGAAGTCAAAGCTGGGGGTGGAAATGCTGAGCGAGTCCCAGCTGTCGGATGGCAAGAA
GTTCAAGTGTGTTACAAGCCACATAGTTGGGCCAGAGTCGGGCGCCAGCTGCATGGTGCAGATCAGGGGT
CCCTCCCTTCTCTCTGAGCCCATGAAGACTTGCTTCACTGGGGGCAATGTGACGCTTACATGCCAGGTGT
CTGGGGCCTACCCCCCTGCCAAGATCCTGTGGCTGAGGAACCTTACCCAGCCCGAGGTGATCATCCAGCC
TAGCAGCCGCCATCTCATTACCCAGGATGGCCAGAACTCCACCCTCACTATCCACAACTGCTCCCAGGAC
CTGGATGAGGGCTACTACATCTGCCGAGCTGACAGCCCTGTAGGGGTGAGGGAGATGGAAATCTGGCTGA
GTGTGAAAGAACCTTTAAATATCGGGGGG

FIG. 1B

VSIG10 Variant skipping exon 3 (101aa presented in Italic and underlined in the figure above) (SEQ ID NO:5):

MAAGGSAPEPRVLVCLGALLAGWVAVGLEAVVIGEVHENVTLHCGNISGLRGQVTWYRNNSEPVFLLSSN
SSLRPAEPRFSLVDATSLHIESLSLGDEGIYTCQEILNVTQWFQVWLQVANPPPSAPQCWAQMASGSFML
QLTCRWDGGYPDPDFLWIEEPGGVIVGKSKLGVEMLSESQLSDGKKFKCVTSHIVGPESGASCMVQIRGP
SLLSEPMKTCFTGGNVTLTCQVSGAYPPAKILWLRNLTQPEVIIQPSSRHLITQDGQNSTLTIHNCSQDL
DEGYYICRADSPVGVREMEIWLSVKEPLNIGGIVGTIVSLLLLGLAIISGLLLHYSPVFCWKVGNTSRGQ
NMDDVMVLVDSEEEEEEEEEEEEDAAVGEQEGAREREELPKEIPKQDHIHRVTALVNGNIEQMGNGFQDL
QDDSSEEQSDIVQEEDRPV

SP - aa 1-30: MAAGGSAPEPRVLVCLGALLAGWVAVGLEA

TM - aa 313-333: IVGTIVSLLLLGLAIISGLLL

VSIG10 Variant skipping exon 3 ECD (without SP) - aa 31-312 (SEQ ID NO:6):

VVIGEVHENVTLHCGNISGLRGQVTWYRNNSEPVFLLSSNSSLRPAEPRFSLVDATSLHIESLSLGDEGI
YTCQEILNVTQWFQVWLQVANPPPSAPQCWAQMASGSFMLQLTCRWDGGYPDPDFLWIEEPGGVIVGKSK
LGVEMLSESQLSDGKKFKCVTSHIVGPESGASCMVQIRGPSLLSEPMKTCFTGGNVTLTCQVSGAYPPAK
ILWLRNLTQPEVIIQPSSRHLITQDGQNSTLTIHNCSQDLDEGYYICRADSPVGVREMEIWLSVKEPLNI
GG

FIG. 1C-1

NA encoding VSIG10 Variant skipping exon 3 (SEQ ID NO:35):

*ATGGCCGCAGGCGGCAGTGCGCCC*
*GAGCCCCGCGTCCTCGTCTGCCTCGGGGCGCTCCTGGCCGGCTGGGTCGCCGTAGGATTGGAGGCTGTTG*
*TCATTGGAGAAGTTCATGAGAATGTTACTCTGCACTGTGGCAACATCTCGGGACTGAGGGGCCAGGTGAC*
*CTGGTACCGGAACAACTCGGAGCCTGTCTTCCTTCTCTCGTCCAACTCTAGCCTCCGGCCAGCTGAGCCT*
*CGCTTCTCTCTAGTGGATGCCACCTCCCTGCACATTGAATCGCTGAGCCTGGGAGATGAGGGAATCTACA*
*CCTGCCAGGAGATCCTGAATGTGACTCAGTGGTTCCAAGTGTGGCTGCAGGTGGCCAATCCCCCTCCATC*
*AGCTCCCCAGTGCTGGGCACAGATGGCATCAGGATCGTTCATGTTGCAGCTTACCTGTCGCTGGGATGGG*
*GGATACCCTGACCCTGACTTCCTGTGGATAGAAGAGCCAGGAGGTGTAATCGTGGGGAAGTCAAAGCTGG*
*GGGTGGAAATGCTGAGCGAGTCCCAGCTGTCGGATGGCAAGAAGTTCAAGTGTGTTACAAGCCACATAGT*
*TGGGCCAGAGTCGGGCGCCAGCTGCATGGTGCAGATCAGGGGTCCCTCCCTTCTCTCTGAGCCCATGAAG*
*ACTTGCTTCACTGGGGGCAATGTGACGCTTACATGCCAGGTGTCTGGGGCCTACCCCCCTGCCAAGATCC*
*TGTGGCTGAGGAACCTTACCCAGCCCGAGGTGATCATCCAGCCTAGCAGCCGCCATCTCATTACCCAGGA*
*TGGCCAGAACTCCACCCTCACTATCCACAACTGCTCCCAGGACCTGGATGAGGGCTACTACATCTGCCGA*
*GCTGACAGCCCTGTAGGGGTGAGGGAGATGGAAATCTGGCTGAGTGTGAAAGAACCTTTAAATATCGGGG*
*GGATTGTGGGAACCATTGTGAGCCTCCTTCTGCTGGGACTGGCCATTATCTCAGGGCTTCTGTTGCATTA*
TAGCCCTGTGTTCTGCTGGAAAGTAGGAAACACTTCCAGGGGACAAAACATGGATGATGTCATGGTTTTG
GTGGATTCAGAAGAGGAAGAGGAGGAGGAGGAGGAGGAGGAAGATGCTGCAGTAGGGGAACAGGAGG
GAGCACGTGAGAGAGAGGAGTTGCCAAAAGAAATACCTAAGCAGGACCACATTCACAGAGTGACCGCCTT
GGTGAATGGGAACATAGAACAGATGGGAAATGGATTCCAGGATCTTCAAGATGACAGCAGTGAGGAGCAA
AGTGACATTGTTCAAGAAGAAGACAGGCCAGTCTGA

FIG. 1C-2

NA encoding VSIG10 Variant skipping exon 3 ECD (SEQ ID NO:36):

```
GTTGTCATTGGAGAAGTTCATGAGAATGTTACTCTGCACTGTGGCAACATCTCGGGACTGAGGGGCCAGG
TGACCTGGTACCGGAACAACTCGGAGCCTGTCTTCCTTCTCTCGTCCAACTCTAGCCTCCGGCCAGCTGA
GCCTCGCTTCTCTCTAGTGGATGCCACCTCCCTGCACATTGAATCGCTGAGCCTGGGAGATGAGGGAATC
TACACCTGCCAGGAGATCCTGAATGTGACTCAGTGGTTCCAAGTGTGGCTGCAGGTGGCCAATCCCCCTC
CATCAGCTCCCCAGTGCTGGGCACAGATGGCATCAGGATCGTTCATGTTGCAGCTTACCTGTCGCTGGGA
TGGGGGATACCCTGACCCTGACTTCCTGTGGATAGAAGAGCCAGGAGGTGTAATCGTGGGGAAGTCAAAG
CTGGGGGTGGAAATGCTGAGCGAGTCCCAGCTGTCGGATGGCAAGAAGTTCAAGTGTGTTACAAGCCACA
TAGTTGGGCCAGAGTCGGGCGCCAGCTGCATGGTGCAGATCAGGGGTCCCTCCCTTCTCTCTGAGCCCAT
GAAGACTTGCTTCACTGGGGGCAATGTGACGCTTACATGCCAGGTGTCTGGGGCCTACCCCCCTGCCAAG
ATCCTGTGGCTGAGGAACCTTACCCAGCCCGAGGTGATCATCCAGCCTAGCAGCCGCCATCTCATTACCC
AGGATGGCCAGAACTCCACCCTCACTATCCACAACTGCTCCCAGGACCTGGATGAGGGCTACTACATCTG
CCGAGCTGACAGCCCTGTAGGGGTGAGGGAGATGGAAATCTGGCTGAGTGTGAAAGAACCTTTAAATATC
GGGGGG
```

FIG. 1C-3

TMEM25 - SEQ ID NO:7

MALPPGPAALRHTLLLLPALLSSGWGELEPQIDGQTWAERALRENERHAFTCRVAGGPGT
PRLAWYLDGQLQEASTSRLLSVGGEAFSGGTSTFTVTAHRAQHELNCSLQDPRSGRSANA
SVILNVQFKPEIAQVGAKYQEAQGPGLLVVLFALVRANPPANVTWIDQDGPVTVNTSDFL
VLDAQNYPWLTNHTVQLQLRSLAHNLSVVATNDVGVTSASLPAPGLLATRVE**VPLLGIVV
AAGLALGTLVGFSTLVACLVC**RKEKKTKGPSRHPSLISSDSNNLKLNNVRLPRENMSLPS
NLQLNDLTPDSRAVKPADRQMAQNNSRPELLDPEPGGLLTSQGFIRLPVLGYIYRVSSVS
SDEIWL

SP - aa 1-26: MALPPGPAALRHTLLLLPALLSSGW

TM - aa 233-261: VPLLGIVVAAGLALGTLVGFSTLVACLVC

TMEM25 ECD (without SP) – aa 27-232 (SEQ ID NO:8):

ELEPQIDGQTWAERALRENERHAFTCRVAGGPGTPRLAWYLDGQLQEASTSRLLSVGGEA
FSGGTSTFTVTAHRAQHELNCSLQDPRSGRSANASVILNVQFKPEIAQVGAKYQEAQGPG
LLVVLFALVRANPPANVTWIDQDGPVTVNTSDFLVLDAQNYPWLTNHTVQLQLRSLAHNL
SVVATNDVGVTSASLPAPGLLATRVE

NA encoding TMEM25 ECD (SEQ ID NO:37):

GAGTTGGAGCCACAAATAGATGGTCAGACCTGGGCTGAGCGGGCACTTCGGGAGAATGAACGCCACGC
CTTCACCTGCCGGGTGGCAGGGGGGCCTGGCACCCCAGATTGGCCTGGTATCTGGATGGACAGCTGCA
GGAGGCCAGCACCTCAAGACTGCTGAGCGTGGGAGGGGAGGCCTTCTCTGGAGGCACCAGCACCTTCA
CTGTCACTGCCCATCGGGCCCAGCATGAGCTCAACTGCTCTCTGCAGGACCCCAGAAGTGGCCGATCAGC
CAACGCCTCTGTCATCCTTAATGTGCAATTCAAGCCAGAGATTGCCCAAGTCGGCGCCAAGTACCAGGAA
GCTCAGGGCCCAGGCCTCCTGGTTGTCCTGTTTGCCCTGGTGCGTGCCAACCCGCCGGCCAATGTCACCT
GGATCGACCAGGATGGGCCAGTGACTGTCAACACCTCTGACTTCCTGGTGCTGGATGCGCAGAACTACC
CCTGGCTCACCAACCACACGGTGCAGCTGCAGCTCCGCAGCCTGGCACACAACCTCTCGGTGGTGGCCAC
CAATGACGTGGGTGTCACCAGTGCGTCGCTTCCAGCCCAGGGCTTCTGGCTACCCGG

FIG. 1D

LSR isoform-a (SEQ ID NO:11):

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLGRTSGVAELLPGFQAGPIE
D<u>WLFVVVVCLAAFLIFLLLGICWC</u>QCCPHTCCCYVRCPCCPDKCCCPEALYAAGKAATSGVPSIYAPSTY
AHLSPAKTPPPPAMIPMGPAYNGYPGGYPGDVRSSSAGGQGSYVPLLRDTDSSVAS<u>E</u>VRSGYRIQASQQ
DDSMRVLYYMEKELANFDPSRPGPPSGRVERAMSEVTSLHEDDWRSRPSRGPALTPIRDEEWGGHSPRSP
RGWDQEPAREQAGGGWRARRPRARSVDALDDLTPPSTAESGSRSPTSNGGRSRAYMPPRSRSRDDLYDQD
DSRDFPRSRDPHYDDFRSRERPPADPRSHHHRTRDPRDNGSRSGDLPYDGRLLEEAVRKKGSEERRRPHK
EEEEEAYYPPAPPPYSETDSQASRERRLKKNLALSRESLVV

SP - aa 1-41: MALLAGGLSRGLGSHPAAAGRDAVVFVWLLLSTWCTAPARA

TM - aa 212-234: <u>WLFVVVVCLAAFLIFLLLGICWC</u>

LSR isoform-a ECD (without SP) - aa 42-211 (SEQ ID NO:12):

IQVTVSNPYHVVILFQPVTLPCTYQMTSTPTQPIVIWKYKSFCRDRIADAFSPASVDNQLNAQLAAGNPG
YNPYVECQDSVRTVRVVATKQGNAVTLGDYYQGRRITITGNADLTFDQTAWGDSGVYYCSVVSAQDLQGN
NEAYAELIVLGRTSGVAELLPGFQAGPIED

NA encoding LSR isoform-a ECD (SEQ ID NO:40):

ATCCAGGTGACCGTGTCCAACCCCTACCACGTGGTGATCCTCTTCCAGCCTGTGACCCTGCCCTGTACCT
ACCAGATGACCTCGACCCCCACGCAACCCATCGTCATCTGGAAGTACAAGTCTTTCTGCCGGGACCGCAT
CGCCGATGCCTTCTCCCCGGCCAGCGTCGACAACCAGCTCAATGCCCAGCTGGCAGCCGGGAACCCAGGC
TACAACCCCTACGTCGAGTGCCAGGACAGCGTGCGCACCGTCAGGGTCGTGGCCACCAAGCAGGGCAACG
CTGTGACCCTGGGAGATTACTACCAGGGCCGGAGGATTACCATCACCGGAAATGCTGACCTGACCTTTGA
CCAGACGGCGTGGGGGGACAGTGGTGTGTATTACTGCTCCGTGGTCTCAGCCCAGGACCTCCAGGGGAAC
AATGAGGCCTACGCAGAGCTCATCGTCCTTGGGAGGACCTCAGGGGTGGCTGAGCTCTTACCTGGTTTTC
AGGCGGGGCCCATAGAAGAC

FIG. 1E

LSR isoform-b, skipping exon 4 (19aa) (SEQ ID NO:13):

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLD<u>WLFVVVVCLAAFLIFLLL
GICWC</u>QCCPHTCCCYVRCPCCPDKCCCPEALYAAGKAATSGVPSIYAPSTYAHLSPAKTPPPPAMIPMGP
AYNGYPGGYPGDVDRSSSAGGQGSYVPLLRDTDSSVASEVRSGYRIQASQQDDSMRVLYYMEKELANFDP
SRPGPPSGRVERAMSEVTSLHEDDWRSRPSRGPALTPIRDEEWGGHSPRSPRGWDQEPAREQAGGGWRAR
RPRARSVDALDDLTPPSTAESGSRSPTSNGGRSRAYMPPRSRSRDDLYDQDDSRDFPRSRDPHYDDFRSR
ERPPADPRSHHHRTRDPRDNGSRSGDLPYDGRLLEEAVRKKGSEERRRPHKEEEEEAYYPPAPPPYSETD
SQASRERRLKKNLALSRESLVV

SP - aa 1-41: MALLAGGLSRGLGSHPAAAGRDAVVFVWLLLSTWCTAPARA

TM - aa 193-215: <u>WLFVVVVCLAAFLIFLLLGICWC</u>

LSR isoform-b ECD (without SP) – aa 42-192 (SEQ ID NO:14):

IQVTVSNPYHVVILFQPVTLPCTYQMTSTPTQPIVIWKYKSFCRDRIADAFSPASVDNQLNAQLAAGNPG
YNPYVECQDSVRTVRVVATKQGNAVTLGDYYQGRRITITGNADLTFDQTAWGDSGVYYCSVVSAQDLQGN
NEAYAELIVLD

NA encoding LSR isoform-b ECD (SEQ ID NO:41):

ATCCAGGTGACCGTGTCCAACCCCTACCACGTGGTGATCCTCTTCCAGCCTGTGACCCTGCCCTGTACCT
ACCAGATGACCTCGACCCCCACGCAACCCATCGTCATCTGGAAGTACAAGTCTTTCTGCCGGGACCGCAT
CGCCGATGCCTTCTCCCCGGCCAGCGTCGACAACCAGCTCAATGCCCAGCTGGCAGCGGGAACCCAGGC
TACAACCCCTACGTCGAGTGCCAGGACAGCGTGCGCACCGTCAGGGTCGTGGCCACCAAGCAGGGCAACG
CTGTGACCCTGGGAGATTACTACCAGGGCCGGAGGATTACCATCACCGGAAATGCTGACCTGACCTTTGA
CCAGACGGCGTGGGGGGACAGTGGTGTGTATTACTGCTCCGTGGTCTCAGCCCAGGACCTCCAGGGGAAC
AATGAGGCCTACGCAGAGCTCATCGTCCTTGAC

FIG. 1F

LSR isoform-c, skipping exons 4 and 5 (19aa and TM) SEQ ID NO:15:

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLVYAAGKAATSGVPSIYAPS
TYAHLSPAKTPPPPAMIPMGPAYNGYPGGYPGDVDRSSSAGGQGSYVPLLRDTDSSVASEVRSGYRIQAS
QQDDSMRVLYYMEKELANFDPSRPGPPSGRVERAMSEVTSLHEDDWRSRPSRGPALTPIRDEEWGGHSPR
SPRGWDQEPAREQAGGGWRARRPRARSVDALDDLTPPSTAESGSRSPTSNGGRSRAYMPPRSRSRDDLYD
QDDSRDFPRSRDPHYDDFRSRERPPADPRSHHHRTRDPRDNGSRSGDLPYDGRLLEEAVRKKGSEERRRP
HKEEEEEAYYPPAPPPYSETDSQASRERRLKKNLALSRESLVV

SP - aa 1-41: MALLAGGLSRGLGSHPAAAGRDAVVFVWLLLSTWCTAPARA

NA encoding LSR isoform-c (SEQ ID NO:42):

**ATGGCGCTGTTGGCCGGCGGGCTCTCCAGAGGGCTGGGCTCCCACCCGGCCGCCGCAGGCCGGGACGCGG
TCGTCTTCGTGTGGCTTCTGCTTAGCACCTGGTGCACAGCTCCTGCCAGGGCC**ATCCAGGTGACCGTGTC
CAACCCCTACCACGTGGTGATCCTCTTCCAGCCTGTGACCCTGCCTGTACCTACCAGATGACCTCGACC
CCCACGCAACCCATCGTCATCTGGAAGTACAAGTCTTTCTGCCGGGACCGCATCGCCGATGCCTTCTCCC
CGGCCAGCGTCGACAACCAGCTCAATGCCCAGCTGGCAGCCGGGAACCCAGGCTACAACCCCTACGTCGA
GTGCCAGGACAGCGTGCGCACCGTCAGGGTCGTGGCCACCAAGCAGGGCAACGCTGTGACCCTGGGAGAT
TACTACCAGGGCCGGAGGATTACCATCACCGGAAATGCTGACCTGACCTTTGACCAGACGGCGTGGGGGG
ACAGTGGTGTGTATTACTGCTCCGTGGTCTCAGCCCAGGACCTCCAGGGGAACAATGAGGCCTACGCAGA
GCTCATCGTCCTTGTGTATGCCGCCGGCAAAGCAGCCACCTCAGGTGTTCCCAGCATTTATGCCCCCAGC
ACCTATGCCCACCTGTCTCCCGCCAAGACCCCACCCCCACCAGCTATGATTCCCATGGGCCCTGCCTACA
ACGGGTACCCTGGAGGATACCCTGGAGACGTTGACAGGAGTAGCTCAGCTGGTGGCCAAGGCTCCTATGT
ACCCCTGCTTCGGGACACGGACAGCAGTGTGGCCTCTGAAGTCCGCAGTGGCTACAGGATTCAGGCCAGC
CAGCAGGACGACTCCATGCGGGTCCTGTACTACATGGAGAAGGAGCTGGCCAACTTCGACCCTTCTCGAC
CTGGCCCCCCAGTGGCCGTGTGGAGCGGGCCATGAGTGAAGTCACCTCCCTCCACGAGGACGACTGGCG
ATCTCGGCCTTCCCGGGGCCCTGCCCTCACCCCGATCCGGGATGAGGAGTGGGGTGGCCACTCCCCCGG
AGTCCCAGGGGATGGGACCAGGAGCCCGCCAGGGAGCAGGCAGCGGGGGCTGGCGGGCCAGCGGCCCC
GGGCCCGCTCCGTGGACGCCCTGGACGACCTCACCCCGCCGAGCACCGCCGAGTCAGGGAGCAGGTCTCC
CACGAGTAATGGTGGGAGAAGCCGGGCCTACATGCCCCCGCGGAGCCGCAGCCGGGACGACCTCTATGAC
CAAGACGACTCGAGGGACTTCCCACGCTCCCGGGACCCCACTACGACGACTTCAGGTCTCGGGAGCGCC
CTCCTGCCGACCCCAGGTCCCACCACCACCGTACCCGGGACCCTCGGGACAACGGCTCCAGGTCCGGGGA
CCTCCCCTATGATGGGCGGCTACTGGAGGAGGCTGTGAGGAAGAAGGGGTCGGAGGAGAGGAGGAGACCC
CACAAGGAGGAGGAGGAAGAGGCCTACTACCCGCCCGCGCCGCCCCCGTACTCGGAGACCGACTCGCAGG
CGTCCCGAGAGCGCAGGCTCAAGAAGAACTTGGCCCTGAGTCGGGAAAGTTTAGTCGTC

FIG. 1G

LSR isoform-d, skipping exons 4 and 5 (19aa exon + TM + 1aa skip) SEQ ID NO:16:

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLVYAAGKAATSGVPSIYAPS
TYAHLSPAKTPPPPAMIPMGPAYNGYPGGYPGDVDRSSSAGGQGSYVPLLRDTDSSVASVRSGYRIQASQ
QDDSMRVLYYMEKELANFDPSRPGPPSGRVERAMSEVTSLHEDDWRSRPSRGPALTPIRDEEWGGHSPRS
PRGWDQEPAREQAGGGWRARRPRARSVDALDDLTPPSTAESGSRSPTSNGGRSRAYMPPRSRSRDDLYDQ
DDSRDFPRSRDPHYDDFRSRERPPADPRSHHHRTRDPRDNGSRSGDLPYDGRLLEEAVRKKGSEERRRPH
KEEEEEAYYPPAPPPYSETDSQASRERRLKKNLALSRESLVV

SP - aa 1-41: MALLAGGLSRGLGSHPAAAGRDAVVFVWLLLSTWCTAPARA

NA encoding LSR isoform-d(SEQ ID NO:43):

**ATGGCGCTGTTGGCCGGCGGGCTCTCCAGAGGGCTGGGCTCCCACCCGGCCGCCGCAGGCCGGGACGCGG
TCGTCTTCGTGTGGCTTCTGCTTAGCACCTGGTGCACAGCTCCTGCCAGGGCC**ATCCAGGTGACCGTGTC
CAACCCCTACCACGTGGTGATCCTCTTCCAGCCTGTGACCCTGCCCTGTACCTACCAGATGACCTCGACCC
CCACGCAACCCATCGTCATCTGGAAGTACAAGTCTTTCTGCCGGGACCGCATCGCCGATGCCTTCTCCCC
GGCCAGCGTCGACAACCAGCTCAATGCCCAGCTGGCAGCCGGGAACCCAGGCTACAACCCCTACGTCGA
GTGCCAGGACAGCGTGCGCACCGTCAGGGTCGTGGCCACCAAGCAGGGCAACGCTGTGACCCTGGGAGAT
TACTACCAGGGCCGGAGGATTACCATCACCGGAAATGCTGACCTGACCTTTGACCAGACGGCGTGGGGGG
ACAGTGGTGTGTATTACTGCTCCGTGGTCTCAGCCCAGGACCTCCAGGGGAACAATGAGGCCTACGCAGA
GCTCATCGTCCTTGTGTATGCCGCCGGCAAAGCAGCCACCTCAGGTGTTCCCAGCATTTATGCCCCCAGC
ACCTATGCCCACCTGTCTCCCGCCAAGACCCCACCCCCACCAGCTATGATTCCCATGGGCCCTGCCTACA
ACGGGTACCCTGGAGGATACCCTGGAGACGTTGACAGGAGTAGCTCAGCTGGTGGCCAAGGCTCCTATGT
ACCCCTGCTTCGGGACACGGACAGCAGTGTGGCCTCTGTCCGCAGTGGCTACAGGATTCAGGCCAGCCAG
CAGGACGACTCCATGCGGGTCCTGTACTACATGGAGAAGGAGCTGGCCAACTTCGACCCTTCTCGACCTG
GCCCCCCCAGTGGCCGTGTGGAGCGGGCCATGAGTGAAGTCACCTCCCTCCACGAGGACGACTGGCGATC
TCGGCCTTCCCGGGGCCCTGCCCTCACCCCGATCCGGGATGAGGAGTGGGGTGGCCACTCCCCCCGGAGT
CCCAGGGGATGGGACCAGGAGCCCGCCAGGGAGCAGGCAGGCGGGGCTGGCGGGCCAGGCGGCCCCGGG
CCCGCTCCGTGGACGCCCTGGACGACCTCACCCCGCCGAGCACCGCCGAGTCAGGGAGCAGGTCTCCCAC
GAGTAATGGTGGGAGAAGCCGGGCCTACATGCCCCGCGGAGCCGCAGCCGGACGACCTCTATGACCAA
GACGACTCGAGGGACTTCCCACGCTCCCGGGACCCCACTACGACGACTTCAGGTCTCGGGAGCGCCCTC
CTGCCGACCCCAGGTCCCACCACCACCGTACCCGGGACCCTCGGGACAACGGCTCCAGGTCCGGGGACCT
CCCCTATGATGGGCGGCTACTGGAGGAGGCTGTGAGGAAGAAGGGGTCGGAGGAGAGGAGGAGACCCCAC
AAGGAGGAGGAGGAAGAGGCCTACTACCCGCCCGCGCCGCCCCCGTACTCGGAGACCGACTCGCAGGCGT
CCCGAGAGCGCAGGCTCAAGAAGAACTTGGCCCTGAGTCGGGAAAGTTTAGTCGTC

LSR isoform-e, skipping exons 3, 4 and 5 (40aa exon + 19aa exon+ TM) SEQ ID NO:17:

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGMYAAGKAATSGVPSIYAPSTYAHLSPAKTPPPPAMIPMGPAYNGYPGGYPGDVDRSSSA
GGQGSYVPLLRDTDSSVASEVRSGYRIQASQQDDSMRVLYYMEKELANFDPSRPGPPSGRVERAMSEVTS
LHEDDWRSRPSRGPALTPIRDEEWGGHSPRSPRGWDQEPAREQAGGGWRARRPRARSVDALDDLTPPSTA
ESGSRSPTSNGGRSRAYMPPRSRSRDDLYDQDDSRDFPRSRDPHYDDFRSRERPPADPRSHHHRTRDPRD
NGSRSGDLPYDGRLLEEAVRKKGSEERRRPHKEEEEAYYPPAPPPYSETDSQASRERRLKKNLALSRES
LVV

SP - aa 1-41: MALLAGGLSRGLGSHPAAAGRDAVVFVWLLLSTWCTAPARA

FIG. 1I-1

NA encoding LSR isoform-e (SEQ ID NO:45):

**ATGGCGCTGTTGGCCGGCGGGCTCTCCAGAGGGCTGGGCTCCCACCCGGCCGCCGCAGGCCGGGACGCGG
TCGTCTTCGTGTGGCTTCTGCTTAGCACCTGGTGCACAGCTCCTGCCAGGGCC**ATCCAGGTGACCGTGTC
CAACCCCTACCACGTGGTGATCCTCTTCCAGCCTGTGACCCTGCCCTGTACCTACCAGATGACCTCGACC
CCCACGCAACCCATCGTCATCTGGAAGTACAAGTCTTTCTGCCGGGACCGCATCGCCGATGCCTTCTCCC
CGGCCAGCGTCGACAACCAGCTCAATGCCCAGCTGGCAGCCGGGAACCCAGGCTACAACCCCTACGTCGA
GTGCCAGGACAGCGTGCGCACCGTCAGGGTCGTGGCCACCAAGCAGGGCAACGCTGTGACCCTGGGAGAT
TACTACCAGGGCCGGAGGATTACCATCACCGGAATGTATGCCGCCGGCAAAGCAGCCACCTCAGGTGTTC
CCAGCATTTATGCCCCCAGCACCTATGCCCACCTGTCTCCCGCCAAGACCCCACCCCCACCAGCTATGAT
TCCCATGGGCCCTGCCTACAACGGGTACCCTGGAGGATACCCTGGAGACGTTGACAGGAGTAGCTCAGCT
GGTGGCCAAGGCTCCTATGTACCCCTGCTTCGGGACACGGACAGCAGTGTGGCCTCTGAAGTCCGCAGTG
GCTACAGGATTCAGGCCAGCCAGCAGGACGACTCCATGCGGGTCCTGTACTACATGGAGAAGGAGCTGGC
CAACTTCGACCCTTCTCGACCTGGCCCCCCAGTGGCCGTGTGGAGCGGGCCATGAGTGAAGTCACCTCC
CTCCACGAGGACGACTGGCGATCTCGGCCTTCCCGGGGCCCTGCCCTCACCCCGATCCGGGATGAGGAGT
GGGGTGGCCACTCCCCCCGGAGTCCCAGGGGATGGGACCAGGAGCCCGCCAGGGAGCAGGCAGGCGGGGG
CTGGCGGGCCAGGCGGCCCCGGGCCCGCTCCGTGGACGCCCTGGACGACCTCACCCCGCCGAGCACCGCC
GAGTCAGGGAGCAGGTCTCCCACGAGTAATGGTGGGAGAAGCCGGGCCTACATGCCCCGCGGAGCCGCA
GCCGGGACGACCTCTATGACCAAGACGACTCGAGGGACTTCCCACGCTCCCGGGACCCCCACTACGACGA
CTTCAGGTCTCGGGAGCGCCCTCCTGCCGACCCCAGGTCCCACCACCACCGTACCCGGGACCCTCGGGAC
AACGGCTCCAGGTCCGGGGACCTCCCCTATGATGGGCGGCTACTGGAGGAGGCTGTGAGGAAGAAGGGGT
CGGAGGAGAGGAGGAGACCCCACAAGGAGGAGGAGGAAGAGGCCTACTACCCGCCCGCGCCGCCCCCGTA
CTCGGAGACCGACTCGCAGGCGTCCCGAGAGCGCAGGCTCAAGAAGAACTTGGCCCTGAGTCGGGAAAGT
TTAGTCGTC

FIG. 1I-2

LSR isoform-f, skipping TM, SEQ ID NO:18:

MALLAGGLSRGLGSHPAAAGRDAVVFVWLLLSTWCTAPARAIQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLGRTSGVAELLPGFQAGPIE
VYAAGKAATSGVPSIYAPSTYAHLSPAKTPPPPAMIPMGPAYNGYPGGYPGDVDRSSSAGGQGSYVPLLR
DTDSSVASEVRSGYRIQASQQDDSMRVLYYMEKELANFDPSRPGPPSGRVERAMSEVTSLHEDDWRSRPS
RGPALTPIRDEEWGGHSPRSPRGWDQEPAREQAGGGWRARRPRARSVDALDDLTPPSTAESGSRSPTSNG
GRSRAYMPPRSRSRDDLYDQDDSRDFPRSRDPHYDDFRSRERPPADPRSHHHRTRDPRDNGSRSGDLPYD
GRLLEEAVRKKGSEERRRPHKEEEEEAYYPPAPPPYSETDSQASRERRLKKNLALSRESLVV

SP- aa 1-41: MALLAGGLSRGLGSHPAAAGRDAVVFVWLLLSTWCTAPARA

NA encoding LSR isoform-f (SEQ ID NO:46):

**ATGGCGCTGTTGGCCGGCGGGCTCTCCAGAGGGCTGGGCTCCCACCCGGCCGCCGCAGGCCGGGACGCGG
TCGTCTTCGTGTGGCTTCTGCTTAGCACCTGGTGCACAGCTCCTGCCAGGGCC**ATCCAGGTGACCGTGTC
CAACCCCTACCACGTGGTGATCCTCTTCCAGCCTGTGACCCTGCCCTGTACCTACCAGATGACCTCGACC
CCCACGCAACCCATCGTCATCTGGAAGTACAAGTCTTTCTGCCGGGACCGCATCGCCGATGCCTTCTCCC
CGGCCAGCGTCGACAACCAGCTCAATGCCCAGCTGGCAGCCGGGAACCCAGGCTACAACCCCTACGTCGA
GTGCCAGGACAGCGTGCGCACCGTCAGGGTCGTGGCCACCAAGCAGGGCAACGCTGTGACCCTGGGAGAT
TACTACCAGGGCCGGAGGATTACCATCACCGGAAATGCTGACCTGACCTTTGACCAGACGGCGTGGGGGG
ACAGTGGTGTGTATTACTGCTCCGTGGTCTCAGCCCAGGACCTCCAGGGGAACAATGAGGCCTACGCAGA
GCTCATCGTCCTTGGAGGACCTCAGGGGTGGCTGAGCTCTTACCTGGTTTTCAGGCGGGGCCCATAGAA

FIG. 1J-1

```
GTGTATGCCGCCGGCAAAGCAGCCACCTCAGGTGTTCCCAGCATTTATGCCCCCAGCACCTATGCCCACC
TGTCTCCCGCCAAGACCCCACCCCCACCAGCTATGATTCCCATGGGCCCTGCCTACAACGGGTACCCTGG
AGGATACCCTGGAGACGTTGACAGGAGTAGCTCAGCTGGTGGCCAAGGCTCCTATGTACCCCTGCTTCGG
GACACGGACAGCAGTGTGGCCTCTGAAGTCCGCAGTGGCTACAGGATTCAGGCCAGCCAGCAGGACGACT
CCATGCGGGTCCTGTACTACATGGAGAAGGAGCTGGCCAACTTCGACCCTTCTCGACCTGGCCCCCCCAG
TGGCCGTGTGGAGCGGGCCATGAGTGAAGTCACCTCCCTCCACGAGGACGACTGGCGATCTCGGCCTTCC
CGGGGCCCTGCCCTCACCCCGATCCGGGATGAGGAGTGGGGTGGCCACTCCCCCCGGAGTCCCAGGGGAT
GGGACCAGGAGCCCGCCAGGGAGCAGGCAGGCGGGGGCTGGCGGGCCAGGCGGCCCCGGGCCCGCTCCGT
GGACGCCCTGGACGACCTCACCCCGCCGAGCACCGCCGAGTCAGGGAGCAGGTCTCCCACGAGTAATGGT
GGGAGAAGCCGGGCCTACATGCCCCGCGGAGCCGCAGCCGGGACGACCTCTATGACCAAGACGACTCGA
GGGACTTCCCACGCTCCCGGGACCCCCACTACGACGACTTCAGGTCTCGGGAGCGCCCTCCTGCCGACCC
CAGGTCCCACCACCACCGTACCCGGGACCCTCGGGACAACGGCTCCAGGTCCGGGACCTCCCCTATGAT
GGGCGGCTACTGGAGGAGGCTGTGAGGAAGAAGGGGTCGGAGGAGAGGAGGAGACCCCACAAGGAGGAGG
AGGAAGAGGCCTACTACCCGCCCGCGCCGCCCCCGTACTCGGAGACCGACTCGCAGGCGTCCCGAGAGCG
CAGGCTCAAGAAGAACTTGGCCCTGAGTCGGGAAAGTTTAGTCGTC
```

FIG. 1J-2

SEQ ID NO:5 (VSIG10_Variant_skipping_exon_3_T95617_P6) versus SEQ ID
NO: 3 (wild type VSIG10, accession number NP_061959.2)

```
  1 MAAGGSAPEPRVLVCLGALLAGWVAVGLEAVVIGEVHENVTLHCGNISGL  50
    ||||||||||||||||||||||||||||||||||||||||||||||||||
  1 MAAGGSAPEPRVLVCLGALLAGWVAVGLEAVVIGEVHENVTLHCGNISGL  50

51 RGQVTWYRNNSEPVFLLSSNSSLRPAEPRFSLVDATSLHIESLSLGDEGI 100
    ||||||||||||||||||||||||||||||||||||||||||||||||||
 51 RGQVTWYRNNSEPVFLLSSNSSLRPAEPRFSLVDATSLHIESLSLGDEGI 100

101 YTCQEILNVTQWFQVWLQVAN............................ 121
    ||||||||||||||||||||:
101 YTCQEILNVTQWFQVWLQVASGPYQIEVHIVATGTLPNGTLYAARGSQVD 150

121 .................................................. 121

151 FSCNSSSRPPPVVEWWFQALNSSSESFGHNLTVNFFSLLLISPNLQGNYT 200

122 ....................PPPSAPQCWAQMASGSFMLQLTCRWDGG 149
                        |||||||||||||||||||||||||||||
201 CLALNQLSKRHRKVTTELLVYYPPPSAPQCWAQMASGSFMLQLTCRWDGG 250

150 YPDPDFLWIEEPGGVIVGKSKLGVEMLSESQLSDGKKFKCVTSHIVGPES 199
    ||||||||||||||||||||||||||||||||||||||||||||||||||
```

FIG. 2A-1

```
251 YPDPDFLWIEEPGGVIVGKSKLGVEMLSESQLSDGKKFKCVTSHIVGPES 300

200 GASCMVQIRGPSLLSEPMKTCFTGGNVTLTCQVSGAYPPAKILWLRNLTQ 249
    |||||||||||||||||||||||||||||||||||||||||||||||||
301 GASCMVQIRGPSLLSEPMKTCFTGGNVTLTCQVSGAYPPAKILWLRNLTQ 350

250 PEVIIQPSSRHLITQDGQNSTLTIHNCSQDLDEGYYICRADSPVGVREME 299
    |||||||||||||||||||||||||||||||||||||||||||||||||
351 PEVIIQPSSRHLITQDGQNSTLTIHNCSQDLDEGYYICRADSPVGVREME 400

300 IWLSVKEPLNIGGIVGTIVSLLLLGLAIISGLLLHYSPVFCWKVGNTSRG 349
    |||||||||||||||||||||||||||||||||||||||||||||||||
401 IWLSVKEPLNIGGIVGTIVSLLLLGLAIISGLLLHYSPVFCWKVGNTSRG 450

350 QNMDDVMVLVDSEEEEEEEEEEEEEDAAVGEQEGAREREELPKEIPKQDHI 399
    |||||||||||||||||||||||||||||||||||||||||||||||||
451 QNMDDVMVLVDSEEEEEEEEEEEEEDAAVGEQEGAREREELPKEIPKQDHI 500

400 HRVTALVNGNIEQMGNGFQDLQDDSSEEQSDIVQEEDRPV 439
    |||||||||||||||||||||||||||||||||||||||
501 HRVTALVNGNIEQMGNGFQDLQDDSSEEQSDIVQEEDRPV 540
```

FIG. 2A-2

SEQ ID NO:11 LSR_isoform a versus SEQ ID NO:62 LSR, accession number
NP_991403

```
Query:   1   MALLAGGLSRGLGSHPAAAGRDAVVFVWLLLSTWCTAPARAIQVTVSNPYHVVILFQPVT   60
             MALLAGGLSRGLGSHPAAAGRDAVVFVWLLLSTWCTAPARAIQVTVSNPYHVVILFQPVT
Sbjct:  49   MALLAGGLSRGLGSHPAAAGRDAVVFVWLLLSTWCTAPARAIQVTVSNPYHVVILFQPVT  108

Query:  61   LPCTYQMTSTPTQPIVIWKYKSFCRDRIADAFSPASVDNQLNAQLAAGNPGYNPYVECQD  120
             LPCTYQMTSTPTQPIVIWKYKSFCRDRIADAFSPASVDNQLNAQLAAGNPGYNPYVECQD
Sbjct: 109   LPCTYQMTSTPTQPIVIWKYKSFCRDRIADAFSPASVDNQLNAQLAAGNPGYNPYVECQD  168

Query: 121   SVRTVRVVATKQGNAVTLGDYYQGRRITITGNADLTFDQTAWGDSGVYYCSVVSAQDLQG  180
             SVRTVRVVATKQGNAVTLGDYYQGRRITITGNADLTFDQTAWGDSGVYYCSVVSAQDLQG
Sbjct: 169   SVRTVRVVATKQGNAVTLGDYYQGRRITITGNADLTFDQTAWGDSGVYYCSVVSAQDLQG  228

Query: 181   NNEAYAELIVLGRTSGVAELLPGFQAGPIEDWLFVVVVCLAAFLIFLLLGICWCQCCPHT  240
             NNEAYAELIVLGRTSGVAELLPGFQAGPIEDWLFVVVVCLAAFLIFLLLGICWCQCCPHT
Sbjct: 229   NNEAYAELIVLGRTSGVAELLPGFQAGPIEDWLFVVVVCLAAFLIFLLLGICWCQCCPHT  288

Query: 241   CCCYVRCPCCPDKCCCPEALYAAGKAATSGVPSIYAPSTYAHLSPAKTPPPPAMIPMGPA  300
             CCCYVRCPCCPDKCCCPEALYAAGKAATSGVPSIYAPSTYAHLSPAKTPPPPAMIPMGPA
Sbjct: 289   CCCYVRCPCCPDKCCCPEALYAAGKAATSGVPSIYAPSTYAHLSPAKTPPPPAMIPMGPA  348
```

FIG. 2B-1(1)

```
Query: 301 YNGYPGGYPGDVDRSSSAGGQGSYVPLLRDTDSSVASEVRSGYRIQASQQDDSMRVLYYM 360
            YNGYPGGYPGDVDRSSSAGGQGSYVPLLRDTDSSVASEVRSGYRIQASQQDDSMRVLYYM
Sbjct: 349 YNGYPGGYPGDVDRSSSAGGQGSYVPLLRDTDSSVASEVRSGYRIQASQQDDSMRVLYYM 408

Query: 361 EKELANFDPSRPGPPSGRVERAMSEVTSLHEDDWRSRPSRGPALTPIRDEEWGGHSPRSP 420
            EKELANFDPSRPGPPSGRVERAMSEVTSLHEDDWRSRPSRGPALTPIRDEEWGGHSPRSP
Sbjct: 409 EKELANFDPSRPGPPSGRVERAMSEVTSLHEDDWRSRPSRGPALTPIRDEEWGGHSPRSP 468

Query: 421 RGWDQEPAREQAGGGWRARRPRARSVDALDDLTPPSTAESGSRSPTSNGGRSRAYMPPRS 480
            RGWDQEPAREQAGGGWRARRPRARSVDALDDLTPPSTAESGSRSPTSNGGRSRAYMPPRS
Sbjct: 469 RGWDQEPAREQAGGGWRARRPRARSVDALDDLTPPSTAESGSRSPTSNGGRSRAYMPPRS 528

Query: 481 RSRDDLYDQDDSRDFPRSRDPHYDDFRSRERPPADPRSHHHRTRDPRDNGSRSGDLPYDG 540
            RSRDDLYDQDDSRDFPRSRDPHYDDFRSRERPPADPRSHHHRTRDPRDNGSRSGDLPYDG
Sbjct: 529 RSRDDLYDQDDSRDFPRSRDPHYDDFRSRERPPADPRSHHHRTRDPRDNGSRSGDLPYDG 588

Query: 541 RLLEEAVRKKGSEERRRPHKEEEEEAYYPPAPPPYSETDSQASRERRLKKNLALSRESLV 600
            RLLEEAVRKKGSEERRRPHKEEEEEAYYPPAPPPYSETDSQASRERRLKKNLALSRESLV
Sbjct: 589 RLLEEAVRKKGSEERRRPHKEEEEEAYYPPAPPPYSETDSQASRERRLKKNLALSRESLV 648

Query: 601 V 601
            V
Sbjct: 649 V 649
```

FIG. 2B-1(2)

SEQ ID NO:11 LSR_isoform-a versus SEQ ID NO:68 LSR, accession number
XP_002829104, [Pongo abelii]

Query: 1    MALLAGGLSRGLGSHPAAAGRDAVVFVWLLLSTWCTAPARAIQVTVSNPYHVVILFQPVT 60
            MALLAGGLSRGLGSHPAA GRDAVVFVWLLLSTWCTAPARAIQVTVSNPYHVVILFQPVT
Sbjct: 1    MALLAGGLSRGLGSHPAAPGRDAVVFVWLLLSTWCTAPARAIQVTVSNPYHVVILFQPVT 60

Query: 61   LPCTYQMTSTPTQPIVIWKYKSFCRDRIADAFSPASVDNQLNAQLAAGNPGYNPYVECQD 120
            LPCTYQMTSTPTQPIVIWKYKSFCRDRIADAFSPASVDNQLNAQLAAGNPGYNPYVECQD
Sbjct: 61   LPCTYQMTSTPTQPIVIWKYKSFCRDRIADAFSPASVDNQLNAQLAAGNPGYNPYVECQD 120

Query: 121  SVRTVRVVATKQGNAVTLGDYYQGRRITITGNADLTFDQTAWGDSGVYYCSVVSAQDLQG 180
            SVRTVRVVATKQGNAVTLGDYYQGRRITITGNADLTFDQTAWGDSGVYYCSVVSAQDLQG
Sbjct: 121  SVRTVRVVATKQGNAVTLGDYYQGRRITITGNADLTFDQTAWGDSGVYYCSVVSAQDLQG 180

Query: 181  NNEAYAELIVLGRTSGVAELLPGFQAGPIEDWLFVVVVCLAAFLIFLLLGICWCQCCPHT 240
            NNEAYAELIVLGRTSGVAELLPGFQAGP+EDWLFVVVVCLAAFLIFLLLGICWCQCCPHT
Sbjct: 181  NNEAYAELIVLGRTSGVAELLPGFQAGPMEDWLFVVVVCLAAFLIFLLLGICWCQCCPHT 240

Query: 241  CCCYVRCPCCPDKCCCPEALYAAGKAATSGVPSIYAPSTYAHLSPAKTPPPPAMIPMGPA 300
            CCCYVRCPCCPDKCCCPEALYAAGKAATSGVPSIYAPSTYAHLSPAKTPPPPAMIPMGPA
Sbjct: 241  CCCYVRCPCCPDKCCCPEALYAAGKAATSGVPSIYAPSTYAHLSPAKTPPPPAMIPMGPA 300

FIG. 2B-2(1)

```
Query: 301 YNGYPGGYPGDVDRSSSAGGQGSYVPLLRDTDSSVASEVRSGYRIQASQQDDSMRVLYYM 360
            YNGYPGGYPGDVDRSSSAGGQGSYVPLLRDTDSSVASEVRSGYRIQASQQDDSMRVLYYM
Sbjct: 301 YNGYPGGYPGDVDRSSSAGGQGSYVPLLRDTDSSVASEVRSGYRIQASQQDDSMRVLYYM 360

Query: 361 EKELANFDPSRPGPPSGRVERAMSEVTSLHEDDWRSRPSRGPALTPIRDEEWGGHSPRSP 420
            EKELANFDPSRPGPP+GRVERAMSEVTSLHEDDWRSRPSRGPALTPIRDEEWGGHSPRSP
Sbjct: 361 EKELANFDPSRPGPPNGRVERAMSEVTSLHEDDWRSRPSRGPALTPIRDEEWGGHSPRSP 420

Query: 421 RGWDQEPAREQAGGGWRARRPRARSVDALDDLTPPSTAESGSRSPTSNGG-RSRAYMPPR 479
            RGWDQEP REQAGGGWRARRPRARSVDALDDLTPPSTAESGSRSPTS+GG R RAYMPPR
Sbjct: 421 RGWDQEPPREQAGGGWRARRPRARSVDALDDLTPPSTAESGSRSPTSSGGRRGRAYMPPR 480

Query: 480 SRSRDDLYDQDDSRDFPRSRDPHYDDFRSRERPPADPRSHHHRTRDPRDNGSRSGDLPYD 539
            SRSRDDLYDQDDSRDFPRSRD HYDDFRSRERPPADPRSHHHRTRDPRD+GSRSGDL YD
Sbjct: 481 SRSRDDLYDQDDSRDFPRSRDSHYDDFRSRERPPADPRSHHHRTRDPRDHGSRSGDLLYD 540

Query: 540 GRLLEEAVRKKGSEERRRPHKEEEEEAYYPPAPPPYSETDSQASRERRLKKNLALSRESL 599
            GRLLEEAVRKKGSEERRRPHKEEEEEAYYPPAPPPYSETDSQASRERRLKKNLALSRESL
Sbjct: 541 GRLLEEAVRKKGSEERRRPHKEEEEEAYYPPAPPPYSETDSQASRERRLKKNLALSRESL 600

Query: 600 VV 601
            VV
Sbjct: 601 VV 602
```

FIG. 2B-2(2)

SEQ ID NO:13 LSR_Isoform_b versus SEQ ID NO:63, LSR accession number
NP_057009

```
Query:   1  MALLAGGLSRGLGSHPAAAGRDAVVFVWLLLSTWCTAPARAIQVTVSNPYHVVILFQPVT  60
            MALLAGGLSRGLGSHPAAAGRDAVVFVWLLLSTWCTAPARAIQVTVSNPYHVVILFQPVT
Sbjct:  49  MALLAGGLSRGLGSHPAAAGRDAVVFVWLLLSTWCTAPARAIQVTVSNPYHVVILFQPVT 108

Query:  61  LPCTYQMTSTPTQPIVIWKYKSFCRDRIADAFSPASVDNQLNAQLAAGNPGYNPYVECQD 120
            LPCTYQMTSTPTQPIVIWKYKSFCRDRIADAFSPASVDNQLNAQLAAGNPGYNPYVECQD
Sbjct: 109  LPCTYQMTSTPTQPIVIWKYKSFCRDRIADAFSPASVDNQLNAQLAAGNPGYNPYVECQD 168

Query: 121  SVRTVRVVATKQGNAVTLGDYYQGRRITITGNADLTFDQTAWGDSGVYYCSVVSAQDLQG 180
            SVRTVRVVATKQGNAVTLGDYYQGRRITITGNADLTFDQTAWGDSGVYYCSVVSAQDLQG
Sbjct: 169  SVRTVRVVATKQGNAVTLGDYYQGRRITITGNADLTFDQTAWGDSGVYYCSVVSAQDLQG 228

Query: 181  NNEAYAELIVLDWLFVVVVCLAAFLIFLLLGICWCQCCPHTCCCYVRCPCCPDKCCCPEA 240
            NNEAYAELIVLDWLFVVVVCLAAFLIFLLLGICWCQCCPHTCCCYVRCPCCPDKCCCPEA
Sbjct: 229  NNEAYAELIVLDWLFVVVVCLAAFLIFLLLGICWCQCCPHTCCCYVRCPCCPDKCCCPEA 288

Query: 241  LYAAGKAATSGVPSIYAPSTYAHLSPAKTPPPPAMIPMGPAYNGYPGGYPGDVDRSSSAG 300
            LYAAGKAATSGVPSIYAPSTYAHLSPAKTPPPPAMIPMGPAYNGYPGGYPGDVDRSSSAG
Sbjct: 289  LYAAGKAATSGVPSIYAPSTYAHLSPAKTPPPPAMIPMGPAYNGYPGGYPGDVDRSSSAG 348
```

FIG. 2C-1(1)

```
Query: 301 GQGSYVPLLRDTDSSVASEVRSGYRIQASQQDDSMRVLYYMEKELANFDPSRPGPPSGRV 360
            GQGSYVPLLRDTDSSVASEVRSGYRIQASQQDDSMRVLYYMEKELANFDPSRPGPPSGRV
Sbjct: 349 GQGSYVPLLRDTDSSVASEVRSGYRIQASQQDDSMRVLYYMEKELANFDPSRPGPPSGRV 408

Query: 361 ERAMSEVTSLHEDDWRSRPSRGPALTPIRDEEWGGHSPRSPRGWDQEPAREQAGGGWRAR 420
            ERAMSEVTSLHEDDWRSRPSRGPALTPIRDEEWGGHSPRSPRGWDQEPAREQAGGGWRAR
Sbjct: 409 ERAMSEVTSLHEDDWRSRPSRGPALTPIRDEEWGGHSPRSPRGWDQEPAREQAGGGWRAR 468

Query: 421 RPRARSVDALDDLTPPSTAESGSRSPTSNGGRSRAYMPPRSRSRDDLYDQDDSRDFPRSR 480
            RPRARSVDALDDLTPPSTAESGSRSPTSNGGRSRAYMPPRSRSRDDLYDQDDSRDFPRSR
Sbjct: 469 RPRARSVDALDDLTPPSTAESGSRSPTSNGGRSRAYMPPRSRSRDDLYDQDDSRDFPRSR 528

Query: 481 DPHYDDFRSRERPPADPRSHHHRTRDPRDNGSRSGDLPYDGRLLEEAVRKKGSEERRRPH 540
            DPHYDDFRSRERPPADPRSHHHRTRDPRDNGSRSGDLPYDGRLLEEAVRKKGSEERRRPH
Sbjct: 529 DPHYDDFRSRERPPADPRSHHHRTRDPRDNGSRSGDLPYDGRLLEEAVRKKGSEERRRPH 588

Query: 541 KEEEEEAYYPPAPPPYSETDSQASRERRLKKNLALSRESLVV 582
            KEEEEEAYYPPAPPPYSETDSQASRERRLKKNLALSRESLVV
Sbjct: 589 KEEEEEAYYPPAPPPYSETDSQASRERRLKKNLALSRESLVV 630
```

FIG. 2C-1(2)

SEQ ID NO:13 LSR_Isoform_b versus SEQ ID NO:65, LSR, accession number
BAC11614

```
Query:   1   MALLAGGLSRGLGSHPAAAGRDAVVFVWLLLSTWCTAPARAIQVTVSNPYHVVILFQPVT  60
             MALLAGGLSRGLGSHPAAAGRDAVVFVWLLLSTWCTAPARAIQVTVSNPYHVVILFQPVT
Sbjct:   1   MALLAGGLSRGLGSHPAAAGRDAVVFVWLLLSTWCTAPARAIQVTVSNPYHVVILFQPVT  60

Query:  61   LPCTYQMTSTPTQPIVIWKYKSFCRDRIADAFSPASVDNQLNAQLAAGNPGYNPYVECQD 120
             LPCTYQMTSTPTQPIVIWKYKSFCRDRIADAFSPASVDNQLNAQLAAGNPGYNPYVECQD
Sbjct:  61   LPCTYQMTSTPTQPIVIWKYKSFCRDRIADAFSPASVDNQLNAQLAAGNPGYNPYVECQD 120

Query: 121   SVRTVRVVATKQGNAVTLGDYYQGRRITITGNADLTFDQTAWGDSGVYYCSVVSAQDLQG 180
             SVRTVRVVATKQGNAVTLGDYYQGRRITITGNADLTFDQTAWGDSGVYYCSVVSAQDLQG
Sbjct: 121   SVRTVRVVATKQGNAVTLGDYYQGRRITITGNADLTFDQTAWGDSGVYYCSVVSAQDLQG 180

Query: 181   NNEAYAELIVLDWLFVVVVCLAAFLIFLLLGICWCQCCPHTCCCYVRCPCCPDKCCCPEA 240
             NNEAYAELIVLDWLFVVVVCLAAFLIFLLLGICWCQCCPHTCCCYVRCPCCPDKCCCPEA
Sbjct: 181   NNEAYAELIVLDWLFVVVVCLAAFLIFLLLGICWCQCCPHTCCCYVRCPCCPDKCCCPEA 240

Query: 241   LYAAGKAATSGVPSIYAPSTYAHLSPAKTPPPPAMIPMGPAYNGYPGGYPGDVDRSSSAG 300
             LYAAGKAATSGVPSIYAPSTYAHLSPAKTPPPPAMIPMGPAYNGYPGGYPGDVDR+SSAG
Sbjct: 241   LYAAGKAATSGVPSIYAPSTYAHLSPAKTPPPPAMIPMGPAYNGYPGGYPGDVDRNSSAG 300
```

FIG. 2C-2(1)

```
Query: 301 GQGSYVPLLRDTDSSVASEVRSGYRIQASQQDDSMRVLYYMEKELANFDPSRPGPPSGRV 360
            GQGSYVPLLRDTDSSVASEVRSGYRIQASQQDDSMRVLYYMEKELANFDPSRPGPPSGRV
Sbjct: 301 GQGSYVPLLRDTDSSVASEVRSGYRIQASQQDDSMRVLYYMEKELANFDPSRPGPPSGRV 360

Query: 361 ERAMSEVTSLHEDDWRSRPSRGPALTPIRDEEWGGHSPRSPRGWDQEPAREQAGGGWRAR 420
            ERAMSEVTSLHEDDWRSRPSRGPALTPIRDEEWGGHSPRSPRGWDQEPAREQAGGGWRAR
Sbjct: 361 ERAMSEVTSLHEDDWRSRPSRGPALTPIRDEEWGGHSPRSPRGWDQEPAREQAGGGWRAR 420

Query: 421 RPRARSVDALDDLTPPSTAESGSRSPTSNGG-RSRAYMPPRSRSRDDLYDQDDSRDFPRS 479
            RPRARSVDALDDLTPPSTAESGSRSPTSNGG RSRAYMPPRSRSRDDLYDQDDSRDFPRS
Sbjct: 421 RPRARSVDALDDLTPPSTAESGSRSPTSNGGRRSRAYMPPRSRSRDDLYDQDDSRDFPRS 480

Query: 480 RDPHYDDFRSRERPPADPRSHHHRTRDPRDNGSRSGDLPYDGRLLEEAVRKKGSEERRRP 539
            RDPHYDDFRSRERPPADPRSHHHRTRDPRDNGSRSGDLPYDGRLLEEAVRKKGSEERRRP
Sbjct: 481 RDPHYDDFRSRERPPADPRSHHHRTRDPRDNGSRSGDLPYDGRLLEEAVRKKGSEERRRP 540

Query: 540 HKEEEEEAYYPPAPPPYSETDSQASRERRLKKNLALSRESLVV 582
            HKEEEEEAYYPPAPPPYSETDSQASRERRLKKNLALSRESLVV
Sbjct: 541 HKEEEEEAYYPPAPPPYSETDSQASRERRLKKNLALSRESLVV 583
```

FIG. 2C-2(2)

SEQ ID NO:15 LSR_Isoform_c_versus SEQ ID NO:66 LSR, accession number:
NP_991404

```
Query:   1  MALLAGGLSRGLGSHPAAAGRDAVVFVWLLLSTWCTAPARAIQVTVSNPYHVVILFQPVT  60
            MALLAGGLSRGLGSHPAAAGRDAVVFVWLLLSTWCTAPARAIQVTVSNPYHVVILFQPVT
Sbjct:  49  MALLAGGLSRGLGSHPAAAGRDAVVFVWLLLSTWCTAPARAIQVTVSNPYHVVILFQPVT 108

Query:  61  LPCTYQMTSTPTQPIVIWKYKSFCRDRIADAFSPASVDNQLNAQLAAGNPGYNPYVECQD 120
            LPCTYQMTSTPTQPIVIWKYKSFCRDRIADAFSPASVDNQLNAQLAAGNPGYNPYVECQD
Sbjct: 109  LPCTYQMTSTPTQPIVIWKYKSFCRDRIADAFSPASVDNQLNAQLAAGNPGYNPYVECQD 168

Query: 121  SVRTVRVVATKQGNAVTLGDYYQGRRITITGNADLTFDQTAWGDSGVYYCSVVSAQDLQG 180
            SVRTVRVVATKQGNAVTLGDYYQGRRITITGNADLTFDQTAWGDSGVYYCSVVSAQDLQG
Sbjct: 169  SVRTVRVVATKQGNAVTLGDYYQGRRITITGNADLTFDQTAWGDSGVYYCSVVSAQDLQG 228

Query: 181  NNEAYAELIVLVYAAGKAATSGVPSIYAPSTYAHLSPAKTPPPPAMIPMGPAYNGYPGGY 240
            NNEAYAELIVLVYAAGKAATSGVPSIYAPSTYAHLSPAKTPPPPAMIPMGPAYNGYPGGY
Sbjct: 229  NNEAYAELIVLVYAAGKAATSGVPSIYAPSTYAHLSPAKTPPPPAMIPMGPAYNGYPGGY 288
```

FIG. 2D-1(1)

```
Query: 241 PGDVDRSSSAGGQGSYVPLLRDTDSSVASEVRSGYRIQASQQDDSMRVLYYMEKELANFD 300
            PGDVDRSSSAGGQGSYVPLLRDTDSSVASEVRSGYRIQASQQDDSMRVLYYMEKELANFD
Sbjct: 289 PGDVDRSSSAGGQGSYVPLLRDTDSSVASEVRSGYRIQASQQDDSMRVLYYMEKELANFD 348

Query: 301 PSRPGPPSGRVERAMSEVTSLHEDDWRSRPSRGPALTPIRDEEWGGHSPRSPRGWDQEPA 360
            PSRPGPPSGRVERAMSEVTSLHEDDWRSRPSRGPALTPIRDEEWGGHSPRSPRGWDQEPA
Sbjct: 349 PSRPGPPSGRVERAMSEVTSLHEDDWRSRPSRGPALTPIRDEEWGGHSPRSPRGWDQEPA 408

Query: 361 REQAGGGWRARRPRARSVDALDDLTPPSTAESGSRSPTSNGGRSRAYMPPRSRSRDDLYD 420
            REQAGGGWRARRPRARSVDALDDLTPPSTAESGSRSPTSNGGRSRAYMPPRSRSRDDLYD
Sbjct: 409 REQAGGGWRARRPRARSVDALDDLTPPSTAESGSRSPTSNGGRSRAYMPPRSRSRDDLYD 468

Query: 421 QDDSRDFPRSRDPHYDDFRSRERPPADPRSHHHRTRDPRDNGSRSGDLPYDGRLLEEAVR 480
            QDDSRDFPRSRDPHYDDFRSRERPPADPRSHHHRTRDPRDNGSRSGDLPYDGRLLEEAVR
Sbjct: 469 QDDSRDFPRSRDPHYDDFRSRERPPADPRSHHHRTRDPRDNGSRSGDLPYDGRLLEEAVR 528

Query: 481 KKGSEERRRPHKEEEEEAYYPPAPPPYSETDSQASRERRLKKNLALSRESLVV 533
            KKGSEERRRPHKEEEEEAYYPPAPPPYSETDSQASRERRLKKNLALSRESLVV
Sbjct: 529 KKGSEERRRPHKEEEEEAYYPPAPPPYSETDSQASRERRLKKNLALSRESLVV 581
```

FIG. 2D-1(2)

SEQ ID NO:15 LSR_Isoform_c versus SEQ ID NO:69 LSR, accession number:
XP_002829105.1, [Pongo abelii]

```
Query: 1    MALLAGGLSRGLGSHPAAAGRDAVVFVWLLLSTWCTAPARAIQVTVSNPYHVVILFQPVT 60
            MALLAGGLSRGLGSHPAA GRDAVVFVWLLLSTWCTAPARAIQVTVSNPYHVVILFQPVT
Sbjct: 1    MALLAGGLSRGLGSHPAAPGRDAVVFVWLLLSTWCTAPARAIQVTVSNPYHVVILFQPVT 60

Query: 61   LPCTYQMTSTPTQPIVIWKYKSFCRDRIADAFSPASVDNQLNAQLAAGNPGYNPYVECQD 120
            LPCTYQMTSTPTQPIVIWKYKSFCRDRIADAFSPASVDNQLNAQLAAGNPGYNPYVECQD
Sbjct: 61   LPCTYQMTSTPTQPIVIWKYKSFCRDRIADAFSPASVDNQLNAQLAAGNPGYNPYVECQD 120

Query: 121  SVRTVRVVATKQGNAVTLGDYYQGRRITITGNADLTFDQTAWGDSGVYYCSVVSAQDLQG 180
            SVRTVRVVATKQGNAVTLGDYYQGRRITITGNADLTFDQTAWGDSGVYYCSVVSAQDLQG
Sbjct: 121  SVRTVRVVATKQGNAVTLGDYYQGRRITITGNADLTFDQTAWGDSGVYYCSVVSAQDLQG 180

Query: 181  NNEAYAELIVLVYAAGKAATSGVPSIYAPSTYAHLSPAKTPPPPAMIPMGPAYNGYPGGY 240
            NNEAYAELIVLVYAAGKAATSGVPSIYAPSTYAHLSPAKTPPPPAMIPMGPAYNGYPGGY
Sbjct: 181  NNEAYAELIVLVYAAGKAATSGVPSIYAPSTYAHLSPAKTPPPPAMIPMGPAYNGYPGGY 240
```

FIG. 2D-2(1)

```
Query: 241 PGDVDRSSSAGGQGSYVPLLRDTDSSVASEVRSGYRIQASQQDDSMRVLYYMEKELANFD 300
            PGDVDRSSSAGGQGSYVPLLRDTDSSVASEVRSGYRIQASQQDDSMRVLYYMEKELANFD
Sbjct: 241 PGDVDRSSSAGGQGSYVPLLRDTDSSVASEVRSGYRIQASQQDDSMRVLYYMEKELANFD 300

Query: 301 PSRPGPPSGRVERAMSEVTSLHEDDWRSRPSRGPALTPIRDEEWGGHSPRSPRGWDQEPA 360
            PSRPGPP+GRVERAMSEVTSLHEDDWRSRPSRGPALTPIRDEEWGGHSPRSPRGWDQEP
Sbjct: 301 PSRPGPPNGRVERAMSEVTSLHEDDWRSRPSRGPALTPIRDEEWGGHSPRSPRGWDQEPP 360

Query: 361 REQAGGGWRARRPRARSVDALDDLTPPSTAESGSRSPTSNGG-RSRAYMPPRSRSRDDLY 419
            REQAGGGWRARRPRARSVDALDDLTPPSTAESGSRSPTS+GG R RAYMPPRSRSRDDLY
Sbjct: 361 REQAGGGWRARRPRARSVDALDDLTPPSTAESGSRSPTSSGGRRGRAYMPPRSRSRDDLY 420

Query: 420 DQDDSRDFPRSRDPHYDDFRSRERPPADPRSHHHRTRDPRDNGSRSGDLPYDGRLLEEAV 479
            DQDDSRDFPRSRD HYDDFRSRERPPADPRSHHHRTRDPRD+GSRSGDL YDGRLLEEAV
Sbjct: 421 DQDDSRDFPRSRDSHYDDFRSRERPPADPRSHHHRTRDPRDHGSRSGDLLYDGRLLEEAV 480

Query: 480 RKKGSEERRRPHKEEEEAYYPPAPPPYSETDSQASRERRLKKNLALSRESLVV 533
            RKKGSEERRRPHKEEEEAYYPPAPPPYSETDSQASRERRLKKNLALSRESLVV
Sbjct: 481 RKKGSEERRRPHKEEEEAYYPPAPPPYSETDSQASRERRLKKNLALSRESLVV 534
```

FIG. 2D-2(2)

SEQ ID NO: 16 LSR_Isoform_d_secreted_R36881_P20 versus SEQ ID NO: 66 LSR
accession number: NP_991404

```
Query:   1   MALLAGGLSRGLGSHPAAAGRDAVVFVWLLLSTWCTAPARAIQVTVSNPYHVVILFQPVT  60
             MALLAGGLSRGLGSHPAAAGRDAVVFVWLLLSTWCTAPARAIQVTVSNPYHVVILFQPVT
Sbjct:  49   MALLAGGLSRGLGSHPAAAGRDAVVFVWLLLSTWCTAPARAIQVTVSNPYHVVILFQPVT  108

Query:  61   LPCTYQMTSTPTQPIVIWKYKSFCRDRIADAFSPASVDNQLNAQLAAGNPGYNPYVECQD  120
             LPCTYQMTSTPTQPIVIWKYKSFCRDRIADAFSPASVDNQLNAQLAAGNPGYNPYVECQD
Sbjct: 109   LPCTYQMTSTPTQPIVIWKYKSFCRDRIADAFSPASVDNQLNAQLAAGNPGYNPYVECQD  168

Query: 121   SVRTVRVVATKQGNAVTLGDYYQGRRITITGNADLTFDQTAWGDSGVYYCSVVSAQDLQG  180
             SVRTVRVVATKQGNAVTLGDYYQGRRITITGNADLTFDQTAWGDSGVYYCSVVSAQDLQG
Sbjct: 169   SVRTVRVVATKQGNAVTLGDYYQGRRITITGNADLTFDQTAWGDSGVYYCSVVSAQDLQG  228

Query: 181   NNEAYAELIVLVYAAGKAATSGVPSIYAPSTYAHLSPAKTPPPPAMIPMGPAYNGYPGGY  240
             NNEAYAELIVLVYAAGKAATSGVPSIYAPSTYAHLSPAKTPPPPAMIPMGPAYNGYPGGY
Sbjct: 229   NNEAYAELIVLVYAAGKAATSGVPSIYAPSTYAHLSPAKTPPPPAMIPMGPAYNGYPGGY  288
```

FIG. 2E-1(1)

```
Query: 241  PGDVDRSSSAGGQGSYVPLLRDTDSSVAS-VRSGYRIQASQQDDSMRVLYYMEKELANFD  299
            PGDVDRSSSAGGQGSYVPLLRDTDSSVAS VRSGYRIQASQQDDSMRVLYYMEKELANFD
Sbjct: 289  PGDVDRSSSAGGQGSYVPLLRDTDSSVASEVRSGYRIQASQQDDSMRVLYYMEKELANFD  348

Query: 300  PSRPGPPSGRVERAMSEVTSLHEDDWRSRPSRGPALTPIRDEEWGGHSPRSPRGWDQEPA  359
            PSRPGPPSGRVERAMSEVTSLHEDDWRSRPSRGPALTPIRDEEWGGHSPRSPRGWDQEPA
Sbjct: 349  PSRPGPPSGRVERAMSEVTSLHEDDWRSRPSRGPALTPIRDEEWGGHSPRSPRGWDQEPA  408

Query: 360  REQAGGGWRARRPRARSVDALDDLTPPSTAESGSRSPTSNGGRSRAYMPPRSRSRDDLYD  419
            REQAGGGWRARRPRARSVDALDDLTPPSTAESGSRSPTSNGGRSRAYMPPRSRSRDDLYD
Sbjct: 409  REQAGGGWRARRPRARSVDALDDLTPPSTAESGSRSPTSNGGRSRAYMPPRSRSRDDLYD  468

Query: 420  QDDSRDFPRSRDPHYDDFRSRERPPADPRSHHHRTRDPRDNGSRSGDLPYDGRLLEEAVR  479
            QDDSRDFPRSRDPHYDDFRSRERPPADPRSHHHRTRDPRDNGSRSGDLPYDGRLLEEAVR
Sbjct: 469  QDDSRDFPRSRDPHYDDFRSRERPPADPRSHHHRTRDPRDNGSRSGDLPYDGRLLEEAVR  528

Query: 480  KKGSEERRRPHKEEEEEAYYPPAPPPYSETDSQASRERRLKKNLALSRESLVV  532
            KKGSEERRRPHKEEEEEAYYPPAPPPYSETDSQASRERRLKKNLALSRESLVV
Sbjct: 529  KKGSEERRRPHKEEEEEAYYPPAPPPYSETDSQASRERRLKKNLALSRESLVV  581
```

FIG. 2E-1(2)

SEQ ID NO: 16 LSR_Isoform_d_secreted_R36881_P20 versus SEQ ID NO:69 LSR, accession number: XP_002829105.1, [Pongo abelii]

```
Query: 1    MALLAGGLSRGLGSHPAAAGRDAVVFVWLLLSTWCTAPARAIQVTVSNPYHVVILFQPVT  60
            MALLAGGLSRGLGSHPAA GRDAVVFVWLLLSTWCTAPARAIQVTVSNPYHVVILFQPVT
Sbjct: 1    MALLAGGLSRGLGSHPAAPGRDAVVFVWLLLSTWCTAPARAIQVTVSNPYHVVILFQPVT  60

Query: 61   LPCTYQMTSTPTQPIVIWKYKSFCRDRIADAFSPASVDNQLNAQLAAGNPGYNPYVECQD  120
            LPCTYQMTSTPTQPIVIWKYKSFCRDRIADAFSPASVDNQLNAQLAAGNPGYNPYVECQD
Sbjct: 61   LPCTYQMTSTPTQPIVIWKYKSFCRDRIADAFSPASVDNQLNAQLAAGNPGYNPYVECQD  120

Query: 121  SVRTVRVVATKQGNAVTLGDYYQGRRITITGNADLTFDQTAWGDSGVYYCSVVSAQDLQG  180
            SVRTVRVVATKQGNAVTLGDYYQGRRITITGNADLTFDQTAWGDSGVYYCSVVSAQDLQG
Sbjct: 121  SVRTVRVVATKQGNAVTLGDYYQGRRITITGNADLTFDQTAWGDSGVYYCSVVSAQDLQG  180

Query: 181  NNEAYAELIVLVYAAGKAATSGVPSIYAPSTYAHLSPAKTPPPPAMIPMGPAYNGYPGGY  240
            NNEAYAELIVLVYAAGKAATSGVPSIYAPSTYAHLSPAKTPPPPAMIPMGPAYNGYPGGY
Sbjct: 181  NNEAYAELIVLVYAAGKAATSGVPSIYAPSTYAHLSPAKTPPPPAMIPMGPAYNGYPGGY  240

Query: 241  PGDVDRSSSAGGQGSYVPLLRDTDSSVAS-VRSGYRIQASQQDDSMRVLYYMEKELANFD  299
            PGDVDRSSSAGGQGSYVPLLRDTDSSVAS VRSGYRIQASQQDDSMRVLYYMEKELANFD
Sbjct: 241  PGDVDRSSSAGGQGSYVPLLRDTDSSVASEVRSGYRIQASQQDDSMRVLYYMEKELANFD  300
```

FIG. 2E-2(1)

```
Query:  300  PSRPGPPSGRVERAMSEVTSLHEDDWRSRPSRGPALTPIRDEEWGGHSPRSPRGWDQEPA  359
             PSRPGPP+GRVERAMSEVTSLHEDDWRSRPSRGPALTPIRDEEWGGHSPRSPRGWDQEP
Sbjct:  301  PSRPGPPNGRVERAMSEVTSLHEDDWRSRPSRGPALTPIRDEEWGGHSPRSPRGWDQEPP  360

Query:  360  REQAGGGWRARRPRARSVDALDDLTPPSTAESGSRSPTSNGG-RSRAYMPPRSRSRDDLY  418
             REQAGGGWRARRPRARSVDALDDLTPPSTAESGSRSPTS+GG R RAYMPPRSRSRDDLY
Sbjct:  361  REQAGGGWRARRPRARSVDALDDLTPPSTAESGSRSPTSSGGRRGRAYMPPRSRSRDDLY  420

Query:  419  DQDDSRDFPRSRDPHYDDFRSRERPPADPRSHHHRTRDPRDNGSRSGDLPYDGRLLEEAV  478
             DQDDSRDFPRSRD HYDDFRSRERPPADPRSHHHRTRDPRD+GSRSGDL YDGRLLEEAV
Sbjct:  421  DQDDSRDFPRSRDSHYDDFRSRERPPADPRSHHHRTRDPRDHGSRSGDLLYDGRLLEEAV  480

Query:  479  RKKGSEERRRPHKEEEEEAYYPPAPPPYSETDSQASRERRLKKNLALSRESLVV  532
             RKKGSEERRRPHKEEEEEAYYPPAPPPYSETDSQASRERRLKKNLALSRESLVV
Sbjct:  481  RKKGSEERRRPHKEEEEEAYYPPAPPPYSETDSQASRERRLKKNLALSRESLVV  534
```

FIG. 2E-2(2)

SEQ ID NO:17 LSR_Isoform_e_secreted_R36881_P27 versus SEQ ID NO:67,
accession number BAG59226.1

```
Query: 1    MALLAGGLSRGLGSHPAAAGRDAVVFVWLLLSTWCTAPARAIQVTVSNPYHVVILFQPVT   60
            MALLAGGLSRGLGSHPAAAGRDAVVFVWLLLSTWCTAPARAIQVTVSNPYHVVILFQPVT
Sbjct: 1    MALLAGGLSRGLGSHPAAAGRDAVVFVWLLLSTWCTAPARAIQVTVSNPYHVVILFQPVT   60

Query: 61   LPCTYQMTSTPTQPIVIWKYKSFCRDRIADAFSPASVDNQLNAQLAAGNPGYNPYVECQD  120
            LPCTYQMTSTPTQPIVIWKYKSFCRDRIADAFSPASVDNQLNAQLAAGNPGYNPYVECQD
Sbjct: 61   LPCTYQMTSTPTQPIVIWKYKSFCRDRIADAFSPASVDNQLNAQLAAGNPGYNPYVECQD  120

Query: 121  SVRTVRVVATKQGNAVTLGDYYQGRRITITGMYAAGKAATSGVPSIYAPSTYAHLSPAKT  180
            SVRTVRVVATKQGNAVTLGDYYQGRRITITGMYAAGKAATSGVPSIYAPSTYAHLSPAKT
Sbjct: 121  SVRTVRVVATKQGNAVTLGDYYQGRRITITGMYAAGKAATSGVPSIYAPSTYAHLSPAKT  180

Query: 181  PPPPAMIPMGPAYNGYPGGYPGDVDRSSSAGGQGSYVPLLRDTDSSVASEVRSGYRIQAS  240
            PPPPAMIPMGPAYNGYPGGYPGDVDRSSSAGGQGSYVPLLRDTDSSVASEVRSGYRIQAS
Sbjct: 181  PPPPAMIPMGPAYNGYPGGYPGDVDRSSSAGGQGSYVPLLRDTDSSVASEVRSGYRIQAS  240
```

FIG. 2F-1

```
Query: 241 QQDDSMRVLYYMEKELANFDPSRPGPPSGRVERAMSEVTSLHEDDWRSRPSRGPALTPIR 300
            QQDDSMRVLYYMEKELANFDPSRPGPPSGRVERAMSEVTSLHEDDWRSRPSRGPALTPIR
Sbjct: 241 QQDDSMRVLYYMEKELANFDPSRPGPPSGRVERAMSEVTSLHEDDWRSRPSRGPALTPIR 300

Query: 301 DEEWGGHSPRSPRGWDQEPAREQAGGGWRARRPRARSVDALDDLTPPSTAESGSRSPTSN 360
            DEEWGGHSPRSPRGWDQEPAREQAGGGWRARRPRARSVDALDDLTPPSTAESGSRSPTSN
Sbjct: 301 DEEWGGHSPRSPRGWDQEPAREQAGGGWRARRPRARSVDALDDLTPPSTAESGSRSPTSN 360

Query: 361 GGRSRAYMPPRSRSRDDLYDQDDSRDFPRSRDPHYDDFRSRERPPADPRSHHHRTRDPRD 420
            GGRSRAYMPPRSRSRDDLYDQDDSRDFPRSRDPHYDDFRSRERPPADPRSHHHRTRDPRD
Sbjct: 361 GGRSRAYMPPRSRSRDDLYDQDDSRDFPRSRDPHYDDFRSRERPPADPRSHHHRTRDPRD 420

Query: 421 NGSRSGDLPYDGRLLEEAVRKKGSEERRRPHKEEEEEAYYPPAPPPYSETDSQASRERRL 480
            NGSRSGDLPYDGRLLEEAVRKKGSEERRRPHKEEEEEAYYPPAPPPYSETDSQASRERRL
Sbjct: 421 NGSRSGDLPYDGRLLEEAVRKKGSEERRRPHKEEEEEAYYPPAPPPYSETDSQASRERRL 480

Query: 481 KKNLALSRESLVV 493
            KKNLALSRESLVV
Sbjct: 481 KKNLALSRESLVV 493
```

FIG. 2F-2

SEQ ID NO: 18 LSR_Isoform_f_secreted_R36881_P14 versus SEQ ID NO:62,
LSR, accession number: NP_991403

```
Query:   1 MALLAGGLSRGLGSHPAAAGRDAVVFVWLLLSTWCTAPARAIQVTVSNPYHVVILFQPVT  60
           MALLAGGLSRGLGSHPAAAGRDAVVFVWLLLSTWCTAPARAIQVTVSNPYHVVILFQPVT
Sbjct:  49 MALLAGGLSRGLGSHPAAAGRDAVVFVWLLLSTWCTAPARAIQVTVSNPYHVVILFQPVT 108

Query:  61 LPCTYQMTSTPTQPIVIWKYKSFCRDRIADAFSPASVDNQLNAQLAAGNPGYNPYVECQD 120
           LPCTYQMTSTPTQPIVIWKYKSFCRDRIADAFSPASVDNQLNAQLAAGNPGYNPYVECQD
Sbjct: 109 LPCTYQMTSTPTQPIVIWKYKSFCRDRIADAFSPASVDNQLNAQLAAGNPGYNPYVECQD 168

Query: 121 SVRTVRVVATKQGNAVTLGDYYQGRRITITGNADLTFDQTAWGDSGVYYCSVVSAQDLQG 180
           SVRTVRVVATKQGNAVTLGDYYQGRRITITGNADLTFDQTAWGDSGVYYCSVVSAQDLQG
Sbjct: 169 SVRTVRVVATKQGNAVTLGDYYQGRRITITGNADLTFDQTAWGDSGVYYCSVVSAQDLQG 228

Query: 181 NNEAYAELIVLGRTSGVAELLPGFQAGPIE------------------------------ 210
           NNEAYAELIVLGRTSGVAELLPGFQAGPIE
Sbjct: 229 NNEAYAELIVLGRTSGVAELLPGFQAGPIEDWLFVVVVCLAAFLIFLLLGICWCQCCPHT 288

Query: 211 -------------------VYAAGKAATSGVPSIYAPSTYAHLSPAKTPPPPAMIPMGPA 251
                              +YAAGKAATSGVPSIYAPSTYAHLSPAKTPPPPAMIPMGPA
Sbjct: 289 CCCYVRCPCCPDKCCCPEALYAAGKAATSGVPSIYAPSTYAHLSPAKTPPPPAMIPMGPA 348
```

FIG. 2G-1(1)

```
Query: 252 YNGYPGGYPGDVDRSSSAGGQGSYVPLLRDTDSSVASEVRSGYRIQASQQDDSMRVLYYM 311
            YNGYPGGYPGDVDRSSSAGGQGSYVPLLRDTDSSVASEVRSGYRIQASQQDDSMRVLYYM
Sbjct: 349 YNGYPGGYPGDVDRSSSAGGQGSYVPLLRDTDSSVASEVRSGYRIQASQQDDSMRVLYYM 408

Query: 312 EKELANFDPSRPGPPSGRVERAMSEVTSLHEDDWRSRPSRGPALTPIRDEEWGGHSPRSP 371
            EKELANFDPSRPGPPSGRVERAMSEVTSLHEDDWRSRPSRGPALTPIRDEEWGGHSPRSP
Sbjct: 409 EKELANFDPSRPGPPSGRVERAMSEVTSLHEDDWRSRPSRGPALTPIRDEEWGGHSPRSP 468

Query: 372 RGWDQEPAREQAGGGWRARRPRARSVDALDDLTPPSTAESGSRSPTSNGGRSRAYMPPRS 431
            RGWDQEPAREQAGGGWRARRPRARSVDALDDLTPPSTAESGSRSPTSNGGRSRAYMPPRS
Sbjct: 469 RGWDQEPAREQAGGGWRARRPRARSVDALDDLTPPSTAESGSRSPTSNGGRSRAYMPPRS 528

Query: 432 RSRDDLYDQDDSRDFPRSRDPHYDDFRSRERPPADPRSHHHRTRDPRDNGSRSGDLPYDG 491
            RSRDDLYDQDDSRDFPRSRDPHYDDFRSRERPPADPRSHHHRTRDPRDNGSRSGDLPYDG
Sbjct: 529 RSRDDLYDQDDSRDFPRSRDPHYDDFRSRERPPADPRSHHHRTRDPRDNGSRSGDLPYDG 588

Query: 492 RLLEEAVRKKGSEERRRPHKEEEEEAYYPPAPPPYSETDSQASRERRLKKNLALSRESLV 551
            RLLEEAVRKKGSEERRRPHKEEEEEAYYPPAPPPYSETDSQASRERRLKKNLALSRESLV
Sbjct: 589 RLLEEAVRKKGSEERRRPHKEEEEEAYYPPAPPPYSETDSQASRERRLKKNLALSRESLV 648

Query: 552 V 552
            V
Sbjct: 649 V 649
```

FIG. 2G-1(2)

SEQ ID NO: 18 LSR_Isoform_f_secreted_R36881_P14 versus SEQ ID NO:66,
LSR, accession number: NP_991404

```
Query:   1  MALLAGGLSRGLGSHPAAAGRDAVVFVWLLLSTWCTAPARAIQVTVSNPYHVVILFQPVT   60
            MALLAGGLSRGLGSHPAAAGRDAVVFVWLLLSTWCTAPARAIQVTVSNPYHVVILFQPVT
Sbjct:  49  MALLAGGLSRGLGSHPAAAGRDAVVFVWLLLSTWCTAPARAIQVTVSNPYHVVILFQPVT  108

Query:  61  LPCTYQMTSTPTQPIVIWKYKSFCRDRIADAFSPASVDNQLNAQLAAGNPGYNPYVECQD  120
            LPCTYQMTSTPTQPIVIWKYKSFCRDRIADAFSPASVDNQLNAQLAAGNPGYNPYVECQD
Sbjct: 109  LPCTYQMTSTPTQPIVIWKYKSFCRDRIADAFSPASVDNQLNAQLAAGNPGYNPYVECQD  168

Query: 121  SVRTVRVVATKQGNAVTLGDYYQGRRITITGNADLTFDQTAWGDSGVYYCSVVSAQDLQG  180
            SVRTVRVVATKQGNAVTLGDYYQGRRITITGNADLTFDQTAWGDSGVYYCSVVSAQDLQG
Sbjct: 169  SVRTVRVVATKQGNAVTLGDYYQGRRITITGNADLTFDQTAWGDSGVYYCSVVSAQDLQG  228

Query: 181  NNEAYAELIVLGRTSGVAELLPGFQAGPIEVYAAGKAATSGVPSIYAPSTYAHLSPAKTP  240
            NNEAYAELIVL                    VYAAGKAATSGVPSIYAPSTYAHLSPAKTP
Sbjct: 229  NNEAYAELIVL-------------------VYAAGKAATSGVPSIYAPSTYAHLSPAKTP  269

Query: 241  PPPAMIPMGPAYNGYPGGYPGDVDRSSSAGGQGSYVPLLRDTDSSVASEVRSGYRIQASQ  300
            PPPAMIPMGPAYNGYPGGYPGDVDRSSSAGGQGSYVPLLRDTDSSVASEVRSGYRIQASQ
Sbjct: 270  PPPAMIPMGPAYNGYPGGYPGDVDRSSSAGGQGSYVPLLRDTDSSVASEVRSGYRIQASQ  329
```

FIG. 2G-2(1)

```
Query: 301 QDDSMRVLYYMEKELANFDPSRPGPPSGRVERAMSEVTSLHEDDWRSRPSRGPALTPIRD 360
            QDDSMRVLYYMEKELANFDPSRPGPPSGRVERAMSEVTSLHEDDWRSRPSRGPALTPIRD
Sbjct: 330 QDDSMRVLYYMEKELANFDPSRPGPPSGRVERAMSEVTSLHEDDWRSRPSRGPALTPIRD 389

Query: 361 EEWGGHSPRSPRGWDQEPAREQAGGGWRARRPRARSVDALDDLTPPSTAESGSRSPTSNG 420
            EEWGGHSPRSPRGWDQEPAREQAGGGWRARRPRARSVDALDDLTPPSTAESGSRSPTSNG
Sbjct: 390 EEWGGHSPRSPRGWDQEPAREQAGGGWRARRPRARSVDALDDLTPPSTAESGSRSPTSNG 449

Query: 421 GRSRAYMPPRSRSRDDLYDQDDSRDFPRSRDPHYDDFRSRERPPADPRSHHHRTRDPRDN 480
            GRSRAYMPPRSRSRDDLYDQDDSRDFPRSRDPHYDDFRSRERPPADPRSHHHRTRDPRDN
Sbjct: 450 GRSRAYMPPRSRSRDDLYDQDDSRDFPRSRDPHYDDFRSRERPPADPRSHHHRTRDPRDN 509

Query: 481 GSRSGDLPYDGRLLEEAVRKKGSEERRRPHKEEEEEAYYPPAPPPYSETDSQASRERRLK 540
            GSRSGDLPYDGRLLEEAVRKKGSEERRRPHKEEEEEAYYPPAPPPYSETDSQASRERRLK
Sbjct: 510 GSRSGDLPYDGRLLEEAVRKKGSEERRRPHKEEEEEAYYPPAPPPYSETDSQASRERRLK 569

Query: 541 KNLALSRESLVV 552
            KNLALSRESLVV
Sbjct: 570 KNLALSRESLVV 581
```

FIG. 2G-2(2)

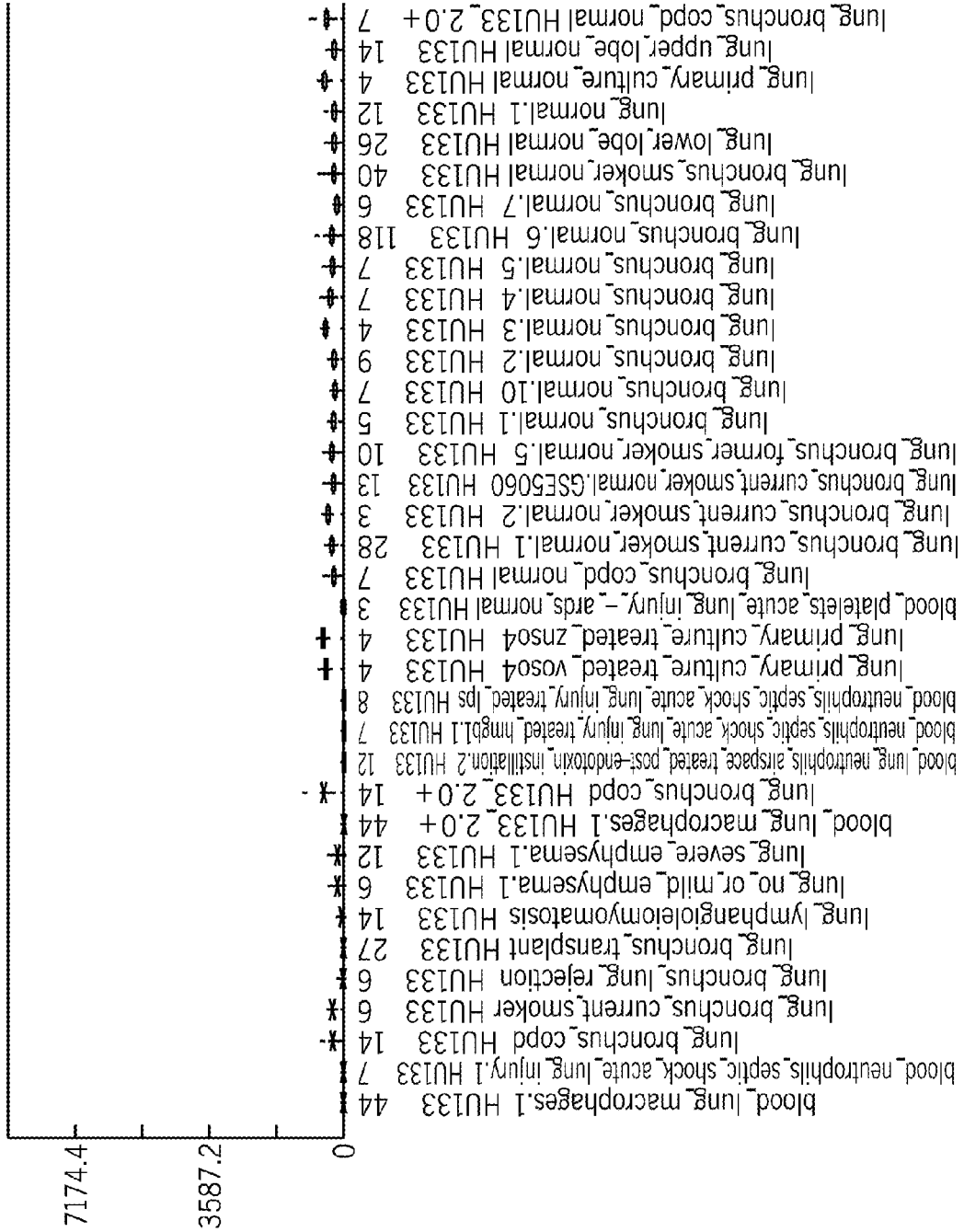

LYG6F human x mouse amino acid sequence comparison

```
Identities = 197/300 (65%), Positives = 230/300 (76%), Gaps = 3/300 (1%)

Query   1    MAVLFLLLFLCGTPQA-ADNMQAIYVALGEAVELPCPSPPTLHGDEHLSWFCSPAAGSFT   59
             MAV+  LLFLCG  QA AD++Q IYVA GE+VE+PCPSPP+L G + L+WF SP AGS T
Sbjct   1    MAVVVFLLFLCGHSQAVADSIQTIYVASGESVEMPCPSPPSLLGGQLLTWFRSPVAGSST   60

Query   60   TLVAQVQVGRPAPDPGKPGRESRLRLLGNYSLWLEGSKEEDAGRYWCAVLGQHHNYQNWR   119
              LVAQVQV +P  D  KP  +SR +L GNYSLWLEGS++EDAGRYWC V+ Q+H YQNWR
Sbjct   61   ILVAQVQVDKPVSDLRKPEPDSRYKLFGNYSLWLEGSRDEDAGRYWCTVMDQNHKYQNWR   120

Query   120  VYDVLVLKGSQLSARAADGSPCNVLLCSVVPSRRMDSVTWQEGKGPVRGRVQSFWGSEAA   179
             VYDV VLKGSQ S ++ DG  C  LLCSVVP+RR+DSVTW EG+  VRG  Q FWG  AA
Sbjct   121  VYDVSVLKGSQFSVKSPDGPSCAALLCSVVPARRLDSVTWLEGRNTVRGHAQYFWGEGAA   180

Query   180  LLLVCPGEGLSEPRSRRPRIIRCLMTHNKGVSFSL-AASIDASPALCAPSTGWDMPWILM   238
             LLLVCP EGL E R+RRPR IRCL+  NK SFSL AAS + SP +CA    WD+PWIL+
Sbjct   181  LLLVCPTEGLPETRARRPRNIRCLLPQNKRFSFSLAAASAEPSPTVCATLPSWDVPWILV   240

Query   239  LLLTMGQGVVILALSIVLW-RQRVRGAPGRDASIPQFKPEIQVYENIHLARLGPPAHKPR   297
             LL T GQGV I+ALSIVLW R+R +G+  R+ S+P FKPE+QVYENIHLARL PP HK R
Sbjct   241  LLFTAGQGVTIIALSIVLWRRRRAQGSRDREPSVPHFKPEVQVYENIHLARLSPPNHKTR   300
```

FIG. 5A

VSIG10 human x mouse amino acid sequence comparison

```
Identities = 365/559 (65%), Positives = 429/559 (76%), Gaps = 34/559 (6%)

Query   11   RVLVCLGALLAGWVAVGL---------------------------EAVVIGEVHENVTLH  43
             RVL+CLGALLA   + GL                           EAV IGEVH+NVTL
Sbjct   5    RVLLCLGALLARQGSAGLQLLLNPSRANLSVRPNSEVLPGIHPDLEAVAIGEVHDNVTLR  64

Query   44   CGNISGLRGQVTWYRNNSEPVFLLSSNSSLRPAEPRFSLVDATSLHIESLSLGDEGIYTC  103
             CG+ SG RG VTWYRN+SEP FL+S NSSL PA PRFSL DA +L IE+L L D+G YTC
Sbjct   65   CGSASGSRGLVTWYRNDSEPAFLVSFNSSLPPAAPRFSLEDAGALRIEALRLEDDGNYTC  124

Query   104  QEILNVTQWFQVWLQVASGPYQIEVHIVATGTLPNGTLYAARGSQVDFSCNSSSRPPPVV  163
             QE+LN T WF V L+VASGP  +EV+I ATGTLPNGTLYAARGSQVDF C S+++PPP V
Sbjct   125  QEVLNETHWFPVRLRVASGPAYVEVNISATGTLPNGTLYAARGSQVDFNCCSAAQPPPEV  184

Query   164  EWWFQALNSSSESFGHNLTVNFFSLLLISPNLQGNYTCLALNQLSKRHRKVTTELLVYYP  223
             EWW Q +S  E  G NL+ N F+L+L+S NLQGNYTC A N LS R RKVTTELLVY+P
Sbjct   185  EWWIQT-HSIPEFLGKNLSANSFTLMLMSQNLQGNYTCSATNVLSGRQRKVTTELLVYWP  243
```

FIG. 5B-1

```
Query  224  PPSAPQCWAQMASGSFMLQLTCRWDGGYPDPDFLWIEEPGGVIVGKSKLGVEMLSESQLS  283
            PPSAPQC +++S S  L+L C WDGGYPDP FLW EEPGG I+G SKL  + LS +QL
Sbjct  244  PPSAPQCSVEVSSESTTLELACNWDGGYPDPTFLWTEEPGGTIMGNSKL--QTLSPAQLL  301

Query  284  DGKKFKCVTSHIVGPESGASCMVQIRGPSLLSEPMKTCFTGGNVTLTCQVSGAYPPAKIL  343
            +GKKFKCV +HI+GPESGASC+V++   P L S+PM+TCF GGNVTLTC+VSGA PPA+I
Sbjct  302  EGKKFKCVGNHILGPESGASCVVKLSSPLLPSQPMRTCFVGGNVTLTCEVSGANPPARIQ  361

Query  344  WLRNLTQPEVIIQPSSRHLITQDGQNSTLTIHNCSQDLDEGYYICRADSPVGVREMEIWL  403
            WLRNLTQP   IQPSS ++ITQ GQ+S+LTIHNCSQDLDEG+Y C+A++ VGVR   IWL
Sbjct  362  WLRNLTQPA--IQPSSHYIITQQGQSSSLTIHNCSQDLDEGFYYCQAENLVGVRATNIWL  419

Query  404  SVKEPLNIGGIVGTIVSLLLLGLAIISGLLLHYSPVFCWKVGNTSRGQNMDDVMVLVDS-  462
            SVKEPLNIGGIVGT+VSLLLLGLA++SGL L+YSP F WK G+T RGQ+M DVMVLVDS
Sbjct  420  SVKEPLNIGGIVGTVVSLLLLGLAVVSGLTLYYSPAFWWKGGSTFRGQDMGDVMVLVDSE  479

Query  463  -EEEEEEEEEEEEDAAVGEQEGAREREELPKEIPKQDHIHRVTALVNGNIEQMGNGFQDL  521
             EEEEEEEEEE+ED A   ++   E EELPK I K  HIHRVTALVNGN+++MGNGFQ+
Sbjct  480  EEEEEEEEEEEKEDVAEEVEQETNETEELPKGISKHGHIHRVTALVNGNLDRMGNGFQEF  539

Query  522  QDDSSEEQSDIVQEEDRPV  540
            QDDS  +QS IVQE+ +PV
Sbjct  540  QDDSDGQQSGIVQEDGKPV  558
```

FIG. 5B-2

LSR human x mouse (ref| NP_059101.1) amino acid sequence comparison

```
Identities = 467/592 (79%), Positives = 496/592 (84%), Gaps = 15/592 (2%)

Query   62  SHPAAAGRDAVVFVWLLLSTWCTAPARAIQVTVSNPYHVVILFQPVTLPCTYQMTSTPTQ  121
            SHPA      +FV L L +C   A AIQVTV +PYHVVILFQPVTL CTYQM++T T
Sbjct   14  SHPAT-----TIFVCLFLIIYCPDRASAIQVTVPDPYHVVILFQPVTLHCTYQMSNTLTA  68

Query  122  PIVIWKYKSFCRDRIADAFSPASVDNQLNAQLAAGNPGYNPYVECQDSVRTVRVVATKQG  181
            PIVIWKYKSFCRDR+ADAFSPASVDNQLNAQLAAGNPGYNPYVECQDSVRTVRVVATKQG
Sbjct   69  PIVIWKYKSFCRDRVADAFSPASVDNQLNAQLAAGNPGYNPYVECQDSVRTVRVVATKQG  128

Query  182  NAVTLGDYYQGRRITITGNADLTFDQTAWGDSGVYYCSVVSAQDLQGNNEAYAELIVLGR  241
            NAVTLGDYYQGRRITITGNADLTF+QTAWGDSGVYYCSVVSAQDL GNNEAYAELIVLGR
Sbjct  129  NAVTLGDYYQGRRITITGNADLTFEQTAWGDSGVYYCSVVSAQDLDGNNEAYAELIVLGR  188

Query  242  TSGVAELLPGFQAGPIEDWLFVVVVCLAAFLIFLLLGICWCQCCPHTCCCYVRCPCCPDK  301
            TS   ELLPGF+AGP+EDWLFVVVVCLA+ L FLLLGICWCQCCPHTCCCYVRCPCCPDK
Sbjct  189  TSEAPELLPGFRAGPLEDWLFVVVVCLASLLFFLLLGICWCQCCPHTCCCYVRCPCCPDK  248

Query  302  CCCPEALYAAGKAATSGVPSIYAPSTYAHLSPAKTPPPPAMIPMGPAYNGYPGGYPGDVD  361
            CCCPEALYAAGKAATSGVPSIYAPS Y HLSPAKT     P       P GYPGD
Sbjct  249  CCCPEALYAAGKAATSGVPSIYAPSIYTHLSPAKT----PPPPPAMIPMRPPYGYPGDFD  304
```

FIG. 5C-1

```
Query  362  RSSSAGGQGSYVPLLRDTDSSVASEVRSGYRIQASQQDDSMRVLYYMEKELANFDPSRPG  421
            R+SS GG  S VPLLR+ D SV+SEVRSGYRIQA+QQDDSMRVLYYMEKELANFDPSRPG
Sbjct  305  RTSSVGGHSSQVPLLREVDGSVSSEVRSGYRIQANQQDDSMRVLYYMEKELANFDPSRPG  364

Query  422  PPSGRVERAMSEVTSLHEDDWRSRPSRGPALTPIRDEEWGGHSPRSPRGWDQEPAREQAG  481
            PP+GRVERAMSEVTSLHEDDWRSRPSR PALTPIRDEEW  HSPRSPR W+QEP +EQ
Sbjct  365  PPNGRVERAMSEVTSLHEDDWRSRPSRAPALTPIRDEEWNRHSPRSPRTWEQEPLQEQPR  424

Query  482  GGWRARRPRARSVDALDDLTPPSTAESGSRSPTSNGGRSRAYMPPRSRSRDDLYDQDDSR  541
            GGW + RPRARSVDALDD+  P + ESG  SP S+G R RAY PPRSRSRDDLYD DD R
Sbjct  425  GGWGSRPRARSVDALDDINRPGSTESGRSSPPSSGRRGRAYAPPRSRSRDDLYDPDDPR  484

Query  542  DFPRSRDPH-YDDFRSRERPPADPRSHHHRTRDPRDNGSRSGDLPYDGRLLEEAVRKKGS  600
            D P SRDPH YDD RSR+ P ADPRS   R+ DPRD G RS D  YDGRLLEEA++KG+
Sbjct  485  DLPHSRDPHYYDDLRSRD-PRADPRS-RQRSHDPRDAGFRSRDPQYDGRLLEEALKKGA  542

Query  601  ---EERRRPHKEEEEEAYYPPAPPPYSETDSQASRERRLKKNLALSRESLVV  649
               R +EEEEE +YPPAPPPYSETDSQASRERR+KKNLALSRESLVV
Sbjct  543  GERRRVYREEEEEEEEGHYPPAPPPYSETDSQASRERRMKKNLALSRESLVV  594
```

FIG. 5C-2

LSR human x mouse (ref| NP_001157656.1) amino acid sequence comparison

Identities = 453/592 (77%), Positives = 480/592 (82%), Gaps = 34/592 (5%)

```
Query   62   SHPAAAGRDAVVFVWLLLSTWCTAPARAIQVTVSNPYHVVILFQPVTLPCTYQMTSTPTQ   121
             SHPA     +FV L L +C   A AIQVTV +PYHVVILFQPVTL CTYQM++T T
Sbjct   14   SHPAT-----TIFVCLFLIIYCPDRASAIQVTVPDPYHVVILFQPVTLHCTYQMSNTLTA   68

Query  122   PIVIWKYKSFCRDRIADAFSPASVDNQLNAQLAAGNPGYNPYVECQDSVRTVRVVATKQG   181
             PIVIWKYKSFCRDR+ADAFSPASVDNQLNAQLAAGNPGYNPYVECQDSVRTVRVVATKQG
Sbjct   69   PIVIWKYKSFCRDRVADAFSPASVDNQLNAQLAAGNPGYNPYVECQDSVRTVRVVATKQG   128

Query  182   NAVTLGDYYQGRRITITGNADLTFDQTAWGDSGVYYCSVVSAQDLQGNNEAYAELIVLGR   241
             NAVTLGDYYQGRRITITGNADLTF+QTAWGDSGVYYCSVVSAQDL GNNEAYAELIVL
Sbjct  129   NAVTLGDYYQGRRITITGNADLTFEQTAWGDSGVYYCSVVSAQDLDGNNEAYAELIVL--   186

Query  242   TSGVAELLPGFQAGPIEDWLFVVVVCLAAFLIFLLLGICWCQCCPHTCCCYVRCPCCPDK   301
                             DWLFVVVVCLA+ L FLLLGICWCQCCPHTCCCYVRCPCCPDK
Sbjct  187   ------------------DWLFVVVVCLASLLFFLLLGICWCQCCPHTCCCYVRCPCCPDK   229

Query  302   CCCPEALYAAGKAATSGVPSIYAPSTYAHLSPAKTPPPPAMIPMGPAYNGYPGGYPGDVD   361
             CCCPEALYAAGKAATSGVPSIYAPS Y HLSPAKT    P        P GYPGD D
Sbjct  230   CCCPEALYAAGKAATSGVPSIYAPSIYTHLSPAKT----PPPPAMIPMRPPYGYPGDFD   285
```

FIG. 5C-3

```
Query  362  RSSSAGGQGSYVPLLRDTDSSVASEVRSGYRIQASQQDDSMRVLYYMEKELANFDPSRPG  421
            R+SS GG  S VPLLR+ D SV+SEVRSGYRIQA+QQDDSMRVLYYMEKELANFDPSRPG
Sbjct  286  RTSSVGGHSSQVPLLREVDGSVSSEVRSGYRIQANQQDDSMRVLYYMEKELANFDPSRPG  345

Query  422  PPSGRVERAMSEVTSLHEDDWRSRPSRGPALTPIRDEEWGGHSPRSPRGWDQEPAREQAG  481
            PP+GRVERAMSEVTSLHEDDWRSRPSR PALTPIRDEEW  HSPRSPR W+QEP +EQ
Sbjct  346  PPNGRVERAMSEVTSLHEDDWRSRPSRAPALTPIRDEEWNRHSPRSPRTWEQEPLQEQPR  405

Query  482  GGWRARRPRARSVDALDDLTPPSTAESGSRSPTSNGGRSRAYMPPRSRSRDDLYDQDDSR  541
            GGW + RPRARSVDALDD+  P + ESG  SP S+G R RAY PPRSRSRDDLYD DD R
Sbjct  406  GGWGSGRPRARSVDALDDINRPGSTESGRSSPPSSGRRGRAYAPPRSRSRDDLYDPDDPR  465

Query  542  DFPRSRDPH-YDDFRSRERPPADPRSHHHRTRDPRDNGSRSGDLPYDGRLLEEAVRKKGS  600
            D P SRDPH YDD RSR+ P ADPRS   R+ DPRD G RS D  YDGRLLEEA++KKG+
Sbjct  466  DLPHSRDPHYYDDLRSRD-PRADPRS-RQRSHDPRDAGFRSRDPQYDGRLLEEALKKKGA  523

Query  601  ---EERRRPHKEEEEEAYYPPAPPPYSETDSQASRERRLKKNLALSRESLVV          649
               R +EEEEE +YPPAPPPYSETDSQASRERR+KKNLALSRESLVV
Sbjct  524  GERRRVYREEEEEEEEGHYPPAPPPYSETDSQASRERRMKKNLALSRESLVV          575
```

FIG. 5C-4

TMEM25 human x mouse (ref:lcl|4109) amino acid sequence comparison

```
Query    1   MALPPGPAALRHTLLLLPALLSSGNGELEPQIDGQTWAERALRENEREAFTCRVAGGPGT   60
             M LP  A LRHTLLLLPALLSSG GEL PQIDGQTWAERALRENE HAFTCRVAGG  T
Sbjct    1   MELPLSQATLRHTLLLLPALLSSGQGELAPQIDGQTWAERALRENEHHAFTCRVAGGSAT   60

Query   61   PRLAWYLDGQLQEASTSRLLSVGGEAFSGGTSTFTVTAHRAQHELNCSLQDPRSGRSANA  120
             PRLAWYLDGQLQEA+TSRLLSVGG+AFSGGTSTFTVTA R+QHELNCSLQDP SGR ANA
Sbjct   61   PRLAWYLDGQLQEATTSRLLSVGGDAFSGGTSTFTVTAQRSQHELNCSLQDPGSGRPANA  120

Query  121   SVILNVQFKPEIAQVGAKYQEAQGPGLLVVLFALVRANPPANVTWIDQDGPVTVNTSDFL  180
             SVILNVQFKPEIAQVGAKYQEAQGPGLLVVLFALVRANPPANVTWIDQDGPVTVN SDFL
Sbjct  121   SVILNVQFKPEIAQVGAKYQEAQGPGLLVVLFALVRANPPANVTWIDQDGPVTVNASDFL  180

Query  181   VLDAQNYPWLTNHTVQLQLRSLAHNLSVVATNDVGVTSASLPAPGLLATRVEVPLLGIVV  240
             VLDAQNYPWLTNHTVQLQLRSLAHNLSVVATNDVGVTSASLPAPGLLATR+EVPLLGIVV
Sbjct  181   VLDAQNYPWLTNHTVQLQLRSLAHNLSVVATNDVGVTSASLPAPGLLATRIEVPLLGIVV  240

Query  241   AAGLALGTLVGFSTLVACLVCRKEKKTKGPSRHPSLISSDSNNLKLNNVRLPRENMSLPS  300
             A GLALGTLVGFSTLVACLVCRKEKKTKGPSR PSLISSDSNNLKLNNVRLPRENMSLPS
Sbjct  241   AGGLALGTLVGFSTLVACLVCRKEKKTKGPSRRPSLISSDSNNLKLNNVRLPRENMSLPS  300

Query  301   NLQLNDLTPDSRAVKPADRQMAQNNSRPELLDPEPGGLLTSQGFIRLPVLGYIYRVSSVS  360
             NLQLNDLTPD R  K  +R MAQ++SRPELL+ EPGGLLTS+GFIRLP+LGYIYRVSSVS
Sbjct  301   NLQLNDLTPDLRG-KATERPMAQHSSRPELLEAEPGGLLTSRGFIRLPMLGYIYRVSSVS  359

Query  361   SDEIWL  366
             SDEIWL
Sbjct  360   SDEIWL  365
```

FIG. 5D

| SEQ ID NO: | Primer ID | Primer sequence | Restriction site |
|---|---|---|---|
| 51 | 100-690 | GAGAACTTGGCAGGCTCTCC | - |
| 52 | 100-691 | CACACTTCCCAGCAGATGTC | - |
| 53 | 100-729 | CTA GCTAGC CACC ATGGCAGTC TTATTCCTCCTC | NheI |
| 54 | 100-730 | CGC GAATTC GCCTGGGCTTGTG GGCAGGTG | EcoRI |

FIG. 6

G6F_EGFP ORF nucleotide sequence in pIRESpuro vector

ATGGCAGTCTTATTCCTCCTCCTGTTCCTATGTGGAACTCCCCAGGCTGCAGACAACATG

CAGGCCATCTATGTGGCCTTGGGGGAGGCAGTAGAGCTGCCATGTCCCTCACCACCTACT

CTACATGGGGACGAACACCTGTCATGGTTCTGCAGCCCTGCAGCAGGCTCCTTCACCACC

CTGGTAGCCCAAGTCCAAGTGGGCAGGCCAGCCCCAGACCCTGGAAAACCAGGAAGGGAA

TCCAGGCTCAGACTGCTGGGGAACTATTCTTTGTGGTTGGAGGGATCCAAAGAGGAAGAT

GCCGGGCGGTACTGGTGCGCTGTGCTAGGTCAGCACCACAACTACCAGAACTGGAGGGTG

TACGACGTCTTGGTGCTCAAAGGATCCCAGTTATCTGCAAGGGCTGCAGATGGATCCCCC

TGCAATGTCCTCCTGTGCTCTGTGGTCCCCAGCAGACGCATGGACTCTGTGACCTGGCAG

GAAGGGAAGGGTCCCGTGAGGGGCCGTGTTCAGTCCTTCTGGGGCAGTGAGGCTGCCCTG

CTCTTGGTGTGTCCTGGGGAGGGGCTTTCTGAGCCCAGGAGCCGAAGACCAAGAATCATC

CGCTGCCTCATGACTCACAACAAAGGGGTCAGCTTTAGCCTGGCAGCCTCCATCGATGCT

TCTCCTGCCCTCTGTGCCCCTTCCACGGGCTGGGACATGCCTTGGATTCTGATGCTGCTG

CTCACAATGGGCCAGGGAGTTGTCATCCTGGCCCTCAGCATCGTGCTCTGGAGGCAGAGG

GTCCGTGGGGCTCCAGGCAGAGATGCCTCGATTCCTCAGTTCAAACCCGAAATCCAGGTC

TATGAGAACATCCATTTGGCCCGTCTTGGCCCACCTGCCCACAAGCCCAGGCGAATTCTG

FIG. 7-1

CAGTCGACGGTACCGCGGGCCCGGGATCCACCGGTCGCCACC*ATGGTGAGCAAGGGCGAG*

*GAGCTGTTCACCGGGGTGGTGCCCATCCTGGTCGAGCTGGACGGCGACGTAAACGGCCAC*

*AAGTTCAGCGTGTCCGGCGAGGGCGAGGGCGATGCCACCTACGGCAAGCTGACCCTGAAG*

*TTCATCTGCACCACCGGCAAGCTGCCCGTGCCCTGGCCCACCCTCGTGACCACCCTGACC*

*TACGGCGTGCAGTGCTTCAGCCGCTACCCCGACCACATGAAGCAGCACGACTTCTTCAAG*

*TCCGCCATGCCCGAAGGCTACGTCCAGGAGCGCACCATCTTCTTCAAGGACGACGGCAAC*

*TACAAGACCCGCGCCGAGGTGAAGTTCGAGGGCGACACCCTGGTGAACCGCATCGAGCTG*

*AAGGGCATCGACTTCAAGGAGGACGGCAACATCCTGGGGCACAAGCTGGAGTACAACTAC*

*AACAGCCACAACGTCTATATCATGGCCGACAAGCAGAAGAACGGCATCAAGGTGAACTTC*

*AAGATCCGCCACAACATCGAGGACGGCAGCGTGCAGCTCGCCGACCACTACCAGCAGAAC*

*ACCCCCATCGGCGACGGCCCCGTGCTGCTGCCCGACAACCACTACCTGAGCACCCAGTCC*

*GCCCTGAGCAAAGACCCCAACGAGAAGCGCGATCACATGGTCCTGCTGGAGTTCGTGACC*

*GCCGCCGGGATCACTCTCGGCATGGACGAGCTGTACAAGTAA*

FIG. 7-2

G6F_EGFP ORF protein sequence in pIRESpuro vector

MAVLFLLLFLCGTPQAADNMQAIYVALGEAVELPCPSPPTLHGDEHLSWFCSPAAGSFTT

LVAQVQVGRPAPDPGKPGRESRLRLLGNYSLWLEGSKEEDAGRYWCAVLGQHHNYQNWRV

YDVLVLKGSQLSARAADGSPCNVLLCSVVPSRRMDSVTWQEGKGPVKGRVQSFWGSEAAL

LLVCPGEGLSEPRSRRPRIIRCLMTHNKGVSFSLAASIDASPALCAPSTGWDMPWILMLL

LTMGQGVVILALSIVLWRQRVRGAPGRDASIPQFKPEIQVYENIHLARLGPPAHKPRRIL

QSTVPRARDPPVAT*MVSKGEELFTGVVPILVELDGDVNGHKFSVSGEGEGDATYGKLTLK*

*FICTTGKLPVPWPTLVTTLTYGVQCFSRYPDHMKQHDFFKSAMPEGYVQERTIFFKDDGN*

*YKTRAEVKFEGDTLVNRIELKGIDFKEDGNILGHKLEYNYNSHNVYIMADKQKNGIKVNF*

*KIRHNIEDGSVQLADHYQQNTPIGDGPVLLPDNHYLSTQSALSKDPNEKRDHMVLLEFVT*

*AAGITLGMDELYK*

FIG. 8

LYG6F-mouse-ECD_FC_mouse IgG2a

SIQTIYVASGESVEMPCPSPPSLLGGQLLTWFRSPVAGSSTILVAQVQVDK

PVSDLRKPEPDSRYKLFGNYSLWLEGSRDEDAGRYWCTVMDQNHKYQNWRVYDVSVLKGSQFSVKSPDGP

SCAALLCSVVPARRLDSVTWLEGRNTVRGHAQYFWGEGAALLLVCPTEGLPETRARRPRNIRCLLPQNKR

FSFSLAAASAEPSPTVCATLPSWDVPEPRGPTIKPCPPCKCPAPNLLGGPSVFIFPPKIKDVLMISLSPIV

TCVVVDVSEDDPDVQISWFVNNVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVEWTNNGKTELNYKNTEPVLDSD

GSYFMYSKLRVEKKNWVERNSYSCSVVHEGLHNHHTTKSFSRTPGK

FIG. 10A

VSIG10-Mouse-ECD_FC_mouse IgG2a

LQLLLNPSRANLSVRPNSEVLPGIHPDLEAVAIGEVHDNVTLRCGSASG

SRGLVTWYRNDSEPAFLVSFNSSLPPAAPRFSLEDAGALRIEALRLEDDGNYTCQEVLNETHWFPVRLRV

ASGPAYVEVNISATGTLPNGTLYAARGSQVDFNCCSAAQPPPEVEWWIQTHSIPEFLGKNLSANSFTLML

MSQNLQGNYTCSATNVLSGRQRKVTTELLVYWPPPSAPQCSVEVSSESTTLELACNWDGGYPDPTFLWTE

EPGGTIMGNSKLQTLSPAQLLEGKKFKCVGNHILGPESGASCVVKLSSPLLPSQPMRTCFVGGNVTLTCE

VSGANPPARIQWLRNLTQPAIQPSSHYIITQQGQSSSLTIHNCSQDLDEGFYYCQAENLVGVRATNIWLS

VKEPLNIGGEPRGPTIKPCPPCKCPAPNLLGGPSVFIFPPKIKDVLMISLSPIVTCVVVDVSEDDPDVQIS

WFVNNVEVHTAQTQTHREDYNSTLRVVSALPIQHQDWMSGKEFKCKVNNKDLPAPIERTISKPKGSVRAPQ

VYVLPPPEEEMTKKQVTLTCMVTDFMPEDIYVEWTNNGKTELNYKNTEPVLDSDGSYFMYSKLRVEKKNWV

ERNSYSCSVVHEGLHNHHTTKSFSRTPGK

FIG. 10B

TMEM25-mouse-ECD_FC_mouse IgG2a

<u>ELAPQIDGQTWAERALRENEHHAFTCRVAGGSATPRLAWYLDGQLQEATTSRLLSVGGDAFSGGTSTFTVT
AQRSQHELNCSLQDPGSGRPANASVILNVQFKPEIAQVGAKYQEAQGPGLLVVLFALVRANPPANVTWIDQ
DGPVTVNASDFLVLDAQNYPWLTNHTVQLQLRSLAHNLSVVATNDVGVTSASLPAPGLLATRIE</u>**EPRGPTI
KPCPPCKCPAPNLLGGPSVFIFPPKIKDVLMISLSPIVTCVVVDSEDDPDVQISWFVNNVEVHTAQTQTH
REDYNSTLRVVSALPIQHQDWMSGKEFKCKVNNKDLPAPIERTISKPKGSVRAPQVYVLPPPEEEMTKKQV
TLTCMVTDFMPEDIYVEWTNNGKTELNYKNTEPVLDSDGSYFMYSKLRVEKKNWVERNSYSCSVVHEGLHN
HHTTKSFSRTPGK**

FIG. 10C

LSR-mouse-ECD_FC_mouse IgG2a

*<u>IQVTVPDPYHVVILFQPVTLHCTYQMSNTLTAPI</u>*

VIWKYKSFCRDRVADAFSPASVDNQLNAQLAAGNPGYNPYVECQDSVRTVRVVATKQGNAVTLGDYYQGR
RITITGNADLTFEQTAWGDSGVYYCSVVSAQDLDGNNEAYAELIVLGRTSEAPELLPGFRAGPLED**EPRGP
TIKPCPPCKCPAPNLLGGPSVFIFPPKIKDVLMISLSPIVTCVVVDSEDDPDVQISWFVNNVEVHTAQTQ
THREDYNSTLRVVSALPIQHQDWMSGKEFKCKVNNKDLPAPIERTISKPKGSVRAPQVYVLPPPEEEMTKK
QVTLTCMVTDFMPEDIYVEWTNNGKTELNYKNTEPVLDSDGSYFMYSKLRVEKKNWVERNSYSCSVVHEGL
HNHHTTKSFSRTPGK**

FIG. 10D

LYG6F_Human ECD_Human IgG1-Fc (C220S)

MAVLFLLLFLCGTPQAADNMQAIYVALGEAVELPCPSPPTLHGDEHLSWFCSPAAGSFTTLVAQVQVGRP
APDPGKPGRESRLRLLGNYSLWLEGSKEEDAGRYWCAVLGQHHNYQNWRVYDVLVLKGSQLSARAADGSP
CNVLLCSVVPSRRMDSVTWQEGKGPVRGRVQSFWGSEAALLLVCPGEGLSEPRSRRPRIIRCLMTHNKGV
SFSLAASIDASPALCAPSTGWDMPEPKSSDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

FIG. 11A

VSIG10_Human ECD_Human IgG1-Fc (C220S)

MAAGGSAPEPRVLVCLGALLAGWVAVGLEAVVIGEVHENVTLHCGNISGLRGQVTWYRNNSEPVFLLSSN
SSLRPAEPRFSLVDATSLHIESLSLGDEGIYTCQEILNVTQWFQVWLQVA*SGPYQIEVHIVATGTLPNGT
LYAARGSQVDFSCNSSSRPPPVVEWWFQALNSSSESFGHNLTVNFFSLLLISPNLQGNYTCLALNQLSKR
HRKVTTELLVYYPPPSAPQCWAQMASGSFMLQLTCRWDGGYPDPDFLWIEEPGGVIVGKSKLGVEMLSES*
QLSDGKKFKCVTSHIVGPESGASCMVQIRGPSLLSEPMKTCFTGGNVTLTCQVSGAYPPAKILWLRNLTQ
PEVIIQPSSRHLITQDGQNSTLTIHNCSQDLDEGYYICRADSPVGVREMEIWLSVKEPLNIGGEPKSSDKT
HTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHY
TQKSLSLSPGK

FIG. 11B

VSIG10 Skipping exon 3_Human ECD_Human IgG1-Fc (C220S)

*MAAGGSAPEPRVLVCLGALLAGWVAVGLEA*VVIGEVHENVTLHCGNISGLRGQVTWYRNNSEPVFLLSSN
SSLRPAEPRFSLVDATSLHIESLSLGDEGIYTCQEILNVTQWFQVWLQVANPPPSAPQCWAQMASGSFML
QLTCRWDGGYPDPDFLWIEEPGGVIVGKSKLGVEMLSESQLSDGKKFKCVTSHIVGPESGASCMVQIRGP
SLLSEPMKTCFTGGNVTLTCQVSGAYPPAKILWLRNLTQPEVIIQPSSRHLITQDGQNSTLTIHNCSQDL
DEGYYICRADSPVGVREMEIWLSVKEPLNIGGEPKSSDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

FIG. 11C

TMEM25_Human ECD_Human IgG1-Fc (C220S)

*MALPPGPAALRHTLLLLPALLSSGWG*ELEPQIDGQTWAERALRENERHAFTCRVAGGPGTPRLAWYLDGQL
QEASTSRLLSVGGEAFSGGTSTFTVTAHRAQHELNCSLQDPRSGRSANASVILNVQFKPEIAQVGAKYQEA
QGPGLLVVLFALVRANPPANVTWIDQDGPVTVNTSDFLVLDAQNYPWLTNHTVQLQLRSLAHNLSVVATND
VGVTSASLPAPGLLATRVEEPKSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 11D

LSR isoform-a_Human ECD_Human IgG1-Fc (C220S)

*MALLAGGLSRGLGSHPAAAGRDAVVFVWLLLSTWCTAPARA*IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLGRTSGVAELLPGFQAGPIE
DEPKSSDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPGK

FIG. 11E

LSR isoform-b_Human ECD_Human IgG1-Fc (C220S)

*MALLAGGLSRGLGSHPAAAGRDAVVFVWLLLSTWCTAPARA*IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLDEPKSSDKTHTCPPCPAPEL
LGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGK

FIG. 11F

LSR isoform-c_Human ECD_Human IgG1-Fc (C220S)

*MALLAGGLSRGLGSHPAAAGRDAVVFVWLLLSTWCTAPARA*<u>IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLVYAAGKAATSGVPSIYAPS
TYAHLSPAKTPPPPAMIPMGPAYNGYPGGYPGDVDRSSSAGGQGSYVPLLRDTDSSVASEVRSGYRIQAS
QQDDSMRVLYYMEKELANFDPSRPGPPSGRVERAMSEVTSLHEDDWRSRPSRGPALTPIRDEEWGGHSPR
SPRGWDQEPAREQAGGGWRARRPRARSVDALDDLTPPSTAESGSRSPTSNGGRSRAYMPPRSRSRDDLYD
QDDSRDFPRSRDPHYDDFRSRERPPADPRSHHHRTRDPRDNGSRSGDLPYDGRLLEEAVRKKGSEERRRP
HKEEEEEAYYPPAPPPYSETDSQASRERRLKKNLALSRESLVV</u>EPKSSDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

FIG. 11G

LSR isoform-d_Human ECD_Human IgG1-Fc (C220S)

*MALLAGGLSRGLGSHPAAAGRDAVVFVWLLLSTWCTAPARA*<u>IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLVYAAGKAATSGVPSIYAPS
TYAHLSPAKTPPPPAMIPMGPAYNGYPGGYPGDVDRSSSAGGQGSYVPLLRDTDSSVASVRSGYRIQASQ
QDDSMRVLYYMEKELANFDPSRPGPPSGRVERAMSEVTSLHEDDWRSRPSRGPALTPIRDEEWGGHSPRS
PRGWDQEPAREQAGGGWRARRPRARSVDALDDLTPPSTAESGSRSPTSNGGRSRAYMPPRSRSRDDLYDQ
DDSRDFPRSRDPHYDDFRSRERPPADPRSHHHRTRDPRDNGSRSGDLPYDGRLLEEAVRKKGSEERRRPH
KEEEEEAYYPPAPPPYSETDSQASRERRLKKNLALSRESLVV</u>EPKSSDKTHTCPPCPAPELLGGPSVFLFPPKP
KDTLMISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK

FIG. 11H

LSR isoform-e_Human ECD_Human IgG1-Fc (C220S)

*MALLAGGLSRGLGSHPAAAGRDAVVFVWLLLSTWCTAPARA*<u>IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGMYAAGKAATSGVPSIYAPSTYAHLSPAKTPPPPAMIPMGPAYNGYPGGYPGDVDRSSSA
GGQGSYVPLLRDTDSSVASEVRSGYRIQASQQDDSMRVLYYMEKELANFDPSRPGPPSGRVERAMSEVTS
LHEDDWRSRPSRGPALTPIRDEEWGGHSPRSPRGWDQEPAREQAGGGWRARRPRARSVDALDDLTPPSTA
ESGSRSPTSNGGRSRAYMPPRSRSRDDLYDQDDSRDFPRSRDPHYDDFRSRERPPADPRSHHHRTRDPRD
NGSRSGDLPYDGRLLEEAVRKKGSEERRRPHKEEEEEAYYPPAPPPYSETDSQASRERRLKKNLALSRES
LVV</u>EPKSSDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSCS
VMHEALHNHYTQKSLSLSPGK

FIG. 11I

LSR isoform-f_Human ECD_Human IgG1-Fc (C220S)

*MALLAGGLSRGLGSHPAAAGRDAVVFVWLLLSTWCTAPARA*<u>IQVTVSNPYHVVILFQPVTLPCTYQMTST
PTQPIVIWKYKSFCRDRIADAFSPASVDNQLNAQLAAGNPGYNPYVECQDSVRTVRVVATKQGNAVTLGD
YYQGRRITITGNADLTFDQTAWGDSGVYYCSVVSAQDLQGNNEAYAELIVLGRTSGVAELLPGFQAGPIE
VYAAGKAATSGVPSIYAPSTYAHLSPAKTPPPPAMIPMGPAYNGYPGGYPGDVDRSSSAGGQGSYVPLLR
DTDSSVASEVRSGYRIQASQQDDSMRVLYYMEKELANFDPSRPGPPSGRVERAMSEVTSLHEDDWRSRPS
RGPALTPIRDEEWGGHSPRSPRGWDQEPAREQAGGGWRARRPRARSVDALDDLTPPSTAESGSRSPTSNG
GRSRAYMPPRSRSRDDLYDQDDSRDFPRSRDPHYDDFRSRERPPADPRSHHHRTRDPRDNGSRSGDLPYD
GRLLEEAVRKKGSEERRRPHKEEEEEAYYPPAPPPYSETDSQASRERRLKKNLALSRESLVV</u>EPKSSDKTH
TCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVMHEALHNHYT
QKSLSLSPGK

FIG. 11J

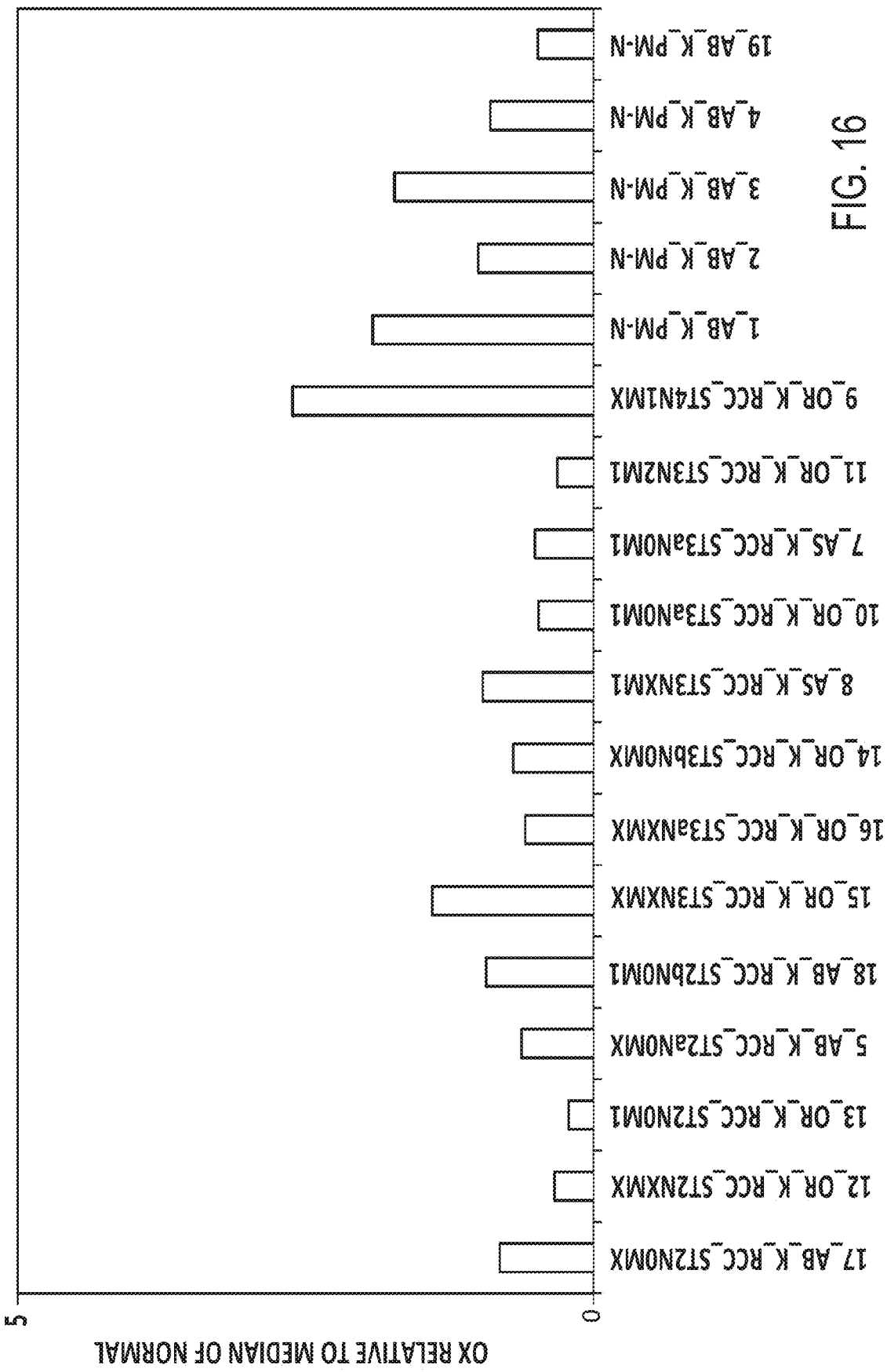

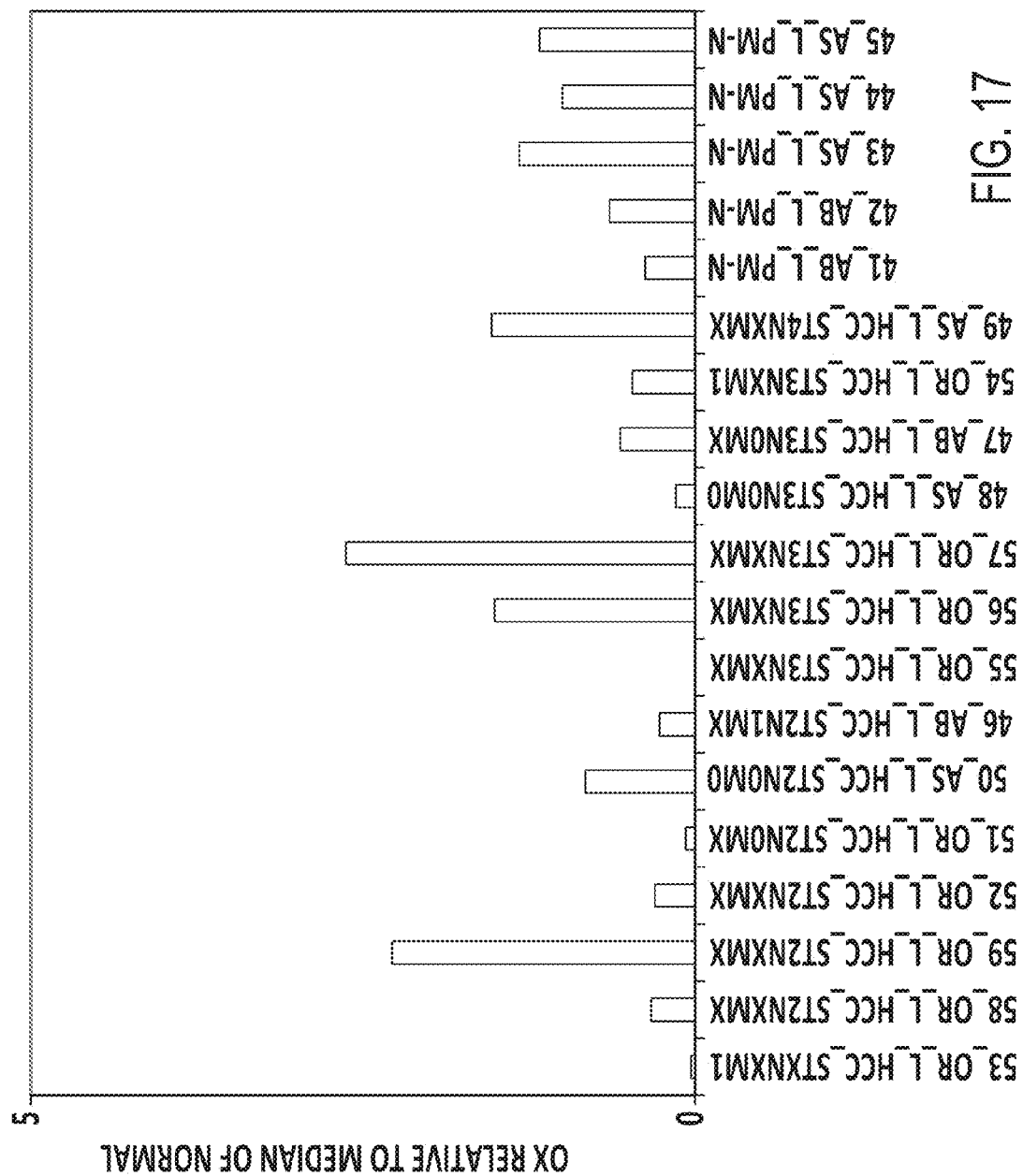

Anti Flag

Anti LSR (Abcam)

Anti LSR (Abnova)

Anti LSR (Sigma)

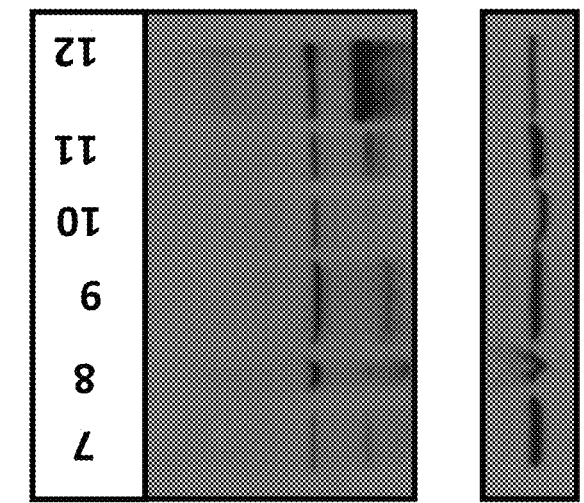
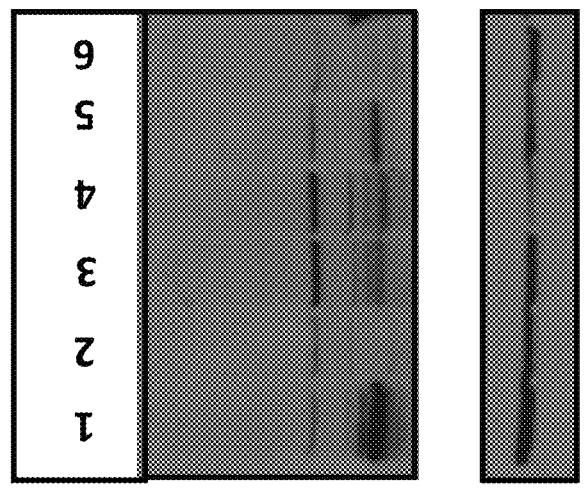
Cell extracts:
1. CaOV3
2. ES-2
3. OV-90
4. OvCAR3
5. SKOV3
6. TOV112D
7. CaCo2
8. HeLa
9. HepG2
10. MCF-7
11. SkBR3
12. 293T_LSR_P5a_Flag
FIG. 20

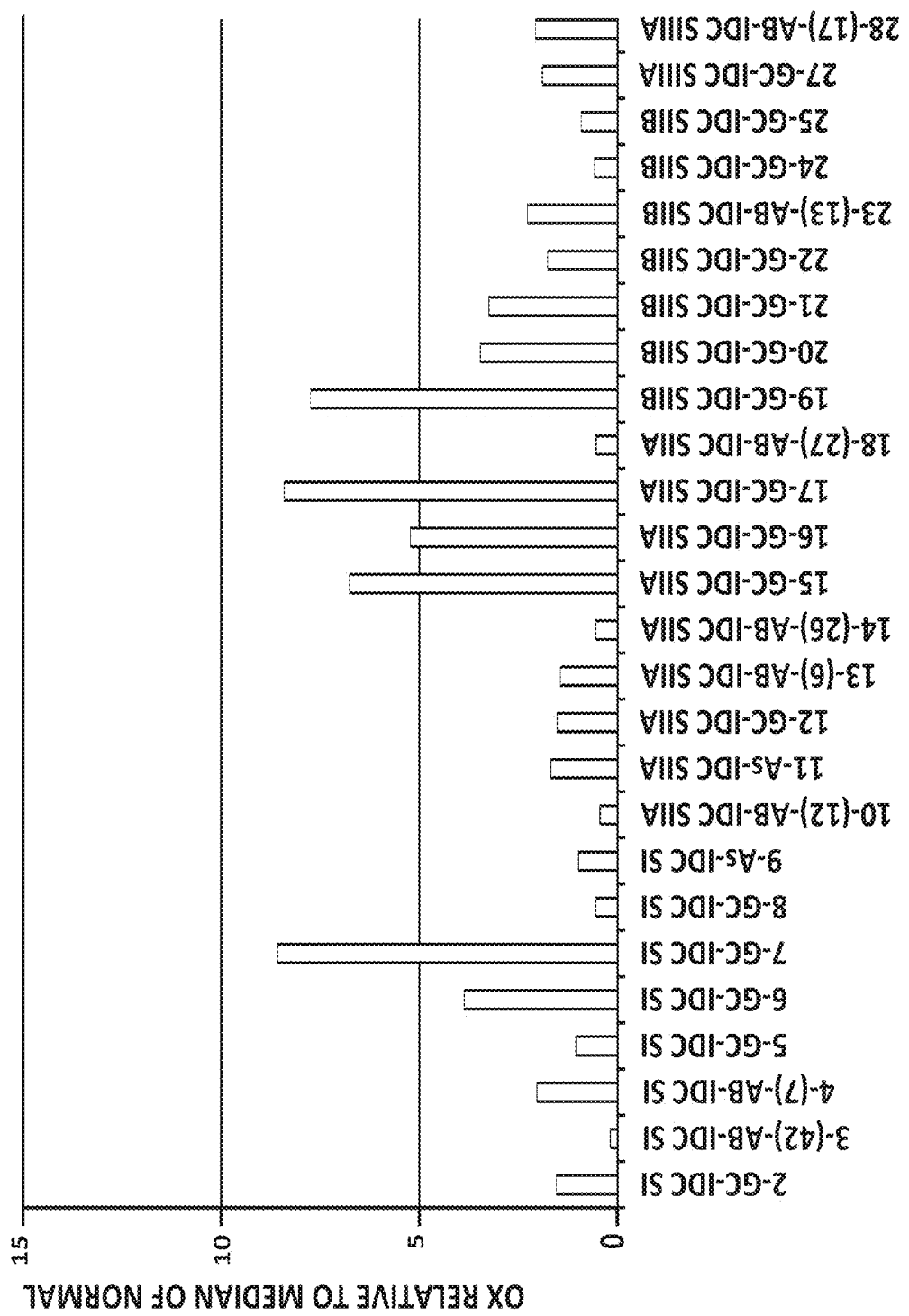

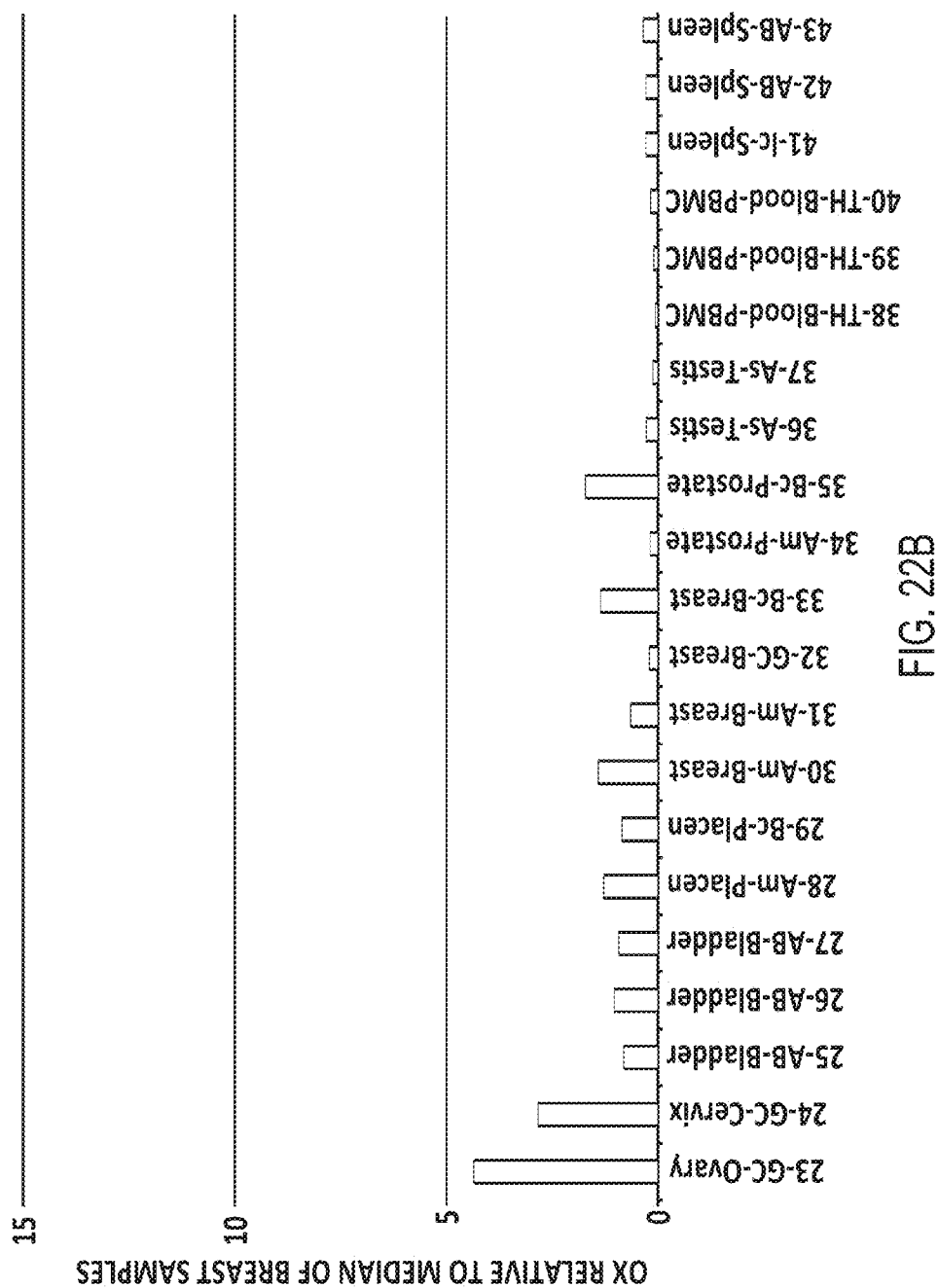

A. HEK293T-TMEM25-P5-Flag+Anti TMEM25 1:2250
B. HEK293T-TMEM25-P5-Flag+Mouse Normal Serum 1:2250

1. HEK293T_pIRESpuro3
2. HEK293T_pIRESpuro3_TMEM25-P5-Flag
3. KARPAS
4. G-361
5. RPMI8226
6. DAUDI
7. JURKAT 1. HEK293T_pIRESpuro3_TMEM25-P5-Flag +Si scrambled
2. HEK293T_pIRESpuro3_TMEM25-P5-Flag+ Si TMEM25

1

3μg/ml ANTIBODY

2

3μg/ml ANTIBODY

1

1μg/ml ANTIBODY

2

1μg/ml ANTIBODY

1

0.3μg/ml ANTIBODY

2

0.3μg/ml ANTIBODY

1

3μg/ml ANTIBODY

2

3μg/ml ANTIBODY

1

1μg/ml ANTIBODY

2

1μg/ml ANTIBODY

1

0.3μg/ml ANTIBODY

2

0.3μg/ml ANTIBODY

SEQUENCE LISTING

```
<160> NUMBER OF SEQ ID NOS: 198

<210> SEQ ID NO 1
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 1

Met Ala Val Leu Phe Leu Leu Leu Phe Leu Cys Gly Thr Pro Gln Ala
1               5                   10                  15

Ala Asp Asn Met Gln Ala Ile Tyr Val Ala Leu Gly Glu Ala Val Glu
            20                  25                  30

Leu Pro Cys Pro Ser Pro Pro Thr Leu His Gly Asp Glu His Leu Ser
        35                  40                  45

Trp Phe Cys Ser Pro Ala Ala Gly Ser Phe Thr Thr Leu Val Ala Gln
    50                  55                  60

Val Gln Val Gly Arg Pro Ala Pro Asp Pro Gly Lys Pro Gly Arg Glu
65                  70                  75                  80

Ser Arg Leu Arg Leu Leu Gly Asn Tyr Ser Leu Trp Leu Glu Gly Ser
                85                  90                  95

Lys Glu Glu Asp Ala Gly Arg Tyr Trp Cys Ala Val Leu Gly Gln His
            100                 105                 110

His Asn Tyr Gln Asn Trp Arg Val Tyr Asp Val Leu Val Leu Lys Gly
        115                 120                 125
```

```
Ser Gln Leu Ser Ala Arg Ala Ala Asp Gly Ser Pro Cys Asn Val Leu
    130                 135                 140
Leu Cys Ser Val Val Pro Ser Arg Arg Met Asp Ser Val Thr Trp Gln
145                 150                 155                 160
Glu Gly Lys Gly Pro Val Arg Gly Arg Val Gln Ser Phe Trp Gly Ser
                165                 170                 175
Glu Ala Ala Leu Leu Leu Val Cys Pro Gly Glu Gly Leu Ser Glu Pro
                180                 185                 190
Arg Ser Arg Arg Pro Arg Ile Ile Arg Cys Leu Met Thr His Asn Lys
            195                 200                 205
Gly Val Ser Phe Ser Leu Ala Ala Ser Ile Asp Ala Ser Pro Ala Leu
    210                 215                 220
Cys Ala Pro Ser Thr Gly Trp Asp Met Pro Trp Ile Leu Met Leu Leu
225                 230                 235                 240
Leu Thr Met Gly Gln Gly Val Val Ile Leu Ala Leu Ser Ile Val Leu
                245                 250                 255
Trp Arg Gln Arg Val Arg Gly Ala Pro Gly Arg Asp Ala Ser Ile Pro
                260                 265                 270
Gln Phe Lys Pro Glu Ile Gln Val Tyr Glu Asn Ile His Leu Ala Arg
            275                 280                 285
Leu Gly Pro Pro Ala His Lys Pro Arg
    290                 295

<210> SEQ ID NO 2
<211> LENGTH: 218
<212> TYPE: PRT
<213> ORGANISM: Artificial sequence
<220> FEATURE:
<223> OTHER INFORMATION: Synthetic polypeptide

<400> SEQUENCE: 2

Ala Asp Asn Met Gln Ala Ile Tyr Val Ala Leu Gly Glu Ala Val Glu
1               5                   10                  15
Leu Pro Cys Pro Ser Pro Pro Thr Leu His Gly Asp Glu His Leu Ser
                20                  25                  30
Trp Phe Cys Ser Pro Ala Ala Gly Ser Phe Thr Thr Leu Val Ala Gln
            35                  40                  45
Val Gln Val Gly Arg Pro Ala Pro Asp Pro Gly Lys Pro Gly Arg Glu
        50                  55                  60
Ser Arg Leu Arg Leu Leu Gly Asn Tyr Ser Leu Trp Leu Glu Gly Ser
65                  70                  75                  80
Lys Glu Glu Asp Ala Gly Arg Tyr Trp Cys Ala Val Leu Gly Gln His
                85                  90                  95
His Asn Tyr Gln Asn Trp Arg Val Tyr Asp Val Leu Val Leu Lys Gly
                100                 105                 110
Ser Gln Leu Ser Ala Arg Ala Ala Asp Gly Ser Pro Cys Asn Val Leu
            115                 120                 125
Leu Cys Ser Val Val Pro Ser Arg Arg Met Asp Ser Val Thr Trp Gln
    130                 135                 140
Glu Gly Lys Gly Pro Val Arg Gly Arg Val Gln Ser Phe Trp Gly Ser
145                 150                 155                 160
Glu Ala Ala Leu Leu Leu Val Cys Pro Gly Glu Gly Leu Ser Glu Pro
                165                 170                 175
Arg Ser Arg Arg Pro Arg Ile Ile Arg Cys Leu Met Thr His Asn Lys
            180                 185                 190
```

```
Gly Val Ser Phe Ser Leu Ala Ala Ser Ile Asp Ala Ser Pro Ala Leu
        195                 200                 205
Cys Ala Pro Ser Thr Gly Trp Asp Met Pro
    210                 215
```

<210> SEQ ID NO 3
<211> LENGTH: 540
<212> TYPE: PRT
<213> ORGANISM: Artificial sequence
<220> FEATURE:
<223> OTHER INFORMATION: Synthetic polypeptide

<400> SEQUENCE: 3

```
Met Ala Ala Gly Gly Ser Ala Pro Glu Pro Arg Val Leu Val Cys Leu
1               5                   10                  15
Gly Ala Leu Leu Ala Gly Trp Val Ala Val Gly Leu Glu Ala Val Val
                20                  25                  30
Ile Gly Glu Val His Glu Asn Val Thr Leu His Cys Gly Asn Ile Ser
            35                  40                  45
Gly Leu Arg Gly Gln Val Thr Trp Tyr Arg Asn Asn Ser Glu Pro Val
        50                  55                  60
Phe Leu Leu Ser Ser Asn Ser Ser Leu Arg Pro Ala Glu Pro Arg Phe
65                  70                  75                  80
Ser Leu Val Asp Ala Thr Ser Leu His Ile Glu Ser Leu Ser Leu Gly
                85                  90                  95
Asp Glu Gly Ile Tyr Thr Cys Gln Glu Ile Leu Asn Val Thr Gln Trp
            100                 105                 110
Phe Gln Val Trp Leu Gln Val Ala Ser Gly Pro Tyr Gln Ile Glu Val
        115                 120                 125
His Ile Val Ala Thr Gly Thr Leu Pro Asn Gly Thr Leu Tyr Ala Ala
    130                 135                 140
Arg Gly Ser Gln Val Asp Phe Ser Cys Asn Ser Ser Ser Arg Pro Pro
145                 150                 155                 160
Pro Val Val Glu Trp Trp Phe Gln Ala Leu Asn Ser Ser Ser Glu Ser
                165                 170                 175
Phe Gly His Asn Leu Thr Val Asn Phe Phe Ser Leu Leu Leu Ile Ser
            180                 185                 190
Pro Asn Leu Gln Gly Asn Tyr Thr Cys Leu Ala Leu Asn Gln Leu Ser
        195                 200                 205
Lys Arg His Arg Lys Val Thr Thr Glu Leu Leu Val Tyr Tyr Pro Pro
    210                 215                 220
Pro Ser Ala Pro Gln Cys Trp Ala Gln Met Ala Ser Gly Ser Phe Met
225                 230                 235                 240
Leu Gln Leu Thr Cys Arg Trp Asp Gly Gly Tyr Pro Asp Pro Asp Phe
                245                 250                 255
Leu Trp Ile Glu Glu Pro Gly Gly Val Ile Val Gly Lys Ser Lys Leu
            260                 265                 270
Gly Val Glu Met Leu Ser Glu Ser Gln Leu Ser Asp Gly Lys Lys Phe
        275                 280                 285
Lys Cys Val Thr Ser His Ile Val Gly Pro Ser Gly Ala Ser Cys
    290                 295                 300
Met Val Gln Ile Arg Gly Pro Ser Leu Leu Ser Glu Pro Met Lys Thr
305                 310                 315                 320
Cys Phe Thr Gly Gly Asn Val Thr Leu Thr Cys Gln Val Ser Gly Ala
                325                 330                 335
```

Tyr Pro Pro Ala Lys Ile Leu Trp Leu Arg Asn Leu Thr Gln Pro Glu
            340                 345                 350

Val Ile Ile Gln Pro Ser Ser Arg His Leu Ile Thr Gln Asp Gly Gln
            355                 360                 365

Asn Ser Thr Leu Thr Ile His Asn Cys Ser Gln Asp Leu Asp Glu Gly
            370                 375                 380

Tyr Tyr Ile Cys Arg Ala Asp Ser Pro Val Gly Val Arg Glu Met Glu
385                 390                 395                 400

Ile Trp Leu Ser Val Lys Glu Pro Leu Asn Ile Gly Gly Ile Val Gly
            405                 410                 415

Thr Ile Val Ser Leu Leu Leu Gly Leu Ala Ile Ser Gly Leu
            420                 425                 430

Leu Leu His Tyr Ser Pro Val Phe Cys Trp Lys Val Gly Asn Thr Ser
            435                 440                 445

Arg Gly Gln Asn Met Asp Asp Val Met Val Leu Val Asp Ser Glu Glu
            450                 455                 460

Glu Glu Glu Glu Glu Glu Glu Glu Glu Asp Ala Ala Val Gly Glu
465                 470                 475                 480

Gln Glu Gly Ala Arg Glu Arg Glu Glu Leu Pro Lys Glu Ile Pro Lys
            485                 490                 495

Gln Asp His Ile His Arg Val Thr Ala Leu Val Asn Gly Asn Ile Glu
            500                 505                 510

Gln Met Gly Asn Gly Phe Gln Asp Leu Gln Asp Asp Ser Ser Glu Glu
            515                 520                 525

Gln Ser Asp Ile Val Gln Glu Glu Asp Arg Pro Val
            530                 535                 540

<210> SEQ ID NO 4
<211> LENGTH: 383
<212> TYPE: PRT
<213> ORGANISM: Artificial sequence
<220> FEATURE:
<223> OTHER INFORMATION: Synthetic polypeptide

<400> SEQUENCE: 4

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
            35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Ser Gly Pro Tyr Gln Ile
            85                  90                  95

Glu Val His Ile Val Ala Thr Gly Thr Leu Pro Asn Gly Thr Leu Tyr
            100                 105                 110

Ala Ala Arg Gly Ser Gln Val Asp Phe Ser Cys Asn Ser Ser Ser Arg
            115                 120                 125

Pro Pro Pro Val Val Glu Trp Trp Phe Gln Ala Leu Asn Ser Ser Ser
            130                 135                 140

Glu Ser Phe Gly His Asn Leu Thr Val Asn Phe Phe Ser Leu Leu Leu
145                 150                 155                 160

```
Ile Ser Pro Asn Leu Gln Gly Asn Tyr Thr Cys Leu Ala Leu Asn Gln
            165                 170                 175

Leu Ser Lys Arg His Arg Lys Val Thr Thr Glu Leu Val Tyr Tyr
        180                 185                 190

Pro Pro Pro Ser Ala Pro Gln Cys Trp Ala Gln Met Ala Ser Gly Ser
        195                 200                 205

Phe Met Leu Gln Leu Thr Cys Arg Trp Asp Gly Gly Tyr Pro Asp Pro
210                 215                 220

Asp Phe Leu Trp Ile Glu Glu Pro Gly Gly Val Ile Val Gly Lys Ser
225                 230                 235                 240

Lys Leu Gly Val Glu Met Leu Ser Glu Ser Gln Leu Ser Asp Gly Lys
            245                 250                 255

Lys Phe Lys Cys Val Thr Ser His Ile Val Gly Pro Glu Ser Gly Ala
            260                 265                 270

Ser Cys Met Val Gln Ile Arg Gly Pro Ser Leu Leu Ser Glu Pro Met
        275                 280                 285

Lys Thr Cys Phe Thr Gly Gly Asn Val Thr Leu Thr Cys Gln Val Ser
        290                 295                 300

Gly Ala Tyr Pro Pro Ala Lys Ile Leu Trp Leu Arg Asn Leu Thr Gln
305                 310                 315                 320

Pro Glu Val Ile Ile Gln Pro Ser Ser Arg His Leu Ile Thr Gln Asp
            325                 330                 335

Gly Gln Asn Ser Thr Leu Thr Ile His Asn Cys Ser Gln Asp Leu Asp
            340                 345                 350

Glu Gly Tyr Tyr Ile Cys Arg Ala Asp Ser Pro Val Gly Val Arg Glu
        355                 360                 365

Met Glu Ile Trp Leu Ser Val Lys Glu Pro Leu Asn Ile Gly Gly
        370                 375                 380

<210> SEQ ID NO 5
<211> LENGTH: 439
<212> TYPE: PRT
<213> ORGANISM: Artificial sequence
<220> FEATURE:
<223> OTHER INFORMATION: Synthetic polypeptide

<400> SEQUENCE: 5

Met Ala Ala Gly Gly Ser Ala Pro Glu Pro Arg Val Leu Val Cys Leu
1               5                   10                  15

Gly Ala Leu Leu Ala Gly Trp Val Ala Val Gly Leu Glu Ala Val Val
            20                  25                  30

Ile Gly Glu Val His Glu Asn Val Thr Leu His Cys Gly Asn Ile Ser
        35                  40                  45

Gly Leu Arg Gly Gln Val Thr Trp Tyr Arg Asn Asn Ser Glu Pro Val
    50                  55                  60

Phe Leu Leu Ser Ser Asn Ser Ser Leu Arg Pro Ala Glu Pro Arg Phe
65                  70                  75                  80

Ser Leu Val Asp Ala Thr Ser Leu His Ile Glu Ser Leu Ser Leu Gly
            85                  90                  95

Asp Glu Gly Ile Tyr Thr Cys Gln Glu Ile Leu Asn Val Thr Gln Trp
        100                 105                 110

Phe Gln Val Trp Leu Gln Val Ala Asn Pro Pro Ser Ala Pro Gln
        115                 120                 125

Cys Trp Ala Gln Met Ala Ser Gly Ser Phe Met Leu Gln Leu Thr Cys
    130                 135                 140
```

```
Arg Trp Asp Gly Gly Tyr Pro Asp Pro Asp Phe Leu Trp Ile Glu Glu
145                 150                 155                 160

Pro Gly Gly Val Ile Val Gly Lys Ser Lys Leu Gly Val Glu Met Leu
                165                 170                 175

Ser Glu Ser Gln Leu Ser Asp Gly Lys Lys Phe Lys Cys Val Thr Ser
            180                 185                 190

His Ile Val Gly Pro Glu Ser Gly Ala Ser Cys Met Val Gln Ile Arg
            195                 200                 205

Gly Pro Ser Leu Leu Ser Glu Pro Met Lys Thr Cys Phe Thr Gly Gly
        210                 215                 220

Asn Val Thr Leu Thr Cys Gln Val Ser Gly Ala Tyr Pro Pro Ala Lys
225                 230                 235                 240

Ile Leu Trp Leu Arg Asn Leu Thr Gln Pro Glu Val Ile Ile Gln Pro
                245                 250                 255

Ser Ser Arg His Leu Ile Thr Gln Asp Gly Gln Asn Ser Thr Leu Thr
            260                 265                 270

Ile His Asn Cys Ser Gln Asp Leu Asp Glu Gly Tyr Tyr Ile Cys Arg
        275                 280                 285

Ala Asp Ser Pro Val Gly Val Arg Glu Met Glu Ile Trp Leu Ser Val
290                 295                 300

Lys Glu Pro Leu Asn Ile Gly Gly Ile Val Gly Thr Ile Val Ser Leu
305                 310                 315                 320

Leu Leu Leu Gly Leu Ala Ile Ile Ser Gly Leu Leu His Tyr Ser
                325                 330                 335

Pro Val Phe Cys Trp Lys Val Gly Asn Thr Ser Arg Gly Gln Asn Met
            340                 345                 350

Asp Asp Val Met Val Leu Val Asp Ser Glu Glu Glu Glu Glu Glu Glu
            355                 360                 365

Glu Glu Glu Glu Glu Asp Ala Ala Val Gly Gln Glu Gly Ala Arg
        370                 375                 380

Glu Arg Glu Glu Leu Pro Lys Glu Ile Pro Lys Gln Asp His Ile His
385                 390                 395                 400

Arg Val Thr Ala Leu Val Asn Gly Asn Ile Gln Met Gly Asn Gly
                405                 410                 415

Phe Gln Asp Leu Gln Asp Asp Ser Ser Glu Glu Gln Ser Asp Ile Val
                420                 425                 430

Gln Glu Glu Asp Arg Pro Val
        435

<210> SEQ ID NO 6
<211> LENGTH: 282
<212> TYPE: PRT
<213> ORGANISM: Artificial sequence
<220> FEATURE:
<223> OTHER INFORMATION: Synthetic polypeptide

<400> SEQUENCE: 6

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60
```

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Asn Pro Pro Ser Ala
                85                  90                  95

Pro Gln Cys Trp Ala Gln Met Ala Ser Gly Ser Phe Met Leu Gln Leu
            100                 105                 110

Thr Cys Arg Trp Asp Gly Gly Tyr Pro Asp Pro Asp Phe Leu Trp Ile
            115                 120                 125

Glu Glu Pro Gly Gly Val Ile Val Gly Lys Ser Lys Leu Gly Val Glu
        130                 135                 140

Met Leu Ser Glu Ser Gln Leu Ser Asp Gly Lys Lys Phe Lys Cys Val
145                 150                 155                 160

Thr Ser His Ile Val Gly Pro Glu Ser Gly Ala Ser Cys Met Val Gln
                165                 170                 175

Ile Arg Gly Pro Ser Leu Leu Ser Glu Pro Met Lys Thr Cys Phe Thr
            180                 185                 190

Gly Gly Asn Val Thr Leu Thr Cys Gln Val Ser Gly Ala Tyr Pro Pro
            195                 200                 205

Ala Lys Ile Leu Trp Leu Arg Asn Leu Thr Gln Pro Glu Val Ile Ile
        210                 215                 220

Gln Pro Ser Ser Arg His Leu Ile Thr Gln Asp Gly Gln Asn Ser Thr
225                 230                 235                 240

Leu Thr Ile His Asn Cys Ser Gln Asp Leu Asp Glu Gly Tyr Tyr Ile
                245                 250                 255

Cys Arg Ala Asp Ser Pro Val Gly Val Arg Glu Met Glu Ile Trp Leu
            260                 265                 270

Ser Val Lys Glu Pro Leu Asn Ile Gly Gly
            275                 280

<210> SEQ ID NO 7
<211> LENGTH: 366
<212> TYPE: PRT
<213> ORGANISM: Artificial sequence
<220> FEATURE:
<223> OTHER INFORMATION: Synthetic polypeptide

<400> SEQUENCE: 7

Met Ala Leu Pro Pro Gly Pro Ala Ala Leu Arg His Thr Leu Leu Leu
1               5                   10                  15

Leu Pro Ala Leu Leu Ser Ser Gly Trp Gly Glu Leu Glu Pro Gln Ile
            20                  25                  30

Asp Gly Gln Thr Trp Ala Glu Arg Ala Leu Arg Glu Asn Glu Arg His
        35                  40                  45

Ala Phe Thr Cys Arg Val Ala Gly Gly Pro Gly Thr Pro Arg Leu Ala
    50                  55                  60

Trp Tyr Leu Asp Gly Gln Leu Gln Glu Ala Ser Thr Ser Arg Leu Leu
65                  70                  75                  80

Ser Val Gly Gly Glu Ala Phe Ser Gly Thr Ser Thr Phe Thr Val
                85                  90                  95

Thr Ala His Arg Ala Gln His Glu Leu Asn Cys Ser Leu Gln Asp Pro
            100                 105                 110

Arg Ser Gly Arg Ser Ala Asn Ala Ser Val Ile Leu Asn Val Gln Phe
        115                 120                 125

Lys Pro Glu Ile Ala Gln Val Gly Ala Lys Tyr Gln Glu Ala Gln Gly
    130                 135                 140

-continued

```
Pro Gly Leu Leu Val Val Leu Phe Ala Leu Val Arg Ala Asn Pro Pro
145                 150                 155                 160

Ala Asn Val Thr Trp Ile Asp Gln Asp Gly Pro Val Thr Val Asn Thr
                165                 170                 175

Ser Asp Phe Leu Val Leu Asp Ala Gln Asn Tyr Pro Trp Leu Thr Asn
            180                 185                 190

His Thr Val Gln Leu Gln Leu Arg Ser Leu Ala His Asn Leu Ser Val
        195                 200                 205

Val Ala Thr Asn Asp Val Gly Val Thr Ser Ala Ser Leu Pro Ala Pro
    210                 215                 220

Gly Leu Leu Ala Thr Arg Val Glu Val Pro Leu Leu Gly Ile Val Val
225                 230                 235                 240

Ala Ala Gly Leu Ala Leu Gly Thr Leu Val Gly Phe Ser Thr Leu Val
                245                 250                 255

Ala Cys Leu Val Cys Arg Lys Glu Lys Lys Thr Lys Gly Pro Ser Arg
                260                 265                 270

His Pro Ser Leu Ile Ser Ser Asp Ser Asn Asn Leu Lys Leu Asn Asn
            275                 280                 285

Val Arg Leu Pro Arg Glu Asn Met Ser Leu Pro Ser Asn Leu Gln Leu
        290                 295                 300

Asn Asp Leu Thr Pro Asp Ser Arg Ala Val Lys Pro Ala Asp Arg Gln
305                 310                 315                 320

Met Ala Gln Asn Asn Ser Arg Pro Glu Leu Leu Asp Pro Glu Pro Gly
                325                 330                 335

Gly Leu Leu Thr Ser Gln Gly Phe Ile Arg Leu Pro Val Leu Gly Tyr
            340                 345                 350

Ile Tyr Arg Val Ser Ser Val Ser Ser Asp Glu Ile Trp Leu
        355                 360                 365

<210> SEQ ID NO 8
<211> LENGTH: 206
<212> TYPE: PRT
<213> ORGANISM: Artificial sequence
<220> FEATURE:
<223> OTHER INFORMATION: Synthetic polypeptide

<400> SEQUENCE: 8

Glu Leu Glu Pro Gln Ile Asp Gly Gln Thr Trp Ala Glu Arg Ala Leu
1               5                   10                  15

Arg Glu Asn Glu Arg His Ala Phe Thr Cys Arg Val Ala Gly Gly Pro
                20                  25                  30

Gly Thr Pro Arg Leu Ala Trp Tyr Leu Asp Gly Gln Leu Gln Glu Ala
            35                  40                  45

Ser Thr Ser Arg Leu Leu Ser Val Gly Gly Glu Ala Phe Ser Gly Gly
        50                  55                  60

Thr Ser Thr Phe Thr Val Thr Ala His Arg Ala Gln His Glu Leu Asn
65                  70                  75                  80

Cys Ser Leu Gln Asp Pro Arg Ser Gly Arg Ser Ala Asn Ala Ser Val
                85                  90                  95

Ile Leu Asn Val Gln Phe Lys Pro Glu Ile Ala Gln Val Gly Ala Lys
                100                 105                 110

Tyr Gln Glu Ala Gln Gly Pro Gly Leu Leu Val Val Leu Phe Ala Leu
            115                 120                 125

Val Arg Ala Asn Pro Pro Ala Asn Val Thr Trp Ile Asp Gln Asp Gly
        130                 135                 140
```

```
Pro Val Thr Val Asn Thr Ser Asp Phe Leu Val Leu Asp Ala Gln Asn
145                 150                 155                 160

Tyr Pro Trp Leu Thr Asn His Thr Val Gln Leu Gln Leu Arg Ser Leu
                165                 170                 175

Ala His Asn Leu Ser Val Val Ala Thr Asn Asp Val Gly Val Thr Ser
            180                 185                 190

Ala Ser Leu Pro Ala Pro Gly Leu Leu Ala Thr Arg Val Glu
        195                 200                 205

<210> SEQ ID NO 9
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 9

Met Glu Leu Pro Leu Ser Gln Ala Thr Leu Arg His Thr Leu Leu Leu
1               5                   10                  15

Leu Pro Ala Leu Leu Ser Ser Gly Gln Gly Glu Leu Ala Pro Gln Ile
            20                  25                  30

Asp Gly Gln Thr Trp Ala Glu Arg Ala Leu Arg Glu Asn Glu His His
        35                  40                  45

Ala Phe Thr Cys Arg Val Ala Gly Gly Ser Ala Thr Pro Arg Leu Ala
    50                  55                  60

Trp Tyr Leu Asp Gly Gln Leu Gln Glu Ala Thr Thr Ser Arg Leu Leu
65                  70                  75                  80

Ser Val Gly Gly Asp Ala Phe Ser Gly Thr Ser Thr Phe Thr Val
                85                  90                  95

Thr Ala Gln Arg Ser Gln His Glu Leu Asn Cys Ser Leu Gln Asp Pro
                100                 105                 110

Gly Ser Gly Arg Pro Ala Asn Ala Ser Val Ile Leu Asn Val Gln Phe
            115                 120                 125

Lys Pro Glu Ile Ala Gln Val Gly Ala Lys Tyr Gln Glu Ala Gln Gly
    130                 135                 140

Pro Gly Leu Leu Val Val Leu Phe Ala Leu Val Arg Ala Asn Pro Pro
145                 150                 155                 160

Ala Asn Val Thr Trp Ile Asp Gln Asp Gly Pro Val Thr Val Asn Ala
                165                 170                 175

Ser Asp Phe Leu Val Leu Asp Ala Gln Asn Tyr Pro Trp Leu Thr Asn
            180                 185                 190

His Thr Val Gln Leu Gln Leu Arg Ser Leu Ala His Asn Leu Ser Val
        195                 200                 205

Val Ala Thr Asn Asp Val Gly Val Thr Ser Ala Ser Leu Pro Ala Pro
    210                 215                 220

Gly Leu Leu Ala Thr Arg Ile Glu
225                 230

<210> SEQ ID NO 10
<211> LENGTH: 211
<212> TYPE: PRT
<213> ORGANISM: Artificial sequence
<220> FEATURE:
<223> OTHER INFORMATION: Synthetic polypeptide

<400> SEQUENCE: 10

Met Ala Leu Leu Ala Gly Gly Leu Ser Arg Gly Leu Gly Ser His Pro
```

```
   1               5                  10                 15
Ala Ala Ala Gly Arg Asp Ala Val Val Phe Val Trp Leu Leu Leu Ser
             20                 25                 30

Thr Trp Cys Thr Ala Pro Ala Arg Ala Ile Gln Val Thr Val Ser Asn
             35                 40                 45

Pro Tyr His Val Val Ile Leu Phe Gln Pro Val Thr Leu Pro Cys Thr
             50                 55                 60

Tyr Gln Met Thr Ser Thr Pro Thr Gln Pro Ile Val Ile Trp Lys Tyr
 65                 70                 75                 80

Lys Ser Phe Cys Arg Asp Arg Ile Ala Asp Ala Phe Ser Pro Ala Ser
             85                 90                 95

Val Asp Asn Gln Leu Asn Ala Gln Leu Ala Ala Gly Asn Pro Gly Tyr
            100                105                110

Asn Pro Tyr Val Glu Cys Gln Asp Ser Val Arg Thr Val Arg Val Val
            115                120                125

Ala Thr Lys Gln Gly Asn Ala Val Thr Leu Gly Asp Tyr Tyr Gln Gly
            130                135                140

Arg Arg Ile Thr Ile Thr Gly Asn Ala Asp Leu Thr Phe Asp Gln Thr
145                150                155                160

Ala Trp Gly Asp Ser Gly Val Tyr Tyr Cys Ser Val Val Ser Ala Gln
            165                170                175

Asp Leu Gln Gly Asn Asn Glu Ala Tyr Ala Glu Leu Ile Val Leu Gly
            180                185                190

Arg Thr Ser Gly Val Ala Glu Leu Leu Pro Gly Phe Gln Ala Gly Pro
            195                200                205

Ile Glu Asp
            210

<210> SEQ ID NO 11
<211> LENGTH: 601
<212> TYPE: PRT
<213> ORGANISM: Artificial sequence
<220> FEATURE:
<223> OTHER INFORMATION: Synthetic polypeptide

<400> SEQUENCE: 11

Met Ala Leu Leu Ala Gly Gly Leu Ser Arg Gly Leu Gly Ser His Pro
 1               5                  10                 15

Ala Ala Ala Gly Arg Asp Ala Val Val Phe Val Trp Leu Leu Leu Ser
             20                 25                 30

Thr Trp Cys Thr Ala Pro Ala Arg Ala Ile Gln Val Thr Val Ser Asn
             35                 40                 45

Pro Tyr His Val Val Ile Leu Phe Gln Pro Val Thr Leu Pro Cys Thr
             50                 55                 60

Tyr Gln Met Thr Ser Thr Pro Thr Gln Pro Ile Val Ile Trp Lys Tyr
 65                 70                 75                 80

Lys Ser Phe Cys Arg Asp Arg Ile Ala Asp Ala Phe Ser Pro Ala Ser
             85                 90                 95

Val Asp Asn Gln Leu Asn Ala Gln Leu Ala Ala Gly Asn Pro Gly Tyr
            100                105                110

Asn Pro Tyr Val Glu Cys Gln Asp Ser Val Arg Thr Val Arg Val Val
            115                120                125

Ala Thr Lys Gln Gly Asn Ala Val Thr Leu Gly Asp Tyr Tyr Gln Gly
            130                135                140

Arg Arg Ile Thr Ile Thr Gly Asn Ala Asp Leu Thr Phe Asp Gln Thr
```

-continued

```
            145                 150                 155                 160
        Ala Trp Gly Asp Ser Gly Val Tyr Tyr Cys Ser Val Val Ser Ala Gln
                            165                 170                 175
        Asp Leu Gln Gly Asn Asn Glu Ala Tyr Ala Glu Leu Ile Val Leu Gly
                            180                 185                 190
        Arg Thr Ser Gly Val Ala Glu Leu Leu Pro Gly Phe Gln Ala Gly Pro
                            195                 200                 205
        Ile Glu Asp Trp Leu Phe Val Val Val Cys Leu Ala Ala Phe Leu
            210                 215                 220
        Ile Phe Leu Leu Leu Gly Ile Cys Trp Cys Gln Cys Cys Pro His Thr
        225                 230                 235                 240
        Cys Cys Cys Tyr Val Arg Cys Pro Cys Cys Pro Asp Lys Cys Cys Cys
                            245                 250                 255
        Pro Glu Ala Leu Tyr Ala Ala Gly Lys Ala Ala Thr Ser Gly Val Pro
                            260                 265                 270
        Ser Ile Tyr Ala Pro Ser Thr Tyr Ala His Leu Ser Pro Ala Lys Thr
                            275                 280                 285
        Pro Pro Pro Pro Ala Met Ile Pro Met Gly Pro Ala Tyr Asn Gly Tyr
                            290                 295                 300
        Pro Gly Gly Tyr Pro Gly Asp Val Asp Arg Ser Ser Ala Gly Gly
        305                 310                 315                 320
        Gln Gly Ser Tyr Val Pro Leu Leu Arg Asp Thr Asp Ser Ser Val Ala
                            325                 330                 335
        Ser Glu Val Arg Ser Gly Tyr Arg Ile Gln Ala Ser Gln Gln Asp Asp
                            340                 345                 350
        Ser Met Arg Val Leu Tyr Tyr Met Glu Lys Glu Leu Ala Asn Phe Asp
                            355                 360                 365
        Pro Ser Arg Pro Gly Pro Pro Ser Gly Arg Val Glu Arg Ala Met Ser
                            370                 375                 380
        Glu Val Thr Ser Leu His Glu Asp Asp Trp Arg Ser Arg Pro Ser Arg
        385                 390                 395                 400
        Gly Pro Ala Leu Thr Pro Ile Arg Asp Glu Glu Trp Gly Gly His Ser
                            405                 410                 415
        Pro Arg Ser Pro Arg Gly Trp Asp Gln Glu Pro Ala Arg Glu Gln Ala
                            420                 425                 430
        Gly Gly Gly Trp Arg Ala Arg Arg Pro Arg Ala Arg Ser Val Asp Ala
                            435                 440                 445
        Leu Asp Asp Leu Thr Pro Pro Ser Thr Ala Glu Ser Gly Ser Arg Ser
            450                 455                 460
        Pro Thr Ser Asn Gly Gly Arg Ser Arg Ala Tyr Met Pro Pro Arg Ser
        465                 470                 475                 480
        Arg Ser Arg Asp Asp Leu Tyr Asp Gln Asp Ser Asp Phe Pro
                            485                 490                 495
        Arg Ser Arg Asp Pro His Tyr Asp Phe Arg Ser Arg Glu Arg Pro
                            500                 505                 510
        Pro Ala Asp Pro Arg Ser His His Arg Thr Arg Asp Pro Arg Asp
                            515                 520                 525
        Asn Gly Ser Arg Ser Gly Asp Leu Pro Tyr Asp Gly Arg Leu Leu Glu
                            530                 535                 540
        Glu Ala Val Arg Lys Lys Gly Ser Glu Glu Arg Arg Pro His Lys
        545                 550                 555                 560
        Glu Glu Glu Glu Glu Ala Tyr Tyr Pro Pro Ala Pro Pro Tyr Ser
                            565                 570                 575
```

```
Glu Thr Asp Ser Gln Ala Ser Arg Glu Arg Arg Leu Lys Lys Asn Leu
            580                 585                 590

Ala Leu Ser Arg Glu Ser Leu Val Val
        595                 600

<210> SEQ ID NO 12
<211> LENGTH: 170
<212> TYPE: PRT
<213> ORGANISM: Artificial sequence
<220> FEATURE:
<223> OTHER INFORMATION: Synthetic polypeptide

<400> SEQUENCE: 12

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
        35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
    130                 135                 140

Ala Glu Leu Ile Val Leu Gly Arg Thr Ser Gly Val Ala Glu Leu Leu
145                 150                 155                 160

Pro Gly Phe Gln Ala Gly Pro Ile Glu Asp
                165                 170

<210> SEQ ID NO 13
<211> LENGTH: 582
<212> TYPE: PRT
<213> ORGANISM: Artificial sequence
<220> FEATURE:
<223> OTHER INFORMATION: Synthetic polypeptide

<400> SEQUENCE: 13

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
```

```
                100             105             110
Asn Pro Tyr Val Glu Cys Gln Asp Ser Val Arg Thr Val Arg Val Val
            115                 120             125
Ala Thr Lys Gln Gly Asn Ala Val Thr Leu Gly Asp Tyr Tyr Gln Gly
        130                 135             140
Arg Arg Ile Thr Ile Thr Gly Asn Ala Asp Leu Thr Phe Asp Gln Thr
145                 150             155                 160
Ala Trp Gly Asp Ser Gly Val Tyr Tyr Cys Ser Val Val Ser Ala Gln
                165             170             175
Asp Leu Gln Gly Asn Asn Glu Ala Tyr Ala Glu Leu Ile Val Leu Asp
            180             185             190
Trp Leu Phe Val Val Val Cys Leu Ala Ala Phe Leu Ile Phe Leu
        195             200             205
Leu Leu Gly Ile Cys Trp Cys Gln Cys Cys Pro His Thr Cys Cys Cys
210             215                 220
Tyr Val Arg Cys Pro Cys Cys Pro Asp Lys Cys Cys Cys Pro Glu Ala
225             230             235                 240
Leu Tyr Ala Ala Gly Lys Ala Ala Thr Ser Gly Val Pro Ser Ile Tyr
            245             250             255
Ala Pro Ser Thr Tyr Ala His Leu Ser Pro Ala Lys Thr Pro Pro Pro
        260             265             270
Pro Ala Met Ile Pro Met Gly Pro Ala Tyr Asn Gly Tyr Pro Gly Gly
        275             280             285
Tyr Pro Gly Asp Val Asp Arg Ser Ser Ala Gly Gly Gln Gly Ser
290             295             300
Tyr Val Pro Leu Leu Arg Asp Thr Asp Ser Ser Val Ala Ser Glu Val
305             310             315             320
Arg Ser Gly Tyr Arg Ile Gln Ala Ser Gln Gln Asp Asp Ser Met Arg
            325             330             335
Val Leu Tyr Tyr Met Glu Lys Glu Leu Ala Asn Phe Asp Pro Ser Arg
            340             345             350
Pro Gly Pro Pro Ser Gly Arg Val Glu Arg Ala Met Ser Glu Val Thr
        355             360             365
Ser Leu His Glu Asp Asp Trp Arg Ser Arg Pro Ser Arg Gly Pro Ala
        370             375             380
Leu Thr Pro Ile Arg Asp Glu Glu Trp Gly Gly His Ser Pro Arg Ser
385                 390             395                 400
Pro Arg Gly Trp Asp Gln Glu Pro Ala Arg Glu Gln Ala Gly Gly
            405             410             415
Trp Arg Ala Arg Arg Pro Arg Ala Arg Ser Val Asp Ala Leu Asp Asp
            420             425             430
Leu Thr Pro Ser Thr Ala Glu Ser Gly Ser Arg Ser Pro Thr Ser
        435             440             445
Asn Gly Gly Arg Ser Arg Ala Tyr Met Pro Pro Arg Ser Arg Ser Arg
        450             455             460
Asp Asp Leu Tyr Asp Gln Asp Asp Ser Arg Asp Phe Pro Arg Ser Arg
465             470             475                 480
Asp Pro His Tyr Asp Asp Phe Arg Ser Arg Glu Arg Pro Pro Ala Asp
            485             490             495
Pro Arg Ser His His His Arg Thr Arg Asp Pro Arg Asp Asn Gly Ser
        500             505             510
Arg Ser Gly Asp Leu Pro Tyr Asp Gly Arg Leu Leu Glu Glu Ala Val
        515             520             525
```

Arg Lys Lys Gly Ser Glu Arg Arg Pro His Lys Glu Glu
        530             535             540
Glu Glu Ala Tyr Tyr Pro Ala Pro Pro Tyr Ser Glu Thr Asp
545             550             555             560
Ser Gln Ala Ser Arg Glu Arg Arg Leu Lys Lys Asn Leu Ala Leu Ser
            565             570             575
Arg Glu Ser Leu Val Val
            580

<210> SEQ ID NO 14
<211> LENGTH: 151
<212> TYPE: PRT
<213> ORGANISM: Artificial sequence
<220> FEATURE:
<223> OTHER INFORMATION: Synthetic polypeptide

<400> SEQUENCE: 14

Ile Gln Val Thr Val Ser Asn Pro Tyr His Val Ile Leu Phe Gln
1               5                   10                  15
Pro Val Thr Leu Pro Cys Thr Tyr Gln Met Thr Ser Thr Pro Thr Gln
                20                  25                  30
Pro Ile Val Ile Trp Lys Tyr Lys Ser Phe Cys Arg Asp Arg Ile Ala
            35                  40                  45
Asp Ala Phe Ser Pro Ala Ser Val Asp Asn Gln Leu Asn Ala Gln Leu
        50                  55                  60
Ala Ala Gly Asn Pro Gly Tyr Asn Pro Tyr Val Glu Cys Gln Asp Ser
65                  70                  75                  80
Val Arg Thr Val Arg Val Ala Thr Lys Gln Gly Asn Ala Val Thr
                85                  90                  95
Leu Gly Asp Tyr Tyr Gln Gly Arg Arg Ile Thr Ile Thr Gly Asn Ala
                100                 105                 110
Asp Leu Thr Phe Asp Gln Thr Ala Trp Gly Asp Ser Gly Val Tyr Tyr
            115                 120                 125
Cys Ser Val Val Ser Ala Gln Asp Leu Gln Gly Asn Asn Glu Ala Tyr
        130                 135                 140
Ala Glu Leu Ile Val Leu Asp
145                 150

<210> SEQ ID NO 15
<211> LENGTH: 533
<212> TYPE: PRT
<213> ORGANISM: Artificial sequence
<220> FEATURE:
<223> OTHER INFORMATION: Synthetic polypeptide

<400> SEQUENCE: 15

Met Ala Leu Leu Ala Gly Gly Leu Ser Arg Gly Leu Gly Ser His Pro
1               5                   10                  15
Ala Ala Ala Gly Arg Asp Ala Val Phe Val Trp Leu Leu Leu Ser
                20                  25                  30
Thr Trp Cys Thr Ala Pro Ala Arg Ala Ile Gln Val Thr Val Ser Asn
            35                  40                  45
Pro Tyr His Val Val Ile Leu Phe Gln Pro Val Thr Leu Pro Cys Thr
        50                  55                  60
Tyr Gln Met Thr Ser Thr Pro Thr Gln Pro Ile Val Ile Trp Lys Tyr
65                  70                  75                  80
Lys Ser Phe Cys Arg Asp Arg Ile Ala Asp Ala Phe Ser Pro Ala Ser

```
                85                  90                  95
Val Asp Asn Gln Leu Asn Ala Gln Leu Ala Ala Gly Asn Pro Gly Tyr
                100                 105                 110

Asn Pro Tyr Val Glu Cys Gln Asp Ser Val Arg Thr Val Arg Val Val
                115                 120                 125

Ala Thr Lys Gln Gly Asn Ala Val Thr Leu Gly Asp Tyr Tyr Gln Gly
                130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Val
                180                 185                 190

Tyr Ala Ala Gly Lys Ala Ala Thr Ser Gly Val Pro Ser Ile Tyr Ala
                195                 200                 205

Pro Ser Thr Tyr Ala His Leu Ser Pro Ala Lys Thr Pro Pro Pro Pro
                210                 215                 220

Ala Met Ile Pro Met Gly Pro Ala Tyr Asn Gly Tyr Pro Gly Gly Tyr
225                 230                 235                 240

Pro Gly Asp Val Asp Arg Ser Ser Ser Ala Gly Gly Gln Gly Ser Tyr
                245                 250                 255

Val Pro Leu Leu Arg Asp Thr Asp Ser Ser Val Ala Ser Glu Val Arg
                260                 265                 270

Ser Gly Tyr Arg Ile Gln Ala Ser Gln Gln Asp Asp Ser Met Arg Val
                275                 280                 285

Leu Tyr Tyr Met Glu Lys Glu Leu Ala Asn Phe Asp Pro Ser Arg Pro
                290                 295                 300

Gly Pro Pro Ser Gly Arg Val Glu Arg Ala Met Ser Glu Val Thr Ser
305                 310                 315                 320

Leu His Glu Asp Asp Trp Arg Ser Arg Pro Ser Arg Gly Pro Ala Leu
                325                 330                 335

Thr Pro Ile Arg Asp Glu Glu Trp Gly Gly His Ser Pro Arg Ser Pro
                340                 345                 350

Arg Gly Trp Asp Gln Glu Pro Ala Arg Glu Gln Ala Gly Gly Gly Trp
                355                 360                 365

Arg Ala Arg Arg Pro Arg Ala Arg Ser Val Asp Ala Leu Asp Asp Leu
                370                 375                 380

Thr Pro Pro Ser Thr Ala Glu Ser Gly Ser Arg Ser Pro Thr Ser Asn
385                 390                 395                 400

Gly Gly Arg Ser Arg Ala Tyr Met Pro Pro Arg Ser Arg Ser Arg Asp
                405                 410                 415

Asp Leu Tyr Asp Gln Asp Asp Ser Asp Phe Pro Arg Ser Arg Arg Asp
                420                 425                 430

Pro His Tyr Asp Asp Phe Arg Ser Arg Glu Arg Pro Ala Asp Pro
                435                 440                 445

Arg Ser His His His Arg Thr Arg Asp Pro Arg Asp Asn Gly Ser Arg
                450                 455                 460

Ser Gly Asp Leu Pro Tyr Asp Gly Arg Leu Leu Glu Glu Ala Val Arg
465                 470                 475                 480

Lys Lys Gly Ser Glu Glu Arg Arg Pro His Lys Glu Glu Glu Glu
                485                 490                 495

Glu Ala Tyr Tyr Pro Pro Ala Pro Pro Pro Tyr Ser Glu Thr Asp Ser
                500                 505                 510
```

Gln Ala Ser Arg Glu Arg Arg Leu Lys Lys Asn Leu Ala Leu Ser Arg
        515                 520                 525

Glu Ser Leu Val Val
    530

<210> SEQ ID NO 16
<211> LENGTH: 532
<212> TYPE: PRT
<213> ORGANISM: Artificial sequence
<220> FEATURE:
<223> OTHER INFORMATION: Synthetic polypeptide

<400> SEQUENCE: 16

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Val
            180                 185                 190

Tyr Ala Ala Gly Lys Ala Ala Thr Ser Gly Val Pro Ser Ile Tyr Ala
        195                 200                 205

Pro Ser Thr Tyr Ala His Leu Ser Pro Ala Lys Thr Pro Pro Pro Pro
    210                 215                 220

Ala Met Ile Pro Met Gly Pro Ala Tyr Asn Gly Tyr Pro Gly Gly Tyr
225                 230                 235                 240

Pro Gly Asp Val Asp Arg Ser Ser Ala Gly Gln Gly Ser Tyr
                245                 250                 255

Val Pro Leu Leu Arg Asp Thr Asp Ser Ser Val Ala Ser Val Arg Ser
            260                 265                 270

Gly Tyr Arg Ile Gln Ala Ser Gln Gln Asp Asp Ser Met Arg Val Leu
        275                 280                 285

Tyr Tyr Met Glu Lys Glu Leu Ala Asn Phe Asp Pro Ser Arg Pro Gly
    290                 295                 300

Pro Pro Ser Gly Arg Val Glu Arg Ala Met Ser Glu Val Thr Ser Leu
305                 310                 315                 320

His Glu Asp Asp Trp Arg Ser Arg Pro Ser Arg Gly Pro Ala Leu Thr
                325                 330                 335

```
Pro Ile Arg Asp Glu Glu Trp Gly Gly His Ser Pro Arg Ser Pro Arg
            340                 345                 350

Gly Trp Asp Gln Glu Pro Ala Arg Glu Gln Ala Gly Gly Trp Arg
        355                 360                 365

Ala Arg Arg Pro Arg Ala Arg Ser Val Asp Ala Leu Asp Asp Leu Thr
370                 375                 380

Pro Pro Ser Thr Ala Glu Ser Gly Ser Arg Ser Pro Thr Ser Asn Gly
385                 390                 395                 400

Gly Arg Ser Arg Ala Tyr Met Pro Pro Arg Ser Arg Ser Arg Asp Asp
                405                 410                 415

Leu Tyr Asp Gln Asp Asp Ser Arg Asp Phe Pro Arg Ser Arg Asp Pro
            420                 425                 430

His Tyr Asp Asp Phe Arg Ser Arg Glu Arg Pro Ala Asp Pro Arg
            435                 440                 445

Ser His His His Arg Thr Arg Asp Pro Arg Asp Asn Gly Ser Arg Ser
        450                 455                 460

Gly Asp Leu Pro Tyr Asp Gly Arg Leu Leu Glu Glu Ala Val Arg Lys
465                 470                 475                 480

Lys Gly Ser Glu Glu Arg Arg Arg Pro His Lys Glu Glu Glu Glu
                485                 490                 495

Ala Tyr Tyr Pro Pro Ala Pro Pro Tyr Ser Glu Thr Asp Ser Gln
                500                 505                 510

Ala Ser Arg Glu Arg Arg Leu Lys Lys Asn Leu Ala Leu Ser Arg Glu
            515                 520                 525

Ser Leu Val Val
        530

<210> SEQ ID NO 17
<211> LENGTH: 493
<212> TYPE: PRT
<213> ORGANISM: Artificial sequence
<220> FEATURE:
<223> OTHER INFORMATION: Synthetic polypeptide

<400> SEQUENCE: 17

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Met Tyr Ala Ala Gly Lys Ala Ala Thr
145                 150                 155                 160
```

```
Ser Gly Val Pro Ser Ile Tyr Ala Pro Ser Thr Tyr Ala His Leu Ser
            165                 170                 175

Pro Ala Lys Thr Pro Pro Pro Ala Met Ile Pro Met Gly Pro Ala
        180                 185                 190

Tyr Asn Gly Tyr Pro Gly Gly Tyr Pro Gly Asp Val Asp Arg Ser Ser
        195                 200                 205

Ser Ala Gly Gly Gln Gly Ser Tyr Val Pro Leu Leu Arg Asp Thr Asp
    210                 215                 220

Ser Ser Val Ala Ser Glu Val Arg Ser Gly Tyr Arg Ile Gln Ala Ser
225                 230                 235                 240

Gln Gln Asp Asp Ser Met Arg Val Leu Tyr Tyr Met Glu Lys Glu Leu
                245                 250                 255

Ala Asn Phe Asp Pro Ser Arg Pro Gly Pro Pro Ser Gly Arg Val Glu
            260                 265                 270

Arg Ala Met Ser Glu Val Thr Ser Leu His Glu Asp Asp Trp Arg Ser
        275                 280                 285

Arg Pro Ser Arg Gly Pro Ala Leu Thr Pro Ile Arg Asp Glu Glu Trp
    290                 295                 300

Gly Gly His Ser Pro Arg Ser Pro Arg Gly Trp Asp Gln Glu Pro Ala
305                 310                 315                 320

Arg Glu Gln Ala Gly Gly Gly Trp Arg Ala Arg Arg Pro Arg Ala Arg
                325                 330                 335

Ser Val Asp Ala Leu Asp Asp Leu Thr Pro Ser Thr Ala Glu Ser
            340                 345                 350

Gly Ser Arg Ser Pro Thr Ser Asn Gly Gly Arg Ser Arg Ala Tyr Met
    355                 360                 365

Pro Pro Arg Ser Arg Ser Arg Asp Asp Leu Tyr Asp Gln Asp Asp Ser
    370                 375                 380

Arg Asp Phe Pro Arg Ser Arg Asp Pro His Tyr Asp Asp Phe Arg Ser
385                 390                 395                 400

Arg Glu Arg Pro Pro Ala Asp Pro Arg Ser His His His Arg Thr Arg
                405                 410                 415

Asp Pro Arg Asp Asn Gly Ser Arg Ser Gly Asp Leu Pro Tyr Asp Gly
            420                 425                 430

Arg Leu Leu Glu Glu Ala Val Arg Lys Lys Gly Ser Glu Glu Arg Arg
        435                 440                 445

Arg Pro His Lys Glu Glu Glu Glu Ala Tyr Tyr Pro Pro Ala Pro
    450                 455                 460

Pro Pro Tyr Ser Glu Thr Asp Ser Gln Ala Ser Arg Glu Arg Arg Leu
465                 470                 475                 480

Lys Lys Asn Leu Ala Leu Ser Arg Glu Ser Leu Val Val
                485                 490

<210> SEQ ID NO 18
<211> LENGTH: 552
<212> TYPE: PRT
<213> ORGANISM: Artificial sequence
<220> FEATURE:
<223> OTHER INFORMATION: Synthetic polypeptide

<400> SEQUENCE: 18

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30
```

```
Thr Trp Cys Thr Ala Pro Ala Arg Ala Ile Gln Val Thr Val Ser Asn
         35                  40                  45

Pro Tyr His Val Val Ile Leu Phe Gln Pro Val Thr Leu Pro Cys Thr
 50                  55                  60

Tyr Gln Met Thr Ser Thr Pro Thr Gln Pro Ile Val Ile Trp Lys Tyr
 65                  70                  75                  80

Lys Ser Phe Cys Arg Asp Arg Ile Ala Asp Ala Phe Ser Pro Ala Ser
                 85                  90                  95

Val Asp Asn Gln Leu Asn Ala Gln Leu Ala Ala Gly Asn Pro Gly Tyr
                100                 105                 110

Asn Pro Tyr Val Glu Cys Gln Asp Ser Val Arg Thr Val Arg Val Val
            115                 120                 125

Ala Thr Lys Gln Gly Asn Ala Val Thr Leu Gly Asp Tyr Tyr Gln Gly
        130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
                180                 185                 190

Arg Thr Ser Gly Val Ala Glu Leu Leu Pro Gly Phe Gln Ala Gly Pro
            195                 200                 205

Ile Glu Val Tyr Ala Ala Gly Lys Ala Ala Thr Ser Gly Val Pro Ser
        210                 215                 220

Ile Tyr Ala Pro Ser Thr Tyr Ala His Leu Ser Pro Ala Lys Thr Pro
225                 230                 235                 240

Pro Pro Pro Ala Met Ile Pro Met Gly Pro Ala Tyr Asn Gly Tyr Pro
                245                 250                 255

Gly Gly Tyr Pro Gly Asp Val Asp Arg Ser Ser Ala Gly Gly Gln
                260                 265                 270

Gly Ser Tyr Val Pro Leu Leu Arg Asp Thr Asp Ser Ser Val Ala Ser
            275                 280                 285

Glu Val Arg Ser Gly Tyr Arg Ile Gln Ala Ser Gln Gln Asp Asp Ser
        290                 295                 300

Met Arg Val Leu Tyr Tyr Met Glu Lys Glu Leu Ala Asn Phe Asp Pro
305                 310                 315                 320

Ser Arg Pro Gly Pro Pro Ser Gly Arg Val Glu Arg Ala Met Ser Glu
                325                 330                 335

Val Thr Ser Leu His Glu Asp Asp Trp Arg Ser Arg Pro Ser Arg Gly
            340                 345                 350

Pro Ala Leu Thr Pro Ile Arg Asp Glu Glu Trp Gly His Ser Pro
        355                 360                 365

Arg Ser Pro Arg Gly Trp Asp Gln Glu Pro Ala Arg Glu Gln Ala Gly
    370                 375                 380

Gly Gly Trp Arg Ala Arg Pro Arg Ala Arg Ser Val Asp Ala Leu
385                 390                 395                 400

Asp Asp Leu Thr Pro Pro Ser Thr Ala Glu Ser Gly Ser Arg Ser Pro
                405                 410                 415

Thr Ser Asn Gly Gly Arg Ser Arg Ala Tyr Met Pro Pro Arg Ser Arg
            420                 425                 430

Ser Arg Asp Asp Leu Tyr Asp Gln Asp Asp Ser Arg Asp Phe Pro Arg
        435                 440                 445
```

```
Ser Arg Asp Pro His Tyr Asp Asp Phe Arg Ser Arg Glu Arg Pro Pro
    450                 455                 460
Ala Asp Pro Arg Ser His His His Arg Thr Arg Asp Pro Arg Asp Asn
465                 470                 475                 480
Gly Ser Arg Ser Gly Asp Leu Pro Tyr Asp Gly Arg Leu Leu Glu Glu
                485                 490                 495
Ala Val Arg Lys Lys Gly Ser Glu Glu Arg Arg Pro His Lys Glu
            500                 505                 510
Glu Glu Glu Ala Tyr Tyr Pro Ala Pro Pro Tyr Ser Glu
        515                 520                 525
Thr Asp Ser Gln Ala Ser Arg Glu Arg Leu Lys Lys Asn Leu Ala
530                 535                 540
Leu Ser Arg Glu Ser Leu Val Val
545                 550

<210> SEQ ID NO 19
<211> LENGTH: 429
<212> TYPE: PRT
<213> ORGANISM: Artificial sequence
<220> FEATURE:
<223> OTHER INFORMATION: Synthetic polypeptide

<400> SEQUENCE: 19

Met Ala Gly Leu Arg Val Leu Leu Cys Leu Gly Ala Leu Leu Ala Arg
1               5                   10                  15
Gln Gly Ser Ala Gly Leu Gln Leu Leu Leu Asn Pro Ser Arg Ala Asn
                20                  25                  30
Leu Ser Val Arg Pro Asn Ser Glu Val Leu Pro Gly Ile His Pro Asp
            35                  40                  45
Leu Glu Ala Val Ala Ile Gly Glu Val His Asp Asn Val Thr Leu Arg
        50                  55                  60
Cys Gly Ser Ala Ser Gly Ser Arg Gly Leu Val Thr Trp Tyr Arg Asn
65                  70                  75                  80
Asp Ser Glu Pro Ala Phe Leu Val Ser Phe Asn Ser Ser Leu Pro Pro
                85                  90                  95
Ala Ala Pro Arg Phe Ser Leu Glu Asp Ala Gly Ala Leu Arg Ile Glu
            100                 105                 110
Ala Leu Arg Leu Glu Asp Asp Gly Asn Tyr Thr Cys Gln Glu Val Leu
        115                 120                 125
Asn Glu Thr His Trp Phe Pro Val Arg Leu Arg Val Ala Ser Gly Pro
130                 135                 140
Ala Tyr Val Glu Val Asn Ile Ser Ala Thr Gly Thr Leu Pro Asn Gly
145                 150                 155                 160
Thr Leu Tyr Ala Ala Arg Gly Ser Gln Val Asp Phe Asn Cys Cys Ser
                165                 170                 175
Ala Ala Gln Pro Pro Pro Glu Val Glu Trp Trp Ile Gln Thr His Ser
            180                 185                 190
Ile Pro Glu Phe Leu Gly Lys Asn Leu Ser Ala Asn Ser Phe Thr Leu
        195                 200                 205
Met Leu Met Ser Gln Asn Leu Gln Gly Asn Tyr Thr Cys Ser Ala Thr
210                 215                 220
Asn Val Leu Ser Gly Arg Gln Arg Lys Val Thr Thr Glu Leu Leu Val
225                 230                 235                 240
Tyr Trp Pro Pro Pro Ser Ala Pro Gln Cys Ser Val Glu Val Ser Ser
                245                 250                 255
```

```
Glu Ser Thr Thr Leu Glu Leu Ala Cys Asn Trp Asp Gly Gly Tyr Pro
            260                 265                 270

Asp Pro Thr Phe Leu Trp Thr Glu Pro Gly Gly Thr Ile Met Gly
        275                 280                 285

Asn Ser Lys Leu Gln Thr Leu Ser Pro Ala Gln Leu Leu Glu Gly Lys
290                 295                 300

Lys Phe Lys Cys Val Gly Asn His Ile Leu Gly Pro Glu Ser Gly Ala
305                 310                 315                 320

Ser Cys Val Val Lys Leu Ser Ser Pro Leu Pro Ser Gln Pro Met
                325                 330                 335

Arg Thr Cys Phe Val Gly Gly Asn Val Thr Leu Thr Cys Glu Val Ser
            340                 345                 350

Gly Ala Asn Pro Pro Ala Arg Ile Gln Trp Leu Arg Asn Leu Thr Gln
        355                 360                 365

Pro Ala Ile Gln Pro Ser Ser His Tyr Ile Ile Thr Gln Gly Gln
370                 375                 380

Ser Ser Ser Leu Thr Ile His Asn Cys Ser Gln Asp Leu Asp Glu Gly
385                 390                 395                 400

Phe Tyr Tyr Cys Gln Ala Glu Asn Leu Val Gly Val Arg Ala Thr Asn
            405                 410                 415

Ile Trp Leu Ser Val Lys Glu Pro Leu Asn Ile Gly Gly
            420                 425

<210> SEQ ID NO 20
<211> LENGTH: 236
<212> TYPE: PRT
<213> ORGANISM: Artificial sequence
<220> FEATURE:
<223> OTHER INFORMATION: Synthetic polypeptide

<400> SEQUENCE: 20

Met Ala Val Val Phe Leu Leu Phe Leu Cys Gly His Ser Gln Ala
1               5                   10                  15

Val Ala Asp Ser Ile Gln Thr Ile Tyr Val Ala Ser Gly Glu Ser Val
                20                  25                  30

Glu Met Pro Cys Pro Ser Pro Pro Ser Leu Leu Gly Gly Gln Leu Leu
            35                  40                  45

Thr Trp Phe Arg Ser Pro Val Ala Gly Ser Ser Thr Ile Leu Val Ala
50                  55                  60

Gln Val Gln Val Asp Lys Pro Val Ser Asp Leu Arg Lys Pro Glu Pro
65                  70                  75                  80

Asp Ser Arg Tyr Lys Leu Phe Gly Asn Tyr Ser Leu Trp Leu Glu Gly
                85                  90                  95

Ser Arg Asp Glu Asp Ala Gly Arg Tyr Trp Cys Thr Val Met Asp Gln
            100                 105                 110

Asn His Lys Tyr Gln Asn Trp Arg Val Tyr Asp Val Ser Val Leu Lys
        115                 120                 125

Gly Ser Gln Phe Ser Val Lys Ser Pro Asp Gly Pro Ser Cys Ala Ala
130                 135                 140

Leu Leu Cys Ser Val Val Pro Ala Arg Arg Leu Asp Ser Val Thr Trp
145                 150                 155                 160

Leu Glu Gly Arg Asn Thr Val Arg Gly His Ala Gln Tyr Phe Trp Gly
                165                 170                 175

Glu Gly Ala Ala Leu Leu Leu Val Cys Pro Thr Glu Gly Leu Pro Glu
            180                 185                 190
```

Thr Arg Ala Arg Arg Pro Arg Asn Ile Arg Cys Leu Leu Pro Gln Asn
            195                 200                 205

Lys Arg Phe Ser Phe Ser Leu Ala Ala Ala Ser Ala Glu Pro Ser Pro
        210                 215                 220

Thr Val Cys Ala Thr Leu Pro Ser Trp Asp Val Pro
225                 230                 235

<210> SEQ ID NO 21
<211> LENGTH: 206
<212> TYPE: PRT
<213> ORGANISM: Artificial sequence
<220> FEATURE:
<223> OTHER INFORMATION: Synthetic polypeptide

<400> SEQUENCE: 21

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp
        195                 200                 205

<210> SEQ ID NO 22
<211> LENGTH: 192
<212> TYPE: PRT
<213> ORGANISM: Artificial sequence
<220> FEATURE:
<223> OTHER INFORMATION: Synthetic polypeptide

<400> SEQUENCE: 22

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

```
Tyr Gln Met Thr Ser Thr Pro Thr Gln Pro Ile Val Ile Trp Lys Tyr
 65                  70                  75                  80

Lys Ser Phe Cys Arg Asp Arg Ile Ala Asp Ala Phe Ser Pro Ala Ser
                 85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Asp
            180                 185                 190

<210> SEQ ID NO 23
<211> LENGTH: 451
<212> TYPE: PRT
<213> ORGANISM: Artificial sequence
<220> FEATURE:
<223> OTHER INFORMATION: Synthetic polypeptide

<400> SEQUENCE: 23

Asp Ser Ile Gln Thr Ile Tyr Val Ala Ser Gly Glu Ser Val Glu Met
1               5                  10                  15

Pro Cys Pro Ser Pro Pro Ser Leu Leu Gly Gly Gln Leu Leu Thr Trp
                 20                  25                  30

Phe Arg Ser Pro Val Ala Gly Ser Ser Thr Ile Leu Val Ala Gln Val
             35                  40                  45

Gln Val Asp Lys Pro Val Ser Asp Leu Arg Lys Pro Glu Pro Asp Ser
    50                  55                  60

Arg Tyr Lys Leu Phe Gly Asn Tyr Ser Leu Trp Leu Glu Gly Ser Arg
65                  70                  75                  80

Asp Glu Asp Ala Gly Arg Tyr Trp Cys Thr Val Met Asp Gln Asn His
                 85                  90                  95

Lys Tyr Gln Asn Trp Arg Val Tyr Asp Val Ser Val Leu Lys Gly Ser
            100                 105                 110

Gln Phe Ser Val Lys Ser Pro Asp Gly Pro Ser Cys Ala Ala Leu Leu
        115                 120                 125

Cys Ser Val Val Pro Ala Arg Arg Leu Asp Ser Val Thr Trp Leu Glu
    130                 135                 140

Gly Arg Asn Thr Val Arg Gly His Ala Gln Tyr Phe Trp Gly Glu Gly
145                 150                 155                 160

Ala Ala Leu Leu Leu Val Cys Pro Thr Glu Gly Leu Pro Glu Thr Arg
                165                 170                 175

Ala Arg Arg Pro Arg Asn Ile Arg Cys Leu Leu Pro Gln Asn Lys Arg
            180                 185                 190

Phe Ser Phe Ser Leu Ala Ala Ala Ser Ala Glu Pro Ser Pro Thr Val
        195                 200                 205

Cys Ala Thr Leu Pro Ser Trp Asp Val Pro Gly Pro Arg Gly Pro Thr
    210                 215                 220

Ile Lys Pro Cys Pro Pro Cys Lys Cys Pro Ala Pro Asn Leu Leu Gly
225                 230                 235                 240
```

```
Gly Pro Ser Val Phe Ile Phe Pro Pro Lys Ile Lys Asp Val Leu Met
                245                 250                 255
Ile Ser Leu Ser Pro Ile Val Thr Cys Val Val Val Asp Val Ser Glu
            260                 265                 270
Asp Asp Pro Asp Val Gln Ile Ser Trp Phe Val Asn Asn Val Glu Val
        275                 280                 285
His Thr Ala Gln Thr Gln Thr His Arg Glu Asp Tyr Asn Ser Thr Leu
    290                 295                 300
Arg Val Val Ser Ala Leu Pro Ile Gln His Gln Asp Trp Met Ser Gly
305                 310                 315                 320
Lys Glu Phe Lys Cys Lys Val Asn Asn Lys Asp Leu Pro Ala Pro Ile
                325                 330                 335
Glu Arg Thr Ile Ser Lys Pro Lys Gly Ser Val Arg Ala Pro Gln Val
            340                 345                 350
Tyr Val Leu Pro Pro Pro Glu Glu Glu Met Thr Lys Lys Gln Val Thr
        355                 360                 365
Leu Thr Cys Met Val Thr Asp Phe Met Pro Glu Asp Ile Tyr Val Glu
    370                 375                 380
Trp Thr Asn Asn Gly Lys Thr Glu Leu Asn Tyr Lys Asn Thr Glu Pro
385                 390                 395                 400
Val Leu Asp Ser Asp Gly Ser Tyr Phe Met Tyr Ser Lys Leu Arg Val
                405                 410                 415
Glu Lys Lys Asn Trp Val Glu Arg Asn Ser Tyr Ser Cys Ser Val Val
            420                 425                 430
His Glu Gly Leu His Asn His His Thr Thr Lys Ser Phe Ser Arg Thr
        435                 440                 445
Pro Gly Lys
    450

<210> SEQ ID NO 24
<211> LENGTH: 641
<212> TYPE: PRT
<213> ORGANISM: Artificial sequence
<220> FEATURE:
<223> OTHER INFORMATION: Synthetic polypeptide

<400> SEQUENCE: 24

Leu Gln Leu Leu Leu Asn Pro Ser Arg Ala Asn Leu Ser Val Arg Pro
1               5                   10                  15
Asn Ser Glu Val Leu Pro Gly Ile His Pro Asp Leu Glu Ala Val Ala
            20                  25                  30
Ile Gly Glu Val His Asp Asn Val Thr Leu Arg Cys Gly Ser Ala Ser
        35                  40                  45
Gly Ser Arg Gly Leu Val Thr Trp Tyr Arg Asn Asp Ser Glu Pro Ala
    50                  55                  60
Phe Leu Val Ser Phe Asn Ser Ser Leu Pro Pro Ala Ala Pro Arg Phe
65                  70                  75                  80
Ser Leu Glu Asp Ala Gly Ala Leu Arg Ile Glu Ala Leu Arg Leu Glu
                85                  90                  95
Asp Asp Gly Asn Tyr Thr Cys Gln Glu Val Leu Asn Glu Thr His Trp
            100                 105                 110
Phe Pro Val Arg Leu Arg Val Ala Ser Gly Pro Ala Tyr Val Glu Val
        115                 120                 125
Asn Ile Ser Ala Thr Gly Thr Leu Pro Asn Gly Thr Leu Tyr Ala Ala
    130                 135                 140
```

-continued

```
Arg Gly Ser Gln Val Asp Phe Asn Cys Cys Ser Ala Gln Pro Pro
145                 150                 155                 160

Pro Glu Val Glu Trp Trp Ile Gln Thr His Ser Ile Pro Glu Phe Leu
            165                 170                 175

Gly Lys Asn Leu Ser Ala Asn Ser Phe Thr Leu Met Leu Met Ser Gln
            180                 185                 190

Asn Leu Gln Gly Asn Tyr Thr Cys Ser Ala Thr Asn Val Leu Ser Gly
            195                 200                 205

Arg Gln Arg Lys Val Thr Thr Glu Leu Leu Val Tyr Trp Pro Pro
210                 215                 220

Ser Ala Pro Gln Cys Ser Val Glu Val Ser Ser Glu Ser Thr Thr Leu
225                 230                 235                 240

Glu Leu Ala Cys Asn Trp Asp Gly Gly Tyr Pro Asp Pro Thr Phe Leu
                245                 250                 255

Trp Thr Glu Glu Pro Gly Gly Thr Ile Met Gly Asn Ser Lys Leu Gln
                260                 265                 270

Thr Leu Ser Pro Ala Gln Leu Leu Glu Gly Lys Lys Phe Lys Cys Val
            275                 280                 285

Gly Asn His Ile Leu Gly Pro Glu Ser Gly Ala Ser Cys Val Val Lys
            290                 295                 300

Leu Ser Ser Pro Leu Leu Pro Ser Gln Pro Met Arg Thr Cys Phe Val
305                 310                 315                 320

Gly Gly Asn Val Thr Leu Thr Cys Glu Val Ser Gly Ala Asn Pro Pro
                325                 330                 335

Ala Arg Ile Gln Trp Leu Arg Asn Leu Thr Gln Pro Ala Ile Gln Pro
                340                 345                 350

Ser Ser His Tyr Ile Ile Thr Gln Gln Gly Gln Ser Ser Ser Leu Thr
            355                 360                 365

Ile His Asn Cys Ser Gln Asp Leu Asp Glu Gly Phe Tyr Tyr Cys Gln
            370                 375                 380

Ala Glu Asn Leu Val Gly Val Arg Ala Thr Asn Ile Trp Leu Ser Val
385                 390                 395                 400

Lys Glu Pro Leu Asn Ile Gly Gly Glu Pro Arg Gly Pro Thr Ile Lys
                405                 410                 415

Pro Cys Pro Pro Cys Lys Cys Pro Ala Pro Asn Leu Leu Gly Gly Pro
                420                 425                 430

Ser Val Phe Ile Phe Pro Pro Lys Ile Lys Asp Val Leu Met Ile Ser
            435                 440                 445

Leu Ser Pro Ile Val Thr Cys Val Val Val Asp Val Ser Glu Asp Asp
450                 455                 460

Pro Asp Val Gln Ile Ser Trp Phe Val Asn Asn Val Glu Val His Thr
465                 470                 475                 480

Ala Gln Thr Gln Thr His Arg Glu Asp Tyr Asn Ser Thr Leu Arg Val
            485                 490                 495

Val Ser Ala Leu Pro Ile Gln His Gln Asp Trp Met Ser Gly Lys Glu
            500                 505                 510

Phe Lys Cys Lys Val Asn Asn Lys Asp Leu Pro Ala Pro Ile Glu Arg
            515                 520                 525

Thr Ile Ser Lys Pro Lys Gly Ser Val Arg Ala Pro Gln Val Tyr Val
            530                 535                 540

Leu Pro Pro Pro Glu Glu Glu Met Thr Lys Lys Gln Val Thr Leu Thr
545                 550                 555                 560
```

```
Cys Met Val Thr Asp Phe Met Pro Glu Asp Ile Tyr Val Glu Trp Thr
                565                 570                 575

Asn Asn Gly Lys Thr Glu Leu Asn Tyr Lys Asn Thr Glu Pro Val Leu
            580                 585                 590

Asp Ser Asp Gly Ser Tyr Phe Met Tyr Ser Lys Leu Arg Val Glu Lys
        595                 600                 605

Lys Asn Trp Val Glu Arg Asn Ser Tyr Ser Cys Ser Val Val His Glu
    610                 615                 620

Gly Leu His Asn His His Thr Thr Lys Ser Phe Ser Arg Thr Pro Gly
625                 630                 635                 640

Lys

<210> SEQ ID NO 25
<211> LENGTH: 439
<212> TYPE: PRT
<213> ORGANISM: Artificial sequence
<220> FEATURE:
<223> OTHER INFORMATION: Synthetic polypeptide

<400> SEQUENCE: 25

Glu Leu Ala Pro Gln Ile Asp Gly Gln Thr Trp Ala Glu Arg Ala Leu
1               5                   10                  15

Arg Glu Asn Glu His His Ala Phe Thr Cys Arg Val Ala Gly Gly Ser
            20                  25                  30

Ala Thr Pro Arg Leu Ala Trp Tyr Leu Asp Gly Gln Leu Gln Glu Ala
        35                  40                  45

Thr Thr Ser Arg Leu Leu Ser Val Gly Gly Asp Ala Phe Ser Gly Gly
    50                  55                  60

Thr Ser Thr Phe Thr Val Thr Ala Gln Arg Ser Gln His Glu Leu Asn
65                  70                  75                  80

Cys Ser Leu Gln Asp Pro Gly Ser Gly Arg Pro Ala Asn Ala Ser Val
                85                  90                  95

Ile Leu Asn Val Gln Phe Lys Pro Glu Ile Ala Gln Val Gly Ala Lys
            100                 105                 110

Tyr Gln Glu Ala Gln Gly Pro Gly Leu Leu Val Val Leu Phe Ala Leu
        115                 120                 125

Val Arg Ala Asn Pro Pro Ala Asn Val Thr Trp Ile Asp Gln Asp Gly
    130                 135                 140

Pro Val Thr Val Asn Ala Ser Asp Phe Leu Val Leu Asp Ala Gln Asn
145                 150                 155                 160

Tyr Pro Trp Leu Thr Asn His Thr Val Gln Leu Gln Leu Arg Ser Leu
                165                 170                 175

Ala His Asn Leu Ser Val Val Ala Thr Asn Asp Val Gly Val Thr Ser
            180                 185                 190

Ala Ser Leu Pro Ala Pro Gly Leu Leu Ala Thr Arg Ile Glu Glu Pro
        195                 200                 205

Arg Gly Pro Thr Ile Lys Pro Cys Pro Pro Cys Lys Cys Pro Ala Pro
    210                 215                 220

Asn Leu Leu Gly Gly Pro Ser Val Phe Ile Phe Pro Pro Lys Ile Lys
225                 230                 235                 240

Asp Val Leu Met Ile Ser Leu Ser Pro Ile Val Thr Cys Val Val Val
                245                 250                 255

Asp Val Ser Glu Asp Asp Pro Asp Val Gln Ile Ser Trp Phe Val Asn
            260                 265                 270

Asn Val Glu Val His Thr Ala Gln Thr Gln Thr His Arg Glu Asp Tyr
```

```
            275                 280                 285
Asn Ser Thr Leu Arg Val Val Ser Ala Leu Pro Ile Gln His Gln Asp
    290                 295                 300

Trp Met Ser Gly Lys Glu Phe Lys Cys Lys Val Asn Asn Lys Asp Leu
305                 310                 315                 320

Pro Ala Pro Ile Glu Arg Thr Ile Ser Lys Pro Lys Gly Ser Val Arg
                325                 330                 335

Ala Pro Gln Val Tyr Val Leu Pro Pro Glu Glu Met Thr Lys
                340                 345                 350    Lys

Lys Gln Val Thr Leu Thr Cys Met Val Thr Asp Phe Met Pro Glu Asp
                355                 360                 365

Ile Tyr Val Glu Trp Thr Asn Asn Gly Lys Thr Glu Leu Asn Tyr Lys
            370                 375                 380

Asn Thr Glu Pro Val Leu Asp Ser Asp Gly Ser Tyr Phe Met Tyr Ser
385                 390                 395                 400

Lys Leu Arg Val Glu Lys Lys Asn Trp Val Glu Arg Asn Ser Tyr Ser
                405                 410                 415

Cys Ser Val Val His Glu Gly Leu His Asn His His Thr Thr Lys Ser
                420                 425                 430

Phe Ser Arg Thr Pro Gly Lys
            435

<210> SEQ ID NO 26
<211> LENGTH: 403
<212> TYPE: PRT
<213> ORGANISM: Artificial sequence
<220> FEATURE:
<223> OTHER INFORMATION: Synthetic polypeptide

<400> SEQUENCE: 26

Ile Gln Val Thr Val Pro Asp Pro Tyr His Val Val Ile Leu Phe Gln
1               5                   10                  15

Pro Val Thr Leu His Cys Thr Tyr Gln Met Ser Asn Thr Leu Thr Ala
                20                  25                  30

Pro Ile Val Ile Trp Lys Tyr Lys Ser Phe Cys Arg Asp Arg Val Ala
            35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Ala Thr Lys Gln Gly Asn Ala Val Thr
                85                  90                  95

Leu Gly Asp Tyr Tyr Gln Gly Arg Arg Ile Thr Ile Thr Gly Asn Ala
                100                 105                 110

Asp Leu Thr Phe Glu Gln Thr Ala Trp Gly Asp Ser Gly Val Tyr Tyr
            115                 120                 125

Cys Ser Val Val Ser Ala Gln Asp Leu Asp Gly Asn Asn Glu Ala Tyr
    130                 135                 140

Ala Glu Leu Ile Val Leu Gly Arg Thr Ser Glu Ala Pro Glu Leu Leu
145                 150                 155                 160

Pro Gly Phe Arg Ala Gly Pro Leu Glu Asp Glu Pro Arg Gly Pro Thr
                165                 170                 175

Ile Lys Pro Cys Pro Pro Cys Lys Cys Pro Ala Pro Asn Leu Leu Gly
            180                 185                 190

Gly Pro Ser Val Phe Ile Phe Pro Pro Lys Ile Lys Asp Val Leu Met
```

```
                195                 200                 205
Ile Ser Leu Ser Pro Ile Val Thr Cys Val Val Asp Val Ser Glu
    210                 215                 220

Asp Asp Pro Asp Val Gln Ile Ser Trp Phe Val Asn Asn Val Glu Val
225                 230                 235                 240

His Thr Ala Gln Thr Gln Thr His Arg Glu Asp Tyr Asn Ser Thr Leu
                245                 250                 255

Arg Val Val Ser Ala Leu Pro Ile Gln His Gln Asp Trp Met Ser Gly
            260                 265                 270

Lys Glu Phe Lys Cys Lys Val Asn Asn Lys Asp Leu Pro Ala Pro Ile
        275                 280                 285

Glu Arg Thr Ile Ser Lys Pro Lys Gly Ser Val Arg Ala Pro Gln Val
    290                 295                 300

Tyr Val Leu Pro Pro Glu Glu Glu Met Thr Lys Lys Gln Val Thr
305                 310                 315                 320

Leu Thr Cys Met Val Thr Asp Phe Met Pro Glu Asp Ile Tyr Val Glu
                325                 330                 335

Trp Thr Asn Asn Gly Lys Thr Glu Leu Asn Tyr Lys Asn Thr Glu Pro
            340                 345                 350

Val Leu Asp Ser Asp Gly Ser Tyr Phe Met Tyr Ser Lys Leu Arg Val
        355                 360                 365

Glu Lys Lys Asn Trp Val Glu Arg Asn Ser Tyr Ser Cys Ser Val Val
    370                 375                 380

His Glu Gly Leu His Asn His His Thr Thr Lys Ser Phe Ser Arg Thr
385                 390                 395                 400

Pro Gly Lys

<210> SEQ ID NO 27
<211> LENGTH: 233
<212> TYPE: PRT
<213> ORGANISM: Artificial sequence
<220> FEATURE:
<223> OTHER INFORMATION: Synthetic polypeptide

<400> SEQUENCE: 27

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160
```

```
Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 28
<211> LENGTH: 365
<212> TYPE: PRT
<213> ORGANISM: Artificial sequence
<220> FEATURE:
<223> OTHER INFORMATION: Synthetic polypeptide

<400> SEQUENCE: 28

```
Met Glu Leu Pro Leu Ser Gln Ala Thr Leu Arg His Thr Leu Leu Leu
1               5                   10                  15

Leu Pro Ala Leu Leu Ser Ser Gly Gln Gly Leu Ala Pro Gln Ile
            20                  25                  30

Asp Gly Gln Thr Trp Ala Glu Arg Ala Leu Arg Glu Asn Glu His His
        35                  40                  45

Ala Phe Thr Cys Arg Val Ala Gly Gly Ser Ala Thr Pro Arg Leu Ala
    50                  55                  60

Trp Tyr Leu Asp Gly Gln Leu Gln Glu Ala Thr Thr Ser Arg Leu Leu
65                  70                  75                  80

Ser Val Gly Gly Asp Ala Phe Ser Gly Gly Thr Ser Thr Phe Thr Val
                85                  90                  95

Thr Ala Gln Arg Ser Gln His Glu Leu Asn Cys Ser Leu Gln Asp Pro
            100                 105                 110

Gly Ser Gly Arg Pro Ala Asn Ala Ser Val Ile Leu Asn Val Gln Phe
        115                 120                 125

Lys Pro Glu Ile Ala Gln Val Gly Ala Lys Tyr Gln Glu Ala Gln Gly
    130                 135                 140

Pro Gly Leu Leu Val Val Leu Phe Ala Leu Val Arg Ala Asn Pro Pro
145                 150                 155                 160

Ala Asn Val Thr Trp Ile Asp Gln Asp Gly Pro Val Thr Val Asn Ala
                165                 170                 175

Ser Asp Phe Leu Val Leu Asp Ala Gln Asn Tyr Pro Trp Leu Thr Asn
            180                 185                 190

His Thr Val Gln Leu Gln Leu Arg Ser Leu Ala His Asn Leu Ser Val
        195                 200                 205

Val Ala Thr Asn Asp Val Gly Val Thr Ser Ala Ser Leu Pro Ala Pro
    210                 215                 220

Gly Leu Leu Ala Thr Arg Ile Glu Val Pro Leu Leu Gly Ile Val Val
225                 230                 235                 240

Ala Gly Gly Leu Ala Leu Gly Thr Leu Val Gly Phe Ser Thr Leu Val
                245                 250                 255

Ala Cys Leu Val Cys Arg Lys Glu Lys Lys Thr Lys Gly Pro Ser Arg
            260                 265                 270

Arg Pro Ser Leu Ile Ser Ser Asp Ser Asn Asn Leu Lys Leu Asn Asn
        275                 280                 285
```

```
Val Arg Leu Pro Arg Glu Asn Met Ser Leu Pro Ser Asn Leu Gln Leu
        290                 295                 300

Asn Asp Leu Thr Pro Asp Leu Arg Gly Lys Ala Thr Glu Arg Pro Met
305                 310                 315                 320

Ala Gln His Ser Ser Arg Pro Glu Leu Leu Glu Ala Glu Pro Gly Gly
                325                 330                 335

Leu Leu Thr Ser Arg Gly Phe Ile Arg Leu Pro Met Leu Gly Tyr Ile
                340                 345                 350

Tyr Arg Val Ser Ser Val Ser Ser Asp Glu Ile Trp Leu
                355                 360                 365

<210> SEQ ID NO 29
<211> LENGTH: 300
<212> TYPE: PRT
<213> ORGANISM: Artificial sequence
<220> FEATURE:
<223> OTHER INFORMATION: Synthetic polypeptide

<400> SEQUENCE: 29

Met Ala Val Val Phe Leu Leu Phe Leu Cys Gly His Ser Gln Ala
1               5                   10                  15

Val Ala Asp Ser Ile Gln Thr Ile Tyr Val Ala Ser Gly Glu Ser Val
                20                  25                  30

Glu Met Pro Cys Pro Ser Pro Pro Ser Leu Leu Gly Gly Gln Leu Leu
            35                  40                  45

Thr Trp Phe Arg Ser Pro Val Ala Gly Ser Ser Thr Ile Leu Val Ala
    50                  55                  60

Gln Val Gln Val Asp Lys Pro Val Ser Asp Leu Arg Lys Pro Glu Pro
65                  70                  75                  80

Asp Ser Arg Tyr Lys Leu Phe Gly Asn Tyr Ser Leu Trp Leu Glu Gly
                85                  90                  95

Ser Arg Asp Glu Asp Ala Gly Arg Tyr Trp Cys Thr Val Met Asp Gln
            100                 105                 110

Asn His Lys Tyr Gln Asn Trp Arg Val Tyr Asp Val Ser Val Leu Lys
        115                 120                 125

Gly Ser Gln Phe Ser Val Lys Ser Pro Asp Gly Pro Ser Cys Ala Ala
130                 135                 140

Leu Leu Cys Ser Val Val Pro Ala Arg Arg Leu Asp Ser Val Thr Trp
145                 150                 155                 160

Leu Glu Gly Arg Asn Thr Val Arg Gly His Ala Gln Tyr Phe Trp Gly
                165                 170                 175

Glu Gly Ala Ala Leu Leu Leu Val Cys Pro Thr Glu Gly Leu Pro Glu
            180                 185                 190

Thr Arg Ala Arg Arg Pro Arg Asn Ile Arg Cys Leu Leu Pro Gln Asn
        195                 200                 205

Lys Arg Phe Ser Phe Ser Leu Ala Ala Ala Ser Ala Glu Pro Ser Pro
210                 215                 220

Thr Val Cys Ala Thr Leu Pro Ser Trp Asp Val Pro Trp Ile Leu Val
225                 230                 235                 240

Leu Leu Phe Thr Ala Gly Gln Gly Val Thr Ile Ile Ala Leu Ser Ile
                245                 250                 255

Val Leu Trp Arg Arg Arg Arg Ala Gln Gly Ser Arg Asp Arg Glu Pro
            260                 265                 270

Ser Val Pro His Phe Lys Pro Glu Val Gln Val Tyr Glu Asn Ile His
        275                 280                 285
```

```
Leu Ala Arg Leu Ser Pro Pro Asn His Lys Thr Arg
        290                 295                 300
```

<210> SEQ ID NO 30
<211> LENGTH: 558
<212> TYPE: PRT
<213> ORGANISM: Artificial sequence
<220> FEATURE:
<223> OTHER INFORMATION: Synthetic polypeptide

<400> SEQUENCE: 30

```
Met Ala Gly Leu Arg Val Leu Leu Cys Leu Gly Ala Leu Leu Ala Arg
1               5                   10                  15

Gln Gly Ser Ala Gly Leu Gln Leu Leu Asn Pro Ser Arg Ala Asn
            20                  25                  30

Leu Ser Val Arg Pro Asn Ser Glu Val Leu Pro Gly Ile His Pro Asp
            35                  40                  45

Leu Glu Ala Val Ala Ile Gly Glu Val His Asp Asn Val Thr Leu Arg
    50                  55                  60

Cys Gly Ser Ala Ser Gly Ser Arg Gly Leu Val Thr Trp Tyr Arg Asn
65                  70                  75                  80

Asp Ser Glu Pro Ala Phe Leu Val Ser Phe Asn Ser Ser Leu Pro Pro
                85                  90                  95

Ala Ala Pro Arg Phe Ser Leu Glu Asp Ala Gly Ala Leu Arg Ile Glu
            100                 105                 110

Ala Leu Arg Leu Glu Asp Asp Gly Asn Tyr Thr Cys Gln Glu Val Leu
        115                 120                 125

Asn Glu Thr His Trp Phe Pro Val Arg Leu Arg Val Ala Ser Gly Pro
    130                 135                 140

Ala Tyr Val Glu Val Asn Ile Ser Ala Thr Gly Thr Leu Pro Asn Gly
145                 150                 155                 160

Thr Leu Tyr Ala Ala Arg Gly Ser Gln Val Asp Phe Asn Cys Cys Ser
                165                 170                 175

Ala Ala Gln Pro Pro Pro Glu Val Glu Trp Trp Ile Gln Thr His Ser
            180                 185                 190

Ile Pro Glu Phe Leu Gly Lys Asn Leu Ser Ala Asn Ser Phe Thr Leu
        195                 200                 205

Met Leu Met Ser Gln Asn Leu Gln Gly Asn Tyr Thr Cys Ser Ala Thr
    210                 215                 220

Asn Val Leu Ser Gly Arg Gln Arg Lys Val Thr Thr Glu Leu Leu Val
225                 230                 235                 240

Tyr Trp Pro Pro Pro Ser Ala Pro Gln Cys Ser Val Glu Val Ser Ser
                245                 250                 255

Glu Ser Thr Thr Leu Glu Leu Ala Cys Asn Trp Asp Gly Gly Tyr Pro
            260                 265                 270

Asp Pro Thr Phe Leu Trp Thr Glu Pro Gly Gly Thr Ile Met Gly
        275                 280                 285

Asn Ser Lys Leu Gln Thr Leu Ser Pro Ala Gln Leu Leu Glu Gly Lys
    290                 295                 300

Lys Phe Lys Cys Val Gly Asn His Ile Leu Gly Pro Glu Ser Gly Ala
305                 310                 315                 320

Ser Cys Val Val Lys Leu Ser Ser Pro Leu Leu Pro Ser Gln Pro Met
                325                 330                 335

Arg Thr Cys Phe Val Gly Gly Asn Val Thr Leu Thr Cys Glu Val Ser
            340                 345                 350
```

Gly Ala Asn Pro Pro Ala Arg Ile Gln Trp Leu Arg Asn Leu Thr Gln
                355                 360                 365

Pro Ala Ile Gln Pro Ser Ser His Tyr Ile Ile Thr Gln Gln Gly Gln
            370                 375                 380

Ser Ser Ser Leu Thr Ile His Asn Cys Ser Gln Asp Leu Asp Glu Gly
385                 390                 395                 400

Phe Tyr Tyr Cys Gln Ala Glu Asn Leu Val Gly Val Arg Ala Thr Asn
                405                 410                 415

Ile Trp Leu Ser Val Lys Glu Pro Leu Asn Ile Gly Ile Val Gly
            420                 425                 430

Thr Val Val Ser Leu Leu Leu Leu Gly Leu Ala Val Ser Gly Leu
                435                 440                 445

Thr Leu Tyr Tyr Ser Pro Ala Phe Trp Trp Lys Gly Gly Ser Thr Phe
    450                 455                 460

Arg Gly Gln Asp Met Gly Asp Val Met Val Leu Val Asp Ser Glu Glu
465                 470                 475                 480

Glu Glu Glu Glu Glu Glu Glu Glu Lys Glu Asp Val Ala Glu
                485                 490                 495

Glu Val Glu Gln Glu Thr Asn Glu Thr Glu Glu Leu Pro Lys Gly Ile
            500                 505                 510

Ser Lys His Gly His Ile His Arg Val Thr Ala Leu Val Asn Gly Asn
    515                 520                 525

Leu Asp Arg Met Gly Asn Gly Phe Gln Glu Phe Gln Asp Asp Ser Asp
    530                 535                 540

Gly Gln Gln Ser Gly Ile Val Gln Glu Asp Gly Lys Pro Val
545                 550                 555

<210> SEQ ID NO 31
<211> LENGTH: 594
<212> TYPE: PRT
<213> ORGANISM: Artificial sequence
<220> FEATURE:
<223> OTHER INFORMATION: Synthetic polypeptide

<400> SEQUENCE: 31

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
                20                  25                  30

Arg Ala Ser Ala Ile Gln Val Thr Val Pro Asp Pro Tyr His Val Val
            35                  40                  45

Ile Leu Phe Gln Pro Val Thr Leu His Cys Thr Tyr Gln Met Ser Asn
50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

```
Gly Val Tyr Tyr Cys Ser Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
            195                 200                 205

Phe Val Val Val Cys Leu Ala Ser Leu Leu Phe Phe Leu Leu Leu
    210                 215                 220

Gly Ile Cys Trp Cys Gln Cys Cys Pro His Thr Cys Cys Cys Tyr Val
225                 230                 235                 240

Arg Cys Pro Cys Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270

Ser Ile Tyr Thr His Leu Ser Pro Ala Lys Thr Pro Pro Pro Pro
            275                 280                 285

Ala Met Ile Pro Met Arg Pro Pro Tyr Gly Tyr Pro Gly Asp Phe Asp
            290                 295                 300

Arg Thr Ser Ser Val Gly Gly His Ser Ser Gln Val Pro Leu Leu Arg
305                 310                 315                 320

Glu Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu
            340                 345                 350

Lys Glu Leu Ala Asn Phe Asp Pro Ser Arg Pro Gly Pro Pro Asn Gly
            355                 360                 365

Arg Val Glu Arg Ala Met Ser Glu Val Thr Ser Leu His Glu Asp Asp
370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Arg Ser Pro Arg Thr Trp Glu Gln
            405                 410                 415

Glu Pro Leu Gln Glu Gln Pro Arg Gly Gly Trp Gly Ser Gly Arg Pro
            420                 425                 430

Arg Ala Arg Ser Val Asp Ala Leu Asp Asp Ile Asn Arg Pro Gly Ser
            435                 440                 445

Thr Glu Ser Gly Arg Ser Ser Pro Ser Ser Gly Arg Arg Gly Arg
            450                 455                 460

Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
            485                 490                 495

Asp Leu Arg Ser Arg Asp Pro Arg Ala Asp Pro Arg Ser Arg Gln Arg
            500                 505                 510

Ser His Asp Pro Arg Asp Ala Gly Phe Arg Ser Arg Asp Pro Gln Tyr
            515                 520                 525

Asp Gly Arg Leu Leu Glu Glu Ala Leu Lys Lys Lys Gly Ala Gly Glu
            530                 535                 540

Arg Arg Arg Val Tyr Arg Glu Glu Glu Glu Glu Glu Glu Gly His
545                 550                 555                 560

Tyr Pro Pro Ala Pro Pro Pro Tyr Ser Glu Thr Asp Ser Gln Ala Ser
            565                 570                 575
```

Arg Glu Arg Arg Met Lys Lys Asn Leu Ala Leu Ser Arg Glu Ser Leu
            580                 585                 590

Val Val

<210> SEQ ID NO 32
<211> LENGTH: 575
<212> TYPE: PRT
<213> ORGANISM: Artificial sequence
<220> FEATURE:
<223> OTHER INFORMATION: Synthetic polypeptide

<400> SEQUENCE: 32

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Asp Trp Leu Phe Val Val
            180                 185                 190

Val Val Cys Leu Ala Ser Leu Leu Phe Phe Leu Leu Leu Gly Ile Cys
        195                 200                 205

Trp Cys Gln Cys Cys Pro His Thr Cys Cys Cys Tyr Val Arg Cys Pro
    210                 215                 220

Cys Cys Pro Asp Lys Cys Cys Cys Pro Glu Ala Leu Tyr Ala Ala Gly
225                 230                 235                 240

Lys Ala Ala Thr Ser Gly Val Pro Ser Ile Tyr Ala Pro Ser Ile Tyr
                245                 250                 255

Thr His Leu Ser Pro Ala Lys Thr Pro Pro Pro Pro Ala Met Ile
            260                 265                 270

Pro Met Arg Pro Pro Tyr Gly Tyr Pro Gly Asp Phe Asp Arg Thr Ser
        275                 280                 285

Ser Val Gly Gly His Ser Ser Gln Val Pro Leu Leu Arg Glu Val Asp
    290                 295                 300

Gly Ser Val Ser Ser Glu Val Arg Ser Gly Tyr Arg Ile Gln Ala Asn
305                 310                 315                 320

Gln Gln Asp Asp Ser Met Arg Val Leu Tyr Tyr Met Glu Lys Glu Leu
                325                 330                 335

Ala Asn Phe Asp Pro Ser Arg Pro Gly Pro Pro Asn Gly Arg Val Glu

```
                340               345               350
Arg Ala Met Ser Glu Val Thr Ser Leu His Glu Asp Asp Trp Arg Ser
                355               360               365
Arg Pro Ser Arg Ala Pro Ala Leu Thr Pro Ile Arg Asp Glu Glu Trp
            370               375               380
Asn Arg His Ser Pro Arg Ser Pro Arg Thr Trp Glu Gln Glu Pro Leu
385               390               395               400
Gln Glu Gln Pro Arg Gly Gly Trp Gly Ser Gly Arg Pro Arg Ala Arg
                405               410               415
Ser Val Asp Ala Leu Asp Asp Ile Asn Arg Pro Gly Ser Thr Glu Ser
                420               425               430
Gly Arg Ser Ser Pro Pro Ser Ser Gly Arg Arg Gly Arg Ala Tyr Ala
                435               440               445
Pro Pro Arg Ser Arg Ser Arg Asp Asp Leu Tyr Asp Pro Asp Asp Pro
            450               455               460
Arg Asp Leu Pro His Ser Arg Asp Pro His Tyr Tyr Asp Asp Leu Arg
465               470               475               480
Ser Arg Asp Pro Arg Ala Asp Pro Arg Ser Arg Gln Arg Ser His Asp
                485               490               495
Pro Arg Asp Ala Gly Phe Arg Ser Arg Asp Pro Gln Tyr Asp Gly Arg
            500               505               510
Leu Leu Glu Glu Ala Leu Lys Lys Gly Ala Gly Leu Arg Arg Arg
            515               520               525
Val Tyr Arg Glu Glu Glu Glu Glu Glu Glu Gly His Tyr Pro Pro
            530               535               540
Ala Pro Pro Pro Tyr Ser Glu Thr Asp Ser Gln Ala Ser Arg Glu Arg
545               550               555               560
Arg Met Lys Lys Asn Leu Ala Leu Ser Arg Glu Ser Leu Val Val
                565               570               575
```

<210> SEQ ID NO 33
<211> LENGTH: 654
<212> TYPE: DNA
<213> ORGANISM: Artificial sequence
<220> FEATURE:
<223> OTHER INFORMATION: Synthetic polynucleotide

<400> SEQUENCE: 33

```
gcagacaaca tgcaggccat ctatgtggcc ttggggagg cagtagagct gccatgtccc      60
tcaccaccta ctctacatgg ggacgaacac ctgtcatggt tctgcagccc tgcagcaggc    120
tccttcacca ccctggtagc ccaagtccaa gtgggcaggc cagccccaga ccctggaaaa    180
ccaggaaggg aatccaggct cagactgctg gggaactatt ctttgtggtt ggagggatcc    240
aaagaggaag atgccgggcg gtactggtgc gctgtgctag gtcagcacca caactaccag    300
aactggaggt gtacgacgt cttggtgctc aaaggatccc agttatctgc aaggggctgca    360
gatggatccc cctgcaatgt cctcctgtgc tctgtggtcc ccagcagacg catggactct    420
gtgacctggc aggaagggaa gggtcccgtg aggggccgtg ttcagtcctt ctggggcagt    480
gaggctgccc tgctcttggt gtgtcctggg gagggctttt ctgagcccag gagccgaaga    540
ccaagaatca tccgctgcct catgactcac aacaaggggg tcagctttag cctggcagcc    600
tccatcgatg cttctcctgc cctctgtgcc ccttccacgg gctgggacat gcct          654
```

<210> SEQ ID NO 34
<211> LENGTH: 1149

<212> TYPE: DNA
<213> ORGANISM: Artificial sequence
<220> FEATURE:
<223> OTHER INFORMATION: Synthetic polynucleotide

<400> SEQUENCE: 34

```
gttgtcattg gagaagttca tgagaatgtt actctgcact gtggcaacat ctcgggactg      60
aggggccagg tgacctggta ccggaacaac tcggagcctg tcttccttct ctcgtccaac     120
tctagcctcc ggccagctga gcctcgcttc tctctagtgg atgccacctc cctgcacatt     180
gaatcgctga gcctgggaga tgagggaatc tacacctgcc aggagatcct gaatgtgact     240
cagtggttcc aagtgtggct gcaggtggcc agcggcccct atcagattga ggtccacatc     300
gtggccaccg gcacactccc caacggcacc ctctatgcag ccaggggctc ccaggtggac     360
ttcagctgca cagcagctc caggccacca cccgtggttg aatggtggtt ccaggccctg     420
aattccagca gcgagtcctt tggccacaac ctgacagtca acttttctc actgttactg     480
atatcgccaa acctccaagg gaactacacc tgtttagcct tgaatcagct cagcaagaga     540
catcgaaagg tgaccaccga gctcctggtc tactatcccc ctccatcagc tccccagtgc     600
tgggcacaga tggcatcagg atcgttcatg ttgcagctta cctgtcgctg ggatggggga     660
taccctgacc ctgacttcct gtggatagaa gagccaggag gtgtaatcgt ggggaagtca     720
aagctggggg tggaaatgct gagcgagtcc cagctgtcgg atgcaagaa gttcaagtgt     780
gttacaagcc acatagttgg gccagagtcg ggcgccagct gcatggtgca gatcagggg     840
ccctcccttc tctctgagcc catgaagact tgcttcactg ggggcaatgt gacgcttaca     900
tgccaggtgt ctggggccta ccccctgcc aagatcctgt ggctgaggaa ccttacccag     960
cccgaggtga tcatccagcc tagcagccgc catctcatta cccaggatgg ccagaactcc    1020
accctcacta tccacaactg ctcccaggac ctggatgagg gctactacat ctgccgagct    1080
gacagccctg tagggtgag ggagatggaa atctggctga gtgtgaaaga acctttaaat     1140
atcgggggg                                                           1149
```

<210> SEQ ID NO 35
<211> LENGTH: 1320
<212> TYPE: DNA
<213> ORGANISM: Artificial sequence
<220> FEATURE:
<223> OTHER INFORMATION: Synthetic polynucleotide

<400> SEQUENCE: 35

```
atggccgcag gcggcagtgc gcccgagccc cgcgtcctcg tctgcctcgg ggcgctcctg      60
gccggctggg tcgccgtagg attggaggct gttgtcattg gagaagttca tgagaatgtt     120
actctgcact gtggcaacat ctcgggactg aggggccagg tgacctggta ccggaacaac     180
tcggagcctg tcttccttct ctcgtccaac tctagcctcc ggccagctga gcctcgcttc     240
tctctagtgg atgccacctc cctgcacatt gaatcgctga gcctgggaga tgagggaatc     300
tacacctgcc aggagatcct gaatgtgact cagtggttcc aagtgtggct gcaggtggcc     360
aatccccctc catcagctcc ccagtgctgg gcacagatgg catcaggatc gttcatgttg     420
cagcttacct gtcgctggga tgggggatac cctgaccctg acttcctgtg gatagaagag     480
ccaggaggtg taatcgtggg gaagtcaaag ctgggggtgg aaatgctgag cgagtcccag     540
ctgtcggatg caagaagtt caagtgtgtt acaagccaca tagttgggcc agagtcgggc     600
gccagctgca tggtgcagat caggggtccc tcccttctct ctgagcccat gaagacttgc     660
```

```
ttcactgggg gcaatgtgac gcttacatgc caggtgtctg gggcctaccc ccctgccaag    720
atcctgtggc tgaggaacct tacccagccc gaggtgatca tccagcctag cagccgccat    780
ctcattaccc aggatggcca gaactccacc ctcactatcc acaactgctc ccaggacctg    840
gatgagggct actacatctg ccgagctgac agccctgtag gggtgaggga gatggaaatc    900
tggctgagtg tgaaagaacc tttaaatatc gggggattg tgggaaccat tgtgagcctc     960
cttctgctgg gactgccat tatctcaggg cttctgttgc attatagccc tgtgttctgc    1020
tggaaagtag gaaacacttc caggggacaa acatggatg atgtcatggt tttggtggat    1080
tcagaagagg aagaggagga ggaggaggag gaggaggaag atgctgcagt aggggaacag    1140
gagggagcac gtgagagaga ggagttgcca aaagaaatac ctaagcagga ccacattcac    1200
agagtgaccg ccttggtgaa tgggaacata aacagatgg gaaatggatt ccaggatctt    1260
caagatgaca gcagtgagga gcaaagtgac attgttcaag aagaagacag gccagtctga    1320
```

<210> SEQ ID NO 36
<211> LENGTH: 846
<212> TYPE: DNA
<213> ORGANISM: Artificial sequence
<220> FEATURE:
<223> OTHER INFORMATION: Synthetic polynucleotide

<400> SEQUENCE: 36

```
gttgtcattg gagaagttca tgagaatgtt actctgcact gtggcaacat ctcgggactg     60
aggggccagg tgacctggta ccggaacaac tcggagcctg tcttccttct ctcgtccaac    120
tctagcctcc ggccagctga gcctcgcttc tctctagtgg atgccacctc cctgcacatt    180
gaatcgctga gcctgggaga tgagggaatc tacacctgcc aggagatcct gaatgtgact    240
cagtggttcc aagtgtggct gcaggtggcc aatcccccctc catcagctcc ccagtgctgg    300
gcacagatgg catcaggatc gttcatgttg cagcttacct gtcgctggga tggggatac    360 cctgaccctg acttcctgtg gatagaagag ccaggaggtg taatcgtggg gaagtcaaag    420
ctgggggtgg aaatgctgag cgagtcccag ctgtcggatg gcaagaagtt caagtgtgtt    480
acaagccaca tagttgggcc agagtcgggc gccagctgca tggtgcagat caggggtccc    540
tcccttctct ctgagcccat gaagacttgc ttcactgggg gcaatgtgac gcttacatgc    600
caggtgtctg gggcctaccc ccctgccaag atcctgtggc tgaggaacct tacccagccc    660
gaggtgatca tccagcctag cagccgccat ctcattaccc aggatggcca gaactccacc    720
ctcactatcc acaactgctc ccaggacctg gatgagggct actacatctg ccgagctgac    780
agccctgtag gggtgaggga gatggaaatc tggctgagtg tgaaagaacc tttaaatatc    840
gggggg                                                               846
```

<210> SEQ ID NO 37
<211> LENGTH: 612
<212> TYPE: DNA
<213> ORGANISM: Artificial sequence
<220> FEATURE:
<223> OTHER INFORMATION: Synthetic polynucleotide

<400> SEQUENCE: 37

```
gagttggagc cacaaataga tggtcagacc tgggctgagc gggcacttcg ggagaatgaa     60
cgccacgcct tcacctgccg ggtggcaggg gggcctggca ccccagatt ggcctggtat    120 ctggatggac agctgcagga ggccagcacc tcaagactgc tgagcgtggg aggggaggcc    180
ttctctggag gcaccagcac cttcactgtc actgcccatc gggcccagca tgagctcaac    240
```

```
tgctctctgc aggaccccag aagtggccga tcagccaacg cctctgtcat ccttaatgtg    300
caattcaagc cagagattgc ccaagtcggc gccaagtacc aggaagctca gggcccaggc    360
ctcctggttg tcctgtttgc cctggtgcgt gccaacccgc cggccaatgt cacctggatc    420
gaccaggatg ggccagtgac tgtcaacacc tctgacttcc tggtgctgga tgcgcagaac    480 taccccctggc tcaccaacca cacggtgcag ctgcagctcc gcagcctggc acacaacctc    540
tcggtggtgg ccaccaatga cgtgggtgtc accagtgcgt cgcttccagc cccagggctt    600
ctggctaccc gg    612
```

<210> SEQ ID NO 38
<211> LENGTH: 1101
<212> TYPE: DNA
<213> ORGANISM: Artificial sequence
<220> FEATURE:
<223> OTHER INFORMATION: Synthetic polynucleotide
<400> SEQUENCE: 38

```
atggcgctgc ctccaggccc agccgccctc cggcacacac tgctgctcct gccagccctt    60
ctgagctcag gttgggggga gttggagcca caaatagatg gtcagacctg ggctgagcgg    120
gcacttcggg agaatgaacg ccacgccttc acctgccggg tggcagggg gcctggcacc     180 cccagattgg cctggtatct ggatggacag ctgcaggagg ccagcacctc aagactgctg    240
agcgtgggag gggaggcctt ctctggaggc accagcacct tcactgtcac tgcccatcgg    300
gcccagcatg agctcaactg ctctctgcag gaccccagaa gtggccgatc agccaacgcc    360
tctgtcatcc ttaatgtgca attcaagcca gagattgccc aagtcggcgc caagtaccag    420
gaagctcagg gcccaggcct cctggttgtc ctgtttgccc tggtgcgtgc caacccgccg    480
gccaatgtca cctggatcga ccaggatggg ccagtgactg tcaacacctc tgacttcctg    540
gtgctggatg cgcagaacta ccccctggct caccaaccac acggtgcagct gcagctccgc    600 agcctggcac acaacctctc ggtggtggcc accaatgacg tgggtgtcac cagtgcgtcg    660
cttccagccc cagggcttct ggctacccgg gtggaagtgc cactgctggg cattgttgtg    720
gctgctgggc ttgcactggg cacccctcgtg gggttcagca ccttggtggc ctgcctggtc    780
tgcagaaaag agaagaaaac caaaggcccc tcccggcacc catctctgat atcaagtgac    840
tccaacaacc taaaactcaa caacgtgcgc ctgccacggg agaacatgtc cctcccgtcc    900
aaccttcagc tcaatgacct cactccagat tccagagcag tgaaaccagc agaccggcag    960
atggctcaga caacagccg ccagagcttc tggacccgg agcccggcgg cctcctcacc    1020
agccaaggtt tcatccgcct cccagtgctg ggctatatct atcgagtgtc cagcgtgagc    1080
agtgatgaga tctggctctg a                                            1101
```

<210> SEQ ID NO 39
<211> LENGTH: 232
<212> TYPE: PRT
<213> ORGANISM: Artificial sequence
<220> FEATURE:
<223> OTHER INFORMATION: Synthetic polypeptide
<400> SEQUENCE: 39

```
Met Ala Leu Pro Pro Gly Pro Ala Ala Leu Arg His Thr Leu Leu Leu
 1               5                  10                  15

Leu Pro Ala Leu Leu Ser Ser Gly Trp Gly Glu Leu Glu Pro Gln Ile
            20                  25                  30
```

```
Asp Gly Gln Thr Trp Ala Glu Arg Ala Leu Arg Glu Asn Glu Arg His
         35                  40                  45
Ala Phe Thr Cys Arg Val Ala Gly Gly Pro Gly Thr Pro Arg Leu Ala
 50                  55                  60
Trp Tyr Leu Asp Gly Gln Leu Gln Glu Ala Ser Thr Ser Arg Leu Leu
 65                  70                  75                  80
Ser Val Gly Gly Glu Ala Phe Ser Gly Thr Ser Thr Phe Thr Val
                 85                  90                  95
Thr Ala His Arg Ala Gln His Glu Leu Asn Cys Ser Leu Gln Asp Pro
                100                 105                 110
Arg Ser Gly Arg Ser Ala Asn Ala Ser Val Ile Leu Asn Val Gln Phe
            115                 120                 125
Lys Pro Glu Ile Ala Gln Val Gly Ala Lys Tyr Gln Glu Ala Gln Gly
        130                 135                 140
Pro Gly Leu Leu Val Val Leu Phe Ala Leu Val Arg Ala Asn Pro Pro
145                 150                 155                 160
Ala Asn Val Thr Trp Ile Asp Gln Asp Gly Pro Val Thr Val Asn Thr
                165                 170                 175
Ser Asp Phe Leu Val Leu Asp Ala Gln Asn Tyr Pro Trp Leu Thr Asn
                180                 185                 190
His Thr Val Gln Leu Gln Leu Arg Ser Leu Ala His Asn Leu Ser Val
            195                 200                 205
Val Ala Thr Asn Asp Val Gly Val Thr Ser Ala Ser Leu Pro Ala Pro
        210                 215                 220
Gly Leu Leu Ala Thr Arg Val Glu
225                 230

<210> SEQ ID NO 40
<211> LENGTH: 510
<212> TYPE: DNA
<213> ORGANISM: Artificial sequence
<220> FEATURE:
<223> OTHER INFORMATION: Synthetic polynucleotide

<400> SEQUENCE: 40
atccaggtga ccgtgtccaa cccctaccac gtggtgatcc tcttccagcc tgtgaccctg      60
ccctgtacct accagatgac ctcgaccccc acgcaaccca tcgtcatctg gaagtacaag     120
tctttctgcc gggaccgcat cgccgatgcc ttctccccgg ccagcgtcga caaccagctc     180
aatgcccagc tggcagccgg gaacccaggc tacaacccct acgtcgagtg ccaggacagc     240
gtgcgcaccg tcagggtcgt ggccaccaag cagggcaacg ctgtgaccct ggagagttac     300
taccagggcc ggaggattac catcaccgga atgctgacct gacctttga ccagacggcg     360 tgggggaca gtggtgtgta ttactgctcc gtggtctcag cccaggacct caggggaac      420 aatgaggcct acgcagagct catcgtcctt ggaggacct caggggtggc tgagctctta     480
cctggttttc aggcgggcc catagaagac                                        510

<210> SEQ ID NO 41
<211> LENGTH: 453
<212> TYPE: DNA
<213> ORGANISM: Artificial sequence
<220> FEATURE:
<223> OTHER INFORMATION: Synthetic polynucleotide

<400> SEQUENCE: 41
atccaggtga ccgtgtccaa cccctaccac gtggtgatcc tcttccagcc tgtgaccctg      60
```

```
ccctgtacct accagatgac ctcgacccccc acgcaaccca tcgtcatctg gaagtacaag    120
tctttctgcc gggaccgcat cgccgatgcc ttctccccgg ccagcgtcga caaccagctc    180
aatgcccagc tggcagccgg aacccaggc tacaacccct acgtcgagtg ccaggacagc     240
gtgcgcaccg tcagggtcgt ggccaccaag cagggcaacg ctgtgaccct gggagattac    300
taccagggcc ggaggattac catcaccgga atgctgacc tgacctttga ccagacggcg     360
tgggggaca gtggtgtgta ttactgctcc gtggtctcag cccaggacct caggggaac      420
aatgaggcct acgcagagct catcgtcctt gac                                 453

<210> SEQ ID NO 42
<211> LENGTH: 1599
<212> TYPE: DNA
<213> ORGANISM: Artificial sequence
<220> FEATURE:
<223> OTHER INFORMATION: Synthetic polynucleotide

<400> SEQUENCE: 42
atggcgctgt tggccggcgg gctctccaga gggctgggct cccacccggc cgccgcaggc     60
cgggacgcgg tcgtcttcgt gtggcttctg cttagcacct ggtgcacagc tcctgccagg    120
gccatccagg tgaccgtgtc caaccccctac acgtggtga tcctcttcca gcctgtgacc    180
ctgcccctgta cctaccagat gacctcgacc cccacgcaac ccatcgtcat ctggaagtac   240
aagtcttttct gccgggaccg catcgccgat gccttctccc cggccagcgt cgacaaccag   300
ctcaatgccc agctggcagc cgggaaccca ggctacaacc cctacgtcga gtgccaggac   360
agcgtgcgca ccgtcagggt cgtggccacc aagcagggca acgctgtgac cctgggagat   420
tactaccagg gccggaggat taccatcacc ggaaatgctg acctgacctt tgaccagacg   480
gcgtgggggg acagtggtgt gtattactgc tccgtggtct cagcccagga cctcagggg    540
aacaatgagg cctacgcaga gctcatcgtc cttgtgtatg ccgccggcaa agcagccacc   600
tcaggtgttc ccagcattta tgcccccagc acctatgccc acctgtctcc cgccaagacc   660
ccaccccccac cagctatgat tcccatgggc cctgcctaca acgggtaccc tggaggatac   720
cctggagacg ttgacaggag tagctcagct ggtggccaag gctcctatgt acccctgctt   780
cgggacacgg acagcagtgt ggcctctgaa gtccgcagtg gctacaggat tcaggccagc   840
cagcaggacg actccatgcg ggtcctgtac tacatggaga aggagctggc caacttcgac   900
ccttctcgac ctggcccccc cagtggccgt gtggagcggg ccatgagtga agtcacctcc   960
ctccacgagg acgactggcg atctcggcct tccgggggcc ctgccctcac ccgatccgg   1020
gatgaggagt ggggtggcca ctcccccgg agtcccaggg gatgggacca ggagcccgcc   1080
agggagcagg caggcgggg ctggcggcc aggcggcccc gggcccgctc cgtgacgcc    1140
ctggacgacc tcacccccgcc gagcaccgcc gagtcaggga gcaggtctcc cacgagtaat   1200
ggtgggagaa gccggggccta catgccccgg cggagccgca gccggacgga cctctatgac   1260
caagacgact cgagggactt cccacgctcc cgggacccccc actacgacga cttcaggtct   1320
cgggagcgcc ctcctgccga ccccaggtcc caccaccacc gtacccggga ccctcgggac   1380
aacggctcca ggtccgggga cctccccctat gatgggcggc tactggagga ggctgtgagg   1440
aagaagggt cggaggagag gaggagaccc cacaaggagg aggaggaaga ggcctactac   1500
ccgcccgcgc cgccccgta ctcggagacc gactcgcagg cgtcccgaga gcgcaggctc   1560
aagaagaact ggccctgag tcgggaaagt ttagtcgtc                          1599
```

<210> SEQ ID NO 43
<211> LENGTH: 1596
<212> TYPE: DNA
<213> ORGANISM: Artificial sequence
<220> FEATURE:
<223> OTHER INFORMATION: Synthetic polynucleotide

<400> SEQUENCE: 43

| | |
|---|---|
| atggcgctgt tggccggcgg gctctccaga gggctgggct cccacccggc cgccgcaggc | 60 |
| cgggacgcgg tcgtcttcgt gtggcttctg cttagcacct ggtgcacagc tcctgccagg | 120 |
| gccatccagg tgaccgtgtc caacccctac acgtggtga tcctcttcca gcctgtgacc | 180 |
| ctgccctgta cctaccagat gacctcgacc cccacgcaac ccatcgtcat ctggaagtac | 240 |
| aagtctttct gccgggaccg catcgccgat gccttctccc cggccagcgt cgacaaccag | 300 |
| ctcaatgccc agctggcagc cgggaaccca ggctacaacc cctacgtcga gtgccaggac | 360 |
| agcgtgcgca ccgtcagggt cgtggccacc aagcagggca cgctgtgac cctgggagat | 420 |
| tactaccagg gccggaggat taccatcacc ggaaatgctg acctgacctt tgaccagacg | 480 |
| gcgtgggggg acagtggtgt gtattactgc tccgtggtct cagcccagga cctccagggg | 540 |
| aacaatgagg cctacgcaga gctcatcgtc cttgtgtatg ccgccggcaa agcagccacc | 600 |
| tcaggtgttc ccagcattta tgccccccagc acctatgccc acctgtctcc cgccaagacc | 660 |
| ccaccccac cagctatgat tcccatgggc cctgcctaca cgggtaccc tggaggatac | 720 |
| cctggagacg ttgacaggag tagctcagct ggtggccaag gctcctatgt accccctgctt | 780 |
| cgggacacgg acagcagtgt ggcctctgtc cgcagtggct acaggattca ggccagccag | 840 |
| caggacgact ccatgcgggt cctgtactac atggagaagg agctggccaa cttcgaccct | 900 |
| tctcgacctg ccccccccag tggccgtgtg gagcgggcca tgagtgaagt cacctcccctc | 960 |
| cacgaggacg actggcgatc tcggccttcc cggggccctg ccctcacccc gatccgggat | 1020 |
| gaggagtggg gtggccactc ccccccggagt cccaggggat gggaccagga gcccgccagg | 1080 |
| gagcaggcag gcggggggctg gcgggccagg cggccccggg cccgctccgt ggacgccctg | 1140 |
| gacgacctca ccccgccgag caccgccgag tcagggagca ggtctcccac gagtaatggt | 1200 |
| gggagaagcc gggcctacat gccccccgcgg agccgcagcc gggacgacct ctatgaccaa | 1260 |
| gacgactcga gggacttccc acgctcccgg gaccccact acgacgactt caggtctcgg | 1320 |
| gagcgccctc ctgccgaccc caggtccac caccaccgta cccgggaccc tcgggacaac | 1380 |
| ggctccaggt ccggggacct cccctatgat gggcggctac tggaggaggc tgtgaggaag | 1440 |
| aaggggtcgg aggagaggag gagacccac aaggaggagg aggaagaggc ctactacccg | 1500 |
| cccgcgccgc ccccgtactc ggagaccgac tcgcaggcgt cccgagagcg caggctcaag | 1560 |
| aagaacttgg ccctgagtcg ggaaagttta gtcgtc | 1596 |

<210> SEQ ID NO 44
<211> LENGTH: 1473
<212> TYPE: DNA
<213> ORGANISM: Artificial sequence
<220> FEATURE:
<223> OTHER INFORMATION: Synthetic polynucleotide

<400> SEQUENCE: 44

| | |
|---|---|
| atccaggtga ccgtgtccaa cccctaccac gtggtgatcc tcttccagcc tgtgaccctg | 60 |
| ccctgtacct accagatgac ctcgaccccc acgcaaccca tcgtcatctg gaagtacaag | 120 |
| tctttctgcc gggaccgcat cgccgatgcc ttctccccgg ccagcgtcga caaccagctc | 180 |

| | |
|---|---|
| aatgcccagc tggcagccgg gaacccaggc tacaaccect acgtcgagtg ccaggacagc | 240 |
| gtgcgcaccg tcagggtcgt ggccaccaag cagggcaacg ctgtgaccct gggagattac | 300 |
| taccagggcc ggaggattac catcaccgga aatgctgacc tgacctttga ccagacggcg | 360 |
| tggggggaca gtggtgtgta ttactgctcc gtggtctcag cccaggacct ccaggggaac | 420 |
| aatgaggcct acgcagagct catcgtcctt gtgtatgccg ccggcaaagc agccacctca | 480 |
| ggtgttccca gcatttatgc ccccagcacc tatgcccacc tgtctcccgc caagacccca | 540 |
| cccccaccag ctatgattcc catgggccct gcctacaacg ggtaccctgg aggatacect | 600 |
| ggagacgttg acaggagtag ctcagctggt ggccaaggct cctatgtacc cctgcttcgg | 660 |
| gacacggaca gcagtgtggc ctctgtccgc agtggctaca ggattcaggc cagcagcag | 720 |
| gacgactcca tgcgggtcct gtactacatg gagaaggagc tggccaactt cgacccttct | 780 |
| cgacctggcc cccccagtgg ccgtgtggag cgggccatga gtgaagtcac ctccctccac | 840 |
| gaggacgact ggcgatctcg gccttcccgg ggccctgccc tcaccccgat ccgggatgag | 900 |
| gagtgggggtg gccactcccc ccggagtccc agggatggg accaggagcc cgccaggag | 960 |
| caggcaggcg ggggctggcg ggccaggcgg cccegggccc gctccgtgga cgccctggac | 1020 |
| gacctcaccc cgccgagcac cgccgagtca gggagcaggt ctcccacgag taatggtggg | 1080 |
| agaagccggg cctacatgcc cccgcggagc cgcagccggg acgacctcta tgaccaagac | 1140 |
| gactcgaggg acttcccacg ctcccgggac ccccactacg acgacttcag gtctcgggag | 1200 |
| cgccctcctg ccgaccccag gtcccaccac caccgtaccc gggaccctcg ggacaacggc | 1260 |
| tccaggtccg ggaccctccc ctatgatggg cggctactgg aggaggctgt gaggaagaag | 1320 |
| gggtcggagg agaggaggag accccacaag gaggaggagg aagaggccta ctacccgccc | 1380 |
| gcgccgcccc cgtactcgga gaccgactcg caggcgtccc gagagcgcag gctcaagaag | 1440 |
| aacttggccc tgagtcggga aagtttagtc gtc | 1473 |

<210> SEQ ID NO 45
<211> LENGTH: 1479
<212> TYPE: DNA
<213> ORGANISM: Artificial sequence
<220> FEATURE:
<223> OTHER INFORMATION: Synthetic polynucleotide

<400> SEQUENCE: 45

| | |
|---|---|
| atggcgctgt tggccggcgg gctctccaga gggctgggct cccacccggc cgccgcaggc | 60 |
| cgggacgcgg tcgtcttcgt gtggcttctg cttagcacct ggtgcacagc tcctgccagg | 120 |
| gccatccagg tgaccgtgtc caaccectac cacgtggtga tcctcttcca gcctgtgacc | 180 |
| ctgccctgta cctaccagat gacctcgacc cccacgcaac ccatcgtcat ctggaagtac | 240 |
| aagtctttct gccgggaccg catcgccgat gccttctccc cggccagcgt cgacaaccag | 300 |
| ctcaatgccc agctggcagc cgggaaccca ggctacaacc cctacgtcga gtgccaggac | 360 |
| agcgtgcgca ccgtcagggt cgtggccacc aagcagggca cgctgtgacc ctgggagat | 420 |
| tactaccagg gccggaggat taccatcacc ggaatgtatg ccgccggcaa agcagccacc | 480 |
| tcaggtgttc ccagcattta tgcccccagc acctatgccc acctgtctcc cgccaagacc | 540 |
| ccaccccac cagctatgat tcccatgggc cctgcctaca cgggtaccc tggaggatac | 600 |
| cctggagacg ttgacaggag tagctcagct ggtggccaag gctcctatgt acccctgctt | 660 |
| cgggacacgg acagcagtgt ggcctctgtg agtccgcagtg gctacaggat tcaggccagc | 720 |
| cagcaggacg actccatgcg ggtcctgtac tacatggaga aggagctggc caacttcgac | 780 |

```
ccttctcgac ctggccccc cagtggccgt gtggagcggg ccatgagtga agtcacctcc      840
ctccacgagg acgactggcg atctcggcct tcccggggcc ctgccctcac ccgatccgg      900 gatgaggagt ggggtggcca ctcccccgg agtcccaggg gatgggacca ggagcccgcc      960
agggagcagg caggcggggg ctggcgggcc aggcggcccc gggcccgctc cgtggacgcc     1020
ctggacgacc tcaccccgcc gagcaccgcc gagtcaggga gcaggtctcc cacgagtaat     1080
ggtgggagaa gccgggccta catgccccg cggagccgca gccggacga cctctatgac       1140 caagacgact cgagggactt cccacgctcc cgggaccccc actacgacga cttcaggtct     1200
cgggagcgcc ctcctgccga ccccaggtcc caccaccacc gtacccggga ccctcgggac     1260
aacggctcca ggtccgggga cctcccctat gatgggcggc tactggagga ggctgtgagg     1320 aagaagggt cggaggagag gaggagaccc cacaaggagg aggaggaaga ggcctactac      1380
ccgcccgcgc cgcccccgta ctcggagacc gactcgcagg cgtcccgaga gcgcaggctc     1440
aagaagaact tggccctgag tcgggaaagt ttagtcgtc                            1479

<210> SEQ ID NO 46
<211> LENGTH: 1656
<212> TYPE: DNA
<213> ORGANISM: Artificial sequence
<220> FEATURE:
<223> OTHER INFORMATION: Synthetic polynucleotide

<400> SEQUENCE: 46
atggcgctgt tggccggcgg gctctccaga gggctgggct cccacccggc cgccgcaggc       60
cgggacgcgg tcgtcttcgt gtggcttctg cttagcacct ggtgcacagc tcctgccagg     120
gccatccagg tgaccgtgtc caaccccctac cacgtggtga tcctcttcca gcctgtgacc     180
ctgccctgta cctaccagat gacctcgacc cccacgcaac ccatcgtcat ctggaagtac     240
aagtctttct gccgggaccg catcgccgat gccttctccc cggccagcgt cgacaaccag     300
ctcaatgccc agctggcagc cgggaaccca ggctacaacc cctacgtcga gtgccaggac     360
agcgtgcgca ccgtcaggg tcgtggccacc aagcagggca acgctgtgac cctgggagat     420
tactaccagg gccggaggat taccatcacc ggaaatgctg acctgacctt tgaccagacg     480
gcgtgggggg acagtggtgt gtattactgc tccgtggtct cagcccagga cctccagggg     540
aacaatgagg cctacgcaga gctcatcgtc cttggggaga cctcaggggt ggctgagctc     600
ttacctggtt tcaggcgggg gcccatagaa gtgtatgccg ccggcaaagc agccacctca     660
ggtgttccca gcatttatgc ccccagcacc tatgcccacc tgtctcccgc caagacccca     720
cccccaccag ctatgattcc catgggccct gcctacaacg gtaccctgg aggatacccc     780 ggagacgttg acaggagtag ctcagctggt ggccaaggct cctatgtacc cctgcttcgg     840
gacacggaca gcagtgtggc ctctgaagtc cgcagtggct acaggattca ggccagccag     900
caggacgact ccatgcgggt cctgtactac atgagaagg agctggccaa cttcgaccct      960
tctcgacctg gccccccag tggccgtgtg gagcgggcca tgagtgaagt cacctccctc     1020
cacgaggacg actggcgatc tcggccttcc cggggcctg ccctcacccc gatccgggat     1080
gaggagtggg gtgccactc cccccggagt cccagggat gggaccagga gcccgccagg     1140
gagcaggcag gcgggggctg gcgggccagg cggcccggg cccgctccgt ggacgccctg     1200
gacgacctca ccccgccgag caccgccgag tcagggagca ggtctcccac gagtaatggt     1260
gggagaagcc gggcctacat gccccgcgg agccgcagcc gggacgacct ctatgaccaa     1320
```

```
gacgactcga gggacttccc acgctcccgg accccccact acgacgactt caggtctcgg    1380
gagcgccctc ctgccgaccc caggtccac caccaccgta cccggaccc tcgggacaac     1440 ggctccaggt ccggggacct cccctatgat gggcggctac tggaggaggc tgtgaggaag    1500
aaggggtcgg aggagaggag gagacccac aaggaggagg aggaagaggc ctactacccg    1560
cccgcgccgc ccccgtactc ggagaccgac tcgcaggcgt cccgagagcg caggctcaag    1620
aagaacttgg ccctgagtcg ggaaagttta gtcgtc                              1656
```

<210> SEQ ID NO 47
<211> LENGTH: 492
<212> TYPE: PRT
<213> ORGANISM: Artificial sequence
<220> FEATURE:
<223> OTHER INFORMATION: Synthetic polypeptide

<400> SEQUENCE: 47

```
Ile Gln Val Thr Val Ser Asn Pro Tyr His Val Ile Leu Phe Gln
 1               5                  10                  15

Pro Val Thr Leu Pro Cys Thr Tyr Gln Met Thr Ser Thr Pro Thr Gln
             20                  25                  30

Pro Ile Val Ile Trp Lys Tyr Lys Ser Phe Cys Arg Asp Arg Ile Ala
         35                  40                  45

Asp Ala Phe Ser Pro Ala Ser Val Asp Asn Gln Leu Asn Ala Gln Leu
     50                  55                  60

Ala Ala Gly Asn Pro Gly Tyr Asn Pro Tyr Val Glu Cys Gln Asp Ser
 65                  70                  75                  80

Val Arg Thr Val Arg Val Ala Thr Lys Gln Gly Asn Ala Val Thr
                 85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
    130                 135                 140

Ala Glu Leu Ile Val Leu Val Tyr Ala Ala Gly Lys Ala Ala Thr Ser
145                 150                 155                 160

Gly Val Pro Ser Ile Tyr Ala Pro Ser Thr Tyr Ala His Leu Ser Pro
                165                 170                 175

Ala Lys Thr Pro Pro Pro Ala Met Ile Pro Met Gly Pro Ala Tyr
            180                 185                 190

Asn Gly Tyr Pro Gly Gly Tyr Pro Gly Asp Val Asp Arg Ser Ser Ser
        195                 200                 205

Ala Gly Gly Gln Gly Ser Tyr Val Pro Leu Leu Arg Asp Thr Asp Ser
    210                 215                 220

Ser Val Ala Ser Glu Val Arg Ser Gly Tyr Arg Ile Gln Ala Ser Gln
225                 230                 235                 240

Gln Asp Asp Ser Met Arg Val Leu Tyr Tyr Met Glu Lys Glu Leu Ala
                245                 250                 255

Asn Phe Asp Pro Ser Arg Pro Gly Pro Pro Ser Gly Arg Val Glu Arg
            260                 265                 270

Ala Met Ser Glu Val Thr Ser Leu His Glu Asp Asp Trp Arg Ser Arg
        275                 280                 285

Pro Ser Arg Gly Pro Ala Leu Thr Pro Ile Arg Asp Glu Glu Trp Gly
    290                 295                 300
```

Gly His Ser Pro Arg Ser Pro Arg Gly Trp Asp Gln Glu Pro Ala Arg
305                 310                 315                 320

Glu Gln Ala Gly Gly Trp Arg Ala Arg Arg Pro Arg Ala Arg Ser
                325                 330                 335

Val Asp Ala Leu Asp Asp Leu Thr Pro Pro Ser Thr Ala Glu Ser Gly
                340                 345                 350

Ser Arg Ser Pro Thr Ser Asn Gly Gly Arg Ser Arg Ala Tyr Met Pro
                355                 360                 365

Pro Arg Ser Arg Ser Arg Asp Leu Tyr Asp Gln Asp Ser Arg
    370                 375                 380

Asp Phe Pro Arg Ser Arg Asp Pro His Tyr Asp Asp Phe Arg Ser Arg
385                 390                 395                 400

Glu Arg Pro Pro Ala Asp Pro Arg Ser His His His Arg Thr Arg Asp
                405                 410                 415

Pro Arg Asp Asn Gly Ser Arg Ser Gly Asp Leu Pro Tyr Asp Gly Arg
                420                 425                 430

Leu Leu Glu Glu Ala Val Arg Lys Lys Gly Ser Glu Arg Arg Arg
                435                 440                 445

Pro His Lys Glu Glu Glu Glu Ala Tyr Tyr Pro Pro Ala Pro Pro
    450                 455                 460

Pro Tyr Ser Glu Thr Asp Ser Gln Ala Ser Arg Glu Arg Arg Leu Lys
465                 470                 475                 480

Lys Asn Leu Ala Leu Ser Arg Glu Ser Leu Val Val
                485                 490

<210> SEQ ID NO 48
<211> LENGTH: 491
<212> TYPE: PRT
<213> ORGANISM: Artificial sequence
<220> FEATURE:
<223> OTHER INFORMATION: Synthetic polypeptide

<400> SEQUENCE: 48

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
                20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Asn Ala
                100                 105                 110

Asp Leu Thr Phe Asp Gln Thr Ala Trp Gly Asp Ser Gly Val Tyr Tyr
            115                 120                 125

Cys Ser Val Val Ser Ala Gln Asp Leu Gln Gly Asn Asn Glu Ala Tyr
    130                 135                 140

Ala Glu Leu Ile Val Leu Val Tyr Ala Ala Gly Lys Ala Ala Thr Ser
145                 150                 155                 160

Gly Val Pro Ser Ile Tyr Ala Pro Ser Thr Tyr Ala His Leu Ser Pro
                165                 170                 175

Ala Lys Thr Pro Pro Pro Ala Met Ile Pro Met Gly Pro Ala Tyr
            180                 185                 190

Asn Gly Tyr Pro Gly Gly Tyr Pro Gly Asp Val Asp Arg Ser Ser Ser
        195                 200                 205

Ala Gly Gly Gln Gly Ser Tyr Val Pro Leu Leu Arg Asp Thr Asp Ser
210                 215                 220

Ser Val Ala Ser Val Arg Ser Gly Tyr Arg Ile Gln Ala Ser Gln Gln
225                 230                 235                 240

Asp Asp Ser Met Arg Val Leu Tyr Tyr Met Glu Lys Glu Leu Ala Asn
            245                 250                 255

Phe Asp Pro Ser Arg Pro Gly Pro Pro Ser Gly Arg Val Glu Arg Ala
            260                 265                 270

Met Ser Glu Val Thr Ser Leu His Glu Asp Asp Trp Arg Ser Arg Pro
            275                 280                 285

Ser Arg Gly Pro Ala Leu Thr Pro Ile Arg Asp Glu Glu Trp Gly Gly
            290                 295                 300

His Ser Pro Arg Ser Pro Arg Gly Trp Asp Gln Glu Pro Ala Arg Glu
305                 310                 315                 320

Gln Ala Gly Gly Gly Trp Arg Ala Arg Arg Pro Arg Ala Arg Ser Val
                    325                 330                 335

Asp Ala Leu Asp Asp Leu Thr Pro Pro Ser Thr Ala Glu Ser Gly Ser
            340                 345                 350

Arg Ser Pro Thr Ser Asn Gly Gly Arg Ser Arg Ala Tyr Met Pro Pro
            355                 360                 365

Arg Ser Arg Ser Arg Asp Asp Leu Tyr Asp Gln Asp Asp Ser Arg Asp
        370                 375                 380

Phe Pro Arg Ser Arg Asp Pro His Tyr Asp Asp Phe Arg Ser Arg Glu
385                 390                 395                 400

Arg Pro Pro Ala Asp Pro Arg Ser His His His Arg Thr Arg Asp Pro
            405                 410                 415

Arg Asp Asn Gly Ser Arg Ser Gly Asp Leu Pro Tyr Asp Gly Arg Leu
            420                 425                 430

Leu Glu Glu Ala Val Arg Lys Lys Gly Ser Glu Glu Arg Arg Arg Pro
            435                 440                 445

His Lys Glu Glu Glu Glu Ala Tyr Tyr Pro Pro Ala Pro Pro Pro
    450                 455                 460

Tyr Ser Glu Thr Asp Ser Gln Ala Ser Arg Glu Arg Leu Lys Lys
465                 470                 475                 480

Asn Leu Ala Leu Ser Arg Glu Ser Leu Val Val
            485                 490

<210> SEQ ID NO 49
<211> LENGTH: 452
<212> TYPE: PRT
<213> ORGANISM: Artificial sequence
<220> FEATURE:
<223> OTHER INFORMATION: Synthetic polypeptide

<400> SEQUENCE: 49

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
        35                  40                  45

```
Asp Ala Phe Ser Pro Ala Ser Val Asp Asn Gln Leu Asn Ala Gln Leu
 50                  55                  60

Ala Ala Gly Asn Pro Gly Tyr Asn Pro Tyr Val Glu Cys Gln Asp Ser
 65                  70                  75                  80

Val Arg Thr Val Arg Val Ala Thr Lys Gln Gly Asn Ala Val Thr
                 85                  90                  95

Leu Gly Asp Tyr Tyr Gln Gly Arg Arg Ile Thr Ile Thr Gly Met Tyr
             100                 105                 110

Ala Ala Gly Lys Ala Ala Thr Ser Gly Val Pro Ser Ile Tyr Ala Pro
             115                 120                 125

Ser Thr Tyr Ala His Leu Ser Pro Ala Lys Thr Pro Pro Pro Ala
             130                 135                 140

Met Ile Pro Met Gly Pro Ala Tyr Asn Gly Tyr Pro Gly Gly Tyr Pro
145                 150                 155                 160

Gly Asp Val Asp Arg Ser Ser Ala Gly Gln Gly Ser Tyr Val
                 165                 170                 175

Pro Leu Leu Arg Asp Thr Asp Ser Ser Val Ala Ser Glu Val Arg Ser
             180                 185                 190

Gly Tyr Arg Ile Gln Ala Ser Gln Gln Asp Ser Met Arg Val Leu
             195                 200                 205

Tyr Tyr Met Glu Lys Glu Leu Ala Asn Phe Asp Pro Ser Arg Pro Gly
210                 215                 220

Pro Pro Ser Gly Arg Val Glu Arg Ala Met Ser Glu Val Thr Ser Leu
225                 230                 235                 240

His Glu Asp Asp Trp Arg Ser Arg Pro Ser Arg Gly Pro Ala Leu Thr
                 245                 250                 255

Pro Ile Arg Asp Glu Glu Trp Gly Gly His Ser Pro Arg Ser Pro Arg
                 260                 265                 270

Gly Trp Asp Gln Glu Pro Ala Arg Glu Gln Ala Gly Gly Trp Arg
             275                 280                 285

Ala Arg Arg Pro Arg Ala Arg Ser Val Asp Ala Leu Asp Asp Leu Thr
             290                 295                 300

Pro Pro Ser Thr Ala Glu Ser Gly Ser Arg Ser Pro Thr Ser Asn Gly
305                 310                 315                 320

Gly Arg Ser Arg Ala Tyr Met Pro Pro Arg Ser Arg Ser Arg Asp Asp
                 325                 330                 335

Leu Tyr Asp Gln Asp Asp Ser Arg Asp Phe Pro Arg Ser Arg Asp Pro
             340                 345                 350

His Tyr Asp Asp Phe Arg Ser Arg Glu Arg Pro Ala Asp Pro Arg
             355                 360                 365

Ser His His His Arg Thr Arg Asp Pro Arg Asp Asn Gly Ser Arg Ser
             370                 375                 380

Gly Asp Leu Pro Tyr Asp Gly Arg Leu Leu Glu Glu Ala Val Arg Lys
385                 390                 395                 400

Lys Gly Ser Glu Glu Arg Arg Pro His Lys Glu Glu Glu Glu
                 405                 410                 415

Ala Tyr Tyr Pro Pro Ala Pro Pro Tyr Ser Glu Thr Asp Ser Gln
                 420                 425                 430

Ala Ser Arg Glu Arg Arg Leu Lys Lys Asn Leu Ala Leu Ser Arg Glu
             435                 440                 445

Ser Leu Val Val
450
```

```
<210> SEQ ID NO 50
<211> LENGTH: 511
<212> TYPE: PRT
<213> ORGANISM: Artificial sequence
<220> FEATURE:
<223> OTHER INFORMATION: Synthetic polypeptide

<400> SEQUENCE: 50

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
        35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
    130                 135                 140

Ala Glu Leu Ile Val Leu Gly Arg Thr Ser Gly Val Ala Glu Leu Leu
145                 150                 155                 160

Pro Gly Phe Gln Ala Gly Pro Ile Glu Val Tyr Ala Ala Gly Lys Ala
                165                 170                 175

Ala Thr Ser Gly Val Pro Ser Ile Tyr Ala Pro Ser Thr Tyr Ala His
            180                 185                 190

Leu Ser Pro Ala Lys Thr Pro Pro Pro Ala Met Ile Pro Met Gly
        195                 200                 205

Pro Ala Tyr Asn Gly Tyr Pro Gly Gly Tyr Pro Gly Asp Val Asp Arg
    210                 215                 220

Ser Ser Ser Ala Gly Gly Gln Gly Ser Tyr Val Pro Leu Leu Arg Asp
225                 230                 235                 240

Thr Asp Ser Ser Val Ala Ser Glu Val Arg Ser Gly Tyr Arg Ile Gln
                245                 250                 255

Ala Ser Gln Gln Asp Asp Ser Met Arg Val Leu Tyr Tyr Met Glu Lys
            260                 265                 270

Glu Leu Ala Asn Phe Asp Pro Ser Arg Pro Gly Pro Pro Ser Gly Arg
        275                 280                 285

Val Glu Arg Ala Met Ser Glu Val Thr Ser Leu His Glu Asp Asp Trp
    290                 295                 300

Arg Ser Arg Pro Ser Arg Gly Pro Ala Leu Thr Pro Ile Arg Asp Glu
305                 310                 315                 320

Glu Trp Gly Gly His Ser Pro Arg Ser Pro Arg Gly Trp Asp Gln Glu
                325                 330                 335

Pro Ala Arg Glu Gln Ala Gly Gly Gly Trp Arg Ala Arg Pro Arg
            340                 345                 350

Ala Arg Ser Val Asp Ala Leu Asp Asp Leu Thr Pro Pro Ser Thr Ala
        355                 360                 365

Glu Ser Gly Ser Arg Ser Pro Thr Ser Asn Gly Gly Arg Ser Arg Ala
```

```
                370             375             380
Tyr Met Pro Pro Arg Ser Arg Ser Arg Asp Asp Leu Tyr Asp Gln Asp
385                 390                 395                 400

Asp Ser Arg Asp Phe Pro Arg Ser Arg Asp Pro His Tyr Asp Asp Phe
                405                 410                 415

Arg Ser Arg Glu Arg Pro Pro Ala Asp Pro Arg Ser His His His Arg
            420                 425                 430

Thr Arg Asp Pro Arg Asp Asn Gly Ser Arg Ser Gly Asp Leu Pro Tyr
        435                 440                 445

Asp Gly Arg Leu Leu Glu Glu Ala Val Arg Lys Lys Gly Ser Glu Glu
    450                 455                 460

Arg Arg Arg Pro His Lys Glu Glu Glu Glu Ala Tyr Tyr Pro Pro
465                 470                 475                 480

Ala Pro Pro Pro Tyr Ser Glu Thr Asp Ser Gln Ala Ser Arg Glu Arg
                485                 490                 495

Arg Leu Lys Lys Asn Leu Ala Leu Ser Arg Glu Ser Leu Val Val
            500                 505                 510

<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 51
gagaacttgg caggctctcc                                             20

<210> SEQ ID NO 52
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 52
cacacttccc agcagatgtc                                             20

<210> SEQ ID NO 53
<211> LENGTH: 34
<212> TYPE: DNA
<213> ORGANISM: Artificial sequence
<220> FEATURE:
<223> OTHER INFORMATION: Synthetic polynucleotide

<400> SEQUENCE: 53
ctagctagcc accatggcag tcttattcct cctc                             34

<210> SEQ ID NO 54
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 54
cgcgaattcg cctgggcttg tgggcaggtg                                  30

<210> SEQ ID NO 55
<211> LENGTH: 1662
<212> TYPE: DNA
<213> ORGANISM: Artificial sequence
```

<220> FEATURE:
<223> OTHER INFORMATION: Synthetic polynucleotide

<400> SEQUENCE: 55

```
atggcagtct tattcctcct cctgttccta tgtggaactc cccaggctgc agacaacatg      60
caggccatct atgtggcctt gggggaggca gtagagctgc catgtccctc accacctact     120
ctacatgggg acgaacacct gtcatggttc tgcagccctg cagcaggctc cttcaccacc     180
ctggtagccc aagtccaagt gggcaggcca gccccagacc tggaaaaacc aggaagggaa     240
tccaggctca gactgctggg gaactattct ttgtggttgg agggatccaa agaggaagat     300
gccgggcggt actggtgcgc tgtgctaggt cagcaccaca actaccagaa ctggagggtg     360
tacgacgtct tggtgctcaa aggatcccag ttatctgcaa gggctgcaga tggatccccc     420
tgcaatgtcc tcctgtgctc tgtggtcccc agcagacgca tggactctgt gacctggcag     480
gaagggaagg gtcccgtgag gggccgtgtt cagtccttct ggggcagtga ggctgccctg     540
ctcttggtgt gtcctgggga ggggctttct gagcccagga ccgaagacc aagaatcatc     600
cgctgcctca tgactcacaa caaagggtc agctttagcc tggcagcctc catcgatgct     660
tctcctgccc tctgtgcccc ttccacgggc tgggacatgc cttggattct gatgctgctg     720
ctcacaatgg ccagggagt tgtcatcctg gccctcagca tcgtgctctg gaggcagagg     780
gtccgtgggg ctccaggcag agatgcctcg attcctcagt tcaaacccga atccaggtc     840
tatgagaaca tccatttggc ccgtcttggc ccacctgccc acaagcccag gcgaattctg     900
cagtcgacgg taccgcgggc ccgggatcca ccggtcgcca ccatggtgag caagggcgag     960
gagctgttca ccggggtggt gcccatcctg gtcgagctgg acggcgacgt aaacggccac    1020
aagttcagcg tgtccggcga gggcgagggc gatgccacct acggcaagct gaccctgaag    1080
ttcatctgca ccaccggcaa gctgcccgtg ccctggccca cctcgtgac cacccctgacc    1140
tacggcgtgc agtgcttcag ccgctacccc gaccacatga gcagcacga cttcttcaag    1200
tccgccatgc ccgaaggcta cgtccaggag cgcaccatct tcttcaagga cgacggcaac    1260
tacaagaccc gcgccgaggt gaagttcgag ggcgacaccc tggtgaaccg catcgagctg    1320
aagggcatcg acttcaagga ggacggcaac atcctggggc acaagctgga gtacaactac    1380
aacagccaca acgtctatat catggccgac aagcagaaga acggcatcaa ggtgaacttc    1440
aagatccgcc acaacatcga ggacggcagc gtgcagctcg ccgaccacta ccagcagaac    1500
accccccatcg gcgacggccc cgtgctgctg cccgacaacc actacctgag cacccagtcc    1560
gccctgagca agaccccaa cgagaagcgc gatcacatgg tcctgctgga gttcgtgacc    1620
gccgccggga tcactctcgg catggacgag ctgtacaagt aa                        1662
```

<210> SEQ ID NO 56
<211> LENGTH: 553
<212> TYPE: PRT
<213> ORGANISM: Artificial sequence
<220> FEATURE:
<223> OTHER INFORMATION: Synthetic polypeptide

<400> SEQUENCE: 56

```
Met Ala Val Leu Phe Leu Leu Leu Phe Leu Cys Gly Thr Pro Gln Ala
1               5                   10                  15

Ala Asp Asn Met Gln Ala Ile Tyr Val Ala Leu Gly Glu Ala Val Glu
            20                  25                  30

Leu Pro Cys Pro Ser Pro Pro Thr Leu His Gly Asp Glu His Leu Ser
        35                  40                  45
```

```
Trp Phe Cys Ser Pro Ala Ala Gly Ser Phe Thr Thr Leu Val Ala Gln
    50                  55                  60

Val Gln Val Gly Arg Pro Ala Pro Asp Pro Gly Lys Pro Gly Arg Glu
65                  70                  75                  80

Ser Arg Leu Arg Leu Leu Gly Asn Tyr Ser Leu Trp Leu Glu Gly Ser
                85                  90                  95

Lys Glu Glu Asp Ala Gly Arg Tyr Trp Cys Ala Val Leu Gly Gln His
                100                 105                 110

His Asn Tyr Gln Asn Trp Arg Val Tyr Asp Val Leu Val Leu Lys Gly
            115                 120                 125

Ser Gln Leu Ser Ala Arg Ala Asp Gly Ser Pro Cys Asn Val Leu
    130                 135                 140

Leu Cys Ser Val Val Pro Ser Arg Arg Met Asp Ser Val Thr Trp Gln
145                 150                 155                 160

Glu Gly Lys Gly Pro Val Lys Gly Arg Val Gln Ser Phe Trp Gly Ser
                165                 170                 175

Glu Ala Ala Leu Leu Leu Val Cys Pro Gly Glu Gly Leu Ser Glu Pro
                180                 185                 190

Arg Ser Arg Arg Pro Arg Ile Ile Arg Cys Leu Met Thr His Asn Lys
        195                 200                 205

Gly Val Ser Phe Ser Leu Ala Ala Ser Ile Asp Ala Ser Pro Ala Leu
    210                 215                 220

Cys Ala Pro Ser Thr Gly Trp Asp Met Pro Trp Ile Leu Met Leu Leu
225                 230                 235                 240

Leu Thr Met Gly Gln Gly Val Val Ile Leu Ala Leu Ser Ile Val Leu
                245                 250                 255

Trp Arg Gln Arg Val Arg Gly Ala Pro Gly Arg Asp Ala Ser Ile Pro
                260                 265                 270

Gln Phe Lys Pro Glu Ile Gln Val Tyr Glu Asn Ile His Leu Ala Arg
        275                 280                 285

Leu Gly Pro Pro Ala His Lys Pro Arg Arg Ile Leu Gln Ser Thr Val
    290                 295                 300

Pro Arg Ala Arg Asp Pro Pro Val Ala Thr Met Val Ser Lys Gly Glu
305                 310                 315                 320

Glu Leu Phe Thr Gly Val Val Pro Ile Leu Val Glu Leu Asp Gly Asp
                325                 330                 335

Val Asn Gly His Lys Phe Ser Val Ser Gly Glu Gly Glu Gly Asp Ala
                340                 345                 350

Thr Tyr Gly Lys Leu Thr Leu Lys Phe Ile Cys Thr Thr Gly Lys Leu
        355                 360                 365

Pro Val Pro Trp Pro Thr Leu Val Thr Thr Leu Thr Tyr Gly Val Gln
    370                 375                 380

Cys Phe Ser Arg Tyr Pro Asp His Met Lys Gln His Asp Phe Phe Lys
385                 390                 395                 400

Ser Ala Met Pro Glu Gly Tyr Val Gln Glu Arg Thr Ile Phe Phe Lys
                405                 410                 415

Asp Asp Gly Asn Tyr Lys Thr Arg Ala Glu Val Lys Phe Glu Gly Asp
                420                 425                 430

Thr Leu Val Asn Arg Ile Glu Leu Lys Gly Ile Asp Phe Lys Glu Asp
        435                 440                 445

Gly Asn Ile Leu Gly His Lys Leu Glu Tyr Asn Tyr Asn Ser His Asn
    450                 455                 460
```

Val Tyr Ile Met Ala Asp Lys Gln Lys Asn Gly Ile Lys Val Asn Phe
465                 470                 475                 480

Lys Ile Arg His Asn Ile Glu Asp Gly Ser Val Gln Leu Ala Asp His
            485                 490                 495

Tyr Gln Gln Asn Thr Pro Ile Gly Asp Gly Pro Val Leu Leu Pro Asp
        500                 505                 510

Asn His Tyr Leu Ser Thr Gln Ser Ala Leu Ser Lys Asp Pro Asn Glu
    515                 520                 525

Lys Arg Asp His Met Val Leu Leu Glu Phe Val Thr Ala Ala Gly Ile
    530                 535                 540

Thr Leu Gly Met Asp Glu Leu Tyr Lys
545                 550

<210> SEQ ID NO 57
<211> LENGTH: 891
<212> TYPE: DNA
<213> ORGANISM: Artificial sequence
<220> FEATURE:
<223> OTHER INFORMATION: Synthetic polynucleotide

<400> SEQUENCE: 57
atggcagtct tattcctcct cctgttccta tgtggaactc cccaggctgc agacaacatg      60
caggccatct atgtggcctt gggggaggca gtagagctgc catgtccctc accacctact     120
ctacatgggg acgaacacct gtcatggttc tgcagccctg cagcaggctc cttcaccacc     180
ctggtagccc aagtccaagt gggcaggcca gccccagacc ctggaaaacc aggaagggaa     240
tccaggctca gactgctggg gaactattct ttgtggttgg agggatccaa agaggaagat     300
gccgggcggt actggtgcgc tgtgctaggt cagcaccaca actaccagaa ctggagggtg     360
tacgacgtct tggtgctcaa aggatcccag ttatctgcaa gggctgcaga tggatccccc     420
tgcaatgtcc tcctgtgctc tgtggtcccc agcagacgca tggactctgt gacctggcag     480
gaagggaagg gtcccgtgag gggccgtgtt cagtccttct ggggcagtga ggctgccctg     540
ctcttggtgt gtcctgggga ggggctttct gagcccagga gccgaagacc aagaatcatc     600
cgctgcctca tgactcacaa caaagggggtc agctttagcc tggcagcctc catcgatgct     660
tctcctgccc tctgtgcccc ttccacgggc tgggacatgc cttggattct gatgctgctg     720
ctcacaatgg ccagggagt tgtcatcctg gccctcagca tcgtgctctg gaggcagagg     780
gtccgtgggg ctccaggcag agatgcctcg attcctcagt tcaaacccga atccaggtc     840 tatgagaaca tccatttggc cgtcttggcc cacctgccc acaagcccag g               891

<210> SEQ ID NO 58
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 58

Met Ala Val Leu Phe Leu Leu Leu Phe Leu Cys Gly Thr Pro Gln Ala
1               5                   10                  15

Ala Asp Asn Met Gln Ala Ile Tyr Val Ala Leu Gly Glu Ala Val Glu
            20                  25                  30

Leu Pro Cys Pro Ser Pro Pro Thr Leu His Gly Asp Glu His Leu Ser
        35                  40                  45

Trp Phe Cys Ser Pro Ala Ala Gly Ser Phe Thr Thr Leu Val Ala Gln
    50                  55                  60

```
Val Gln Val Gly Arg Pro Ala Pro Asp Pro Gly Lys Pro Gly Arg Glu
 65                  70                  75                  80

Ser Arg Leu Arg Leu Leu Gly Asn Tyr Ser Leu Trp Leu Glu Gly Ser
                 85                  90                  95

Lys Glu Glu Asp Ala Gly Arg Tyr Trp Cys Ala Val Leu Gly Gln His
            100                 105                 110

His Asn Tyr Gln Asn Trp Arg Val Tyr Asp Val Leu Val Leu Lys Gly
        115                 120                 125

Ser Gln Leu Ser Ala Arg Ala Ala Asp Gly Ser Pro Cys Asn Val Leu
    130                 135                 140

Leu Cys Ser Val Val Pro Ser Arg Arg Met Asp Ser Val Thr Trp Gln
145                 150                 155                 160

Glu Gly Lys Gly Pro Val Lys Gly Arg Val Gln Ser Phe Trp Gly Ser
                165                 170                 175

Glu Ala Ala Leu Leu Leu Val Cys Pro Gly Glu Gly Leu Ser Glu Pro
            180                 185                 190

Arg Ser Arg Arg Pro Arg Ile Ile Arg Cys Leu Met Thr His Asn Lys
        195                 200                 205

Gly Val Ser Phe Ser Leu Ala Ala Ser Ile Asp Ala Ser Pro Ala Leu
    210                 215                 220

Cys Ala Pro Ser Thr Gly Trp Asp Met Pro Trp Ile Leu Met Leu Leu
225                 230                 235                 240

Leu Thr Met Gly Gln Gly Val Val Ile Leu Ala Leu Ser Ile Val Leu
                245                 250                 255

Trp Arg Gln Arg Val Arg Gly Ala Pro Gly Arg Asp Ala Ser Ile Pro
            260                 265                 270

Gln Phe Lys Pro Glu Ile Gln Val Tyr Glu Asn Ile His Leu Ala Arg
        275                 280                 285

Leu Gly Pro Pro Ala His Lys Pro Arg
    290                 295

<210> SEQ ID NO 59
<211> LENGTH: 234
<212> TYPE: PRT
<213> ORGANISM: Artificial sequence
<220> FEATURE:
<223> OTHER INFORMATION: Synthetic polypeptide

<400> SEQUENCE: 59

Met Ala Val Leu Phe Leu Leu Phe Leu Cys Gly Thr Pro Gln Ala
 1               5                  10                  15

Ala Asp Asn Met Gln Ala Ile Tyr Val Ala Leu Gly Glu Ala Val Glu
            20                  25                  30

Leu Pro Cys Pro Ser Pro Pro Thr Leu His Gly Asp Glu His Leu Ser
        35                  40                  45

Trp Phe Cys Ser Pro Ala Ala Gly Ser Phe Thr Thr Leu Val Ala Gln
    50                  55                  60

Val Gln Val Gly Arg Pro Ala Pro Asp Pro Gly Lys Pro Gly Arg Glu
 65                  70                  75                  80

Ser Arg Leu Arg Leu Leu Gly Asn Tyr Ser Leu Trp Leu Glu Gly Ser
                 85                  90                  95

Lys Glu Glu Asp Ala Gly Arg Tyr Trp Cys Ala Val Leu Gly Gln His
            100                 105                 110

His Asn Tyr Gln Asn Trp Arg Val Tyr Asp Val Leu Val Leu Lys Gly
        115                 120                 125
```

```
Ser Gln Leu Ser Ala Arg Ala Ala Asp Gly Ser Pro Cys Asn Val Leu
        130                 135                 140

Leu Cys Ser Val Val Pro Ser Arg Arg Met Asp Ser Val Thr Trp Gln
145                 150                 155                 160

Glu Gly Lys Gly Pro Val Arg Gly Arg Val Gln Ser Phe Trp Gly Ser
                165                 170                 175

Glu Ala Ala Leu Leu Val Cys Pro Gly Glu Gly Leu Ser Glu Pro
                180                 185                 190

Arg Ser Arg Arg Pro Arg Ile Ile Arg Cys Leu Met Thr His Asn Lys
            195                 200                 205

Gly Val Ser Phe Ser Leu Ala Ala Ser Ile Asp Ala Ser Pro Ala Leu
        210                 215                 220

Cys Ala Pro Ser Thr Gly Trp Asp Met Pro
225                 230
```

<210> SEQ ID NO 60
<211> LENGTH: 413
<212> TYPE: PRT
<213> ORGANISM: Artificial sequence
<220> FEATURE:
<223> OTHER INFORMATION: Synthetic polypeptide

<400> SEQUENCE: 60

```
Met Ala Ala Gly Gly Ser Ala Pro Glu Pro Arg Val Leu Val Cys Leu
1               5                   10                  15

Gly Ala Leu Leu Ala Gly Trp Val Ala Val Gly Leu Glu Ala Val Val
            20                  25                  30

Ile Gly Glu Val His Glu Asn Val Thr Leu His Cys Gly Asn Ile Ser
        35                  40                  45

Gly Leu Arg Gly Gln Val Thr Trp Tyr Arg Asn Asn Ser Glu Pro Val
    50                  55                  60

Phe Leu Leu Ser Ser Asn Ser Ser Leu Arg Pro Ala Glu Pro Arg Phe
65                  70                  75                  80

Ser Leu Val Asp Ala Thr Ser Leu His Ile Glu Ser Leu Ser Leu Gly
                85                  90                  95

Asp Glu Gly Ile Tyr Thr Cys Gln Glu Ile Leu Asn Val Thr Gln Trp
            100                 105                 110

Phe Gln Val Trp Leu Gln Val Ala Ser Gly Pro Tyr Gln Ile Glu Val
        115                 120                 125

His Ile Val Ala Thr Gly Thr Leu Pro Asn Gly Thr Leu Tyr Ala Ala
    130                 135                 140

Arg Gly Ser Gln Val Asp Phe Ser Cys Asn Ser Ser Ser Arg Pro Pro
145                 150                 155                 160

Pro Val Val Glu Trp Trp Phe Gln Ala Leu Asn Ser Ser Ser Glu Ser
                165                 170                 175

Phe Gly His Asn Leu Thr Val Asn Phe Phe Ser Leu Leu Leu Ile Ser
            180                 185                 190

Pro Asn Leu Gln Gly Asn Tyr Thr Cys Leu Ala Leu Asn Gln Leu Ser
        195                 200                 205

Lys Arg His Arg Lys Val Thr Thr Glu Leu Leu Val Tyr Tyr Pro Pro
    210                 215                 220

Pro Ser Ala Pro Gln Cys Trp Ala Gln Met Ala Ser Gly Ser Phe Met
225                 230                 235                 240

Leu Gln Leu Thr Cys Arg Trp Asp Gly Gly Tyr Pro Asp Pro Asp Phe
                245                 250                 255
```

-continued

```
Leu Trp Ile Glu Glu Pro Gly Val Ile Val Gly Lys Ser Lys Leu
            260                 265                 270

Gly Val Glu Met Leu Ser Glu Ser Gln Leu Ser Asp Gly Lys Lys Phe
        275                 280                 285

Lys Cys Val Thr Ser His Ile Val Gly Pro Glu Ser Gly Ala Ser Cys
    290                 295                 300

Met Val Gln Ile Arg Gly Pro Ser Leu Leu Ser Glu Pro Met Lys Thr
305                 310                 315                 320

Cys Phe Thr Gly Gly Asn Val Thr Leu Thr Cys Gln Val Ser Gly Ala
                325                 330                 335

Tyr Pro Pro Ala Lys Ile Leu Trp Leu Arg Asn Leu Thr Gln Pro Glu
            340                 345                 350

Val Ile Ile Gln Pro Ser Ser Arg His Leu Ile Thr Gln Asp Gly Gln
        355                 360                 365

Asn Ser Thr Leu Thr Ile His Asn Cys Ser Gln Asp Leu Asp Glu Gly
    370                 375                 380

Tyr Tyr Ile Cys Arg Ala Asp Ser Pro Val Gly Val Arg Glu Met Glu
385                 390                 395                 400

Ile Trp Leu Ser Val Lys Glu Pro Leu Asn Ile Gly Gly
                405                 410
```

```
<210> SEQ ID NO 61
<211> LENGTH: 312
<212> TYPE: PRT
<213> ORGANISM: Artificial sequence
<220> FEATURE:
<223> OTHER INFORMATION: Synthetic polypeptide

<400> SEQUENCE: 61
```

```
Met Ala Ala Gly Gly Ser Ala Pro Glu Pro Arg Val Leu Val Cys Leu
1               5                   10                  15

Gly Ala Leu Leu Ala Gly Trp Val Ala Val Gly Leu Glu Ala Val Val
            20                  25                  30

Ile Gly Glu Val His Glu Asn Val Thr Leu His Cys Gly Asn Ile Ser
        35                  40                  45

Gly Leu Arg Gly Gln Val Thr Trp Tyr Arg Asn Asn Ser Glu Pro Val
    50                  55                  60

Phe Leu Leu Ser Ser Asn Ser Ser Leu Arg Pro Ala Glu Pro Arg Phe
65                  70                  75                  80

Ser Leu Val Asp Ala Thr Ser Leu His Ile Glu Ser Leu Ser Leu Gly
                85                  90                  95

Asp Glu Gly Ile Tyr Thr Cys Gln Glu Ile Leu Asn Val Thr Gln Trp
            100                 105                 110

Phe Gln Val Trp Leu Gln Val Ala Asn Pro Pro Ser Ala Pro Gln
        115                 120                 125

Cys Trp Ala Gln Met Ala Ser Gly Ser Phe Met Leu Gln Leu Thr Cys
    130                 135                 140

Arg Trp Asp Gly Gly Tyr Pro Asp Pro Asp Phe Leu Trp Ile Glu Glu
145                 150                 155                 160

Pro Gly Gly Val Ile Val Gly Lys Ser Lys Leu Gly Val Glu Met Leu
                165                 170                 175

Ser Glu Ser Gln Leu Ser Asp Gly Lys Lys Phe Lys Cys Val Thr Ser
            180                 185                 190

His Ile Val Gly Pro Glu Ser Gly Ala Ser Cys Met Val Gln Ile Arg
        195                 200                 205
```

```
Gly Pro Ser Leu Leu Ser Glu Pro Met Lys Thr Cys Phe Thr Gly Gly
        210                 215                 220

Asn Val Thr Leu Thr Cys Gln Val Ser Gly Ala Tyr Pro Pro Ala Lys
225                 230                 235                 240

Ile Leu Trp Leu Arg Asn Leu Thr Gln Pro Glu Val Ile Ile Gln Pro
                245                 250                 255

Ser Ser Arg His Leu Ile Thr Gln Asp Gly Gln Asn Ser Thr Leu Thr
        260                 265                 270

Ile His Asn Cys Ser Gln Asp Leu Asp Glu Gly Tyr Tyr Ile Cys Arg
    275                 280                 285

Ala Asp Ser Pro Val Gly Val Arg Glu Met Glu Ile Trp Leu Ser Val
    290                 295                 300

Lys Glu Pro Leu Asn Ile Gly Gly
305                 310
```

<210> SEQ ID NO 62
<211> LENGTH: 649
<212> TYPE: PRT
<213> ORGANISM: Artificial sequence
<220> FEATURE:
<223> OTHER INFORMATION: Synthetic polypeptide

<400> SEQUENCE: 62

```
Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
                20                  25                  30

Arg Tyr Phe Gly Arg Asp Ala Arg Ala Arg Ala Gln Thr Ala Ala
            35                  40                  45

Met Ala Leu Leu Ala Gly Gly Leu Ser Arg Gly Leu Gly Ser His Pro
    50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
                100                 105                 110

Tyr Gln Met Thr Ser Thr Pro Thr Gln Pro Ile Val Ile Trp Lys Tyr
            115                 120                 125

Lys Ser Phe Cys Arg Asp Arg Ile Ala Asp Ala Phe Ser Pro Ala Ser
        130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Ser Ala Gln
    210                 215                 220

Asp Leu Gln Gly Asn Asn Glu Ala Tyr Ala Glu Leu Ile Val Leu Gly
225                 230                 235                 240

Arg Thr Ser Gly Val Ala Glu Leu Leu Pro Gly Phe Gln Ala Gly Pro
                245                 250                 255
```

-continued

Ile Glu Asp Trp Leu Phe Val Val Val Cys Leu Ala Ala Phe Leu
            260                 265                 270

Ile Phe Leu Leu Gly Ile Cys Trp Cys Gln Cys Cys Pro His Thr
        275                 280                 285

Cys Cys Cys Tyr Val Arg Cys Pro Cys Pro Asp Lys Cys Cys Cys
    290                 295                 300

Pro Glu Ala Leu Tyr Ala Ala Gly Lys Ala Thr Ser Gly Val Pro
305                 310                 315                 320

Ser Ile Tyr Ala Pro Ser Thr Tyr Ala His Leu Ser Pro Ala Lys Thr
                325                 330                 335

Pro Pro Pro Pro Ala Met Ile Pro Met Gly Pro Ala Tyr Asn Gly Tyr
                340                 345                 350

Pro Gly Gly Tyr Pro Gly Asp Val Asp Arg Ser Ser Ala Gly Gly
            355                 360                 365

Gln Gly Ser Tyr Val Pro Leu Leu Arg Asp Thr Asp Ser Ser Val Ala
    370                 375                 380

Ser Glu Val Arg Ser Gly Tyr Arg Ile Gln Ala Ser Gln Gln Asp Asp
385                 390                 395                 400

Ser Met Arg Val Leu Tyr Tyr Met Glu Lys Glu Leu Ala Asn Phe Asp
            405                 410                 415

Pro Ser Arg Pro Gly Pro Pro Ser Gly Arg Val Glu Arg Ala Met Ser
            420                 425                 430

Glu Val Thr Ser Leu His Glu Asp Asp Trp Arg Ser Arg Pro Ser Arg
            435                 440                 445

Gly Pro Ala Leu Thr Pro Ile Arg Asp Glu Glu Trp Gly Gly His Ser
450                 455                 460

Pro Arg Ser Pro Arg Gly Trp Asp Gln Glu Pro Ala Arg Glu Gln Ala
465                 470                 475                 480

Gly Gly Gly Trp Arg Ala Arg Arg Pro Arg Ala Arg Ser Val Asp Ala
            485                 490                 495

Leu Asp Asp Leu Thr Pro Pro Ser Thr Ala Glu Ser Gly Ser Arg Ser
            500                 505                 510

Pro Thr Ser Asn Gly Gly Arg Ser Arg Ala Tyr Met Pro Pro Arg Ser
            515                 520                 525

Arg Ser Arg Asp Leu Tyr Asp Gln Asp Asp Ser Arg Asp Phe Pro
530                 535                 540

Arg Ser Arg Asp Pro His Tyr Asp Asp Phe Arg Ser Arg Glu Arg Pro
545                 550                 555                 560

Pro Ala Asp Pro Arg Ser His His His Arg Thr Arg Asp Pro Arg Asp
                565                 570                 575

Asn Gly Ser Arg Ser Gly Asp Leu Pro Tyr Asp Gly Arg Leu Leu Glu
            580                 585                 590

Glu Ala Val Arg Lys Lys Gly Ser Glu Glu Arg Arg Pro His Lys
            595                 600                 605

Glu Glu Glu Glu Ala Tyr Tyr Pro Ala Pro Pro Tyr Ser
            610                 615                 620

Glu Thr Asp Ser Gln Ala Ser Arg Glu Arg Arg Leu Lys Lys Asn Leu
625                 630                 635                 640

Ala Leu Ser Arg Glu Ser Leu Val Val
                645

<210> SEQ ID NO 63
<211> LENGTH: 630

```
<212> TYPE: PRT
<213> ORGANISM: Artificial sequence
<220> FEATURE:
<223> OTHER INFORMATION: Synthetic polypeptide

<400> SEQUENCE: 63

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
            20                  25                  30

Arg Tyr Phe Gly Arg Asp Ala Arg Ala Arg Ala Gln Thr Ala Ala
        35                  40                  45

Met Ala Leu Leu Ala Gly Gly Leu Ser Arg Gly Leu Gly Ser His Pro
50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
                85                  90                  95

Pro Tyr His Val Val Ile Leu Phe Gln Pro Val Thr Leu Pro Cys Thr
            100                 105                 110

Tyr Gln Met Thr Ser Thr Pro Thr Gln Pro Ile Val Ile Trp Lys Tyr
            115                 120                 125

Lys Ser Phe Cys Arg Asp Arg Ile Ala Asp Ala Phe Ser Pro Ala Ser
130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
            165                 170                 175

Ala Thr Lys Gln Gly Asn Ala Val Thr Leu Gly Asp Tyr Tyr Gln Gly
            180                 185                 190

Arg Arg Ile Thr Ile Thr Gly Asn Ala Asp Leu Thr Phe Asp Gln Thr
        195                 200                 205

Ala Trp Gly Asp Ser Gly Val Tyr Tyr Cys Ser Val Val Ser Ala Gln
210                 215                 220

Asp Leu Gln Gly Asn Asn Glu Ala Tyr Ala Glu Leu Ile Val Leu Asp
225                 230                 235                 240

Trp Leu Phe Val Val Val Val Cys Leu Ala Ala Phe Leu Ile Phe Leu
                245                 250                 255

Leu Leu Gly Ile Cys Trp Cys Gln Cys Cys Pro His Thr Cys Cys Cys
            260                 265                 270

Tyr Val Arg Cys Pro Cys Cys Pro Asp Lys Cys Cys Cys Pro Glu Ala
        275                 280                 285

Leu Tyr Ala Ala Gly Lys Ala Thr Ser Gly Val Pro Ser Ile Tyr
290                 295                 300

Ala Pro Ser Thr Tyr Ala His Leu Ser Pro Ala Lys Thr Pro Pro
305                 310                 315                 320

Pro Ala Met Ile Pro Met Gly Pro Ala Tyr Asn Gly Tyr Pro Gly Gly
                325                 330                 335

Tyr Pro Gly Asp Val Asp Arg Ser Ser Ser Ala Gly Gly Gln Gly Ser
            340                 345                 350

Tyr Val Pro Leu Leu Arg Asp Thr Asp Ser Ser Val Ala Ser Glu Val
            355                 360                 365

Arg Ser Gly Tyr Arg Ile Gln Ala Ser Gln Gln Asp Asp Ser Met Arg
        370                 375                 380
```

-continued

Val Leu Tyr Tyr Met Glu Lys Glu Leu Ala Asn Phe Asp Pro Ser Arg
385                 390                 395                 400

Pro Gly Pro Pro Ser Gly Arg Val Glu Arg Ala Met Ser Glu Val Thr
        405                 410                 415

Ser Leu His Glu Asp Asp Trp Arg Ser Arg Pro Ser Arg Gly Pro Ala
            420                 425                 430

Leu Thr Pro Ile Arg Asp Glu Glu Trp Gly Gly His Ser Pro Arg Ser
        435                 440                 445

Pro Arg Gly Trp Asp Gln Glu Pro Ala Arg Glu Gln Ala Gly Gly Gly
450                 455                 460

Trp Arg Ala Arg Arg Pro Arg Ala Arg Ser Val Asp Ala Leu Asp Asp
465                 470                 475                 480

Leu Thr Pro Pro Ser Thr Ala Glu Ser Gly Ser Arg Ser Pro Thr Ser
            485                 490                 495

Asn Gly Gly Arg Ser Arg Ala Tyr Met Pro Pro Arg Ser Arg Ser Arg
        500                 505                 510

Asp Asp Leu Tyr Asp Gln Asp Ser Arg Asp Phe Pro Arg Ser Arg
        515                 520                 525

Asp Pro His Tyr Asp Asp Phe Arg Ser Arg Glu Arg Pro Pro Ala Asp
        530                 535                 540

Pro Arg Ser His His His Arg Thr Arg Asp Pro Arg Asp Asn Gly Ser
545                 550                 555                 560

Arg Ser Gly Asp Leu Pro Tyr Asp Gly Arg Leu Leu Glu Glu Ala Val
            565                 570                 575

Arg Lys Lys Gly Ser Glu Glu Arg Arg Pro His Lys Glu Glu Glu
        580                 585                 590

Glu Glu Ala Tyr Tyr Pro Pro Ala Pro Pro Tyr Ser Glu Thr Asp
        595                 600                 605

Ser Gln Ala Ser Arg Glu Arg Arg Leu Lys Lys Asn Leu Ala Leu Ser
610                 615                 620

Arg Glu Ser Leu Val Val
625                 630

<210> SEQ ID NO 64
<211> LENGTH: 588
<212> TYPE: PRT
<213> ORGANISM: Artificial sequence
<220> FEATURE:
<223> OTHER INFORMATION: Synthetic polypeptide

<400> SEQUENCE: 64

Ala Gln Thr Ala Ala Met Ala Leu Leu Ala Gly Gly Leu Ser Arg Gly
1               5                   10                  15

Leu Gly Ser His Pro Ala Ala Gly Arg Asp Ala Val Val Phe Val
            20                  25                  30

Trp Leu Leu Leu Ser Thr Trp Cys Thr Ala Pro Ala Arg Ala Ile Gln
        35                  40                  45

Val Thr Val Ser Asn Pro Tyr His Val Val Ile Leu Phe Gln Pro Val
    50                  55                  60

Thr Leu Pro Cys Thr Tyr Gln Met Thr Ser Thr Pro Thr Gln Pro Ile
65                  70                  75                  80

Val Ile Trp Lys Tyr Lys Ser Phe Cys Arg Asp Arg Ile Ala Asp Ala
                85                  90                  95

Phe Ser Pro Ala Ser Val Asp Asn Gln Leu Asn Ala Gln Leu Ala Ala
            100                 105                 110

-continued

Gly Asn Pro Gly Tyr Asn Pro Tyr Val Glu Cys Gln Asp Ser Val Arg
            115                 120                 125

Thr Val Arg Val Val Ala Thr Lys Gln Gly Asn Ala Val Thr Leu Gly
130                 135                 140

Asp Tyr Tyr Gln Gly Arg Arg Ile Thr Ile Thr Gly Asn Ala Asp Leu
145                 150                 155                 160

Thr Phe Asp Gln Thr Ala Trp Gly Asp Ser Gly Val Tyr Tyr Cys Ser
                165                 170                 175

Val Val Ser Ala Gln Asp Leu Gln Gly Asn Asn Glu Ala Tyr Ala Glu
            180                 185                 190

Leu Ile Val Leu Asp Trp Leu Phe Val Val Val Cys Leu Ala Ala
        195                 200                 205

Phe Leu Ile Phe Leu Leu Gly Ile Cys Trp Cys Gln Cys Cys Pro
210                 215                 220

His Thr Cys Cys Cys Tyr Val Arg Cys Pro Cys Cys Pro Asp Lys Cys
225                 230                 235                 240

Cys Cys Pro Glu Ala Leu Tyr Ala Ala Gly Lys Ala Ala Thr Ser Gly
                245                 250                 255

Val Pro Ser Ile Tyr Ala Pro Ser Thr Tyr Ala His Leu Ser Pro Ala
            260                 265                 270

Lys Thr Pro Pro Pro Ala Met Ile Pro Met Gly Pro Ala Tyr Asn
        275                 280                 285

Gly Tyr Pro Gly Gly Tyr Pro Gly Asp Val Asp Arg Ser Ser Ser Ala
            290                 295                 300

Gly Gly Gln Gly Ser Tyr Val Pro Leu Leu Arg Asp Thr Asp Ser Ser
305                 310                 315                 320

Val Ala Ser Glu Val Arg Ser Gly Tyr Arg Ile Gln Ala Ser Gln Gln
                325                 330                 335

Asp Asp Ser Met Arg Val Leu Tyr Tyr Met Glu Lys Glu Leu Ala Asn
            340                 345                 350

Phe Asp Pro Ser Arg Pro Gly Pro Pro Ser Gly Arg Val Glu Arg Ala
        355                 360                 365

Met Ser Glu Val Thr Ser Leu His Glu Asp Asp Trp Arg Ser Arg Pro
370                 375                 380

Ser Arg Gly Pro Ala Leu Thr Pro Ile Arg Asp Glu Glu Trp Gly Gly
385                 390                 395                 400

His Ser Pro Arg Ser Pro Arg Gly Trp Asp Gln Glu Pro Ala Arg Glu
                405                 410                 415

Gln Ala Gly Gly Gly Trp Arg Ala Arg Arg Pro Arg Ala Arg Ser Val
            420                 425                 430

Asp Ala Leu Asp Asp Leu Thr Pro Pro Ser Thr Ala Glu Ser Gly Ser
        435                 440                 445

Arg Ser Pro Thr Ser Asn Gly Gly Arg Arg Ser Arg Ala Tyr Met Pro
450                 455                 460

Pro Arg Ser Arg Ser Arg Asp Asp Leu Tyr Asp Gln Asp Ser Arg
465                 470                 475                 480

Asp Phe Pro Arg Ser Arg Asp Pro His Tyr Asp Phe Arg Ser Arg
                485                 490                 495

Glu Arg Pro Pro Ala Asp Pro Arg Ser His His His Arg Thr Arg Asp
            500                 505                 510

Pro Arg Asp Asn Gly Ser Arg Ser Gly Asp Leu Pro Tyr Asp Gly Arg
        515                 520                 525

Leu Leu Glu Glu Ala Val Arg Lys Lys Gly Ser Glu Glu Arg Arg Arg

```
                         530                 535                 540
Pro His Lys Glu Glu Glu Glu Ala Tyr Tyr Pro Ala Pro Pro
545                 550                 555                 560

Pro Tyr Ser Glu Thr Asp Ser Gln Ala Ser Arg Glu Arg Leu Lys
                565                 570                 575

Lys Asn Leu Ala Leu Ser Arg Glu Ser Leu Val Val
            580                 585

<210> SEQ ID NO 65
<211> LENGTH: 583
<212> TYPE: PRT
<213> ORGANISM: Artificial sequence
<220> FEATURE:
<223> OTHER INFORMATION: Synthetic polypeptide

<400> SEQUENCE: 65

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Asp
            180                 185                 190

Trp Leu Phe Val Val Val Cys Leu Ala Ala Phe Leu Ile Phe Leu
        195                 200                 205

Leu Leu Gly Ile Cys Trp Cys Gln Cys Cys Pro His Thr Cys Cys Cys
210                 215                 220

Tyr Val Arg Cys Pro Cys Cys Pro Asp Lys Cys Cys Cys Pro Glu Ala
225                 230                 235                 240

Leu Tyr Ala Ala Gly Lys Ala Thr Ser Gly Val Pro Ser Ile Tyr
            245                 250                 255

Ala Pro Ser Thr Tyr Ala His Leu Ser Pro Ala Lys Thr Pro Pro Pro
        260                 265                 270

Pro Ala Met Ile Pro Met Gly Pro Ala Tyr Asn Gly Tyr Pro Gly Gly
            275                 280                 285

Tyr Pro Gly Asp Val Asp Arg Asn Ser Ser Ala Gly Gly Gln Gly Ser
        290                 295                 300

Tyr Val Pro Leu Leu Arg Asp Thr Asp Ser Ser Val Ala Ser Glu Val
```

```
                305                 310                 315                 320
        Arg Ser Gly Tyr Arg Ile Gln Ala Ser Gln Gln Asp Asp Ser Met Arg
                        325                 330                 335

Val Leu Tyr Tyr Met Glu Lys Glu Leu Ala Asn Phe Asp Pro Ser Arg
                        340                 345                 350

Pro Gly Pro Pro Ser Gly Arg Val Glu Arg Ala Met Ser Glu Val Thr
                        355                 360                 365

Ser Leu His Glu Asp Asp Trp Arg Ser Arg Pro Ser Arg Gly Pro Ala
                370                 375                 380

Leu Thr Pro Ile Arg Asp Glu Glu Trp Gly Gly His Ser Pro Arg Ser
        385                 390                 395                 400

Pro Arg Gly Trp Asp Gln Glu Pro Ala Arg Glu Gln Ala Gly Gly
                        405                 410                 415

Trp Arg Ala Arg Arg Pro Arg Ala Arg Ser Val Asp Ala Leu Asp Asp
                        420                 425                 430

Leu Thr Pro Pro Ser Thr Ala Glu Ser Gly Ser Arg Ser Pro Thr Ser
                        435                 440                 445

Asn Gly Gly Arg Arg Ser Arg Ala Tyr Met Pro Pro Arg Ser Arg Ser
                450                 455                 460

Arg Asp Asp Leu Tyr Asp Gln Asp Ser Arg Asp Phe Pro Arg Ser
        465                 470                 475                 480

Arg Asp Pro His Tyr Asp Asp Phe Arg Ser Arg Glu Arg Pro Pro Ala
                        485                 490                 495

Asp Pro Arg Ser His His His Arg Thr Arg Asp Pro Arg Asp Asn Gly
                        500                 505                 510

Ser Arg Ser Gly Asp Leu Pro Tyr Asp Gly Arg Leu Leu Glu Glu Ala
                        515                 520                 525

Val Arg Lys Lys Gly Ser Glu Glu Arg Arg Pro His Lys Glu Glu
                        530                 535                 540

Glu Glu Glu Ala Tyr Tyr Pro Pro Ala Pro Pro Pro Tyr Ser Glu Thr
        545                 550                 555                 560

Asp Ser Gln Ala Ser Arg Glu Arg Arg Leu Lys Lys Asn Leu Ala Leu
                        565                 570                 575

Ser Arg Glu Ser Leu Val Val
                        580

<210> SEQ ID NO 66
<211> LENGTH: 581
<212> TYPE: PRT
<213> ORGANISM: Artificial sequence
<220> FEATURE:
<223> OTHER INFORMATION: Synthetic polypeptide

<400> SEQUENCE: 66

Met Gln Gln Asp Gly Leu Gly Val Gly Thr Arg Asn Gly Ser Gly Lys
1               5                   10                  15

Gly Arg Ser Val His Pro Ser Trp Pro Trp Cys Ala Pro Arg Pro Leu
                20                  25                  30

Arg Tyr Phe Gly Arg Asp Ala Arg Ala Arg Ala Gln Thr Ala Ala
            35                  40                  45

Met Ala Leu Leu Ala Gly Gly Leu Ser Arg Gly Leu Gly Ser His Pro
        50                  55                  60

Ala Ala Ala Gly Arg Asp Ala Val Val Phe Val Trp Leu Leu Leu Ser
65                  70                  75                  80

Thr Trp Cys Thr Ala Pro Ala Arg Ala Ile Gln Val Thr Val Ser Asn
```

```
                    85                  90                  95
Pro Tyr His Val Val Ile Leu Phe Gln Pro Val Thr Leu Pro Cys Thr
                100                 105                 110

Tyr Gln Met Thr Ser Thr Pro Thr Gln Pro Ile Val Ile Trp Lys Tyr
                115                 120                 125

Lys Ser Phe Cys Arg Asp Arg Ile Ala Asp Ala Phe Ser Pro Ala Ser
            130                 135                 140

Val Asp Asn Gln Leu Asn Ala Gln Leu Ala Ala Gly Asn Pro Gly Tyr
145                 150                 155                 160

Asn Pro Tyr Val Glu Cys Gln Asp Ser Val Arg Thr Val Arg Val Val
                165                 170                 175

Ala Thr Lys Gln Gly Asn Ala Val Thr Leu Gly Asp Tyr Tyr Gln Gly
                180                 185                 190

Arg Arg Ile Thr Ile Thr Gly Asn Ala Asp Leu Thr Phe Asp Gln Thr
                195                 200                 205

Ala Trp Gly Asp Ser Gly Val Tyr Tyr Cys Ser Val Val Ser Ala Gln
            210                 215                 220

Asp Leu Gln Gly Asn Asn Glu Ala Tyr Ala Glu Leu Ile Val Leu Val
225                 230                 235                 240

Tyr Ala Ala Gly Lys Ala Ala Thr Ser Gly Val Pro Ser Ile Tyr Ala
                245                 250                 255

Pro Ser Thr Tyr Ala His Leu Ser Pro Ala Lys Thr Pro Pro Pro Pro
                260                 265                 270

Ala Met Ile Pro Met Gly Pro Ala Tyr Asn Gly Tyr Pro Gly Gly Tyr
            275                 280                 285

Pro Gly Asp Val Asp Arg Ser Ser Ala Gly Gly Gln Gly Ser Tyr
            290                 295                 300

Val Pro Leu Leu Arg Asp Thr Asp Ser Ser Val Ala Ser Glu Val Arg
305                 310                 315                 320

Ser Gly Tyr Arg Ile Gln Ala Ser Gln Gln Asp Asp Ser Met Arg Val
                325                 330                 335

Leu Tyr Tyr Met Glu Lys Glu Leu Ala Asn Phe Asp Pro Ser Arg Pro
                340                 345                 350

Gly Pro Pro Ser Gly Arg Val Glu Arg Ala Met Ser Glu Val Thr Ser
            355                 360                 365

Leu His Glu Asp Trp Arg Ser Arg Pro Ser Arg Gly Pro Ala Leu
            370                 375                 380

Thr Pro Ile Arg Asp Glu Glu Trp Gly Gly His Ser Pro Arg Ser Pro
385                 390                 395                 400

Arg Gly Trp Asp Gln Glu Pro Ala Arg Glu Gln Ala Gly Gly Trp
            405                 410                 415

Arg Ala Arg Arg Pro Arg Ala Arg Ser Val Asp Ala Leu Asp Asp Leu
            420                 425                 430

Thr Pro Pro Ser Thr Ala Glu Ser Gly Ser Arg Ser Pro Thr Ser Asn
            435                 440                 445

Gly Gly Arg Ser Arg Ala Tyr Met Pro Pro Arg Ser Arg Ser Arg Asp
            450                 455                 460

Asp Leu Tyr Asp Gln Asp Asp Ser Arg Asp Phe Pro Arg Ser Arg Asp
465                 470                 475                 480

Pro His Tyr Asp Asp Phe Arg Ser Arg Glu Arg Pro Ala Asp Pro
                485                 490                 495

Arg Ser His His His Arg Thr Arg Asp Pro Arg Asp Asn Gly Ser Arg
            500                 505                 510
```

```
Ser Gly Asp Leu Pro Tyr Asp Gly Arg Leu Glu Glu Ala Val Arg
            515                 520                 525

Lys Lys Gly Ser Glu Arg Arg Pro His Lys Glu Glu Glu Glu
        530                 535                 540

Glu Ala Tyr Tyr Pro Pro Ala Pro Pro Tyr Ser Glu Thr Asp Ser
545                 550                 555                 560

Gln Ala Ser Arg Glu Arg Leu Lys Lys Asn Leu Ala Leu Ser Arg
                565                 570                 575

Glu Ser Leu Val Val
            580

<210> SEQ ID NO 67
<211> LENGTH: 493
<212> TYPE: PRT
<213> ORGANISM: Artificial sequence
<220> FEATURE:
<223> OTHER INFORMATION: Synthetic polypeptide

<400> SEQUENCE: 67

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
                20                  25                  30

Thr Trp Cys Thr Ala Pro Ala Arg Ala Ile Gln Val Thr Val Ser Asn
            35                  40                  45

Pro Tyr His Val Val Ile Leu Phe Gln Pro Val Thr Leu Pro Cys Thr
        50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Met Tyr Ala Ala Gly Lys Ala Ala Thr
145                 150                 155                 160

Ser Gly Val Pro Ser Ile Tyr Ala Pro Ser Thr Tyr Ala His Leu Ser
                165                 170                 175

Pro Ala Lys Thr Pro Pro Pro Ala Met Ile Pro Met Gly Pro Ala
            180                 185                 190

Tyr Asn Gly Tyr Pro Gly Gly Tyr Pro Gly Asp Val Asp Arg Ser Ser
        195                 200                 205

Ser Ala Gly Gly Gln Ser Tyr Val Pro Leu Leu Arg Asp Thr Asp
    210                 215                 220

Ser Ser Val Ala Ser Glu Val Arg Ser Gly Tyr Arg Ile Gln Ala Ser
225                 230                 235                 240

Gln Gln Asp Asp Ser Met Arg Val Leu Tyr Tyr Met Glu Lys Glu Leu
                245                 250                 255

Ala Asn Phe Asp Pro Ser Arg Pro Gly Pro Pro Ser Gly Arg Val Glu
            260                 265                 270

Arg Ala Met Ser Glu Val Thr Ser Leu His Glu Asp Asp Trp Arg Ser
        275                 280                 285
```

-continued

```
Arg Pro Ser Arg Gly Pro Ala Leu Thr Pro Ile Arg Asp Glu Glu Trp
        290                 295                 300

Gly Gly His Ser Pro Arg Ser Pro Arg Gly Trp Asp Gln Glu Pro Ala
305                 310                 315                 320

Arg Glu Gln Ala Gly Gly Gly Trp Arg Ala Arg Arg Pro Arg Ala Arg
                325                 330                 335

Ser Val Asp Ala Leu Asp Asp Leu Thr Pro Pro Ser Thr Ala Glu Ser
            340                 345                 350

Gly Ser Arg Ser Pro Thr Ser Asn Gly Gly Arg Ser Arg Ala Tyr Met
        355                 360                 365

Pro Pro Arg Ser Arg Ser Arg Asp Asp Leu Tyr Asp Gln Asp Asp Ser
    370                 375                 380

Arg Asp Phe Pro Arg Ser Arg Asp Pro His Tyr Asp Asp Phe Arg Ser
385                 390                 395                 400

Arg Glu Arg Pro Pro Ala Asp Pro Arg Ser His His Arg Thr Arg
                405                 410                 415

Asp Pro Arg Asp Asn Gly Ser Arg Ser Gly Asp Leu Pro Tyr Asp Gly
            420                 425                 430

Arg Leu Leu Glu Glu Ala Val Arg Lys Lys Gly Ser Glu Glu Arg Arg
        435                 440                 445

Arg Pro His Lys Glu Glu Glu Glu Ala Tyr Tyr Pro Pro Ala Pro
    450                 455                 460

Pro Pro Tyr Ser Glu Thr Asp Ser Gln Ala Ser Arg Glu Arg Arg Leu
465                 470                 475                 480

Lys Lys Asn Leu Ala Leu Ser Arg Glu Ser Leu Val Val
                485                 490

<210> SEQ ID NO 68
<211> LENGTH: 602
<212> TYPE: PRT
<213> ORGANISM: Artificial sequence
<220> FEATURE:
<223> OTHER INFORMATION: Synthetic polypeptide

<400> SEQUENCE: 68

Met Ala Leu Leu Ala Gly Gly Leu Ser Arg Gly Leu Gly Ser His Pro
1               5                   10                  15

Ala Ala Pro Gly Arg Asp Ala Val Val Phe Val Trp Leu Leu Leu Ser
                20                  25                  30

Thr Trp Cys Thr Ala Pro Ala Arg Ala Ile Gln Val Thr Val Ser Asn
            35                  40                  45

Pro Tyr His Val Val Ile Leu Phe Gln Pro Val Thr Leu Pro Cys Thr
        50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160
```

-continued

```
Ala Trp Gly Asp Ser Gly Val Tyr Tyr Cys Ser Val Ser Ala Gln
            165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
            195                 200                 205

Met Glu Asp Trp Leu Phe Val Val Val Cys Leu Ala Ala Phe Leu
            210                 215                 220

Ile Phe Leu Leu Leu Gly Ile Cys Trp Cys Gln Cys Cys Pro His Thr
225                 230                 235                 240

Cys Cys Cys Tyr Val Arg Cys Pro Cys Pro Asp Lys Cys Cys Cys
            245                 250                 255

Pro Glu Ala Leu Tyr Ala Ala Gly Lys Ala Ala Thr Ser Gly Val Pro
            260                 265                 270

Ser Ile Tyr Ala Pro Ser Thr Tyr Ala His Leu Ser Pro Ala Lys Thr
            275                 280                 285

Pro Pro Pro Ala Met Ile Pro Met Gly Pro Ala Tyr Asn Gly Tyr
            290                 295                 300

Pro Gly Gly Tyr Pro Gly Asp Val Asp Arg Ser Ser Ala Gly Gly
305                 310                 315                 320

Gln Gly Ser Tyr Val Pro Leu Leu Arg Asp Thr Asp Ser Ser Val Ala
            325                 330                 335

Ser Glu Val Arg Ser Gly Tyr Arg Ile Gln Ala Ser Gln Gln Asp Asp
            340                 345                 350

Ser Met Arg Val Leu Tyr Tyr Met Glu Lys Glu Leu Ala Asn Phe Asp
            355                 360                 365

Pro Ser Arg Pro Gly Pro Pro Asn Gly Arg Val Glu Arg Ala Met Ser
            370                 375                 380

Glu Val Thr Ser Leu His Glu Asp Asp Trp Arg Ser Arg Pro Ser Arg
385                 390                 395                 400

Gly Pro Ala Leu Thr Pro Ile Arg Asp Glu Glu Trp Gly Gly His Ser
            405                 410                 415

Pro Arg Ser Pro Arg Gly Trp Asp Gln Glu Pro Arg Glu Gln Ala
            420                 425                 430

Gly Gly Gly Trp Arg Ala Arg Arg Pro Arg Ala Arg Ser Val Asp Ala
            435                 440                 445

Leu Asp Asp Leu Thr Pro Pro Ser Thr Ala Glu Ser Gly Ser Arg Ser
450                 455                 460

Pro Thr Ser Ser Gly Gly Arg Arg Gly Arg Ala Tyr Met Pro Pro Arg
465                 470                 475                 480

Ser Arg Ser Arg Asp Asp Leu Tyr Asp Gln Asp Asp Ser Arg Asp Phe
            485                 490                 495

Pro Arg Ser Arg Asp Ser His Tyr Asp Asp Phe Arg Ser Arg Glu Arg
            500                 505                 510

Pro Pro Ala Asp Pro Arg Ser His His His Arg Thr Arg Asp Pro Arg
            515                 520                 525

Asp His Gly Ser Arg Ser Gly Asp Leu Leu Tyr Asp Gly Arg Leu Leu
            530                 535                 540

Glu Glu Ala Val Arg Lys Lys Gly Ser Glu Glu Arg Arg Pro His
545                 550                 555                 560

Lys Glu Glu Glu Glu Ala Tyr Tyr Pro Ala Pro Pro Tyr
            565                 570                 575
```

Ser Glu Thr Asp Ser Gln Ala Ser Glu Arg Arg Leu Lys Lys Asn
              580                 585                 590

Leu Ala Leu Ser Arg Glu Ser Leu Val Val
              595                 600

<210> SEQ ID NO 69
<211> LENGTH: 534
<212> TYPE: PRT
<213> ORGANISM: Artificial sequence
<220> FEATURE:
<223> OTHER INFORMATION: Synthetic polypeptide

<400> SEQUENCE: 69

Met Ala Leu Leu Ala Gly Gly Leu Ser Arg Gly Leu Gly Ser His Pro
1               5                   10                  15

Ala Ala Pro Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Val
            180                 185                 190

Tyr Ala Ala Gly Lys Ala Ala Thr Ser Gly Val Pro Ser Ile Tyr Ala
        195                 200                 205

Pro Ser Thr Tyr Ala His Leu Ser Pro Ala Lys Thr Pro Pro Pro Pro
    210                 215                 220

Ala Met Ile Pro Met Gly Pro Ala Tyr Asn Gly Tyr Pro Gly Gly Tyr
225                 230                 235                 240

Pro Gly Asp Val Asp Arg Ser Ser Ala Gly Gly Gln Gly Ser Tyr
                245                 250                 255

Val Pro Leu Leu Arg Asp Thr Asp Ser Ser Val Ala Ser Glu Val Arg
            260                 265                 270

Ser Gly Tyr Arg Ile Gln Ala Ser Gln Gln Asp Asp Ser Met Arg Val
        275                 280                 285

Leu Tyr Tyr Met Glu Lys Glu Leu Ala Asn Phe Asp Pro Ser Arg Pro
    290                 295                 300

Gly Pro Pro Asn Gly Arg Val Glu Arg Ala Met Ser Glu Val Thr Ser
305                 310                 315                 320

Leu His Glu Asp Asp Trp Arg Ser Arg Pro Ser Arg Gly Pro Ala Leu
                325                 330                 335

Thr Pro Ile Arg Asp Glu Glu Trp Gly His Ser Pro Arg Ser Pro
         340                 345                 350

Arg Gly Trp Asp Gln Glu Pro Pro Arg Glu Gln Ala Gly Gly Gly Trp
    355                 360                 365

Arg Ala Arg Arg Pro Arg Ala Arg Ser Val Asp Ala Leu Asp Asp Leu
    370                 375                 380

Thr Pro Pro Ser Thr Ala Glu Ser Gly Ser Arg Ser Pro Thr Ser Ser
385                 390                 395                 400

Gly Gly Arg Arg Gly Arg Ala Tyr Met Pro Pro Arg Ser Arg Ser Arg
                405                 410                 415

Asp Asp Leu Tyr Asp Gln Asp Ser Arg Asp Phe Pro Arg Ser Arg
        420                 425                 430

Asp Ser His Tyr Asp Asp Phe Arg Ser Arg Glu Arg Pro Pro Ala Asp
        435                 440                 445

Pro Arg Ser His His His Arg Thr Arg Asp Pro Arg Asp His Gly Ser
    450                 455                 460

Arg Ser Gly Asp Leu Leu Tyr Asp Gly Arg Leu Leu Glu Glu Ala Val
465                 470                 475                 480

Arg Lys Lys Gly Ser Glu Glu Arg Arg Pro His Lys Glu Glu
                485                 490                 495

Glu Glu Ala Tyr Tyr Pro Pro Ala Pro Pro Pro Tyr Ser Glu Thr Asp
                500                 505                 510

Ser Gln Ala Ser Arg Glu Arg Leu Lys Lys Asn Leu Ala Leu Ser
            515                 520                 525

Arg Glu Ser Leu Val Val
    530

<210> SEQ ID NO 70
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 70

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 71
<211> LENGTH: 466
<212> TYPE: PRT
<213> ORGANISM: Artificial sequence
<220> FEATURE:
<223> OTHER INFORMATION: Synthetic polypeptide

<400> SEQUENCE: 71

Met Ala Val Leu Phe Leu Leu Phe Leu Cys Gly Thr Pro Gln Ala
1               5                   10                  15

Ala Asp Asn Met Gln Ala Ile Tyr Val Ala Leu Gly Glu Ala Val Glu
            20                  25                  30

Leu Pro Cys Pro Ser Pro Pro Thr Leu His Gly Asp Glu His Leu Ser
        35                  40                  45

Trp Phe Cys Ser Pro Ala Ala Gly Ser Phe Thr Thr Leu Val Ala Gln
    50                  55                  60

Val Gln Val Gly Arg Pro Ala Pro Asp Pro Gly Lys Pro Gly Arg Glu
65                  70                  75                  80

Ser Arg Leu Arg Leu Leu Gly Asn Tyr Ser Leu Trp Leu Glu Gly Ser
                85                  90                  95

Lys Glu Glu Asp Ala Gly Arg Tyr Trp Cys Ala Val Leu Gly Gln His
            100                 105                 110

His Asn Tyr Gln Asn Trp Arg Val Tyr Asp Val Leu Val Leu Lys Gly
        115                 120                 125

Ser Gln Leu Ser Ala Arg Ala Ala Asp Gly Ser Pro Cys Asn Val Leu
    130                 135                 140

Leu Cys Ser Val Val Pro Ser Arg Arg Met Asp Ser Val Thr Trp Gln
145                 150                 155                 160

Glu Gly Lys Gly Pro Val Arg Gly Arg Val Gln Ser Phe Trp Gly Ser
                165                 170                 175

Glu Ala Ala Leu Leu Leu Val Cys Pro Gly Glu Gly Leu Ser Glu Pro
            180                 185                 190

Arg Ser Arg Arg Pro Arg Ile Ile Arg Cys Leu Met Thr His Asn Lys
        195                 200                 205

Gly Val Ser Phe Ser Leu Ala Ala Ser Ile Asp Ala Ser Pro Ala Leu
    210                 215                 220

Cys Ala Pro Ser Thr Gly Trp Asp Met Pro Glu Pro Lys Ser Ser Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285
```

```
Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
    355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
    450                 455                 460

Gly Lys
465

<210> SEQ ID NO 72
<211> LENGTH: 645
<212> TYPE: PRT
<213> ORGANISM: Artificial sequence
<220> FEATURE:
<223> OTHER INFORMATION: Synthetic polypeptide

<400> SEQUENCE: 72

Met Ala Ala Gly Gly Ser Ala Pro Glu Pro Arg Val Leu Val Cys Leu
1               5                   10                  15

Gly Ala Leu Leu Ala Gly Trp Val Ala Val Gly Leu Glu Ala Val Val
                20                  25                  30

Ile Gly Glu Val His Glu Asn Val Thr Leu His Cys Gly Asn Ile Ser
            35                  40                  45

Gly Leu Arg Gly Gln Val Thr Trp Tyr Arg Asn Asn Ser Glu Pro Val
    50                  55                  60

Phe Leu Leu Ser Ser Asn Ser Ser Leu Arg Pro Ala Glu Pro Arg Phe
65                  70                  75                  80

Ser Leu Val Asp Ala Thr Ser Leu His Ile Glu Ser Leu Ser Leu Gly
                85                  90                  95

Asp Glu Gly Ile Tyr Thr Cys Gln Glu Ile Leu Asn Val Thr Gln Trp
            100                 105                 110

Phe Gln Val Trp Leu Gln Val Ala Ser Gly Pro Tyr Gln Ile Glu Val
        115                 120                 125

His Ile Val Ala Thr Gly Thr Leu Pro Asn Gly Thr Leu Tyr Ala Ala
    130                 135                 140

Arg Gly Ser Gln Val Asp Phe Ser Cys Asn Ser Ser Ser Arg Pro Pro
145                 150                 155                 160

Pro Val Val Glu Trp Trp Phe Gln Ala Leu Asn Ser Ser Ser Glu Ser
                165                 170                 175
```

-continued

```
Phe Gly His Asn Leu Thr Val Asn Phe Phe Ser Leu Leu Ile Ser
            180                 185                 190

Pro Asn Leu Gln Gly Asn Tyr Thr Cys Leu Ala Leu Asn Gln Leu Ser
        195                 200                 205

Lys Arg His Arg Lys Val Thr Thr Glu Leu Leu Val Tyr Tyr Pro Pro
    210                 215                 220

Pro Ser Ala Pro Gln Cys Trp Ala Gln Met Ala Ser Gly Ser Phe Met
225                 230                 235                 240

Leu Gln Leu Thr Cys Arg Trp Asp Gly Gly Tyr Pro Asp Pro Asp Phe
                245                 250                 255

Leu Trp Ile Glu Glu Pro Gly Gly Val Ile Val Gly Lys Ser Lys Leu
            260                 265                 270

Gly Val Glu Met Leu Ser Glu Ser Gln Leu Ser Asp Gly Lys Lys Phe
        275                 280                 285

Lys Cys Val Thr Ser His Ile Val Gly Pro Glu Ser Gly Ala Ser Cys
    290                 295                 300

Met Val Gln Ile Arg Gly Pro Ser Leu Leu Ser Glu Pro Met Lys Thr
305                 310                 315                 320

Cys Phe Thr Gly Gly Asn Val Thr Leu Thr Cys Gln Val Ser Gly Ala
                325                 330                 335

Tyr Pro Pro Ala Lys Ile Leu Trp Leu Arg Asn Leu Thr Gln Pro Glu
            340                 345                 350

Val Ile Ile Gln Pro Ser Ser Arg His Leu Ile Thr Gln Asp Gly Gln
        355                 360                 365

Asn Ser Thr Leu Thr Ile His Asn Cys Ser Gln Asp Leu Asp Glu Gly
    370                 375                 380

Tyr Tyr Ile Cys Arg Ala Asp Ser Pro Val Gly Val Arg Glu Met Glu
385                 390                 395                 400

Ile Trp Leu Ser Val Lys Glu Pro Leu Asn Ile Gly Gly Glu Pro Lys
                405                 410                 415

Ser Ser Asp Lys Thr His Thr Cys Pro Pro Cys Pro Ala Pro Glu Leu
            420                 425                 430

Leu Gly Gly Pro Ser Val Phe Leu Phe Pro Pro Lys Pro Lys Asp Thr
        435                 440                 445

Leu Met Ile Ser Arg Thr Pro Glu Val Thr Cys Val Val Val Asp Val
    450                 455                 460

Ser His Glu Asp Pro Glu Val Lys Phe Asn Trp Tyr Val Asp Gly Val
465                 470                 475                 480

Glu Val His Asn Ala Lys Thr Lys Pro Arg Glu Glu Gln Tyr Asn Ser
                485                 490                 495

Thr Tyr Arg Val Val Ser Val Leu Thr Val Leu His Gln Asp Trp Leu
            500                 505                 510

Asn Gly Lys Glu Tyr Lys Cys Lys Val Ser Asn Lys Ala Leu Pro Ala
        515                 520                 525

Pro Ile Glu Lys Thr Ile Ser Lys Ala Lys Gly Gln Pro Arg Glu Pro
    530                 535                 540

Gln Val Tyr Thr Leu Pro Pro Ser Arg Asp Glu Leu Thr Lys Asn Gln
545                 550                 555                 560

Val Ser Leu Thr Cys Leu Val Lys Gly Phe Tyr Pro Ser Asp Ile Ala
                565                 570                 575

Val Glu Trp Glu Ser Asn Gly Gln Pro Glu Asn Asn Tyr Lys Thr Thr
            580                 585                 590

Pro Pro Val Leu Asp Ser Asp Gly Ser Phe Phe Leu Tyr Ser Lys Leu
```

```
                595                 600                 605
Thr Val Asp Lys Ser Arg Trp Gln Gln Gly Asn Val Phe Ser Cys Ser
610                 615                 620
Val Met His Glu Ala Leu His Asn His Tyr Thr Gln Lys Ser Leu Ser
625                 630                 635                 640
Leu Ser Pro Gly Lys
            645

<210> SEQ ID NO 73
<211> LENGTH: 544
<212> TYPE: PRT
<213> ORGANISM: Artificial sequence
<220> FEATURE:
<223> OTHER INFORMATION: Synthetic polypeptide

<400> SEQUENCE: 73

Met Ala Ala Gly Gly Ser Ala Pro Glu Pro Arg Val Leu Val Cys Leu
1               5                   10                  15
Gly Ala Leu Leu Ala Gly Trp Val Ala Val Gly Leu Glu Ala Val Val
            20                  25                  30
Ile Gly Glu Val His Glu Asn Val Thr Leu His Cys Gly Asn Ile Ser
        35                  40                  45
Gly Leu Arg Gly Gln Val Thr Trp Tyr Arg Asn Asn Ser Glu Pro Val
    50                  55                  60
Phe Leu Leu Ser Ser Asn Ser Ser Leu Arg Pro Ala Glu Pro Arg Phe
65                  70                  75                  80
Ser Leu Val Asp Ala Thr Ser Leu His Ile Glu Ser Leu Ser Leu Gly
                85                  90                  95
Asp Glu Gly Ile Tyr Thr Cys Gln Glu Ile Leu Asn Val Thr Gln Trp
            100                 105                 110
Phe Gln Val Trp Leu Gln Val Ala Asn Pro Pro Ser Ala Pro Gln
        115                 120                 125
Cys Trp Ala Gln Met Ala Ser Gly Ser Phe Met Leu Gln Leu Thr Cys
130                 135                 140
Arg Trp Asp Gly Gly Tyr Pro Asp Pro Asp Phe Leu Trp Ile Glu Glu
145                 150                 155                 160
Pro Gly Gly Val Ile Val Gly Lys Ser Lys Leu Gly Val Glu Met Leu
                165                 170                 175
Ser Glu Ser Gln Leu Ser Asp Gly Lys Lys Phe Lys Cys Val Thr Ser
            180                 185                 190
His Ile Val Gly Pro Glu Ser Gly Ala Ser Cys Met Val Gln Ile Arg
        195                 200                 205
Gly Pro Ser Leu Leu Ser Glu Pro Met Lys Thr Cys Phe Thr Gly Gly
    210                 215                 220
Asn Val Thr Leu Thr Cys Gln Val Ser Gly Ala Tyr Pro Pro Ala Lys
225                 230                 235                 240
Ile Leu Trp Leu Arg Asn Leu Thr Gln Pro Glu Val Ile Ile Gln Pro
                245                 250                 255
Ser Ser Arg His Leu Ile Thr Gln Asp Gly Gln Asn Ser Thr Leu Thr
            260                 265                 270
Ile His Asn Cys Ser Gln Asp Leu Asp Glu Gly Tyr Tyr Ile Cys Arg
        275                 280                 285
Ala Asp Ser Pro Val Gly Val Arg Glu Met Glu Ile Trp Leu Ser Val
    290                 295                 300
Lys Glu Pro Leu Asn Ile Gly Gly Glu Pro Lys Ser Ser Asp Lys Thr
```

His Thr Cys Pro Pro Cys Pro Ala Pro Glu Leu Leu Gly Gly Pro Ser
            325                 330                 335

Val Phe Leu Phe Pro Lys Pro Lys Asp Thr Leu Met Ile Ser Arg
            340                 345                 350

Thr Pro Glu Val Thr Cys Val Val Val Asp Val Ser His Glu Asp Pro
            355                 360                 365

Glu Val Lys Phe Asn Trp Tyr Val Asp Gly Val Glu Val His Asn Ala
            370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Ala Pro Ile Glu Lys Thr
            420                 425                 430

Ile Ser Lys Ala Lys Gly Gln Pro Arg Glu Pro Gln Val Tyr Thr Leu
            435                 440                 445

Pro Pro Ser Arg Asp Glu Leu Thr Lys Asn Gln Val Ser Leu Thr Cys
            450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
            515                 520                 525

Leu His Asn His Tyr Thr Gln Lys Ser Leu Ser Leu Ser Pro Gly Lys
            530                 535                 540

<210> SEQ ID NO 74
<211> LENGTH: 464
<212> TYPE: PRT
<213> ORGANISM: Artificial sequence
<220> FEATURE:
<223> OTHER INFORMATION: Synthetic polypeptide

<400> SEQUENCE: 74

Met Ala Leu Pro Pro Gly Pro Ala Ala Leu Arg His Thr Leu Leu Leu
1               5                   10                  15

Leu Pro Ala Leu Leu Ser Ser Gly Trp Gly Glu Leu Glu Pro Gln Ile
            20                  25                  30

Asp Gly Gln Thr Trp Ala Glu Arg Ala Leu Arg Glu Asn Glu Arg His
            35                  40                  45

Ala Phe Thr Cys Arg Val Ala Gly Gly Pro Gly Thr Pro Arg Leu Ala
    50                  55                  60

Trp Tyr Leu Asp Gly Gln Leu Gln Glu Ala Ser Thr Ser Arg Leu Leu
65                  70                  75                  80

Ser Val Gly Gly Glu Ala Phe Ser Gly Thr Ser Thr Phe Thr Val
                85                  90                  95

Thr Ala His Arg Ala Gln His Glu Leu Asn Cys Ser Leu Gln Asp Pro
            100                 105                 110

Arg Ser Gly Arg Ser Ala Asn Ala Ser Val Ile Leu Asn Val Gln Phe
            115                 120                 125

Lys Pro Glu Ile Ala Gln Val Gly Ala Lys Tyr Gln Glu Ala Gln Gly

```
                130                 135                 140
Pro Gly Leu Leu Val Val Leu Phe Ala Leu Val Arg Ala Asn Pro Pro
145                 150                 155                 160

Ala Asn Val Thr Trp Ile Asp Gln Asp Gly Pro Val Thr Val Asn Thr
                165                 170                 175

Ser Asp Phe Leu Val Leu Asp Ala Gln Asn Tyr Pro Trp Leu Thr Asn
            180                 185                 190

His Thr Val Gln Leu Gln Leu Arg Ser Leu Ala His Asn Leu Ser Val
        195                 200                 205

Val Ala Thr Asn Asp Val Gly Val Thr Ser Ala Ser Leu Pro Ala Pro
    210                 215                 220

Gly Leu Leu Ala Thr Arg Val Glu Glu Pro Lys Ser Ser Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 75
<211> LENGTH: 443
<212> TYPE: PRT
<213> ORGANISM: Artificial sequence
<220> FEATURE:
<223> OTHER INFORMATION: Synthetic polypeptide

<400> SEQUENCE: 75

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
```

```
            35                  40                  45
Pro Tyr His Val Val Ile Leu Phe Gln Pro Val Thr Leu Pro Cys Thr
 50                  55                  60

Tyr Gln Met Thr Ser Thr Pro Thr Gln Pro Ile Val Ile Trp Lys Tyr
 65                  70                  75                  80

Lys Ser Phe Cys Arg Asp Arg Ile Ala Asp Ala Phe Ser Pro Ala Ser
                 85                  90                  95

Val Asp Asn Gln Leu Asn Ala Gln Leu Ala Ala Gly Asn Pro Gly Tyr
                100                 105                 110

Asn Pro Tyr Val Glu Cys Gln Asp Ser Val Arg Thr Val Arg Val Val
                115                 120                 125

Ala Thr Lys Gln Gly Asn Ala Val Thr Leu Gly Asp Tyr Tyr Gln Gly
            130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
                180                 185                 190

Arg Thr Ser Gly Val Ala Glu Leu Leu Pro Gly Phe Gln Ala Gly Pro
            195                 200                 205

Ile Glu Asp Glu Pro Lys Ser Ser Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 76
```

```
<211> LENGTH: 424
<212> TYPE: PRT
<213> ORGANISM: Artificial sequence
<220> FEATURE:
<223> OTHER INFORMATION: Synthetic polypeptide

<400> SEQUENCE: 76

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Asp
            180                 185                 190

Glu Pro Lys Ser Ser Asp Lys Thr His Thr Cys Pro Pro Cys Pro Ala
        195                 200                 205

Pro Glu Leu Leu Gly Gly Pro Ser Val Phe Leu Phe Pro Pro Lys Pro
    210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Asn Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
    290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Asp Glu Leu Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
    370                 375                 380
```

```
Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
            405                 410                 415

Ser Leu Ser Leu Ser Pro Gly Lys
            420

<210> SEQ ID NO 77
<211> LENGTH: 765
<212> TYPE: PRT
<213> ORGANISM: Artificial sequence
<220> FEATURE:
<223> OTHER INFORMATION: Synthetic polypeptide

<400> SEQUENCE: 77

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Val
            180                 185                 190

Tyr Ala Ala Gly Lys Ala Ala Thr Ser Gly Val Pro Ser Ile Tyr Ala
        195                 200                 205

Pro Ser Thr Tyr Ala His Leu Ser Pro Ala Lys Thr Pro Pro Pro Pro
    210                 215                 220

Ala Met Ile Pro Met Gly Pro Ala Tyr Asn Gly Tyr Pro Gly Gly Tyr
225                 230                 235                 240

Pro Gly Asp Val Asp Arg Ser Ser Ser Ala Gly Gly Gln Gly Ser Tyr
                245                 250                 255

Val Pro Leu Leu Arg Asp Thr Asp Ser Ser Val Ala Ser Glu Val Arg
            260                 265                 270

Ser Gly Tyr Arg Ile Gln Ala Ser Gln Gln Asp Asp Ser Met Arg Val
        275                 280                 285

Leu Tyr Tyr Met Glu Lys Glu Leu Ala Asn Phe Asp Pro Ser Arg Pro
    290                 295                 300

Gly Pro Pro Ser Gly Arg Val Glu Arg Ala Met Ser Glu Val Thr Ser
305                 310                 315                 320
```

```
Leu His Glu Asp Asp Trp Arg Ser Arg Pro Ser Arg Gly Pro Ala Leu
                325                 330                 335

Thr Pro Ile Arg Asp Glu Glu Trp Gly Gly His Ser Pro Arg Ser Pro
            340                 345                 350

Arg Gly Trp Asp Gln Glu Pro Ala Arg Glu Gln Ala Gly Gly Gly Trp
        355                 360                 365

Arg Ala Arg Arg Pro Arg Ala Arg Ser Val Asp Ala Leu Asp Asp Leu
    370                 375                 380

Thr Pro Pro Ser Thr Ala Glu Ser Gly Ser Arg Ser Pro Thr Ser Asn
385                 390                 395                 400

Gly Gly Arg Ser Arg Ala Tyr Met Pro Pro Arg Ser Arg Ser Arg Asp
                405                 410                 415

Asp Leu Tyr Asp Gln Asp Asp Ser Arg Asp Phe Pro Arg Ser Arg Asp
                420                 425                 430

Pro His Tyr Asp Asp Phe Arg Ser Arg Glu Arg Pro Pro Ala Asp Pro
            435                 440                 445

Arg Ser His His His Arg Thr Arg Asp Pro Arg Asp Asn Gly Ser Arg
    450                 455                 460

Ser Gly Asp Leu Pro Tyr Asp Gly Arg Leu Leu Glu Glu Ala Val Arg
465                 470                 475                 480

Lys Lys Gly Ser Glu Glu Arg Arg Pro His Lys Glu Glu Glu Glu
                485                 490                 495

Glu Ala Tyr Tyr Pro Pro Ala Pro Pro Tyr Ser Glu Thr Asp Ser
                500                 505                 510

Gln Ala Ser Arg Glu Arg Arg Leu Lys Lys Asn Leu Ala Leu Ser Arg
                515                 520                 525

Glu Ser Leu Val Val Glu Pro Lys Ser Ser Asp Lys Thr His Thr Cys
530                 535                 540

Pro Pro Cys Pro Ala Pro Glu Leu Leu Gly Gly Pro Ser Val Phe Leu
545                 550                 555                 560

Phe Pro Pro Lys Pro Lys Asp Thr Leu Met Ile Ser Arg Thr Pro Glu
                565                 570                 575

Val Thr Cys Val Val Val Asp Val Ser His Glu Asp Pro Glu Val Lys
                580                 585                 590

Phe Asn Trp Tyr Val Asp Gly Val Glu Val His Asn Ala Lys Thr Lys
            595                 600                 605

Pro Arg Glu Glu Gln Tyr Asn Ser Thr Tyr Arg Val Val Ser Val Leu
    610                 615                 620

Thr Val Leu His Gln Asp Trp Leu Asn Gly Lys Glu Tyr Lys Cys Lys
625                 630                 635                 640

Val Ser Asn Lys Ala Leu Pro Ala Pro Ile Glu Lys Thr Ile Ser Lys
                645                 650                 655

Ala Lys Gly Gln Pro Arg Glu Pro Gln Val Tyr Thr Leu Pro Pro Ser
            660                 665                 670

Arg Asp Glu Leu Thr Lys Asn Gln Val Ser Leu Thr Cys Leu Val Lys
    675                 680                 685

Gly Phe Tyr Pro Ser Asp Ile Ala Val Glu Trp Glu Ser Asn Gly Gln
690                 695                 700

Pro Glu Asn Asn Tyr Lys Thr Thr Pro Pro Val Leu Asp Ser Asp Gly
705                 710                 715                 720

Ser Phe Phe Leu Tyr Ser Lys Leu Thr Val Asp Lys Ser Arg Trp Gln
                725                 730                 735
```

```
Gln Gly Asn Val Phe Ser Cys Ser Val Met His Glu Ala Leu His Asn
                740                 745                 750

His Tyr Thr Gln Lys Ser Leu Ser Leu Ser Pro Gly Lys
        755                 760                 765

<210> SEQ ID NO 78
<211> LENGTH: 764
<212> TYPE: PRT
<213> ORGANISM: Artificial sequence
<220> FEATURE:
<223> OTHER INFORMATION: Synthetic polypeptide

<400> SEQUENCE: 78

Met Ala Leu Leu Ala Gly Gly Leu Ser Arg Gly Leu Gly Ser His Pro
1               5                   10                  15

Ala Ala Ala Gly Arg Asp Ala Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Val
            180                 185                 190

Tyr Ala Ala Gly Lys Ala Ala Thr Ser Gly Val Pro Ser Ile Tyr Ala
        195                 200                 205

Pro Ser Thr Tyr Ala His Leu Ser Pro Ala Lys Thr Pro Pro Pro Pro
    210                 215                 220

Ala Met Ile Pro Met Gly Pro Ala Tyr Asn Gly Tyr Pro Gly Gly Tyr
225                 230                 235                 240

Pro Gly Asp Val Asp Arg Ser Ser Ala Gly Gly Gln Gly Ser Tyr
                245                 250                 255

Val Pro Leu Leu Arg Asp Thr Asp Ser Ser Val Ala Ser Val Arg Ser
            260                 265                 270

Gly Tyr Arg Ile Gln Ala Ser Gln Gln Asp Asp Ser Met Arg Val Leu
        275                 280                 285

Tyr Tyr Met Glu Lys Glu Leu Ala Asn Phe Asp Pro Ser Arg Pro Gly
    290                 295                 300

Pro Pro Ser Gly Arg Val Glu Arg Ala Met Ser Glu Val Thr Ser Leu
305                 310                 315                 320

His Glu Asp Asp Trp Arg Ser Arg Pro Ser Arg Gly Pro Ala Leu Thr
                325                 330                 335
```

```
Pro Ile Arg Asp Glu Glu Trp Gly Gly His Ser Pro Arg Ser Pro Arg
                340                 345                 350

Gly Trp Asp Gln Glu Pro Ala Arg Glu Gln Ala Gly Gly Gly Trp Arg
            355                 360                 365

Ala Arg Arg Pro Arg Ala Arg Ser Val Asp Ala Leu Asp Asp Leu Thr
        370                 375                 380

Pro Pro Ser Thr Ala Glu Ser Gly Ser Arg Ser Pro Thr Ser Asn Gly
385                 390                 395                 400

Gly Arg Ser Arg Ala Tyr Met Pro Pro Arg Ser Arg Ser Arg Asp Asp
                405                 410                 415

Leu Tyr Asp Gln Asp Asp Ser Arg Asp Phe Pro Arg Ser Arg Asp Pro
            420                 425                 430

His Tyr Asp Asp Phe Arg Ser Arg Glu Arg Pro Pro Ala Asp Pro Arg
        435                 440                 445

Ser His His His Arg Thr Arg Asp Pro Arg Asp Asn Gly Ser Arg Ser
    450                 455                 460

Gly Asp Leu Pro Tyr Asp Gly Arg Leu Leu Glu Glu Ala Val Arg Lys
465                 470                 475                 480

Lys Gly Ser Glu Glu Arg Arg Arg Pro His Lys Glu Glu Glu Glu Glu
                485                 490                 495

Ala Tyr Tyr Pro Pro Ala Pro Pro Tyr Ser Glu Thr Asp Ser Gln
            500                 505                 510

Ala Ser Arg Glu Arg Arg Leu Lys Lys Asn Leu Ala Leu Ser Arg Glu
        515                 520                 525

Ser Leu Val Val Glu Pro Lys Ser Ser Asp Lys Thr His Thr Cys Pro
    530                 535                 540

Pro Cys Pro Ala Pro Glu Leu Leu Gly Gly Pro Ser Val Phe Leu Phe
545                 550                 555                 560

Pro Pro Lys Pro Lys Asp Thr Leu Met Ile Ser Arg Thr Pro Glu Val
                565                 570                 575

Thr Cys Val Val Val Asp Val Ser His Glu Asp Pro Glu Val Lys Phe
            580                 585                 590

Asn Trp Tyr Val Asp Gly Val Glu Val His Asn Ala Lys Thr Lys Pro
        595                 600                 605

Arg Glu Glu Gln Tyr Asn Ser Thr Tyr Arg Val Val Ser Val Leu Thr
    610                 615                 620

Val Leu His Gln Asp Trp Leu Asn Gly Lys Glu Tyr Lys Cys Lys Val
625                 630                 635                 640

Ser Asn Lys Ala Leu Pro Ala Pro Ile Glu Lys Thr Ile Ser Lys Ala
                645                 650                 655

Lys Gly Gln Pro Arg Glu Pro Gln Val Tyr Thr Leu Pro Pro Ser Arg
            660                 665                 670

Asp Glu Leu Thr Lys Asn Gln Val Ser Leu Thr Cys Leu Val Lys Gly
        675                 680                 685

Phe Tyr Pro Ser Asp Ile Ala Val Glu Trp Ser Asn Gly Gln Pro
    690                 695                 700

Glu Asn Asn Tyr Lys Thr Thr Pro Pro Val Leu Asp Ser Asp Gly Ser
705                 710                 715                 720

Phe Phe Leu Tyr Ser Lys Leu Thr Val Asp Lys Ser Arg Trp Gln Gln
                725                 730                 735

Gly Asn Val Phe Ser Cys Ser Val Met His Glu Ala Leu His Asn His
            740                 745                 750

Tyr Thr Gln Lys Ser Leu Ser Leu Ser Pro Gly Lys
```

-continued

```
          755                 760
```

<210> SEQ ID NO 79
<211> LENGTH: 725
<212> TYPE: PRT
<213> ORGANISM: Artificial sequence
<220> FEATURE:
<223> OTHER INFORMATION: Synthetic polypeptide

<400> SEQUENCE: 79

```
Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Met Tyr Ala Ala Gly Lys Ala Ala Thr
145                 150                 155                 160

Ser Gly Val Pro Ser Ile Tyr Ala Pro Ser Thr Tyr Ala His Leu Ser
                165                 170                 175

Pro Ala Lys Thr Pro Pro Pro Ala Met Ile Pro Met Gly Pro Ala
            180                 185                 190

Tyr Asn Gly Tyr Pro Gly Gly Tyr Pro Gly Asp Val Asp Arg Ser Ser
        195                 200                 205

Ser Ala Gly Gly Gln Gly Ser Tyr Val Pro Leu Leu Arg Asp Thr Asp
    210                 215                 220

Ser Ser Val Ala Ser Glu Val Arg Ser Gly Tyr Arg Ile Gln Ala Ser
225                 230                 235                 240

Gln Gln Asp Asp Ser Met Arg Val Leu Tyr Tyr Met Glu Lys Glu Leu
                245                 250                 255

Ala Asn Phe Asp Pro Ser Arg Pro Gly Pro Pro Ser Gly Arg Val Glu
            260                 265                 270

Arg Ala Met Ser Glu Val Thr Ser Leu His Glu Asp Asp Trp Arg Ser
        275                 280                 285

Arg Pro Ser Arg Gly Pro Ala Leu Thr Pro Ile Arg Asp Glu Glu Trp
    290                 295                 300

Gly Gly His Ser Pro Arg Ser Pro Arg Gly Trp Asp Gln Glu Pro Ala
305                 310                 315                 320

Arg Glu Gln Ala Gly Gly Gly Trp Arg Ala Arg Arg Pro Arg Ala Arg
                325                 330                 335

Ser Val Asp Ala Leu Asp Asp Leu Thr Pro Pro Ser Thr Ala Glu Ser
            340                 345                 350

Gly Ser Arg Ser Pro Thr Ser Asn Gly Gly Arg Ser Arg Ala Tyr Met
```

```
            355                 360                 365
Pro Pro Arg Ser Arg Ser Arg Asp Asp Leu Tyr Asp Gln Asp Asp Ser
    370                 375                 380

Arg Asp Phe Pro Arg Ser Arg Asp Pro His Tyr Asp Asp Phe Arg Ser
385                 390                 395                 400

Arg Glu Arg Pro Pro Ala Asp Pro Arg Ser His His Arg Thr Arg
                405                 410                 415

Asp Pro Arg Asp Asn Gly Ser Arg Ser Gly Asp Leu Pro Tyr Asp Gly
            420                 425                 430

Arg Leu Leu Glu Glu Ala Val Arg Lys Lys Gly Ser Glu Glu Arg Arg
        435                 440                 445

Arg Pro His Lys Glu Glu Glu Glu Ala Tyr Tyr Pro Pro Ala Pro
    450                 455                 460

Pro Pro Tyr Ser Glu Thr Asp Ser Gln Ala Ser Arg Glu Arg Arg Leu
465                 470                 475                 480

Lys Lys Asn Leu Ala Leu Ser Arg Glu Ser Leu Val Val Glu Pro Lys
            485                 490                 495

Ser Ser Asp Lys Thr His Thr Cys Pro Pro Cys Pro Ala Pro Glu Leu
        500                 505                 510

Leu Gly Gly Pro Ser Val Phe Leu Phe Pro Pro Lys Pro Lys Asp Thr
    515                 520                 525

Leu Met Ile Ser Arg Thr Pro Glu Val Thr Cys Val Val Val Asp Val
530                 535                 540

Ser His Glu Asp Pro Glu Val Lys Phe Asn Trp Tyr Val Asp Gly Val
545                 550                 555                 560

Glu Val His Asn Ala Lys Thr Lys Pro Arg Glu Glu Gln Tyr Asn Ser
            565                 570                 575

Thr Tyr Arg Val Val Ser Val Leu Thr Val Leu His Gln Asp Trp Leu
        580                 585                 590

Asn Gly Lys Glu Tyr Lys Cys Lys Val Ser Asn Lys Ala Leu Pro Ala
    595                 600                 605

Pro Ile Glu Lys Thr Ile Ser Lys Ala Lys Gly Gln Pro Arg Glu Pro
610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
            645                 650                 655

Val Glu Trp Glu Ser Asn Gly Gln Pro Glu Asn Asn Tyr Lys Thr Thr
        660                 665                 670

Pro Pro Val Leu Asp Ser Asp Gly Ser Phe Phe Leu Tyr Ser Lys Leu
    675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly Lys
            725

<210> SEQ ID NO 80
<211> LENGTH: 784
<212> TYPE: PRT
<213> ORGANISM: Artificial sequence
<220> FEATURE:
<223> OTHER INFORMATION: Synthetic polypeptide
```

```
<400> SEQUENCE: 80

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Ile Glu Val Tyr Ala Ala Gly Lys Ala Ala Thr Ser Gly Val Pro Ser
    210                 215                 220

Ile Tyr Ala Pro Ser Thr Tyr Ala His Leu Ser Pro Ala Lys Thr Pro
225                 230                 235                 240

Pro Pro Pro Ala Met Ile Pro Met Gly Pro Ala Tyr Asn Gly Tyr Pro
                245                 250                 255

Gly Gly Tyr Pro Gly Asp Val Asp Arg Ser Ser Ala Gly Gly Gln
            260                 265                 270

Gly Ser Tyr Val Pro Leu Leu Arg Asp Thr Asp Ser Ser Val Ala Ser
        275                 280                 285

Glu Val Arg Ser Gly Tyr Arg Ile Gln Ala Ser Gln Gln Asp Asp Ser
    290                 295                 300

Met Arg Val Leu Tyr Tyr Met Glu Lys Glu Leu Ala Asn Phe Asp Pro
305                 310                 315                 320

Ser Arg Pro Gly Pro Ser Gly Arg Val Glu Arg Ala Met Ser Glu
                325                 330                 335

Val Thr Ser Leu His Glu Asp Asp Trp Arg Ser Arg Pro Ser Arg Gly
            340                 345                 350

Pro Ala Leu Thr Pro Ile Arg Asp Glu Glu Trp Gly Gly His Ser Pro
        355                 360                 365

Arg Ser Pro Arg Gly Trp Asp Gln Glu Pro Ala Arg Glu Gln Ala Gly
    370                 375                 380

Gly Gly Trp Arg Ala Arg Arg Pro Arg Ala Arg Ser Val Asp Ala Leu
385                 390                 395                 400

Asp Asp Leu Thr Pro Pro Ser Thr Ala Glu Ser Gly Ser Arg Ser Pro
                405                 410                 415
```

Thr Ser Asn Gly Gly Arg Ser Arg Ala Tyr Met Pro Pro Arg Ser Arg
            420                 425                 430

Ser Arg Asp Asp Leu Tyr Asp Gln Asp Asp Ser Arg Asp Phe Pro Arg
        435                 440                 445

Ser Arg Asp Pro His Tyr Asp Asp Phe Arg Ser Arg Glu Arg Pro Pro
        450                 455                 460

Ala Asp Pro Arg Ser His His His Arg Thr Arg Asp Pro Arg Asp Asn
465                 470                 475                 480

Gly Ser Arg Ser Gly Asp Leu Pro Tyr Asp Gly Arg Leu Leu Glu Glu
                485                 490                 495

Ala Val Arg Lys Lys Gly Ser Glu Glu Arg Arg Pro His Lys Glu
                500                 505                 510

Glu Glu Glu Glu Ala Tyr Tyr Pro Pro Ala Pro Pro Tyr Ser Glu
            515                 520                 525

Thr Asp Ser Gln Ala Ser Arg Glu Arg Arg Leu Lys Lys Asn Leu Ala
    530                 535                 540

Leu Ser Arg Glu Ser Leu Val Val Glu Pro Lys Ser Ser Asp Lys Thr
545                 550                 555                 560

His Thr Cys Pro Pro Cys Pro Ala Pro Glu Leu Leu Gly Gly Pro Ser
                565                 570                 575

Val Phe Leu Phe Pro Pro Lys Pro Lys Asp Thr Leu Met Ile Ser Arg
            580                 585                 590

Thr Pro Glu Val Thr Cys Val Val Val Asp Val Ser His Glu Asp Pro
            595                 600                 605

Glu Val Lys Phe Asn Trp Tyr Val Asp Gly Val Glu Val His Asn Ala
            610                 615                 620

Lys Thr Lys Pro Arg Glu Glu Gln Tyr Asn Ser Thr Tyr Arg Val Val
625                 630                 635                 640

Ser Val Leu Thr Val Leu His Gln Asp Trp Leu Asn Gly Lys Glu Tyr
                645                 650                 655

Lys Cys Lys Val Ser Asn Lys Ala Leu Pro Ala Pro Ile Glu Lys Thr
                660                 665                 670

Ile Ser Lys Ala Lys Gly Gln Pro Arg Glu Pro Gln Val Tyr Thr Leu
                675                 680                 685

Pro Pro Ser Arg Asp Glu Leu Thr Lys Asn Gln Val Ser Leu Thr Cys
            690                 695                 700

Leu Val Lys Gly Phe Tyr Pro Ser Asp Ile Ala Val Glu Trp Glu Ser
705                 710                 715                 720

Asn Gly Gln Pro Glu Asn Asn Tyr Lys Thr Thr Pro Pro Val Leu Asp
                725                 730                 735

Ser Asp Gly Ser Phe Phe Leu Tyr Ser Lys Leu Thr Val Asp Lys Ser
                740                 745                 750

Arg Trp Gln Gln Gly Asn Val Phe Ser Cys Ser Val Met His Glu Ala
            755                 760                 765

Leu His Asn His Tyr Thr Gln Lys Ser Leu Ser Leu Ser Pro Gly Lys
                770                 775                 780

<210> SEQ ID NO 81
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 81

```
Ala Asp Asn Met Gln Ala Ile Tyr Val Ala Leu Gly Glu Ala Val Glu
1               5                   10                  15

Leu Pro Cys Pro Ser Pro Thr Leu His Gly Asp Glu His Leu Ser
            20                  25                  30

Trp Phe Cys Ser Pro Ala Ala Gly Ser Phe Thr Thr Leu Val Ala Gln
            35                  40                  45

Val Gln Val Gly Arg Pro Ala Pro Asp Pro Gly Lys Pro Gly Arg Glu
    50                  55                  60

Ser Arg Leu Arg Leu Leu Gly Asn Tyr Ser Leu Trp Leu Glu Gly Ser
65                  70                  75                  80

Lys Glu Glu Asp Ala Gly Arg Tyr Trp Cys Ala Val Leu Gly Gln His
                85                  90                  95

His Asn Tyr Gln Asn Trp Arg Val Tyr Asp
                100                 105

<210> SEQ ID NO 82
<211> LENGTH: 89
<212> TYPE: PRT
<213> ORGANISM: Artificial sequence
<220> FEATURE:
<223> OTHER INFORMATION: Synthetic polypeptide

<400> SEQUENCE: 82

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
            35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val
                85

<210> SEQ ID NO 83
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 83

Pro Tyr Gln Ile Glu Val His Ile Val Ala Thr Gly Thr Leu Pro Asn
1               5                   10                  15

Gly Thr Leu Tyr Ala Ala Arg Gly Ser Gln Val Asp Phe Ser Cys Asn
            20                  25                  30

Ser Ser Ser Arg Pro Pro Val Val Glu Trp Trp Phe Gln Ala Leu
            35                  40                  45

Asn Ser Ser Ser Glu Ser Phe Gly His Asn Leu Thr Val Asn Phe Phe
    50                  55                  60

Ser Leu Leu Leu Ile Ser Pro Asn Leu Gln Gly Asn Tyr Thr Cys Leu
65                  70                  75                  80

Ala Leu Asn Gln Leu Ser Lys Arg His Arg Lys Val Thr
                85                  90
```

<210> SEQ ID NO 84
<211> LENGTH: 87
<212> TYPE: PRT
<213> ORGANISM: Artificial sequence
<220> FEATURE:
<223> OTHER INFORMATION: Synthetic polypeptide

<400> SEQUENCE: 84

```
Pro Pro Pro Ser Ala Pro Gln Cys Trp Ala Gln Met Ala Ser Gly Ser
1               5                   10                  15

Phe Met Leu Gln Leu Thr Cys Arg Trp Asp Gly Tyr Pro Asp Pro
            20                  25                  30

Asp Phe Leu Trp Ile Glu Glu Pro Gly Gly Val Ile Val Gly Lys Ser
            35                  40                  45

Lys Leu Gly Val Glu Met Leu Ser Glu Ser Gln Leu Ser Asp Gly Lys
        50                  55                  60

Lys Phe Lys Cys Val Thr Ser His Ile Val Gly Pro Glu Ser Gly Ala
65                  70                  75                  80

Ser Cys Met Val Gln Ile Arg
            85
```

<210> SEQ ID NO 85
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 85

```
Pro Ser Leu Leu Ser Glu Pro Met Lys Thr Cys Phe Thr Gly Gly Asn
1               5                   10                  15

Val Thr Leu Thr Cys Gln Val Ser Gly Ala Tyr Pro Pro Ala Lys Ile
            20                  25                  30

Leu Trp Leu Arg Asn Leu Thr Gln Pro Glu Val Ile Ile Gln Pro Ser
            35                  40                  45

Ser Arg His Leu Ile Thr Gln Asp Gly Gln Asn Ser Thr Leu Thr Ile
        50                  55                  60

His Asn Cys Ser Gln Asp Leu Asp Glu Gly Tyr Tyr Ile Cys Arg Ala
65                  70                  75                  80

Asp Ser Pro Val Gly Val Arg Glu Met Glu Ile Trp Leu Ser
            85                  90
```

<210> SEQ ID NO 86
<211> LENGTH: 185
<212> TYPE: PRT
<213> ORGANISM: Artificial sequence
<220> FEATURE:
<223> OTHER INFORMATION: Synthetic polypeptide

<400> SEQUENCE: 86

```
Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
            35                  40                  45

Arg Phe Ser Leu Val Asp Ala Thr Ser Leu His Ile Glu Ser Leu Ser
        50                  55                  60

Leu Gly Asp Glu Gly Ile Tyr Thr Cys Gln Glu Ile Leu Asn Val Thr
65                  70                  75                  80
```

```
Gln Trp Phe Gln Val Trp Leu Gln Val Ala Ser Gly Pro Tyr Gln Ile
                85                  90                  95

Glu Val His Ile Val Ala Thr Gly Thr Leu Pro Asn Gly Thr Leu Tyr
            100                 105                 110

Ala Ala Arg Gly Ser Gln Val Asp Phe Ser Cys Asn Ser Ser Ser Arg
        115                 120                 125

Pro Pro Pro Val Val Glu Trp Trp Phe Gln Ala Leu Asn Ser Ser Ser
    130                 135                 140

Glu Ser Phe Gly His Asn Leu Thr Val Asn Phe Phe Ser Leu Leu Leu
145                 150                 155                 160

Ile Ser Pro Asn Leu Gln Gly Asn Tyr Thr Cys Leu Ala Leu Asn Gln
                165                 170                 175

Leu Ser Lys Arg His Arg Lys Val Thr
            180                 185
```

<210> SEQ ID NO 87
<211> LENGTH: 279
<212> TYPE: PRT
<213> ORGANISM: Artificial sequence
<220> FEATURE:
<223> OTHER INFORMATION: Synthetic polypeptide

<400> SEQUENCE: 87

```
Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65              70                  75                  80

Gln Trp Phe Gln Val Trp Leu Gln Val Ala Ser Gly Pro Tyr Gln Ile
                85                  90                  95

Glu Val His Ile Val Ala Thr Gly Thr Leu Pro Asn Gly Thr Leu Tyr
            100                 105                 110

Ala Ala Arg Gly Ser Gln Val Asp Phe Ser Cys Asn Ser Ser Ser Arg
        115                 120                 125

Pro Pro Pro Val Val Glu Trp Trp Phe Gln Ala Leu Asn Ser Ser Ser
    130                 135                 140

Glu Ser Phe Gly His Asn Leu Thr Val Asn Phe Phe Ser Leu Leu Leu
145                 150                 155                 160

Ile Ser Pro Asn Leu Gln Gly Asn Tyr Thr Cys Leu Ala Leu Asn Gln
                165                 170                 175

Leu Ser Lys Arg His Arg Lys Val Thr Thr Glu Leu Leu Val Tyr Tyr
            180                 185                 190

Pro Pro Pro Ser Ala Pro Gln Cys Trp Ala Gln Met Ala Ser Gly Ser
        195                 200                 205

Phe Met Leu Gln Leu Thr Cys Arg Trp Asp Gly Gly Tyr Pro Asp Pro
    210                 215                 220

Asp Phe Leu Trp Ile Glu Glu Pro Gly Gly Val Ile Val Gly Lys Ser
225                 230                 235                 240

Lys Leu Gly Val Glu Met Leu Ser Glu Ser Gln Leu Ser Asp Gly Lys
                245                 250                 255
```

```
Lys Phe Lys Cys Val Thr Ser His Ile Val Gly Pro Glu Ser Gly Ala
            260                 265                 270

Ser Cys Met Val Gln Ile Arg
        275
```

<210> SEQ ID NO 88
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 88

```
Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Ser Gly Pro Tyr Gln Ile
                85                  90                  95

Glu Val His Ile Val Ala Thr Gly Thr Leu Pro Asn Gly Thr Leu Tyr
            100                 105                 110

Ala Ala Arg Gly Ser Gln Val Asp Phe Ser Cys Asn Ser Ser Ser Arg
        115                 120                 125

Pro Pro Pro Val Val Glu Trp Trp Phe Gln Ala Leu Asn Ser Ser Ser
    130                 135                 140

Glu Ser Phe Gly His Asn Leu Thr Val Asn Phe Phe Ser Leu Leu Leu
145                 150                 155                 160

Ile Ser Pro Asn Leu Gln Gly Asn Tyr Thr Cys Leu Ala Leu Asn Gln
                165                 170                 175

Leu Ser Lys Arg His Arg Lys Val Thr Thr Glu Leu Leu Val Tyr Tyr
            180                 185                 190

Pro Pro Pro Ser Ala Pro Gln Cys Trp Ala Gln Met Ala Ser Gly Ser
        195                 200                 205

Phe Met Leu Gln Leu Thr Cys Arg Trp Asp Gly Gly Tyr Pro Asp Pro
    210                 215                 220

Asp Phe Leu Trp Ile Glu Pro Gly Gly Val Ile Val Gly Lys Ser
225                 230                 235                 240

Lys Leu Gly Val Glu Met Leu Ser Glu Ser Gln Leu Ser Asp Gly Lys
                245                 250                 255

Lys Phe Lys Cys Val Thr Ser His Ile Val Gly Pro Glu Ser Gly Ala
            260                 265                 270

Ser Cys Met Val Gln Ile Arg Gly Pro Ser Leu Leu Ser Glu Pro Met
        275                 280                 285

Lys Thr Cys Phe Thr Gly Gly Asn Val Thr Leu Thr Cys Gln Val Ser
    290                 295                 300

Gly Ala Tyr Pro Pro Ala Lys Ile Leu Trp Leu Arg Asn Leu Thr Gln
305                 310                 315                 320

Pro Glu Val Ile Ile Gln Pro Ser Ser Arg His Leu Ile Thr Gln Asp
                325                 330                 335
```

```
Gly Gln Asn Ser Thr Leu Thr Ile His Asn Cys Ser Gln Asp Leu Asp
                340                 345                 350

Glu Gly Tyr Tyr Ile Cys Arg Ala Asp Ser Pro Val Gly Val Arg Glu
            355                 360                 365

Met Glu Ile Trp Leu Ser
    370

<210> SEQ ID NO 89
<211> LENGTH: 187
<212> TYPE: PRT
<213> ORGANISM: Artificial sequence
<220> FEATURE:
<223> OTHER INFORMATION: Synthetic polypeptide

<400> SEQUENCE: 89

Pro Tyr Gln Ile Glu Val His Ile Val Ala Thr Gly Thr Leu Pro Asn
1               5                   10                  15

Gly Thr Leu Tyr Ala Ala Arg Gly Ser Gln Val Asp Phe Ser Cys Asn
            20                  25                  30

Ser Ser Ser Arg Pro Pro Val Glu Trp Trp Phe Gln Ala Leu
            35                  40                  45

Asn Ser Ser Glu Ser Phe Gly His Asn Leu Thr Val Asn Phe Phe
 50                 55                  60

Ser Leu Leu Leu Ile Ser Pro Asn Leu Gln Gly Asn Tyr Thr Cys Leu
65                  70                  75                  80

Ala Leu Asn Gln Leu Ser Lys Arg His Arg Lys Val Thr Thr Glu Leu
                85                  90                  95

Leu Val Tyr Tyr Pro Pro Ser Ala Pro Gln Cys Trp Ala Gln Met
            100                 105                 110

Ala Ser Gly Ser Phe Met Leu Gln Leu Thr Cys Arg Trp Asp Gly Gly
            115                 120                 125

Tyr Pro Asp Pro Asp Phe Leu Trp Ile Glu Pro Gly Gly Val Ile
            130                 135                 140

Val Gly Lys Ser Lys Leu Gly Val Glu Met Leu Ser Glu Ser Gln Leu
145                 150                 155                 160

Ser Asp Gly Lys Lys Phe Lys Cys Val Thr Ser His Ile Val Gly Pro
                165                 170                 175

Glu Ser Gly Ala Ser Cys Met Val Gln Ile Arg
            180                 185

<210> SEQ ID NO 90
<211> LENGTH: 282
<212> TYPE: PRT
<213> ORGANISM: Artificial sequence
<220> FEATURE:
<223> OTHER INFORMATION: Synthetic polypeptide

<400> SEQUENCE: 90

Pro Tyr Gln Ile Glu Val His Ile Val Ala Thr Gly Thr Leu Pro Asn
1               5                   10                  15

Gly Thr Leu Tyr Ala Ala Arg Gly Ser Gln Val Asp Phe Ser Cys Asn
            20                  25                  30

Ser Ser Ser Arg Pro Pro Val Glu Trp Trp Phe Gln Ala Leu
            35                  40                  45

Asn Ser Ser Glu Ser Phe Gly His Asn Leu Thr Val Asn Phe Phe
 50                 55                  60

Ser Leu Leu Leu Ile Ser Pro Asn Leu Gln Gly Asn Tyr Thr Cys Leu
```

```
                65                  70                  75                  80
Ala Leu Asn Gln Leu Ser Lys Arg His Arg Lys Val Thr Thr Glu Leu
                85                  90                  95

Leu Val Tyr Tyr Pro Pro Ser Ala Pro Gln Cys Trp Ala Gln Met
            100                 105                 110

Ala Ser Gly Ser Phe Met Leu Gln Leu Thr Cys Arg Trp Asp Gly Gly
            115                 120                 125

Tyr Pro Asp Pro Asp Phe Leu Trp Ile Glu Glu Pro Gly Gly Val Ile
        130                 135                 140

Val Gly Lys Ser Lys Leu Gly Val Glu Met Leu Ser Glu Ser Gln Leu
145                 150                 155                 160

Ser Asp Gly Lys Lys Phe Lys Cys Val Thr Ser His Ile Val Gly Pro
                165                 170                 175

Glu Ser Gly Ala Ser Cys Met Val Gln Ile Arg Gly Pro Ser Leu Leu
            180                 185                 190

Ser Glu Pro Met Lys Thr Cys Phe Thr Gly Gly Asn Val Thr Leu Thr
        195                 200                 205

Cys Gln Val Ser Gly Ala Tyr Pro Pro Ala Lys Ile Leu Trp Leu Arg
    210                 215                 220

Asn Leu Thr Gln Pro Glu Val Ile Ile Gln Pro Ser Ser Arg His Leu
225                 230                 235                 240

Ile Thr Gln Asp Gly Gln Asn Ser Thr Leu Thr Ile His Asn Cys Ser
                245                 250                 255

Gln Asp Leu Asp Glu Gly Tyr Tyr Ile Cys Arg Ala Asp Ser Pro Val
            260                 265                 270

Gly Val Arg Glu Met Glu Ile Trp Leu Ser
        275                 280

<210> SEQ ID NO 91
<211> LENGTH: 182
<212> TYPE: PRT
<213> ORGANISM: Artificial sequence
<220> FEATURE:
<223> OTHER INFORMATION: Synthetic polypeptide

<400> SEQUENCE: 91

Pro Pro Pro Ser Ala Pro Gln Cys Trp Ala Gln Met Ala Ser Gly Ser
1               5                   10                  15

Phe Met Leu Gln Leu Thr Cys Arg Trp Asp Gly Gly Tyr Pro Asp Pro
            20                  25                  30

Asp Phe Leu Trp Ile Glu Glu Pro Gly Gly Val Ile Val Gly Lys Ser
        35                  40                  45

Lys Leu Gly Val Glu Met Leu Ser Glu Ser Gln Leu Ser Asp Gly Lys
    50                  55                  60

Lys Phe Lys Cys Val Thr Ser His Ile Val Gly Pro Glu Ser Gly Ala
65                  70                  75                  80

Ser Cys Met Val Gln Ile Arg Gly Pro Ser Leu Leu Ser Glu Pro Met
                85                  90                  95

Lys Thr Cys Phe Thr Gly Gly Asn Val Thr Leu Thr Cys Gln Val Ser
            100                 105                 110

Gly Ala Tyr Pro Pro Ala Lys Ile Leu Trp Leu Arg Asn Leu Thr Gln
        115                 120                 125

Pro Glu Val Ile Ile Gln Pro Ser Ser Arg His Leu Ile Thr Gln Asp
    130                 135                 140

Gly Gln Asn Ser Thr Leu Thr Ile His Asn Cys Ser Gln Asp Leu Asp
```

```
                145                 150                 155                 160
Glu Gly Tyr Tyr Ile Cys Arg Ala Asp Ser Pro Val Gly Val Arg Glu
            165                 170                 175

Met Glu Ile Trp Leu Ser
            180

<210> SEQ ID NO 92
<211> LENGTH: 178
<212> TYPE: PRT
<213> ORGANISM: Artificial sequence
<220> FEATURE:
<223> OTHER INFORMATION: Synthetic polypeptide

<400> SEQUENCE: 92

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Asn Pro Pro Ser Ala
            85                  90                  95

Pro Gln Cys Trp Ala Gln Met Ala Ser Gly Ser Phe Met Leu Gln Leu
            100                 105                 110

Thr Cys Arg Trp Asp Gly Gly Tyr Pro Asp Pro Asp Phe Leu Trp Ile
        115                 120                 125

Glu Glu Pro Gly Gly Val Ile Val Gly Lys Ser Lys Leu Gly Val Glu
    130                 135                 140

Met Leu Ser Glu Ser Gln Leu Ser Asp Gly Lys Lys Phe Lys Cys Val
145                 150                 155                 160

Thr Ser His Ile Val Gly Pro Glu Ser Gly Ala Ser Cys Met Val Gln
            165                 170                 175

Ile Arg

<210> SEQ ID NO 93
<211> LENGTH: 273
<212> TYPE: PRT
<213> ORGANISM: Artificial sequence
<220> FEATURE:
<223> OTHER INFORMATION: Synthetic polypeptide

<400> SEQUENCE: 93

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Asn Pro Pro Ser Ala
```

```
                85                  90                  95
Pro Gln Cys Trp Ala Gln Met Ala Ser Gly Ser Phe Met Leu Gln Leu
            100                 105                 110

Thr Cys Arg Trp Asp Gly Gly Tyr Pro Asp Pro Asp Phe Leu Trp Ile
            115                 120                 125

Glu Glu Pro Gly Gly Val Ile Val Gly Lys Ser Lys Leu Gly Val Glu
            130                 135                 140

Met Leu Ser Glu Ser Gln Leu Ser Asp Gly Lys Lys Phe Lys Cys Val
145                 150                 155                 160

Thr Ser His Ile Val Gly Pro Glu Ser Gly Ala Ser Cys Met Val Gln
                165                 170                 175

Ile Arg Gly Pro Ser Leu Leu Ser Glu Pro Met Lys Thr Cys Phe Thr
                180                 185                 190

Gly Gly Asn Val Thr Leu Thr Cys Gln Val Ser Gly Ala Tyr Pro Pro
                195                 200                 205

Ala Lys Ile Leu Trp Leu Arg Asn Leu Thr Gln Pro Glu Val Ile Ile
                210                 215                 220

Gln Pro Ser Ser Arg His Leu Ile Thr Gln Asp Gly Gln Asn Ser Thr
225                 230                 235                 240

Leu Thr Ile His Asn Cys Ser Gln Asp Leu Asp Glu Gly Tyr Tyr Ile
                245                 250                 255

Cys Arg Ala Asp Ser Pro Val Gly Val Arg Glu Met Glu Ile Trp Leu
                260                 265                 270

Ser

<210> SEQ ID NO 94
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 94

Pro Gln Ile Asp Gly Gln Thr Trp Ala Glu Arg Ala Leu Arg Glu Asn
1               5                   10                  15

Glu Arg His Ala Phe Thr Cys Arg Val Ala Gly Gly Pro Gly Thr Pro
                20                  25                  30

Arg Leu Ala Trp Tyr Leu Asp Gly Gln Leu Gln Glu Ala Ser Thr Ser
            35                  40                  45

Arg Leu Leu Ser Val Gly Gly Glu Ala Phe Ser Gly Gly Thr Ser Thr
        50                  55                  60

Phe Thr Val Thr Ala His Arg Ala Gln His Glu Leu Asn Cys Ser Leu
65                  70                  75                  80

Gln Asp Pro Arg Ser Gly Arg Ser Ala Asn Ala Ser Val Ile
                85                  90

<210> SEQ ID NO 95
<211> LENGTH: 145
<212> TYPE: PRT
<213> ORGANISM: Artificial sequence
<220> FEATURE:
<223> OTHER INFORMATION: Synthetic polypeptide

<400> SEQUENCE: 95

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
```

```
                20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
        50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
    130                 135                 140

Ala
145

<210> SEQ ID NO 96
<211> LENGTH: 72
<212> TYPE: PRT
<213> ORGANISM: Artificial sequence
<220> FEATURE:
<223> OTHER INFORMATION: Synthetic polypeptide

<400> SEQUENCE: 96

Cys Pro Ser Pro Pro Thr Leu His Gly Asp Glu His Leu Ser Trp Phe
1               5                   10                  15

Cys Ser Pro Ala Ala Gly Ser Phe Thr Thr Leu Val Ala Gln Val Gln
                20                  25                  30

Val Gly Arg Pro Ala Pro Asp Pro Gly Lys Pro Gly Arg Glu Ser Arg
            35                  40                  45

Leu Arg Leu Leu Gly Asn Tyr Ser Leu Trp Leu Glu Gly Ser Lys Glu
        50                  55                  60

Glu Asp Ala Gly Arg Tyr Trp Cys
65                  70

<210> SEQ ID NO 97
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 97

Cys Gly Asn Ile Ser Gly Leu Arg Gly Gln Val Thr Trp Tyr Arg Asn
1               5                   10                  15

Asn Ser Glu Pro Val Phe Leu Leu Ser Ser Asn Ser Ser Leu Arg Pro
                20                  25                  30

Ala Glu Pro Arg Phe Ser Leu Val Asp Ala Thr Ser Leu His Ile Glu
            35                  40                  45

Ser Leu Ser Leu Gly Asp Glu Gly Ile Tyr Thr Cys
        50                  55                  60

<210> SEQ ID NO 98
<211> LENGTH: 49
<212> TYPE: PRT
<213> ORGANISM: Artificial sequence
<220> FEATURE:
```

<223> OTHER INFORMATION: Synthetic polypeptide

<400> SEQUENCE: 98

Cys Asn Ser Ser Ser Arg Pro Pro Val Val Glu Trp Trp Phe Gln
1               5                   10                  15

Ala Leu Asn Ser Ser Ser Glu Ser Phe Gly His Asn Leu Thr Val Asn
            20                  25                  30

Phe Phe Ser Leu Leu Leu Ile Ser Pro Asn Leu Gln Gly Asn Tyr Thr
        35                  40                  45

Cys

<210> SEQ ID NO 99
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 99

Cys Arg Trp Asp Gly Gly Tyr Pro Asp Pro Asp Phe Leu Trp Ile Glu
1               5                   10                  15

Glu Pro Gly Gly Val Ile Val Gly Lys Ser Lys Leu Gly Val Glu Met
            20                  25                  30

Leu Ser Glu Ser Gln Leu Ser Asp Gly Lys Lys Phe Lys Cys
        35                  40                  45

<210> SEQ ID NO 100
<211> LENGTH: 58
<212> TYPE: PRT
<213> ORGANISM: Artificial sequence
<220> FEATURE:
<223> OTHER INFORMATION: Synthetic polypeptide

<400> SEQUENCE: 100

Cys Gln Val Ser Gly Ala Tyr Pro Pro Ala Lys Ile Leu Trp Leu Arg
1               5                   10                  15

Asn Leu Thr Gln Pro Glu Val Ile Ile Gln Pro Ser Ser Arg His Leu
            20                  25                  30

Ile Thr Gln Asp Gly Gln Asn Ser Thr Leu Thr Ile His Asn Cys Ser
        35                  40                  45

Gln Asp Leu Asp Glu Gly Tyr Tyr Ile Cys
    50                  55

<210> SEQ ID NO 101
<211> LENGTH: 56
<212> TYPE: PRT
<213> ORGANISM: Artificial sequence
<220> FEATURE:
<223> OTHER INFORMATION: Synthetic polypeptide

<400> SEQUENCE: 101

Cys Arg Val Ala Gly Gly Pro Gly Thr Pro Arg Leu Ala Trp Tyr Leu
1               5                   10                  15

Asp Gly Gln Leu Gln Glu Ala Ser Thr Ser Arg Leu Leu Ser Val Gly
            20                  25                  30

Gly Glu Ala Phe Ser Gly Gly Thr Ser Thr Phe Thr Val Thr Ala His
        35                  40                  45

Arg Ala Gln His Glu Leu Asn Cys
    50                  55

<210> SEQ ID NO 102
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 102

```
Cys Thr Tyr Gln Met Thr Ser Thr Pro Thr Gln Pro Ile Val Ile Trp
1               5                   10                  15

Lys Tyr Lys Ser Phe Cys Arg Asp Arg Ile Ala Asp Ala Phe Ser Pro
            20                  25                  30

Ala Ser Val Asp Asn Gln Leu Asn Ala Gln Leu Ala Ala Gly Asn Pro
        35                  40                  45

Gly Tyr Asn Pro Tyr Val Glu Cys Gln Asp Ser Val Arg Thr Val Arg
    50                  55                  60

Val Val Ala Thr Lys Gln Gly Asn Ala Val Thr Leu Gly Asp Tyr Tyr
65                  70                  75                  80

Gln Gly Arg Arg Ile Thr Ile Thr Gly Asn Ala Asp Leu Thr Phe Asp
                85                  90                  95

Gln Thr Ala Trp Gly Asp Ser Gly Val Tyr Tyr Cys
            100                 105
```

<210> SEQ ID NO 103
<211> LENGTH: 2405
<212> TYPE: DNA
<213> ORGANISM: Artificial sequence
<220> FEATURE:
<223> OTHER INFORMATION: Synthetic polynucleotide

<400> SEQUENCE: 103

| | | | | | |
|---|---|---|---|---|---|
| tccggcgtgg | tgcgcaggcg | cggtatcccc | cctcccccgc | cagctcgacc | ccggtgtggt | 60 |
| gcgcaggcgc | agtctgcgca | gggactggcg | ggactgcgcg | gcggcaacag | cagacatgtc | 120 |
| gggggtccgg | ggcctgtcgc | ggctgctgag | cgctcggcgc | ctggcgctgg | ccaaggcgtg | 180 |
| gccaacagtg | ttgcaaacag | gaacccgagg | ttttcacttc | actgttgatg | ggaacaagag | 240 |
| ggcatctgct | aaagtttcag | attccatttc | tgctcagtat | ccagtagtgg | atcatgaatt | 300 |
| tgatgcagtg | gtggtaggcg | ctggaggggc | aggcttgcga | gctgcatttg | gccttctga | 360 |
| ggcagggttt | aatacagcat | gtgttaccaa | gctgtttcct | accaggtcac | acactgttgc | 420 |
| agcacaggga | ggaatcaatg | ctgctctggg | aacatggag | gaggacaact | ggaggtggca | 480 |
| tttctacgac | accgtgaagg | ctccgactg | gctggggggac | caggatgcca | tccactacat | 540 |
| gacggagcag | gcccccgccg | ccgtggtcga | gctagaaaat | tatggcatgc | cgtttagcag | 600 |
| aactgaagat | gggaagattt | atcagcgtgc | atttggtgga | cagagcctca | gtttggaaa | 660 |
| gggcgggcag | gcccatcggt | gctgctgtgt | ggctgatcgg | actggccact | cgctattgca | 720 |
| caccttatat | ggaaggtctc | tgcgatatga | taccagctat | tttgtggagt | attttgcctt | 780 |
| ggatctcctg | atggagaatg | gggagtgccg | tggtgtcatc | gcactgtgca | tagaggacgg | 840 |
| gtccatccat | cgcataagag | caaagaacac | tgttgttgcc | acaggaggct | acgggcgcac | 900 |
| ctacttcagc | tgcacgtctg | cccacaccag | cactggcgac | ggcacggcca | tgatcaccag | 960 |
| ggcaggcctt | ccttgccagg | acctagagtt | tgttcagttc | caccctacag | gcatatatgg | 1020 |
| tgctggttgt | ctcattacgg | aaggatgtcg | tggagaggga | ggcattctca | ttaacagtca | 1080 |
| aggcgaaagg | tttatggagc | gatacgcccc | tgtcgcgaag | gacctggcgt | ctagagatgt | 1140 |
| ggtgtctcgg | tccatgactc | tggagatccg | agaaggaaga | ggctgtggcc | ctgagaaaga | 1200 |

```
tcacgtctac ctgcagctgc accacctacc tccagagcag ctggccacgc gcctgcctgg    1260
catttcagag acagccatga tcttcgctgg cgtggacgtc acgaaggagc cgatccctgt    1320
cctccccacc gtgcattata acatgggcgg cattcccacc aactacaagg ggcaggtcct    1380
gaggcacgtg aatggccagg atcagattgt gcccggcctg tacgcctgtg gggaggccgc    1440
ctgtgcctcg gtacatggtg ccaaccgcct cggggcaaac tcgctcttgg acctggttgt    1500 cttttggtcgg gcatgtgccc tgagcatcga agagtcatgc aggcctggag ataaagtccc    1560
tccaattaaa ccaaacgctg gggaagaatc tgtcatgaat cttgacaaat tgagatttgc    1620
tgatggaagc ataagaacat cggaactgcg actcagcatg cagaagtcaa tgcaaaatca    1680
tgctgccgtg ttccgtgtgg aagcgtgtt gcaagaaggt tgtgggaaaa tcagcaagct    1740
ctatggagac ctaaagcacc tgaagacgtt cgaccgggga atggtctgga cacggacct    1800 ggtggagacc ctggagctgc agaacctgat gctgtgtgcg ctgcagacca tctacggagc    1860
agaggcacgg aaggagtcac ggggcgcgca tgccagggaa gactacaagg tgcggattga    1920
tgagtacgat tactccaagc ccatccaggg gcaacagaag aagcccttg aggagcactg    1980 gaggaagcac accctgtcct atgtggacgt tggcactggg aaggtcactc tggaatatag    2040
acccgtgatc gacaaaactt tgaacgaggc tgactgtgcc accgtcccgc cagccattcg    2100
ctcctactga tgagacaaga tgtggtgatg acagaatcag cttttgtaat tatgtataat    2160
agctcatgca tgtgtccatg tcataactgt cttcatacgc ttctgcactc tggggaagaa    2220
ggagtacatt gaagggagat tggcacctag tggctgggag cttgccagga acccagtggc    2280
cagggagcgt ggcacttacc tttgtccctt gcttcattct tgtgagatga taaaactggg    2340
cacagctctt aaataaaata taaatgaaca aactttcttt tatttccaaa aaaaaaaaa    2400 aaaaa                                                                2405

<210> SEQ ID NO 104
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 104
tgggaacaag agggcatctg                                                 20

<210> SEQ ID NO 105
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 105
ccaccactgc atcaaattca tg                                              22

<210> SEQ ID NO 106
<211> LENGTH: 86
<212> TYPE: DNA
<213> ORGANISM: Artificial sequence
<220> FEATURE:
<223> OTHER INFORMATION: Synthetic polynucleotide

<400> SEQUENCE: 106
tgggaacaag agggcatctg ctaaagtttc agattccatt tctgctcagt atccagtagt    60
```
ggatcatgaa tttgatgcag tggtgg        86

<210> SEQ ID NO 107
<211> LENGTH: 1435
<212> TYPE: DNA
<213> ORGANISM: Artificial sequence
<220> FEATURE:
<223> OTHER INFORMATION: Synthetic polynucleotide

<400> SEQUENCE: 107
ggcggggcct gcttctcctc agcttcaggc ggctgcgacg agccctcagg cgaacctctc      60
ggctttcccg cgcggcgccg cctcttgctg cgcctccgcc tcctcctctg ctccgccacc     120
ggcttcctcc tcctgagcag tcagcccgcg cgccggccgg ctccgttatg gcgacccgca     180
gccctggcgt cgtgattagt gatgatgaac caggttatga ccttgattta ttttgcatac     240
ctaatcatta tgctgaggat ttggaaaggg tgtttattcc tcatggacta attatggaca     300
ggactgaacg tcttgctcga gatgtgatga aggagatggg aggccatcac attgtagccc     360
tctgtgtgct caagggggc tataaattct ttgctgacct gctggattac atcaaagcac      420
tgaatagaaa tagtgataga tccattccta tgactgtaga ttttatcaga ctgaagagct     480
attgtaatga ccagtcaaca ggggacataa agtaattgg tggagatgat ctctcaactt      540
taactggaaa gaatgtcttg attgtggaag atataattga cactggcaaa acaatgcaga     600
cttttgctttc cttggtcagg cagtataatc aaagatggt caaggtcgca agcttgctgg     660
tgaaaaggac cccacgaagt gttggatata agccagactt tgttggattt gaaattccag     720
acaagtttgt tgtaggatat gcccttgact ataatgaata cttcagggat ttgaatcatg     780
tttgtgtcat tagtgaaact ggaaaagcaa atacaaagc ctaagatgag agttcaagtt      840
gagtttggaa acatctggag tcctattgac atcgccagta aaattatcaa tgttctagtt     900
ctgtggccat ctgcttagta gagcttttg catgtatctt ctaagaattt tatctgtttt      960
gtactttaga aatgtcagtt gctgcattcc taaactgttt atttgcacta tgagcctata    1020
gactatcagt tcccttgg cggattgttg tttaacttgt aaatgaaaaa attctcttaa      1080
accacagcac tattgagtga acattgaac tcatatctgt aagaaataaa gagaagatat     1140
attagttttt taattggtat ttaatttttt atatatgcag gaaagaatag aagtgattga    1200
atattgttaa ttataccacc gtgtgttaga aaagtaagaa gcagtcaatt ttcacatcaa    1260
agacagcatc taagaagttt tgttctgtcc tggaattatt ttagtagtgt tcagtaatg     1320
ttgactgtat tttccaactt gttcaaatta ttaccagtga atctttgtca gcagttccct    1380
tttaaatgca aatcaataaa ttcccaaaaa tttaaaaaaa aaaaaaaaaa aaaaa          1435

<210> SEQ ID NO 108
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 108
tgacactggc aaaacaatgc a        21

<210> SEQ ID NO 109
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 109
ggtccttttc accagcaagc t                                                      21

<210> SEQ ID NO 110
<211> LENGTH: 94
<212> TYPE: DNA
<213> ORGANISM: Artificial sequence
<220> FEATURE:
<223> OTHER INFORMATION: Synthetic polynucleotide

<400> SEQUENCE: 110
tgacactggc aaaacaatgc agactttgct ttccttggtc aggcagtata atccaaagat            60
ggtcaaggtc gcaagcttgc tggtgaaaag gacc                                        94

<210> SEQ ID NO 111
<211> LENGTH: 2395
<212> TYPE: DNA
<213> ORGANISM: Artificial sequence
<220> FEATURE:
<223> OTHER INFORMATION: Synthetic polynucleotide

<400> SEQUENCE: 111
agaggcaggg gctggcctgg gatgcgcgcg cacctgccct cgccccgccc cgcccgcacg            60
aggggtggtg gccgaggccc cgccccgcac gcctcgcctg aggcgggtcc gctcagccca          120
ggcgcccgcc cccgcccccg ccgattaaat gggccggcgg ggctcagccc ccggaaacgg          180
tcgtacactt cggggctgcg agcgcggagg gcgacgacga cgaagcgcag acagcgtcat          240
ggcagagcag gtggccctga gccggaccca ggtgtgcggg atcctgcggg aagagctttt          300
ccagggcgat gccttccatc agtcggatac acacatattc atcatcatgg gtgcatcggg          360
tgacctggcc aagaagaaga tctacccacc catctggtgg ctgttccggg atggccttct          420
gcccgaaaac accttcatcg tgggctatgc ccgttcccgc ctcacagtgg ctgacatccg          480
caaacagagt gagcccttct tcaaggccac cccagaggag aagctcaagc tggaggactt          540 cttttgcccgc aactcctatg tggctggcca gtacgatgat gcagcctcct accagcgcct          600
caacagccac atgaatgccc tccacctggg gtcacaggcc aaccgcctct tctacctggc          660 cttgccccg accgtctacg aggccgtcac caagaacatt cacgagtcct gcatgagcca          720
gataggctgg aaccgcatca tcgtggagaa gcccttcggg agggacctgc agagctctga          780
ccggctgtcc aaccacatct cctccctgtt ccgtgaggac cagatctacc gcatcgacca          840
ctacctgggc aaggagatgg tgcagaacct catggtgctg agatttgcca acaggatctt          900
cggccccatc tggaaccggg acaacatcgc ctgcgttatc ctcaccttca aggagccctt          960
tggcactgag ggtcgcgggg gctatttcga tgaatttggg atcatccggg acgtgatgca         1020
gaaccaccta ctgcagatgc tgtgtctggt ggccatggag aagcccgcct ccaccaactc         1080
agatgacgtc cgtgatgaga aggtcaaggt gttgaaatgc atctcagagg tgcaggccaa         1140
caatgtggtc ctgggccagt acgtggggaa ccccgatgga gagggcgagg ccaccaaagg         1200
gtacctggac gacccacgg tgccccgcgg gtccaccacc gccacttttg cagccgtcgt         1260
cctctatgtg gagaatgaga ggtgggatgg ggtgccttc atcctgcgct gcggcaaggc         1320
cctgaacgag cgcaaggccg aggtgaggct gcagttccat gatgtggccg gcgacatctt         1380
ccaccagcag tgcaagcgca acgagctggt gatccgcgtg cagcccaacg aggccgtgta         1440
caccaagatg atgaccaaga agccgggcat gttcttcaac cccgaggagt cggagctgga         1500

```
cctgacctac ggcaacagat acaagaacgt gaagctccct gacgcctacg agcgcctcat    1560
cctggacgtc ttctgcggga gccagatgca cttcgtgcgc agcgacgagc tccgtgaggc    1620
ctggcgtatt ttcaccccac tgctgcacca gattgagctg gagaagccca agcccatccc    1680
ctatatttat ggcagccgag gccccacgga ggcagacgag ctgatgaaga gagtgggttt    1740
ccagtatgag ggcacctaca agtgggtgaa ccccacaag ctctgagccc tgggcaccca     1800
cctccacccc cgccacggcc accctccttc ccgccgcccg accccgagtc gggaggactc    1860
cgggaccatt gacctcagct gcacattcct ggccccgggc tctggccacc ctggcccgcc    1920
cctcgctgct gctactaccc gagcccagct acattcctca gctgccaagc actcgagacc    1980
atcctggccc ctccagaccc tgcctgagcc caggagctga gtcacctcct ccactcactc    2040
cagcccaaca gaaggaagga ggagggcgcc cattcgtctg tcccagagct tattggccac    2100
tgggtctcac tcctgagtgg ggccagggtg ggagggaggg acaaggggga ggaaaggggc    2160
gagcacccac gtgagagaat ctgcctgtgg ccttgcccgc cagcctcagt gccacttgac    2220
attccttgtc accagcaaca tctcgagccc cctggatgtc ccctgtccca ccaactctgc    2280
actccatggc caccccgtgc cacccgtagg cagcctctct gctataagaa aagcagacgc    2340
agcagctggg acccctccca acctcaatgc cctgccatta aatccgcaaa cagcc         2395

<210> SEQ ID NO 112
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 112
gaggccgtca ccaagaacat                                                  20

<210> SEQ ID NO 113
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 113
ggacagccgg tcagagctc                                                   19

<210> SEQ ID NO 114
<211> LENGTH: 111
<212> TYPE: DNA
<213> ORGANISM: Artificial sequence
<220> FEATURE:
<223> OTHER INFORMATION: Synthetic polynucleotide

<400> SEQUENCE: 114
gaggccgtca ccaagaacat tcacgagtcc tgcatgagcc agataggctg gaaccgcatc     60
atcgtggaga agcccttcgg gagggacctg cagagctctg accggctgtc c             111

<210> SEQ ID NO 115
<211> LENGTH: 1536
<212> TYPE: DNA
<213> ORGANISM: Artificial sequence
<220> FEATURE:
<223> OTHER INFORMATION: Synthetic polynucleotide

<400> SEQUENCE: 115
gtgacgcgag gctctgcgga gaccaggagt cagactgtag gacgacctcg ggtcccacgt     60
```

```
gtccccggta ctcgccggcc ggagccccg gcttcccggg gccggggac cttagcggca      120
cccacacaca gcctactttc caagcggagc catgtctggt aacggcaatg cggctgcaac      180
ggcggaagaa aacagcccaa agatgagagt gattcgcgtg ggtacccgca agagccagct      240
tgctcgcata cagacggaca gtgtggtggc aacattgaaa gcctcgtacc ctggcctgca      300
gtttgaaatc attgctatgt ccaccacagg ggacaagatt cttgatactg cactctctaa      360
gattggagag aaaagcctgt ttaccaagga gcttgaacat gccctggaga agaatgaagt      420
ggacctggtt gttcactcct tgaaggacct gcccactgtg cttcctcctg cttcaccat      480
cggagccatc tgcaagcggg aaaaccctca tgatgctgtt gtctttcacc caaaatttgt      540
tgggaagacc ctagaaaccc tgccagagaa gagtgtggtg ggaaccagct ccctgcgaag      600
agcagcccag ctgcagagaa agttcccgca tctggagttc aggagtattc ggggaaacct      660
caacacccgg cttcggaagc tggacgagca gcaggagttc agtgccatca tcctggcaac      720
agctggcctg cagcgcatgg gctggcacaa ccgggtgggg cagatcctgc accctgagga      780
atgcatgtat gctgtgggcc agggggcctt gggcgtggaa gtgcgagcca aggaccagga      840
catcttggat ctggtgggtg tgctgcacga tcccgagact ctgcttcgct gcatcgctga      900
aagggccttc ctgaggcacc tggaaggagg ctgcagtgtg ccagtagccg tgcatacagc      960
tatgaaggat gggcaactgt acctgactgg aggagtctgg agtctagacg gctcagatag     1020
catacaagag accatgcagg ctaccatcca tgtccctgcc cagcatgaag atggccctga     1080
ggatgaccca cagttggtag gcatcactgc tcgtaacatt ccacgagggc cccagttggc     1140
tgcccagaac ttgggcatca gcctggccaa cttgttgctg agcaaaggag ccaaaaacat     1200
cctggatgtt gcacggcagc ttaacgatgc ccattaactg gtttgtgggg cacagatgcc     1260
tgggttgctg ctgtccagtg cctacatccc gggcctcagt gccccattct cactgctatc     1320
tggggagtga ttaccccggg agactgaact gcagggttca agccttccag ggatttgcct     1380
caccttgggg ccttgatgac tgccttgcct cctcagtatg tggggcttc atctctttag     1440
agaagtccaa gcaacagcct ttgaatgtaa ccaatcctac taataaacca gttctgaagg     1500
taaaaaaaaa aaaaaaaaa aaaaaaaaaa aaaaaa                                 1536

<210> SEQ ID NO 116
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 116
tgagagtgat tcgcgtggg                                                    19

<210> SEQ ID NO 117
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 117
ccagggtacg aggctttcaa t                                                 21

<210> SEQ ID NO 118
<211> LENGTH: 91
<212> TYPE: DNA
```

<213> ORGANISM: Artificial sequence
<220> FEATURE:
<223> OTHER INFORMATION: Synthetic polynucleotide

<400> SEQUENCE: 118

```
tgagagtgat tcgcgtgggt acccgcaaga gccagcttgc tcgcatacag acggacagtg      60
tggtggcaac attgaaagcc tcgtaccctg g                                     91
```

<210> SEQ ID NO 119
<211> LENGTH: 748
<212> TYPE: DNA
<213> ORGANISM: Artificial sequence
<220> FEATURE:
<223> OTHER INFORMATION: Synthetic polynucleotide

<400> SEQUENCE: 119

```
gcagataatg ggaggagccg ggcccgagcg agctctttcc tttcgctgct gcggccgcag      60
ccatgagtat gctcaggctt cagaagaggc tcgcctctag tgtcctccgc tgtggcaaga     120
agaaggtctg gttagacccc aatgagacca atgaaatcgc caatgccaac tcccgtcagc     180
agatccggaa gctcatcaaa gatgggctga tcatccgcaa gcctgtgacg gtccattccc     240
gggctcgatg ccggaaaaac accttggccc gccggaaggg caggcacatg gcataggta      300 agcggaaggg tacagccaat gcccgaatgc agagaaggt cacatggatg aggagaatga      360
ggattttgcg ccggctgctc agaagatacc gtgaatctaa aagatcgat cgccacatgt      420 atcacagcct gtacctgaag gtgaagggga atgtgttcaa aaacaagcgg attctcatgg     480
aacacatcca aagctgaag gcagacaagg cccgcaagaa gctcctggct gaccaggctg      540 aggccccgcag gtctaagacc aaggaagcac gcaagcgccg tgaagagcgc ctccaggcca     600
agaaggagga gatcatcaag actttatcca aggaggaaga gaccaagaaa taaaacctcc     660
cactttgtct gtacatactg gcctctgtga ttacatagat cagccattaa aataaaacaa     720
gccttaatct gcaaaaaaaa aaaaaaaa                                        748
```

<210> SEQ ID NO 120
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 120

```
tggcaagaag aaggtctggt tag                                              23
```

<210> SEQ ID NO 121
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 121

```
tgatcagccc atctttgatg ag                                               22
```

<210> SEQ ID NO 122
<211> LENGTH: 101
<212> TYPE: DNA
<213> ORGANISM: Artificial sequence
<220> FEATURE:
<223> OTHER INFORMATION: Synthetic polynucleotide

<400> SEQUENCE: 122

```
tggcaagaag aaggtctggt tagaccccaa tgagaccaat gaaatcgcca atgccaactc    60
ccgtcagcag atccggaagc tcatcaaaga tgggctgatc a                       101
```

<210> SEQ ID NO 123
<211> LENGTH: 186
<212> TYPE: DNA
<213> ORGANISM: Artificial sequence
<220> FEATURE:
<223> OTHER INFORMATION: Synthetic polynucleotide

<400> SEQUENCE: 123

```
ttcactgtca ctgcccatcg ggcccagcat gagctcaact gctctctgca ggaccccaga    60
agtggccgat cagccaacgc ctctgtcatc cttaatgtgc aattcaagcc agagattgcc   120
caagtcggcg ccaagtacca ggaagctcag ggcccaggcc tcctggttgt cctgtttgcc   180
ctggtg                                                              186
```

<210> SEQ ID NO 124
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 124

```
ttcactgtca ctgcccatcg g                                              21
```

<210> SEQ ID NO 125
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 125

```
caccagggca aacaggacaa c                                              21
```

<210> SEQ ID NO 126
<211> LENGTH: 1125
<212> TYPE: DNA
<213> ORGANISM: Artificial sequence
<220> FEATURE:
<223> OTHER INFORMATION: Synthetic polynucleotide

<400> SEQUENCE: 126

```
atggcgctgc ctccaggccc agccgccctc cggcacacac tgctgctcct gccagcccett    60 ctgagctcag gttgggggga gttggagcca caaatagatg gtcagacctg ggctgagcgg   120
gcacttcggg agaatgaacg ccacgccttc acctgccggg tggcagggg  gcctggcacc   180 cccagattgg cctggtatct ggatggacag ctgcaggagg ccagcacctc aagactgctg   240
agcgtgggag gggaggcctt ctctggaggc cagcaccct tcactgtcac tgcccatcgg   300
gcccagcatg agctcaactg ctctctgcag gaccccagaa gtggccgatc agccaacgcc   360
tctgtcatcc ttaatgtgca attcaagcca gagattgccc aagtcggcgc caagtaccag   420
gaagctcagg gccaggcct cctggttgtc ctgtttgccc tggtgcgtgc aacccgccg   480 gccaatgtca cctggatcga ccaggatggg ccagtgactg tcaacacctc tgacttcctg   540
gtgctggatg cgcagaacta cccctggctc accaaccaca cggtgcagct gcagctccgc   600
agcctggcac acaacctctc ggtggtggcc accaatgacg tgggtgtcac cagtgcgtcg   660
```

```
cttccagccc cagggcttct ggctacccgg gtggaagtgc cactgctggg cattgttgtg    720
gctgctgggc ttgcactggg caccctcgtg gggttcagca ccttggtggc ctgcctggtc    780
tgcagaaaag agaagaaaac caaaggcccc tcccggcacc catctctgat atcaagtgac    840
tccaacaacc taaaactcaa caacgtgcgc ctgccacggg agaacatgtc cctcccgtcc    900
aaccttcagc tcaatgacct cactccagat tccagagcag tgaaaccagc agaccggcag    960
atggctcaga caacagccg gccagagctt ctggacccgg agcccggcgg cctcctcacc    1020
agccaaggtt tcatccgcct cccagtgctg ggctatatct atcgagtgtc cagcgtgagc    1080
agtgatgaga tctggctcga ctacaaagac gatgacgaca agtga                    1125
```

<210> SEQ ID NO 127
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 127

```
aaagctagcg ccaccatggc gctgcctcca ggcccag                              37
```

<210> SEQ ID NO 128
<211> LENGTH: 53
<212> TYPE: DNA
<213> ORGANISM: Artificial sequence
<220> FEATURE:
<223> OTHER INFORMATION: Synthetic polynucleotide

<400> SEQUENCE: 128

```
aaagaattct cacttgtcgt catcgtcttt gtagtcgagc cagatctcat cac            53
```

<210> SEQ ID NO 129
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 129

```
Met Ala Leu Pro Pro Gly Pro Ala Ala Leu Arg His Thr Leu Leu Leu
1               5                   10                  15

Leu Pro Ala Leu Leu Ser Ser Gly Trp Gly Glu Leu Glu Pro Gln Ile
            20                  25                  30

Asp Gly Gln Thr Trp Ala Glu Arg Ala Leu Arg Glu Asn Glu Arg His
        35                  40                  45

Ala Phe Thr Cys Arg Val Ala Gly Gly Pro Gly Thr Pro Arg Leu Ala
    50                  55                  60

Trp Tyr Leu Asp Gly Gln Leu Gln Glu Ala Ser Thr Ser Arg Leu Leu
65                  70                  75                  80

Ser Val Gly Gly Glu Ala Phe Ser Gly Gly Thr Ser Thr Phe Thr Val
                85                  90                  95

Thr Ala His Arg Ala Gln His Glu Leu Asn Cys Ser Leu Gln Asp Pro
            100                 105                 110

Arg Ser Gly Arg Ser Ala Asn Ala Ser Val Ile Leu Asn Val Gln Phe
        115                 120                 125

Lys Pro Glu Ile Ala Gln Val Gly Ala Lys Tyr Gln Glu Ala Gln Gly
    130                 135                 140

Pro Gly Leu Leu Val Val Leu Phe Ala Leu Val Arg Ala Asn Pro Pro
145                 150                 155                 160
```

Ala Asn Val Thr Trp Ile Asp Gln Asp Gly Pro Val Thr Val Asn Thr
            165                 170                 175

Ser Asp Phe Leu Val Leu Asp Ala Gln Asn Tyr Pro Trp Leu Thr Asn
        180                 185                 190

His Thr Val Gln Leu Gln Leu Arg Ser Leu Ala His Asn Leu Ser Val
        195                 200                 205

Val Ala Thr Asn Asp Val Gly Val Thr Ser Ala Ser Leu Pro Ala Pro
    210                 215                 220

Gly Leu Leu Ala Thr Arg Val Glu Val Pro Leu Leu Gly Ile Val Val
225                 230                 235                 240

Ala Ala Gly Leu Ala Leu Gly Thr Leu Val Gly Phe Ser Thr Leu Val
            245                 250                 255

Ala Cys Leu Val Cys Arg Lys Glu Lys Lys Thr Lys Gly Pro Ser Arg
        260                 265                 270

His Pro Ser Leu Ile Ser Ser Asp Ser Asn Asn Leu Lys Leu Asn Asn
        275                 280                 285

Val Arg Leu Pro Arg Glu Asn Met Ser Leu Pro Ser Asn Leu Gln Leu
    290                 295                 300

Asn Asp Leu Thr Pro Asp Ser Arg Ala Val Lys Pro Ala Asp Arg Gln
305                 310                 315                 320

Met Ala Gln Asn Asn Ser Arg Pro Glu Leu Leu Asp Pro Glu Pro Gly
            325                 330                 335

Gly Leu Leu Thr Ser Gln Gly Phe Ile Arg Leu Pro Val Leu Gly Tyr
        340                 345                 350

Ile Tyr Arg Val Ser Ser Val Ser Ser Asp Glu Ile Trp Leu Asp Tyr
        355                 360                 365

Lys Asp Asp Asp Asp Lys
    370

<210> SEQ ID NO 130
<211> LENGTH: 1100
<212> TYPE: DNA
<213> ORGANISM: Artificial sequence
<220> FEATURE:
<223> OTHER INFORMATION: Synthetic polynucleotide

<400> SEQUENCE: 130
atggcgctgc ctccaggccc agccgccctc cggcacacac tgctgctcct gccagccctt      60
ctgagctcag gttgggggga gttggagcca caaatagatg gtcagacctg ggctgagcgg     120
gcacttcggg agaatgaacg ccacgccttc acctgccggg tggcagggg gcctggcacc      180 cccagattgg cctggtatct ggatggacag ctgcaggagg ccagcacctc aagactgctg     240
agcgtgggag gggaggcctt ctctggaggc accagcacct tcactgtcac tgcccatcgg     300
gcccagcatg agctcaactg ctctctgcag gaccccagaa gtggccgatc agccaacgcc     360
tctgtcatcc ttaatgtgca attcaagcca gagattgccc aagtcggcgc caagtaccag     420
gaagctcagg gccaggcct cctggttgtc ctgtttgccc tggtgcgtgc caacccgccg     480
gccaatgtca cctggatcga ccaggatggg ccagtgactg tcaacacctc tgacttcctg     540
gtgctggatg cgcagaacta ccctggctc accaaccaca cggtgcagct gcagctccgc     600
agcctggcac acaacctctc ggtggtggcc accaatgacg tgggtgtcac cagtgcgtcg     660
cttccagccc cagggcttct ggctacccgg gtggaagtgc cactgctggg cattgttgtg     720
gctgctgggc ttgcactggg caccctcgtg gggttcagca ccttggtggc ctgcctggtc     780

```
tgcagaaaag agaagaaaac caaaggcccc tcccggcacc catctctgat atcaagtgac    840
tccaacaacc taaaactcaa caacgtgcgc ctgccacggg agaacatgtc cctcccgtcc    900
aaccttcagc tcaatgacct cactccagat tccagagcag tgaaaccagc agaccggcag    960
atggctcaga caacagccg gccagagctt ctggacccgg agcccggcgg cctcctcacc     1020
agccaaggtt tcatccgcct cccagtgctg ggctatatct atcgagtgtc cagcgtgagc    1080
agtgatgaga tctggctctg                                                1100
```

<210> SEQ ID NO 131
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 131

```
aaagaattct cagagccaga tctcatcac                                       29
```

<210> SEQ ID NO 132
<211> LENGTH: 1476
<212> TYPE: DNA
<213> ORGANISM: Artificial sequence
<220> FEATURE:
<223> OTHER INFORMATION: Synthetic polynucleotide

<400> SEQUENCE: 132

```
atccaggtga ccgtgtccaa cccctaccac gtggtgatcc tcttccagcc tgtgaccctg     60
ccctgtacct accagatgac ctcgaccccc acgcaaccca tcgtcatctg gaagtacaag    120
tctttctgcc gggaccgcat cgccgatgcc ttctccccgg ccagcgtcga caccagctc    180 aatgcccagc tggcagccgg gaacccaggc tacaacccct acgtcgagtg ccaggacagc    240
gtgcgcaccg tcagggtcgt ggccaccaag cagggcaacg ctgtgaccct gggagattac    300
taccagggcc ggaggattac catcaccgga aatgctgacc tgacctttga ccagacggcg    360 tgggggggaca gtggtgtgta ttactgctcc gtggtctcag cccaggacct ccaggggaac    420
aatgaggcct acgcagagct catcgtcctt gtgtatgccg ccggcaaagc agccacctca    480
ggtgttccca gcatttatgc ccccagcacc tatgcccacc tgtctcccgc caagacccca    540 ccccaccag ctatgattcc catgggccct gcctacaacg gtaccctgg aggataccct     600 ggagacgttg acaggagtag ctcagctggt ggccaaggct cctatgtacc cctgcttcgg    660
gacacggaca gcagtgtggc ctctgaagtc cgcagtggct acaggattca ggccagccag    720
caggacgact ccatgcgggt cctgtactac atggagaagg agctggccaa cttcgaccct    780
tctcgacctg gccccccag tggccgtgtg gagcgggcca tgagtgaagt cacctccctc    840
cacgaggacg actggcgatc tcggccttcc cggggccctg ccctcacccc gatccgggat    900
gaggagtggg gtggccactc ccccggagt cccaggggat gggaccagga gcccgccagg    960
gagcaggcag gcggggctg gcgggccagg cggcccggg cccgctccgt ggacgccctg    1020
gacgacctca ccccgccgag caccgccgag tcagggagca ggtctcccac gagtaatggt    1080
gggagaagcc gggcctacat gccccgcgcg agccgcagcc gggacgacct ctatgaccaa    1140
gacgactcga gggacttccc acgctcccgg acccccact acgacgactt caggtctcgg    1200
gagcgccctc ctgccgaccc caggtccac caccaccgta cccgggaccc tcgggacaac    1260
ggctccaggt ccggggacct cccctatgat gggcggctac tggaggaggc tgtgaggaag    1320 aagggtcgg aggagaggag gagacccca aaggaggagg aggaagaggc ctactacccg    1380
```

```
cccgcgccgc ccccgtactc ggagaccgac tcgcaggcgt cccgagagcg caggctcaag   1440
aagaacttgg ccctgagtcg ggaaagttta gtcgtc                             1476

<210> SEQ ID NO 133
<211> LENGTH: 2201
<212> TYPE: DNA
<213> ORGANISM: Artificial sequence
<220> FEATURE:
<223> OTHER INFORMATION: Synthetic polynucleotide

<400> SEQUENCE: 133
cgggatttgg gtcgcggttc ttgtttgtgg atcgctgtga tcgtcacttg acaatgcaga     60
tcttcgtgaa gactctgact ggtaagacca tcaccctcga ggttgagccc agtgacacca    120
tcgagaatgt caaggcaaag atccaagata aggaaggcat ccctcctgac cagcagaggc    180
tgatctttgc tggaaaacag ctggaagatg gcgcaccct gtctgactac aacatccaga    240
aagagtccac cctgcacctg gtgctccgtc tcagaggtgg gatgcaaatc ttcgtgaaga    300
cactcactgg caagaccatc acccttgagg tggagcccag tgacaccatc gagaacgtca    360
aagcaaagat ccaggacaag gaaggcattc ctcctgacca gcagaggttg atctttgccg    420
gaaagcagct ggaagatggg cgcaccctgt ctgactacaa catccagaaa gagtctaccc    480
tgcacctggt gctccgtctc agaggtggga tgcagatctt cgtgaagacc ctgactggta    540
agaccatcac cctcgaggtg gagcccagtg acaccatcga gaatgtcaag gcaaagatcc    600
aagataagga aggcattcct cctgatcagc agaggttgat ctttgccgga aaacagctgg    660
aagatggtcg taccctgtct gactacaaca tccagaaaga gtccaccttg cacctggtac    720
tccgtctcag aggtgggatg caaatcttcg tgaagacact cactggcaag accatcaccc    780
ttgaggtcga gcccagtgac actatcgaga cgtcaaagc aaagatccaa gacaaggaag    840
gcattcctcc tgaccagcag aggttgatct ttgccggaaa gcagctggaa gatgggcgca    900
ccctgtctga ctacaacatc cagaaagagt ctaccctgca cctggtgctc cgtctcagag    960
gtgggatgca gatcttcgtg aagaccctga ctggtaagac catcaccctc gaagtggagc   1020
cgagtgacac cattgagaat gtcaaggcaa agatccaaga caaggaaggc atccctcctg   1080
accagcagag gttgatcttt gccggaaaac agctggaaga tggtcgtacc ctgtctgact   1140
acaacatcca gaaagagtcc accttgcacc tggtgctccg tctcagaggt gggatgcaga   1200
tcttcgtgaa gaccctgact ggtaagacca tcactctcga ggtggagccg agtgacacca   1260
ttgagaatgt caaggcaaag atccaagaca aggaaggcat ccctcctgat cagcagaggt   1320
tgatctttgc tgggaaacag ctggaagatg gacgcaccct gtctgactac aacatccaga   1380
aagagtccac cctgcacctg gtgctccgtc ttagaggtgg gatgcagatc ttcgtgaaga   1440
ccctgactgg taagaccatc actctcgaag tggagccgag tgacaccatt gagaatgtca   1500
aggcaaagat ccaagacaag gaaggcatcc ctcctgacca gcagaggttg atctttgctg   1560
ggaaacagct ggaagatgga cgcaccctgt ctgactacaa catccagaaa gagtccaccc   1620
tgcacctggt gctccgtctt agaggtggga tgcagatctt cgtgaagacc ctgactggta   1680
agaccatcac tctcgaagtg gagccgagtg acaccattga gaatgtcaag gcaaagatcc   1740
aagacaagga aggcatccct cctgaccagc agaggttgat ctttgctggg aaacagctgg   1800
aagatggacg caccctgtct gactacaaca tccagaaaga gtccaccctg cacctggtgc   1860
tccgtctcag aggtgggatg cagatcttcg tgaagaccct gactggtaag accatcaccc   1920
```

```
tcgaggtgga gcccagtgac accatcgaga atgtcaaggc aaagatccaa gataaggaag    1980
gcatccctcc tgatcagcag aggttgatct ttgctgggaa acagctggaa gatggacgca    2040
ccctgtctga ctacaacatc cagaaagagt ccactctgca cttggtcctg cgcttgaggg    2100
ggggtgtcta agtttcccct tttaaggttt caacaaattt cattgcactt tcctttcaat    2160
aaagttgttg cattcccaaa aaaaaaaaaa aaaaaaaaa a                         2201
```

```
<210> SEQ ID NO 134
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 134
atttgggtcg cggttcttg                                                 19
```

```
<210> SEQ ID NO 135
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 135
tgccttgaca ttctcgatgg t                                              21
```

```
<210> SEQ ID NO 136
<211> LENGTH: 133
<212> TYPE: DNA
<213> ORGANISM: Artificial sequence
<220> FEATURE:
<223> OTHER INFORMATION: Synthetic polynucleotide

<400> SEQUENCE: 136
atttgggtcg cggttcttgt ttgtggatcg ctgtgatcgt cacttgacaa tgcagatctt    60
cgtgaagact ctgactggta agaccatcac cctcgaggtt gagcccagtg acaccatcga    120
gaatgtcaag gca                                                       133
```

```
<210> SEQ ID NO 137
<211> LENGTH: 182
<212> TYPE: DNA
<213> ORGANISM: Artificial sequence
<220> FEATURE:
<223> OTHER INFORMATION: Synthetic polynucleotide

<400> SEQUENCE: 137
gtcgacaacc agctcaatgc ccagctggca gccgggaacc caggctacaa cccctacgtc    60
gagtgccagg acagcgtgcg caccgtcagg gtcgtggcca ccaagcaggg caacgctgtg    120
accctgggag attactacca gggccggagg attaccatca ccggaaatgc tgacctgacc    180
tt                                                                   182
```

```
<210> SEQ ID NO 138
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 138
gtcgacaacc agctcaatgc                                                20
```

<210> SEQ ID NO 139
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 139
aaggtcaggt cagcatttcc                                                 20

<210> SEQ ID NO 140
<211> LENGTH: 154
<212> TYPE: DNA
<213> ORGANISM: Artificial sequence
<220> FEATURE:
<223> OTHER INFORMATION: Synthetic polynucleotide

<400> SEQUENCE: 140
atgctgacct gacctttgac cagacggcgt gggggggacag tggtgtgtat tactgctccg     60
tggtctcagc ccaggacctc caggggaaca tgaggccta cgcagagctc atcgtccttg     120
ggaggacctc aggggtggct gagctcttac ctgg                                154

<210> SEQ ID NO 141
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 141
atgctgacct gacctttgac                                                 20

<210> SEQ ID NO 142
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 142
ccaggtaaga gctcagccac                                                 20

<210> SEQ ID NO 143
<211> LENGTH: 601
<212> TYPE: PRT
<213> ORGANISM: Artificial sequence
<220> FEATURE:
<223> OTHER INFORMATION: Synthetic polypeptide

<400> SEQUENCE: 143

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser

```
                    85                  90                  95
Val Asp Asn Gln Leu Asn Ala Gln Leu Ala Ala Gly Asn Pro Gly Tyr
                100                 105                 110
Asn Pro Tyr Val Glu Cys Gln Asp Ser Val Arg Thr Arg Val Val
                115                 120                 125
Ala Thr Lys Gln Gly Asn Ala Val Thr Leu Gly Asp Tyr Tyr Gln Gly
            130                 135                 140
Arg Arg Ile Thr Ile Thr Gly Asn Ala Asp Leu Thr Phe Asp Gln Thr
145                 150                 155                 160
Ala Trp Gly Asp Ser Gly Val Tyr Tyr Cys Ser Val Val Ser Ala Gln
                165                 170                 175
Asp Leu Gln Gly Asn Asn Glu Ala Tyr Ala Glu Leu Ile Val Leu Gly
                180                 185                 190
Arg Thr Ser Gly Val Ala Glu Leu Leu Pro Gly Phe Gln Ala Gly Pro
            195                 200                 205
Met Glu Asp Trp Leu Phe Val Val Val Cys Leu Ala Ala Phe Leu
        210                 215                 220
Ile Phe Leu Leu Leu Gly Ile Cys Trp Cys Gln Cys Cys Pro His Thr
225                 230                 235                 240
Cys Cys Cys Tyr Val Arg Cys Pro Cys Cys Pro Asp Lys Cys Cys Cys
                245                 250                 255
Pro Glu Ala Leu Tyr Ala Ala Gly Lys Ala Ala Thr Ser Gly Val Pro
                260                 265                 270
Ser Ile Tyr Ala Pro Ser Thr Tyr Ala His Leu Ser Pro Ala Lys Thr
            275                 280                 285
Pro Pro Pro Pro Ala Met Ile Pro Met Gly Pro Ala Tyr Asn Gly Tyr
            290                 295                 300
Pro Gly Gly Tyr Pro Gly Asp Val Asp Arg Ser Ser Ala Gly Gly
305                 310                 315                 320
Gln Gly Ser Tyr Val Pro Leu Leu Arg Asp Thr Asp Ser Ser Val Ala
                325                 330                 335
Ser Glu Val Arg Ser Gly Tyr Arg Ile Gln Ala Ser Gln Gln Asp Asp
                340                 345                 350
Ser Met Arg Val Leu Tyr Tyr Met Glu Lys Glu Leu Ala Asn Phe Asp
            355                 360                 365
Pro Ser Arg Pro Gly Pro Pro Ser Gly Arg Val Glu Arg Ala Met Ser
            370                 375                 380
Glu Val Thr Ser Leu His Glu Asp Asp Trp Arg Ser Arg Pro Ser Arg
385                 390                 395                 400
Gly Pro Ala Leu Thr Pro Ile Arg Asp Glu Glu Trp Gly Gly His Ser
                405                 410                 415
Pro Arg Ser Pro Arg Gly Trp Asp Gln Glu Pro Ala Arg Glu Gln Ala
            420                 425                 430
Gly Gly Gly Trp Arg Ala Arg Arg Pro Arg Ala Arg Ser Val Asp Ala
            435                 440                 445
Leu Asp Asp Leu Thr Pro Pro Ser Thr Ala Glu Ser Gly Ser Arg Ser
        450                 455                 460
Pro Thr Ser Asn Gly Gly Arg Ser Arg Ala Tyr Met Pro Pro Arg Ser
465                 470                 475                 480
Arg Ser Arg Asp Asp Leu Tyr Asp Gln Asp Asp Ser Arg Asp Phe Pro
                485                 490                 495
Arg Ser Arg Asp Pro His Tyr Asp Asp Phe Arg Ser Arg Glu Arg Pro
                500                 505                 510
```

```
Pro Ala Asp Pro Arg Ser His His Arg Thr Arg Asp Pro Arg Asp
            515                 520                 525

Asn Gly Ser Arg Ser Gly Asp Leu Pro Tyr Asp Gly Arg Leu Leu Glu
530                 535                 540

Glu Ala Val Arg Lys Lys Gly Ser Glu Arg Arg Arg Pro His Lys
545                 550                 555                 560

Glu Glu Glu Glu Glu Ala Tyr Tyr Pro Pro Ala Pro Pro Tyr Ser
                565                 570                 575

Glu Thr Asp Ser Gln Ala Ser Arg Gly Arg Arg Leu Lys Lys Asn Leu
            580                 585                 590

Ala Leu Ser Arg Glu Ser Leu Val Val
            595                 600

<210> SEQ ID NO 144
<211> LENGTH: 609
<212> TYPE: PRT
<213> ORGANISM: Artificial sequence
<220> FEATURE:
<223> OTHER INFORMATION: Synthetic polypeptide

<400> SEQUENCE: 144

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Met Glu Asp Trp Leu Phe Val Val Val Cys Leu Ala Ala Phe Leu
    210                 215                 220

Ile Phe Leu Leu Leu Gly Ile Cys Trp Cys Gln Cys Cys Pro His Thr
225                 230                 235                 240

Cys Cys Cys Tyr Val Arg Cys Pro Cys Cys Pro Asp Lys Cys Cys Cys
                245                 250                 255

Pro Glu Ala Leu Tyr Ala Ala Gly Lys Ala Ala Thr Ser Gly Val Pro
            260                 265                 270
```

```
Ser Ile Tyr Ala Pro Ser Thr Tyr Ala His Leu Ser Pro Ala Lys Thr
        275                 280                 285

Pro Pro Pro Ala Met Ile Pro Met Gly Pro Ala Tyr Asn Gly Tyr
290                 295                 300

Pro Gly Gly Tyr Pro Gly Asp Val Asp Arg Ser Ser Ala Gly Gly
305                 310                 315                 320

Gln Gly Ser Tyr Val Pro Leu Leu Arg Asp Thr Asp Ser Ser Val Ala
            325                 330                 335

Ser Glu Val Arg Ser Gly Tyr Arg Ile Gln Ala Ser Gln Gln Asp Asp
        340                 345                 350

Ser Met Arg Val Leu Tyr Tyr Met Glu Lys Glu Leu Ala Asn Phe Asp
            355                 360                 365

Pro Ser Arg Pro Gly Pro Pro Ser Gly Arg Val Glu Arg Ala Met Ser
370                 375                 380

Glu Val Thr Ser Leu His Glu Asp Asp Trp Arg Ser Arg Pro Ser Arg
385                 390                 395                 400

Gly Pro Ala Leu Thr Pro Ile Arg Asp Glu Glu Trp Gly Gly His Ser
                405                 410                 415

Pro Arg Ser Pro Arg Gly Trp Asp Gln Glu Pro Ala Arg Glu Gln Ala
            420                 425                 430

Gly Gly Gly Trp Arg Ala Arg Arg Pro Arg Ala Arg Ser Val Asp Ala
        435                 440                 445

Leu Asp Asp Leu Thr Pro Pro Ser Thr Ala Glu Ser Gly Ser Arg Ser
    450                 455                 460

Pro Thr Ser Asn Gly Gly Arg Ser Arg Ala Tyr Met Pro Pro Arg Ser
465                 470                 475                 480

Arg Ser Arg Asp Asp Leu Tyr Asp Gln Asp Asp Ser Arg Asp Phe Pro
                485                 490                 495

Arg Ser Arg Asp Pro His Tyr Asp Asp Phe Arg Ser Arg Glu Arg Pro
            500                 505                 510

Pro Ala Asp Pro Arg Ser His His His Arg Thr Arg Asp Pro Arg Asp
        515                 520                 525

Asn Gly Ser Arg Ser Gly Asp Leu Pro Tyr Asp Gly Arg Leu Leu Glu
    530                 535                 540

Glu Ala Val Arg Lys Lys Gly Ser Glu Arg Arg Pro His Lys
545                 550                 555                 560

Glu Glu Glu Glu Glu Ala Tyr Tyr Pro Pro Ala Pro Pro Tyr Ser
                565                 570                 575

Glu Thr Asp Ser Gln Ala Ser Arg Glu Arg Arg Leu Lys Lys Asn Leu
            580                 585                 590

Ala Leu Ser Arg Glu Ser Leu Val Val Asp Tyr Lys Asp Asp Asp Asp
        595                 600                 605

Lys

<210> SEQ ID NO 145
<211> LENGTH: 1806
<212> TYPE: DNA
<213> ORGANISM: Artificial sequence
<220> FEATURE:
<223> OTHER INFORMATION: Synthetic polynucleotide

<400> SEQUENCE: 145
atggcgctgt tggccggcgg gctctccaga gggctgggct cccacccggc cgccgcaggc    60
cgggacgcgg tcgtcttcgt gtggcttctg cttagcacct ggtgcacagc tcctgccaga   120
```

```
gccatccagg tgaccgtgtc aacccctac acgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
ctcaatgccc agctggcagc cgggaaccca ggctacaacc cctacgtcga gtgccaggac    360
agcgtgcgca ccgtcagggt cgtggccacc aagcagggca cgctgtgacc cctgggagat    420
tactaccagg gccggaggat taccatcacc ggaaatgctg acctgacctt tgaccagacg    480
gcgtgggggg acagtggtgt gtattactgc tccgtggtct cagcccagga cctccagggg    540
aacaatgagg cctacgcaga gctcatcgtc cttggggagg cctcaggggt ggctgagctc    600
ttacctggtt ttcaggcggg gcccatggaa gactggctct cgtggttgt ggtatgcctg    660 gctgccttcc tcatcttcct cctcctgggc atctgctggt gccagtgctg cccgcacact    720
tgctgctgct acgtcaggtg cccctgctgc ccagacaagt gctgctgccc cgaggccctg    780
tatgccgccg gcaaagcagc cacctcaggt gttcccagca tttatgcccc cagcacctat    840
gcccacctgt ctcccgccaa gaccccaccc ccaccagcta tgattcccat gggccctgcc    900
tacaacgggt accctggagg ataccctgga gacgttgaca ggagtagctc agctggtggc    960
caaggctcct atgtacccct gcttcgggac acggacagca gtgtggcctc tgaagtccgc   1020
agtggctaca ggattcaggc cagccagcag gacgactcca tgcgggtcct gtactacatg   1080
gagaaggagc tggccaactt cgaccttct cgacctggcc cccccagtgg ccgtgtggag   1140
cgggccatga gtgaagtcac ctccctccac gaggacgact ggcgatctcg gccttcccgg   1200
ggccctgccc tcacccccgat ccgggatgag gagtgggtg gccactcccc ccggagtccc   1260
aggggatggg accaggagcc cgccaggag caggcaggcg ggggctggcg ggccaggcgg   1320
ccccgggccc gctccgtgga cgccctggac gacctcacc cgccgagcac cgccgagtca   1380
gggagcaggt ctcccacgag taatggtggg agaagccggg cctacatgcc cccgcggagc   1440
cgcagccggg acgacctcta tgaccaagac gactcgaggg acttcccacg ctcccgggac   1500
ccccactacg acgacttcag gtctcggag cgccctcctg ccgacccag gtcccaccac   1560 caccgtaccc gggaccctcg ggacaacggc tccaggtccg ggacctccc ctatgatggg   1620 cggctactgg aggagctgt gaggaagaag gggtcggagg agaggaggag accccacaag   1680
gaggaggagg aagaggccta ctacccgccc gcgccgcccc cgtactcgga gaccgactcg   1740
caggcgtccc gagagcgcag gctcaagaag aacttggccc tgagtcggga aagtttagtc   1800
gtctga                                                              1806

<210> SEQ ID NO 146
<211> LENGTH: 1830
<212> TYPE: DNA
<213> ORGANISM: Artificial sequence
<220> FEATURE:
<223> OTHER INFORMATION: Synthetic polynucleotide

<400> SEQUENCE: 146
atggcgctgt tggccggcgg gctctccaga gggctgggct cccacccggc cgccgcaggc     60
cgggacgcgg tcgtcttcgt gtggcttctg cttagcacct ggtgcacagc tcctgccaga    120
gccatccagg tgaccgtgtc aacccctac acgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
```

| | |
|---|---|
| ctcaatgccc agctggcagc cgggaaccca ggctacaacc cctacgtcga gtgccaggac | 360 |
| agcgtgcgca ccgtcaggt cgtggccacc aagcagggca acgctgtgac cctgggagat | 420 |
| tactaccagg gccggaggat taccatcacc ggaaatgctg acctgacctt tgaccagacg | 480 |
| gcgtgggggg acagtggtgt gtattactgc tccgtggtct cagcccagga cctccagggg | 540 |
| aacaatgagg cctacgcaga gctcatcgtc cttggagga cctcagggt ggctgagctc | 600 |
| ttacctggtt ttcaggcggg gcccatggaa gactggctct tcgtggttgt ggtatgcctg | 660 |
| gctgccttcc tcatcttcct cctcctgggc atctgctggt gccagtgctg cccgcacact | 720 |
| tgctgctgct acgtcaggtg ccctgctgc cagacaagt gctgctgccc cgaggccctg | 780 |
| tatgccgccg gcaaagcagc cacctcaggt gttcccagca tttatgcccc cagcacctat | 840 |
| gcccacctgt ctcccgccaa gaccccaccc ccaccagcta tgattcccat gggccctgcc | 900 |
| tacaacgggt accctggagg atacctggga gacgttgaca ggagtagctc agctggtggc | 960 |
| caaggctcct atgtaccct gcttcgggac acggacagca gtgtggcctc tgaagtccgc | 1020 |
| agtggctaca ggattcaggc cagccagcag gacgactcca tgcgggtcct gtactacatg | 1080 |
| gagaaggagc tggccaactt cgacccttct cgacctggcc ccccagtgg ccgtgtggag | 1140 |
| cgggccatga gtgaagtcac ctccctccac gaggacgact ggcgatctcg gccttccgg | 1200 |
| ggccctgccc tcaccccgat ccgggatgag gagtggggtg ccactcccc ccggagtccc | 1260 |
| aggggatggg accaggagcc cgccaggag caggcaggcg ggggctggcg ggccaggcgg | 1320 |
| ccccgggccc gctccgtgga cgccctggac gacctcaccc cgccgagcac cgccgagtca | 1380 |
| gggagcaggt ctcccacgag taatggtggg agaagccggg cctacatgcc cccgcggagc | 1440 |
| cgcagccggg acgacctcta tgaccaagac gactcgaggg acttcccacg ctcccgggac | 1500 |
| ccccactacg acgacttcag gtctcggag cgccctcctg ccgacccag gtcccaccac | 1560 |
| caccgtaccc gggaccctcg ggacaacggc tccaggtccg gggacctccc ctatgatggg | 1620 |
| cggctactgg aggaggctgt gaggaagaag gggtcggagg agaggaggag accccacaag | 1680 |
| gaggaggagg aagaggccta ctacccgccc gcgccgcccc cgtactcgga gaccgactcg | 1740 |
| caggcgtccc gagagcgcag gctcaagaag aacttggccc tgagtcggga aagtttagtc | 1800 |
| gtcgactaca agacgatga cgacaagtga | 1830 |

<210> SEQ ID NO 147
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 147

| | |
|---|---|
| tatgctagcg ccaccatggc gctgttggcc gg | 32 |

<210> SEQ ID NO 148
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 148

| | |
|---|---|
| tcagacgact aaactttccc gactc | 25 |

<210> SEQ ID NO 149
<211> LENGTH: 20

<212> TYPE: DNA
<213> ORGANISM: Artificial sequence
<220> FEATURE:
<223> OTHER INFORMATION: Synthetic polynucleotide

<400> SEQUENCE: 149
caggtaagag ctcagccacc                                          20

<210> SEQ ID NO 150
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 150
ggtggctgag ctcttacctg                                          20

<210> SEQ ID NO 151
<211> LENGTH: 58
<212> TYPE: DNA
<213> ORGANISM: Artificial sequence
<220> FEATURE:
<223> OTHER INFORMATION: Synthetic polynucleotide

<400> SEQUENCE: 151
gatggatcct cacttgtcgt catcgtcttt gtagtcgacg actaaacttt cccgactc    58

<210> SEQ ID NO 152
<211> LENGTH: 34
<212> TYPE: DNA
<213> ORGANISM: Artificial sequence
<220> FEATURE:
<223> OTHER INFORMATION: Synthetic polynucleotide

<400> SEQUENCE: 152
gatggatcct cagacgacta aactttcccg actc                          34

<210> SEQ ID NO 153
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 153

Asp Tyr Lys Asp Asp Asp Asp Lys
1               5

<210> SEQ ID NO 154
<211> LENGTH: 1950
<212> TYPE: DNA
<213> ORGANISM: Artificial sequence
<220> FEATURE:
<223> OTHER INFORMATION: Synthetic polynucleotide

<400> SEQUENCE: 154
atgcaacagg acggacttgg agtagggaca aggaacggaa gtgggaaggg gaggagcgtg    60 caccccctcct ggccttggtg cgcgccgcgc cccctaaggt actttggaag ggacgcgcgg   120
gccagacgcg cccagacggc cgcgatggcg ctgttggccg gcgggctctc cagagggctg   180
ggctcccacc cggccgccgc aggccgggac gcggtcgtct tcgtgtggct tctgcttagc   240
acctggtgca cagctcctgc cagggccatc caggtgaccg tgtccaaccc ctaccacgtg    300
gtgatcctct tccagcctgt gaccctgccc tgtacctacc agatgacctc gacccccacg   360

```
caacccatcg tcatctggaa gtacaagtct ttctgccggg accgcatcgc cgatgccttc    420
tccccggcca gcgtcgacaa ccagctcaat gcccagctgg cagccgggaa cccaggctac    480
aaccccctacg tcgagtgcca ggacagcgtg cgcaccgtca gggtcgtggc caccaagcag   540
ggcaacgctg tgaccctggg agattactac cagggccgga ggattaccat caccggaaat    600
gctgacctga cctttgacca gacggcgtgg ggggacagtg gtgtgtatta ctgctccgtg    660
gtctcagccc aggacctcca ggggaacaat gaggcctacg cagagctcat cgtccttggg    720
aggacctcag gggtggctga gctcttacct ggttttcagg cggggcccat agaagactgg    780
ctcttcgtgg ttgtggtatg cctggctgcc ttcctcatct cctcctcct gggcatctgc     840
tggtgccagt gctgcccgca cacttgctgc tgctacgtca ggtgcccctg ctgcccagac    900
aagtgctgct gccccgaggc cctgtatgcc gccggcaaag cagccacctc aggtgttccc    960
agcatttatg cccccagcac ctatgcccac ctgtctcccg ccaagacccc acccccacca   1020
gctatgattc ccatgggccc tgcctacaac gggtaccctg aggatacccc tggagacgtt   1080
gacaggagta gctcagctgg tggccaaggc tcctatgtac ccctgcttcg ggacacggac   1140
agcagtgtgg cctctgaagt ccgcagtggc tacaggattc aggccagcca gcaggacgac   1200
tccatgcggg tcctgtacta catggagaag gagctggcca acttcgaccc ttctcgacct   1260
ggccccccca gtggccgtgt ggagcgggcc atgagtgaag tcacctccct ccacgaggac   1320
gactggcgat ctcggccttc ccggggccct gccctcaccc cgatccggga tgaggagtgg   1380
ggtggccact cccccggag tcccaggga tgggaccagg agcccgccag ggagcaggca    1440
ggcggggggct ggcgggccag gcggcccccgg gcccgctccg tggacgccct ggacgacctc  1500
accccgccga gcaccgccga gtcagggagc aggtctccca cgagtaatgg tgggagaagc   1560
cgggcctaca tgccccgcg gagccgcagc cgggacgacc tctatgacca agacgactcg    1620
agggacttcc cacgctcccg ggaccccac tacgacgact tcaggtctcg ggagcgccct    1680
cctgccgacc ccaggtccca ccaccaccgt acccgggacc ctcgggacaa cggctccagg   1740
tccggggacc tcccctatga tgggcggcta ctggaggagg ctgtgaggaa gagggtcg    1800
gaggagagga ggagacccca caaggaggag gaggaagagg cctactaccc gcccgcgccg   1860
ccccccgtact cggagaccga ctcgcaggcg tcccgagagc gcaggctcaa gaagaacttg   1920
gccctgagtc gggaaagttt agtcgtctga                                    1950

<210> SEQ ID NO 155
<211> LENGTH: 1356
<212> TYPE: DNA
<213> ORGANISM: Artificial sequence
<220> FEATURE:
<223> OTHER INFORMATION: Synthetic polynucleotide

<400> SEQUENCE: 155
atccaggtga ccgtgtccaa cccctaccac gtggtgatcc tcttccagcc tgtgaccctg     60
ccctgtacct accagatgac ctcgaccccc acgcaaccca tcgtcatctg gaagtacaag    120
tctttctgcc gggaccgcat cgccgatgcc ttctccccgg ccagcgtcga caaccagctc    180
aatgcccagc tggcagccgg gaacccaggc tacaacccct acgtcgagtg ccaggacagc    240
gtgcgcaccg tcagggtcgt ggccaccaag cagggcaacg ctgtgaccct gggagattac    300
taccagggcc ggaggattac catcaccgga atgtatgccg ccggcaaagc agccacctca    360
ggtgttccca gcatttatgc ccccagcacc tatgcccacc tgtctcccgc caagacccca    420
```

```
cccccaccag ctatgattcc catgggccct gcctacaacg ggtaccctgg aggataccct    480
ggagacgttg acaggagtag ctcagctggt ggccaaggct cctatgtacc cctgcttcgg    540
gacacggaca gcagtgtggc ctctgaagtc cgcagtggct acaggattca ggccagccag    600
caggacgact ccatgcgggt cctgtactac atggagaagg agctggccaa cttcgaccct    660
tctcgacctg gccccccag tggccgtgtg gagcgggcca tgagtgaagt cacctccctc     720
cacgaggacg actggcgatc tcggccttcc cggggccctg ccctcacccc gatccgggat    780
gaggagtggg gtggccactc ccccggagt cccaggggat gggaccagga gcccgccagg     840
gagcaggcag gcggggctg gcgggccagg cggccccggg cccgctccgt ggacgccctg     900
gacgacctca ccccgccgag caccgccgag tcagggagca ggtctcccac gagtaatggt    960
gggagaagcc gggcctacat gccccgcgcg agccgcagcc gggacgacct ctatgaccaa   1020
gacgactcga gggacttccc acgctcccgg gaccccact acgacgactt caggtctcgg    1080
gagcgccctc ctgccgaccc caggtccac caccaccgta cccgggaccc tcgggacaac    1140
ggctccaggt ccggggacct cccctatgat gggcggctac tggaggaggc tgtgaggaag   1200
aaggggtcgg aggagaggag gagaccccac aaggaggagg aggaagaggc ctactacccg   1260
cccgcgccgc ccccgtactc ggagaccgac tcgcaggcgt cccgagagcg caggctcaag   1320
aagaacttgg ccctgagtcg ggaaagttta gtcgtc                             1356

<210> SEQ ID NO 156
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 156

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
```

```
                195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 157
<211> LENGTH: 217
<212> TYPE: PRT
<213> ORGANISM: Artificial sequence
<220> FEATURE:
<223> OTHER INFORMATION: Synthetic polypeptide

<400> SEQUENCE: 157

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 158
<211> LENGTH: 217
<212> TYPE: PRT
<213> ORGANISM: Artificial sequence
<220> FEATURE:
<223> OTHER INFORMATION: Synthetic polypeptide

<400> SEQUENCE: 158

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45
```

-continued

```
Val Asn Asn Val Glu Val His Thr Ala Gln Thr Gln Thr His Arg Glu
 50                  55                  60
Asp Tyr Asn Ser Thr Leu Arg Val Val Ser Ala Leu Pro Ile Gln His
 65                  70                  75                  80
Gln Asp Trp Met Ser Gly Lys Glu Phe Lys Cys Lys Val Asn Asn Lys
                 85                  90                  95
Asp Leu Pro Ala Pro Ile Glu Arg Thr Ile Ser Lys Pro Lys Gly Ser
            100                 105                 110
Val Arg Ala Pro Gln Val Tyr Val Leu Pro Pro Glu Glu Glu Met
        115                 120                 125
Thr Lys Lys Gln Val Thr Leu Thr Cys Met Val Thr Asp Phe Met Pro
130                 135                 140
Glu Asp Ile Tyr Val Glu Trp Thr Asn Asn Gly Lys Thr Glu Leu Asn
145                 150                 155                 160
Tyr Lys Asn Thr Glu Pro Val Leu Asp Ser Asp Gly Ser Tyr Phe Met
                165                 170                 175
Tyr Ser Lys Leu Arg Val Glu Lys Asn Trp Val Glu Arg Asn Ser
            180                 185                 190
Tyr Ser Cys Ser Val Val His Glu Gly Leu His Asn His His Thr Thr
        195                 200                 205
Lys Ser Phe Ser Arg Thr Pro Gly Lys
210                 215

<210> SEQ ID NO 159
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 159

Gly Ser
1

<210> SEQ ID NO 160
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 160

Gly Ser Gly Ser
1

<210> SEQ ID NO 161
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 161

Ala Ser
1

<210> SEQ ID NO 162
<211> LENGTH: 4
<212> TYPE: PRT
<213> ORGANISM: Artificial sequence
<220> FEATURE:
<223> OTHER INFORMATION: Synthetic polypeptide
```

<400> SEQUENCE: 162

Gly Gly Gly Ser
1

<210> SEQ ID NO 163
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 163

Gly Gly Gly Gly Ser
1               5

<210> SEQ ID NO 164
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 164

Gly Gly Gly Gly Ser Gly Gly Gly Gly Ser
1               5                   10

<210> SEQ ID NO 165
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 165

Gly Gly Gly Gly Ser Gly Gly Gly Gly Ser Gly Gly Gly Gly Ser
1               5                   10                  15

<210> SEQ ID NO 166
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 166

Gly Gly Gly Gly Ser Gly Gly Gly Gly Ser Gly Gly Gly Gly Ser Gly
1               5                   10                  15

Gly Gly Gly Ser
            20

<210> SEQ ID NO 167
<211> LENGTH: 7
<212> TYPE: DNA
<213> ORGANISM: Artificial sequence
<220> FEATURE:
<223> OTHER INFORMATION: Synthetic polynucleotide

<400> SEQUENCE: 167 agaaaka                                                                 7

<210> SEQ ID NO 168
<211> LENGTH: 12
<212> TYPE: PRT
<213> ORGANISM: Artificial sequence
<220> FEATURE:

<223> OTHER INFORMATION: Synthetic polypeptide

<400> SEQUENCE: 168

Ala Gly Ala Ala Ala Lys Gly Ala Ala Lys Ala
1               5                   10

<210> SEQ ID NO 169
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 169

Ala Gly Ala Ala Ala Lys Gly Ala Ala Ala Lys Gly Ala Ala Ala Lys
1               5                   10                  15

Ala

<210> SEQ ID NO 170
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 170

Ala Gly Ala Ala Ala Lys Gly Ala Ala Ala Lys Gly Ala Ala Ala Lys
1               5                   10                  15

Gly Ala Ala Ala Lys Ala
            20

<210> SEQ ID NO 171
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 171

Ala Gly Ala Ala Ala Lys Gly Ala Ala Ala Lys Gly Ala Ala Ala Lys
1               5                   10                  15

Gly Ala Ala Ala Lys Gly Ala Ala Ala Lys Ala
            20                  25

<210> SEQ ID NO 172
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 172

Ala Asp Asn Met Gln Ala Ile Tyr Val Ala Leu Gly Glu Ala Val Glu
1               5                   10                  15

Leu Pro Cys Pro Ser Pro Pro Thr Leu His Gly Asp Glu His Leu Ser
            20                  25                  30

Trp Phe Cys Ser Pro Ala Ala Gly Ser Phe Thr Thr Leu Val Ala Gln
            35                  40                  45

Val Gln Val Gly Arg Pro Ala Pro Asp Pro Gly Lys Pro Gly Arg Glu
        50                  55                  60

Ser Arg Leu Arg Leu Leu Gly Asn Tyr Ser Leu Trp Leu Glu Gly Ser
65                  70                  75                  80

```
Lys Glu Glu Asp Ala Gly Arg Tyr Trp Cys Ala Val Leu Gly Gln His
             85                  90                  95

His Asn Tyr Gln Asn Trp Arg Val Tyr Asp Val Leu Val Leu Lys Gly
            100                 105                 110

Ser Gln Leu Ser Ala Arg Ala Ala Asp Gly Ser Pro Cys Asn Val Leu
            115                 120                 125

Leu Cys Ser Val Val Pro Ser Arg Arg Met Asp Ser Val Thr Trp Gln
130                 135                 140

Glu Gly Lys Gly Pro Val Arg Gly Arg Val Gln Ser Phe Trp Gly Ser
145                 150                 155                 160

Glu Ala Ala Leu Leu Leu Val Cys Pro Gly Glu Gly Leu Ser Glu Pro
                165                 170                 175

Arg Ser Arg Arg Pro Arg Ile Ile Arg Cys Leu Met Thr His Asn Lys
                180                 185                 190

Gly Val Ser Phe Ser Leu Ala Ala Ser Ile Asp Ala Ser Pro Ala Leu
            195                 200                 205

Cys Ala Pro Ser Thr Gly Trp Asp Met Pro Pro Lys Ser Ser Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 173
<211> LENGTH: 615
<212> TYPE: PRT
<213> ORGANISM: Artificial sequence
<220> FEATURE:
<223> OTHER INFORMATION: Synthetic polypeptide
```

<400> SEQUENCE: 173

```
Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Ser Gly Pro Tyr Gln Ile
                85                  90                  95

Glu Val His Ile Val Ala Thr Gly Thr Leu Pro Asn Gly Thr Leu Tyr
                100                 105                 110

Ala Ala Arg Gly Ser Gln Val Asp Phe Ser Cys Asn Ser Ser Ser Arg
            115                 120                 125

Pro Pro Pro Val Val Glu Trp Trp Phe Gln Ala Leu Asn Ser Ser Ser
130                 135                 140

Glu Ser Phe Gly His Asn Leu Thr Val Asn Phe Ser Leu Leu Leu
145                 150                 155                 160

Ile Ser Pro Asn Leu Gln Gly Asn Tyr Thr Cys Leu Ala Leu Asn Gln
                165                 170                 175

Leu Ser Lys Arg His Arg Lys Val Thr Thr Glu Leu Leu Val Tyr Tyr
            180                 185                 190

Pro Pro Pro Ser Ala Pro Gln Cys Trp Ala Gln Met Ala Ser Gly Ser
            195                 200                 205

Phe Met Leu Gln Leu Thr Cys Arg Trp Asp Gly Gly Tyr Pro Asp Pro
210                 215                 220

Asp Phe Leu Trp Ile Glu Glu Pro Gly Gly Val Ile Val Gly Lys Ser
225                 230                 235                 240

Lys Leu Gly Val Glu Met Leu Ser Glu Ser Gln Leu Ser Asp Gly Lys
                245                 250                 255

Lys Phe Lys Cys Val Thr Ser His Ile Val Gly Pro Glu Ser Gly Ala
            260                 265                 270

Ser Cys Met Val Gln Ile Arg Gly Pro Ser Leu Leu Ser Glu Pro Met
            275                 280                 285

Lys Thr Cys Phe Thr Gly Gly Asn Val Thr Leu Thr Cys Gln Val Ser
            290                 295                 300

Gly Ala Tyr Pro Pro Ala Lys Ile Leu Trp Leu Arg Asn Leu Thr Gln
305                 310                 315                 320

Pro Glu Val Ile Ile Gln Pro Ser Ser Arg His Leu Ile Thr Gln Asp
                325                 330                 335

Gly Gln Asn Ser Thr Leu Thr Ile His Asn Cys Ser Gln Asp Leu Asp
            340                 345                 350

Glu Gly Tyr Tyr Ile Cys Arg Ala Asp Ser Pro Val Gly Val Arg Glu
            355                 360                 365

Met Glu Ile Trp Leu Ser Val Lys Glu Pro Leu Asn Ile Gly Gly Glu
            370                 375                 380

Pro Lys Ser Ser Asp Lys Thr His Thr Cys Pro Pro Cys Pro Ala Pro
385                 390                 395                 400

Glu Leu Leu Gly Gly Pro Ser Val Phe Leu Phe Pro Pro Lys Pro Lys
```

```
                405                 410                 415
Asp Thr Leu Met Ile Ser Arg Thr Pro Glu Val Thr Cys Val Val
            420                 425                 430

Asp Val Ser His Glu Asp Pro Glu Val Lys Phe Asn Trp Tyr Val Asp
            435                 440                 445

Gly Val Glu Val His Asn Ala Lys Thr Lys Pro Arg Glu Glu Gln Tyr
450                 455                 460

Asn Ser Thr Tyr Arg Val Val Ser Val Leu Thr Val Leu His Gln Asp
465                 470                 475                 480

Trp Leu Asn Gly Lys Glu Tyr Lys Cys Lys Val Ser Asn Lys Ala Leu
                485                 490                 495

Pro Ala Pro Ile Glu Lys Thr Ile Ser Lys Ala Lys Gly Gln Pro Arg
            500                 505                 510

Glu Pro Gln Val Tyr Thr Leu Pro Pro Ser Arg Asp Glu Leu Thr Lys
            515                 520                 525

Asn Gln Val Ser Leu Thr Cys Leu Val Lys Gly Phe Tyr Pro Ser Asp
530                 535                 540

Ile Ala Val Glu Trp Glu Ser Asn Gly Gln Pro Glu Asn Asn Tyr Lys
545                 550                 555                 560

Thr Thr Pro Pro Val Leu Asp Ser Asp Gly Ser Phe Phe Leu Tyr Ser
                565                 570                 575

Lys Leu Thr Val Asp Lys Ser Arg Trp Gln Gln Gly Asn Val Phe Ser
                580                 585                 590

Cys Ser Val Met His Glu Ala Leu His Asn His Tyr Thr Gln Lys Ser
                595                 600                 605

Leu Ser Leu Ser Pro Gly Lys
            610                 615

<210> SEQ ID NO 174
<211> LENGTH: 514
<212> TYPE: PRT
<213> ORGANISM: Artificial sequence
<220> FEATURE:
<223> OTHER INFORMATION: Synthetic polypeptide

<400> SEQUENCE: 174

Val Val Ile Gly Glu Val His Glu Asn Val Thr Leu His Cys Gly Asn
1               5                   10                  15

Ile Ser Gly Leu Arg Gly Gln Val Thr Trp Tyr Arg Asn Asn Ser Glu
            20                  25                  30

Pro Val Phe Leu Leu Ser Ser Asn Ser Ser Leu Arg Pro Ala Glu Pro
        35                  40                  45

Arg Phe Ser Leu Val Asp Ala Thr Ser Leu His Ile Glu Ser Leu Ser
    50                  55                  60

Leu Gly Asp Glu Gly Ile Tyr Thr Cys Gln Glu Ile Leu Asn Val Thr
65                  70                  75                  80

Gln Trp Phe Gln Val Trp Leu Gln Val Ala Asn Pro Pro Ser Ala
                85                  90                  95

Pro Gln Cys Trp Ala Gln Met Ala Ser Gly Ser Phe Met Leu Gln Leu
            100                 105                 110

Thr Cys Arg Trp Asp Gly Gly Tyr Pro Asp Pro Asp Phe Leu Trp Ile
            115                 120                 125

Glu Glu Pro Gly Gly Val Ile Val Gly Lys Ser Lys Leu Gly Val Glu
        130                 135                 140

Met Leu Ser Glu Ser Gln Leu Ser Asp Gly Lys Lys Phe Lys Cys Val
```

```
                145                 150                 155                 160
Thr Ser His Ile Val Gly Pro Glu Ser Gly Ala Ser Cys Met Val Gln
                165                 170                 175
Ile Arg Gly Pro Ser Leu Leu Ser Glu Pro Met Lys Thr Cys Phe Thr
                180                 185                 190
Gly Gly Asn Val Thr Leu Thr Cys Gln Val Ser Gly Ala Tyr Pro Pro
                195                 200                 205
Ala Lys Ile Leu Trp Leu Arg Asn Leu Thr Gln Pro Glu Val Ile Ile
                210                 215                 220
Gln Pro Ser Ser Arg His Leu Ile Thr Gln Asp Gly Gln Asn Ser Thr
225                 230                 235                 240
Leu Thr Ile His Asn Cys Ser Gln Asp Leu Asp Glu Gly Tyr Tyr Ile
                245                 250                 255
Cys Arg Ala Asp Ser Pro Val Gly Val Arg Glu Met Glu Ile Trp Leu
                260                 265                 270
Ser Val Lys Glu Pro Leu Asn Ile Gly Gly Glu Pro Lys Ser Ser Asp
                275                 280                 285
Lys Thr His Thr Cys Pro Pro Cys Pro Ala Pro Glu Leu Leu Gly Gly
                290                 295                 300
Pro Ser Val Phe Leu Phe Pro Pro Lys Pro Lys Asp Thr Leu Met Ile
305                 310                 315                 320
Ser Arg Thr Pro Glu Val Thr Cys Val Val Val Asp Val Ser His Glu
                325                 330                 335
Asp Pro Glu Val Lys Phe Asn Trp Tyr Val Asp Gly Val Glu Val His
                340                 345                 350
Asn Ala Lys Thr Lys Pro Arg Glu Glu Gln Tyr Asn Ser Thr Tyr Arg
                355                 360                 365
Val Val Ser Val Leu Thr Val Leu His Gln Asp Trp Leu Asn Gly Lys
                370                 375                 380
Glu Tyr Lys Cys Lys Val Ser Asn Lys Ala Leu Pro Ala Pro Ile Glu
385                 390                 395                 400
Lys Thr Ile Ser Lys Ala Lys Gly Gln Pro Arg Glu Pro Gln Val Tyr
                405                 410                 415
Thr Leu Pro Pro Ser Arg Asp Glu Leu Thr Lys Asn Gln Val Ser Leu
                420                 425                 430
Thr Cys Leu Val Lys Gly Phe Tyr Pro Ser Asp Ile Ala Val Glu Trp
                435                 440                 445
Glu Ser Asn Gly Gln Pro Glu Asn Asn Tyr Lys Thr Thr Pro Pro Val
450                 455                 460
Leu Asp Ser Asp Gly Ser Phe Phe Leu Tyr Ser Lys Leu Thr Val Asp
465                 470                 475                 480
Lys Ser Arg Trp Gln Gln Gly Asn Val Phe Ser Cys Ser Val Met His
                485                 490                 495
Glu Ala Leu His Asn His Tyr Thr Gln Lys Ser Leu Ser Leu Ser Pro
                500                 505                 510
Gly Lys

<210> SEQ ID NO 175
<211> LENGTH: 438
<212> TYPE: PRT
<213> ORGANISM: Artificial sequence
<220> FEATURE:
<223> OTHER INFORMATION: Synthetic polypeptide

<400> SEQUENCE: 175
```

-continued

```
Glu Leu Glu Pro Gln Ile Asp Gly Gln Thr Trp Ala Glu Arg Ala Leu
1               5                   10                  15
Arg Glu Asn Glu Arg His Ala Phe Thr Cys Arg Val Ala Gly Gly Pro
            20                  25                  30
Gly Thr Pro Arg Leu Ala Trp Tyr Leu Asp Gly Gln Leu Gln Glu Ala
        35                  40                  45
Ser Thr Ser Arg Leu Leu Ser Val Gly Gly Glu Ala Phe Ser Gly Gly
    50                  55                  60
Thr Ser Thr Phe Thr Val Thr Ala His Arg Ala Gln His Glu Leu Asn
65                  70                  75                  80
Cys Ser Leu Gln Asp Pro Arg Ser Gly Arg Ser Ala Asn Ala Ser Val
                85                  90                  95
Ile Leu Asn Val Gln Phe Lys Pro Glu Ile Ala Gln Val Gly Ala Lys
                100                 105                 110
Tyr Gln Glu Ala Gln Gly Pro Gly Leu Leu Val Val Leu Phe Ala Leu
                115                 120                 125
Val Arg Ala Asn Pro Pro Ala Asn Val Thr Trp Ile Asp Gln Asp Gly
        130                 135                 140
Pro Val Thr Val Asn Thr Ser Asp Phe Leu Val Leu Asp Ala Gln Asn
145                 150                 155                 160
Tyr Pro Trp Leu Thr Asn His Thr Val Gln Leu Gln Leu Arg Ser Leu
                165                 170                 175
Ala His Asn Leu Ser Val Val Ala Thr Asn Asp Val Gly Val Thr Ser
            180                 185                 190
Ala Ser Leu Pro Ala Pro Gly Leu Leu Ala Thr Arg Val Glu Glu Pro
        195                 200                 205
Lys Ser Ser Asp Lys Thr His Thr Cys Pro Pro Cys Pro Ala Pro Glu
    210                 215                 220
Leu Leu Gly Gly Pro Ser Val Phe Leu Phe Pro Pro Lys Pro Lys Asp
225                 230                 235                 240
Thr Leu Met Ile Ser Arg Thr Pro Glu Val Thr Cys Val Val Val Asp
                245                 250                 255
Val Ser His Glu Asp Pro Glu Val Lys Phe Asn Trp Tyr Val Asp Gly
                260                 265                 270
Val Glu Val His Asn Ala Lys Thr Lys Pro Arg Glu Glu Gln Tyr Asn
            275                 280                 285
Ser Thr Tyr Arg Val Val Ser Val Leu Thr Val Leu His Gln Asp Trp
        290                 295                 300
Leu Asn Gly Lys Glu Tyr Lys Cys Lys Val Ser Asn Lys Ala Leu Pro
305                 310                 315                 320
Ala Pro Ile Glu Lys Thr Ile Ser Lys Ala Lys Gly Gln Pro Arg Glu
                325                 330                 335
Pro Gln Val Tyr Thr Leu Pro Pro Ser Arg Asp Glu Leu Thr Lys Asn
                340                 345                 350
Gln Val Ser Leu Thr Cys Leu Val Lys Gly Phe Tyr Pro Ser Asp Ile
            355                 360                 365
Ala Val Glu Trp Glu Ser Asn Gly Gln Pro Glu Asn Asn Tyr Lys Thr
        370                 375                 380
Thr Pro Pro Val Leu Asp Ser Asp Gly Ser Phe Phe Leu Tyr Ser Lys
385                 390                 395                 400
Leu Thr Val Asp Lys Ser Arg Trp Gln Gln Gly Asn Val Phe Ser Cys
                405                 410                 415
```

-continued

Ser Val Met His Glu Ala Leu His Asn His Tyr Thr Gln Lys Ser Leu
        420                 425                 430

Ser Leu Ser Pro Gly Lys
        435

<210> SEQ ID NO 176
<211> LENGTH: 402
<212> TYPE: PRT
<213> ORGANISM: Artificial sequence
<220> FEATURE:
<223> OTHER INFORMATION: Synthetic polypeptide

<400> SEQUENCE: 176

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
        35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
    130                 135                 140

Ala Glu Leu Ile Val Leu Gly Arg Thr Ser Gly Val Ala Glu Leu Leu
145                 150                 155                 160

Pro Gly Phe Gln Ala Gly Pro Ile Glu Asp Glu Pro Lys Ser Ser Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
    210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Ala Leu Pro Ala Pro Ile Glu
        275                 280                 285

Lys Thr Ile Ser Lys Ala Lys Gly Gln Pro Arg Glu Pro Gln Val Tyr
    290                 295                 300

Thr Leu Pro Pro Ser Arg Asp Glu Leu Thr Lys Asn Gln Val Ser Leu
305                 310                 315                 320

Thr Cys Leu Val Lys Gly Phe Tyr Pro Ser Asp Ile Ala Val Glu Trp
                325                 330                 335

```
Glu Ser Asn Gly Gln Pro Glu Asn Asn Tyr Lys Thr Thr Pro Pro Val
                340                 345                 350

Leu Asp Ser Asp Gly Ser Phe Phe Leu Tyr Ser Lys Leu Thr Val Asp
            355                 360                 365

Lys Ser Arg Trp Gln Gln Gly Asn Val Phe Ser Cys Ser Val Met His
    370                 375                 380

Glu Ala Leu His Asn His Tyr Thr Gln Lys Ser Leu Ser Leu Ser Pro
385                 390                 395                 400

Gly Lys

<210> SEQ ID NO 177
<211> LENGTH: 383
<212> TYPE: PRT
<213> ORGANISM: Artificial sequence
<220> FEATURE:
<223> OTHER INFORMATION: Synthetic polypeptide

<400> SEQUENCE: 177

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
        50                  55                  60

Ala Ala Gly Asn Pro Gly Tyr Asn Pro Tyr Val Glu Cys Gln Asp Ser
65                  70                  75                  80

Val Arg Thr Val Arg Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
130                 135                 140

Ala Glu Leu Ile Val Leu Asp Glu Pro Lys Ser Ser Asp Lys Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
        210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
```

```
            290                 295                 300
Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 178
<211> LENGTH: 724
<212> TYPE: PRT
<213> ORGANISM: Artificial sequence
<220> FEATURE:
<223> OTHER INFORMATION: Synthetic polypeptide

<400> SEQUENCE: 178

Ile Gln Val Thr Val Ser Asn Pro Tyr His Val Ile Leu Phe Gln
1               5                   10                  15

Pro Val Thr Leu Pro Cys Thr Tyr Gln Met Thr Ser Thr Pro Thr Gln
                20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
        50                  55                  60

Ala Ala Gly Asn Pro Gly Tyr Asn Pro Tyr Val Glu Cys Gln Asp Ser
65                  70                  75                  80

Val Arg Thr Val Arg Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
        115                 120                 125

Cys Ser Val Val Ser Ala Gln Asp Leu Gln Gly Asn Asn Glu Ala Tyr
130                 135                 140

Ala Glu Leu Ile Val Leu Val Tyr Ala Ala Gly Lys Ala Ala Thr Ser
145                 150                 155                 160

Gly Val Pro Ser Ile Tyr Ala Pro Ser Thr Tyr Ala His Leu Ser Pro
                165                 170                 175

Ala Lys Thr Pro Pro Pro Ala Met Ile Pro Met Gly Pro Ala Tyr
            180                 185                 190

Asn Gly Tyr Pro Gly Gly Tyr Pro Gly Asp Val Asp Arg Ser Ser Ser
        195                 200                 205

Ala Gly Gly Gln Gly Ser Tyr Val Pro Leu Leu Arg Asp Thr Asp Ser
    210                 215                 220

Ser Val Ala Ser Glu Val Arg Ser Gly Tyr Arg Ile Gln Ala Ser Gln
225                 230                 235                 240

Gln Asp Asp Ser Met Arg Val Leu Tyr Tyr Met Glu Lys Glu Leu Ala
                245                 250                 255

Asn Phe Asp Pro Ser Arg Pro Gly Pro Pro Ser Gly Arg Val Glu Arg
            260                 265                 270

Ala Met Ser Glu Val Thr Ser Leu His Glu Asp Asp Trp Arg Ser Arg
```

```
                275                 280                 285
Pro Ser Arg Gly Pro Ala Leu Thr Pro Ile Arg Asp Glu Glu Trp Gly
290                 295                 300

Gly His Ser Pro Arg Ser Pro Arg Gly Trp Asp Gln Glu Pro Ala Arg
305                 310                 315                 320

Glu Gln Ala Gly Gly Trp Arg Ala Arg Pro Arg Ala Arg Ser
                325                 330                 335

Val Asp Ala Leu Asp Asp Leu Thr Pro Pro Ser Thr Ala Glu Ser Gly
                340                 345                 350

Ser Arg Ser Pro Thr Ser Asn Gly Gly Arg Ser Arg Ala Tyr Met Pro
                355                 360                 365

Pro Arg Ser Arg Ser Arg Asp Leu Tyr Asp Gln Asp Asp Ser Arg
370                 375                 380

Asp Phe Pro Arg Ser Arg Asp Pro His Tyr Asp Asp Phe Arg Ser Arg
385                 390                 395                 400

Glu Arg Pro Pro Ala Asp Pro Arg Ser His His His Arg Thr Arg Asp
                405                 410                 415

Pro Arg Asp Asn Gly Ser Arg Ser Gly Asp Leu Pro Tyr Asp Gly Arg
                420                 425                 430

Leu Leu Glu Glu Ala Val Arg Lys Lys Gly Ser Glu Glu Arg Arg Arg
                435                 440                 445

Pro His Lys Glu Glu Glu Glu Ala Tyr Tyr Pro Ala Pro Pro
                450                 455                 460

Pro Tyr Ser Glu Thr Asp Ser Gln Ala Ser Arg Glu Arg Arg Leu Lys
465                 470                 475                 480

Lys Asn Leu Ala Leu Ser Arg Glu Ser Leu Val Glu Pro Lys Ser
                485                 490                 495

Ser Asp Lys Thr His Thr Cys Pro Pro Cys Pro Ala Pro Glu Leu Leu
                500                 505                 510

Gly Gly Pro Ser Val Phe Leu Phe Pro Pro Lys Pro Lys Asp Thr Leu
                515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
                580                 585                 590

Gly Lys Glu Tyr Lys Cys Lys Val Ser Asn Lys Ala Leu Pro Ala Pro
                595                 600                 605

Ile Glu Lys Thr Ile Ser Lys Ala Lys Gly Gln Pro Arg Glu Pro Gln
                610                 615                 620

Val Tyr Thr Leu Pro Pro Ser Arg Asp Glu Leu Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
                660                 665                 670

Pro Val Leu Asp Ser Asp Gly Ser Phe Phe Leu Tyr Ser Lys Leu Thr
                675                 680                 685

Val Asp Lys Ser Arg Trp Gln Gln Gly Asn Val Phe Ser Cys Ser Val
                690                 695                 700
```

```
Met His Glu Ala Leu His Asn His Tyr Thr Gln Lys Ser Leu Ser Leu
705                 710                 715                 720

Ser Pro Gly Lys

<210> SEQ ID NO 179
<211> LENGTH: 723
<212> TYPE: PRT
<213> ORGANISM: Artificial sequence
<220> FEATURE:
<223> OTHER INFORMATION: Synthetic polypeptide

<400> SEQUENCE: 179

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
                20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
        50                  55                  60

Ala Ala Gly Asn Pro Gly Tyr Asn Pro Tyr Val Glu Cys Gln Asp Ser
65                  70                  75                  80

Val Arg Thr Val Arg Val Ala Thr Lys Gln Gly Asn Ala Val Thr
                85                  90                  95

Leu Gly Asp Tyr Tyr Gln Gly Arg Arg Ile Thr Ile Thr Gly Asn Ala
                100                 105                 110

Asp Leu Thr Phe Asp Gln Thr Ala Trp Gly Asp Ser Gly Val Tyr Tyr
            115                 120                 125

Cys Ser Val Val Ser Ala Gln Asp Leu Gln Gly Asn Asn Glu Ala Tyr
    130                 135                 140

Ala Glu Leu Ile Val Leu Val Tyr Ala Ala Gly Lys Ala Ala Thr Ser
145                 150                 155                 160

Gly Val Pro Ser Ile Tyr Ala Pro Ser Thr Tyr Ala His Leu Ser Pro
                165                 170                 175

Ala Lys Thr Pro Pro Pro Ala Met Ile Pro Met Gly Pro Ala Tyr
            180                 185                 190

Asn Gly Tyr Pro Gly Gly Tyr Pro Gly Asp Val Asp Arg Ser Ser Ser
        195                 200                 205

Ala Gly Gly Gln Gly Ser Tyr Val Pro Leu Leu Arg Asp Thr Asp Ser
    210                 215                 220

Ser Val Ala Ser Val Arg Ser Gly Tyr Arg Ile Gln Ala Ser Gln Gln
225                 230                 235                 240

Asp Asp Ser Met Arg Val Leu Tyr Tyr Met Glu Lys Glu Leu Ala Asn
                245                 250                 255

Phe Asp Pro Ser Arg Pro Gly Pro Ser Gly Arg Val Glu Arg Ala
            260                 265                 270

Met Ser Glu Val Thr Ser Leu His Glu Asp Asp Trp Arg Ser Arg Pro
        275                 280                 285

Ser Arg Gly Pro Ala Leu Thr Pro Ile Arg Asp Glu Glu Trp Gly Gly
    290                 295                 300

His Ser Pro Arg Ser Pro Arg Gly Trp Asp Gln Glu Pro Ala Arg Glu
305                 310                 315                 320

Gln Ala Gly Gly Gly Trp Arg Ala Arg Arg Pro Arg Ala Arg Ser Val
                325                 330                 335
```

```
Asp Ala Leu Asp Asp Leu Thr Pro Pro Ser Thr Ala Glu Ser Gly Ser
            340                 345                 350

Arg Ser Pro Thr Ser Asn Gly Gly Arg Ser Arg Ala Tyr Met Pro Pro
        355                 360                 365

Arg Ser Arg Ser Arg Asp Asp Leu Tyr Asp Gln Asp Asp Ser Arg Asp
    370                 375                 380

Phe Pro Arg Ser Arg Asp Pro His Tyr Asp Asp Phe Arg Ser Arg Glu
385                 390                 395                 400

Arg Pro Pro Ala Asp Pro Arg Ser His His Arg Thr Arg Asp Pro
                405                 410                 415

Arg Asp Asn Gly Ser Arg Ser Gly Asp Leu Pro Tyr Asp Gly Arg Leu
            420                 425                 430

Leu Glu Glu Ala Val Arg Lys Lys Gly Ser Glu Arg Arg Arg Pro
        435                 440                 445

His Lys Glu Glu Glu Glu Ala Tyr Tyr Pro Pro Ala Pro Pro Pro
    450                 455                 460

Tyr Ser Glu Thr Asp Ser Gln Ala Ser Arg Glu Arg Arg Leu Lys Lys
465                 470                 475                 480

Asn Leu Ala Leu Ser Arg Glu Ser Leu Val Val Glu Pro Lys Ser Ser
                485                 490                 495

Asp Lys Thr His Thr Cys Pro Pro Cys Pro Ala Pro Glu Leu Leu Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Asp Glu Leu Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys

<210> SEQ ID NO 180
<211> LENGTH: 684
<212> TYPE: PRT
<213> ORGANISM: Artificial sequence
```

```
<220> FEATURE:
<223> OTHER INFORMATION: Synthetic polypeptide

<400> SEQUENCE: 180

Ile Gln Val Thr Val Ser Asn Pro Tyr His Val Ile Leu Phe Gln
1               5                   10                  15

Pro Val Thr Leu Pro Cys Thr Tyr Gln Met Thr Ser Thr Pro Thr Gln
                20                  25                  30

Pro Ile Val Ile Trp Lys Tyr Lys Ser Phe Cys Arg Asp Arg Ile Ala
            35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80

Val Arg Thr Val Arg Val Val Ala Thr Lys Gln Gly Asn Ala Val Thr
                85                  90                  95

Leu Gly Asp Tyr Tyr Gln Gly Arg Arg Ile Thr Ile Thr Gly Met Tyr
                100                 105                 110

Ala Ala Gly Lys Ala Ala Thr Ser Gly Val Pro Ser Ile Tyr Ala Pro
            115                 120                 125

Ser Thr Tyr Ala His Leu Ser Pro Ala Lys Thr Pro Pro Pro Ala
    130                 135                 140

Met Ile Pro Met Gly Pro Ala Tyr Asn Gly Tyr Pro Gly Gly Tyr Pro
145                 150                 155                 160

Gly Asp Val Asp Arg Ser Ser Ala Gly Gly Gln Gly Ser Tyr Val
                165                 170                 175

Pro Leu Leu Arg Asp Thr Asp Ser Ser Val Ala Ser Glu Val Arg Ser
                180                 185                 190

Gly Tyr Arg Ile Gln Ala Ser Gln Gln Asp Asp Ser Met Arg Val Leu
            195                 200                 205

Tyr Tyr Met Glu Lys Glu Leu Ala Asn Phe Asp Pro Ser Arg Pro Gly
    210                 215                 220

Pro Pro Ser Gly Arg Val Glu Arg Ala Met Ser Glu Val Thr Ser Leu
225                 230                 235                 240

His Glu Asp Asp Trp Arg Ser Arg Pro Ser Arg Gly Pro Ala Leu Thr
                245                 250                 255

Pro Ile Arg Asp Glu Glu Trp Gly Gly His Ser Pro Ser Pro Arg
            260                 265                 270

Gly Trp Asp Gln Glu Pro Ala Arg Glu Gln Ala Gly Gly Trp Arg
            275                 280                 285

Ala Arg Arg Pro Arg Ala Arg Ser Val Asp Ala Leu Asp Asp Leu Thr
290                 295                 300

Pro Pro Ser Thr Ala Glu Ser Gly Ser Arg Ser Pro Thr Ser Asn Gly
305                 310                 315                 320

Gly Arg Ser Arg Ala Tyr Met Pro Pro Arg Ser Arg Ser Arg Asp Asp
            325                 330                 335

Leu Tyr Asp Gln Asp Asp Ser Arg Asp Phe Pro Arg Ser Arg Asp Pro
                340                 345                 350

His Tyr Asp Asp Phe Arg Ser Arg Glu Arg Pro Pro Ala Asp Pro Arg
            355                 360                 365

Ser His His His Arg Thr Arg Asp Pro Arg Asp Asn Gly Ser Arg Ser
            370                 375                 380

Gly Asp Leu Pro Tyr Asp Gly Arg Leu Leu Glu Glu Ala Val Arg Lys
385                 390                 395                 400
```

```
Lys Gly Ser Glu Glu Arg Arg Pro His Lys Glu Glu Glu Glu
                405                 410                 415

Ala Tyr Tyr Pro Pro Ala Pro Pro Tyr Ser Glu Thr Asp Ser Gln
            420                 425                 430

Ala Ser Arg Glu Arg Arg Leu Lys Lys Asn Leu Ala Leu Ser Arg Glu
        435                 440                 445

Ser Leu Val Val Glu Pro Lys Ser Ser Asp Lys Thr His Thr Cys Pro
    450                 455                 460

Pro Cys Pro Ala Pro Glu Leu Leu Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
                500                 505                 510

Asn Trp Tyr Val Asp Gly Val Glu Val His Asn Ala Lys Thr Lys Pro
            515                 520                 525

Arg Glu Glu Gln Tyr Asn Ser Thr Tyr Arg Val Val Ser Val Leu Thr
        530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Asp Glu Leu Thr Lys Asn Gln Val Ser Leu Thr Cys Leu Val Lys Gly
        595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680

<210> SEQ ID NO 181
<211> LENGTH: 743
<212> TYPE: PRT
<213> ORGANISM: Artificial sequence
<220> FEATURE:
<223> OTHER INFORMATION: Synthetic polypeptide

<400> SEQUENCE: 181

Ile Gln Val Thr Val Ser Asn Pro Tyr His Val Val Ile Leu Phe Gln
1               5                   10                  15

Pro Val Thr Leu Pro Cys Thr Tyr Gln Met Thr Ser Thr Pro Thr Gln
            20                  25                  30

Pro Ile Val Ile Trp Lys Tyr Lys Ser Phe Cys Arg Asp Arg Ile Ala
        35                  40                  45

Asp Ala Phe Ser Pro Ala Ser Val Asp Asn Gln Leu Asn Ala Gln Leu
    50                  55                  60

Ala Ala Gly Asn Pro Gly Tyr Asn Pro Tyr Val Glu Cys Gln Asp Ser
65                  70                  75                  80
```

```
Val Arg Thr Val Arg Val Ala Thr Lys Gln Gly Asn Ala Val Thr
                85                  90                  95

Leu Gly Asp Tyr Tyr Gln Gly Arg Arg Ile Thr Ile Thr Gly Asn Ala
            100                 105                 110

Asp Leu Thr Phe Asp Gln Thr Ala Trp Gly Asp Ser Gly Val Tyr Tyr
            115                 120                 125

Cys Ser Val Val Ser Ala Gln Asp Leu Gln Gly Asn Asn Glu Ala Tyr
130                 135                 140

Ala Glu Leu Ile Val Leu Gly Arg Thr Ser Gly Val Ala Glu Leu Leu
145                 150                 155                 160

Pro Gly Phe Gln Ala Gly Pro Ile Glu Val Tyr Ala Ala Gly Lys Ala
                165                 170                 175

Ala Thr Ser Gly Val Pro Ser Ile Tyr Ala Pro Ser Thr Tyr Ala His
            180                 185                 190

Leu Ser Pro Ala Lys Thr Pro Pro Pro Ala Met Ile Pro Met Gly
            195                 200                 205

Pro Ala Tyr Asn Gly Tyr Pro Gly Gly Tyr Pro Gly Asp Val Asp Arg
210                 215                 220

Ser Ser Ser Ala Gly Gly Gln Gly Ser Tyr Val Pro Leu Leu Arg Asp
225                 230                 235                 240

Thr Asp Ser Ser Val Ala Ser Glu Val Arg Ser Gly Tyr Arg Ile Gln
                245                 250                 255

Ala Ser Gln Gln Asp Asp Ser Met Arg Val Leu Tyr Tyr Met Glu Lys
            260                 265                 270

Glu Leu Ala Asn Phe Asp Pro Ser Arg Pro Gly Pro Pro Ser Gly Arg
            275                 280                 285

Val Glu Arg Ala Met Ser Glu Val Thr Ser Leu His Glu Asp Asp Trp
290                 295                 300

Arg Ser Arg Pro Ser Arg Gly Pro Ala Leu Thr Pro Ile Arg Asp Glu
305                 310                 315                 320

Glu Trp Gly Gly His Ser Pro Arg Ser Pro Arg Gly Trp Asp Gln Glu
                325                 330                 335

Pro Ala Arg Glu Gln Ala Gly Gly Gly Trp Arg Ala Arg Arg Pro Arg
            340                 345                 350

Ala Arg Ser Val Asp Ala Leu Asp Asp Leu Thr Pro Pro Ser Thr Ala
            355                 360                 365

Glu Ser Gly Ser Arg Ser Pro Thr Ser Asn Gly Gly Arg Ser Arg Ala
370                 375                 380

Tyr Met Pro Pro Arg Ser Arg Ser Arg Asp Asp Leu Tyr Asp Gln Asp
385                 390                 395                 400

Asp Ser Arg Asp Phe Pro Arg Ser Arg Asp Pro His Tyr Asp Asp Phe
                405                 410                 415

Arg Ser Arg Glu Arg Pro Pro Ala Asp Pro Arg Ser His His His Arg
            420                 425                 430

Thr Arg Asp Pro Arg Asp Asn Gly Ser Arg Ser Gly Asp Leu Pro Tyr
            435                 440                 445

Asp Gly Arg Leu Leu Glu Glu Ala Val Arg Lys Lys Gly Ser Glu Glu
450                 455                 460

Arg Arg Arg Pro His Lys Glu Glu Glu Glu Ala Tyr Tyr Pro Pro
465                 470                 475                 480

Ala Pro Pro Pro Tyr Ser Glu Thr Asp Ser Gln Ala Ser Arg Glu Arg
                485                 490                 495
```

Arg Leu Lys Lys Asn Leu Ala Leu Ser Arg Glu Ser Leu Val Val Glu
            500                 505                 510

Pro Lys Ser Ser Asp Lys Thr His Thr Cys Pro Cys Pro Ala Pro
        515                 520                 525

Glu Leu Leu Gly Gly Pro Ser Val Phe Leu Phe Pro Pro Lys Pro Lys
        530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
            580                 585                 590

Asn Ser Thr Tyr Arg Val Val Ser Val Leu Thr Val Leu His Gln Asp
        595                 600                 605

Trp Leu Asn Gly Lys Glu Tyr Lys Cys Lys Val Ser Asn Lys Ala Leu
    610                 615                 620

Pro Ala Pro Ile Glu Lys Thr Ile Ser Lys Ala Lys Gly Gln Pro Arg
625                 630                 635                 640

Glu Pro Gln Val Tyr Thr Leu Pro Pro Ser Arg Asp Glu Leu Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Val Leu Asp Ser Asp Gly Ser Phe Phe Leu Tyr Ser
    690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 182
<211> LENGTH: 702
<212> TYPE: DNA
<213> ORGANISM: Artificial sequence
<220> FEATURE:
<223> OTHER INFORMATION: Synthetic polynucleotide

<400> SEQUENCE: 182
atggcagtct tattcctcct cctgttccta tgtggaactc cccaggctgc agacaacatg      60
caggccatct atgtggcctt gggggaggca gtagagctgc catgtccctc accacctact     120
ctacatgggg acgaacacct gtcatggttc tgcagccctg cagcaggctc cttcaccacc     180
ctggtagccc aagtccaagt gggcaggcca gccccagacc tggaaaaacc aggaagggaa     240
tccaggctca gactgctggg gaactattct ttgtggttgg agggatccaa agaggaagat     300
gccgggcggt actggtgcgc tgtgctaggt cagcaccaca actaccagaa ctggagggtg     360
tacgacgtct tggtgctcaa aggatcccag ttatctgcaa gggctgcaga tgatccccc     420 tgcaatgtcc tcctgtgctc tgtggtcccc agcagacgca tggactctgt gacctggcag     480
gaagggaagg gtcccgtgag ggccgtgtt cagtccttct ggggcagtga ggctgccctg     540
ctcttggtgt gtcctgggga ggggcttttct gagcccagga ccgaagacc aagaatcatc     600 cgctgcctca tgactcacaa caaaggggtc agctttagcc tggcagcctc catcgatgct     660
tctcctgccc tctgtgcccc ttccacgggc tgggacatgc ct        702

<210> SEQ ID NO 183
<211> LENGTH: 1239
<212> TYPE: DNA
<213> ORGANISM: Artificial sequence
<220> FEATURE:
<223> OTHER INFORMATION: Synthetic polynucleotide

<400> SEQUENCE: 183

| | |
|---|---|
| atggccgcag gcggcagtgc gcccgagccc cgcgtcctcg tctgcctcgg ggcgctcctg | 60 |
| gccggctggg tcgccgtagg attggaggct gttgtcattg gagaagttca tgagaatgtt | 120 |
| actctgcact gtggcaacat ctcgggactg aggggccagg tgacctggta ccggaacaac | 180 |
| tcggagcctg tcttccttct ctcgtccaac tctagcctcc ggccagctga gcctcgcttc | 240 |
| tctctagtgg atgccacctc cctgcacatt gaatcgctga gcctgggaga tgagggaatc | 300 |
| tacacctgcc aggagatcct gaatgtgact cagtggttcc aagtgtggct gcaggtggcc | 360 |
| agcggcccct atcagattga ggtccacatc gtggccaccg gcacactccc caacggcacc | 420 |
| ctctatgcag ccaggggctc ccaggtggac ttcagctgca acagcagctc caggccacca | 480 |
| cccgtggttg aatggtggtt ccaggccctg aattccagca gcgagtcctt tggccacaac | 540 |
| ctgacagtca acttttctc actgttactg atatcgccaa acctccaagg gaactacacc | 600 |
| tgtttagcct tgaatcagct cagcaagaga catcgaaagg tgaccaccga gctcctggtc | 660 |
| tactatcccc ctccatcagc tccccagtgc tgggcacaga tggcatcagg atcgttcatg | 720 |
| ttgcagctta cctgtcgctg ggatggggga taccctgacc ctgacttcct gtggatagaa | 780 |
| gagccaggag gtgtaatcgt ggggaagtca aagctggggg tggaaatgct gagcgagtcc | 840 |
| cagctgtcgg atggcaagaa gttcaagtgt gttacaagcc acatagttgg gccagagtcg | 900 |
| ggcgccagct gcatggtgca gatcaggggt ccctcccttc tctctgagcc catgaagact | 960 |
| tgcttcactg ggggcaatgt gacgcttaca tgccaggtgt ctggggccta cccccctgcc | 1020 |
| aagatcctgt ggctgaggaa ccttacccag cccgaggtga tcatccagcc tagcagccgc | 1080 |
| catctcatta cccaggatgg ccagaactcc accctcacta tccacaactg ctcccaggac | 1140 |
| ctggatgagg gctactacat ctgccgagct gacagccctg tagggggtgag ggagatggaa | 1200 |
| atctggctga gtgtgaaaga acctttaaat atcgggggg | 1239 |

<210> SEQ ID NO 184
<211> LENGTH: 936
<212> TYPE: DNA
<213> ORGANISM: Artificial sequence
<220> FEATURE:
<223> OTHER INFORMATION: Synthetic polynucleotide

<400> SEQUENCE: 184

| | |
|---|---|
| atggccgcag gcggcagtgc gcccgagccc cgcgtcctcg tctgcctcgg ggcgctcctg | 60 |
| gccggctggg tcgccgtagg attggaggct gttgtcattg gagaagttca tgagaatgtt | 120 |
| actctgcact gtggcaacat ctcgggactg aggggccagg tgacctggta ccggaacaac | 180 |
| tcggagcctg tcttccttct ctcgtccaac tctagcctcc ggccagctga gcctcgcttc | 240 |
| tctctagtgg atgccacctc cctgcacatt gaatcgctga gcctgggaga tgagggaatc | 300 |
| tacacctgcc aggagatcct gaatgtgact cagtggttcc aagtgtggct gcaggtggcc | 360 |
| aatccccctc catcagctcc ccagtgctgg gcacagatgg catcaggatc gttcatgttg | 420 |

```
cagcttacct gtcgctggga tgggggatac cctgaccctg acttcctgtg gatagaagag     480
ccaggaggtg taatcgtggg gaagtcaaag ctgggggtgg aaatgctgag cgagtcccag     540
ctgtcggatg gcaagaagtt caagtgtgtt acaagccaca tagttgggcc agagtcgggc     600
gccagctgca tggtgcagat caggggtccc tcccttctct ctgagcccat gaagacttgc     660
ttcactgggg gcaatgtgac gcttacatgc caggtgtctg gggcctaccc ccctgccaag     720
atcctgtggc tgaggaacct tacccagccc gaggtgatca tccagcctag cagccgccat     780
ctcattaccc aggatggcca gaactccacc ctcactatcc acaactgctc ccaggacctg     840
gatgagggct actacatctg ccgagctgac agccctgtag gggtgaggga gatggaaatc     900
tggctgagtg tgaaagaacc tttaaatatc gggggg                                936

<210> SEQ ID NO 185
<211> LENGTH: 690
<212> TYPE: DNA
<213> ORGANISM: Artificial sequence
<220> FEATURE:
<223> OTHER INFORMATION: Synthetic polynucleotide

<400> SEQUENCE: 185
atggcgctgc ctccaggccc agccgccctc cggcacacac tgctgctcct gccagccctt      60
ctgagctcag gttgggggga gttggagcca caaatagatg gtcagacctg ggctgagcgg     120
gcacttcggg agaatgaacg ccacgccttc acctgccggg tggcaggggg gcctggcacc     180
cccagattgg cctggtatct ggatggacag ctgcaggagg ccagcacctc aagactgctg     240
agcgtgggag gggaggcctt ctctggaggc accagcacct tcactgtcac tgcccatcgg     300
gcccagcatg agctcaactg ctctctgcag gaccccagaa gtggccgatc agccaacgcc     360
tctgtcatcc ttaatgtgca attcaagcca gagattgccc aagtcggcgc caagtaccag     420
gaagctcagg gccaggcct cctggttgtc ctgtttgccc tggtgcgtgc caacccgccg     480
gccaatgtca cctggatcga ccaggatggg ccagtgactg tcaacacctc tgacttcctg     540
gtgctggatg cgcagaacta cccctggctc accaaccaca cggtgcagct gcagctccgc     600
agcctggcac acaacctctc ggtggtggcc accaatgacg tgggtgtcac cagtgcgtcg     660
cttccagccc cagggcttct ggctacccgg                                      690

<210> SEQ ID NO 186
<211> LENGTH: 633
<212> TYPE: DNA
<213> ORGANISM: Artificial sequence
<220> FEATURE:
<223> OTHER INFORMATION: Synthetic polynucleotide

<400> SEQUENCE: 186
atggcgctgt tggccggcgg gctctccaga gggctgggct cccacccggc cgccgcaggc      60
cgggacgcgg tcgtcttcgt gtggcttctg cttagcacct ggtgcacagc tcctgccagg     120
gccatccagg tgaccgtgtc caaccectac acgtgtgtga tcctcttcca gcctgtgacc     180
ctgccctgta cctaccagat gacctcgacc cccacgcaac ccatcgtcat ctggaagtac     240 aagtcttttct gccgggaccg catcgccgat gccttctccc cggccagcgt cgacaaccag     300
ctcaatgccc agctggcagc cgggaaccca ggctacaacc cctacgtcga gtgccaggac     360
agcgtgcgca ccgtcagggt cgtggccacc aagcagggca acgctgtgac cctgggagat     420
tactaccagg gccggaggat taccatcacc ggaaatgctg acctgacctt tgaccagacg     480
gcgtgggggg acagtggtgt gtattactgc tccgtggtct cagcccagga cctccagggg     540
```

```
aacaatgagg cctacgcaga gctcatcgtc cttgggagga cctcaggggt ggctgagctc    600
ttacctggtt ttcaggcggg gcccatagaa gac                                 633

<210> SEQ ID NO 187
<211> LENGTH: 576
<212> TYPE: DNA
<213> ORGANISM: Artificial sequence
<220> FEATURE:
<223> OTHER INFORMATION: Synthetic polynucleotide

<400> SEQUENCE: 187
atggcgctgt tggccggcgg gctctccaga gggctgggct cccacccggc cgccgcaggc     60
cgggacgcgg tcgtcttcgt gtggcttctg cttagcacct ggtgcacagc tcctgccagg    120
gccatccagg tgaccgtgtc caaccoctac cacgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
ctcaatgccc agctggcagc cgggaaccca ggctacaacc cctacgtcga gtgccaggac    360
agcgtgcgca ccgtcagggt cgtggccacc aagcagggca cgctgtgac cctgggagat    420 tactaccagg gccggaggat taccatcacc ggaaatgctg acctgaccct tgaccagacg    480
gcgtgggggg acagtggtgt gtattactgc tccgtggtct cagcccagga cctccagggg    540
aacaatgagg cctacgcaga gctcatcgtc cttgac                              576

<210> SEQ ID NO 188
<211> LENGTH: 1533
<212> TYPE: DNA
<213> ORGANISM: Artificial sequence
<220> FEATURE:
<223> OTHER INFORMATION: Synthetic polynucleotide

<400> SEQUENCE: 188
atccaggtga ccgtgtccaa ccoctaccac gtggtgatcc tcttccagcc tgtgaccctg     60
ccctgtacct accagatgac ctcgaccccc acgcaaccca tcgtcatctg gaagtacaag    120
tctttctgcc gggaccgcat cgccgatgcc ttctccccgg ccagcgtcga caaccagctc    180
aatgcccagc tggcagccgg gaacccaggc tacaacccct acgtcgagtg ccaggacagc    240
gtgcgcaccg tcagggtcgt ggccaccaag cagggcaacg ctgtgaccct gggagattac    300
taccagggcc ggaggattac catcaccgga aatgctgacc tgacctttga ccagacggcg    360
tggggggaca gtggtgtgta ttactgctcc gtggtctcag cccaggacct caggggaac    420 aatgaggcct acgcagagct catcgtcctt ggaggacct cagggtggc tgagctctta     480 cctggttttc aggcggggcc catagaagtg tatgccgccg gcaaagcagc cacctcaggt    540
gttcccagca tttatgcccc cagcacctat gcccacctgt ctcccgccaa gacccccaccc    600 ccaccagcta tgattcccat gggccctgcc tacaacgggt accctggagg ataccctgga    660
gacgttgaca ggagtagctc agctggtggc caaggctcct atgtacccct gcttcgggac    720
acggacagca gtgtggcctc tgaagtccgc agtggctaca ggattcaggc cagccagcag    780
gacgactcca tgcgggtcct gtactacatg agaaggagc tggccaactt cgacccttct    840
cgacctggcc ccccagtggc cgtgtggag cgggcatga gtgaagtcac ctccctccac    900
gaggacgact ggcgatctcg gccttccgg ggccctgccc tcaccccgat ccggatgag    960 gagtggggtg gccactcccc ccggagtccc aggggatggg accaggagcc cgccaggag   1020
```

```
caggcaggcg ggggctggcg ggccaggcgg ccccgggccc gctccgtgga cgccctggac    1080
gacctcaccc cgccgagcac cgccgagtca gggagcaggt ctcccacgag taatggtggg    1140
agaagccggg cctacatgcc cccgcggagc cgcagccggg acgacctcta tgaccaagac    1200
gactcgaggg acttcccacg ctcccgggac ccccactacg acgacttcag gtctcgggag    1260
cgccctcctg ccgacccag gtcccaccac caccgtaccc gggaccctcg ggacaacggc    1320
tccaggtccg ggaccctccc ctatgatggg cggctactgg aggaggctgt gaggaagaag    1380
gggtcggagg agaggaggag accccacaag gaggaggagg aagaggccta ctacccgccc    1440
gcgccgcccc cgtactcgga gaccgactcg caggcgtccc gagagcgcag gctcaagaag    1500
aacttggccc tgagtcggga aagtttagtc gtc                                 1533

<210> SEQ ID NO 189
<211> LENGTH: 1398
<212> TYPE: DNA
<213> ORGANISM: Artificial sequence
<220> FEATURE:
<223> OTHER INFORMATION: Synthetic polynucleotide

<400> SEQUENCE: 189
atggcagtct tattcctcct cctgttccta tgtggaactc cccaggctgc agacaacatg      60
caggccatct atgtggcctt gggggaggca gtagagctgc catgtccctc accacctact     120
ctacatgggg acgaacacct gtcatggttc tgcagccctg cagcaggctc cttcaccacc     180
ctggtagccc aagtccaagt gggcaggcca gccccagacc ctggaaaacc aggaagggaa     240
tccaggctca gactgctggg gaactattct ttgtggttgg agggatccaa agaggaagat     300
gccgggcggt actggtgcgc tgtgctaggt cagcaccaca actaccagaa ctggagggtg     360
tacgacgtct tggtgctcaa aggatcccag ttatctgcaa gggctgcaga tggatccccc     420
tgcaatgtcc tcctgtgctc tgtggtcccc agcagacgca tggactctgt gacctggcag     480
gaagggaagg gtcccgtgag gggccgtgtt cagtccttct ggggcagtga ggctgccctg     540
ctcttggtgt gtcctgggga ggggctttct gagcccagga gccgaagacc aagaatcatc     600
cgctgcctca tgactcacaa caaagggtc agctttagcc tggcagcctc catcgatgct     660
tctcctgccc tctgtgcccc ttccacgggc tgggacatgc ctgagcccaa atcttctgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggatgagct gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcagggaac    1320 gtcttctcat gctccgtgat gcatgaggct ctgcacaacc actacacgca gaagagcctc    1380
tccctgtctc cgggtaaa                                                  1398

<210> SEQ ID NO 190
<211> LENGTH: 1935
```

<212> TYPE: DNA
<213> ORGANISM: Artificial sequence
<220> FEATURE:
<223> OTHER INFORMATION: Synthetic polynucleotide

<400> SEQUENCE: 190

| | | | | | |
|---|---|---|---|---|---|
| atggccgcag | gcggcagtgc | gcccgagccc | cgcgtcctcg | tctgcctcgg | ggcgctcctg | 60 |
| gccggctggg | tcgccgtagg | attggaggct | gttgtcattg | gagaagttca | tgagaatgtt | 120 |
| actctgcact | gtggcaacat | ctcgggactg | aggggccagg | tgacctggta | ccggaacaac | 180 |
| tcggagcctg | tcttccttct | ctcgtccaac | tctagcctcc | ggccagctga | gcctcgcttc | 240 |
| tctctagtgg | atgccacctc | cctgcacatt | gaatcgctga | gcctgggaga | tgagggaatc | 300 |
| tacacctgcc | aggagatcct | gaatgtgact | cagtggttcc | aagtgtggct | gcaggtggcc | 360 |
| agcggcccct | atcagattga | ggtccacatc | gtggccaccg | gcacactccc | caacggcacc | 420 |
| ctctatgcag | ccaggggctc | ccaggtggac | ttcagctgca | acagcagctc | caggccacca | 480 |
| cccgtggttg | aatggtggtt | ccaggccctg | aattccagca | gcgagtcctt | tggccacaac | 540 |
| ctgacagtca | acttttctc | actgttactg | atatcgccaa | acctccaagg | gaactacacc | 600 |
| tgtttagcct | tgaatcagct | cagcaagaga | atcgaaagg | tgaccaccga | gctcctggtc | 660 |
| tactatcccc | ctccatcagc | tccccagtgc | tgggcacaga | tggcatcagg | atcgttcatg | 720 |
| ttgcagctta | cctgtcgctg | ggatggggga | taccctgacc | ctgacttcct | gtggatagaa | 780 |
| gagccaggag | gtgtaatcgt | ggggaagtca | agctggggg | tggaaatgct | gagcgagtcc | 840 |
| cagctgtcgg | atggcaagaa | gttcaagtgt | gttacaagcc | acatagttgg | ccagagtcg | 900 |
| ggcgccagct | gcatggtgca | gatcaggggt | ccctcccttc | tctctgagcc | catgaagact | 960 |
| tgcttcactg | ggggcaatgt | gacgcttaca | tgccaggtgt | ctggggccta | ccccctgcc | 1020 |
| aagatcctgt | ggctgaggaa | ccttacccag | cccgaggtga | tcatccagcc | tagcagccgc | 1080 |
| catctcatta | cccaggatgg | ccagaactcc | accctcacta | tccacaactg | ctcccaggac | 1140 |
| ctggatgagg | gctactacat | ctgccgagct | gacagccctg | taggggtgag | ggagatggaa | 1200 |
| atctggctga | gtgtgaaaga | acctttaaat | atcgggggg | agcccaaatc | ttctgacaaa | 1260 |
| actcacacat | gcccaccgtg | cccagcacct | gaactcctgg | ggggaccgtc | agtcttcctc | 1320 |
| ttccccccaa | aacccaagga | caccctcatg | atctcccgga | cccctgaggt | cacatgcgtg | 1380 |
| gtggtggacg | tgagccacga | agaccctgag | gtcaagttca | actggtacgt | ggacggcgtg | 1440 |
| gaggtgcata | atgccaagac | aaagccgcgg | gaggagcagt | acaacagcac | gtaccgtgtg | 1500 |
| gtcagcgtcc | tcaccgtcct | gcaccaggac | tggctgaatg | gcaaggagta | caagtgcaag | 1560 |
| gtctccaaca | aagccctccc | agcccccatc | gagaaaacca | tctccaaagc | caagggcag | 1620 |
| ccccgagaac | cacaggtgta | caccctgccc | ccatcccggg | atgagctgac | caagaaccag | 1680 |
| gtcagcctga | cctgcctggt | caaaggcttc | tatcccagcg | acatcgccgt | ggagtgggag | 1740 |
| agcaatgggc | agccggagaa | caactacaag | accacgcctc | ccgtgctgga | ctccgacggc | 1800 |
| tccttcttcc | tctacagcaa | gctcaccgtg | gacaagagca | ggtggcagca | ggggaacgtc | 1860 |
| ttctcatgct | ccgtgatgca | tgaggctctg | cacaaccact | acacgcagaa | gagcctctcc | 1920 |
| ctgtctccgg | gtaaa | | | | | 1935 |

<210> SEQ ID NO 191
<211> LENGTH: 1632
<212> TYPE: DNA
<213> ORGANISM: Artificial sequence
<220> FEATURE:

<223> OTHER INFORMATION: Synthetic polynucleotide

<400> SEQUENCE: 191

| | |
|---|---|
| atggccgcag gcggcagtgc gcccgagccc cgcgtcctcg tctgcctcgg ggcgctcctg | 60 |
| gccggctggg tcgccgtagg attggaggct gttgtcattg gagaagttca tgagaatgtt | 120 |
| actctgcact gtggcaacat ctcgggactg aggggccagg tgacctggta ccggaacaac | 180 |
| tcggagcctg tcttccttct ctcgtccaac tctagcctcc ggccagctga gcctcgcttc | 240 |
| tctctagtgg atgccacctc cctgcacatt gaatcgctga gcctgggaga tgagggaatc | 300 |
| tacacctgcc aggagatcct gaatgtgact cagtggttcc aagtgtggct gcaggtggcc | 360 |
| aatccccctc catcagctcc ccagtgctgg gcacagatgg catcaggatc gttcatgttg | 420 |
| cagcttacct gtcgctggga tgggggatac cctgaccctg acttcctgtg atagaagag | 480 |
| ccaggaggtg taatcgtggg gaagtcaaag ctggggtgg aaatgctgag cgagtcccag | 540 |
| ctgtcggatg caagaagtt caagtgtgtt acaagccaca tagttgggcc agagtcgggc | 600 |
| gccagctgca tggtgcagat cagggtccc tcccttctct ctgagcccat gaagacttgc | 660 |
| ttcactgggg gcaatgtgac gcttacatgc caggtgtctg ggcctaccc ccctgccaag | 720 |
| atcctgtggc tgaggaacct tacccagccc gaggtgatca tccagcctag cagccgccat | 780 |
| ctcattaccc aggatggcca gaactccacc ctcactatcc acaactgctc ccaggacctg | 840 |
| gatgagggct actacatctg ccgagctgac agccctgtag gggtgaggga gatggaaatc | 900 |
| tggctgagtg tgaagaacc tttaaatatc gggggggagc ccaaatcttc tgacaaaact | 960 |
| cacacatgcc caccgtgccc agcacctgaa ctcctggggg gaccgtcagt cttcctcttc | 1020 |
| cccccaaaac ccaaggacac cctcatgatc tcccggaccc ctgaggtcac atgcgtggtg | 1080 |
| gtggacgtga gccacgaaga ccctgaggtc aagttcaact ggtacgtgga cggcgtggag | 1140 |
| gtgcataatg ccaagacaaa gccgcgggag gagcagtaca acagcacgta ccgtgtggtc | 1200 |
| agcgtcctca ccgtcctgca ccaggactgg ctgaatggca aggagtacaa gtgcaaggtc | 1260 |
| tccaacaaag ccctcccagc ccccatcgag aaaaccatct ccaaagccaa agggcagccc | 1320 |
| cgagaaccac aggtgtacac cctgccccca tcccgggatg agctgaccaa gaaccaggtc | 1380 |
| agcctgacct gcctggtcaa aggcttctat cccagcgaca tcgccgtgga gtgggagagc | 1440 |
| aatgggcagc cggagaacaa ctacaagacc acgcctcccg tgctggactc cgacggctcc | 1500 |
| ttcttcctct acagcaagct caccgtggac aagagcaggt ggcagcaggg gaacgtcttc | 1560 |
| tcatgctccg tgatgcatga ggctctgcac aaccactaca cgcagaagag cctctccctg | 1620 |
| tctccgggta aa | 1632 |

<210> SEQ ID NO 192
<211> LENGTH: 1386
<212> TYPE: DNA
<213> ORGANISM: Artificial sequence
<220> FEATURE:
<223> OTHER INFORMATION: Synthetic polynucleotide

<400> SEQUENCE: 192

| | |
|---|---|
| atggcgctgc ctccaggccc agccgccctc cggcacacac tgctgctcct gccagccctt | 60 |
| ctgagctcag gttgggggga gttggagcca caaatagatg gtcagacctg gctgagcgg | 120 |
| gcacttcggg agaatgaacg ccacgccttc acctgccggg tggcaggggg gcctggcacc | 180 |
| cccagattgg cctggtatct ggatggacag ctgcaggagg ccagcacctc aagactgctg | 240 |
| agcgtgggag gggaggcctt ctctggaggc accagcacct tcactgtcac tgccatcgg | 300 |

-continued

```
gcccagcatg agctcaactg ctctctgcag gaccccagaa gtggccgatc agccaacgcc    360
tctgtcatcc ttaatgtgca attcaagcca gagattgccc aagtcggcgc caagtaccag    420
gaagctcagg gcccaggcct cctggttgtc ctgtttgccc tggtgcgtgc aacccgccg     480 gccaatgtca cctggatcga ccaggatggg ccagtgactg tcaacacctc tgacttcctg    540
gtgctggatg cgcagaacta cccctggctc accaaccaca cggtgcagct gcagctccgc    600
agcctggcac acaacctctc ggtggtggcc accaatgacg tgggtgtcac cagtgcgtcg    660
cttccagccc cagggcttct ggctacccgg agcccaaat cttctgacaa aactcacaca     720
tgcccaccgt gcccagcacc tgaactcctg ggggaccgt cagtcttcct cttccccca     780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaagggca gccccgagaa    1080 ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc     1260
ctctacagca agctcaccgt ggacaagagc aggtggcagc aggggaacgt cttctcatgc   1320
tccgtgatgc atgaggctct gcacaaccac tacacgcaga gagcctctc cctgtctccg    1380 ggtaaa                                                              1386
```

<210> SEQ ID NO 193
<211> LENGTH: 1329
<212> TYPE: DNA
<213> ORGANISM: Artificial sequence
<220> FEATURE:
<223> OTHER INFORMATION: Synthetic polynucleotide

<400> SEQUENCE: 193

```
atggcgctgt tggccggcgg gctctccaga gggctgggct cccacccggc cgccgcaggc     60
cgggacgcgg tcgtcttcgt gtggcttctg cttagcacct ggtgcacagc tcctgccagg    120
gccatccagg tgaccgtgtc caaccccttac cacgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
ctcaatgccc agctggcagc cgggaaccca ggctacaacc cctacgtcga gtgccaggac    360
agcgtgcgca ccgtcaggt cgtggccacc aagcagggca acgctgtgac cctgggagat    420
tactaccagg gccggaggat taccatcacc ggaaatgctg acctgaccct tgaccagacg    480
gcgtgggggg acagtggtgt gtattactgc tccgtggtct cagcccagga cctccagggg   540
aacaatgagg cctacgcaga gctcatcgtc cttgggagga cctcaggggt ggctgagctc   600
ttacctggtt ttcaggcggg gcccatagaa gacgagccca atcttctga caaaactcac     660 acatgcccac cgtgcccagc acctgaactc ctggggggac cgtcagtctt cctcttcccc    720
ccaaaaccca aggacaccct catgatctcc cggacccctg aggtcacatg cgtggtggtg    780
gacgtgagcc acgaagaccc tgaggtcaag ttcaactggt acgtggacgg cgtggaggtg    840
cataatgcca agacaaagcc gcgggaggag cagtacaaca gcacgtaccg tgtggtcagc    900
```

```
gtcctcaccg tcctgcacca ggactggctg aatggcaagg agtacaagtg caaggtctcc    960
aacaaagccc tcccagcccc catcgagaaa accatctcca agccaaaggc agcccccga   1020 gaaccacagg tgtacaccct gccccatcc cgggatgagc tgaccaagaa ccaggtcagc   1080
ctgacctgcc tggtcaaagg cttctatccc agcgacatcg ccgtggagtg ggagagcaat   1140
gggcagccgg agaacaacta caagaccacg cctcccgtgc tggactccga cggctccttc   1200
ttcctctaca gcaagctcac cgtggacaag agcaggtggc agcaggggaa cgtcttctca   1260
tgctccgtga tgcatgaggc tctgcacaac cactacacgc agaagagcct ctccctgtct   1320
ccgggtaaa                                                           1329
```

<210> SEQ ID NO 194
<211> LENGTH: 1272
<212> TYPE: DNA
<213> ORGANISM: Artificial sequence
<220> FEATURE:
<223> OTHER INFORMATION: Synthetic polynucleotide

<400> SEQUENCE: 194

```
atggcgctgt tggccggcgg gctctccaga gggctgggct cccacccggc cgccgcaggc     60
cgggacgcgg tcgtcttcgt gtggcttctg cttagcacct ggtgcacagc tcctgccagg    120
gccatccagg tgaccgtgtc caaccctac cacgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
ctcaatgccc agctggcagc cgggaaccca ggctacaacc cctacgtcga gtgccaggac    360
agcgtgcgca ccgtcagggt cgtggccacc aagcagggca cgctgtgac cctgggagat    420 tactaccagg gccggaggat taccatcacc ggaaatgctg acctgacctt tgaccagacg    480 gcgtggggg acagtggtgt gtattactgc tccgtggtct cagcccagga cctccagggg    540
aacaatgagg cctacgcaga gctcatcgtc cttgacgagc ccaaatcttc tgacaaaact    600
cacacatgcc caccgtgccc agcacctgaa ctcctggggg gaccgtcagt cttcctcttc    660
cccccaaaac ccaaggacac cctcatgatc tcccggaccc ctgaggtcac atgcgtggtg    720
gtggacgtga gccacgaaga ccctgaggtc aagttcaact ggtacgtgga cggcgtggag    780
gtgcataatg ccaagacaaa gccgcgggag gagcagtaca acagcacgta ccgtgtggtc    840
agcgtcctca ccgtcctgca ccaggactgg ctgaatggca aggagtacaa gtgcaaggtc    900
tccaacaaag ccctcccagc ccccatcgag aaaaccatct ccaaagccaa agggcagccc    960
cgagaaccac aggtgtacac cctgccccca tcccgggatg agctgaccaa gaaccaggtc   1020
agcctgacct gcctggtcaa aggcttctat cccagcgaca tcgccgtgga gtgggagagc   1080
aatgggcagc cggagaacaa ctacaagacc acgcctcccg tgctggactc cgacggctcc   1140
ttcttcctct acagcaagct caccgtggac aagagcaggt ggcagcaggg gaacgtcttc   1200
tcatgctccg tgatgcatga ggctctgcac aaccactaca cgcagaagag cctctccctg   1260
tctccgggta aa                                                       1272
```

<210> SEQ ID NO 195
<211> LENGTH: 2295
<212> TYPE: DNA
<213> ORGANISM: Artificial sequence
<220> FEATURE:
<223> OTHER INFORMATION: Synthetic polynucleotide

<400> SEQUENCE: 195

-continued

```
atggcgctgt tggccggcgg gctctccaga gggctgggct cccacccggc cgccgcaggc      60
cgggacgcgg tcgtcttcgt gtggcttctg cttagcacct ggtgcacagc tcctgccagg     120
gccatccagg tgaccgtgtc caacccctac cacgtggtga tcctcttcca gcctgtgacc     180
ctgccctgta cctaccagat gacctcgacc cccacgcaac ccatcgtcat ctggaagtac     240
aagtctttct gccgggaccg catcgccgat gccttctccc cggccagcgt cgacaaccag     300
ctcaatgccc agctggcagc cgggaaccca ggctacaacc cctacgtcga gtgccaggac     360
agcgtgcgca ccgtcagggt cgtggccacc aagcagggca acgctgtgac cctgggagat     420
tactaccagg gccggaggat taccatcacc ggaaatgctg acctgacctt tgaccagacg     480
gcgtgggggg acagtggtgt gtattactgc tccgtggtct cagcccagga cctccagggg     540
aacaatgagg cctacgcaga gctcatcgtc cttgtgtatg ccgccggcaa agcagccacc     600
tcaggtgttc ccagcattta tgccccagc acctatgccc acctgtctcc cgccaagacc     660
ccacccccac cagctatgat tcccatgggc cctgcctaca cgggtaccc tggaggatac     720
cctggagacg ttgacaggag tagctcagct ggtggccaag gctcctatgt accectgctt     780
cgggacacgg acagcagtgt ggcctctgaa gtccgcagtg gctacaggat tcaggccagc     840
cagcaggacg actccatgcg ggtcctgtac tacatggaga aggagctggc caacttcgac     900
ccttctcgac ctggcccccc cagtggccgt gtggagcggg ccatgagtga agtcacctcc     960
ctccacgagg acgactggcg atctcggcct tcccggggcc ctgccctcac ccgatccgg    1020
gatgaggagt ggggtggcca ctcccccgg agtcccaggg gatgggacca ggagcccgcc    1080
agggagcagg caggcggggg ctggcgggcc aggcggcccc gggcccgctc cgtggacgcc    1140
ctggacgacc tcaccccgcc gagcaccgcc gagtcaggga gcaggtctcc cacgagtaat    1200
ggtgggagaa gccgggccta catgccccg cggagccgca gccgggacga cctctatgac    1260
caagacgact cgagggactt ccacgctcc cgggaccccc actacgacga cttcaggtct    1320
cgggagcgcc ctcctgccga ccccaggtcc caccaccacc gtacccggga ccctcgggac    1380
aacggctcca ggtccgggga cctcccctat gatgggcggc tactggagga ggctgtgagg    1440
aagaagggt cggaggagag gaggagaccc cacaaggagg aggaggaaga ggcctactac    1500
ccgcccgcgc cgcccccgta ctcggagacc gactcgcagg cgtcccgaga gcgcaggctc    1560
aagaagaact tggccctgag tcgggaaagt ttagtcgtcg agcccaaatc ttctgacaaa    1620
actcacacat gcccaccgtg cccagcacct gaactcctgg ggggaccgtc agtcttcctc    1680
ttccccccaa aacccaagga caccctcatg atctcccgga cccctgaggt cacatgcgtg    1740
gtggtggacg tgagccacga agaccctgag gtcaagttca actggtacgt ggacggcgtg    1800
gaggtgcata atgccaagac aaagccgcgg gaggagcagt acaacagcac gtaccgtgtg    1860
gtcagcgtcc tcaccgtcct gcaccaggac tggctgaatg gcaaggagta caagtgcaag    1920
gtctccaaca aagccctccc agccccatc gagaaaacca tctccaaagc caaagggcag    1980
ccccgagaac cacaggtgta caccctgccc ccatcccggg atgagctgac caagaaccag    2040
gtcagcctga cctgcctggt caaaggcttc tatcccagcg acatcgccgt ggagtgggag    2100
agcaatgggc agccggagaa caactacaag accacgcctc ccgtgctgga ctccgacggc    2160
tccttcttcc tctacagcaa gctcaccgtg gacaagagca ggtggcagca ggggaacgtc    2220
ttctcatgct ccgtgatgca tgaggctctg cacaaccact acacgcagaa gagcctctcc    2280
ctgtctccgg gtaaa                                                    2295
```

<210> SEQ ID NO 196
<211> LENGTH: 2292
<212> TYPE: DNA
<213> ORGANISM: Artificial sequence
<220> FEATURE:
<223> OTHER INFORMATION: Synthetic polynucleotide

<400> SEQUENCE: 196

| | | | | | |
|---|---|---|---|---|---|
| atggcgctgt | tggccggcgg | gctctccaga | gggctgggct | cccacccggc | cgccgcaggc | 60 |
| cgggacgcgg | tcgtcttcgt | gtggcttctg | cttagcacct | ggtgcacagc | tcctgccagg | 120 |
| gccatccagg | tgaccgtgtc | caaccctac | cacgtggtga | tcctcttcca | gcctgtgacc | 180 |
| ctgccctgta | cctaccagat | gacctcgacc | cccacgcaac | ccatcgtcat | ctggaagtac | 240 |
| aagtctttct | gccgggaccg | catcgccgat | gccttctccc | cggccagcgt | cgacaaccag | 300 |
| ctcaatgccc | agctggcagc | cgggaaccca | ggctacaacc | cctacgtcga | gtgccaggac | 360 |
| agcgtgcgca | ccgtcagggt | cgtggccacc | aagcagggca | acgctgtgac | cctgggagat | 420 |
| tactaccagg | gccggaggat | taccatcacc | ggaaatgctg | acctgacctt | tgaccagacg | 480 |
| gcgtgggggg | acagtggtgt | gtattactgc | tccgtggtct | cagcccagga | cctccagggg | 540 |
| aacaatgagg | cctacgcaga | gctcatcgtc | cttgtgtatg | ccgccggcaa | agcagccacc | 600 |
| tcaggtgttc | ccagcattta | tgcccccagc | acctatgccc | acctgtctcc | cgccaagacc | 660 |
| ccacccccac | cagctatgat | tcccatgggc | cctgcctaca | cgggtacccc | tggaggatac | 720 |
| cctggagacg | ttgacaggag | tagctcagct | ggtggccaag | gctcctatgt | accoctgctt | 780 |
| cgggacacgg | acagcagtgt | ggcctctgtc | cgcagtggct | acaggattca | ggccagccag | 840 |
| caggacgact | ccatgcgggt | cctgtactac | atggagaagg | agctggccaa | cttcgaccct | 900 |
| tctcgacctg | gccccccag | tggccgtgtg | gagcgggcca | tgagtgaagt | cacctccctc | 960 |
| cacgaggacg | actggcgatc | tcggccttcc | cggggccctg | ccctcacccc | gatccgggat | 1020 |
| gaggagtggg | gtggccactc | ccccggagt | cccaggggat | gggaccagga | gcccgccagg | 1080 |
| gagcaggcag | gcggggctg | gcgggccagg | cggccccggg | cccgctccgt | ggacgccctg | 1140 |
| gacgacctca | ccccgccgag | caccgccgag | tcagggagca | ggtctcccac | gagtaatggt | 1200 |
| gggagaagcc | gggcctacat | gccccgcgg | agccgcagcc | gggacgacct | ctatgaccaa | 1260 |
| gacgactcga | gggacttccc | acgctcccgg | gaccccact | acgacgactt | caggtctcgg | 1320 |
| gagcgccctc | ctgccgaccc | caggtcccac | caccaccgta | cccgggaccc | tcgggacaac | 1380 |
| ggctccaggt | ccggggacct | cccctatgat | gggcggctac | tggaggaggc | tgtgaggaag | 1440 |
| aaggggtcgg | aggagaggag | gagaccccac | aaggaggagg | aggaagaggc | ctactacccg | 1500 |
| cccgcgccgc | ccccgtactc | ggagaccgac | tcgcaggcgt | cccgagagcg | caggctcaag | 1560 |
| aagaacttgg | ccctgagtcg | ggaaagttta | gtcgtcgagc | ccaaatcttc | tgacaaaact | 1620 |
| cacacatgcc | caccgtgccc | agcacctgaa | ctcctgggg | gaccgtcagt | cttcctcttc | 1680 |
| cccccaaaac | ccaaggacac | cctcatgatc | tcccggaccc | ctgaggtcac | atgcgtggtg | 1740 |
| gtggacgtga | gccacgaaga | ccctgaggtc | aagttcaact | ggtacgtgga | cggcgtggag | 1800 |
| gtgcataatg | ccaagacaaa | gccgcggag | gagcagtaca | acagcacgta | ccgtgtggtc | 1860 |
| agcgtcctca | ccgtcctgca | ccaggactgg | ctgaatggca | aggagtacaa | gtgcaaggtc | 1920 |
| tccaacaaag | ccctcccagc | ccccatcgag | aaaaccatct | ccaaagccaa | agggcagccc | 1980 |
| cgagaaccac | aggtgtacac | cctgcccca | tcccgggatg | agctgaccaa | gaaccaggtc | 2040 |
| agcctgacct | gcctggtcaa | aggcttctat | cccagcgaca | tcgccgtgga | gtgggagagc | 2100 |

```
aatgggcagc cggagaacaa ctacaagacc acgcctcccg tgctggactc cgacggctcc   2160
ttcttcctct acagcaagct caccgtggac aagagcaggt ggcagcaggg gaacgtcttc   2220
tcatgctccg tgatgcatga ggctctgcac aaccactaca cgcagaagag cctctccctg   2280
tctccgggta aa                                                       2292

<210> SEQ ID NO 197
<211> LENGTH: 2175
<212> TYPE: DNA
<213> ORGANISM: Artificial sequence
<220> FEATURE:
<223> OTHER INFORMATION: Synthetic polynucleotide

<400> SEQUENCE: 197
atggcgctgt tggccggcgg gctctccaga gggctgggct cccacccggc cgccgcaggc     60
cgggacgcgg tcgtcttcgt gtggcttctg cttagcacct ggtgcacagc tcctgccagg    120
gccatccagg tgaccgtgtc caaccctac cacgtggtga tcctcttcca gcctgtgacc    180
ctgccctgta cctaccagat gacctcgacc cccacgcaac ccatcgtcat ctggaagtac    240
aagtctttct gccgggaccg catcgccgat gccttctccc cggccagcgt cgacaaccag    300
ctcaatgccc agctggcagc cgggaaccca ggctacaacc cctacgtcga gtgccaggac    360
agcgtgcgca ccgtcaggt cgtggccacc aagcagggca acgctgtgac cctgggagat    420
tactaccagg gccggaggat taccatcacc ggaatgtatg ccgccggcaa agcagccacc    480
tcaggtgttc ccagcattta tgcccccagc acctatgccc acctgtctcc cgccaagacc    540 ccaccccca cagctatgat tcccatgggc cctgcctaca cgggtaccc tggaggatac    600 cctggagacg ttgacaggag tagctcagct ggtggccaag gctcctatgt acccctgctt    660
cgggacacgg acagcagtgt ggcctctgaa gtccgcagtg gctacaggat tcaggccagc    720
cagcaggacg actccatgcg ggtcctgtac tacatggaga aggagctggc caacttcgac    780
ccttctcgac ctggccccc cagtggccgt gtggagcggg ccatgagtga agtcacctcc    840
ctccacgagg acgactggcg atctcggcct tccggggcc ctgccctcac cccgatccgg    900
gatgaggagt ggggtggcca ctccccccgg agtcccaggg gatgggacca ggagcccgcc    960
agggagcagg caggcggggg ctggcgggcc aggcggcccc gggcccgctc cgtggacgcc   1020
ctggacgacc tcaccccgcc gagcaccgcc gagtcaggga gcaggtctcc cacgagtaat   1080
ggtgggagaa gccgggccta catgcccccg cggagccgca gccggacga cctctatgac   1140 caagacgact cgagggactt cccacgctcc cggaccccc actacgacga cttcaggtct   1200
cgggagcgcc ctcctgccga ccccaggtcc caccaccacc gtacccggga ccctcgggac   1260
aacggctcca ggtccgggga cctccctat gatgggcggc tactggagga ggctgtgagg   1320 aagaagggt cggaggagag gaggagaccc cacaaggagg aggaggaaga ggcctactac   1380
ccgcccgcgc cgccccgta ctcggagacc gactcgcagg cgtcccgaga gcgcaggctc   1440
aagaagaact ggccctgag tcgggaaagt ttagtcgtcg agcccaaatc ttctgacaaa   1500
actcacacat gcccaccgtg cccagcacct gaactcctgg ggggaccgtc agtcttcctc   1560
ttccccccaa aacccaagga caccctcatg atctcccgga cccctgaggt cacatgcgtg   1620
gtggtggacg tgagccacga agaccctgag gtcaagttca actggtacgt ggacggcgtg   1680
gaggtgcata atgccaagac aaagccgcgg gaggagcagt acaacagcac gtaccgtgtg   1740
gtcagcgtcc tcaccgtcct gcaccaggac tggctgaatg gcaaggagta caagtgcaag   1800
```

| | | |
|---|---|---|
| gtctccaaca | aagccctccc agcccccatc gagaaaacca tctccaaagc caaagggcag | 1860 |
| ccccgagaac | cacaggtgta caccctgccc ccatcccggg atgagctgac caagaaccag | 1920 |
| gtcagcctga | cctgcctggt caaaggcttc tatcccagcg acatcgccgt ggagtgggag | 1980 |
| agcaatgggc | agccggagaa caactacaag accacgcctc ccgtgctgga ctccgacggc | 2040 |
| tccttcttcc | tctacagcaa gctcaccgtg gacaagagca ggtggcagca ggggaacgtc | 2100 |
| ttctcatgct | ccgtgatgca tgaggctctg cacaaccact acacgcagaa gagcctctcc | 2160 |
| ctgtctccgg gtaaa | | 2175 |

<210> SEQ ID NO 198
<211> LENGTH: 2352
<212> TYPE: DNA
<213> ORGANISM: Artificial sequence
<220> FEATURE:
<223> OTHER INFORMATION: Synthetic polynucleotide

<400> SEQUENCE: 198

| | | |
|---|---|---|
| atggcgctgt | tggccggcgg gctctccaga gggctgggct cccacccggc cgccgcaggc | 60 |
| cgggacgcgg | tcgtcttcgt gtggcttctg cttagcacct ggtgcacagc tcctgccagg | 120 |
| gccatccagg | tgaccgtgtc caacccctac acgtggtga tcctcttcca gcctgtgacc | 180 |
| ctgccctgta | cctaccagat gacctcgacc cccacgcaac ccatcgtcat ctggaagtac | 240 |
| aagtctttct | gccgggaccg catcgccgat gccttctccc cggccagcgt cgacaaccag | 300 |
| ctcaatgccc | agctggcagc cgggaaccca ggctacaacc cctacgtcga gtgccaggac | 360 |
| agcgtgcgca | ccgtcaggat cgtggccacc aagcagggca acgctgtgac cctgggagat | 420 |
| tactaccagg | gccggaggat taccatcacc ggaaatgctg acctgacctt tgaccagacg | 480 |
| gcgtgggggg | acagtggtgt gtattactgc tccgtggtct cagcccagga cctccagggg | 540 |
| aacaatgagg | cctacgcaga gctcatcgtc cttggagga cctcaggggt ggctgagctc | 600 |
| ttacctggtt | ttcaggcggg gcccatagaa gtgtatgccg ccggcaaagc agccacctca | 660 |
| ggtgttccca | gcatttatgc ccccagcacc tatgcccacc tgtctcccgc caagacccca | 720 |
| cccccaccag | ctatgattcc catgggccct gcctacaacg gtaccctgg aggataccct | 780 |
| ggagacgttg | acaggagtag ctcagctggt ggccaaggct cctatgtacc cctgcttcgg | 840 |
| gacacggaca | gcagtgtggc ctctgaagtc cgcagtggct acaggattca ggccagccag | 900 |
| caggacgact | ccatgcgggt cctgtactac atggagaagg agctggccaa cttcgaccct | 960 |
| tctcgacctg | gccccccag tggccgtgtg gagcgggcca tgagtgaagt cacctcccctc | 1020 |
| cacgaggacg | actggcgatc tcggccttcc cggggccctg ccctcacccc gatccgggat | 1080 |
| gaggagtggg | gtggccactc ccccggagt cccaggggat gggaccagga gcccgccagg | 1140 |
| gagcaggcag | gcggggctg gcgggccagg cggccccggg cccgctccgt ggacgccctg | 1200 |
| gacgacctca | ccccgccgag caccgccgag tcagggagca ggtctcccac gagtaatggt | 1260 |
| gggagaagcc | gggcctacat gccccgcgcg agccgcagcc gggacgacct ctatgaccaa | 1320 |
| gacgactcga | gggacttccc acgctcccgg gacccccact acgacgactt caggtctcgg | 1380 |
| gagcgccctc | ctgccgaccc caggtccac caccaccgta cccgggaccc tcggacaac | 1440 |
| ggctccaggt | ccggggacct cccctatgat gggcggctac tggaggaggc tgtgaggaag | 1500 |
| aaggggtcgg | aggagaggag gagacccac aaggaggagg aggaagaggc ctactacccg | 1560 |
| cccgcgccgc | ccccgtactc ggagaccgac tcgcaggcgt cccgagagcg caggctcaag | 1620 |
| aagaacttgg | ccctgagtcg ggaaagttta gtcgtcgagc ccaaatcttc tgacaaaact | 1680 |

```
cacacatgcc caccgtgccc agcacctgaa ctcctggggg gaccgtcagt cttcctcttc    1740
cccccaaaac ccaaggacac cctcatgatc tcccggaccc ctgaggtcac atgcgtggtg    1800
gtggacgtga gccacgaaga ccctgaggtc aagttcaact ggtacgtgga cggcgtggag    1860
gtgcataatg ccaagacaaa gccgcgggag gagcagtaca acagcacgta ccgtgtggtc    1920
agcgtcctca ccgtcctgca ccaggactgg ctgaatggca aggagtacaa gtgcaaggtc    1980
tccaacaaag ccctcccagc ccccatcgag aaaaccatct ccaaagccaa agggcagccc    2040
cgagaaccac aggtgtacac cctgccccca tcccgggatg agctgaccaa gaaccaggtc    2100
agcctgacct gcctggtcaa aggcttctat cccagcgaca tcgccgtgga gtgggagagc    2160
aatgggcagc cggagaacaa ctacaagacc acgcctcccg tgctggactc cgacggctcc    2220
ttcttcctct acagcaagct caccgtggac aagagcaggt ggcagcaggg gaacgtcttc    2280
tcatgctccg tgatgcatga ggctctgcac aaccactaca cgcagaagag cctctccctg    2340
tctccgggta aa                                                         2352
```

POLYPEPTIDES AND POLYNUCLEOTIDES, AND USES THEREOF FOR TREATMENT OF IMMUNE RELATED DISORDERS AND CANCER

REFERENCE TO SEQUENCE LISTING

The Sequence Listing is filed herewith electronically as a separate ASCII file entitled "2585-seq-listing.txt", created on Apr. 16 2012, having 427000 bytes in size; the contents of which are hereby incorporated by reference as if fully set forth herein.

FIELD OF THE INVENTION

This invention relates to LY6G6F, VSIG10, TMEM25 and LSR proteins, which are suitable targets for immunotherapy, treatment of cancer, infectious disorders, and/or immune related disorders, and drug development, as well as soluble molecules and conjugates thereof, and antibodies against such.

BACKGROUND OF THE INVENTION

Naïve T cells must receive two independent signals from antigen-presenting cells (APC) in order to become productively activated. The first, Signal 1, is antigen-specific and occurs when T cell antigen receptors encounter the appropriate antigen-MHC complex on the APC. The fate of the immune response is determined by a second, antigen-independent signal (Signal 2) which is delivered through a T cell costimulatory molecule that engages its APC-expressed ligand. This second signal could be either stimulatory (positive costimulation) or inhibitory (negative costimulation or coinhibition). In the absence of a costimulatory signal, or in the presence of a coinhibitory signal, T-cell activation is impaired or aborted, which may lead to a state of antigen-specific unresponsiveness (known as T-cell anergy), or may result in T-cell apoptotic death.

Costimulatory molecule pairs usually consist of ligands expressed on APCs and their cognate receptors expressed on T cells. The prototype ligand/receptor pairs of costimulatory molecules are B7/CD28 and CD40/CD40L. The B7 family consists of structurally related, cell-surface protein ligands, which may provide stimulatory or inhibitory input to an immune response. Members of the B7 family are structurally related, with the extracellular domain containing at least one variable or constant immunoglobulin domain.

Both positive and negative costimulatory signals play critical roles in the regulation of cell-mediated immune responses, and molecules that mediate these signals have proven to be effective targets for immunomodulation. Based on this knowledge, several therapeutic approaches that involve targeting of costimulatory molecules have been developed, and were shown to be useful for prevention and treatment of cancer by turning on, or preventing the turning off, of immune responses in cancer patients and for prevention and treatment of autoimmune diseases and inflammatory diseases, as well as rejection of allogenic transplantation, each by turning off uncontrolled immune responses, or by induction of "off signal" by negative costimulation (or coinhibition) in subjects with these pathological conditions.

Manipulation of the signals delivered by B7 ligands has shown potential in the treatment of autoimmunity, inflammatory diseases, and transplant rejection. Therapeutic strategies include blocking of costimulation using monoclonal antibodies to the ligand or to the receptor of a costimulatory pair, or using soluble fusion proteins composed of the costimulatory receptor that may bind and block its appropriate ligand. Another approach is induction of co-inhibition using soluble fusion protein of an inhibitory ligand. These approaches rely, at least partially, on the eventual deletion of auto- or allo-reactive T cells (which are responsible for the pathogenic processes in autoimmune diseases or transplantation, respectively), presumably because in the absence of costimulation (which induces cell survival genes) T cells become highly susceptible to induction of apoptosis. Thus, novel agents that are capable of modulating costimulatory signals, without compromising the immune system's ability to defend against pathogens, are highly advantageous for treatment and prevention of such pathological conditions.

Costimulatory pathways play an important role in tumor development. Interestingly, tumors have been shown to evade immune destruction by impeding T cell activation through inhibition of co-stimmulatory factors in the B7-CD28 and TNF families, as well as by attracting regulatory T cells, which inhibit anti-tumor T cell responses (see Wang (2006) Immune Suppression by Tumor Specific CD4+ Regulatory T cells in Cancer. Semin Cancer. Biol. 16:73-79; Greenwald, et al. (2005) The B7 Family Revisited. Ann. Rev. Immunol. 23:515-48; Watts (2005) TNF/TNFR Family Members in Co-stimulation of T Cell Responses Ann. Rev. Immunol. 23:23-68; Sadum, et al. (2007) Immune Signatures of Murine and Human Cancers Reveal Unique Mechanisms of Tumor Escape and New Targets for Cancer Immunotherapy. Clin. Canc. Res. 13(13): 4016-4025). Such tumor expressed co-stimulatory molecules have become attractive cancer biomarkers and may serve as tumor-associated antigens (TAAs). Furthermore, costimulatory pathways have been identified as immunologic checkpoints that attenuate T cell dependent immune responses, both at the level of initiation and effector function within tumor metastases. As engineered cancer vaccines continue to improve, it is becoming clear that such immunologic checkpoints are a major barrier to the vaccines' ability to induce therapeutic anti-tumor responses. In that regard, costimulatory molecules can serve as adjuvants for active (vaccination) and passive (antibody-mediated) cancer immunotherapy, providing strategies to thwart immune tolerance and stimulate the immune system.

In addition, such agents could be of use in other types of cancer immunotherapy, such as adoptive immunotherapy, in which tumor-specific T cell populations are expanded and directed to attack and kill tumor cells. Agents capable of augmenting such anti-tumor response have great therapeutic potential and may be of value in the attempt to overcome the obstacles to tumor immunotherapy. Recently, novel agents that modulate several costimulatory pathways were indeed introduced to the clinic as cancer immunotherapy.

Emerging data from a wide range of studies on acute and chronic infections support an important role for negative costimulatory receptors also in controlling infection. Memory CD8 T cells generated after an acute viral infection are highly functional and constitute an important component of protective immunity. Modulation of costimulatory pathway has also been proven effective in optimizing antiviral immunity by limiting the memory T cell response to its protective capacities (Teijaro et al., J Immunol. 2009: 182; 5430-5438). This has been demonstrated in models of influenza infection in which inhibiting CD28 costimulation with CTLA4-Ig suppressed primary immune responses in naive mice infected with influenza, but was remarkably curative for memory CD4 T cell-mediated secondary responses to influenza leading to improved clinical outcome and increased survival to influenza challenge.

Chronic infections are often characterized by varying degrees of functional impairment of virus-specific T-cell responses, and this defect is a principal reason for the inability of the host to eliminate the persisting pathogen. Although functional effector T cells are initially generated during the early stages of infection, they gradually lose function during the course of the chronic infection as a result of persistent exposure to foreign antigen, giving rise to T cell exhaustion. Exhausted T cells express high levels of multiple co-inhibitory receptors such as CTLA-4, PD-1, and LAG3 (Crawford et al., Curr Opin Immunol. 2009; 21:179-186; Kaufmann et al., J Immunol 2009; 182:5891-5897, Sharpe et al., Nat Immunol 2007; 8:239-245). PD-1 overexpression by exhausted T cells was observed clinically in patients suffering from chronic viral infections including HIV, HCV and HBV (Crawford et al., Curr Opin Immunol 2009; 21:179-186; Kaufmann et al., J Immunol 2009; 182:5891-5897, Sharpe et al., Nat Immunol 2007; 8:239-245). There has been some investigation into this pathway in additional pathogens, including other viruses, bacteria, and parasites (Hofmeyer et al., J Biomed Biotechnol. Vol 2011, Art. ID 451694, Bhadra et al., Proc Natl Acad. Sci. 2011; 108(22):9196-201). For example, the PD-1 pathway was shown to be involved in controlling bacterial infection using a sepsis model induced by the standard cecal ligation and puncture method. The absence of PD-1 in knockout mice protected from sepsis-induced death in this model (Huang et al., PNAS 2009: 106; 6303-6308).

T cell exhaustion can be reversed by blocking co-inhibitory pathways such as PD-1 or CTLA-4 (Rivas et al., J Immunol. 2009; 183:4284-91; Golden-Mason et al., J Virol. 2009; 83:9122-30; Hofmeyer et al., J Biomed Biotechnol. Vol 2011, Art. ID 451694), thus allowing restoration of anti viral immune function. The therapeutic potential of co-inhibition blockade for treating viral infection was extensively studied by blocking the PD-1/PD-L1 pathway, which was shown to be efficacious in several animal models of infection including acute and chronic simian immunodeficiency virus (SIV) infection in rhesus macaques (Valu et al., Nature 2009; 458: 206-210) and in mouse models of chronic viral infection, such as lymphocytic choriomeningitis virus (LCMV) (Barber et al., Nature. 2006; 439:682-7), and Theiler's murine encephalomyelitis virus (TMEV) model in SJL/J mice (Duncan and Miller PLoS One. 2011; 6:e18548). In these models PD-1/PD-L1 blockade improved anti viral responses and promoted clearance of the persisting viruses. In addition, PD-1/PD-L1 blockade increased the humoral immunity manifested as elevated production of specific anti-virus antibodies in the plasma, which in combination with the improved cellular responses leads to decrease in plasma viral loads and increased survival.

Blocking negative signaling pathways, such as PD-1 and CTLA-4, can restore the host immune system, enabling it to respond to further stimulation. Combining therapeutic vaccination along with the blockade of inhibitory signals could synergistically enhance functional CD8 T-cell responses and improve viral control in chronically infected individuals, providing a promising strategy for the treatment of chronic viral infections, such as human immunodeficiency virus, hepatitis B virus, and hepatitis C virus (Ha et al, Immunol Rev. 2008 June; 223:317-33). The results of a recent study indicate that blocking of the PD-1 pathway improved T cell responses to HBV vaccination in subjects with HCV infection, and raise the possibility that blocking this pathway might improve success rates of immunization in the setting of chronic viral infection (Moorman et al, Vaccine. 2011 Apr. 12; 29(17): 3169-76). Antibodies to PD-1 and CTLA-4 are currently in clinical trials in chronic hepatitis C, as promising candidates for combination with both prophylactic and therapeutic vaccines (Diepolder and Obst, Expert Rev Vaccines. 2010 March; 9(3):243-7). PD-1 blockade also enhances the effectiveness of prophylactic vaccination leading to an increase in epitope specific T cells (Finnefrock et al., J Immunol 2009; 182; 980-987)

In addition to blockade of co-inhibitory pathways for treatment of chronic infections, recent studies using viral infection models have highlighted the importance of positive costimulatory signals during memory responses against viruses. Costimulatory molecules such as CD28, 4-1BB, and OX40 have also been implicated in the survival, generation, maintenance, and quality of virus-specific memory CD8+ T cells. The delivery of costimulatory signals can help boost the generation and function of virus-specific memory CD8+ T cells. The use of costimulatory molecules as adjuvants, along with viral antigens in vaccines, may facilitate the generation of effective antigen-specific memory CD8+ T-cell responses, and may therefore lead to improved vaccines (Duttagupta et al, Crit Rev Immunol. 2009; 29(6):469-86).

A recent study also evaluated the effects of soluble PD-1 (sPD-1) as a blockade of PD-1 and PD-L1 on vaccine-elicited antigen-specific T-cell responses in mice. Coadministration of sPD-1 with a DNA vaccine or with an adenovirus-based vaccine, increased antigen-specific CD8(+) T-cell responses, indicating vaccine type-independent adjuvant effect of sPD-1 (Song et al, J Immunother. 2011 April; 34(3):297-306). These and additional results of this study suggest that an immunization strategy using the soluble extracellular domain (ECD) of a negative costimulatory protein as an adjuvant, could be used to increase antigen-specific T-cell immunity elicited by vaccination.

B cells have also long been considered to have a key role in the development and maintenance of many autoimmune diseases through production of pathogenic autoantibodies, such as systemic lupus erythomatosus (SLE) and Sjogren's disease. However, it is clear that a number of other B cell functions are also critical in the pathogenesis of organ-specific autoimmune diseases that were previously thought to be mainly T cell mediated, such as rheumatoid arthritis (RA) and type 1 diabetes (T1D) (Wong et al 2010, Curr Opin Immunol. 22:723-731).

T cell help to B cells is a pivotal process of adaptive immune responses. Follicular helper T (Tfh) cells are a subset of CD4+ T cells specialized in B cell help (reviewed by Crotty, Annu. Rev. Immunol. 29: 621-663, 2011). Tfh cells express the B cell homing chemokine receptor, CXCR5, which drives Tfh cell migration into B cell follicles within lymph nodes in a CXCL13-dependent manner. Tfh cells first interact with cognate B cells at the T cell-B cell border and subsequently induce germinal center B cell differentiation and germinal center formation within the follicle (Reviewed by Crotty, Annu. Rev. Immunol. 29: 621-663, 2011). The requirement of Tfh cells for B cell help and T cell-dependent antibody responses indicates that this cell type is of great importance for protective immunity against various types of infectious agents, as well as for rational vaccine design. Not surprisingly, dysregulation and aberrant accumulation of Tfh cells has also been linked with autoimmune diseases, such as Sjogren's disease and autoimmune arthritis (Yu and Vinuesa, 2010, Cell. Mol. Immunol. 7: 198-203).

Tfh cells selectively express a wealth of surface proteins, which are involved in their selective localization (such as CXCR5) and in direct physical interactions with B cells to provide B cell help. Among the latter group are several members of the costimulatory proteins family which are highly expressed in Tfh cells, including the inducible co-stimulatory receptor ICOS, and the negative costimulators (inhibitory receptors) PD-1 and BTLA (Crotty, Annu. Rev. Immunol. 29: 621-663, 2011), thus this cell subset may be also controlled by modulation of costimulatory and coinhibitory pathways, contributing to the effect on B cell function.

Regulating costimulation using agonists and/or antagonists to various costimulatory proteins has been extensively studied as a strategy for treating autoimmune diseases, graft rejection, allergy and cancer. This field has been clinically pioneered by CTLA4-Ig (Abatacept, Orencia®) which is approved for treatment of RA, mutated CTLA4-Ig (Belatacept, Nulojix®) for prevention of acute kidney transplant rejection and by the anti-CTLA4 antibody (Ipilimumab, Yervoy®), recently approved for the treatment of melanoma. Other costimulation regulators are currently in advanced stages of clinical development including anti-PD-1 antibody (MDX-1106) which is in development for treatment of advanced/metastatic clear-cell renal cell carcinoma (RCC) and anti-CD40L Antibody (BG9588, Antova®) for treatment of renal allograft transplantation. Furthermore, such agents are also in clinical development for viral infections, for example the anti PD-1 Ab, MDX-1106, which is being tested for treatment of hepatitis C, and the anti-CTLA-4 Ab CP-675, 206 (tremelimumab) which is in a clinical trial in hepatitis C virus-infected patients with hepatocellular carcinoma; the goals of the study are to test its effect on the carcinoma and on the replication of the virus.

BRIEF SUMMARY OF THE INVENTION

According to at least some embodiments, the invention provides novel therapeutic and diagnostic compositions containing an ectodomain or soluble or secreted form of the LY6G6F, VSIG10, TMEM25 and/or LSR proteins and/or variants and/or orthologs and/or fragments, and/or conjugate containing same, and/or nucleic acid sequences encoding for same.

The full length amino acid sequence of the known (wild type) LY6G6F protein (lymphocyte antigen 6 complex locus protein G6f, genbank accession number: NP_001003693, SEQ ID NO:1) is shown in FIG. 1A. The full length amino acid sequence of known (wild type) VSIG10 protein (V-set and immunoglobulin domain-containing protein 10, genbank accession number: NP_061959, SEQ ID NO:3), and the amino acid sequence of VSIG10 novel variant (SEQ ID NO:5) are shown in FIGS. 1B and 1C, respectively. The amino acid sequence alignment of VSIG10 novel variant (SEQ ID NO:5) and the known (wild type) VSIG10 protein (SEQ ID NO:3) is shown in FIG. 2A. The full length amino acid sequence of known (wild type) TMEM25 protein (Transmembrane protein 25, Swiss-Prot accession number: Q86YD3, SEQ ID NO:7) is shown in FIG. 1D. The full length amino acid sequence of known (wild type) LSR protein (lipolysis-stimulated lipoprotein receptor isoform 2, genbank accession number: NP_991403) is provided in SEQ ID NO:62. The amino acid sequences of LSR variants SEQ ID NOs:11, 13, 15, 16, 17 and 18 are shown in FIGS. 1E, 1F, 1G, 1H, 1I, and 1J, respectively. The amino acid sequence alignment of the LSR variants SEQ ID NOs: 11, 13, 15, 16, 17 and 18 with previously known LSR sequences (SEQ ID NOs: 62-67) is demonstrated in FIGS. 2B, 2C, 2D, 2E, 2F, 2G, respectively.

According to at least some embodiments, there is provided an isolated polypeptide comprising at least 98 amino acids of the soluble ectodomain of a sequence selected from the group consisting of SEQ ID NOs:11, 13, 15-18, 67, and 143; at least 62 amino acids of the soluble ectodomain of a sequence selected from the group consisting of SEQ ID NOs:1 and 58; at least 36 amino acids of the soluble ectodomain of a sequence selected from the group consisting of SEQ ID NOs:3 and 5; or at least 46 amino acids of the soluble ectodomain of SEQ ID NO:7, or an isolated polypeptide consisting essentially of an amino acid sequence as set forth in SEQ ID NO:5 or variant thereof that possesses at least 95% sequence identity therewith; or variants, or orthologs, or fragments thereof.

Optionally the isolated polypeptide comprises only between 98 to 180 amino acids of the sequence selected from the group consisting of SEQ ID NOs:11, 13, 15-18, 67, and 143; between 62 to 228 amino acids of the sequence selected from the group consisting of SEQ ID NOs:1 and 58; between 36 and 393 of the sequence selected from the group consisting of SEQ ID NOs:3 and 5; or between 46 and 216 amino acids of SEQ ID NO:7.

Also optionally, the isolated polypeptide is selected from the group consisting of a polypeptide comprising only between 98 to 118, 135 to 155, and 160 to 180 amino acids of the sequence selected from the group consisting of SEQ ID NOs:11, 13, 15-18, 67, and 143; between 62 to 82, 95 to 115, 208 to 228 amino acids of the sequence selected from the group consisting of SEQ ID NOs:1 and 58; between 36 to 70, 80 to 100, 170 to 200, 265 to 290, 365 to 393 amino acids of the sequence selected from the group consisting of SEQ ID NOs:3 and 5; or between 46 to 66, 84 to 104, 196 to 216 amino acids of SEQ ID NO:7.

Also optionally, the isolated polypeptide comprises only about 72, 106, or 218 amino acids of the sequence selected from the group consisting of SEQ ID NOs:1 and 58; about 108, 145, or 170 amino acids of the sequence selected from the group consisting of SEQ ID NOs:11, 13, 15-18, 67, and 143; about 56, 94, or 206 amino acids of SEQ ID NO:7; or about 46, 49, 58, 60, 87, 89, 93, 94, 178, 182, 185, 187, 273, 279, 282, 374 or 383 amino acids of SEQ ID NOs:3 and 5.

Also optionally, the isolated polypeptide consists essentially of an amino acid sequence having at least 95% sequence identity with amino acid sequences set forth in any one of SEQ ID NOs: 12, 2, 4-6, 8, 14, 47-50, 10, 15-18, 22, 39, 59-61; 81-102. Optionally and preferably, the isolated polypeptide consists essentially of the amino acid sequence set forth in any one of SEQ ID NOs: 12, 2, 4-6, 8, 14, 47-50, 10, 15-18, 22, 39, 59-61; 81-102.

Optionally, the isolated polypeptide blocks or inhibits the interaction of LSR, TMEM25, VSIG10, LY6G6F, or a fragment or variant thereof with a corresponding functional counterpart.

Optionally, the isolated polypeptide replaces or augments the interaction of LSR, TMEM25, VSIG10, LY6G6F, or a fragment or variant thereof with a corresponding functional counterpart.

Optionally, the isolated ortholog is a mouse polypeptide selected from SEQ ID NOs: 9 and 19-21.

According to at least some embodiments, the present invention provides isolated polypeptides comprising discrete portions (fragments) of VSIG10 proteins, corresponding to:

A. An isolated chimeric polypeptide, comprising a first amino acid sequence being at least 95% homologous to MAAGGSAPEPRVLVCLGALLAG-WVAVGLEAVVIGEVHENVTLHCGNISGLRGQ VTW-YRNNSEPVFLLSSNSSLRPAEPRFSLV-DATSLHIESLSLGDEGIYTCQEILNVT QWFQVWLQVA corresponding to amino acids 1-120 of known VSIG10 protein (SEQ ID NO:3), which also corresponds to amino acids 1-120 of VSIG10 variant (SEQ ID NO:5), a second bridging amino acid sequence comprising of N, and a third amino acid sequence being at least 95% homologous to PPP-SAPQCWAQMASGSFMLQLTCRWDGGYPD-PDFLWIEEPGGVIVGKSKLGVE MLSESQLS-DGKKFKCVTSHIVGPESGASCMVQIRGPSLLSEPMK-TCFTGGNVTLT CQVSGAYPPAKILWLRNLTQPEVI-IQPSSRHLITQDGQNSTLTIHNCSQDLDEGYYI CRAD-SPVGVREMEIWLSVKEPLNIGGIVG-TIVSLLLLGLAIISGLLLHYSPVFCWK VGNTSRGQNMDDVMVLVD-SEEEEEEEEEEEEDAAVGEQEGAREREELPKEIPKQ DHIHRVTALVNGNIEQMGNGFQDLQDDS-SEEQSDIVQEEDRPV corresponding to amino acids 223-540 of known VSIG10 protein (SEQ ID NO:3), which also corresponds to amino acids 122-439 of VSIG10 variant (SEQ ID NO:5), wherein said first amino acid sequence, second bridging amino acid sequence and third amino acid sequence are contiguous and in a sequential order.

B. An isolated polypeptide of an edge portion of VSIG10 variant (SEQ ID NO:5), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least 3 amino acids comprise ANP having a structure as follows (numbering according to VSIG10 variant (SEQ ID NO:5)): a sequence starting from any of amino acid numbers 120-x to 120; and ending at any of amino acid numbers 122+((n−3)−x), in which x varies from 0 to n−3.

According to at least some embodiments, the subject invention further provides isolated polypeptides comprising a sequence of amino acid residues corresponding to discrete portions of VSIG10 proteins, corresponding to the new junction and edge portions of VSIG10 variant (SEQ ID NO: 5). The unique sequence of the new junction of VSIG10 variant (SEQ ID NO: 5) is demonstrated in protein sequence alignment in FIG. 2A.

According to at least some embodiments, the subject invention provides isolated polypeptides comprising discrete portions (fragments) of LSR proteins, corresponding to:

A. An isolated chimeric polypeptide, comprising a first amino acid sequence being at least 95% homologous to MALLAGGLSRGLGSHPAAAGRDAV-VFVWLLLSTWCTAPARAIQVTVSNPYHVV ILFQPVTLPCTYQMTSTPTQPIVI-WKYKSFCRDRIADAFSPASVDNQLNAQLAAGN PGY-NPYVECQDSVRTVRVVATKQG-NAVTLGDYYQGRRITITGNADLTFDQTAW GDSGVYYCSVVSAQDLQGNNEAYAELIV-LGRTSGVAELLPGFQAGPIE corresponding to amino acids 49-258 of known LSR protein (SEQ ID NO:62), which also corresponds to amino acids 1-210 of LSR variant isoform f (SEQ ID NO:18), a second bridging amino acid sequence comprising of V, and a third amino acid sequence being at least 95% homologous to YAAGKAATSGVPSIYAP-STYAHLSPAKTPPPPAMIPMGPAYN-GYPGGYPGDVDRS SSAGGQGSYVPLLRDTDSS-VASEVRSGYRIQASQQDDSMRVLYYMEKELANFDP SRPGPPSGRVERAMSEVTSLHED-DWRSRPSRGPALTPIRDEEWGGHSPRSPRGWD QEPAREQAGGGWRARRPRARSVDALD-DLTPPSTAESGSRSPTSNGGRSRAYMPP RSRSRDDLY-DQDDSRDFPRSRDPHYDDFRSRERPPAD-PRSHHHRTRDPRDNGSRS GDLPYDGRLLEEAVRKKGSEERRRPH-KEEEEEAYYPPAPPPYSETDSQASRERRL KKNLA-LSRESLVV corresponding to amino acids 309-649 of known LSR protein (SEQ ID NO:62), which also corresponds to amino acids 212-552 of LSR variant isoform f (SEQ ID NO:18), wherein said first amino acid sequence, second bridging amino acid and third amino acid sequence are contiguous and in a sequential order.

B. An isolated polypeptide of an edge portion of LSR variant isoform f (SEQ ID NO:18), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least 3 amino acids comprise EVY having a structure as follows (numbering according to SEQ ID NO:18): a sequence starting from any of amino acid numbers 210-x to 210; and ending at any of amino acid numbers 212+((n−3)−x), in which x varies from 0 to n−3.

C. An isolated chimeric polypeptide comprising a first amino acid sequence being at least 95% homologous to MALLAGGLSRGLGSHPAAAGRDAV-VFVWLLLSTWCTAPARAIQVTVSNPYHVV ILFQPVTLPCTYQMTSTPTQPIVI-WKYKSFCRDRIADAFSPASVDNQLNAQLAAGN PGY-NPYVECQDSVRTVRVVATKQG-NAVTLGDYYQGRRITITGNADLTEDQTAW GDSGVYYCSVVSAQDLQGNNEAYAELIVL corresponding to amino acids 49-239 of known LSR protein (SEQ ID NO:66), which also corresponds to amino acids 1-191 of LSR variant isoform f (SEQ ID NO:18), a second amino acid sequence being at least 80%, preferably at least 85%, more preferably at least 90% and most preferably at least 95% homologous to a polypeptide having the sequence GRTSG-VAELLPGFQAGPIE corresponding to amino acids 192-218 of LSR variant isoform f (SEQ ID NO:18), and a third amino acid sequence being at least 95% homologous to VYAAG-KAATSGVPSIYAPSTYAHLSPAKTPPP-PAMIPMGPAYNGYPGGYPGDVD RSSSAGGGQGSYV-PLLRDTDSSVASEVRSGYRIQASQQDDSMRVLYYME-KELANF DPSRPGPPSGRVERAMSEVTSLHED-DWRSRPSRGPALTPIRDEEWGGHSPRSPRG WDQE-PAREQAGGGWRARRPRARSVDALDDLT-PPSTAESGSRSPTSNGGRSRAY MPPRSRSRDDLYDQDDSRDFPRSRDPHY-DDFRSRERPPADPRSHHHRTRDPRDN GSRS-GDLPYDGRLLEEAVRKKGSEERRRPH-KEEEEEAYYPPAPPPYSETDSQASR ERRLKKNLALSRESLVV corresponding to amino acids 240-581 of known LSR protein SEQ ID NO:66, which also corresponds to amino acids 211-552 of LSR variant isoform f (SEQ ID NO:18), wherein said first amino acid sequence, second amino acid sequence and third amino acid sequence are contiguous and in a sequential order.

D. An isolated polypeptide of an edge portion of LSR variant isoform f (SEQ ID NO:18), comprising an amino acid sequence being at least about 80%, preferably at least about 85%, more preferably at least about 90% and most preferably at least about 95% homologous to the sequence GRTSG-VAELLPGFQAGPIE of LSR variant isoform f (SEQ ID NO:18).

According to at least some embodiments, the subject invention further provides isolated polypeptides comprising a sequence of amino acid residues corresponding to discrete portions of LSR, corresponding to the new junction and edge portions of LSR variant LSR isoform-f (SEQ ID NO: 18). The unique sequences of the new junction of the LSR isoform-f (SEQ ID NO: 18) is demonstrated in protein sequence alignment in FIG. 2G.

According to at least some embodiments, the subject invention provides polypeptides comprising a sequence of amino acid residues corresponding to discrete portions of LY6G6F, VSIG10, TMEM25 and/or LSR proteins, including different portions of the extracellular domain corresponding to residues 17-234 of LY6G6F (SEQ ID NO:1), corresponding to amino acid sequence depicted in SEQ ID NO:2; residues 31-413 of VSIG10 (SEQ ID NO:3), corresponding to amino acid sequence depicted in SEQ ID NO:4; residues 31-312 of VSIG10 (SEQ ID NO:5), corresponding to amino acid sequence depicted in SEQ ID NO:6; residues 27-232 of TMEM25 (SEQ ID NO:7), corresponding to amino acid sequence depicted in SEQ ID NO:8; residues 42-211 of LSR (SEQ ID NO:11, and/or SEQ ID NO:143), corresponding to amino acid sequence depicted in SEQ ID NO:12; residues 42-192 of LSR (SEQ ID NO:13), corresponding to amino acid sequence depicted in SEQ ID NO:14, residues 42-533 of LSR (SEQ ID NO:15), corresponding to amino acid sequence depicted in SEQ ID NO:47, residues 42-532 of LSR (SEQ ID NO:16), corresponding to amino acid sequence depicted in SEQ ID NO:48, residues 42-493 of LSR (SEQ ID NO:17), corresponding to amino acid sequence depicted in SEQ ID NO:49, residues 42-552 of LSR (SEQ ID NO:18), corresponding to amino acid sequence depicted in SEQ ID NO:50, and/or fragments and/or variants thereof possessing at least 85%, 90%, 95, 96, 97, 98 or 99% sequence homology therewith. According to still further embodiments, the LY6G6F ECD fragments are selected from any one of SEQ ID NOs 81, 96, and variants thereof, as described herein. According to still further embodiments, the VSIG10 ECD fragments are selected from any one of SEQ ID NOs 82-93, 97-100, and variants thereof, as described herein. According to still further embodiments, the LSR ECD fragments are selected from any one of SEQ ID NOs 95, 102, and variants thereof, as described herein. According to still further embodiments, the TMEM25 ECD fragments are selected from any one of SEQ ID NOs 94, 101, and variants thereof, as described herein. According to still further embodiments, the discrete portions of LY6G6F, VSIG10, TMEM25 and/or LSR proteins may or may not include a signal (leader) peptide (SP) sequence (FIG. 1). According to at least some embodiments of the invention, there are provided examples of the ECD portions including SP sequences of LY6G6F, VSIG10, TMEM25 and/or LSR proteins. An example of ECD portion including SP sequence of LY6G6F protein (SEQ ID NO:1) is amino acid sequence set forth in SEQ ID NO:59. An example of ECD portion including SP sequence of VSIG10 protein (SEQ ID NO:3) is amino acid sequence set forth in SEQ ID NO:60. An example of ECD portion including SP sequence of VSIG10 protein (SEQ ID NO:5) is amino acid sequence set forth in SEQ ID NO:61. An example of ECD portion including SP sequence of TMEM25 protein (SEQ ID NO:7) is amino acid sequence set forth in SEQ ID NO: 39. An example of ECD portion including SP sequence of LSR protein (SEQ ID NO:11) is amino acid sequence set forth in SEQ ID NO:10. An example of ECD portion including SP sequence of LSR protein (SEQ ID NO:14) is amino acid sequence set forth in SEQ ID NO:22.

According to further embodiments, the invention provides polypeptides comprising a sequence of amino acid residues corresponding to soluble LSR proteins depicted in SEQ ID NO: 18, including different portions thereof or variants thereof possessing at least 85%, 90%, 95, 96, 97, 98 or 99% sequence homology therewith. According to further embodiments, the invention provides polypeptides comprising a sequence of amino acid residues corresponding to soluble LSR proteins depicted in any one of SEQ ID NOs:15-16, including different portions thereof or variants thereof possessing at least 95, 96, 97, 98 or 99% sequence homology therewith. According to further embodiments, the invention provides polypeptides comprising a sequence of amino acid residues corresponding to soluble LSR proteins depicted in any one of SEQ ID NOs:15-18. According to still further embodiments, the soluble LSR proteins depicted in any one of SEQ ID NOs:15-18 may or may not include a signal (leader) peptide sequence (FIGS. 1G, G, I and J).

According to still further embodiments, the invention provides polypeptides comprising a sequence of amino acid residues corresponding to extracellular domains of orthologs of TMEM25, LY6G6F, VSIG10, LSR variant 1 and/or LSR variant 2 proteins, particularly mouse orthologs (SEQ ID NOs: 28, 29, 30, 31 and/or 32, respectively), including but not limited to mouse orthologs extracellular domains corresponding to amino acid sequence depicted in SEQ ID NOs: 9, 19-21, or portions or variants thereof possessing at least 85%, 90%, 95, 96, 97, 98 or 99% sequence homology therewith.

According to still further embodiments, the invention provides polypeptides comprising an amino acid sequence corresponding to any one of novel variants of VSIG10 (SEQ ID NO: 5), and LSR (SEQ ID NOs: 11, 13, 15, 16 and 18).

According to at least some embodiments, the present invention provides a fusion protein comprising any of the above polypeptides joined to a heterologous sequence. Optionally, the heterologous sequence comprises at least a portion of an immunoglobulin molecule. Optionally and preferably, the immunoglobulin molecule portion is an immunoglobulin heavy chain constant region Fc fragment. Optionally and more preferably, the immunoglobulin heavy chain constant region is derived from an immunoglobulin isotype selected from the group consisting of an IgG1, IgG2, IgG3, IgG4, IgM, IgE, IgA and IgD. Optionally and most preferably, the fusion protein has the amino acid sequence set forth in any one of SEQ ID NOs: 71-80, 172-181 or set forth in any one of SEQ ID NOs:23-26 and also optionally modulates immune cell response in vitro or in vivo.

According to at least some embodiments, the subject invention provides isolated nucleic acid sequences encoding any one of the foregoing novel variants of TMEM25, VSIG10, and/or LSR and/or any one of the foregoing LY6G6F, VSIG10, TMEM25 and/or LSR extracellular domain polypeptides or fragments or homologs or orthologs thereof.

According to at least some embodiments, there is provided an isolated nucleic acid sequence selected from the group consisting of SEQ ID NOs: 33-37, 40-46, 132, 155, 182-198, or variant thereof that possesses at least 95% sequence identity therewith, or a degenerative variant thereof.

According to at least some embodiments, the subject invention provides an isolated polynucleotide encoding a polypeptide comprising any one of the amino acid sequences, as set forth in SEQ ID NOs: 2, 4, 5, 6, 8-16, 18-22, 39, 47-50, 59-61, 143, or a fragment or variant thereof that possesses at least 85, 90, 95, 96, 97, 98 or 99% sequence identity therewith, or a degenerative variant thereof.

According to at least some embodiments, the subject invention provides an isolated polynucleotide comprising a nucleic acid as set forth in any one of SEQ ID NO:33-37, 40-46, 132, 145, 155, 182-188, or a sequence homologous thereto or degenerative variants thereof. According to another embodiment, the isolated polynucleotide is at least 85, 90, 95, 96, 97, 98 or 99% homologous to a nucleic acid sequence as set forth in any one of SEQ ID NOs: 33-37, 40-46, 145.

According to at least some embodiments, there is provided an expression vector or a virus, containing at least one isolated nucleic acid sequence as described herein. According to at least some embodiments, there is provided a recombinant cell comprising an expression vector or a virus containing an isolated nucleic acid sequence as described herein, wherein the cell constitutively or inducibly expresses the polypeptide encoded by the DNA segment. According to at least some embodiments, there is provided a method of producing a LSR, TMEM25, VSIG10, LY6G6F soluble ectodomain polypeptide, or fragment or fusion protein thereof, comprising culturing the recombinant cell as described herein, under conditions whereby the cell expresses the polypeptide encoded by the DNA segment or nucleic acid and recovering said polypeptide.

According to at least some embodiments of the present invention, there is provided a pharmaceutical composition comprising an isolated amino acid sequence of ectodomain or soluble or secreted forms of any one of LY6G6F, VSIG10, TMEM25, LSR proteins or variants or orthologs or fragments or conjugates containing same.

According to at least some embodiments, the invention provides an isolated or purified amino acid sequence of soluble and/or extracellular domain of LY6G6F, VSIG10, TMEM25 and/or LSR protein or nucleic acid sequence encoding same, which optionally may be directly or indirectly attached to a non-LY6G6F, VSIG10, TMEM25 and/or LSR protein or nucleic acid sequence, such as a soluble immunoglobulin domain or fragment.

According to at least some embodiments, the invention provides vectors such as plasmids and recombinant viral vectors and host cells containing that express secreted or soluble form and/or the ECD of the LY6G6F, VSIG10, TMEM25 and/or LSR protein or fragments or variants or orthologs thereof or polypeptide conjugates containing any of the foregoing.

According to at least some embodiments the invention provides a use of these vectors such as plasmids and recombinant viral vectors and host cells containing that express any one of LY6G6F, VSIG10, TMEM25 and/or LSR, secreted and/or soluble form and/or the ECD and/or fragments thereof and/or variants, and/or orthologs thereof and/or polypeptide conjugates containing any of the foregoing to produce any one of said LY6G6F, VSIG10, TMEM25 and/or LSR proteins.

According to at least some embodiments, the invention provides pharmaceutical or diagnostic compositions containing any of the foregoing.

According to at least some embodiments, the invention provides a use of any one of the compounds containing at least one of LY6G6F, VSIG10, TMEM25 and/or LSR ectodomains, soluble or secreted form or fragments or orthologs or variants thereof, or conjugates, or nucleic acid sequence encoding same, or pharmaceutical composition comprising same, as therapeutics for treatment or prevention of cancer as recited herein, infectious disorder as recited herein, and/or immune related disorder, including but not limited to autoimmune diseases as recited herein, transplant rejection and graft versus host disease and/or for blocking or promoting immune costimulation mediated by any one of the LY6G6F, VSIG10, TMEM25 and/or LSR polypeptides, immune related diseases as recited herein and/or for immunotherapy (promoting or inhibiting immune costimulation). According to at least some embodiments, the autoimmune disease includes any autoimmune disease, and optionally and preferably includes but is not limited to any of the types and subtypes of any of multiple sclerosis, rheumatoid arthritis, type I diabetes, psoriasis, systemic lupus erythematosus, inflammatory bowel disease, uveitis, or Sjogren's syndrome.

According to at least some embodiments, the invention provides a use of any one of the compounds containing at least one of LY6G6F, VSIG10, TMEM25 and/or LSR ectodomains, soluble or secreted form or fragments or orthologs or variants thereof, or conjugates, or nucleic acid sequence encoding same, or pharmaceutical composition comprising same, for administration as an anti-cancer vaccine, as an adjuvant for anti cancer vaccine, and/or for adoptive immunotherapy, and/or for immunotherapy of cancer as recited herein.

According to at least some embodiments, the invention provides a use of any of the LY6G6F, VSIG10, TMEM25 and/or LSR proteins, and/or nucleic acid sequences as targets for development of drugs which specifically bind to any one of the LY6G6F, VSIG10, TMEM25 and/or LSR proteins and/or drugs which agonize or antagonize the binding of other moieties to the LY6G6F, VSIG10, TMEM25 and/or LSR proteins.

According to at least some embodiments, the present invention provides drugs which modulate (agonize or antagonize) at least one of the LY6G6F, VSIG10, TMEM25 and/or LSR related biological activity. Such drugs include by way of example antibodies, small molecules, peptides, ribozymes, aptamers, antisense molecules, siRNA's and the like. These molecules may directly bind or modulate an activity elicited by the any one of the LY6G6F, VSIG10, TMEM25 and/or LSR proteins or the LY6G6F, VSIG10, TMEM25 and/or LSR DNA or portions or variants thereof or may indirectly modulate any one of the LY6G6F, VSIG10, TMEM25 and/or LSR associated activity or binding of molecules to any one of the LY6G6F, VSIG10, TMEM25 and/or LSR and portions and variants thereof such as by modulating the binding of any one of LY6G6F, VSIG10, TMEM25 and/or LSR to its counter-receptor or endogenous ligand.

According to at least some embodiments, the invention provides novel monoclonal or polyclonal antibodies and antigen binding fragments and conjugates containing same, and/or alternative scaffolds, that specifically bind any one of LY6G6F, VSIG10, TMEM25 and/or LSR proteins as described herein or polypeptides having at least 95% homology thereto. Optionally such antibodies bind to proteins selected from the group consisting of any one of SEQ ID NOs: 1-8, 10-18, 22, 39, 47-50, 59-61, 9, 19-21, and/or the amino acid sequences corresponding to the unique edges of any one of SEQ ID NOs: 5 and 18, particularly wherein these antibodies, antigen binding fragments and conjugates containing same, and/or alternative scaffolds, are adapted to be used as therapeutic and/or diagnostic agents (both in vitro and in vivo diagnostic methods), particularly for treatment and/or diagnosis of infectious disorder as recited herein, and/or immune related disorder, including but not limited to autoimmune diseases as recited herein, immune related diseases as recited herein, transplant rejection and graft versus host disease, as well as cancers and malignancies as recited herein.

According to at least some embodiments, there are provided antibodies in which the antigen binding site comprises a conformational or linear epitope, and wherein the antigen binding site contains about 3-7 contiguous or non-contiguous amino acids. Optionally, the antibody is a fully human antibody, chimeric antibody, humanized or primatized antibody.

Also optionally, the antibody is selected from the group consisting of Fab, Fab', F(ab')2, F(ab'), F(ab), Fv or scFv fragment and minimal recognition unit.

Also optionally, the antibody is coupled to a moiety selected from a drug, a radionuclide, a fluorophore, an enzyme, a toxin, a therapeutic agent, or a chemotherapeutic agent; and wherein the detectable marker is a radioisotope, a metal chelator, an enzyme, a fluorescent compound, a bioluminescent compound or a chemiluminescent compound.

Also optionally the antibody blocks or inhibits the interaction of any one of LSR, TMEM25, VSIG10, LY6G6F polypeptides, or a fragment or variant thereof with a counterpart.

Also optionally the antibody replaces or augments the interaction of LSR, TMEM25, VSIG10, LY6G6F polypeptides, or a fragment or variant thereof with a counterpart.

Also optionally the antibody elicits apoptosis or lysis of cancer cells that express any one of LSR, TMEM25, VSIG10, LY6G6F protein.

Also optionally the apoptosis or lysis involves CDC or ADCC activity of the antibody, wherein CDC (complement dependent cytotoxicity) or ADCC (antibody dependent cellular cytotoxicity) activities are used to target the immune cells.

According to at least some embodiments, the invention provides antibodies and antigen binding fragments and conjugates containing same, and/or alternative scaffolds, against discrete portions of the LY6G6F protein including different portions of the extracellular domain corresponding to residues 17-234 of LY6G6F (SEQ ID NO:1), set forth in SEQ ID NO: 2, and/or corresponding to amino acid sequences set forth in any one of SEQ ID NOs: 81, 96. According to further embodiments the invention provides antibodies antigen binding fragments and conjugates containing same, and/or alternative scaffolds, against discrete portions of the mouse LY6G6F protein (SEQ ID NO: 29), including different portions of the extracellular domain corresponding to SEQ ID NO:20.

According to at least some embodiments, the invention provides antibodies and antigen binding fragments and conjugates containing same, and/or alternative scaffolds, against discrete portions of the VSIG10 protein including different portions of the extracellular domain corresponding to amino acid residues 31-413 of VSIG10 (SEQ ID NO:3), depicted in SEQ ID NO:4; amino acid residues 31-312 of VSIG10 (SEQ ID NO:5), depicted in SEQ ID NO:6, and/or corresponding to amino acid sequences set forth in any one of SEQ ID NOs: 82-93, 97-100. According to further embodiments the invention provides antibodies antigen binding fragments and conjugates containing same, and/or alternative scaffolds, against discrete portions of the mouse VSIG10 protein (SEQ ID NO: 30), including different portions of the extracellular domain corresponding to SEQ ID NO:19. According to at least some embodiments, the invention provides antibodies, antigen binding fragments and conjugates containing same, and/or alternative scaffolds, against discrete portions of the VSIG10 protein including the edge portion of VSIG10 variant (SEQ ID NO:5), as described herein.

According to at least some embodiments, the invention provides antibodies, antigen binding fragments and conjugates containing same, and/or alternative scaffolds, against discrete portions of the TMEM25 proteins including different portions of the extracellular domain corresponding to amino acid residues 27-232 of TMEM25 (SEQ ID NO:7), depicted in SEQ ID NO:8, and/or corresponding to amino acid sequences set forth in any one of SEQ ID NOs: 94, 101. According to further embodiments the invention provides antibodies and antigen binding fragments and conjugates containing same, and/or alternative scaffolds, against discrete portions of the mouse TMEM25 protein (SEQ ID NO: 28), including different portions of the extracellular domain, set forth in SEQ ID NO:9.

According to at least some embodiments, the invention provides antibodies and antigen binding fragments and conjugates containing same, and/or alternative scaffolds, against discrete portions of the LSR proteins including different portions of the extracellular domain corresponding to amino acid residues 42-211 of LSR (SEQ ID NO:11), depicted in SEQ ID NO:12; amino acid residues 42-192 of LSR (SEQ ID NO:13), depicted in SEQ ID NO:14, amino acid residues 42-533 of LSR (SEQ ID NO:15), depicted in SEQ ID NO:47, amino acid residues 42-532 of LSR (SEQ ID NO:16), depicted in SEQ ID NO:48, amino acid residues 42-493 of LSR (SEQ ID NO:17), depicted in SEQ ID NO:49, amino acid residues 42-552 of LSR (SEQ ID NO:18), depicted in SEQ ID NO:50, and/or corresponding to amino acid sequences set forth in any one of SEQ ID NOs:95, 102. According to further embodiments the invention provides antibodies and antigen binding fragments and conjugates containing same, and/or alternative scaffolds, against discrete portions of the mouse LY6G6F proteins (SEQ ID NOs: 31-32), including different portions of the extracellular domain corresponding to SEQ ID NO:21.

According to at least some embodiments, the invention provides antibodies and antigen binding fragments and conjugates containing same, and/or alternative scaffolds, against discrete portions of the LSR proteins including the unique edge portion of LSR variant isoform-f (SEQ ID NO:18), as described herein.

According to at least some embodiments, the invention provides antibodies and antigen binding fragments and conjugates containing same, and/or alternative scaffolds, against discrete portions of the soluble LSR proteins including different portions of the LSR proteins depicted in any one of SEQ ID NOs:15-18, 47-50.

According to at least some embodiments the invention relates to protein scaffolds with specificities and affinities in a range similar to specific antibodies. According to at least some embodiments the present invention relates to an antigen-binding construct comprising a protein scaffold which is linked to one or more epitope-binding domains. Such engineered protein scaffolds are usually obtained by designing a random library with mutagenesis focused at a loop region or at an otherwise permissible surface area and by selection of variants against a given target via phage display or related techniques. According to at least some embodiments the invention relates to alternative scaffolds including, but not limited to, anticalins, DARPins, Armadillo repeat proteins, protein A, lipocalins, fibronectin domain, ankyrin consensus repeat domain, thioredoxin, chemically constrained peptides and the like. According to at least some embodiments the invention relates to alternative scaffolds that are used as therapeutic agents for treatment of cancer as recited herein, immune related diseases as recited herein, autoimmune disease as recited herein and infectious diseases, as well as for in vivo diagnostics.

According to at least some embodiments of the present invention, there is provided a pharmaceutical composition comprising an isolated polypeptide as described herein, or a fusion protein as described herein; a nucleotide sequence as described herein; an expression vector as described herein; a host cell as described herein, or an antibody as described herein, and further comprising a pharmaceutically acceptable diluent or carrier.

According to at least some embodiments, there is provided use of any of any one of an isolated polypeptide as described herein, or a fusion protein as described herein; a nucleotide sequence as described herein; an expression vector as described herein; a host cell as described herein, or an antibody as described herein or a pharmaceutical composition as described herein, wherein administration of such to the subject inhibits or reduces activation of T cells.

According to at least some embodiments, there is provided use of any of any one of an isolated polypeptide as described herein, or a fusion protein as described herein; a nucleotide sequence as described herein; an expression vector as described herein; a host cell as described herein, or an antibody as described herein or a pharmaceutical composition as described herein, for treatment of cancer.

According to at least some embodiments, there is provided use of an isolated polypeptide as described herein, or a fusion protein as described herein; a nucleotide sequence as described herein; an expression vector as described herein; a host cell as described herein, or an antibody as described herein or a pharmaceutical composition as described herein, for treatment of infectious disorder.

According to at least some embodiments, there is provided a method of performing one or more of the following in a subject:
 a. upregulating cytokines;
 b. inducing expansion of T cells;
 c. promoting antigenic specific T cell immunity;
 d. promoting CD4+ and/or CD8+ T cell activation;
comprising administering any of an isolated polypeptide as described herein, or a fusion protein as described herein; a nucleotide sequence as described herein; an expression vector as described herein; a host cell as described herein, or an antibody as described herein or a pharmaceutical composition as described hereinto the subject.

According to at least some embodiments, there is provided a method for treating or preventing immune system related condition comprising administering to a subject in need thereof an effective amount of any of an isolated polypeptide as described herein, or a fusion protein as described herein; a nucleotide sequence as described herein; an expression vector as described herein; a host cell as described herein, or an antibody as described herein or a pharmaceutical composition.

Optionally, the immune system related condition comprises an immune related condition, autoimmune diseases as recited herein, transplant rejection and graft versus host disease and/or for blocking or promoting immune costimulation mediated by any one of the LSR, TMEM25, VSIG10, and/or LY6G6F polypeptides, immune related diseases as recited herein and/or for immunotherapy (promoting or inhibiting immune costimulation).

Optionally the treatment is combined with another moiety useful for treating immune related condition.

Optionally the moiety is selected from the group consisting of immunosuppressants such as corticosteroids, cyclosporin, cyclophosphamide, prednisone, azathioprine, methotrexate, rapamycin, tacrolimus, biological agents such as TNF-alpha blockers or antagonists, or any other biological agent targeting any inflammatory cytokine, nonsteroidal antiinflammatory drugs/Cox-2 inhibitors, hydroxychloroquine, sulphasalazopryine, gold salts, etanercept, infliximab, mycophenolate mofetil, basiliximab, atacicept, rituximab, cytoxan, interferon beta-1a, interferon beta-1b, glatiramer acetate, mitoxantrone hydrochloride, anakinra and/or other biologics and/or intravenous immunoglobulin (IVIG), interferons such as IFN-beta-1a (REBIF®. and AVONEX®) and IFN-beta-1b (BETASERON®); glatiramer acetate (COPAXONE®), a polypeptide; natalizumab (TYSABRI®), mitoxantrone (NOVANTRONE®), a cytotoxic agent, a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g. CTLA4-Ig (abatacept, ORENCIA®), CD28-Ig, B7-H4-Ig, or other costimulatory agents, or adhesion molecule inhibitors, e.g. mAbs or low molecular weight inhibitors including LFA-1 antagonists, Selectin antagonists and VLA-4 antagonists, or another immunomodulatory agent.

Optionally the immune condition is selected from autoimmune disease, transplant rejection, or graft versus host disease.

Optionally the autoimmune disease is selected from a group consisting of multiple sclerosis, including relapsing-remiting multiple sclerosis, primary progressive multiple sclerosis, and secondary progressive multiple sclerosis; psoriasis; rheumatoid arthritis; psoriatic arthritis, systemic lupus erythematosus (SLE); ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune haemolytic anaemia, Guillian-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anaemia, pemphigus, pemphigus vulgarus, cirrhosis, primary biliary cirrhosis, dermatomyositis, polymyositis, fibromyositis, myogelosis, celiac disease, immunoglobulin A nephropathy, Henoch-Schonlein purpura, Evans syndrome, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis nodosa, chondrocalcinosis, Wegener's granulomatosis, microscopic polyangiitis, chronic urticaria, bullous skin disorders, pemphigoid, atopic eczema, Devic's disease, childhood autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne, normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, autoimmune retinopathy, age-related macular degeneration, atherosclerosis, chronic prostatitis and TNF receptor-associated periodic syndrome (TRAPS).

Optionally the autoimmune disease is selected from the group consisting of any of the types and subtypes of any of multiple sclerosis, rheumatoid arthritis, type I diabetes, psoriasis, systemic lupus erythematosus, inflammatory bowel disease, uveitis, and Sjogren's syndrome.

According to at least some embodiments there is provided a method for treating or preventing an infectious disease comprising administering to a subject in need thereof an effective amount of any of an isolated polypeptide as described herein, or a fusion protein as described herein; a nucleotide sequence as described herein; an expression vector as described herein; a host cell as described herein, or an antibody as described herein or a pharmaceutical composition.

Optionally the infectious disease is selected from the disease caused by bacterial infection, viral infection, fungal infection and/or other parasite infection.

Optionally the infectious disease is selected from hepatitis B, hepatitis C, infectious mononucleosis, EBV, cytomegalovirus, AIDS, HIV-1, HIV-2, tuberculosis, malaria and schistosomiasis.

According to at least some embodiments, there is provided a method for treating or preventing cancer comprising administering to a subject in need thereof an effective amount of any of an isolated polypeptide as described herein, or a fusion protein as described herein; a nucleotide sequence as described herein; an expression vector as described herein; a host cell as described herein, or an antibody as described herein or a pharmaceutical composition.

Optionally the treatment is combined with another moiety or therapy useful for treating cancer.

Optionally the therapy is radiation therapy, antibody therapy, chemotherapy, photodynamic therapy, adoptive T cell therapy, Treg depletion, surgery or in combination therapy with conventional drugs.

Optionally the moiety is selected from the group consisting of immunosuppressants, cytotoxic drugs, tumor vaccines, antibodies (e.g. bevacizumab, erbitux), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immunostimulatory antibodies, growth hormones or other cytokines, folic acid, vitamins, minerals, aromatase inhibitors, RNAi, Histone Deacetylase Inhibitors, and proteasome inhibitors.

Optionally the cancer is selected from a group consisting of breast cancer, cervical cancer, ovary cancer, endometrial cancer, melanoma, bladder cancer, lung cancer, pancreatic cancer, colon cancer, prostate cancer, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma, benign tumor of the skin, keratoacanthomas, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL), and wherein the cancer is non-metastatic, invasive or metastatic.

Optionally the cancer is any of melanoma, cancer of liver, renal, brain, breast, colon, lung, ovary, pancreas, prostate, stomach, multiple myeloma, Hodgkin's lymphoma, non Hodgkin's lymphoma, acute and chronic lymphoblastic leukemia and acute and chronic myeloid leukemia.

According to at least some embodiments, there is provided a method for potentiating a secondary immune response to an antigen in a patient, which method comprises administering effective amount of any of an isolated polypeptide as described herein, or a fusion protein as described herein; a nucleotide sequence as described herein; an expression vector as described herein; a host cell as described herein, or an antibody as described herein or a pharmaceutical composition.

Optionally the antigen is a cancer antigen, a viral antigen or a bacterial antigen, and the patient has received treatment with an anticancer vaccine or a viral vaccine.

A method of immunotherapy in a patient, comprising:

in vivo or ex vivo tolerance induction, comprising administering effective amount of any of an isolated polypeptide as described herein, or a fusion protein as described herein; a nucleotide sequence as described herein; an expression vector as described herein; a host cell as described herein, or an antibody as described herein or a pharmaceutical composition, to a patient or to leukocytes isolated from the patient, in order to induce differentiation of tolerogenic regulatory cells;

ex-vivo enrichment and expansion of said cells;

reinfusion of the tolerogenic regulatory cells to said patient.

A method of using at least one of: any of an isolated polypeptide as described herein, or a fusion protein as described herein; a nucleotide sequence as described herein; an expression vector as described herein; a host cell as described herein, or an antibody as described herein or a pharmaceutical composition; as a cancer vaccine adjuvant, comprising administration to a patient an immunogenic amount of a tumor associated antigen preparation of interest; and a cancer vaccine adjuvant in a formulation suitable for immunization, wherein the immune response against the tumor associated antigen in the presence of the cancer vaccine adjuvant is stronger than in the absence of the cancer vaccine adjuvant.

According to at least some embodiments there is provided a method for combining therapeutic vaccination with an antigen along with administration of any of an isolated polypeptide as described herein, or a fusion protein as described herein; a nucleotide sequence as described herein; an expression vector as described herein; a host cell as described herein, or an antibody as described herein or a pharmaceutical composition, for treatment of infection.

According to at least some embodiments, there is provided a method for combining any of an isolated polypeptide as described herein, or a fusion protein as described herein; a nucleotide sequence as described herein; an expression vector as described herein; a host cell as described herein, or an antibody as described herein or a pharmaceutical composition, an adjuvant, and an antigen in a vaccine, in order to increase the immune response.

Optionally the antigen is a viral antigen, bacterial antigen, fungal antigen, parasite antigen, and/or other pathogen's antigen.

According to at least some embodiments, any one of the foregoing therapeutic agents according to at least some embodiments of the present invention, including antibodies and antigen binding fragments and conjugates containing same, and/or alternative scaffolds, against any one of LY6G6F, VSIG10, TMEM25 and/or LSR proteins; LY6G6F, VSIG10, TMEM25 and/or LSR secreted or soluble form or ECD and/or variants, and/or orthologs, and/or conjugates thereof, can be used for adoptive immunotherapy. Immune tolerance or immunological tolerance is the process by which the immune system does not attack an antigen. It can be either 'natural' or 'self tolerance', where the body does not mount an immune response to self antigens, or 'induced tolerance', where tolerance to external antigens can be created by manipulating the immune system. It occurs in three forms: central tolerance, peripheral tolerance and acquired tolerance. Without wishing to be bound by a single theory, tolerance employs regulatory immune cells—including Tregs— that directly suppress autoreactive cells, as well as several other immune cell subsets with immunoregulatory properties—including CD8+ T cells and other types of CD4+ T cells (Tr1, Th3), in addition to natural killer (NK), NKT cells, dendritic cells (DC) and B cells.

Tolerance can be induced by blocking costimulation or upon engagement of a co-inhibitory B7 with its counter receptor. Transfer of tolerance involves isolation of the cells that have been induced for tolerance either in vivo (i.e. prior to cell isolation) or ex-vivo, enrichment and expansion of these cells ex vivo, followed by reinfusion of the expanded cells to the patient. This method can be used for treatment of autoimmune diseases as recited herein, immune related diseases as recited herein, transplantation and graft rejection. Thus, according to at least some embodiments, the invention provides methods for tolerance induction, comprising in vivo or ex vivo treatment administration of effective amount of any one of isolated soluble LY6G6F, VSIG10, TMEM25, LSR polypeptide, or a polypeptide comprising the extracellular domain of LY6G6F, VSIG10, TMEM25, LSR, or fragment thereof, or a fusion thereof to a heterologous sequence, and/or a polyclonal or monoclonal antibody or antigen binding fragments and conjugates containing same, and/or alternative scaffolds, specific to any one of LY6G6F, VSIG10, TMEM25 and/or LSR proteins, to a patient or to leukocytes isolated from the patient, in order to induce differentiation of tolerogenic regulatory cells, followed by ex-vivo enrichment and expansion of said cells and reinfusion of the tolerogenic regulatory cells to said patient.

According to at least some embodiments, the invention provides assays for detecting the presence of LY6G6F, VSIG10, TMEM25 and/or LSR proteins in vitro or in vivo in a biological sample or an individual, comprising contacting the sample with an antibody and/or antigen binding fragments and/or conjugates containing same, and/or alternative scaffolds, having specificity for LY6G6F, VSIG10, TMEM25 and/or LSR polypeptides, and detecting the binding of LY6G6F, VSIG10, TMEM25 and/or LSR protein in the sample and/or in the individual.

According to at least some embodiments, there is provided an assay for detecting the presence of any one of the polypeptides of any of SEQ ID NOs:1-8, 11-18, 47-50, 58, 143, or a variant thereof that is at least 95% identical thereto, in a sample.

According to at least some embodiments, there is provided a method for diagnosing a disease in a subject, comprising detecting in the subject or in a sample obtained from said subject any one of the polypeptides of any of SEQ ID NOs: 1-8, 11-18, 47-50, 58, 143, or a variant thereof that is at least 95% identical thereto, or fragments thereof.

Optionally detecting the polypeptide is performed in vivo or in vitro.

Optionally the detection is conducted by immunoassay.

Optionally the detection is conducted using antibodies or fragments as described herein.

According to at least some embodiments, the invention provides methods for detecting a disease, diagnosing a disease, monitoring disease progression or treatment efficacy or relapse of a disease, or selecting a therapy for a disease, detect cells affected by the foregoing disease, comprising detecting expression of a LY6G6F, VSIG10, TMEM25 and/or LSR, wherein the disease is selected from cancer, infectious disorder as recited herein, and/or immune related disorder.

According to one embodiment, detecting the presence of the polypeptide is indicative of the presence of the disease and/or its severity and/or its progress. According to another embodiment, a change in the expression and/or the level of the polypeptide compared to its expression and/or level in a healthy subject or a sample obtained therefrom is indicative of the presence of the disease and/or its severity and/or its progress. According to a further embodiment, a change in the expression and/or level of the polypeptide compared to its level and/or expression in said subject or in a sample obtained therefrom at earlier stage is indicative of the progress of the disease. According to still further embodiment, detecting the presence and/or relative change in the expression and/or level of the polypeptide is useful for selecting a treatment and/or monitoring a treatment of the disease.

BRIEF DESCRIPTION OF THE FIGURES

FIG. 5A presents LY6G6F human (SEQ ID NO: 1) and mouse (refINP_001156664.1, SEQ ID NO:29) amino acid sequence comparison. FIG. 5B presents VSIG10 human (SEQ ID NO: 3) and mouse (sp|D3YX43.2, SEQ ID NO:30) amino acid sequence comparison. FIG. 5C presents LSR human (SEQ ID NO:11) and either mouse (refINP_059101.1, SEQ ID NO:31) or mouse (refINP_001157656.1, SEQ ID NO:32) amino acid sequence comparison. FIG. 5D presents TMEM25 human (SEQ ID NO:7) and mouse (ref: 1cl|4109, SEQ ID NO:28) amino acid sequence comparison.

FIG. 6 presents a table summarizing the primers which were used for cloning of LY6G6F transcript fused to EGFP. Gene specific sequences are shown in bold face; the restriction site extensions utilized for cloning purposes are in Italic; and Kozak sequence are underlined.

FIG. 7 presents the DNA sequence of LY6G6F full length_fused to EGFP. The gene specific sequence corresponding to the LY6G6F full length sequence is marked in bold faced, EGFP sequence is unbold Italic underline.

FIG. 8 presents the amino acid sequence of the resulting LY6G6F full length fused to EGFP. The gene specific sequence corresponding to the full length sequence of LY6G6F is marked in bold faced; EGFP sequence is unbold Italic underline.

FIG. 11 presents amino acid sequences of human ECDs fused to human IgG1 Fc with the Cys at position 220 (according to full length human IgG1, position 5 in SEQ ID NO:70) replaced with a Ser (SEQ ID NO:156), as follows: human LY6G6F (FIG. 11A), human VSIG10 (FIG. 11B), human VSIG10-skipping exon 3 variant (FIG. 11C), human TMEM25 (FIG. 11D), human LSR isoform a (FIG. 11E), human LSR isoform b (FIG. 11F), human LSR isoform c (FIG. 11G), human LSR isoform d (FIG. 11H), human LSR isoform e (FIG. 11I), human LSR isoform f (FIG. 11J) ECD fused to human IgG1 Fc (SEQ ID NOs: 71-80, respectively) Amino acid residues corresponding to signal peptide (SP) are shown in bold Italics. Amino acid residues corresponding to human ECD sequence are underlined Amino acid residues corresponding to human IgG1 Fc with the Cys at position 220 replaced with a Ser (SEQ ID NO:156) are unmarked.

FIG. 16 is a histogram showing over expression of the LSR transcripts detectable by or according to LSR_seg24-36_200-309/310_Amplicon (SEQ ID:140) in cancerous kidney samples relative to the normal samples.

FIG. 17 is a histogram showing over expression of the LSR transcripts detectable by or according to LSR_seg24-36_200-309/310_Amplicon (SEQ ID:140) in cancerous liver samples relative to the normal samples.

Figure 19A:
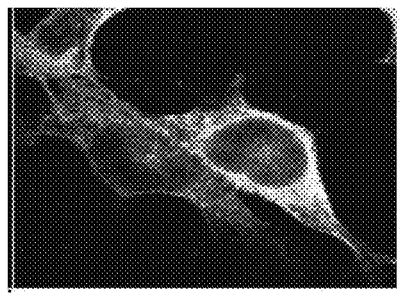
FIG. 19 demonstrates the subcellular localization of LSR_P5a_Flag_m. LSR_P5a_Flag_m (SEQ ID NO: 144) is localized mainly to the cell cytoplasm, but can also be detected on the cell surface as detected with anti Flag (Sigma cat#A9594) (FIG. 19A) and anti LSR antibodies as follows.
Figure 19B:
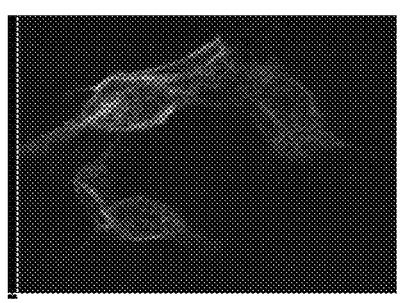
Figure 19C:
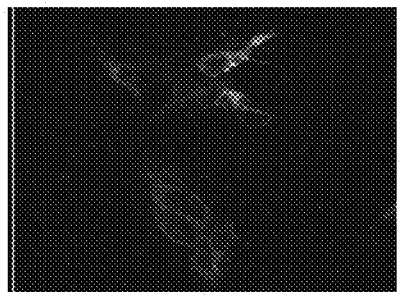
Figure 19D:
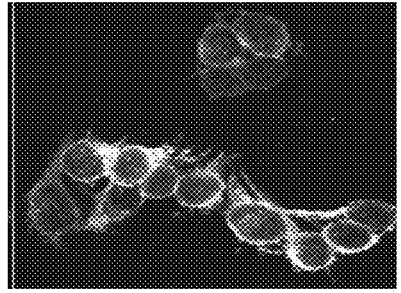

Abcam, cat ab59646 (FIG. 19B) Abnova, cat#H00051599-B01P (FIG. 19C) and Sigma cat#HPA007270 (FIG. 19D).

FIG. 20 demonstrates the endogenous expression of LSR in various cell lines. A band at 72 kDa corresponding to LSR was detected with anti LSR antibody in extracts of (1) Caov3, (2) ES2, (3) OV-90, (4) OVCAR3, (5) SK-OV3, (6) TOV112D, (7) CaCo2, (8) HeLa, (9) Hep G2, (10) MCF-7, (11) SkBR3 and (12) 293T_LSR_P5a_Flag (FIG. 20A). Anti GAPDH (Abcam cat#ab9484) served as a loading control (FIG. 20B).

Figure 21B:
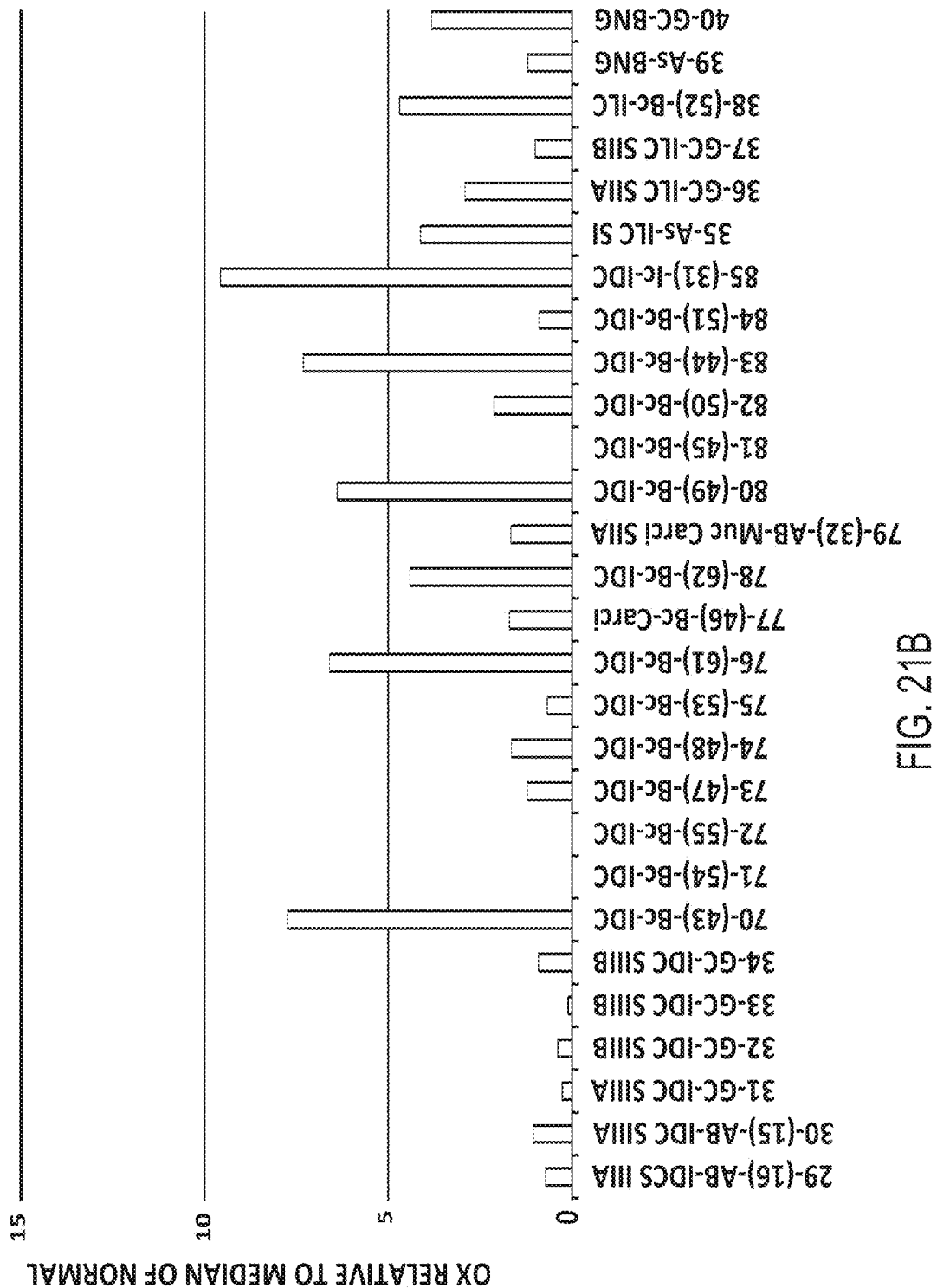
Figure 21C:
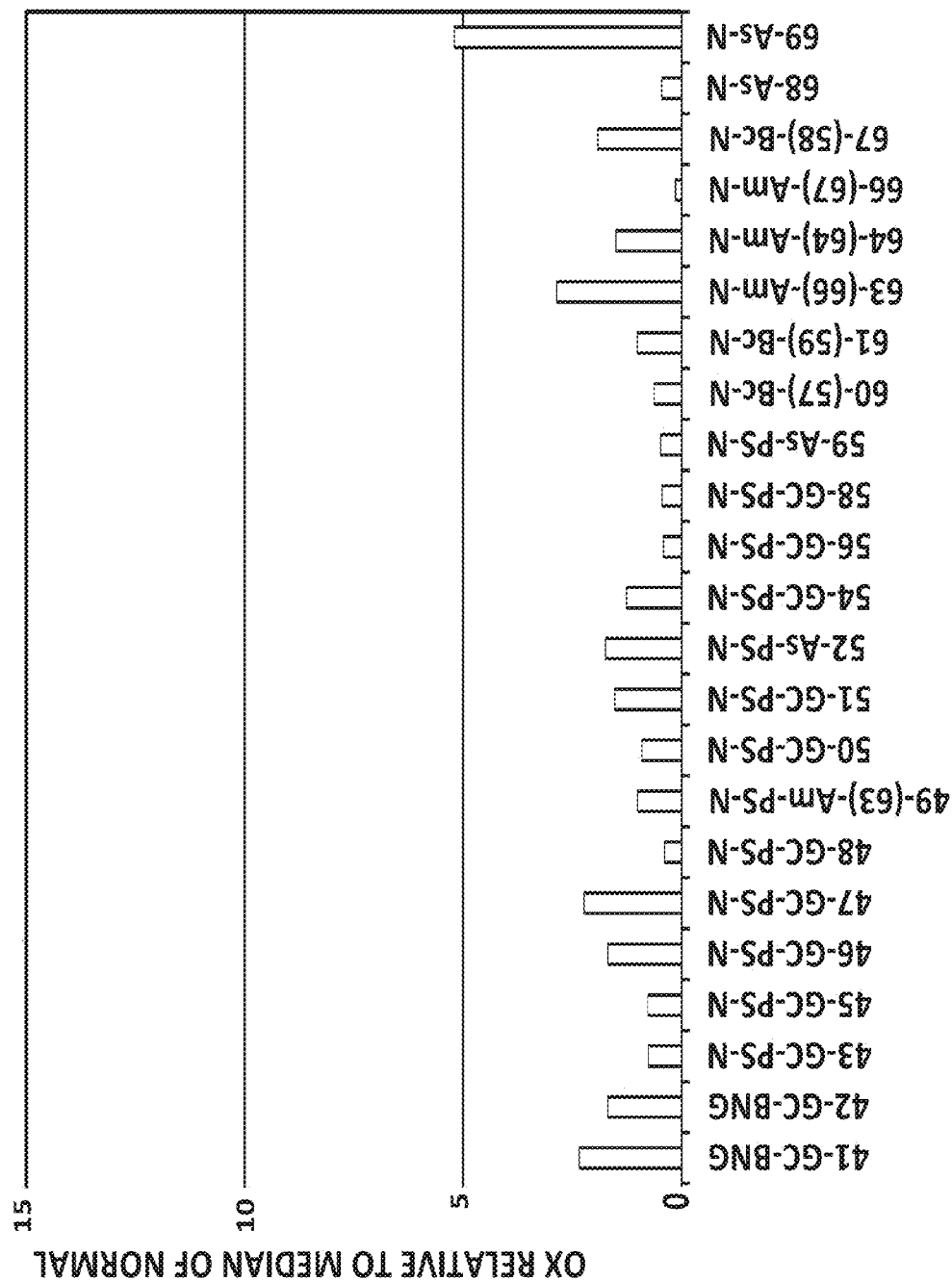

FIG. 21 is a histogram showing expression of TMEM25 transcripts detectable by or according to seg21-27—TMEM25_seg_21-27_200-344/346_Amplicon (SEQ ID NO: 123) in normal and cancerous Breast tissues.

Figure 22A:
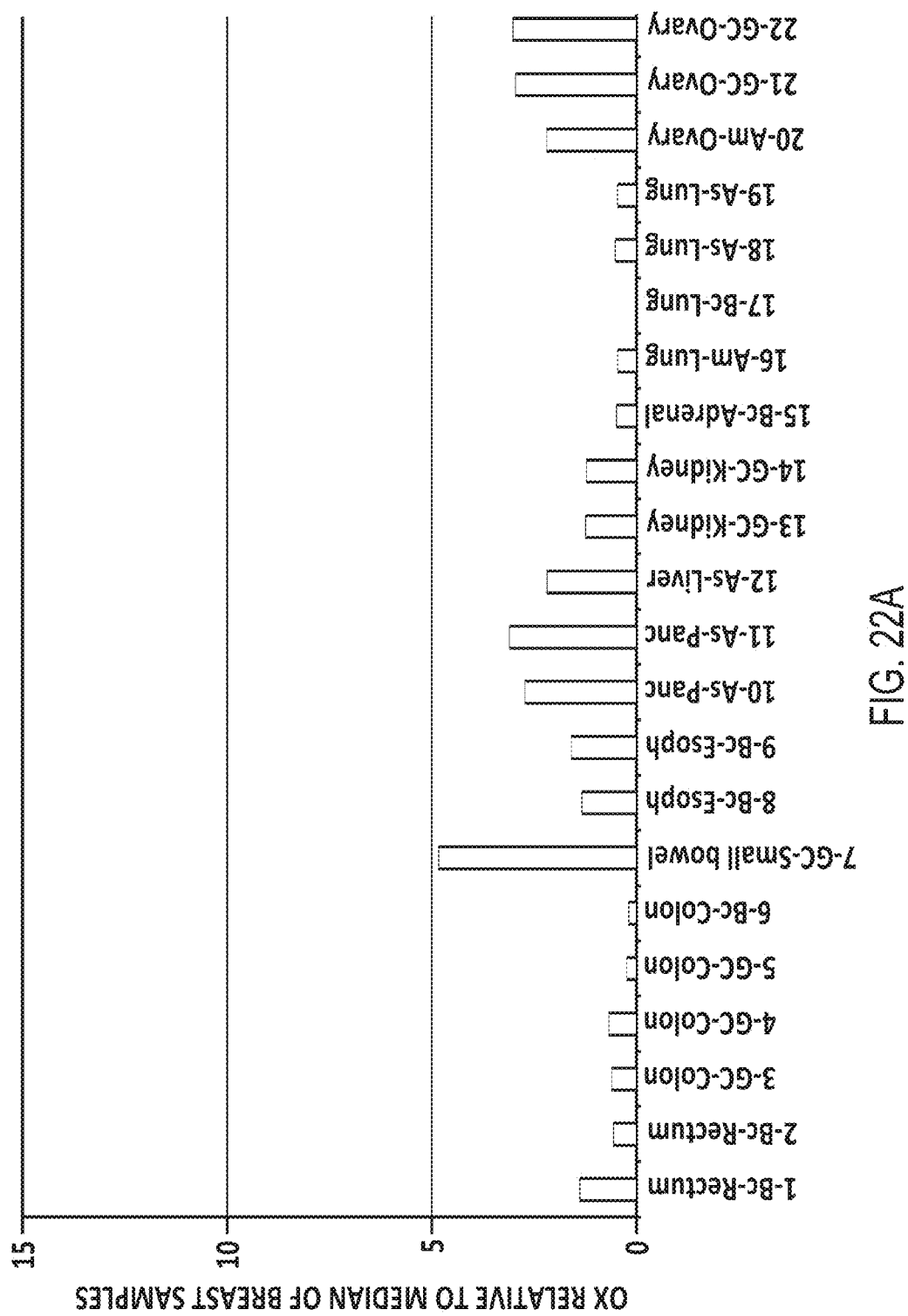
Figure 22C:
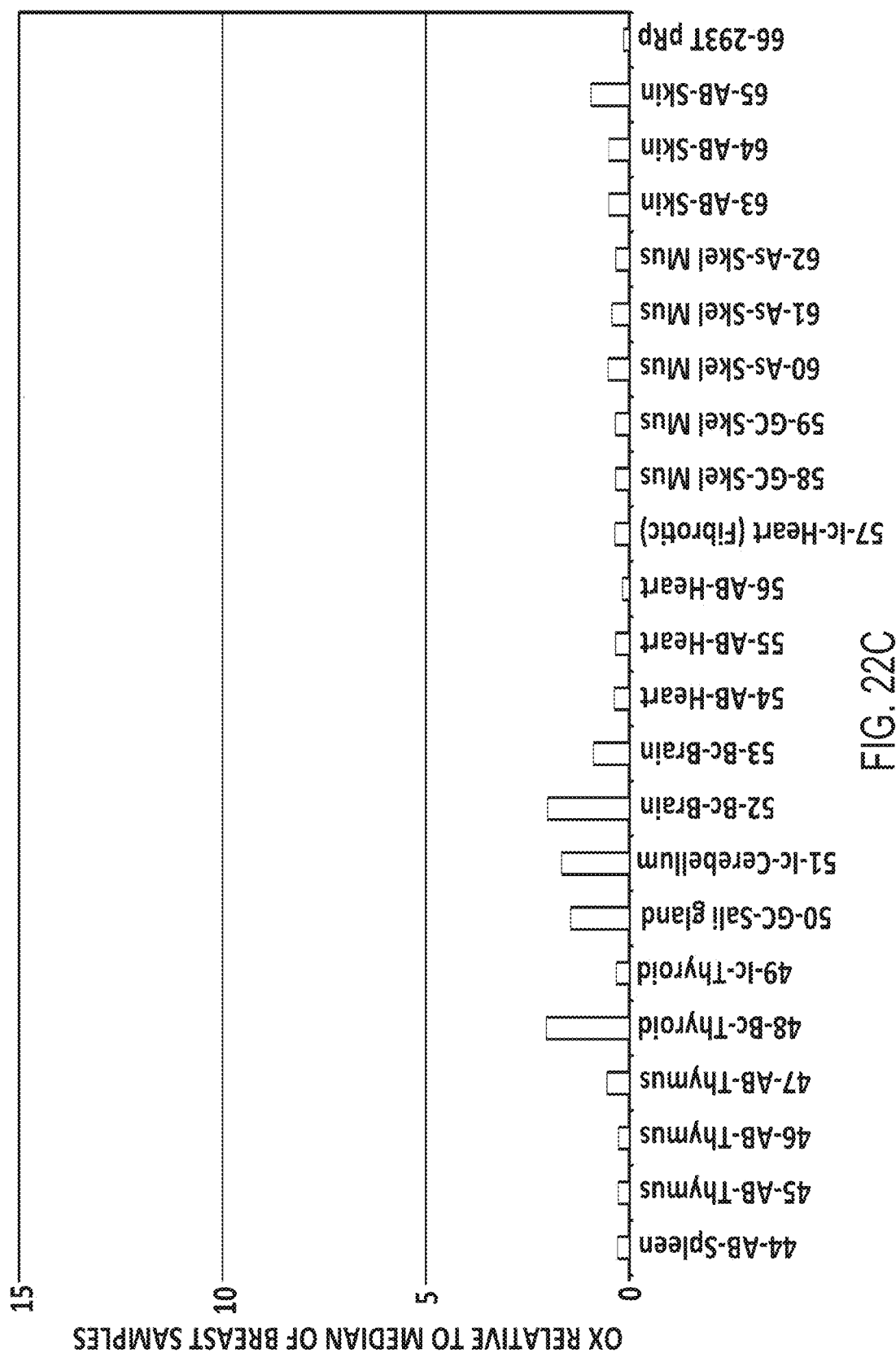

FIG. 22 is a histogram showing expression of TMEM25 transcripts detectable by or according to seg21-27—TMEM25_seg_21-27_200-344/346_Amplicon (SEQ ID NO: 123) in different normal tissues.

FIG. 23 demonstrates Western blot results showing (A) specific interaction between Rabbit anti TMEM25 antibodies and TMEM25_P5 protein (SEQ ID NO: 7) and TMEM25_P5_Flag (SEQ ID NO: 129), but not HEK_293T_pRp3. (B) specific interaction between TMEM25_P5_Flag protein (SEQ ID NO: 129) and anti-Flag antibodies. Lane1: HEK293T_pIRESpuro3; lane 2: HEK293T_pIRESpuro3_TMEM25-P5, lane 3: HEK293T_pIRESpuro3_TMEM25-P5-Flag.

Figure 24C:
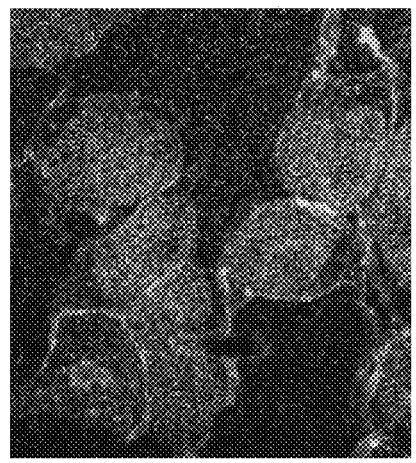
Figure 24B:
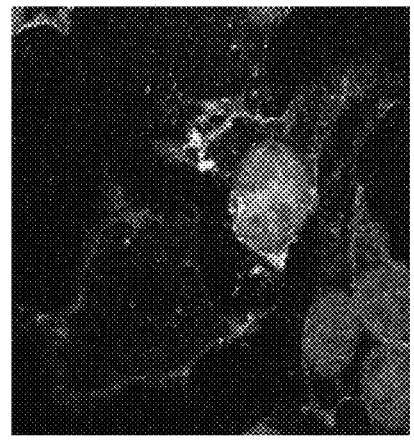
Figure 24A:
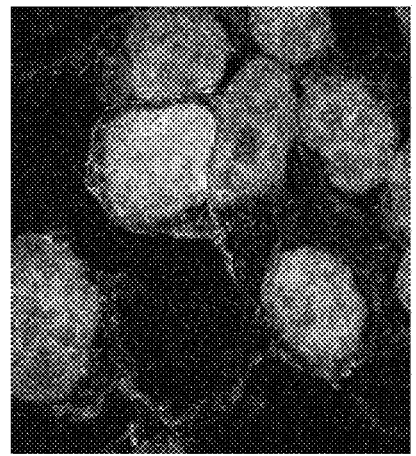

FIG. 24 presents the cell surface localization of TMEM25_P5 (SEQ ID NO:132) (FIG. 24A) and TMEM25_P5_Flag (SEQ ID NO: 129) (FIG. 24B) using anti TMEM25 Abs. FIG. 24C demonstrate TMEM25_P5_Flag (SEQ ID NO: 129) localization using anti flag Abs (Sigma, catalog number: A9594).

Figure 25:
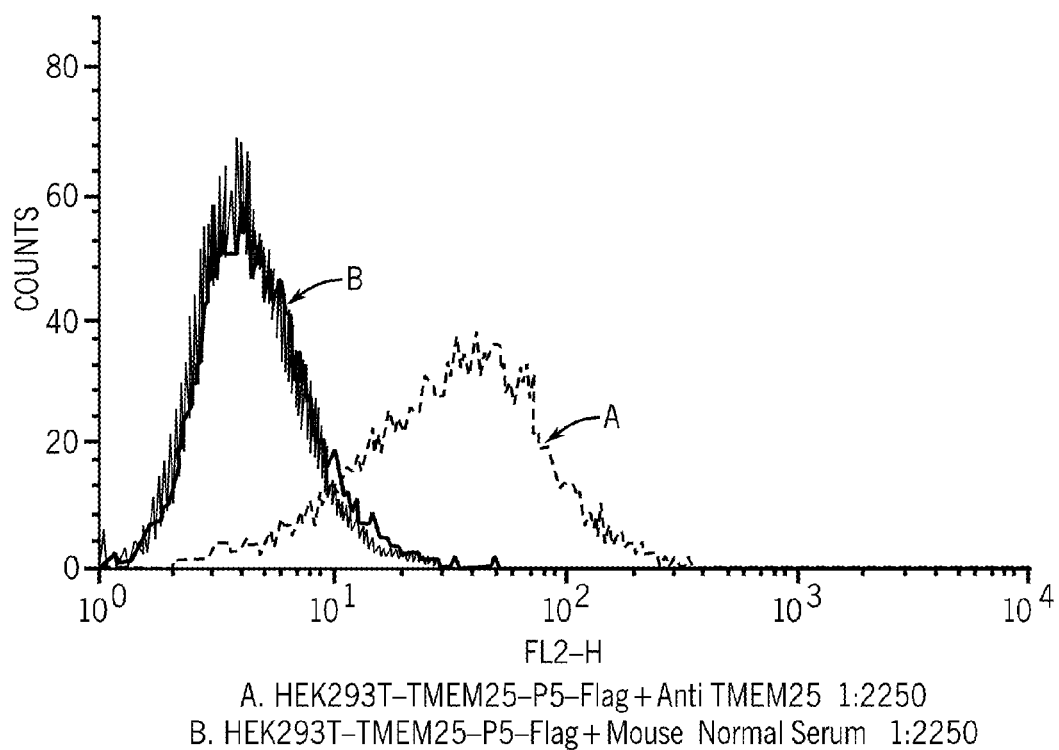

FIG. 25 demonstrates that anti TMEM25 antibodies bind to the full length TMEM25 protein, in HEK293T recombinant cells expressing TMEM25_P5_Flag protein (1:2250) (FIG. 25A), as compared to mouse serum (1:2250) (FIG. 25B) used as a negative control, indicating membrane localization of TMEM25 protein.

Figure 26:
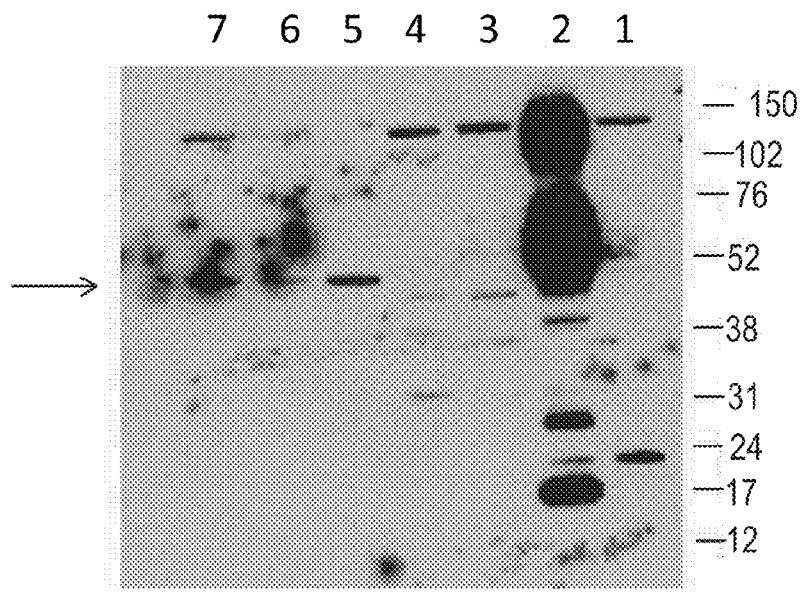

FIG. 26 presents Western Blot results showing the expression of endogenous TMEM25 protein in various cell lines: (1): HEK293T_pIRESpuro3, (2) HEK293T_pIRESpuro3_TMEM25-P5-Flag, (3) KARPAS, (4) G-361, (5) RPMI8226, (6) DAUDI, (7) Jurkat.

Figure 27:
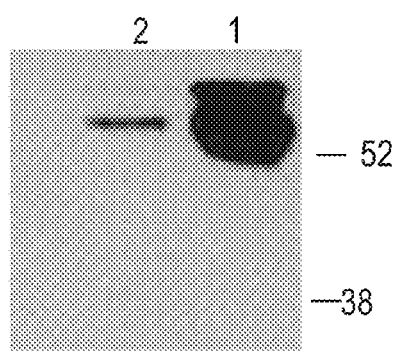
Figure 28A:
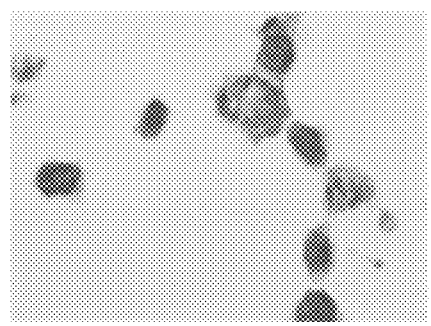
Figure 28B:
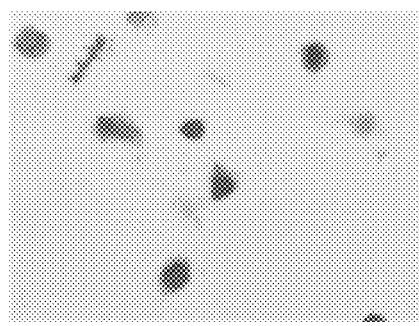
Figure 28C:
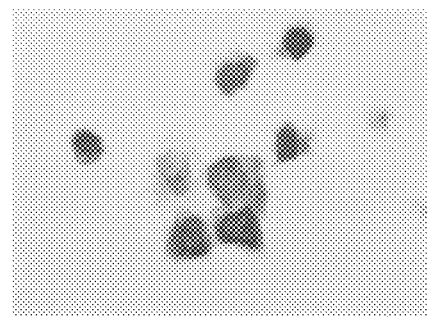
Figure 28D:
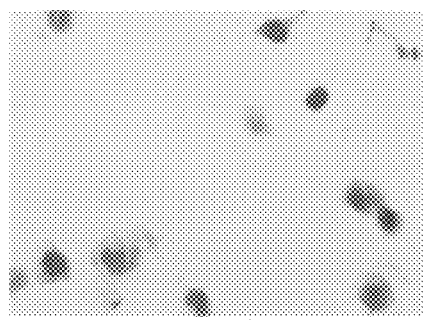
Figure 28E:
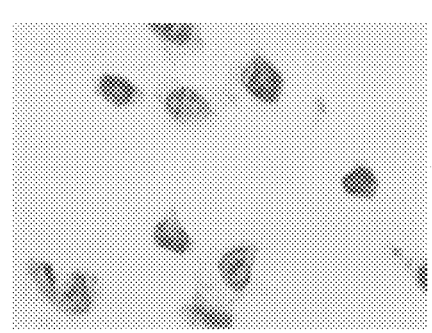
Figure 28F:
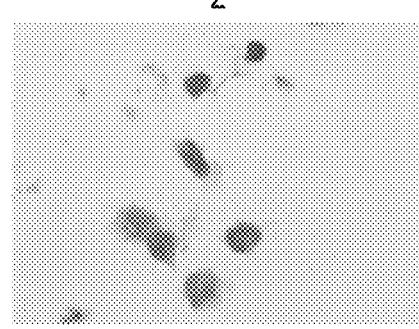
Figure 29A:
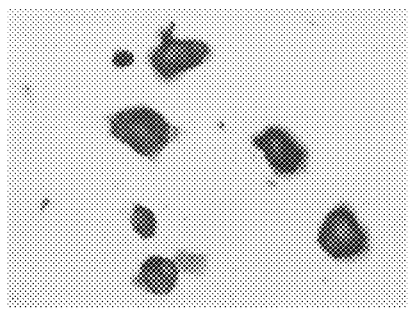
Figure 29B:
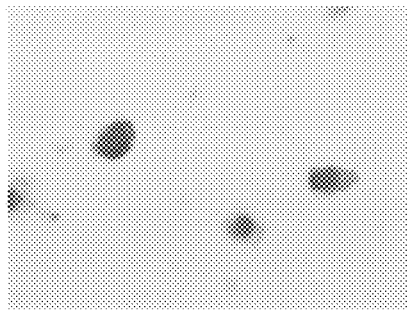
Figure 29C:
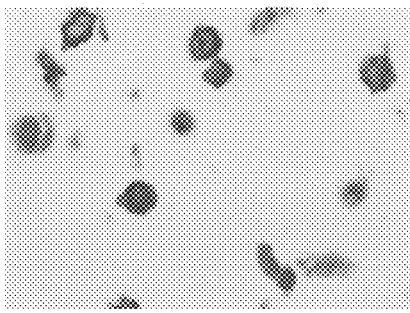
Figure 29D:
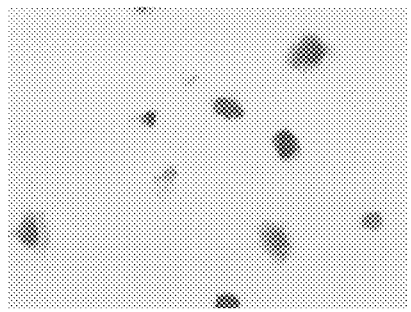
Figure 29E:
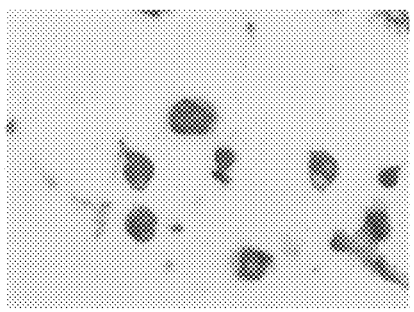
Figure 29F:
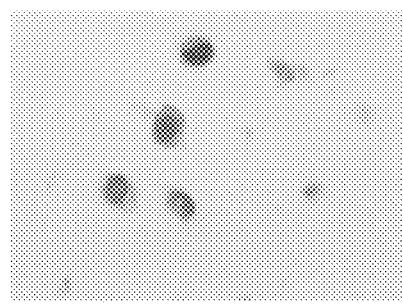
Figure 30A:
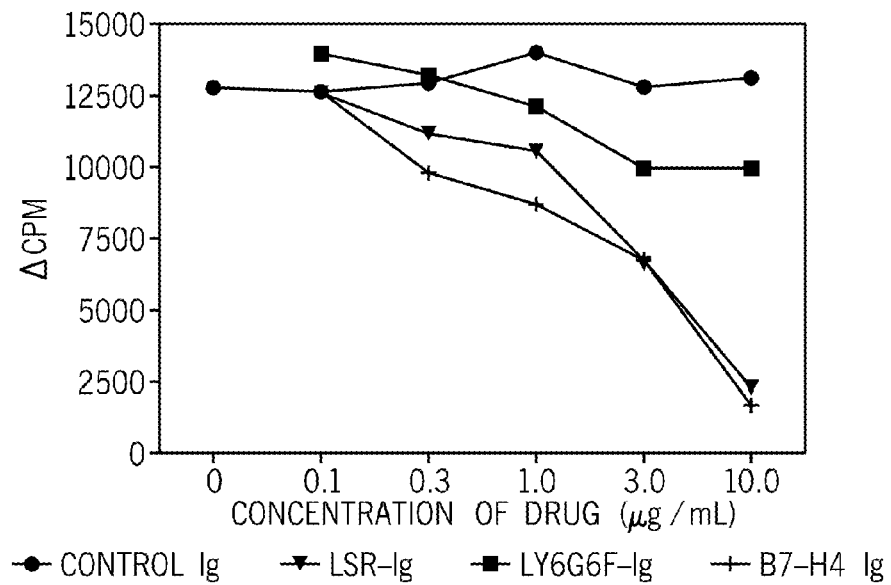
Figure 30B:
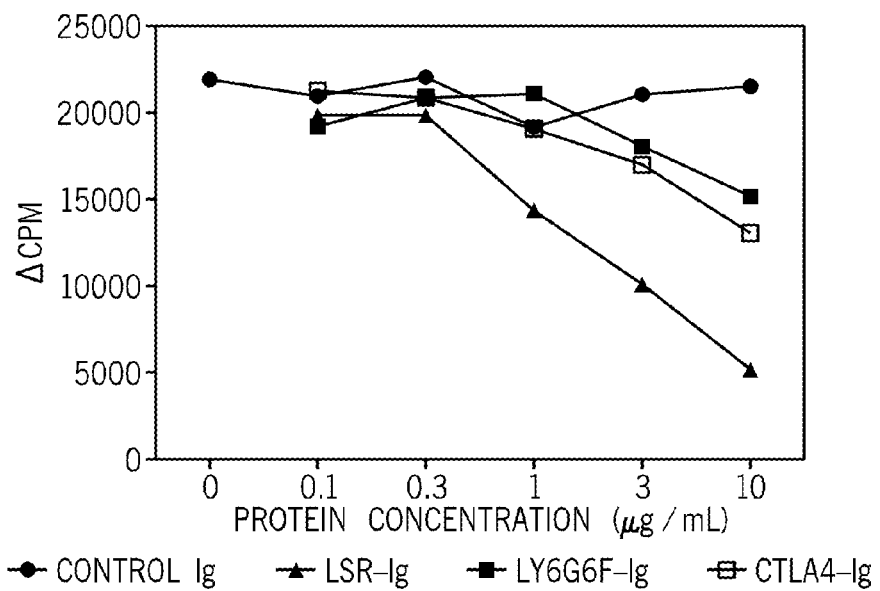
Figure 30C:
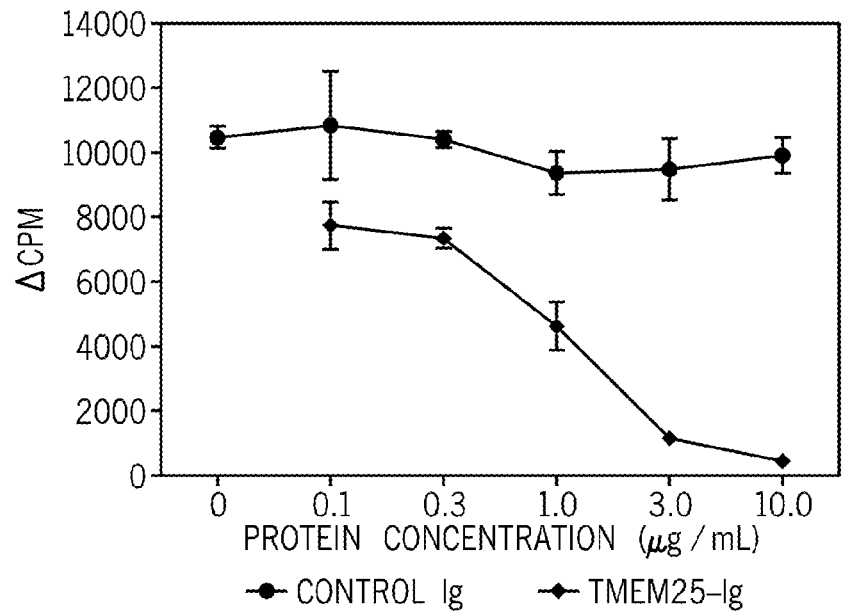
Figure 30D:
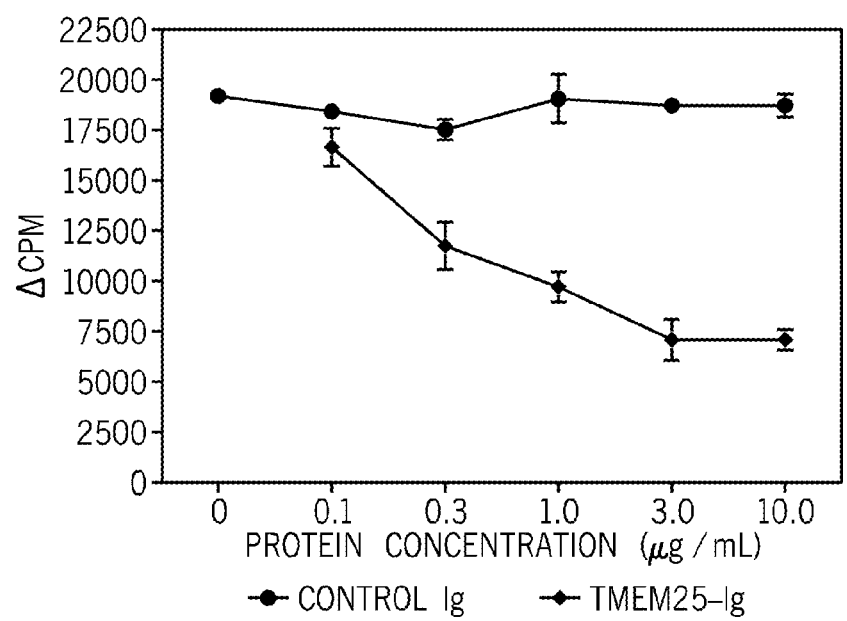
Figure 30E:
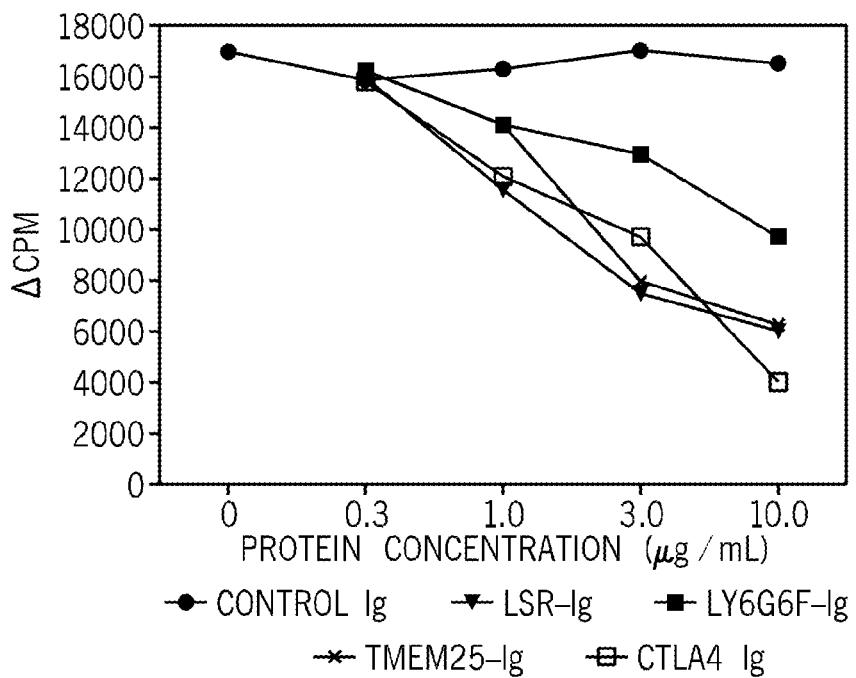

FIG. 27 demonstrates specific knockdown of TMEM25_P5_Flag protein (SEQ ID NO: 129) in HEK293T cells stably expressing TMEM25_P5_Flag (SEQ ID NO 129) transfected with TMEM25_P5 siRNA (L-018183-00-0005, Dharmacon) (Lane 2) compared to HEK293T cells stably expressing TMEM25_P5_FLAG transfected with Scrambled-SiRNA (Lane 1) (Dharmacon, D-001810-10-05), using anti TMEM25 antibodies (Sigma, cat#HPA012163).

FIG. 28 demonstrates that anti LSR (Cat no. ab59646, Abcam) in sections of positive control cell line (LSR_P5a_Flag_m transfected HEK293T cells (column 1, panels A, C and E) shows specific immunoreactivity in a dose dependent concentrations of 3, 1 and 0.3 ug/ml respectively, as compared to the negative control cell line empty vector HEK293T cells (column 2, panels B, D and F), in pH 9 antigen retrieval method.

FIG. 29 demonstrates that anti TMEM25 (Cat no. HPA012163, Sigma) in sections of positive control cell line TMEM25_P5_Flag transfected HEK293T cells (column 1, panels A, C and E) shows specific immunoreactivity in a dose dependent concentrations of 3, 1 and 0.3 ug/ml respectively, as compared to the negative control cell line empty vector HEK293T cells (column 2 panels B, D and F), in pH 9 antigen retrieval method.

FIG. 30A-F shows the in vitro inhibitory effect of soluble LY6G6F-Ig (SEQ ID NO:23), TMEM25-Ig (SEQ ID NO:25) and LSR-Ig (SEQ ID NO:26) on mouse T cells activation. Activation of T cells isolated from spleens of D011.10 mice was induced with 20 ug/ml (FIGS. 30A-C, E) or 2 ug/ml (FIGS. D and F) OVA323-339 in the presence of irradiated splenocytes from Balb/c mice that serve as APCs. In these studies CTLA4-Ig or B7-H4-Ig were used as positive controls while mouse IgG2a was used as Ig control.

Figure 31:
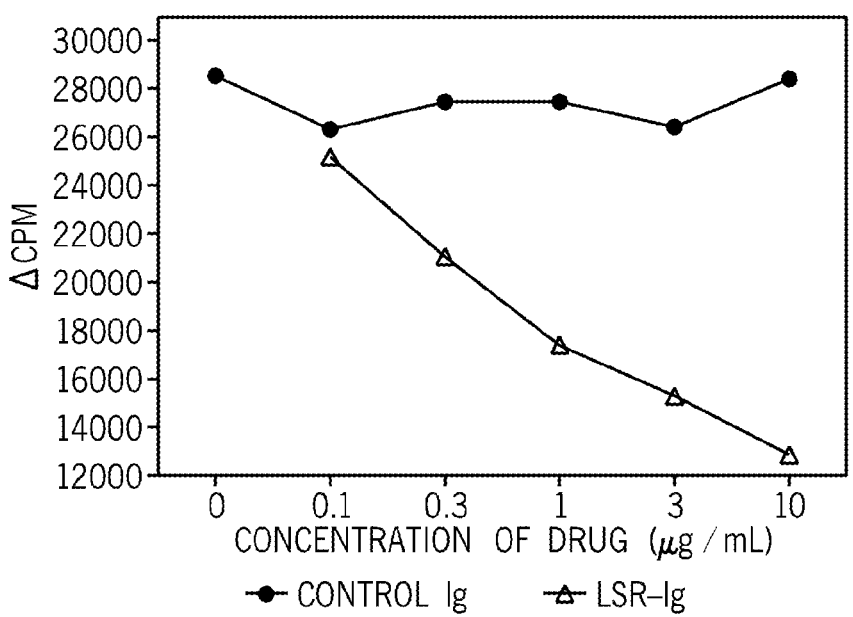

FIG. 31 shows the in vitro inhibitory effect of bead bound LSR-Ig (SEQ ID NO:26) on T cell proliferation induced by anti-CD3 and anti-CD28 coated beads.

Figure 32A:
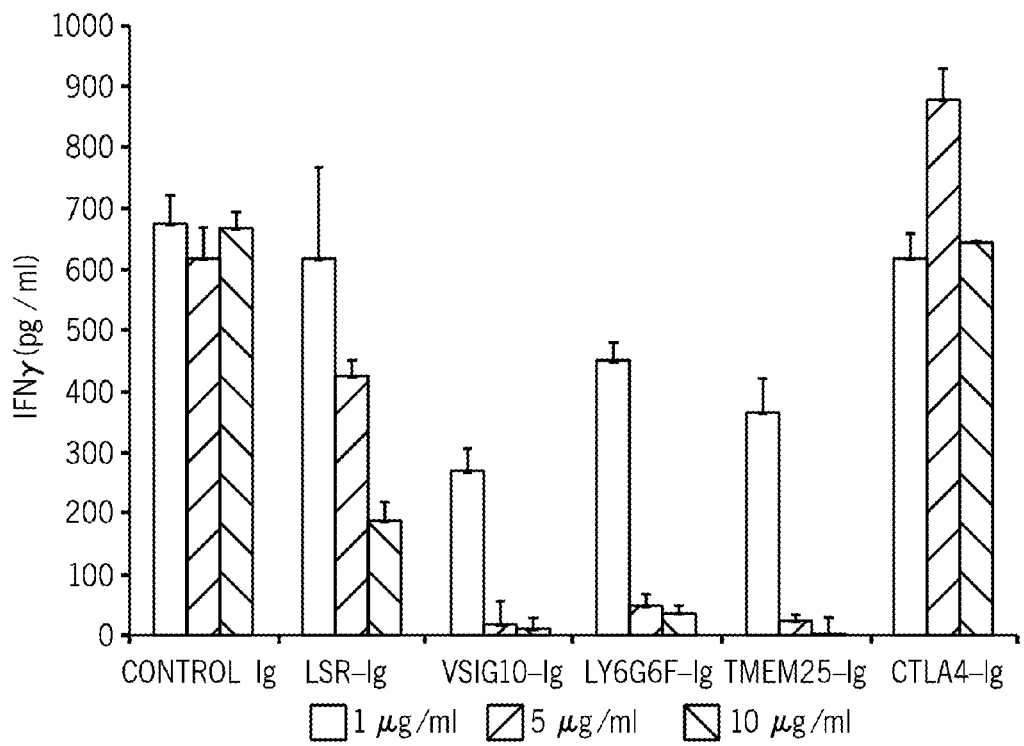
Figure 32B:
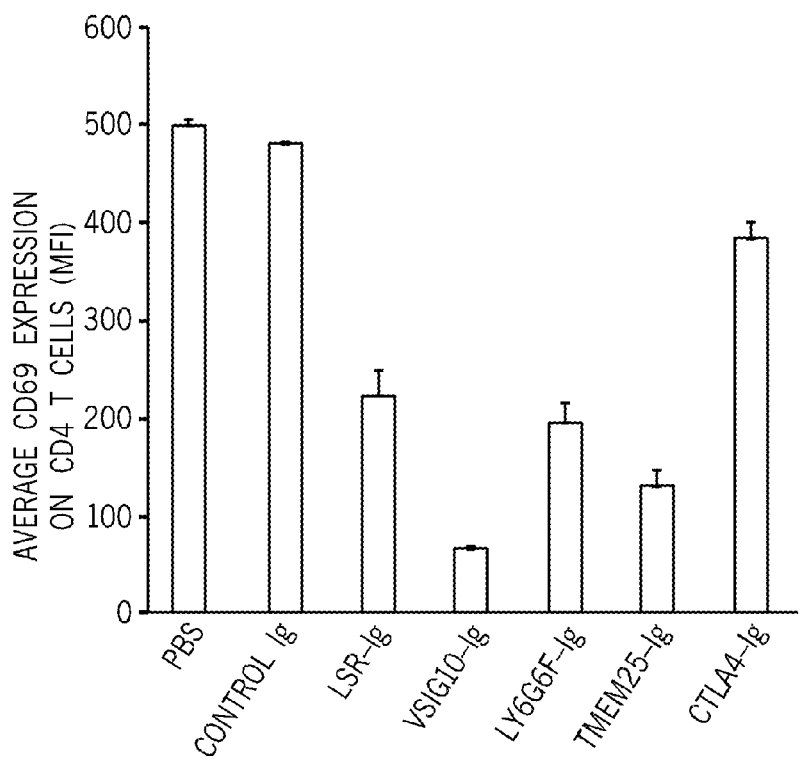

FIG. 32 shows the effect of LY6G6F, VSIG10, TMEM25 and LSR fusion proteins (SEQ ID NO:23-26, respectively) on CD4 T cell activation, as manifested by reduced IFNγ secretion (A) and reduced expression of the activation marker CD69 (B). Each bar is the mean of duplicate cultures, the error bars indicating the standard deviation (Student t-test, *P<0.05, **p<0.01, compared with control mIgG2a.

Figure 33A:
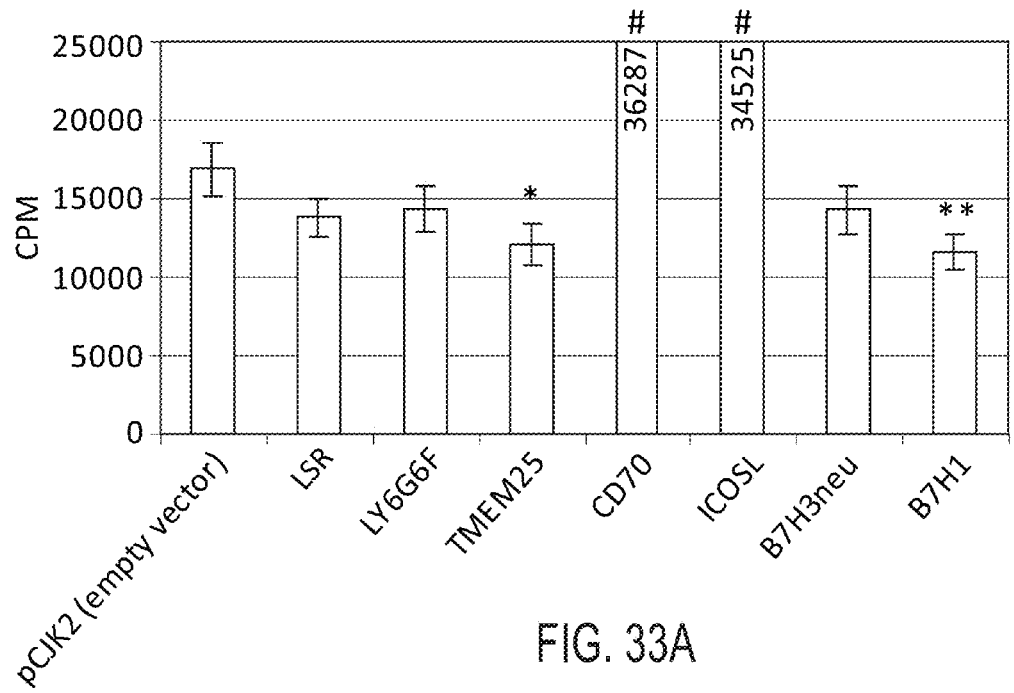
Figure 33B:
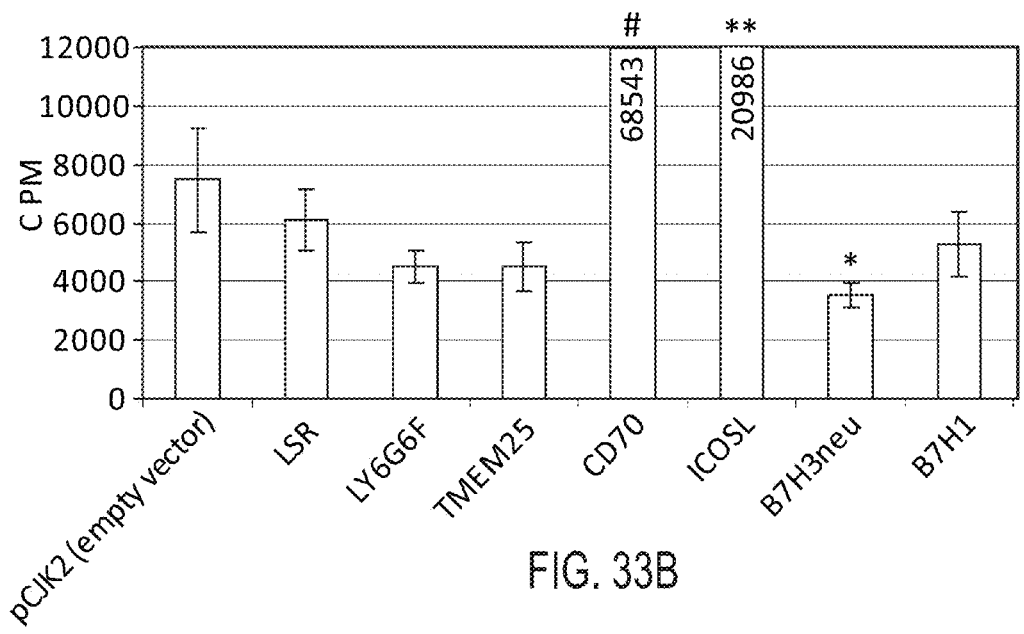
Figure 33C:
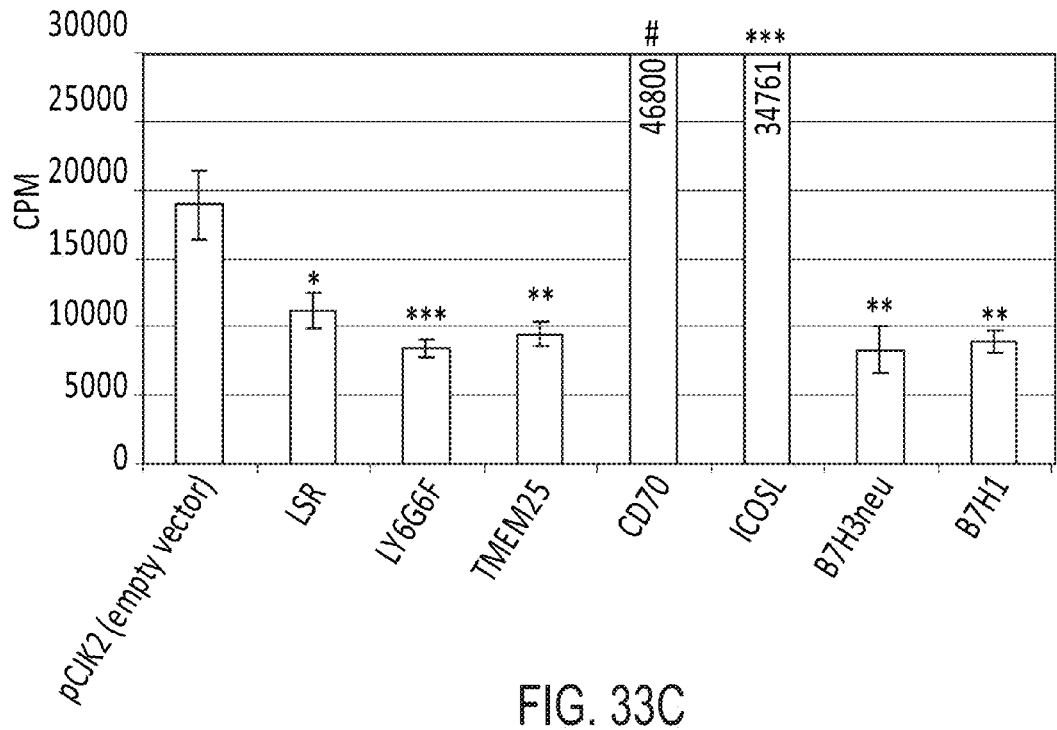
Figure 33D:
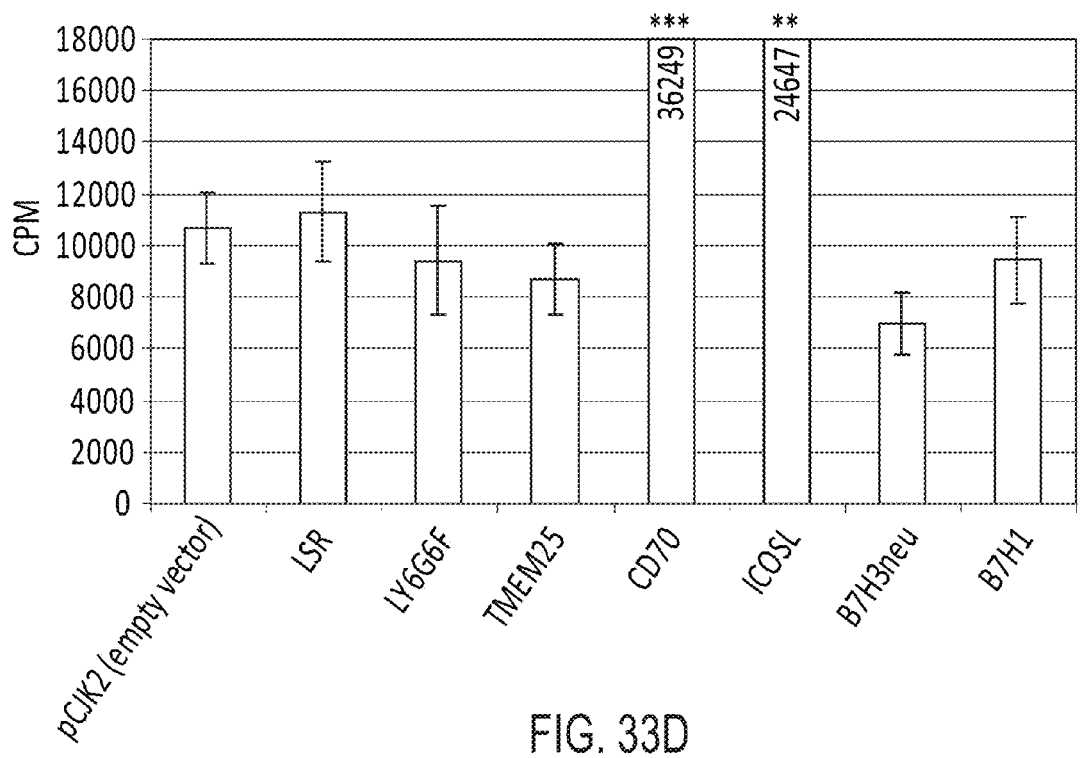

FIG. 33 shows the effect of stimulator cells (a murine thymoma cell line, Bw5147, which were engineered to express membrane-bound anti-human CD3 antibody fragments) expressing the cDNAs encoding human LY6G6F, TMEM25 or LSR (SEQ ID NOs: 1, 7 or 11, respectively) on the proliferation (CPM) of bulk human T cells (FIG. 33A), CD4+ human T cells (FIG. 33B), CD8+ human T cells (FIG. 33C), or naïve CD4CD45RA+ human T cells (FIG. 33D). Results are displayed as the mean+/−SEM of 6 (FIG. 337A) or 3 (FIGS. 33B, C, and D) experiments. *P<0.05, p<0.01, *p<0.001, and #p<0.0001 (Students T-test) represent significantly different results compared to empty vector.

Figure 34A:
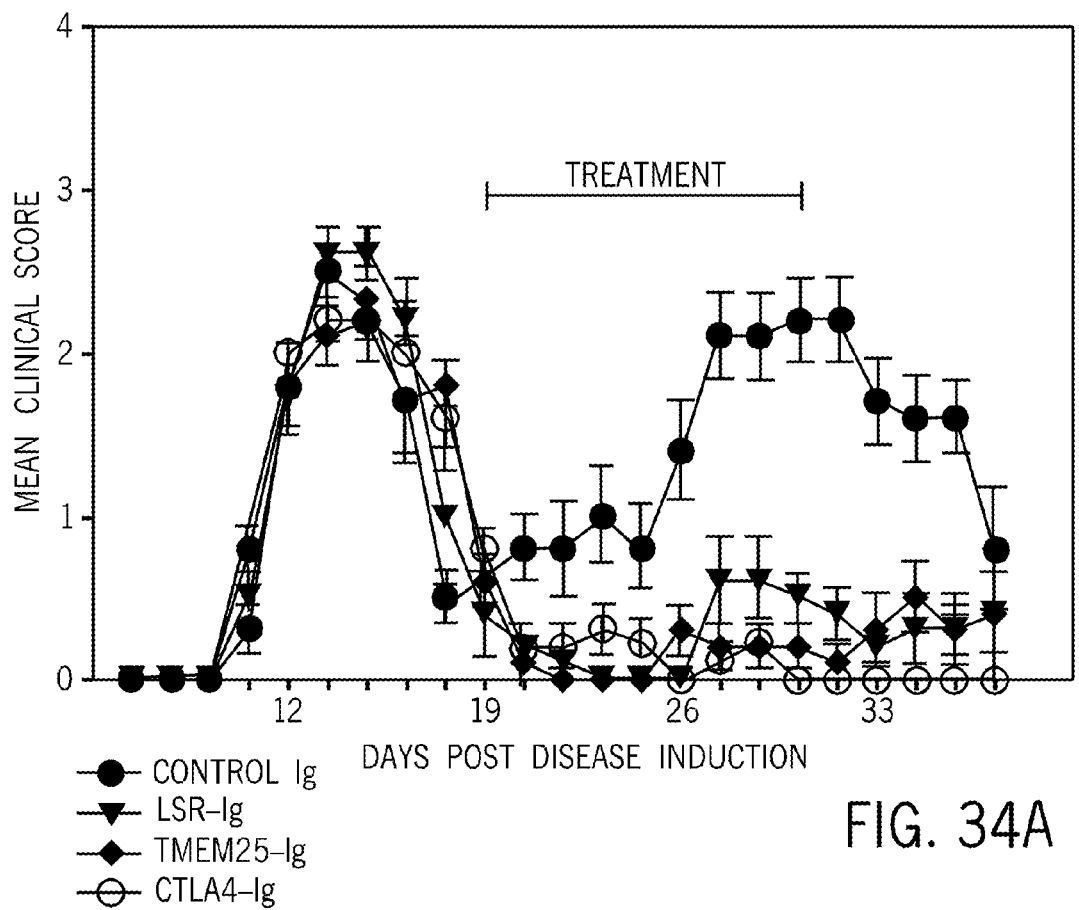
Figure 34B:
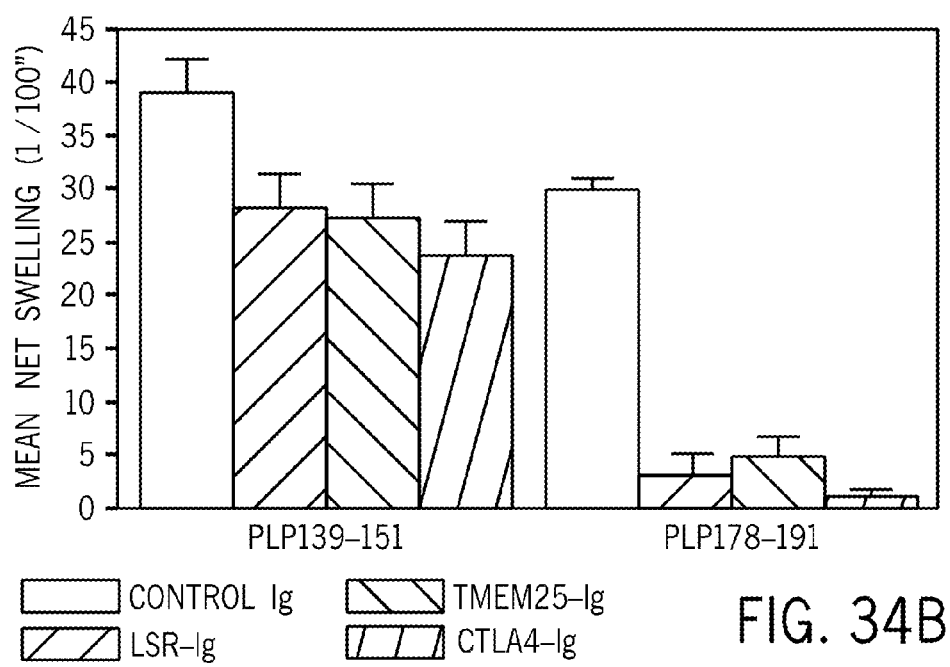

FIG. 34 shows the therapeutic effect of LSR-Ig (SEQ ID NO:26) or TMEM25-Ig (SEQ ID NO:25) treatment in the PLP139-151-induced R-EAE model in SJL mice. LSR-Ig (SEQ ID NO:26) or TMEM25-Ig (SEQ ID NO:25) were administered in a therapeutic mode from the onset of disease remission (day 18), at 100 microg/mouse i.p. 3 times per week for two weeks. Therapeutic effects of LSR-Ig and TMEM25-Ig on clinical symptoms are demonstrated as reduction in Mean Clinical Score (FIG. 34A). In addition, LSR-Ig and TMEM25-Ig treatment inhibited DTH responses to inducing epitope (PLP139-151) or spread epitope (PLP178-191), on day 35 after R-EAE induction (FIG. 34B). In this study the effect of LSR-Ig or TMEM25-Ig was studied in comparison to mIgG2a Ig negative control and CTLA4-Ig positive control that were administered at a similar regimen as the test proteins.

FIG. 35 shows the dose dependency and mode of action of the effect of TMEM25-Ig (SEQ ID NO:25) in the R-EAE model in SJL mice. In this study, treatments were given from onset of disease remission (day 19) at 100, 30 or 10 microg/mouse i.p. 3 times per week for two weeks, as compared to 100 microg/mouse IgG2a control that was given at a similar schedule. shown are effects of TMEM25-Ig treatment on disease course (FIG. 35A), DTH responses to spread epitopes PLP178-191 and MBP84-104 on days 45 and 76 post R-EAE induction (FIG. 35B), ex-vivo recall responses of splenocytes isolated on day 45 and 75 post disease induction (FIG. 35C) and LN cells isolated on day 45 post disease induction (FIG. 35D) as manifested by the effect of TMEM25-Ig treatment on cell proliferation and cytokine secretion (IFNg, IL-17, IL-10 and IL-4). The effect of TMEM25-Ig on cell counts in the spleen, lymph nodes and CNS as well as the different linages present in the CNS upon treatment with TMEM25-Ig at 100 ug/dose is shown in FIG. 35E.

FIG. 36 shows the therapeutic effect of VSIG10-Ig (SEQ ID NO:24) treatment in the PLP139-151-induced R-EAE model in SJL mice. VSIG10-Ig (SEQ ID NO:24) was administered in a therapeutic mode from the onset of disease remission (day 19), at 100 microg/mouse i.p. 3 times per week for two weeks. Therapeutic effects of VSIG10-Ig on clinical symptoms is demonstrated as reduction in Mean Clinical Score (FIG. 36A). In addition, VSIG10-Ig treatment inhibited DTH responses to spread epitopes (PLP178-191 and MBP MBP84-104), on days 45 and 76 after R-EAE induction (FIG. 36B). Also shown is the effect of VSIG10-Ig on ex-vivo recall responses of splenocytes isolated on day 45 and 75 post disease induction (FIG. 36C) and LN cells isolated on day 45 post disease induction (FIG. 36D) as manifested by the effect of VSIG10-Ig treatment on cell proliferation and cytokine secretion (IFNg, IL-17, IL-10 and IL-4). The effect of VSIG10-Ig on cell counts in the spleen, lymph nodes and CNS as well as the different linages present within each of these tissues upon treatment with VSIG10-Ig at 100 ug/dose is shown in FIG. 36E. In this study the effect of VSIG10-Ig was studied in comparison to mIgG2a Ig control that was administered at similar dose and regimen as VSIG10-Ig.

Figure 37A:
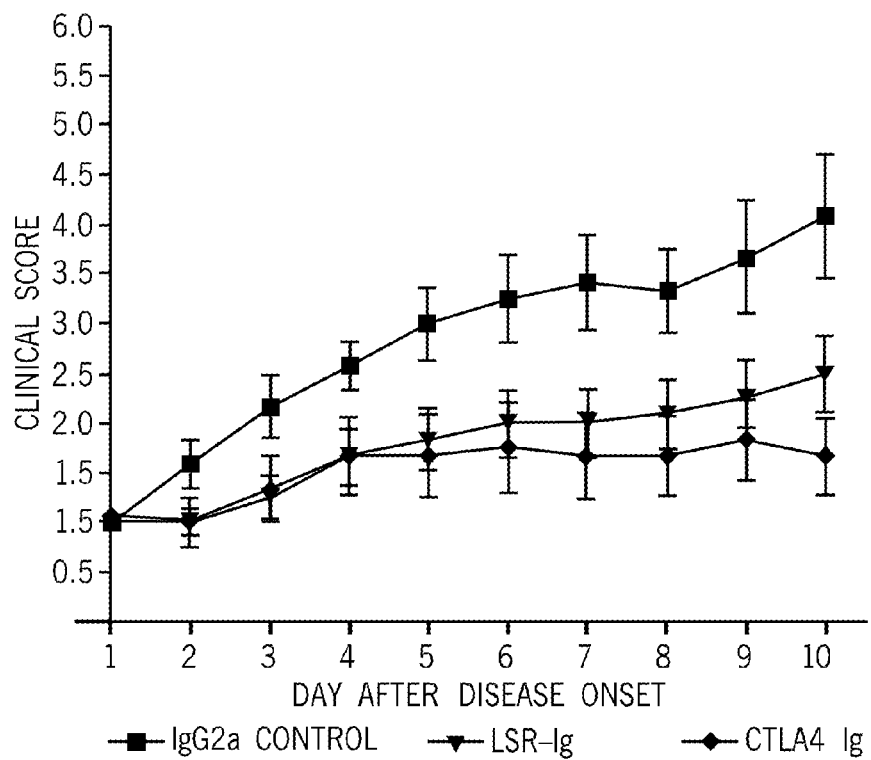
Figure 37B:
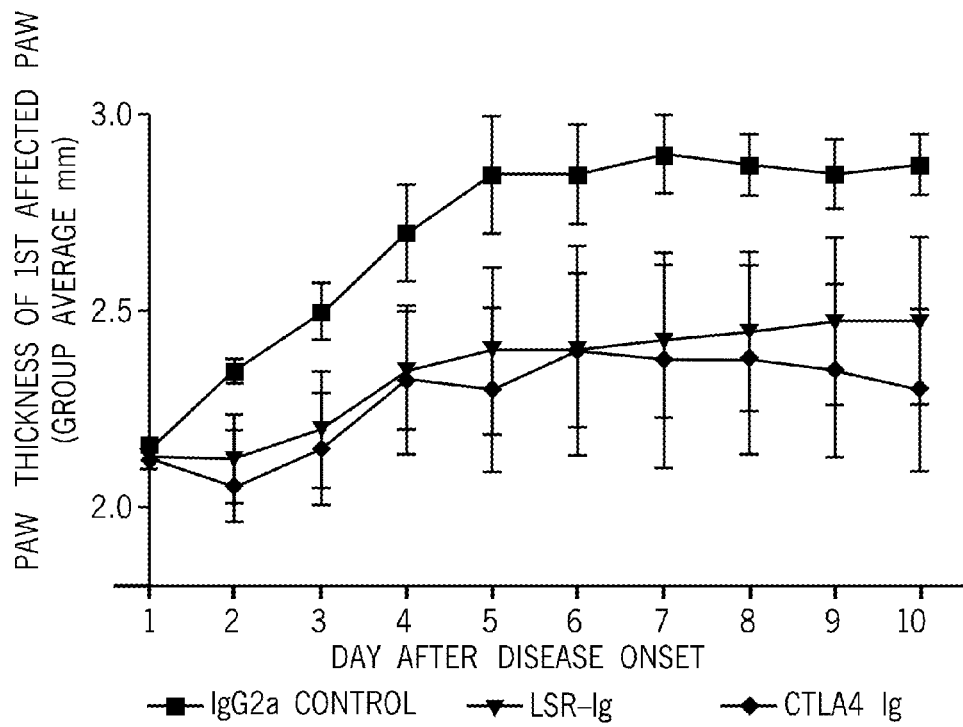

FIG. 37 shows the therapeutic effect of LSR-Ig (SEQ ID NO:26) administered at 100 microg/mouse, i.p, 3 times per week for 10 days in collagen induced arthritis (CIA) model of Rhematoid Arthritis. Measured are clinical score (A) paw swelling (B) and histological damage (C) CTLA4-Ig, (100 microg/mouse) and TNFR-Ig (etanercept) were used as a positive control while mIgG2a Ig control (100 microg/mouse) was used as negative control.

Figure 38:
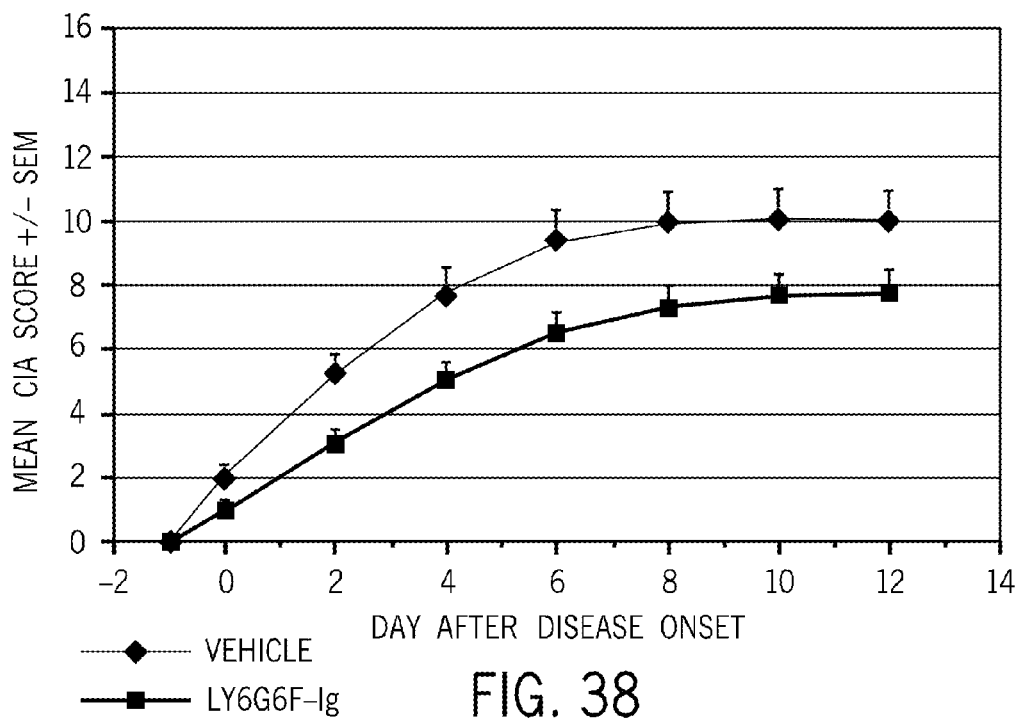

FIG. 38 shows the therapeutic effect of LY6G6F-Ig (SEQ ID NO:23) administered at 25 mg/kg, i.p, 3 times per week for 2 weeks in collagen induced arthritis (CIA) model of Rhematoid Arthritis, with measurements given according to clinical scores.

For FIGS. 12-17, 21, 22, division was made into separate parts "A", "B" and so forth for reasons of space only, so as to be able to show all results.

DETAILED DESCRIPTION OF THE INVENTION

The present invention, in at least some embodiments, relates to any one of the proteins referred to as LY6G6F, VSIG10, TMEM25 and/or LSR, and its corresponding nucleic acid sequence, and portions and variants thereof and fusion proteins and conjugates containing, and/or polyclonal and monoclonal antibodies and/or antigen binding fragments and/or conjugates containing same, and/or alternative scaffolds thereof that bind LY6G6F, VSIG10, TMEM25 and/or LSR and/or portions and/or variants thereof, and the use thereof as a therapeutic and/or diagnostic agent, and various uses as described herein.

US Patent Application Nos. US2009117566, US20090017473, and other family members, assigned to GENENTECH INC., disclose a 382 amino acid LY6G6F protein sequence (DNA234441, tumor-associated antigenic target (TAT) TAT201, SEQ ID NO:92 therein) having a transmembrane domain between residues 234-254 and 354-374. '566, '473, applications and other applications from this patent family disclose that TAT201 is over expressed in colon and rectal cancers. PCT Application Nos WO2003083074 and WO2004046342 disclose a 382 amino acid LY6G6F protein sequence as one of many genes that are over expressed in colon cancer cells. These patent applications further purportedly relate to methods of use of LY6G6F for detecting and treating colon cancer. However, these patent applications do not teach or suggest or provide any incentive that would direct a skilled artisan to use antibodies specific to the LY6G6F and/or LY6G6F ECD for treatment and/or diagnosis of cancer other than colorectal cancer, and/or infectious disorders, and/or immune related disorders. These patent applications do not describe LY6G6F ECD and do not teach or suggest or provide any incentive that would direct a skilled artisan to use the LY6G6F ECD for treatment of cancer and/or infectious disorders, and/or immune related disorders.

TMEM25 is disclosed in PCT Application Nos WO9958642 and WO2003087300, and US Patent Application Nos. US2007041963 and US2005202526, as one of many (hundreds to thousands) proteins, useful for diagnosing, preventing, and treating disorders associated with an abnormal expression or activity of these proteins. However, these applications do not teach or suggest or provide any incentive that would direct a skilled artisan to use antibodies specific to the TMEM25 and/or TMEM25 ECD for treatment and/or diagnosis of cancer and/or infectious disorders, and/or immune related disorders. TMEM25 is also disclosed in US Patent Application No. US2004010134, as one of hundreds of albumin fusion proteins, useful for diagnosing, treating, preventing or ameliorating diseases or disorders e.g. cancer, anemia, arthritis, asthma, inflammatory bowel disease or Alzheimer's disease. However, this application does not teach or suggest or provide any incentive that would direct a skilled artisan to use antibodies specific to the TMEM25 and/or TMEM25 ECD for treatment and/or diagnosis of cancer and/or infectious disorders, and/or immune related disorders. TMEM25 is also described in Doolan P, et al., Tumour Biol. 2009, 30(4):200-9 as a favourable prognostic and predictive biomarker for breast cancer diagnosis. However, this publication does not teach or suggest or provide any incentive that would direct a skilled artisan to use the antibodies specific to TMEM25 and/or TMEM25 ECD for treatment of cancer and/or infectious disorders, and/or immune related disorders.

In order that the present invention in various embodiments may be more readily understood, certain terms are first defined. Additional definitions are set forth throughout the detailed description.

As used herein the term "isolated" refers to a compound of interest (for example a polynucleotide or a polypeptide) that is in an environment different from that in which the compound naturally occurs e.g. separated from its natural milieu such as by concentrating a peptide to a concentration at which it is not found in nature. "Isolated" includes compounds that are within samples that are substantially enriched for the compound of interest and/or in which the compound of interest is partially or substantially purified.

An "immune cell" refers to any cell from the hemopoietic origin including but not limited to T cells, B cells, monocytes, dendritic cells, and macrophages.

As used herein, the term "polypeptide" refers to a chain of amino acids of any length, regardless of modification (e.g., phosphorylation or glycosylation).

As used herein, a "costimulatory polypeptide" or "costimulatory molecule" is a polypeptide that, upon interaction with a cell-surface molecule on T cells, modulates T cell responses.

As used herein, a "costimulatory signaling" is the signaling activity resulting from the interaction between costimulatory polypeptides on antigen presenting cells and their receptors on T cells during antigen-specific T cell responses. Without wishing to be limited by a single hypothesis, the antigen-specific T cell response is believed to be mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). Without wishing to be limited by a single hypothesis, this "second signal" is critical in determining the type of T cell response (activation vs inhibition) as well as the strength and duration of that response, and is regulated by both positive and negative signals from costimulatory molecules, such as the B7 family of proteins.

As used herein, the term "B7" polypeptide means a member of the B7 family of proteins that costimulate T cells including, but not limited to B7-1, B7-2, B7-DC, B7-H5, B7-H1, B7-H2, B7-H3, B7-H4, B7-H6, B7-S3 and biologically active fragments and/or variants thereof. Representative biologically active fragments include the extracellular domain or fragments of the extracellular domain that costimulate T cells.

As used herein, a "variant" polypeptide contains at least one amino acid sequence alteration as compared to the amino acid sequence of the corresponding wild-type polypeptide.

As used herein, "conservative" amino acid substitutions are substitutions wherein the substituted amino acid has similar structural or chemical properties. As used herein, the term "host cell" refers to prokaryotic and eukaryotic cells into which a recombinant vector can be introduced.

As used herein, the term "an edge portion" or "a new junction" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a head and a "known protein" portion of a variant, or a join between a tail and a "known protein" portion of a variant, or a join between an insertion and a "known protein" portion of a variant.

In some embodiments, a bridge between a tail or a head or a unique insertion, and a "known protein" portion of a variant, comprises at least about 10 amino acids, or in some embodiments at least about 20 amino acids, or in some embodiments at least about 30 amino acids, or in some embodiments at least about 40 amino acids, in which at least one amino acid is from the tail/head/insertion and at least one amino acid is from the "known protein" portion of a variant. In some embodiments, the bridge may comprise any number of amino acids from about 10 to about 40 amino acids (for example, 10, 11, 12, 13 . . . 37, 38, 39, 40 amino acids in length, or any number in between).

It should be noted that a bridge cannot be extended beyond the length of the sequence in either direction, and it should be assumed that every bridge description is to be read in such manner that the bridge length does not extend beyond the sequence itself.

Furthermore, bridges are described with regard to a sliding window in certain contexts below. For example, certain descriptions of the bridges feature the following format: a bridge between two edges (in which a portion of the known protein is not present in the variant) may optionally be described as follows: a bridge portion of CONTIG-NAME_P1 (representing the name of the protein), comprising a polypeptide having a length "n", wherein n is at least about 10 amino acids in length, optionally at least about 20 amino acids, at least about 30 amino acids, at least about 40 amino acids, or at least about 50 amino acids in length, wherein at least two amino acids comprise XX (2 amino acids in the center of the bridge, one from each end of the edge), having a structure as follows (numbering according to the sequence of CONTIG-NAME_PD: a sequence starting from any of amino acid numbers 49-x to 49 (for example); and ending at any of amino acid numbers 50+((n−2)−x) (for example), in which x varies from 0 to n−2. In this example, it should also be read as including bridges in which n is any number of amino acids between 10-50 amino acids in length. Furthermore, the bridge polypeptide cannot extend beyond the sequence, so it should be read such that 49-x (for example) is not less than 1, nor 50+((n−2)−x) (for example) greater than the total sequence length.

The term "cancer" as used herein should be understood to encompass any neoplastic disease (whether invasive or metastatic) which is characterized by abnormal and uncontrolled cell division causing malignant growth or tumor. Non-limiting examples of cancer which may be treated with a compound according to at least some embodiments of the present invention are solid tumors, sarcomas and hematological malignancies, including but not limited to breast cancer (e.g. breast carcinoma), cervical cancer, ovary cancer (ovary carcinoma), endometrial cancer, melanoma, bladder cancer (bladder carcinoma), lung cancer (e.g. adenocarcinoma and non-small cell lung cancer), pancreatic cancer (e.g. pancreatic carcinoma such as exocrine pancreatic carcinoma), colon cancer (e.g. colorectal carcinoma, such as colon adenocarcinoma and colon adenoma), prostate cancer including the advanced disease, hematopoietic tumors of lymphoid lineage (e.g. leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma), myeloid leukemia (for example, acute myelogenous leukemia (AML), chronic myelogenous leukemia), thyroid cancer, thyroid follicular cancer, myelodysplastic syndrome (MDS), tumors of mesenchymal origin (e.g. fibrosarcomas and rhabdomyosarcomas), melanoma, uveal melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), and a hereditary cancer syndrome such as Li-Fraumeni syndrome and Von Hippel-Lindau syndrome (VHL), and wherein the cancer may be non-metastatic, invasive or metastatic.

According to at least some preferred embodiments of the present invention, the cancer is selected from the group consisting of melanoma, cancers of liver, renal, brain, breast, colon, lung, ovary, pancreas, prostate, stomach, multiple myeloma and hematopoietic cancer, including but not limited to lymphoma (Hodgkin's and non Hodgkin's), acute and chronic lymphoblastic leukemia and acute and chronic myeloid leukemia, and wherein the cancer may be non-metastatic, invasive or metastatic.

The term "autoimmune disease" as used herein should be understood to encompass any autoimmune disease and chronic inflammatory conditions. According to at least some embodiments of the invention, the autoimmune diseases should be understood to encompass any disease disorder or condition selected from the group including but not limited to multiple sclerosis, including relapsing-remiting multiple sclerosis, primary progressive multiple sclerosis, and secondary progressive multiple sclerosis; psoriasis; rheumatoid arthritis; psoriatic arthritis, systemic lupus erythematosus (SLE); ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune haemolytic anaemia, Guillian-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anaemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis nodosa, chondrocalcinosis, Wegener's granulomatosis, microscopic polyangiitis, chronic urticaria, bullous skin disorders, pemphigoid, atopic eczema, Devic's disease, childhood autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne, normocomplementemic urticarial vasculitis, pericarditis, myositis, antisynthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, autoimmune retinopathy, age-related macular degeneration, atherosclerosis, chronic prostatitis and TNF receptor-associated periodic syndrome (TRAPS).

Optionally and preferably, the autoimmune disease includes but is not limited to any of the types and subtypes of any of multiple sclerosis, rheumatoid arthritis, type I diabetes, psoriasis, systemic lupus erythematosus, inflammatory bowel disease, uveitis, or Sjogren's syndrome.

As used herein, "multiple sclerosis" comprises one or more of multiple sclerosis, benign multiple sclerosis, relapsing remitting multiple sclerosis, secondary progressive multiple sclerosis, primary progressive multiple sclerosis, progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, and acute multiple sclerosis. Optionally, "conditions relating to multiple sclerosis" include, e.g., Devic's disease, also known as Neuromyelitis Optica; acute disseminated encephalomyelitis, acute demyelinating optic neuritis, demyelinative transverse myelitis, Miller-Fisher syndrome, encephalomyelradiculoneuropathy, acute demyelinative polyneuropathy, tumefactive multiple sclerosis and Balo's concentric sclerosis.

As used herein, "rheumatoid arthritis" comprises one or more of rheumatoid arthritis, gout and pseudo-gout, juvenile idiopathic arthritis, juvenile rheumatoid arthritis, Still's disease, ankylosing spondylitis, rheumatoid vasculitis. Optionally, conditions relating to rheumatoid arthritis include, e.g., osteoarthritis, sarcoidosis, Henoch-Schönlein purpura, Psoriatic arthritis, Reactive arthritis, Spondyloarthropathy, septic arthritis, Haemochromatosis, Hepatitis, vasculitis, Wegener's granulomatosis, Lyme disease, Familial Mediterranean fever, Hyperimmunoglobulinemia D with recurrent fever, TNF receptor associated periodic syndrome, and Enteropathic arthritis associated with inflammatory bowel disease.

As used herein, "Uveitis" comprises one or more of uveitis, anterior uveitis (or iridocyclitis), intermediate uveitis (pars planitis), posterior uveitis (or chorioretinitis) and the panuveitic form.

As used herein, "inflammatory bowel disease" comprises one or more of inflammatory bowel disease Crohn's disease, ulcerative colitis (UC), Collagenous colitis, Lymphocytic colitis, Ischaemic colitis, Diversion colitis, Behçet's disease, Indeterminate colitis.

As used herein, "psoriasis" comprises one or more of psoriasis, Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplantar pustulosis, pustular psoriasis of the Barber type, pustular psoriasis of the extremities), Annular pustular psoriasis, Acrodermatitis continua, Impetigo herpetiformis. Optionally, conditions relating to psoriasis include, e.g., drug-induced psoriasis, Inverse psoriasis, Napkin psoriasis, Seborrheic-like psoriasis, Guttate psoriasis, Nail psoriasis, Psoriatic arthritis.

As used herein, "type 1 diabetes" comprises one or more of type 1 diabetes, insulin-dependent diabetes mellitus, idiopathic diabetes, juvenile type 1 diabetes, maturity onset diabetes of the young, latent autoimmune diabetes in adults, gestational diabetes. Conditions relating to type 1 diabetes include, neuropathy including polyneuropathy, mononeuropathy, peripheral neuropathy and autonomicneuropathy; eye complications: glaucoma, cataracts, retinopathy.

As used herein, "Sjogren's syndrome" comprises one or more of Sjogren's syndrome, Primary Sjogren's syndrome and Secondary Sjogren's syndrome, as well as conditions relating to Sjogren's syndrome including connective tissue disease, such as rheumatoid arthritis, systemic lupus erythematosus, or scleroderma. Other complications include pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, Inflammation in the esophagus, stomach, pancreas, and liver (including hepatitis), Polymyositis, Raynaud's phenomenon, Vasculitis, Autoimmune thyroid problems, lymphoma.

As used herein, "systemic lupus erythematosus", comprises one or more of systemic lupus erythematosus, discoid lupus, lupus arthritis, lupus pneumonitis, lupus nephritis. Conditions relating to systemic lupus erythematosus include osteoarticular tuberculosis, antiphospholipid antibody syndrome, inflammation of various parts of the heart, such as pericarditis, myocarditis, and endocarditis, Lung and pleura inflammation, pleuritis, pleural effusion, chronic diffuse interstitial lung disease, pulmonary hypertension, pulmonary emboli, pulmonary hemorrhage, and shrinking lung syndrome, lupus headache, Guillain-Barré syndrome, aseptic meningitis, demyelinating syndrome, mononeuropathy, mononeuritis multiplex, myasthenia gravis, myelopathy, cranial neuropathy, polyneuropathy, vasculitis.

The term "immune related disease (or disorder or condition)" as used herein should be understood to encompass any disease disorder or condition selected from the group including but not limited to autoimmune diseases, inflammatory disorders and immune disorders associated with graft transplantation rejection, such as acute and chronic rejection of organ transplantation, allogenic stem cell transplantation, autologous stem cell transplantation, bone marrow transplantation, and graft versus host disease.

As used herein the term "inflammatory disorders" and/or "inflammation", used interchangeably, includes inflammatory abnormalities characterized by disregulated immune response to harmful stimuli, such as pathogens, damaged cells, or irritants. Inflammatory disorders underlie a vast variety of human diseases. Non-immune diseases with etiological origins in inflammatory processes include cancer, atherosclerosis, and ischaemic heart disease. Examples of disorders associated with inflammation include: Chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

As used herein the term "infectious disorder and/or disease" and/or "infection", used interchangeably, includes any disorder, disease and/or condition caused by presence and/or growth of pathogenic biological agent in an individual host organism. As used herein the term "infection" comprises the disorder, disease and/or condition as above, exhibiting clinically evident illness (i.e., characteristic medical signs and/or symptoms of disease) and/or which is asymptomatic for much or all of it course. As used herein the term "infection" also comprises disorder, disease and/or condition caused by persistence of foreign antigen that lead to exhaustion T cell phenotype characterized by impaired functionality which is manifested as reduced proliferation and cytokine production. As used herein the term "infectious disorder and/or disease" and/or "infection", further includes any of the below listed infectious disorders, diseases and/or conditions, caused by a bacterial infection, viral infection, fungal infection and/or parasite infection.

As used herein the term "viral infection" comprises any infection caused by a virus, optionally including but not limited to Retroviridae (e.g., human immunodeficiency viruses, such as HIV-1 or HIV-2, acquired immune deficiency (AIDS) also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxyiridae (variola virsues, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1-internally transmitted; class 2-parenterally transmitted (i.e., Hepatitis C); Norwalk and related viruses, and astroviruses) as well as Severe acute respiratory syndrome virus and respiratory syncytial virus (RSV).

As used herein the term "fungal infection" comprises any infection caused by a fungi, optionally including but not limited to *Cryptococcus neoformans, Histoplasma capsulatum, Coccidioides immitis, Blastomyces dermatitidis, Chlamydia trachomatis, Candida albicans.*

As used herein the term "parasite infection" comprises any infection caused by a parasite, optionally including but not limited to protozoa, such as Amebae, Flagellates, *Plasmodium falciparum, Toxoplasma gondii, Ciliates, Coccidia, Microsporidia, Sporozoa;* helminthes, *Nematodes* (Roundworms), *Cestodes* (Tapeworms), *Trematodes* (Flukes), Arthropods, and aberrant proteins known as prions.

An infectious disorder and/or disease caused by bacteria may optionally comprise one or more of Sepsis, septic shock, sinusitis, skin infections, pneumonia, bronchitis, meningitis, Bacterial vaginosis, Urinary tract infection (UCI), Bacterial gastroenteritis, Impetigo and erysipelas, Erysipelas, Cellulitis, anthrax, whooping cough, lyme disease, Brucellosis, enteritis, acute enteritis, Tetanus, diphtheria, Pseudomembranous colitis, Gas gangrene, Acute food poisoning, Anaerobic cellulitis, Nosocomial infections, Diarrhea, Meningitis in infants, Traveller's diarrhea, Hemorrhagic colitis, Hemolytic-uremic syndrome, Tularemia, Peptic ulcer, Gastric and Duodenal ulcers, Legionnaire's Disease, Pontiac fever, Leptospirosis, Listeriosis, Leprosy (Hansen's disease), Tuberculosis, Gonorrhea, Ophthalmia neonatorum, Septic arthritis, Meningococcal disease including meningitis, Waterhouse-Friderichsen syndrome, *Pseudomonas* infection, Rocky mountain spotted fever, Typhoid fever type salmonellosis, Salmonellosis with gastroenteritis and enterocolitis, Bacillary dysentery/Shigellosis, Coagulase-positive staphylococcal infections: Localized skin infections including Diffuse skin infection (Impetigo), Deep localized infections, Acute infective endocarditis, Septicemia, Necrotizing pneumonia, Toxinoses such as Toxic shock syndrome and Staphylococcal food poisoning, Cystitis, Endometritis, Otitis media, Streptococcal pharyngitis, Scarlet fever, Rheumatic fever, Puerperal fever, Necrotizing fasciitis, Cholera, Plague (including Bubonic plague and Pneumonic plague), as well as any infection caused by a bacteria selected from but not limited to *Helicobacter pyloris, Boreliai burgdorferi, Legionella pneumophilia, Mycobacteria* sps (e.g., *M. tuberculosis, M. avium, M. Intracellulare, M. kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter erogenes, Klebsiella pneuomiae, Pasturella multicoda, Bacteroides* sp., *Fusobacterium nucleatum, Sreptobacillus moniliformis, Treponema pallidium, Treponema pertenue, Leptospira,* and *Actinomyces israelli.*

Non limiting examples of infectious disorder and/or disease caused by virus is selected from the group consisting of but not limited to acquired immune deficiency (AIDS), West Nile encephalitis, coronavirus infection, rhinovirus infection, influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, EBV infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus Infection, Paramyxovirus, Parvovirus B 19 Infection, Picornavirus, Poxviruses infection, Rotavirus diarrhea, Rubella, Rubeola, Varicella, Variola infection.

An infectious disorder and/or disease caused by fungi optionally includes but is not limited to Allergic bronchopulmonary aspergillosis, Aspergilloma, Aspergillosis, Basidiobolomycosis, Blastomycosis, Candidiasis, Chronic pulmonary aspergillosis, Chytridiomycosis, Coccidioidomycosis, Conidiobolomycosis, Covered smut (barley), Cryptococcosis, Dermatophyte, Dermatophytid, Dermatophytosis, Endothrix, Entomopathogenic fungus, Epizootic lymphangitis, Epizootic ulcerative syndrome, Esophageal candidiasis, Exothrix, Fungemia, Histoplasmosis, Lobomycosis, Massospora cicadina, Mycosis, Mycosphaerella fragariae, Myringomycosis, Paracoccidioidomycosis, Pathogenic fungi, Penicilliosis, Thousand cankers disease, Tinea, Zeaspora, Zygomycosis. Non limiting examples of infectious disorder and/or disease caused by parasites is selected from the group consisting of but not limited to Acanthamoeba, Amoebiasis, Ascariasis, Ancylostomiasis, Anisakiasis, Babesiosis, Balantidiasis, Baylisascariasis, Blastocystosis, Candiru, Chagas disease, Clonorchiasis, Cochliomyia, Coccidia, Chinese Liver Fluke Cryptosporidiosis, Dientamoebiasis, Diphyllobothriasis, Dioctophyme renalis infection, Dracunculiasis, Echinococcosis, Elephantiasis, Enterobiasis, Fascioliasis, Fasciolopsiasis, Filariasis, Giardiasis, Gnathostomiasis, Hymenolepiasis, Halzoun Syndrome, Isosporiasis, Katayama fever, Leishmaniasis, lymphatic filariasis, Malaria, Metagonimiasis, Myiasis, Onchocerciasis, Pediculosis, Primary amoebic meningoencephalitis, Parasitic pneumonia, Paragonimiasis, Scabies, Schistosomiasis, Sleeping sickness, Strongyloidiasis, Sparganosis, Rhinosporidiosis, River blindness, Taeniasis (cause of Cysticercosis), Toxocariasis, Toxoplasmosis, Trichinosis, Trichomoniasis, Trichuriasis, Trypanosomiasis, Tapeworm infection.

A preferred example of infectious disease is a disease caused by any of hepatitis B, hepatitis C, infectious mononucleosis, EBV, cytomegalovirus, AIDS, HIV-1, HIV-2, tuberculosis, malaria and schistosomiasis.

As used herein, the term "vaccine" refers to a biological preparation that improves immunity to a particular disease, wherein the vaccine includes an antigen, such as weakened or killed forms of pathogen, its toxins or one of its surface proteins, against which immune responses are elicited. A vaccine typically includes an adjuvant as immune potentiator to stimulate the immune system. As used herein, the term "therapeutic vaccine" and/or "therapeutic vaccination" refers to a vaccine used to treat ongoing disease, such as infectious disease or cancer.

As used herein, the term "adjuvant" refers to an agent used to stimulate the immune system and increase the response to a vaccine, without having any specific antigenic effect in itself.

As used herein, the term LY6G6F and/or LY6G6F protein(s) refers to any one of the proteins set forth in SEQ ID NO:1, and/or variants thereof, and/or orthologs and/or fragments thereof, and/or nucleic acid sequences encoding for same, that are differentially expressed in cancers as recited herein and/or in infectious disorders as recited herein, and/or immune related disorders as recited herein, and/or that play a role in the etiology of cancers, and/or in infectious disorders, and/or immune related disorders.

According to preferred embodiments, a LY6G6F fragment comprises an amino acid sequence of LY6G6F ectodomain, set forth in any one of SEQ ID NOs: 2, 59, 81, 96, and/or variants thereof. According to preferred embodiments, a LY6G6F ortholog comprises any one of SEQ ID NOs:20, 29. According to preferred embodiments, a nucleic acid sequence encoding LY6G6F protein comprises SEQ ID NO:33, 57 or 182.

As used herein, the term VSIG10 and/or VSIG10 protein(s) refers to any one of the proteins set forth in any one of SEQ ID NOs:3, 5, and/or variants thereof, and/or orthologs and/or fragments thereof, and/or nucleic acid sequences encoding for same, that are differentially expressed in cancers as recited herein and/or in infectious disorders as recited herein, and/or immune related disorders as recited herein, and/or that play a role in the etiology of cancers and/or in infectious disorders, and/or immune related disorders.

Figures 1, 4A:
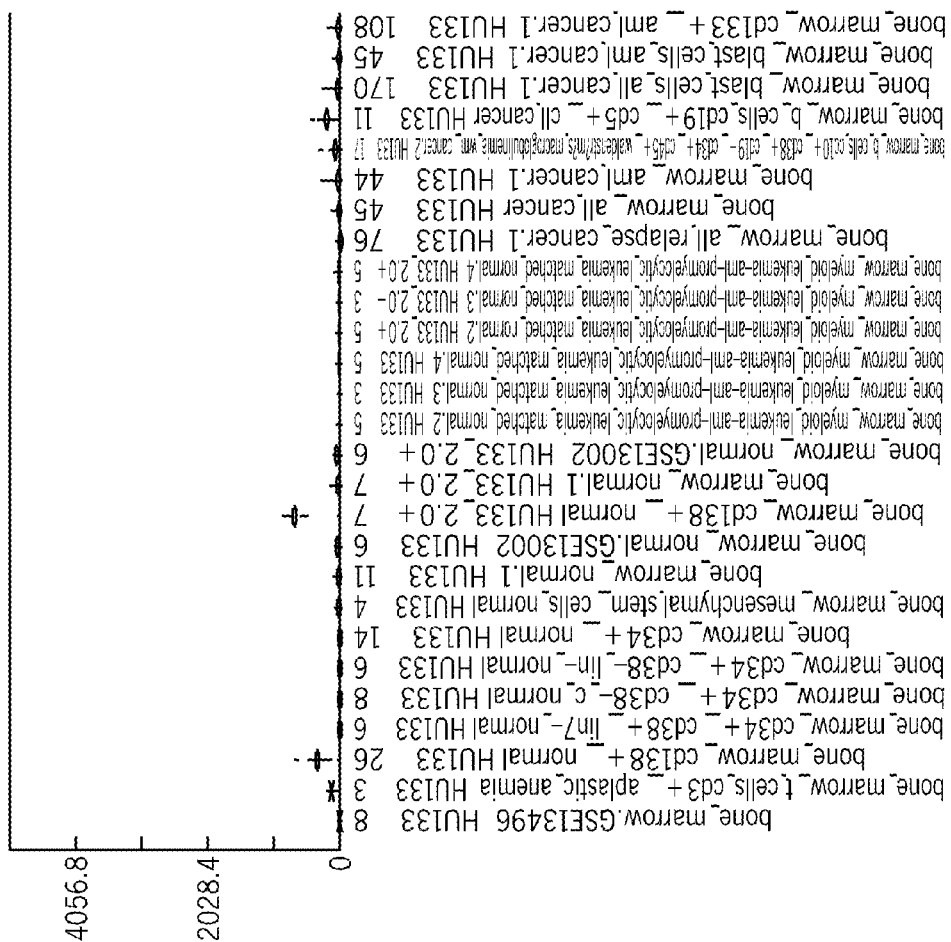
FIG. 1 presents amino acid sequences of LY6G6F (FIG. 1A, SEQ ID NO:1), VSIG10 (FIG. 1B, SEQ ID NO:3, and 1C, SEQ ID NO:5), TMEM25 (FIG. 1D, SEQ ID NO:7), LSR (FIG. 1E (SEQ ID NO:11), 1F (SEQ ID NO:13), 1G (SEQ ID NO:15), 1H (SEQ ID NO:16), 1I (SEQ ID NO:17), and 1J (SEQ ID NO:18)) proteins, fragments, ECDs and the corresponding nucleic acid sequences encoding same Amino acid residues corresponding to signal peptide (SP) appear in bold Italics. Ig-V and/or Ig-C domains are shown in boxes. Amino acid residues corresponding to thransmembrane region (TM) appear in bold and underlined Amino acid residues corresponding to alternative exons skipping in some of the isoforms (in FIGS. 1B, and 1E) appear in Italics and underlined. Nucleic acid sequence corresponding to alternative exons skipping variants of VSIG10 (skiping exon 3), and LSR (isoform-e, skipping exons 3, 4 and 5) appears in bold in FIGS. 1C, and 1I, respectively. Nucleic acid sequence corresponding to transmembrane region (TM) appears in bold and underlined in FIG. 1C. Nucleic acid sequence corresponding to signal peptide (SP) appears in bold Italics in FIGS. 1C, 1E, 1G, 1H, 1I, and 1J. TGA stop codon is highlighted in FIGS. 1C, and 1I.
Figures 2, 4A:
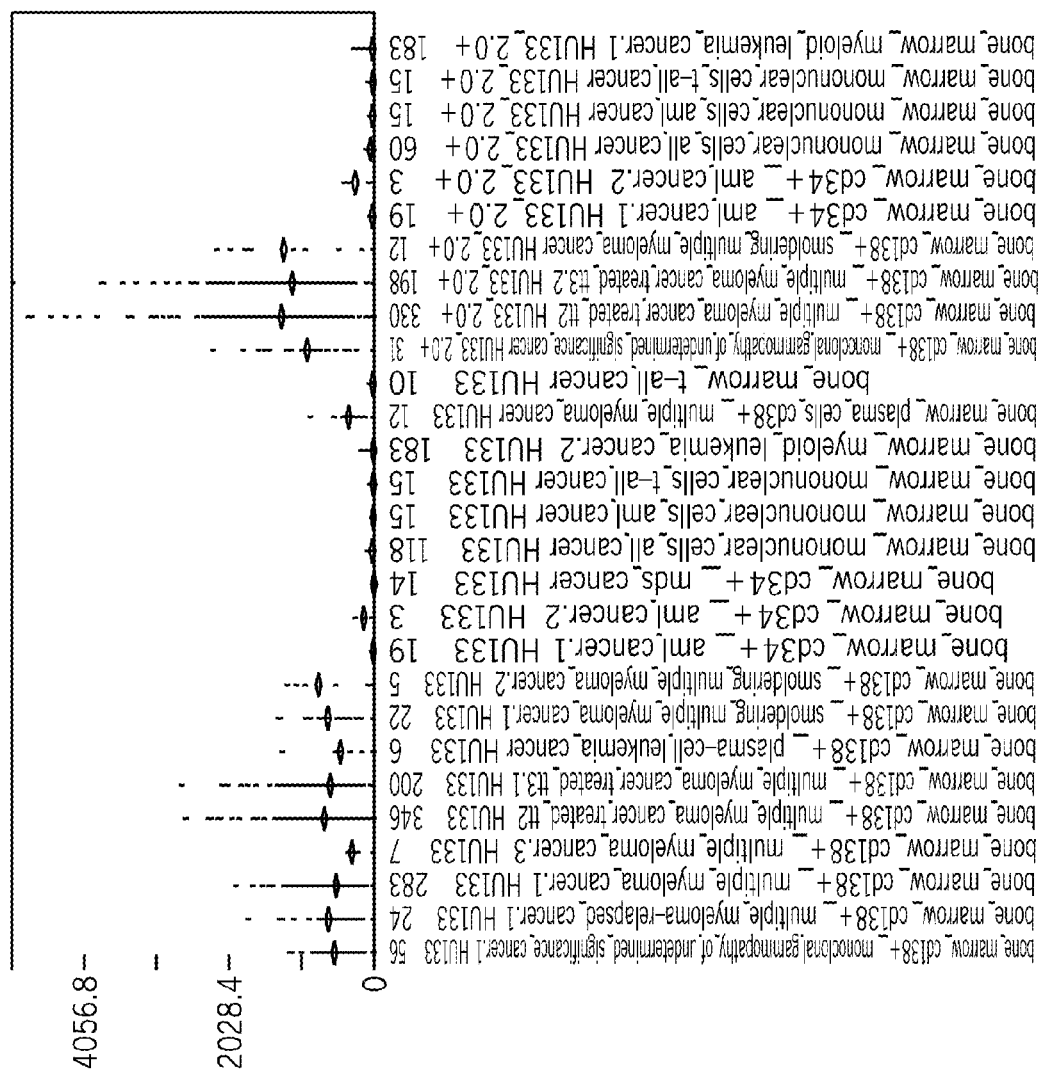
FIG. 2 presents amino acid sequence comparison between: the VSIG10 variant SEQ ID NO:5 and the known VSIG10 protein, SEQ ID NO: 3 (genbank accession number NP_061959.2) (FIG. 2A); LSR_isoform-a, SEQ ID NO:11 and known LSR protein, genbank accession number NP_991403 SEQ ID NO:62 (FIG. 2B-1); LSR_isoform-a, SEQ ID NO:11 and known LSR protein, genbank accession number XP_002829104, SEQ ID NO:68 (FIG. 2B-2); LSR_isoform-b, SEQ ID NO:13 and known LSR protein, genbank accession number NP_057009, SEQ ID NO:63 (FIG. 2C-1); LSR_isoform-b, SEQ ID NO:13 and known LSR protein, genbank accession number BAC11614, SEQ ID NO:65 (FIG. 2C-2); LSR_isoform-c, SEQ ID NO:15 and known LSR protein, genbank accession number NP_991404, SEQ ID NO:66 (FIG. 2D-1); LSR_isoform-c, SEQ ID NO:15 and known LSR protein, genbank accession number XP_002829105.1, SEQ ID NO:69 (FIG. 2D-2); LSR_isoform-d, SEQ ID NO:16 and known LSR protein, genbank accession number NP_991404, SEQ ID NO:66 (FIG. 2E-1); LSR_isoform-d, SEQ ID NO:16 and known LSR protein, genbank accession number XP_002829105.1, SEQ ID NO:69 (FIG. 2E-2); LSR_isoform-e, SEQ ID NO:17 and known LSR protein, genbank accession number BAG59226.1, SEQ ID NO:67 (FIG. 2F); LSR_isoform-f, SEQ ID NO:18 and known LSR protein, genbank accession number NP_991403, SEQ ID NO:62 (FIG. 2G-1); LSR_isoform-f, SEQ ID NO:18 and known LSR protein, genbank accession number NP_991404, SEQ ID NO:66 (FIG. 2G-2). The sequence of the unique edge portions (unique junction) of the VSIG10 variant (SEQ ID NO:5) and LSR variant (SEQ ID NO:18) are bold and highlighted (FIGS. 2A and 2G, respectively).
Figures 1, 4B:
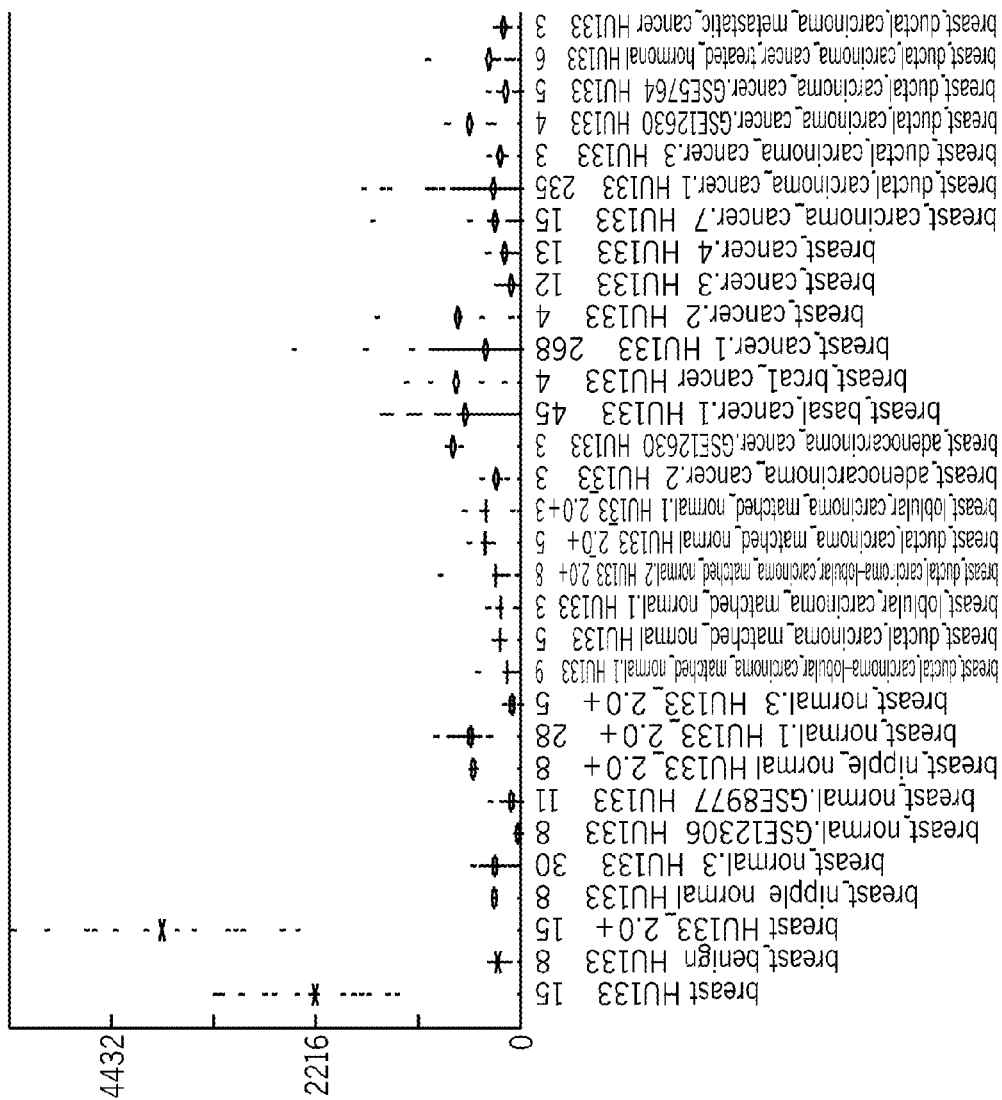
Figures 2, 4B:
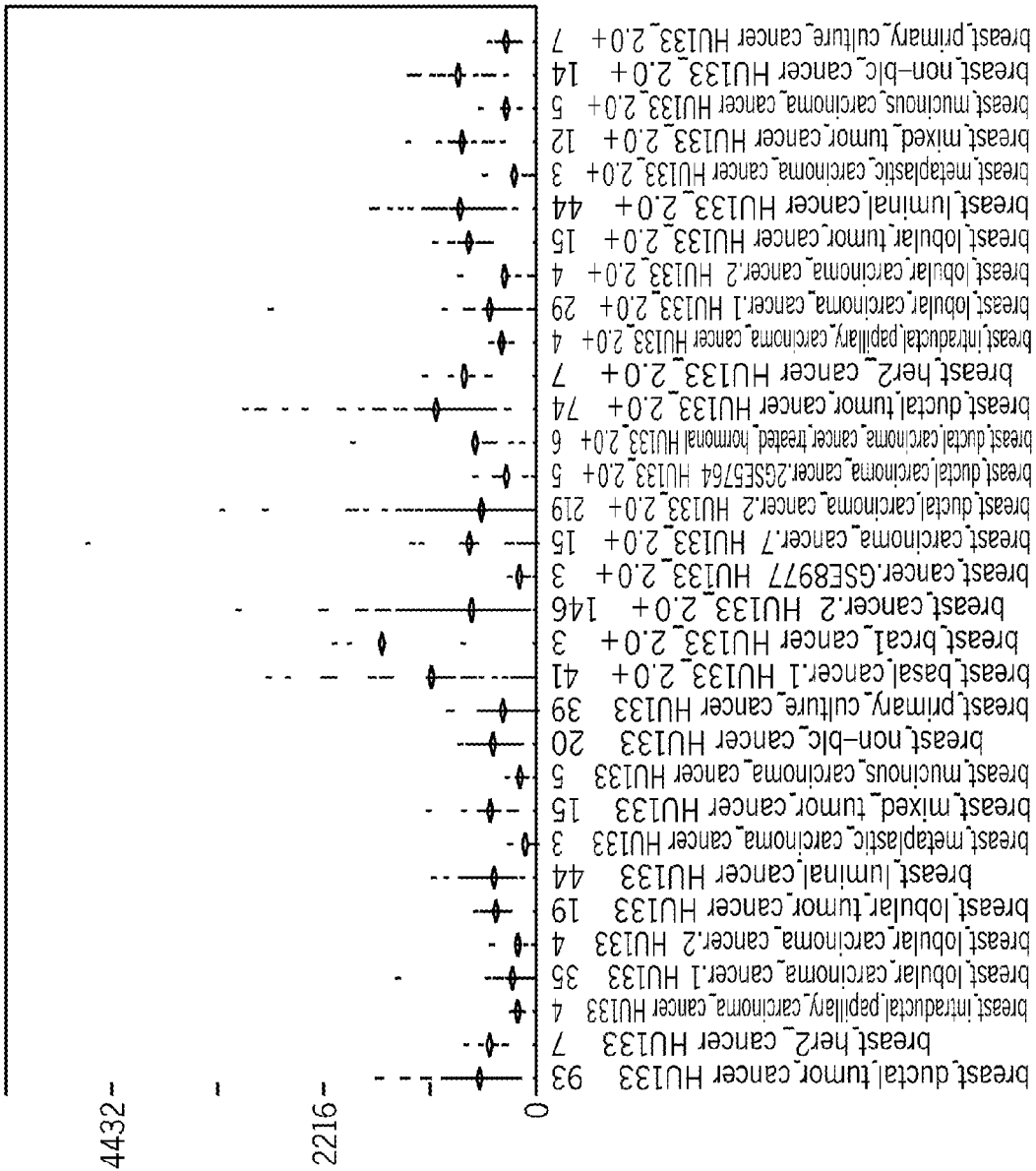
Figures 2, 4C:
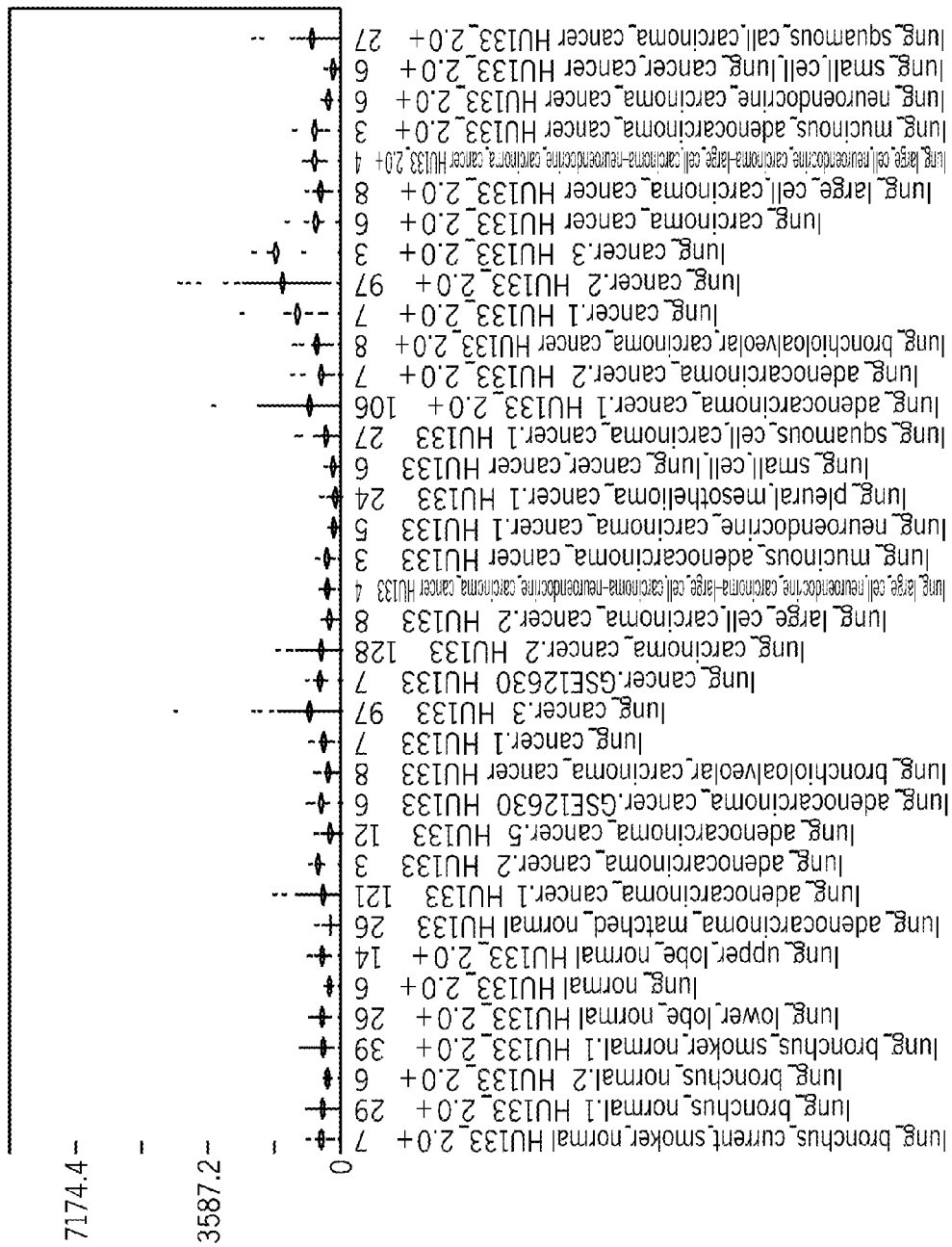
Figures 1, 4D:
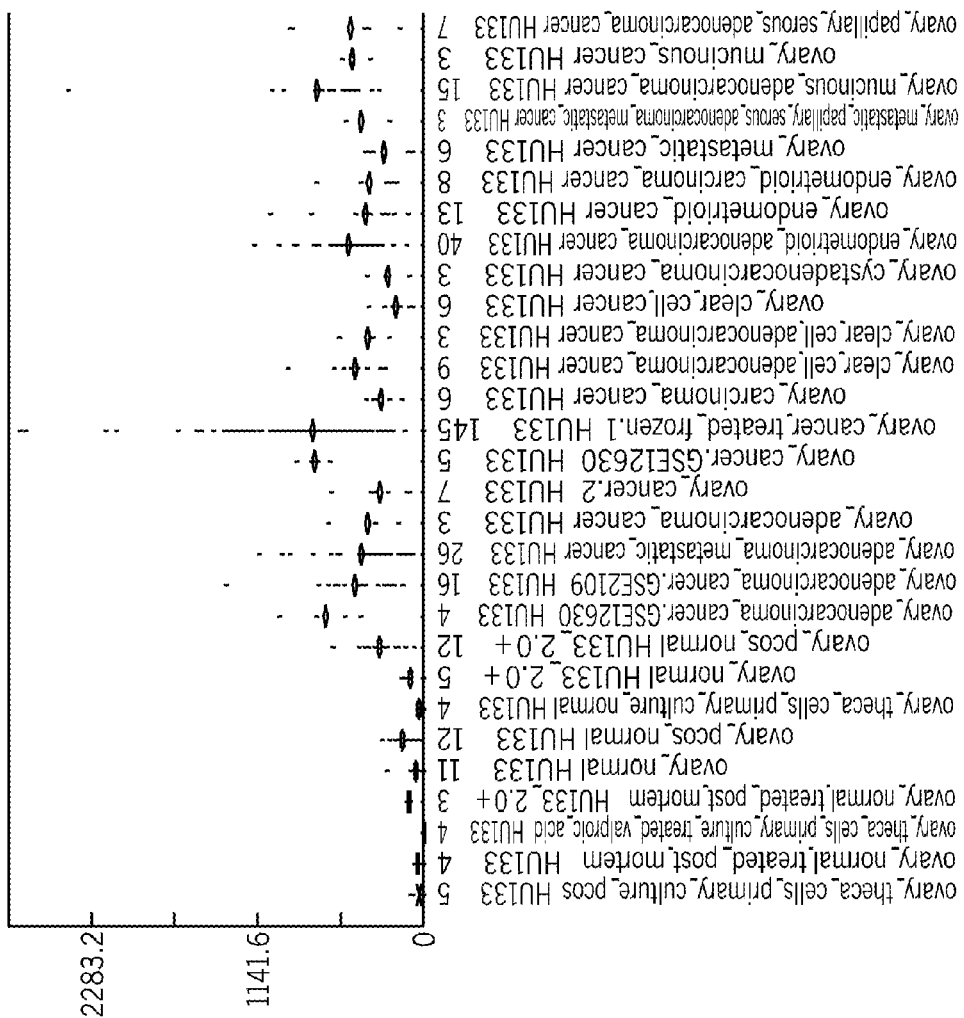
Figures 2, 4D:
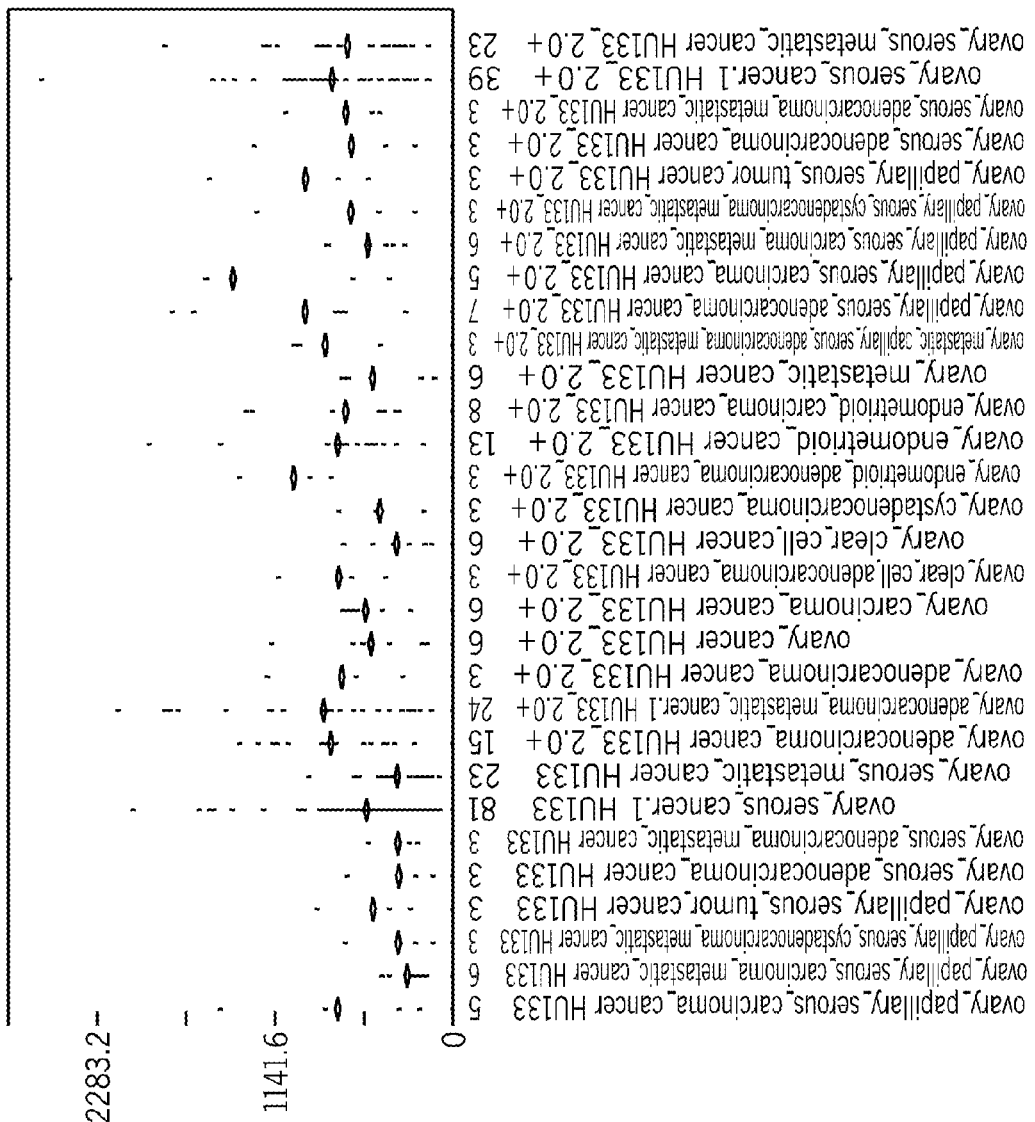
Figure 4E:
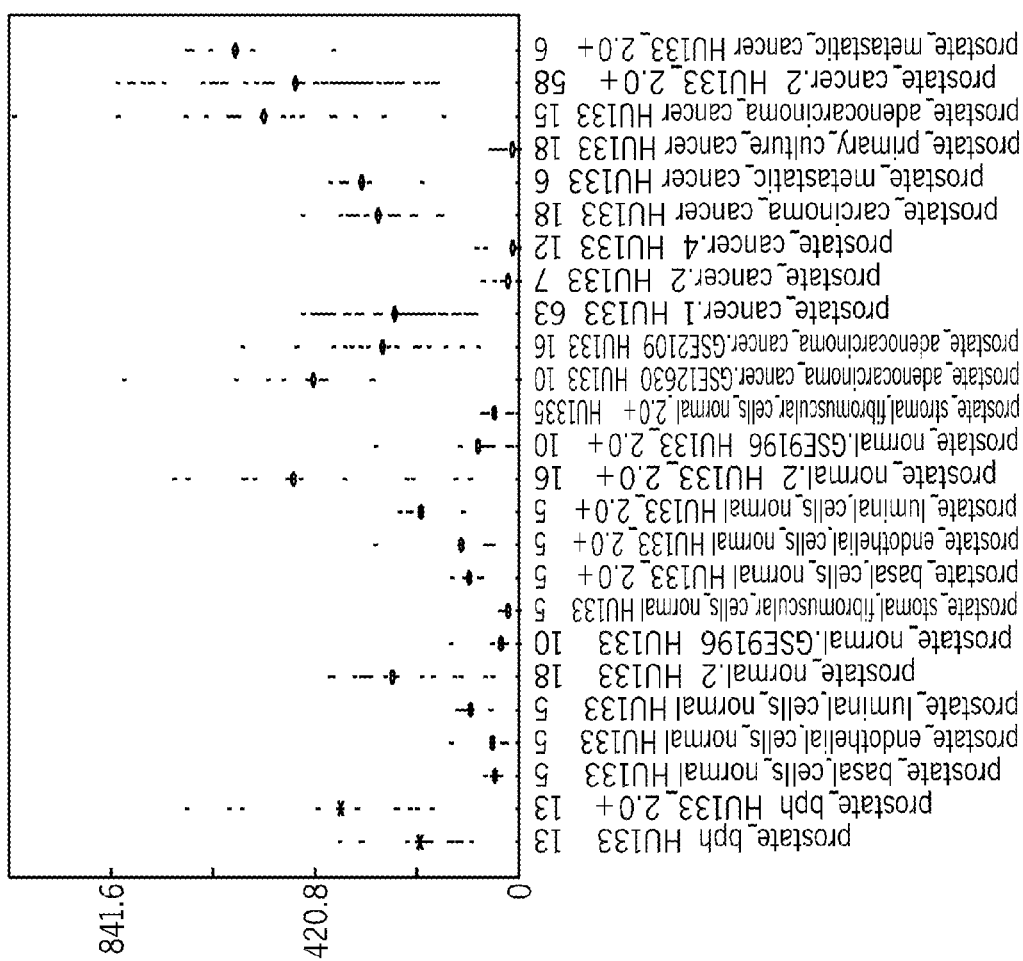
FIG. 4 shows a scatter plot, demonstrating the expression of LSR transcripts, that encode the LSR proteins, on a virtual panel of all tissues and conditions using MED discovery engine, demonstrating differential expression of LSR transcripts in several groups of cells from the immune system, mainly in bone marrow cells, and in various cancerous conditions of tissues, such as in breast, lung, ovary, pancreas, prostate and skin cancers.

According to preferred embodiments, a VSIG10 fragment comprises an amino acid sequence of VSIG10 ectodomain, set forth in any one of SEQ ID NOs: 4, 6, 60, 61, 82-93, 97-100, and/or variants thereof, and/or an amino acid sequence comprising a VSIG10 variant (SEQ ID NO:5) unique edge portion, demonstrated in FIG. 2A. According to preferred embodiments, a VSIG10 ortholog comprises any one of SEQ ID NOs: 19, 30. According to preferred embodiments, a nucleic acid sequence encoding VSIG10 protein comprises any one of SEQ ID NOs: 34, 35, 36, 183, or 184.

As used herein, the term TMEM25 and/or TMEM25 protein(s) refers to any one of the proteins set forth in any one of SEQ ID NOs: 7, 39, and/or variants thereof, and/or orthologs and/or fragments thereof, and/or nucleic acid sequences encoding for same, that are differentially expressed in cancers as recited herein and/or in infectious disorders as recited herein, and/or immune related disorders as recited herein, and/or that play a role in the etiology of cancers and/or in infectious disorders, and/or immune related disorders.

According to preferred embodiments, a TMEM25 fragment comprises an amino acid sequence of TMEM25 ectodomain, set forth in any one of SEQ ID NOs: 8, 39, 94, 101 and/or variants thereof. According to preferred embodiments, a TMEM25 ortholog comprises a protein having a sequence according to any of SEQ ID NO: 9, and/or 28. According to preferred embodiments, a nucleic acid sequence encoding TMEM25 protein comprises any one of SEQ ID NOs:37 or 185.

As used herein, the term LSR and/or LSR protein(s) refers to any one of the proteins set forth in any one of SEQ ID NOs: 11, 13, 15-18, 143, and/or variants thereof, and/or orthologs and/or fragments thereof, and/or nucleic acid sequences encoding for same, that are differentially expressed in cancers as recited herein and/or in infectious disorders as recited herein, and/or immune related disorders as recited herein, and/or that play a role in the etiology of cancers and/or in infectious disorders, and/or immune related disorders.

According to preferred embodiments, a LSR fragment comprises an amino acid sequence of LSR ectodomain, set forth in any one of SEQ ID NOs:10, 12, 14, 22, 47-50, 95, 102, and/or variants thereof, and/or an amino acid sequence comprising a LSR variant (SEQ ID NO:18) unique edge portion, demonstrated in FIG. 2G. An example of LSR orthologs is presented in any one of SEQ ID NOs: 21, 31, 32. According to preferred embodiments, a nucleic acid sequence encoding LSR protein comprises any one of SEQ ID NOs: 40-46, 132, 155, 188, 186, 187, 145, 154.

Without wishing to be limited by a single hypothesis, each of the LY6G6F, VSIG10, TMEM25 and/or LSR proteins according to at least some embodiments of the present invention, was predicted to be an immune costimulatory protein, e.g., a B7 protein family member that is involved in B7 immune co-stimulation including for example T cell responses elicited against cancer cells and that elicit effects on immunity such as triggering of autoimmune effects.

As used herein, the term the "soluble ectodomain (ECD)" or "ectodomain" or "soluble LY6G6F, VSIG10, TMEM25 and/or LSR protein(s)/molecule(s)" of LY6G6F, VSIG10, TMEM25 and/or LSR means non-cell-surface-bound (i.e. circulating) LY6G6F, VSIG10, TMEM25 and/or LSR molecules or any portion thereof, including, but not limited to: LY6G6F, VSIG10, TMEM25 and/or LSR-Ig fusion proteins, wherein the extracellular domain of LY6G6F, VSIG10, TMEM25 and/or LSR is fused to an immunoglobulin (Ig) moiety rendering the fusion molecule soluble, or fragments and derivatives thereof, proteins with the extracellular domain of LY6G6F, VSIG10, TMEM25 and/or LSR fused or joined with a portion of a biologically active or chemically active protein such as the papillomavirus E7 gene product, melanoma-associated antigen p97 or HIV env protein, or fragments and derivatives thereof; hybrid (chimeric) fusion proteins such as LY6G6F, VSIG10, TMEM25 and/or LSR-Ig, or fragments and derivatives thereof. Such fusion proteins are described in greater detail below.

"Soluble LY6G6F, VSIG10, TMEM25 and/or LSR protein(s)/molecule(s)" also include LY6G6F, VSIG10, TMEM25 and/or LSR molecules with the transmembrane domain removed to render the protein soluble, or fragments and derivatives thereof; fragments, portions or derivatives thereof, and soluble LY6G6F, VSIG10, TMEM25 and/or LSR mutant molecules. The soluble LY6G6F, VSIG10, TMEM25 and/or LSR molecules used in the methods according to at least some embodiments of the invention may or may not include a signal (leader) peptide sequence.

Fragments of LY6G6F Polypeptides

The term the "soluble ectodomain (ECD)" or "ectodomain" or "soluble" form of LY6G6F refers also to the nucleic acid sequences encoding the corresponding proteins of LY6G6F "soluble ectodomain (ECD)" or "ectodomain" or "soluble LY6G6F proteins/molecules"). Optionally, the LY6G6F ECD refers to any one of the polypeptide sequences below and/or listed in Table A below, and/or or fragments or variants thereof possessing at least 80% sequence identity, more preferably at least 90% sequence identity therewith and even more preferably at least 95, 96, 97, 98 or 99% sequence identity therewith, and/or conjugates thereof, and/or polynucleotides encoding same:

SEQ ID NO: 2, amino acid residues 17-234 (not including signal peptide, up till transmembrane) (FIG. 1A):
ADNMQAIYVALGEAVELPCPSPPTLHGDEHLSWFCSPAAGSFTTLVAQV

QVGRPAPDPGKPGRESRLRLLGNYSLWLEGSKEEDAGRYWCAVLGQHHN

YQNWRVYDVLVLKGSQLSARAADGSPCNVLLCSVVPSRRMDSVTWQEGK

GPVRGRVQSFWGSEAALLLVCPGEGLSEPRSRRPRIIRCLMTHNKGVSF

SLAASIDASPALCAPSTGWDMP, and fragments and variants thereof possessing at least 80% sequence identity, more preferably at least 90% sequence identity therewith and even more preferably at least 95, 96, 97, 98 or 99% sequence identity therewith. SEQ ID NO:59 represents an example of the LY6G6F ECD including signal peptide.

TABLE A

| SEQ ID NO: | Amino acid sequence | Description |
|---|---|---|
| 81 | ADNMQAIYVALGEAVELPCPSPPTLHGDEHLSWFCSPAAG SFTTLVAQVQVGRPAPDPGKPGRESRLRLLGNYSLWLEGS KEEDAGRYWCAVLGQHHNYQNWRVYD | LY6G6F_IgV_domain aa 17-122 of seq id: 1 |

Optionally, the fragment is of at least about 62, 63, 64, 65 and so forth amino acids of the extracellular domain of LY6G6F protein, set forth in SEQ ID NO: 1, up to 228 amino acids of the LY6G6F protein extracellular domain, optionally including any integral value between 62 and 228 amino acids in length. Preferably, the fragment is of at least about 62 and up to 82 amino acids of the LY6G6F protein extracellular domain, optionally including any integral value between 62 and 82 amino acids in length. Also preferably the fragment is of at least about 95 up to 115 amino acids of the LY6G6F protein extracellular domain, optionally including any integral value between 95 and 115 amino acids in length. Also preferably the fragment is of at least about 208 up to 228 amino acids of the LY6G6F protein extracellular domain, optionally including any integral value between 208 and 228 amino acids in length. More preferably, the fragment is about 72 or 106 or 218 amino acids. The LY6G6F fragment protein according to at least some embodiments of the invention may or may not include a signal peptide sequence, and may or may not include 1, 2, 3, 4, or 5 contiguous amino acids from the LY6G6F transmembrane domain.

In particular, the fragments of the extracellular domain of LY6G6F can include any sequence corresponding to any portion of or comprising the IgV domain of the extracellular domain of LY6G6F, having any sequence corresponding to residues of LY6G6F (SEQ ID NO:1) starting from any position between 14 and 27 and ending at any position between 112 and 132.

The LY6G6F proteins contain an immunoglobulin domain within the extracellular domain, the IgV domain (or V domain), shown in FIG. 1A in a box, which is related to the variable domain of antibodies. The IgV domain may be responsible for receptor binding, by analogy to the other B7 family members. The Ig domain of the extracellular domain includes one disulfide bond formed between intradomain cystein residues, as is typical for this fold and may be important for structure-function. In SEQ ID NO: 1 these cysteines are located at residues 35 and 106.

In one embodiment, there is provided a soluble fragment of LY6G6F; as described in greater detail below with regard to the section on fusion proteins, such a soluble fragment may optionally be described as a first fusion partner. Useful fragments are those that retain the ability to bind to their natural receptor or receptors and/or retain the ability to inhibit T cell activation. A LY6G6F polypeptide that is a fragment of full-length LY6G6F typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or of the ability to inhibit T cell activation as compared to full-length LY6G6F. Soluble LY6G6F polypeptide fragments are fragments of LY6G6F polypeptides that may be shed, secreted or otherwise extracted from the producing cells. In other embodiments, the soluble fragments of LY6G6F polypeptides include fragments of the LY6G6F extracellular domain that retain LY6G6F biological activity, such as fragments that retain the ability to bind to their natural receptor or receptors and/or retain the ability to inhibit T cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments the LY6G6F extracellular domain polypeptide comprises the amino acid sequence of the IgV domain as set forth in any one of SEQ ID NO: 81, or fragments or variants thereof, or the region between the conserved cysteines of the IgV domain located at residues 35 and 106 of the full-length protein SEQ ID NO:1, corresponding to the sequence set forth in SEQ ID NO: 96: CPSPPTLHGDE-HLSWFCSPAAGSFTTLVAQVQVGRPAPD-PGKPGRESRLRLLGNY SLWLEGSKEEDAGRYWC. In other embodiments the LY6G6F extracellular domain polypeptide consists essentially of the amino acid sequence of the IgV domain as set forth in any one of SEQ ID NOs: 81 and 96.

Generally, the LY6G6F polypeptide fragments are expressed from nucleic acids that include sequences that encode a signal sequence. The signal sequence is generally cleaved from the immature polypeptide to produce the mature polypeptide lacking the signal sequence. The signal sequence of LY6G6F can be replaced by the signal sequence of another polypeptide using standard molecule biology techniques to affect the expression levels, secretion, solubility, or other property of the polypeptide. The signal peptide sequence that is used to replace the LY6G6F signal peptide sequence can be any known in the art.

Optionally, the LY6G6F ECD refers to any one of the nucleic acid sequences encoding LY6G6F ECD polypeptides, optionally to the nucleic acid sequences set forth in SEQ ID NO:33, or fragments thereof and/or degenerative variants thereof, encoding LY6G6F ECD polypeptides set forth in SEQ ID NO:2.

Optionally, the LY6G6F ECD refers to orthologous ECD polypeptides. Optionally, the LY6G6F ECD refers to mouse LY6G6F ECD polypeptides, set forth in SEQ ID NOs:20, and/or a mouse LY6G6F ECD-IgG2a-Fc-fused polypeptide, set forth in SEQ ID NOs:23.

Fragments of VSIG10 Polypeptides

The term the "soluble ectodomain (ECD)" or "ectodomain" or "soluble" form of VSIG10 refers also to the nucleic acid sequences encoding the corresponding proteins of VSIG10 "soluble ectodomain (ECD)" or "ectodomain" or "soluble VSIG10 proteins/molecules"). Optionally, the VSIG10 ECD refers to any one of the polypeptide sequences below and/or listed in Table B below, and/or fragments or variants thereof possessing at least 80% sequence identity, more preferably at least 90% sequence identity therewith and even more preferably at least 95, 96, 97, 98 or 99% sequence identity therewith, and/or conjugates thereof, and/or polynucleotides encoding same:

```
SEQ ID NO: 4, amino acid residues 31-413 (not
including signal peptide, up till transmembrane)
(FIG. 1B):
VVIGEVHENVTLHCGNISGLRGQVTWYRNNSEPVFLLSSNSSLRPAEPR

FSLVDATSLHIESLSLGDEGIYTCQEILNVTQWFQVWLQVASGPYQIEV

HIVATGTLPNGTLYAARGSQVDFSCNSSSRPPPVVEWWFQALNSSSESF

GHNLTVNFFSLLLISPNLQGNYTCLALNQLSKRHRKVTTELLVYYPPPS

APQCWAQMASGSFMLQLTCRWDGGYPDPDFLWIEEPGGVIVGKSKLGVE

MLSESQLSDGKKFKCVTSHIVGPESGASCMVQIRGPSLLSEPMKTCFTG

GNVTLTCQVSGAYPPAKILWLRNLTQPEVIIQPSSRHLITQDGQNSTLT

IHNCSQDLDEGYYICRADSPVGVREMEIWLSVKEPLNIGG;
```

SEQ ID NO: 6, amino acid residues 31-312 (skipping exon 3 variant, not including signal peptide, up till transmembrane) (FIG. 1C):
VVIGEVHENVTLHCGNISGLRGQVTWYRNNSEPVFLLSSNSSLRPAEPR

FSLVDATSLHIESLSLGDEGIYTCQEILNVTQWFQVWLQVANPPPSAPQ

CWAQMASGSFMLQLTCRWDGGYPDPDFLWIEEPGGVIVGKSKLGVEMLS

ESQLSDGKKFKCVTSHIVGPESGASCMVQIRGPSLLSEPMKTCFTGGNV

TLTCQVSGAYPPAKILWLRNLTQPEVIIQPSSRHLITQDGQNSTLTIHN

CSQDLDEGYYICRADSPVGVREMEIWLSVKEPLNIGG, and variants thereof possessing at least 80% sequence identity, more preferably at least 90% sequence identity therewith and even more preferably at least 95, 96, 97, 98 or 99% sequence identity therewith. SEQ ID NOs:60-61 represent examples of the VSIG10 ECD including signal peptide.

TABLE B

| SEQ ID NO: | Amino acid sequence | Description |
|---|---|---|
| 82 | VVIGEVHENVTLHCGNISGLRGQVTWYRNNSEP VFLLSSNSSLRPAEPRFSLVDATSLHIESLSLG DEGIYTCQEILNVTQWFQVWLQV | VSIG10_IgC2_domain_1 aa 31-119 of seq id:3 aa 31-119 of seq id: 5 |
| 83 | PYQIEVHIVATGTLPNGTLYAARGSQVDFSCNS SSRPPPVVEWWFQALNSSSESFGHNLTVNFFSL LLISPNLQGNYTCLALNQLSKRHRKVT | VSIG10_IgC2_domain_2 aa 123-215 of seq id: 3 |
| 84 | PPPSAPQCWAQMASGSFMLQLTCRWDGGYPDPD FLWIEEPGGVIVGKSKLGVEMLSESQLSDGKKF KCVTSHIVGPESGASCMVQIR | VSIG10_IgC2_domain_3 aa 223-309 of seq id: 3 aa 122-208 of seq id: 5 |
| 85 | PSLLSEPMKTCFTGGNVTLTCQVSGAYPPAKIL WLRNLTQPEVIIQPSSRHLITQDGQNSTLTIHN CSQDLDEGYYICRADSPVGVREMEIWLS | VSIG10_IgC2_domain_4 aa 311-404 of seq id:3 aa 210-303 of seq id:5 |
| 86 | VVIGEVHENVTLHCGNISGLRGQVTWYRNNSEP VFLLSSNSSLRPAEPRFSLVDATSLHIESLSLG DEGIYTCQEILNVTQWFQVWLQVASGPYQIEVH IVATGTLPNGTLYAARGSQVDFSCNSSSRPPPV VEWWFQALNSSSESFGHNLTVNFFSLLLISPNL QGNYTCLALNQLSKRHRKVT | VSIG10_WT_IgC2_domains_1-2 aa 31-215 of seq id: 3 |
| 87 | VVIGEVHENVTLHCGNISGLRGQVTWYRNNSEP VFLLSSNSSLRPAEPRFSLVDATSLHIESLSLG DEGIYTCQEILNVTQWFQVWLQVASGPYQIEVH IVATGTLPNGTLYAARGSQVDFSCNSSSRPPPV VEWWFQALNSSSESFGHNLTVNFFSLLLISPNL QGNYTCLALNQLSKRHRKVTTELLVYYPPPSAP QCWAQMASGSFMLQLTCRWDGGYPDPDFLWIEE PGGVIVGKSKLGVEMLSESQLSDGKKFKCVTSH IVGPESGASCMVQIR | VSIG10_WT_IgC2_domains_1-3 aa 31-309 of seq id: 3 |
| 88 | VVIGEVHENVTLHCGNISGLRGQVTWYRNNSEP VFLLSSNSSLRPAEPRFSLVDATSLHIESLSLG DEGIYTCQEILNVTQWFQVWLQVASGPYQIEVH IVATGTLPNGTLYAARGSQVDFSCNSSSRPPPV VEWWFQALNSSSESFGHNLTVNFFSLLLISPNL QGNYTCLALNQLSKRHRKVTTELLVYYPPPSAP QCWAQMASGSFMLQLTCRWDGGYPDPDFLWIEE PGGVIVGKSKLGVEMLSESQLSDGKKFKCVTSH IVGPESGASCMVQIRGPSLLSEPMKTCFTGGNV TLTCQVSGAYPPAKILWLRNLTQPEVIIQPSSR HLITQDGQNSTLTIHNCSQDLDEGYYICRADSP VGVREMEIWLS | VSIG10_WT_IgC2_domains_1-4 aa 31-404 of seq id: 3 |
| 89 | PYQIEVHIVATGTLPNGTLYAARGSQVDFSCNS SSRPPPVVEWWFQALNSSSESFGHNLTVNFFSL LLISPNLQGNYTCLALNQLSKRHRKVTTELLVY YPPPSAPQCWAQMASGSFMLQLTCRWDGGYPDP DFLWIEEPGGVIVGKSKLGVEMLSESQLSDGKK FKCVTSHIVGPESGASCMVQIR | VSIG10_WT_IgC2_domains_2-3 aa 123-309 of seq id: 3 |
| 90 | PYQIEVHIVATGTLPNGTLYAARGSQVDFSCNS SSRPPPVVEWWFQALNSSSESFGHNLTVNFFSL LLISPNLQGNYTCLALNQLSKRHRKVTTELLVY YPPPSAPQCWAQMASGSFMLQLTCRWDGGYPDP DFLWIEEPGGVIVGKSKLGVEMLSESQLSDGKK FKCVTSHIVGPESGASCMVQIRGPSLLSEPMKT CFTGGNVTLTCQVSGAYPPAKILWLRNLTQPEV | VSIG10_WT_IgC2_domains_2-4 aa 123-404 of seq id: 3 |

TABLE B -continued

| SEQ ID NO: | Amino acid sequence | Description |
|---|---|---|
| | IIQPSSRHLITQDGQNSTLTIHNCSQDLDEGYY ICRADSPVGVREMEIWLS | |
| 91 | PPPSAPQCWAQMASGSFMLQLTCRWDGGYPDPD FLWIEEPGGVIVGKSKLGVEMLSESQLSDGKKF KCVTSHIVGPESGASCMVQIRGPSLLSEPMKTC FTGGNVTLTCQVSGAYPPAKILWLRNLTQPEVI IQPSSRHLITQDGQNSTLTIHNCSQDLDEGYYI CRADSPVGVREMEIWLS | VSIG10_IgC2_domains_3-4 aa 223-404 of seq id: 3 aa 122-303 of seq id: 5 |
| 92 | VVIGEVHENVTLHCGNISGLRGQVTWYRNNSEP VFLLSSNSSLRPAEPRFSLVDATSLHI ESLSLGDEGIYTCQEILNVTQWFQVWLQVANPP PSAPQCWAQMASGSFMLQLTCRWDGGY PDPDFLWIEEPGGVIVGKSKLGVEMLSESQLSD GKKFKCVTSHIVGPESGASCMVQIR | VSIG10_Variant_skipping_ exon_3_T95617_P6_IgC2_ domains_1,3 aa 31-208 of seq id: 5 |
| 93 | VVIGEVHENVTLHCGNISGLRGQVTWYRNNSEP VFLLSSNSSLRPAEPRFSLVDATSLHI ESLSLGDEGIYTCQEILNVTQWFQVWLQVANPP PSAPQCWAQMASGSFMLQLTCRWDGGY PDPDFLWIEEPGGVIVGKSKLGVEMLSESQLSD GKKFKCVTSHIVGPESGASCMVQIRGP SLLSEPMKTCFTGGNVTLTCQVSGAYPPAKILW LRNLTQPEVIIQPSSRHLITQDGQNST LTIHNCSQDLDEGYYICRADSPVGVREMEIWLS | VSIG10_Variant_skipping_ exon_3_T95617_P6_IgC2_ domains_1,3-4 aa 31-303 of seq id: 5 |

Optionally, the fragment is of at least about 36, 37, 38, 39, 40, 41, 42, 43, and so forth amino acids of the extracellular domain of VSIG10 protein, set forth in SEQ ID NO:3, up to 393 amino acids of the VSIG10 protein extracellular domain, optionally, including any integral value between 36 and 393 amino acids in length. Preferably, the fragment is of at least about 36 up to 70 amino acids of the VSIG10 protein extracellular domain, optionally including any integral value between 36 and 70 amino acids in length. Also preferably the fragment is of at least about 80 up to 100 amino acids of the VSIG10 protein extracellular domain, optionally including any integral value between 80 and 100 amino acids in length. Also preferably the fragment is of at least about 170 up to 200 amino acids of the VSIG10 protein extracellular domain, optionally including any integral value between 170 and 200 amino acids in length. Also preferably the fragment is of at least about 265 up to 290 amino acids of the VSIG10 protein extracellular domain, optionally including any integral value between 265 and 290 amino acids in length. Also preferably the fragment is of at least about 365 up to 393 amino acids of the VSIG10 protein extracellular domain, optionally including any integral value between 365 and 393 amino acids in length. More preferably, the fragment is about 46, 49, 58, 60, 87, 89, 93, 94, 178, 182, 185, 187, 273, 279, 282, 374, 383 amino acids. The VSIG10 fragment protein according to at least some embodiments of the invention may or may not include a signal peptide sequence, and may or may not include 1, 2, 3, 4, or 5 contiguous amino acids from the VSIG10 transmembrane domain.

In particular, the fragments of the extracellular domain of VSIG10 can include any sequence corresponding to any portion of or comprising of one or more of the IgC2 domains of the extracellular domain of VSIG10, having any sequence corresponding to residues of VSIG10 (SEQ ID NO:3) starting from any position between 28 and 41 and ending at any position between 109 and 122 or starting from any position between 120 and 133 and ending at any position between 205 and 222 or starting from any position between 216 and 233 and ending at any position between 299 and 310 or starting from any position between 310 and 321 and ending at any position between 394 and 414 or starting from any position between 28 and 41 and ending at any position between 205 and 222 or starting from any position between 28 and 41 and ending at any position between 299 and 310 or starting from any position between 28 and 41 and ending at any position between 394 and 414 or starting from any position between 120 and 133 and ending at any position between 299 and 310 or starting from any position between 120 and 133 and ending at any position between 394 and 414 or starting from any position between 216 and 233 and ending at any position between 394 and 414, or having any sequence corresponding to residues of VSIG10_Variant_skipping_exon_3_T95617_P6 (SEQ ID NO:5) starting from any position between 28 and 41 and ending at any position between 198 and 209 or starting from any position between 28 and 41 and ending at any position between 293 and 313.

The VSIG10 proteins contain immunoglobulin domains within the extracellular domain, IgC2 domain (or Ig-like C2 domain or Ig C2-set domain), which is related to the constant domain of antibodies. The domains are illustrated in FIG. 1B (for SEQ ID NO:3) and in FIG. 1C (for SEQ ID NO:5). The Ig domains of the extracellular domain include one disulfide bond formed between intradomain cystein residues, as is typical for this fold and may be important for structure-function. In SEQ ID NO: 3 these cysteines are located at residues 44 and 103 and at residues 153 and 201 and at residues 245 and 290 and at residues 331 and 388. In SEQ ID NO:5 these cysteines are located at residues 44 and 103 and 144 and 189 and at residues 230 and 287.

In one embodiment, there is provided a soluble fragment of VSIG10, which may optionally be described as a first fusion partner in the below section on fusion proteins. Useful fragments are those that retain the ability to bind to their natural receptor or receptors and/or retain the ability to inhibit T cell activation. A VSIG10 polypeptide that is a fragment of full-length VSIG10 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or of the ability to inhibit T cell activation as compared to full-length VSIG10. Soluble VSIG10 polypeptide fragments are fragments of VSIG10 polypeptides that may be shed, secreted or otherwise extracted from the producing cells. In other embodiments, the soluble fragments of VSIG10 polypeptides include fragments of the VSIG10 extracellular domain that retain VSIG10 biological activity, such as fragments that retain the ability to bind to their natural receptor or receptors and/or retain the ability to inhibit T cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments the VSIG10 extracellular domain polypeptide comprises the amino acid sequence of at least one of the IgC2 domains as set forth in any one of SEQ IDS NO: 82, 83, 84 and 85, or fragments or variants thereof, or the regions between the conserved cysteines of the IgC2 domains located at residues 44 and 103 of the full-length protein SEQ ID NO:3, corresponding to the sequence set forth in SEQ ID NO: 97: CGNISGLRGQVTWYRNNSEPVFLLSSNS-SLRPAEPRFSLVDATSLHIESLSLGDEGI YTC, or located at residues 153 and 201 of the full-length protein SEQ ID NO:3, corresponding to the sequence set forth in SEQ ID NO: 98: CNSSSRPPPVVEWWFQALNSSSESF-GHNLTVNFFSLLLISPNLQGNYTC or located at residues 245 and 209 of the full-length protein SEQ ID NO:3, corresponding to the sequence set forth in SEQ ID NO: 99: CRWDGGYPDPDFLWIEEPGGVIVGK-SKLGVEMLSESQLSDGKKFKC or located at residues 331 and 388 of the full-length protein SEQ ID NO:3, corresponding to the sequence set forth in SEQ ID NO: 100: CQVSGAY-PPAKILWLRNLTQPEVIIQPSSRHL-ITQDGQNSTLTIHNCSQDLDEGYYI C. In some further embodiments the VSIG10 extracellular domain polypeptide consists essentially of amino acid sequence of at least one of SEQ IDS NOs: 82-93, 97-100.

Generally, the VSIG10 polypeptide fragments are expressed from nucleic acids that include sequences that encode a signal sequence. The signal sequence is generally cleaved from the immature polypeptide to produce the mature polypeptide lacking the signal sequence. The signal sequence of VSIG10 can be replaced by the signal sequence of another polypeptide using standard molecule biology techniques to affect the expression levels, secretion, solubility, or other property of the polypeptide. The signal peptide sequence that is used to replace the VSIG10 signal peptide sequence can be any known in the art.

Optionally, the VSIG10 ECD refers also to any one of the nucleic acid sequences encoding VSIG10 ECD polypeptides, optionally to the nucleic acid sequences set forth in SEQ ID NOs:34, 36, or fragments thereof and/or degenerative variants thereof, encoding VSIG10 ECD polypeptides set forth in SEQ ID NOs:4, 6, respectively.

Optionally, the VSIG10 ECD refers to orthologous ECD polypeptides. Optionally, the VSIG10 ECD refers to mouse VSIG10 ECD polypeptides, set forth in SEQ ID NO:19, and/or a mouse VSIG10 ECD-IgG2a-Fc-fused polypeptide, set forth in SEQ ID NO:24.

Fragments of TMEM25 Polypeptides

The term the "soluble ectodomain (ECD)" or "ectodomain" or "soluble" form of TMEM25 refers also to the nucleic acid sequences encoding the corresponding proteins of TMEM25 "soluble ectodomain (ECD)" or "ectodomain" or "soluble TMEM25 proteins/molecules"). Optionally, the TMEM25 ECD refers to any one of the polypeptide sequences below and/or listed in Table C below, and/or fragments or variants thereof possessing at least 80% sequence identity, more preferably at least 90% sequence identity therewith and even more preferably at least 95, 96, 97, 98 or 99% sequence identity therewith, and/or conjugates thereof, and/or polynucleotides encoding same:

```
SEQ ID NO: 8, amino acid residues 27-232 (not
including signal peptide, up till transmembrane)
(FIG. 1D):
ELEPQIDGQTWAERALRENERHAFTCRVAGGPGTPRLAWYLDGQLQEAS

TSRLLSVGGEAFSGGTSTFTVTAHRAQHELNCSLQDPRSGRSANASVIL

NVQFKPEIAQVGAKYQEAQGPGLLVVLFALVRANPPANVTWIDQDGPVT

VNTSDFLVLDAQNYPWLTNHTVQLQLRSLAHNLSVVATNDVGVTSASLP

APGLLATRVE,
``` and variants thereof possessing at least 80% sequence identity, more preferably at least 90% sequence identity therewith and even more preferably at least 95, 96, 97, 98 or 99% sequence identity therewith. SEQ ID NO:39 represents example of the TMEM25 ECD including signal peptide.

TABLE C

| SEQ ID NO: | Amino acid sequence | Description |
|---|---|---|
| 94 | PQIDGQTWAERALRENERHAFTCRVAGGPGTPR LAWYLDGQLQEASTSRLLSVGGEAFSGGTSTFT VTAHRAQHELNCSLQDPRSGRSANASVI | TMEM25_IgC2_domain aa 30-123 of seq id: 7 |

Optionally, the fragment is of at least about 46, 47, 48, 49, 50, 51, 52, and so forth amino acids of the extracellular domain of TMEM25 protein, set forth in SEQ ID NO:7, up to 216 amino acids of the TMEM25 protein extracellular domain, optionally including any integral value between 46 and 216 amino acids in length. Preferably, the fragment is of at least about 46 up to 66 amino acids of the TMEM25 protein extracellular domain, optionally including any integral value between 46 and 66 amino acids in length. Also preferably the fragment is of at least about 84 up to 104 amino acids of the TMEM25 protein extracellular domain, optionally including any integral value between 84 and 104 amino acids in length. Also preferably the fragment is of at least about 196 up to 216 amino acids of the TMEM25 protein extracellular domain, optionally including any integral value between 196 and 216 amino acids in length. More preferably, the fragment is about 56 or 94 or 206 amino acids. The TMEM25 fragment protein according to at least some embodiments of the invention may or may not include a signal peptide sequence, and may or may not include 1, 2, 3, 4, or 5 contiguous amino acids from the TMEM25 transmembrane domain.

In particular, the fragments of the extracellular domain of TMEM25 can include any sequence corresponding to any portion of or comprising the IgC2 domain of the extracellular domain of TMEM25, having any sequence corresponding to residues of TMEM25 (SEQ ID NO:7) starting from any position between 27 and 40 and ending at any position between 113 and 133.

The TMEM25 proteins contain an immunoglobulin domain within the extracellular domain, IgC2 domain (or Ig-like C2 domain or Ig C2-set domain), which is related to the constant domain of antibodies. The domain is shown in FIG. 1D in a box. The Ig domain of the extracellular domain includes one disulfide bond formed between intradomain cystein residues, as is typical for this fold and may be important for structure-function. In SEQ ID NO: 7 these cysteines are located at residues 52 and 107.

In one embodiment, there is provided a soluble fragment of TMEM25, which may optionally be described as a first fusion partner, as for example in the detailed section on fusion proteins below. Useful fragments are those that retain the ability to bind to their natural receptor or receptors and/or retain the ability to inhibit T cell activation. A TMEM25 polypeptide that is a fragment of full-length TMEM25 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or of the ability to inhibit T cell activation as compared to full-length TMEM25. Soluble TMEM25 polypeptide fragments are fragments of TMEM25 polypeptides that may be shed, secreted or otherwise extracted from the producing cells. In other embodiments, the soluble fragments of TMEM25 polypeptides include fragments of the TMEM25 extracellular domain that retain TMEM25 biological activity, such as fragments that retain the ability to bind to their natural receptor or receptors and/or retain the ability to inhibit T cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments the TMEM25 extracellular domain polypeptide comprises the amino acid sequence of IgC2 domain, as set forth in any one of SEQ ID NO: 94, or fragments or variants thereof, or the region between the conserved cysteines of the IgC2 domain located at residues 52 and 107 of the full-length protein SEQ ID NO:7, corresponding to the sequence set forth in SEQ ID NO: 101: CRVAGGPGT-PRLAWYLDGQLQEASTSRLLSVGGEAF-SGGTSTFTVTAHRAQHEL NC. In other embodiments the TMEM25 extracellular domain polypeptide consists essentially of the amino acid sequence of the IgC2 domain as set forth in any one of SEQ ID NOs: 94 and 101.

Generally, the TMEM25 polypeptide fragments are expressed from nucleic acids that include sequences that encode a signal sequence. The signal sequence is generally cleaved from the immature polypeptide to produce the mature polypeptide lacking the signal sequence. The signal sequence of TMEM25 can be replaced by the signal sequence of another polypeptide using standard molecule biology techniques to affect the expression levels, secretion, solubility, or other property of the polypeptide. The signal peptide sequence that is used to replace the TMEM25 signal peptide sequence can be any known in the art.

Optionally, the TMEM25 ECD refers also to any one of the nucleic acid sequences encoding TMEM25 ECD polypeptides, optionally to the nucleic acid sequences set forth in SEQ ID NO:37, or fragments thereof and/or degenerative variants thereof, encoding TMEM25 ECD polypeptides set forth in SEQ ID NO:8

Optionally, the TMEM25 ECD refers to orthologous ECD polypeptides. Optionally, the TMEM25 ECD refers to mouse TMEM25 ECD polypeptides, set forth in SEQ ID NOs:9, and/or a mouse TMEM25 ECD-IgG2a-Fc-fused polypeptide, set forth in SEQ ID NOs:25.

Fragments of LSR Polypeptides

The term the "soluble ectodomain (ECD)" or "ectodomain" or "soluble" form of LSR refers also to the nucleic acid sequences encoding the corresponding proteins of LSR "soluble ectodomain (ECD)" or "ectodomain" or "soluble LSR proteins/molecules"). Optionally, the LSR ECD refers to any one of the polypeptide sequences below and/or listed in Table D below, and/or fragments or variants thereof possessing at least 80% sequence identity, more preferably at least 90% sequence identity therewith and even more preferably at least 95, 96, 97, 98 or 99% sequence identity therewith, and/or conjugates thereof, and/or polynucleotides encoding same:

```
SEQ ID NO: 12, LSR isoform A ECD (not including
signal peptide, up till transmembrane) amino
acid residues 42-211 (FIG. 1E):
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

DYYQGRRITITGNADLTFDQTAWGDSGVYYCSVVSAQDLQGNNEAYAEL

IVLGRTSGVAELLPGFQAGPIED;

SEQ ID NO: 14, LSR isoform B ECD (not including
signal peptide, up till transmembrane) amino acid
residues 42-192 (FIG. 1F):
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

DYYQGRRITITGNADLTFDQTAWGDSGVYYCSVVSAQDLQGNNEAYAEL

IVLD;

SEQ ID NO: 47, LSR isoform C secreted variant
amino acid residues 42-533 (FIG. 1G):
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

DYYQGRRITITGNADLTFDQTAWGDSGVYYCSVVSAQDLQGNNEAYAEL

IVLVYAAGKAATSGVPSIYAPSTYAHLSPAKTPPPPAMIPMGPAYNGYP

GGYPGDVDRSSSAGGQGSYVPLLRDTDSSVASEVRSGYRIQASQQDDSM

RVLYYMEKELANFDPSRPGPPSGRVERAMSEVTSLHEDDWRSRPSRGPA

LTPIRDEEWGGHSPRSPRGWDQEPAREQAGGGWRARRPRARSVDALDDL

TPPSTAESGSRSPTSNGGRSRAYMPPRSRSRDDLYDQDDSRDFPRSRDP

HYDDFRSRERPPADPRSHHHRTRDPRDNGSRSGDLPYDGRLLEEAVRKK

GSEERRRPHKEEEEEAYYPPAPPPYSETDSQASRERRLKKNLALSRESL

VV;
```

-continued

SEQ ID NO: 48, LSR isoform D secreted variant
amino acid residues 42-532 (FIG. 1H)
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

DYYQGRRITITGNADLTFDQTAWGDSGVYYCSVVSAQDLQGNNEAYAEL

IVLVYAAGKAATSGVPSIYAPSTYAHLSPAKTPPPPAMIPMGPAYNGYP

GGYPGDVDRSSSAGGQGSYVPLLRDTDSSVASVRSGYRIQASQQDDSMR

VLYYMEKELANFDPSRPGPPSGRVERAMSEVTSLHEDDWRSRPSRGPAL

TPIRDEEWGGHSPRSPRGWDQEPAREQAGGGWRARRPRARSVDALDDLT

PPSTAESGSRSPTSNGGRSRAYMPPRSRSRDDLYDQDDSRDFPRSRDPH

YDDERSRERPPADPRSHHHRTRDPRDNGSRSGDLPYDGRLLEEAVRKKG

SEERRRPHKEEEEEAYYPPAPPPYSETDSQASRERRLKKNLALSRESLV

V;

SEQ ID NO: 49, LSR isoform E secreted variant
amino acid residues 42-493 (FIG. 1I):
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

-continued
DYYQGRRITITGMYAAGKAATSGVPSIYAPSTYAHLSPAKTPPPPAMIP

MGPAYNGYPGGYPGDVDRSSSAGGQGSYVPLLRDTDSSVASEVRSGYRI

QASQQDDSMRVLYYMEKELANEDPSRPGPPSGRVERAMSEVTSLHEDDW

RSRPSRGPALTPIRDEEWGGHSPRSPRGWDQEPAREQAGGGWRARRPRA

RSVDALDDLTPPSTAESGSRSPTSNGGRSRAYMPPRSRSRDDLYDQDDS

RDFPRSRDPHYDDFRSRERPPADPRSHHHRTRDPRDNGSRSGDLPYDGR

LLEEAVRKKGSEERRRPHKEEEEEAYYPPAPPPYSETDSQASRERRLKK

NLALSRESLVV;

SEQ ID NO: 50, LSR isoform F secreted variant
amino acid residues 42-552 (FIG. 1J):
IQVTVSNPYHVVILFQPVTLPCTYQMTSTPTQPIVIWKYKSFCRDRIAD

AFSPASVDNQLNAQLAAGNPGYNPYVECQDSVRTVRVVATKQGNAVTLG

DYYQGRRITITGNADLTFDQTAWGDSGVYYCSVVSAQDLQGNNEAYAEL

IVLGRTSGVAELLPGFQAGPIEVYAAGKAATSGVPSIYAPSTYAHLSPA

KTPPPPAMIPMGPAYNGYPGGYPGDVDRSSSAGGQGSYVPLLRDTDSSV

ASEVRSGYRIQASQQDDSMRVLYYMEKELANFDPSRPGPPSGRVERAMS

EVTSLHEDDWRSRPSRGPALTPIRDEEWGGHSPRSPRGWDQEPAREQAG

GGWRARRPRARSVDALDDLTPPSTAESGSRSPTSNGGRSRAYMPPRSRS

-continued
RDDLYDQDDSRDFPRSRDPHYDDFRSRERPPADPRSHHHRTRDPRDNGS

RSGDLPYDGRLLEEAVRKKGSEERRRPHKEEEEEAYYPPAPPPYSETDS

QASRERRLKKNLALSRESLVV, and variants thereof possessing at least 80% sequence identity, more preferably at least 90% sequence identity therewith and even more preferably at least 95, 96, 97, 98 or 99% sequence identity therewith. SEQ ID NOs:10, 22 represent example of the LSR ECD including signal peptide.

Optionally, the fragment is of at least about 100, 101, 102, 103, 104, 105, 106, 107, 108, 109, 110 and so forth amino acids of the extracellular domain of LSR protein, set forth in SEQ ID NO:11 and/or 143, up to 198 amino acids of the extracellular domain, optionally including any integral value between 100 and 198 amino acids in length. The LSR fragment protein according to at least some embodiments of the invention may or may not include a signal peptide sequence, and may or may not include 1, 2, 3, 4, or 5 contiguous amino acids from the LSR transmembrane domain.

TABLE D

| SEQ ID NO: | Amino acid sequence | Description |
| --- | --- | --- |
| 95 | IQVTVSNPYHVVILFQPVTLPCTYQMTSTPTQP IVIWKYKSFCRDRIADAFSPASVDNQLNAQLAA GNPGYNPYVECQDSVRTVRVVATKQGNAVTLGD YYQGRRITITGNADLTFDQTAWGDSGVYYCSVV SAQDLQGNNEAYA | LSR_IgV_domain aa 42-186 of seq id : 11, 13 , 15, 16 , 17, 18 |

Optionally, the fragment is of at least about 98, 99, 100, 101, 102 and so forth amino acids of the extracellular domain of LSR protein, set forth in SEQ ID NO: 11, up to 180 amino acids of the LY6G6F protein extracellular domain, optionally including any integral value between 98 and 180 amino acids in length Preferably, the fragment is of at least about 98 up to 118 amino acids of the LSR protein extracellular domain, optionally including any integral value between 98 and 118 amino acids in length. Also preferably the fragment is of at least about 135 up to 155 amino acids of the LSR protein extracellular domain, optionally including any integral value between 135 and 155 amino acids in length. Also preferably the fragment is of at least about 160 up to 180 amino acids of the LSR protein extracellular domain, optionally including any integral value between 160 and 180 amino acids in length. More preferably, the fragment is about 108 or 145 or 170 amino acids. The LSR fragment protein according to at least some embodiments of the invention may or may not include a signal peptide sequence, and may or may not include 1, 2, 3, 4, or 5 contiguous amino acids from the LSR transmembrane domain.

The LSR proteins contain an immunoglobulin domain within the extracellular domain, the IgV domain (or V domain), which is related to the variable domain of antibodies. The Ig domain is shown in a box in FIGS. 1E, 1F, 1G, 1H, and 1J, for SEQ ID NOs: 11, 13, 15, 16, and 18, respectively. The Ig domain of the extracellular domain includes one disulfide bond formed between intradomain cystein residues, as is typical for this fold and may be important for structure-function. In SEQ ID NO: 11 these cysteines are located at residues 63 and 170.

In one embodiment, there is provided a soluble fragment of LSR, which may optionally be described as a first fusion partner, as for example in the below section on fusion proteins. Useful fragments are those that retain the ability to bind to their natural receptor or receptors and/or retain the ability to inhibit T cell activation. A LSR polypeptide that is a fragment of full-length LSR typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or of the ability to inhibit T cell activation as compared to full-length LSR. Soluble LSR polypeptide fragments are fragments of LSR polypeptides that may be shed, secreted or otherwise extracted from the producing cells. In other embodiments, the soluble fragments of LSR polypeptides include fragments of the LSR extracellular domain that retain LSR biological activity, such as fragments that retain the ability to bind to their natural receptor or receptors and/or retain the ability to inhibit T cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments the LSR extracellular domain polypeptide comprises the amino acid of the IgV domain as set forth in any one of SEQ ID NO: 95, or fragments or variants thereof, or the region between the conserved cysteines of the IgV domain located at residues 63 and 170 of the full-length protein SEQ ID NO:11, corresponding to the sequence set forth in SEQ ID NO: 102: CTYQMT-STPTQPIVIWKYKSFCRDRIADAFSPAS-VDNQLNAQLAAGNPGYNPYVE CQDSVRTVRVVAT-KQGNAVTLGDYYQGRRITITGNADLTFDQTAWGDSG-VYYC. In some further embodiments the LSR extracellular domain polypeptide consists essentially of the amino acid of the IgV domain as set forth in any one of SEQ ID NO: 95, and SEQ ID NO: 102.

Generally, the LSR polypeptide fragments are expressed from nucleic acids that include sequences that encode a signal sequence. The signal sequence is generally cleaved from the immature polypeptide to produce the mature polypeptide lacking the signal sequence. The signal sequence of LSR can be replaced by the signal sequence of another polypeptide using standard molecule biology techniques to affect the expression levels, secretion, solubility, or other property of the polypeptide. The signal peptide sequence that is used to replace the LSR signal peptide sequence can be any known in the art.

Optionally, the LSR ECD refers also to any one of the nucleic acid sequences encoding LSR ECD polypeptides, optionally to the nucleic acid sequences set forth in SEQ ID NO:40, 41, 132, 44, 155, 188, or fragments thereof and/or degenerative variants thereof, encoding LSR ECD polypeptides set forth in any one of SEQ ID NO:12, 14, 47, 48, 49, 50, respectively.

Optionally, the LSR ECD refers to orthologous ECD polypeptides. Optionally, the LSR ECD refers to mouse LSR ECD polypeptides, set forth in SEQ ID NOs:21, and/or a mouse LSR ECD-IgG2a-Fc-fused polypeptide, set forth in SEQ ID NOs:26.

Variants of LY6G6F, VSIG10, TMEM25 and/or LSR Polypeptides

The present invention encompasses useful variants of LY6G6F, VSIG10, TMEM25 and/or LSR polypeptides including those that increase biological activity, as indicated by any of the assays described herein, or that increase half life or stability of the protein. Soluble LY6G6F, VSIG10, TMEM25 and/or LSR proteins or fragments, or fusions thereof having LY6G6F, VSIG10, TMEM25 and/or LSR proteins activity, respectively, can be engineered to increase biological activity. In a further embodiment, the LY6G6F, VSIG10, TMEM25 and/or LSR proteins or fusion protein is modified with at least one amino acid substitution, deletion, or insertion that increases the binding of the molecule to an immune cell, for example a T cell, and transmits an inhibitory signal into the T cell.

Other optional variants are those LY6G6F, VSIG10, TMEM25 and/or LSR proteins that are engineered to selectively bind to one type of T cell versus other immune cells. For example, the LY6G6F, VSIG10, TMEM25 and/or LSR polypeptide can be engineered to bind optionally to Tregs, Th0, Th1, Th17, Th2 or Th22 cells. Preferential binding refers to binding that is at least 10%, 20%, 30%, 40%, 50%, 60% f 70%, 80%, 90%, 95%, or greater for one type of cell over another type of cell. Still other variants of LY6G6F, VSIG10, TMEM25 and/or LSR protein can be engineered to have reduced binding to immune cells relative to wildtype LY6G6F, VSIG10, TMEM25 and/or LSR protein, respectively. These variants can be used in combination with variants having stronger binding properties to modulate the immune response with a moderate impact.

Also optionally, variant LY6G6F, VSIG10, TMEM25 and/or LSR protein can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art.

The LY6G6F protein (SEQ ID NO:1) also has the following non-silent SNPs (Single Nucleotide Polymorphism) as listed in Table E, (given according to their position(s) on the amino acid sequence, with the alternative amino acid listed the presence of SNPs in LY6G6F protein (SEQ ID NO:1) sequence provides support for alternative sequence(s) of this protein according to the present invention. SEQ ID NO:58 is an example of such a alternative sequence, with alternative amino-acids, using part of the SNPs below

TABLE E

Amino acid mutations

| SNP position(s) on amino acid sequence | Alternative amino acid(s) |
|---|---|
| 34 | P -> Q |
| 39 | P -> S |
| 107 | A -> T |
| 167 | R -> K |

The LSR protein (SEQ ID NO:11) also has the following non-silent SNPs (Single Nucleotide Polymorphism) as listed in Table F, (given according to their position(s) on the amino acid sequence, with the alternative amino acid listed; the presence of SNPs in LSR protein (SEQ ID NO:11) sequence provides support for alternative sequence(s) of this protein according to the present invention. SEQ ID NO:143 is an example of such a alternative sequence, with alternative amino-acids, using part of the SNPs below

TABLE F

Amino acid mutations

| SNP position(s) on amino acid sequence | Alternative amino acid(s) |
| --- | --- |
| 209 | I -> M |
| 211 | D -> G |
| 260 | L -> R |
| 315 | S -> N |
| 382 | A -> G |
| 591 | N -> D |

The VSIG10 protein (SEQ ID NO:3) also has the following non-silent SNPs (Single Nucleotide Polymorphism) as listed in Table G, (given according to their position(s) on the amino acid sequence, with the alternative amino acid listed; the presence of SNPs in VSIG10 protein (SEQ ID NO:3) sequence provides support for alternative sequence(s) of this protein according to the present invention.

TABLE G

Amino acid mutations

| SNP position(s) on amino acid sequence | Alternative amino acid(s) |
| --- | --- |
| 333 | V -> M |
| 435 | H -> Y |

The TMEM25 protein (SEQ ID NO:7) also has the following non-silent SNPs (Single Nucleotide Polymorphism) as listed in Table H, (given according to their position(s) on the amino acid sequence, with the alternative amino acid listed; the presence of SNPs in TMEM25 protein (SEQ ID NO:7) sequence provides support for alternative sequence(s) of this protein according to the present invention.

TABLE H

Amino acid mutations

| SNP position(s) on amino acid sequence | Alternative amino acid(s) |
| --- | --- |
| 25 | W -> C |
| 342 | Q -> R |

Various aspects of the invention are described in further detail in the following subsections.

Nucleic Acids

A "nucleic acid fragment" or an "oligonucleotide" or a "polynucleotide" are used herein interchangeably to refer to a polymer of nucleic acid residues. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

Thus, the present invention encompasses nucleic acid sequences described hereinabove; fragments thereof, sequences hybridizable therewith, sequences homologous thereto [e.g., at least 90%, at least 95, 96, 97, 98 or 99% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention), which include sequence regions unique to the polynucleotides of the present invention.

Thus, the present invention also encompasses polypeptides encoded by the polynucleotide sequences of the present invention. The present invention also encompasses homologues of these polypeptides, such homologues can be at least 90%, at least 95, 96, 97, 98 or 99% or more homologous to the amino acid sequences set forth below, as can be determined using BlastP software of the National Center of Biotechnology Information (NCBI) using default parameters. As mentioned hereinabove, biomolecular sequences of the present invention can be efficiently utilized as tissue or pathological markers and as putative drugs or drug targets for treating or preventing a disease.

Oligonucleotides designed for carrying out the methods of the present invention for any of the sequences provided herein (designed as described above) can be generated according to any oligonucleotide synthesis method known in the art such as enzymatic synthesis or solid phase synthesis. Oligonucleotides used according to this aspect of the present invention are those having a length selected from a range of about 10 to about 200 bases preferably about 15 to about 150 bases, more preferably about 20 to about 100 bases, most preferably about 20 to about 50 bases.

The oligonucleotides of the present invention may comprise heterocyclic nucleosides consisting of purines and the pyrimidines bases, bonded in a 3' to 5' phosphodiester linkage.

Preferable oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds according to at least some embodiments of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [SanghviY S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides according to at least some embodiments of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

Expression Systems

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining elements, or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptides of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Recombinant Expression Vectors and Host Cells

Another aspect of the invention pertains to vectors, preferably expression vectors, containing a nucleic acid encoding a protein according to at least some embodiments of the invention, or derivatives, fragments, analogs or homologs thereof. As used herein, the term "vector" refers to a nucleic acid molecule capable of transporting another nucleic acid to which it has been linked. Examples of vector types are plasmids and viral vectors. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". The invention is intended to include such forms of expression vectors, such as plasmids, viral vectors (e.g., replication defective retroviruses, adenoviruses and adeno-associated viruses), which serve equivalent functions.

The recombinant expression vectors according to at least some embodiments of the invention comprise a nucleic acid according to at least some embodiments of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequences in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors according to at least some embodiments of the invention can be introduced into host cells to thereby produce proteins or peptides, including fusion proteins or peptides, encoded by nucleic acids as described herein.

The recombinant expression vectors according to at least some embodiments of the invention can be designed for production of variant proteins in prokaryotic or eukaryotic cells. For example, proteins according to at least some embodiments of the invention can be expressed in bacterial cells such as Escherichia coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

In another embodiment, the expression vector encoding for the protein of the invention is a yeast expression vector. Examples of vectors for expression in yeast Saccharomyces cerevisiae include pYepSec1 (Baldari, et al., 1987. EMBO J. 6: 229-234), pMFa (Kurj an and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, polypeptides of the present invention can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

According to at least some embodiments the invention further provides a recombinant expression vector comprising a DNA molecule according to at least some embodiments of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for protein according to at least some embodiments of the invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

According to at least some embodiments the invention pertains to host cells into which a recombinant expression vector according to at least some embodiments of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, protein according to at least some embodiments of the invention can be produced in bacterial cells such as *E. coli*, insect cells, yeast, plant or mammalian cells (such as Chinese hamster ovary cells (CHO) or COS or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein according to at least some embodiments of the invention or can be introduced on a separate vector. Cells stably transfected with the introduced nucleic acid can be identified by drug selection (e.g., cells that have incorporated the selectable marker gene will survive, while the other cells die).

A host cell according to at least some embodiments of the invention, such as a prokaryotic or eukaryotic host cell in culture, can be used to produce (i.e., express) protein according to at least some embodiments of the invention. Accordingly, the invention further provides methods for producing proteins according to at least some embodiments of the invention using the host cells according to at least some embodiments of the invention. In one embodiment, the method comprises culturing the host cell of the present invention (into which a recombinant expression vector encoding protein according to at least some embodiments of the invention has been introduced) in a suitable medium such that the protein according to at least some embodiments of the invention is produced. In another embodiment, the method further comprises isolating protein according to at least some embodiments of the invention from the medium or the host cell.

For efficient production of the protein, it is preferable to place the nucleotide sequences encoding the protein according to at least some embodiments of the invention under the control of expression control sequences optimized for expression in a desired host. For example, the sequences may include optimized transcriptional and/or translational regulatory sequences (such as altered Kozak sequences).

It should be noted, that according to at least some embodiments of the present invention the LY6G6F, VSIG10, TMEM25 and/or LSR proteins according to at least some embodiments of the invention may be isolated as naturally-occurring polypeptides, or from any source whether natural, synthetic, semi-synthetic or recombinant. Accordingly, the LY6G6F, VSIG10, TMEM25 and/or LSR proteins may be isolated as naturally-occurring proteins from any species, particularly mammalian, including bovine, ovine, porcine, murine, equine, and preferably human. Alternatively, the LY6G6F, VSIG10, TMEM25 and/or LSR proteins may be isolated as recombinant polypeptides that are expressed in prokaryote or eukaryote host cells, or isolated as a chemically synthesized polypeptide.

A skilled artisan can readily employ standard isolation methods to obtain isolated LY6G6F, VSIG10, TMEM25 and/or LSR proteins. The nature and degree of isolation will depend on the source and the intended use of the isolated molecules.

Transgenic Animals and Plants

According to at least some embodiments the invention also provides transgenic non-human animals and transgenic plants comprising one or more nucleic acid molecules according to at least some embodiments of the invention that may be used to produce the polypeptides according to at least some embodiments of the invention. The polypeptides can be produced in and recovered from tissue or bodily fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957.

Non-human transgenic animals and transgenic plants are produced by introducing one or more nucleic acid molecules according to at least some embodiments of the invention into the animal or plant by standard transgenic techniques. The transgenic cells used for making the transgenic animal can be embryonic stem cells, somatic cells or fertilized egg cells.

The transgenic non-human organisms can be chimeric, non-chimeric heterozygotes, and nonchimeric homozygotes. See, e.g., Hogan et al. Manipulating the Mouse Embryo: A Laboratory Manual 2ed. Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999).

Gene Therapy

According to at least some embodiments of the present invention, nucleic acid sequences encoding soluble LY6G6F, VSIG10, TMEM25 and/or LSR proteins can be used in gene therapy for treatment of infectious disorders, and/or immune related disorders, and or cancer.

As used herein, "gene therapy" is a process to treat a disease by genetic manipulation so that a sequence of nucleic acid is transferred into a cell, the cell then expressing any genetic product encoded by the nucleic acid. For example, as is well known by those skilled in the art, nucleic acid transfer may be performed by inserting an expression vector containing the nucleic acid of interest into cells ex vivo or in vitro by a variety of methods including, for example, calcium phosphate precipitation, diethylaminoethyl dextran, polyethylene glycol (PEG), electroporation, direct injection, lipofection or viral infection (Sambrook et al., Molecular Cloning: A Laboratory Manual (Cold Spring Harbor Laboratory Press 1989); Kriegler M. Gene Transfer ad Expression: A Laboratory Manual (W. H. Freeman and Co, New York, N.Y., 1993) and Wu, Methods in Enzymology (Academic Press, New York, 1993). Alternatively, nucleic acid sequences of interest may be transferred into a cell in vivo in a variety of vectors and by a variety of methods including, for example, direct administration of the nucleic acid into a subject, or insertion of the nucleic acid into a viral vector and infection of the subject with the virus. Other methods used for in vivo transfer include encapsulation of the nucleic acid into liposomes, and direct transfer of the liposomes, or liposomes combined with a hemagglutinating Sendai virus, to a subject. The transfected or infected cells express the protein products encoded by the nucleic acid in order to ameliorate a disease or the symptoms of a disease.

Antibodies and Immune System Response

As used herein, the terms "immunologic", "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. Without wishing to be limited by a single hypothesis, a cellular immune response is elicited by the presentation of polypeptide epitopes in association with Class I or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

A "signal, transduction pathway" refers to the biochemical relationship between varieties of signal transduction molecules that play a role in the transmission of a signal from one portion of a cell to another portion of a cell.

As used herein, the phrase "cell surface receptor" includes, for example, molecules and complexes of molecules capable of receiving a signal and the transmission of such a signal across the plasma membrane of a cell.

The term "antibody" as referred to herein includes whole polyclonal and monoclonal antibodies and any antigen binding fragment (i.e., "antigen-binding portion") or single chains thereof. An "antibody" refers to a glycoprotein comprising at least two heavy (H) chains and two light (L) chains interconnected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., LY6G6F, VSIG10, TMEM25 and/or LSR molecules, and/or a fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V Light, V Heavy, Constant light (CL) and CH1 domains; (ii) a F(ab').2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds LY6G6F, VSIG10, TMEM25 or LSR proteins and/or fragments thereof, and is substantially free of antibodies that specifically bind antigens other than LY6G6F, VSIG10, TMEM25 or LSR, respectively. An isolated antibody that specifically binds LY6G6F, VSIG10, TMEM25 or LSR proteins may, however, have cross-reactivity to other antigens, such as LY6G6F, VSIG10, TMEM25 or LSR molecules from other species, respectively. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies according to at least some embodiments of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human LY6G6F, VSIG10, TMEM25 or LSR proteins" is intended to refer to an antibody that binds to LY6G6F, VSIG10, TMEM25 or LSR proteins, respectively, such as for example, one with a KD of $5 \times 10^{-8}$ M, $3 \times 10^{-8}$ M, $1 \times 0.10^{-9}$ M or less.

The term "K-assoc" or "Ka", as used herein, is intended to refer to the association rate of a particular antibody-antigen interaction, whereas the term "Kdiss" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface Plasmon resonance, preferably using a biosensor system such as a Biacore® system.

As used herein, the term "high affinity" for an IgG antibody refers to an antibody having a KD of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a KD of $10^{-7}$ M or less, more preferably $10^{-8}$ M or less.

As used herein, the term "subject" or "patient" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Anti-LY6G6F, Anti-VSIG10, Anti-TMEM25 and Anti-LSR Antibodies

The antibodies according to at least some embodiments of the invention including those having the particular germline sequences, homologous antibodies, antibodies with conservative modifications, engineered and modified antibodies are characterized by particular functional features or properties of the antibodies. For example, the antibodies bind specifically to human LY6G6F, VSIG10, TMEM25 or LSR. Preferably, an antibody according to at least some embodiments of the invention binds to corresponding LY6G6F, VSIG10, TMEM25 or LSR with high affinity, for example with a KD of $10^{-8}$ M or less or $10^{-9}$ M or less or even $10^{-10}$ M or less. The anti-LY6G6F, anti-VSIG10, anti-TMEM25 and anti-LSR antibodies according to at least some embodiments of the present invention preferably exhibit one or more of the following characteristics:

(i) binds to corresponding human LY6G6F, VSIG10, TMEM25 or LSR with a KD of $5 \times 10^{-8}$ M or less;

(ii) modulates (enhances or inhibits) B7 immune costimulation and related activities and functions such a T cell responses involved in antitumor immunity and autoimmunity, and/or (iii) binds to LY6G6F, VSIG10, TMEM25 or LSR antigen expressed by cancer cells including for example melanoma, cancers of liver, renal, brain, breast, colon, lung, ovary, pancreas, prostate, stomach, multiple myeloma, and hematopoietic cancer, including but not limited to lymphoma (Hodgkin's and non Hodgkin's), acute and chronic lymphoblastic leukemia and acute and chronic myeloid leukemia., but does not substantially bind to normal cells. In addition, preferably these antibodies and conjugates thereof will be effective in eliciting selective killing of such cancer cells and for modulating immune responses involved in autoimmunity and cancer.

More preferably, the antibody binds to corresponding human LY6G6F, VSIG10, TMEM25 or LSR antigen with a KD of $3\times10^{-8}$ M or less, or with a KD of $1\times10^{-9}$ M or less, or with a KD of $0.1.\times10^{-9}$ M or less, or with a KD Of $0.05.\times10^{-9}$ M or less or with a KD of between $1\times10^{-9}$ and $1\times10^{-11}$ M.

Standard assays to evaluate the binding ability of the antibodies toward LY6G6F, VSIG10, TMEM25 or LSR are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Upon production of anti-LY6G6F, anti-VSIG10, anti-TMEM25 and anti-LSR antibody sequences from antibodies can bind to LY6G6F, VSIG10, TMEM25 or LSR the VH and VL sequences can be "mixed and matched" to create other anti-LY6G6F, anti-VSIG10, anti-TMEM25 and anti-LSR, binding molecules according to at least some embodiments of the invention. LY6G6F, VSIG10, TMEM25 or LSR binding of such "mixed and matched" antibodies can be tested using the binding assays described above. e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. For example, the VH and VL sequences of homologous antibodies are particularly amenable for mixing and matching.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, 96, 97, 98 or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to isolated anti-LY6G6F, anti-VSIG10, anti-TMEM25 or anti-LSR amino acid sequences of preferred anti-LY6G6F, anti-VSIG10, anti-TMEM25 or anti-LSR antibodies, respectively, wherein the antibodies retain the desired functional properties of the parent anti-LY6G6F, anti-VSIG10, anti-TMEM25 or anti-LSR antibodies.

As used herein, the percent homology between two amino acid sequences is equivalent to the percent identity between the two sequences. The percent identity between the two sequences is a function of the number of identical positions shared by the sequences (i.e., % homology=# of identical positions/total # of positions$\times$100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules according to at least some embodiments of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on preferred anti-LY6G6F, anti-VSIG10, anti-TMEM25 or anti-LSR antibodies isolated and produced using methods herein, or conservative modifications thereof, and wherein the antibodies retain the desired functional properties of the anti-LY6G6F, anti-VSIG10, anti-TMEM25 or anti-LSR antibodies according to at least some embodiments of the invention, respectively.

In various embodiments, the anti-LY6G6F, anti-VSIG10, anti-TMEM25 or anti-LSR antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody according to at least some embodiments of the invention can be replaced with other amino acid residues from the same side chain family and the altered antibody can be tested for retained function (i.e., the functions set forth in (c) through (j) above) using the functional assays described herein.

Antibodies that Bind to the Same Epitope as Anti-LY6G6F, Anti-VSIG10, Anti-TMEM25 or Anti-LSR According to at Least Some Embodiments of the Invention.

In another embodiment, the invention provides antibodies that bind to preferred epitopes on human LY6G6F, VSIG10, TMEM25 or LSR which possess desired functional properties such as modulation of B7 co-stimulation and related functions. Other antibodies with desired epitope specificity may be selected and will have the ability to cross-compete for binding to LY6G6F, VSIG10, TMEM25 or LSR antigen with the desired antibodies.

Engineered and Modified Antibodies

An antibody according to at least some embodiments of the invention further can be prepared using an antibody having one or more of the VH and/or VL sequences derived from an anti-LY6G6F, anti-VSIG10, anti-TMEM25 or anti-LSR antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germline VH Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fc gamma RI, Fc gamma RII, Fc gammaRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve Fcgamma.RIII binding: T256A/S298A, S298A/E333A, S298A/K224A and S298A/E333A/K334A. Furthermore, mutations such as M252Y/S254T/T256E or M428L/N434S improve binding to FcRn and increase antibody circulation half-life (see Chan C A and Carter P J (2010) Nature Rev Immunol 10:301-316).

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277: 26733-26740). PCT Publication WO 99/54342 by Umana et al. describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Methods of Engineering Antibodies

As discussed above, anti-LY6G6F, anti-VSIG10, anti-TMEM25 or anti-LSR antibodies having VH and VK sequences disclosed herein can be used to create new anti-LY6G6F, anti-VSIG10, anti-TMEM25 or anti-LSR antibodies, respectively, by modifying the VH and/or VL sequences, or the constant regions attached thereto. Thus, in another aspect according to at least some embodiments of the invention, the structural features of an anti-LY6G6F, anti-VSIG10, anti-TMEM25 or anti-LSR antibody according to at least some embodiments of the invention, are used to create structurally related anti-LY6G6F, anti-VSIG10, anti-TMEM25 or anti-LSR antibodies that retain at least one functional property of the antibodies according to at least some embodiments of the invention, such as binding to human LY6G6F, VSIG10, TMEM25 or LSR, respectively. For example, one or more CDR regions of one LY6G6F, VSIG10, TMEM25 or LSR antibody or mutations thereof, can be combined recombinantly with known framework regions and/or other CDRs to create additional, recombinantly-engineered, anti-LY6G6F, anti-VSIG10, anti-TMEM25 or anti-LSR antibodies according to at least some embodiments of the invention, as discussed above. Other types of modifications include those described in the previous section. The starting material for the engineering method is one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence.

Preferably, the antibody encoded by the altered antibody sequences is one that retains one, some or all of the functional properties of the anti-LY6G6F, anti-VSIG10, anti-TMEM25 or anti-LSR antibodies, respectively, produced by methods and with sequences provided herein, which functional properties include binding to LY6G6F, VSIG10, TMEM25 or LSR antigen with a specific KD level or less and/or modulating B7 costimulation and/or selectively binding to desired target cells such as for example melanoma, cancers of liver, renal, brain, breast, colon, lung, ovary, pancreas, prostate, stomach, multiple myeloma and hematopoietic cancer, including but not limited to lymphoma (Hodgkin's and non Hodgkin's), acute and chronic lymphoblastic leukemia and acute and chronic myeloid leukemia, that express LY6G6F, VSIG10, TMEM25 and/or LSR antigen.

The functional properties of the altered antibodies can be assessed using standard assays available in the art and/or described herein.

In certain embodiments of the methods of engineering antibodies according to at least some embodiments of the invention, mutations can be introduced randomly or selectively along all or part of an anti-LY6G6F, anti-VSIG10, anti-TMEM25 or anti-LSR antibody coding sequence and the resulting modified anti-LY6G6F, anti-VSIG10, anti-TMEM25 or anti-LSR antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

Another aspect of the invention pertains to nucleic acid molecules that encode the antibodies according to at least some embodiments of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Anti-LY6G6F, Anti-VSIG10, Anti-TMEM25 or Anti-LSR Monoclonal Antibodies Monoclonal antibodies (mAbs) of the present invention can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

According to at least some embodiments of the invention, the antibodies are human monoclonal antibodies. Such human monoclonal antibodies directed against LY6G6F, VSIG10, TMEM25 and/or LSR can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice." The HuMAb Mouse™ (Medarex. Inc.) contains human immunoglobulin gene miniloci that encode unrearranged human heavy (.mu. and .gamma.) and .kappa. light chain immunoglobulin sequences, together with targeted mutations that inactivate the endogenous .mu. and .kappa. chain loci (see e.g., Lonberg, et al. (1994) Nature 368(6474): 856-859). Accordingly, the mice exhibit reduced expression of mouse IgM or. kappa., and in response to immunization, the introduced human heavy and light chain transgenes undergo class switching and somatic mutation to generate high affinity human IgGkappa. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann N.Y. Acad. Sci. 764:536-546). The preparation and use of the HuMab Mouse®, and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-LY6G6F, anti-VSIG10, anti-TMEM25 and/or anti-LSR antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-LY6G6F, anti-VSIG10, anti-TMEM25 and/or anti-LSR antibodies according to at least some embodiments of the invention. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-LY6G6F, anti-VSIG10, anti-TMEM25 and/or anti-LSR antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies according to at least some embodiments of the invention, such mice can be immunized with a purified or enriched preparation of LY6G6F, VSIG10, TMEM25 and/or LSR antigen and/or recombinant LY6G6F, VSIG10, TMEM25 and/or LSR, or LY6G6F, VSIG10, TMEM25 and/or LSR fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 .mu.g) of LY6G6F, VSIG10, TMEM25 and/or LSR antigen can be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-LY6G6F, anti-VSIG10, anti-TMEM25 and/or anti-LSR human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used.

Generation of Hybridomas Producing Human Monoclonal Antibodies

To generate hybridomas producing human monoclonal antibodies according to at least some embodiments of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3x63-Ag8.653 nonsecreting mouse myeloma cells (ATCC, CRL 1580) with 50% PEG. Cells are plated at approximately 2×10-5 in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

Generation of Transfectomas Producing Monoclonal Antibodies

Antibodies according to at least some embodiments according to at least some embodiments of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors according to at least some embodiments of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or .beta.-globin promoter. Still further, regulatory elements composed of sequences from different sources, such as the SR alpha. promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vectors encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies according to at least some embodiments of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies according to at least some embodiments of the invention include Chinese Hamster Ovary (CHO cells) (including dhfr-CHO cells, described in Urlaub and ChasM, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies according to at least some embodiments of the invention can be tested for binding to LY6G6F, VSIG10, TMEM25 and/or LSR by, for example, standard ELISA. Briefly, microtiter plates are coated with purified LY6G6F, VSIG10, TMEM25 and/or LSR at 0.25 .mu.g/ml in PBS, and then blocked with 5% bovine serum albumin in PBS. Dilutions of antibody (e.g., dilutions of plasma from-immunized mice) are added to each well and incubated for 1-2 hours at 37 degrees C. The plates are washed with PBS/Tween and then incubated with secondary reagent (e.g., for human antibodies, a goat-anti-human IgG Fc-specific polyclonal reagent) conjugated to alkaline phosphatase for 1 hour at 37 degrees C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with LY6G6F, VSIG10, TMEM25 and/or LSR immunogen. Hybridomas that bind with high avidity to LY6G6F, VSIG10, TMEM25 and/or LSR are subcloned and further characterized. One clone from each hybridoma, which retains the reactivity of the parent cells (by ELISA), can be chosen for making a 5-10 vial cell bank stored at −140 degrees C., and for antibody purification.

To purify anti-LY6G6F, anti-VSIG10, anti-TMEM25 and/or anti-LSR antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

To determine if the selected anti-LY6G6F, anti-VSIG10, anti-TMEM25 and/or anti-LSRmonoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using LY6G6F, VSIG10, TMEM25 and/or LSR coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 .mu.g/ml of anti-human immunoglobulin overnight at 4 degrees C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-LY6G6F, anti-VSIG10, anti-TMEM25 and/or anti-LSRhuman IgGs can be further tested for reactivity with LY6G6F, VSIG10, TMEM25 and/or LSR antigen, respectively, by Western blotting. Briefly, LY6G6F, VSIG10, TMEM25 and/or LSRantigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Alternative Scaffolds

According to at least some embodiments the invention relates to protein scaffolds with specificities and affinities in a range similar to specific antibodies. According to at least some embodiments the present invention relates to an antigen-binding construct comprising a protein scaffold which is linked to one or more epitope-binding domains. Such engineered protein scaffolds are usually obtained by designing a random library with mutagenesis focused at a loop region or at an otherwise permissible surface area and by selection of variants against a given target via phage display or related techniques. According to at least some embodiments the invention relates to alternative scaffolds including, but not limited to, anticalins, DARPins, Armadillo repeat proteins, protein A, lipocalins, fibronectin domain, ankyrin consensus repeat domain, thioredoxin, chemically constrained peptides and the like. According to at least some embodiments the invention relates to alternative scaffolds that are used as therapeutic agents for treatment of cancer, autoimmune and infectious diseases as well as for in vivo diagnostics.

According to at least some embodiments the invention further provides a pharmaceutical composition comprising an antigen binding construct as described herein a pharmaceutically acceptable carrier.

The term 'Protein Scaffold' as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. Such protein scaffolds may comprise antigen-binding sites in addition to the one or more constant regions, for example where the protein scaffold comprises a full IgG. Such protein scaffolds will be capable of being linked to other protein domains, for example protein domains which have antigen-binding sites, for example epitope-binding domains or ScFv domains.

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, V HH, V L) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid V HH dAbs. Camelid V HH are immunoglobulin single variable domain polypeptides that are derived from species including camel, llama, alpaca, dromedary, and guanaco, which produce heavy chain antibodies naturally devoid of light chains. Such V HH domains may be humanised according to standard techniques available in the art, and such domains are still considered to be "domain antibodies" according to the invention. As used herein "VH includes camelid V HH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ -crystallin and human ubiquitin (affilins); PDZ domains; scorpion toxinkunitz type domains of human protease inhibitors; Armadillo repeat proteins, thioredoxin, and fibronectin (adnectin); which has been subjected to protein engineering in order to obtain binding to a ligand other than the natural ligand.

Loops corresponding to CDRs of antibodies can be substituted with heterologous sequence to confer different binding properties i.e. Evibodies. For further details see Journal of Immunological Methods 248 (1-2), 31-45 (2001) Lipocalins are a family of extracellular proteins which transport small hydrophobic molecules such as steroids, bilins, retinoids and lipids. They have a rigid secondary structure with a numer of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1 Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007) A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem. 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha helices; -beta turn. They can be engineered to bind different target antigens by randomising residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the beta; -sandwich can be engineered to enable an Adnectin to specifically recognize a therapeutic target of interest. For further details see Protein Eng. Des. Sel. 18, 435-444 (2005), US200801 39791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5. 783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human γ beta-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7-Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

Conjugates or Immunoconjugates

The present invention encompasses conjugates for use in immune therapy comprising the LY6G6F, VSIG10, TMEM25 and/or LSR antigen and soluble portions thereof including the ectodomain or portions or variants thereof. For example the invention encompasses conjugates wherein the ECD of the LY6G6F, VSIG10, TMEM25 and/or LSR antigen is attached to an immunoglobulin or fragment thereof. The invention contemplates the use thereof for promoting or inhibiting LY6G6F, VSIG10, TMEM25 and/or LSR antigen activities such as immune costimulation and the use thereof in treating transplant, autoimmune, and cancer indications described herein.

In another aspect, the present invention features antibody-drug conjugates (ADCs), used for example for treatment of cancer, consisting of an antibody (or antibody fragment such as a single-chain variable fragment [scFv]) linked to a payload drug (often cytotoxic). The antibody causes the ADC to bind to the target cancer cells. Often the ADC is then internalized by the cell and the drug is released into the cell. Because of the targeting, the side effects are lower and give a wider therapeutic window. Hydrophilic linkers (e.g., PEG4Ma1) help prevent the drug being pumped out of resistant cancer cells through MDR (multiple drug resistance) transporters. ADCs based on cleavable linkers are thought to have a less favorable therapeutic window, but targets (tumor cell surface antigens) that do not get internalized efficiently seem more suitable for cleavable linkers.

In another aspect, the present invention features immunoconjugates comprising an anti-LY6G6F, anti-VSIG10, anti-TMEM25 and/or anti-LSR antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody according to at least some embodiments of the invention include duocarmycins, calicheamicins, maytansines and auristatins, and derivatives thereof. An example of a calicheamicin antibody conjugate is commercially available (Mylotarg™; Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Methods for preparing radioimmunconjugates are established in the art. Examples of radioimmunoconjugates are commercially available, including Zevalin (IDEC Pharmaceuticals) and Bexxar. (Corixa Pharmaceuticals), and similar methods can be used to prepare radioimmunoconjugates using the antibodies according to at least some embodiments of the invention.

The antibody conjugates according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-LY6G6F, anti-VSIG10, anti-TMEM25 and/or anti-LSR antibody, or a fragment thereof, according to at least some embodiments of the invention. An antibody according to at least some embodiments of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the invention, an antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for LY6G6F, VSIG10, TMEM25 and/or LSR and a second binding specificity for a second target epitope. According to at least some embodiments of the invention, the second target epitope is an Fc receptor, e.g., human Fc gamma RI (CD64) or a human Fc alpha receptor (CD89). Therefore, the invention includes bispecific molecules capable of binding both to Fc gamma. R, Fc alpha R or Fc epsilon R expressing effector cells (e.g., monocytes, macrophages or polymorphonuclear cells (PMNs)), and to target cells expressing LY6G6F, VSIG10, TMEM25 and/or LSR, respectively. These bispecific molecules target LY6G6F, VSIG10, TMEM25 and/or LSR expressing cells to effector cell and trigger Fc receptor-mediated effector cell activities, such as phagocytosis of an LY6G6F, VSIG10, TMEM25 and/or LSR expressing cells, antibody dependent cell-mediated cytotoxicity (ADCC), cytokine release, or generation of superoxide anion.

According to at least some embodiments of the invention in which the bispecific molecule is multispecific, the molecule can further include a third binding specificity, in addition to an anti-Fc binding specificity and an anti-6f binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

According to at least some embodiments of the invention, the bispecific molecules comprise as a binding specificity at least one antibody, or an antibody fragment thereof, including, e.g., an Fab, Fab', F(ab').sub.2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight .gamma.-chain genes located on chromosome 1. These genes encode a total of twelve transmembrane or soluble receptor isoforms which are grouped into three Fc .gamma. receptor classes: Fc gamma R1 (CD64), Fc gamma RII(CD32), and Fc gamma.RIII (CD 16). In one preferred embodiment, the Fc gamma. receptor a human high affinity Fc.gamma RI. The human Fc gammaRI is a 72 kDa molecule, which shows high affinity for monomeric IgG (10 8-10-9M.-1).

The production and characterization of certain preferred anti-Fc gamma. monoclonal antibodies are described by Fanger et al. in PCT Publication WO 88/00052 and in U.S. Pat. No. 4,954,617, the teachings of which are fully incorporated by reference herein. These antibodies bind to an epitope of Fc.gamma.R1, FcγRII or FcγRIII at a site which is distinct from the Fc.gamma. binding site of the receptor and, thus, their binding is not blocked substantially by physiological levels of IgG. Specific anti-Fc.gamma.RI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HAO22CL1 and has the accession no. CRL 11177.

In still other preferred embodiments, the binding specificity for an Fc receptor is provided by an antibody that binds to a human IgA receptor, e.g., an Fc-alpha receptor (Fc alpha.RI (CD89)), the binding of which is preferably not blocked by human immunoglobulin A (IgA). The term "IgA receptor" is intended to include the gene product of one alpha.-gene (Fc alpha.RI) located on chromosome 19. This gene is known to encode several alternatively spliced transmembrane isoforms of 55 to 10 kDa.

Fc.alpha.RI (CD89) is constitutively expressed on monocytes/macrophages, eosinophilic and neutrophilic granulocytes, but not on non-effector cell populations. Fc alpha RI has medium affinity (Approximately 5×10-7 M-1) for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind Fc.alpha.RI outside the IgA ligand binding domain, have been described (Monteiro, R. C. et al. (1992) J. Immunol. 148:1764).

Fc. alpha. RI and Fc gamma. RI are preferred trigger receptors for use in the bispecific molecules according to at least some embodiments of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments of the invention are murine, chimeric and humanized monoclonal antibodies.

The bispecific molecules of the present invention can be prepared by conjugating the constituent binding specificities, e.g., the anti-FcR and anti-LY6G6F, anti-VSIG10, anti-TMEM25 and/or anti-LSR binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyld-ithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF(ab')2 or ligandXFab fusion protein. A bispecific molecule according to at least some embodiments of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma. counter or a scintillation counter or by autoradiography.

Protein Modifications

Fusion Proteins

According to at least some embodiments, LY6G6F, VSIG10, TMEM25 and/or LSR fusion polypeptides have a first fusion partner comprising all or a part of a LY6G6F, VSIG10, TMEM25 and/or LSR protein fused to a second polypeptide directly or via a linker peptide sequence or a chemical linker useful to connect the two proteins. The LY6G6F, VSIG10, TMEM25 and/or LSR polypeptide may optionally be fused to a second polypeptide to form a fusion protein as described herein. The presence of the second polypeptide can alter the solubility, stability, affinity and/or valency of the LY6G6F, VSIG10, TMEM25 and/or LSR fusion polypeptide. As used herein, "valency" refers to the number of binding sites available per molecule. In one embodiment the second polypeptide is a polypeptide from a different source or different protein.

According to at least some embodiments, the LY6G6F, VSIG10, TMEM25 and/or LSR protein or fragment is selected for its activity for the treatment of immune related disorder and/or infectious disorder, and/or cancer as described herein.

In one embodiment, the second polypeptide contains one or more domains of an immunoglobulin heavy chain constant region, preferably having an amino acid sequence corresponding to the hinge, CH2 and CH3 regions of a human immunoglobulin Cγ1, Cγ2, Cγ3 or Cγ4 chain or to the hinge, CH2 and CH3 regions of a murine immunoglobulin Cγ2a chain. SEQ ID NO: 70 provides exemplary sequence for the hinge, CH2 and CH3 regions of a human immunoglobulin Cγ1.

According to at least some embodiments, the fusion protein is a dimeric fusion protein. In an optional dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as LY6G6F, VSIG10, TMEM25 and/or LSR polypeptides, fragments or fusion proteins thereof.

In one embodiment, the immunoglobulin constant domain may contain one or more amino acid insertions, deletions or substitutions that enhance binding to specific cell types, increase the bioavailablity, or increase the stability of the LY6G6F, VSIG10, TMEM25 and/or LSR polypeptides, fusion proteins, or fragments thereof. Suitable amino acid substitutions include conservative and non-conservative substitutions, as described above.

The fusion proteins optionally contain a domain that functions to dimerize or multimerize two or more fusion proteins. The peptide/polypeptide linker domain can either be a separate domain, or alternatively can be contained within one of the other domains (LY6G6F, VSIG10, TMEM25 and/or LSR polypeptide or second polypeptide) of the fusion protein. Similarly, the domain that functions to dimerize or multimerize the fusion proteins can either be a separate domain, or alternatively can be contained within one of the other domains (LY6G6F, VSIG10, TMEM25 and/or LSR polypeptide, second polypeptide or peptide/polypeptide linker domain) of the fusion protein. In one embodiment, the dimerization/multimerization domain and the peptide/polypeptide linker domain are the same. Further specific, illustrative and non-limiting examples of dimerization/multimerization domains and linkers are given below.

Fusion proteins disclosed herein according to at least some embodiments of the present invention are of formula I: N-R1-R2-R3-C wherein "N" represents the N-terminus of the fusion protein, "C" represents the C-terminus of the fusion protein. In the further embodiment, "R1" is a LY6G6F, VSIG10, TMEM25 and/or LSR polypeptide, "R2" is an optional peptide/polypeptide or chemical linker domain, and "R3" is a second polypeptide. Alternatively, R3 may be a LY6G6F, VSIG10, TMEM25 and/or LSR polypeptide and R1 may be a second polypeptide. Various non-limiting examples of linkers are described in greater detail below.

Optionally, the fusion protein comprises the LY6G6F, VSIG10, TMEM25 and/or LSR polypeptide fragments as described herein, fused, optionally by a linker peptide of one or more amino acids (e.g. GS) to one or more "half-life extending moieties". A "half-life extending moiety" is any moiety, for example, a polypeptide, small molecule or polymer, that, when appended to protein, extends the in vivo half-life of that protein in the body of a subject (e.g., in the plasma of the subject). For example, a half-life extending moiety is, in an embodiment of the invention, polyethylene glycol (PEG), monomethoxy PEG (mPEG) or an immunoglobulin (Ig). In an embodiment of the invention, PEG is a 5, 10, 12, 20, 30, 40 or 50 kDa moiety or larger or comprises about 12000 ethylene glycol units (PEG12000).

The fusion protein may also optionally be prepared by chemical synthetic methods and the "join" effected chemically, either during synthesis or post-synthesis. Cross-linking and other such methods may optionally be used (optionally also with the above described genetic level fusion methods), as described for example in U.S. Pat. No. 5,547,853 to Wallner et al, which is hereby incorporated by reference as if fully set forth herein as a non-limiting example only.

According to the present invention, a fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises the hinge, CH2 and CH3 domains. The Fc chain may optionally be a known or "wild type" Fc chain, or alternatively may be mutated or truncated. The Fc portion of the fusion protein may optionally be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al, MoI. Immun., 34(6):441-452 (1997), Swann, et al., Cur. Opin. Immun, 20:493-499 (2008), and Presta, Cur. Opin. Immun 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions.

Modications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host or substuting the Asn at position 297), and IgG1 with altered pH-dependent binding to FcRn. The Fc region may include the entire hinge region, or less than the entire hinge region.

In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA)

Another embodiment includes IgG2-4 hybrids and IgG4 mutants that have reduced binding to FcR (Fc receptor) which increase their half life. Representative IgG2-4 hybrids and IgG4 mutants are described in Angal, S. et al., Molecular Immunology, 30(1):105-108 (1993); Mueller, J. et al., Molecular Immunology, 34(6): 441-452 (1997); and U.S. Pat. No. 6,982,323 to Wang et al. In some embodiments the IgG1 and/or IgG2 domain is deleted; for example, Angal et al. describe IgG1 and IgG2 having serine 241 replaced with a proline.

In a further embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination.

In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297A/Q substitution, as these mutations abolishFcγR binding. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331 proline for serine may block the ability to activate complement, which may optionally be considered an undesired function (see M. Clark, "Chemical Immunol and Antibody Engineering", pp 1-31). Changing 330 alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to another amino acid residue (e.g., serine), to avoid any type of covalent linkage (see M. Clark, "Chemical Immunol and Antibody Engineering", pp 1-31) or by deletion or truncation.

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

In a further embodiment, the fusion protein includes the extracellular domain of LY6G6F, or a fragment thereof fused to an Ig Fc region. Recombinant IgLY6G6F polypeptides, fragments or fusion proteins thereof fusion proteins can be prepared by fusing the coding region of the extracellular domain of LY6G6F or a fragment thereof to the Fc region of human IgG1 or mouse IgG2a, as described previously (Chapoval, et al., Methods MoI. Med, 45:247-255 (2000)).

Optionally, LY6G6F ECD refers also to fusion protein, comprising an amino acid sequence of human LY6G6F ECD fused to human immunoglobulin Fc. Optionally, said fusion protein comprises the amino acid sequence of the human LY6G6F ECD set forth in SEQ ID NO: 2 fused to human IgG1 Fc set forth in any one of SEQ ID NOs:70, 156. Optionally, the amino acid sequence of said fusion protein is set forth in SEQ ID NO:71 or SEQ ID NO:172.

In a further embodiment, the fusion protein includes the extracellular domain of VSIG10, or a fragment thereof fused to an Ig Fc region. Recombinant IgVSIG10 polypeptides, fragments or fusion proteins thereof fusion proteins can be prepared by fusing the coding region of the extracellular domain of VSIG10 or a fragment thereof to the Fc region of human IgG1 or mouse IgG2a, as described previously (Chapoval, et al., Methods Mol. Med, 45:247-255 (2000)).

Optionally, VSIG10 ECD refers also to fusion protein, comprising an amino acid sequence of human VSIG10 ECD fused to human immunoglobulin Fc. Optionally, said fusion protein comprises the amino acid sequence of the human VSIG10 ECD, selected from the amino acid sequences set forth in any one of SEQ ID NOs: 4 and 6, fused to human IgG1 Fc set forth in any one of SEQ ID NOs:70, 156. Optionally, the amino acid sequence of said fusion protein is set forth in any one of SEQ ID NOs:72, 73, 173 and 174.

In a further embodiment, the fusion protein includes the extracellular domain of TMEM25, or a fragment thereof fused to an Ig Fc region. Recombinant IgTMEM25 polypeptides, fragments or fusion proteins thereof fusion proteins can be prepared by fusing the coding region of the extracellular domain of TMEM25 or a fragment thereof to the Fc region of human IgG1 or mouse IgG2a, as described previously (Chapoval, et al., Methods Mol. Med, 45:247-255 (2000)).

Optionally, TMEM25 ECD refers also to fusion protein, comprising an amino acid sequence of human TMEM25 ECD fused to human immunoglobulin Fc. Optionally, said fusion protein comprises the amino acid sequence of the human TMEM25 ECD set forth in SEQ ID NO: 8 fused to human IgG1 Fc set forth in any one of SEQ ID NOs:70, 156. Optionally, the amino acid sequence of said fusion protein is set forth in any one of SEQ ID NOs:74, 175.

In a further embodiment, the fusion protein includes the extracellular domain of LSR, or a fragment thereof fused to an Ig Fc region. Recombinant Ig LSR polypeptides, fragments or fusion proteins thereof fusion proteins can be prepared by fusing the coding region of the extracellular domain of LSR or a fragment thereof to the Fc region of human IgG1 or mouse IgG2a, as described previously (Chapoval, et al., Methods Mol. Med, 45:247-255. (2000)).

Optionally, LSR ECD refers also to fusion protein, comprising an amino acid sequence of human LSR ECD fused to human immunoglobulin Fc. Optionally, said fusion protein comprises the amino acid sequence of the human LSR ECD, The disclosed fusion proteins can be isolated using standard molecular biology techniques. For example, an expression vector containing a DNA sequence encoding a LY6G6F, VSIG10, TMEM25 and/or LSR polypeptides, fragments or fusion proteins thereof fusion protein is transfected into 293 cells by calcium phosphate precipitation and cultured in serum-free DMEM. The supernatant is collected at 72 h and the fusion protein is purified by Protein G, or preferably Protein A SEPHAROSE® columns (Pharmacia, Uppsala, Sweden). Optionally, a DNA sequence encoding a LY6G6F, VSIG10, TMEM25 and/or LSR polypeptides, fragments or fusion proteins thereof fusion protein is transfected into GPEx® retrovectors and expressed in CHO-S cells following four rounds of retrovector transduction. The protein is clarified from supernatants using protein A chromatography.

In another embodiment the second polypeptide may have a conjugation domain through which additional molecules can be bound to the LY6G6F, VSIG10, TMEM25 and/or LSR fusion proteins. In one such embodiment, the conjugated molecule is capable of targeting the fusion protein to a particular organ or tissue; further specific, illustrative, non-limiting examples of such targeting domains and/or molecules are given below.

In another such embodiment the conjugated molecule is another immunomodulatory agent that can enhance or augment the effects of the LY6G6F, VSIG10, TMEM25 and/or LSR fusion protein. In another embodiment the conjugated molecule is Polyethylene Glycol (PEG).

Peptide or Polypeptide Linker Domain

The disclosed LY6G6F, VSIG10, TMEM25 and/or LSR fusion proteins optionally contain a peptide or polypeptide linker domain that separates the LY6G6F, VSIG10, TMEM25 and/or LSR polypeptide from the second polypeptide. In one embodiment, the linker domain contains the hinge region of an immunoglobulin. In a further embodiment, the hinge region is derived from a human immunoglobulin. Suitable human immunoglobulins that the hinge can be derived from include IgG, IgD and IgA. In a further embodiment, the hinge region is derived from human IgG. Amino acid sequences of immunoglobulin hinge regions and other domains are well known in the art. In one embodiment, LY6G6F, VSIG10, TMEM25 and/or LSR fusion polypeptides contain the hinge, CH2 and CH3 regions of a human immunoglobulin Cγ1 chain, optionally with the Cys at position 220 (according to full length human IgG1, position 5 in SEQ ID NO:70) replaced with a Ser (SEQ ID NO: 156) having at least 85%, 90%, 95%, 99% or 100% sequence homology to amino acid sequence set forth in SEQ ID NO:70:

EPKSCDKTHTCPPCPAPELLGGPSVFLEPPKPKDTLMISRTPEVTCVVVDVSHEDPEVKENNYVDGVEVHNA

KTKPREEQYNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVFSCSVMHEA

LHNHYTQKSLSLSPGK selected from the amino acid sequences set forth in any one of SEQ ID NOs: 12, 14, 15, 16, 17, 18, 47, 48, 49 and 50, fused to human IgG1 Fc set forth in any one of SEQ ID NOs:70, 156. Optionally, the amino acid sequence of said fusion protein is set forth in any one of SEQ ID NOs:75, 76, 77, 78, 79, 80, 176, 177, 178, 179, 180, and 181.

The aforementioned exemplary fusion proteins can incorporate any combination of the variants described herein. In another embodiment the terminal lysine of the aforementioned exemplary fusion proteins is deleted.

The hinge can be further shortened to remove amino acids 1, 2, 3, 4, 5, or combinations thereof of any one of SEQ ID NOs: 70 or 156. In one embodiment, amino acids 1-5 of any one of SEQ ID NOs: 70 or 156 are deleted. Exemplary LY6G6F, VSIG10, TMEM25 and/or LSR fusion polypeptides comprised of the hinge, CH2 and CH3 regions of a human immunoglobulin Cγ1 chain with the Cys at position 220 replaced with a Ser are set forth in SEQ ID NOs:71, 72, 73, 74, 75, 76, 77, 78, 79, 80.

In another embodiment, LY6G6F, VSIG10, TMEM25 and/ or LSR fusion polypeptides contain the CH2 and CH3 regions of a human immunoglobulin Cγ1 chain having at least 85%, 90%, 95%, 99% or 100% sequence homology to amino acid sequence set forth in SEQ ID NO:157: APELLGGPSVFLF-PPKPKDTLMISRTPEVTCVVVDVSHED-PEVKFNWYVDGVEVH NAKTKPREEQYNSTYRVVS-VLTVLHQDWLNGKEYKCKVSNKALPAPIEKTISKA KGQPREPQVYTLPPSRDELTKNQVSLT-CLVKGFYPSDIAVEWESNGQPENNYKTT PPVLDS-DGSFFLYSKLTVDKSRWQQGNVFSCSVM-HEALHNHYTQKSLSLSPGK In another embodiment, the LY6G6F, VSIG10, TMEM25 and/or LSR fusion polypeptides contain the CH2 and CH3 regions of a murine immunoglobulin Cγ2a chain at least 85%, 90%, 95%, 99% or 100% sequence homology to amino acid sequence set forth in SEQ ID NO: 158: EPRGPTIKPCPPCKCPAPNLLGGPS-VFIFPPKIKDVLMISLSPIVTCVVVDVSEDDPD VQISWFVNNVEVHTAQTQTHREDYNSTL-RVVSALPIQHQDWMSGKEFKCKVNN KDLPAPIER-TISKPKGSVRAPQVYVLPPPEEEMT-KKQVTLTCMVTDFMPEDIYVE WTNNGKTELNYKNTEPVLDSDGSY-FMYSKLRVEKKNWVERNSYSCSVVHEGLH NHHT-TKSFSRTPGK. In another embodiment, the linker domain contains a hinge region of an immunoglobulin as described above, and further includes one or more additional immunoglobulin domains.

Other suitable peptide/polypeptide linker domains include naturally occurring or non-naturally occurring peptides or polypeptides. Peptide linker sequences are at least 2 amino acids in length. Optionally the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser (SEQ ID NO:159), Gly-Ser-Gly-Ser (SEQ ID NO:160), Ala-Ser (SEQ ID NO:161), Gly-Gly-Gly-Ser (SEQ ID NO:162), Gly4-Ser (SEQ ID NO:163), (Gly4-Ser)2 (SEQ ID NO:164), (Gly4-Ser)$_3$ (SEQ ID NO:165) and (Gly4-Ser)$_4$ (SEQ ID NO: 166). Additional flexible peptide/polypeptide sequences are well known in the art. Other suitable peptide linker domains include helix forming linkers such as Ala-(Glu-Ala-Ala-Ala-Lys)n-Ala (n=1-5). Additional helix forming peptide/polypeptide sequences are well known in the art. Non-limiting examples of such linkers are depicted in SEQ ID NO:167-171.

Dimerization, Multimerization and Targeting Domains

The fusion proteins disclosed herein optionally contain a dimerization or multimerization domain that functions to dimerize or multimerize two or more fusion proteins. The domain that functions to dimerize or multimerize the fusion proteins can either be a separate domain, or alternatively can be contained within one of the other domains (LY6G6F, VSIG10, TMEM25 and/or LSR polypeptide, second polypeptide, or peptide/polypeptide linker domain) of the fusion protein.

Dimerization or multinierization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the LY6G6F, VSIG10, TMEM25 and/or LSR fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gp120). The "partner" is optionally selected to provide a soluble dimer/multimer and/or for one or more other biological activities as described herein.

A "dimerization domain" is formed by the association of at least two amino acid residues or of at least two peptides or polypeptides (which may have the same, or different, amino acid sequences). The peptides or polypeptides may interact with each other through covalent and/or non-covalent associations). Optional dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a further embodiment, the dimerization domain is the hinge region of an immunoglobulin.

Additional exemplary dimerization domains can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), and/or the yeast transcriptional activator GCN4, SH2 (src homology 2), SH3 (src Homology 3) (Vidal, et al, Biochemistry, 43, 7336-44 ((2004)), phosphotyrosine binding (PTB) (Zhou, et al., Nature, 378:584-592 (1995)), WW (Sudol, Prog, Biochys. Mol. Bio., 65:113-132 (1996)), PDZ (Kim, et al., Nature, 378: 85-88 (1995); Komau, et al, Science, 269.1737-1740 (1995)) 14-3-3, WD40 (Hu5 et al., J Biol. Chem., 273, 33489-33494 (1998)) EH, Lim, an isoleucine zipper, a receptor dimer pair (e.g., interleukin-8 receptor (IL-8R); and integrin heterodimers such as LFA-I and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., J Biol. Chem., 269(45): 27833-27839 (1994) and Radziejewski, et al., Biochem., 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et at, J. Biol Chem, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-I and TSP-2) or five (TSP-3, TSP-4 and TSP-5) chains are connected, or from COMP (COMPcc) (Guo, et at., EMBO J, 1998, 17: 5265-5272) which folds into a parallel five-stranded coiled coil (Malashkevich, et al., Science, 274: 761-765 (1996)). Additional non limiting examples of coiled-coil domains derived from other proteins, and other domains that mediate polypeptide multimerization are known in the art such as the vasodialator-stimulated phosphoprotein (VASP) domain, matrilin-1 (CMP), viral fusion peptides, soluble NSF (N-ethylmaleimide-sensitive factor) Attachment Protein receptor (SNARE) complexes, leucine-rich repeats, certain tRNA synthetases, are suitable for use in the disclosed fusion proteins.

In another embodiment, LY6G6F, VSIG10, TMEM25 and/or LSR polypeptides, fusion proteins, or fragments thereof can be induced to form multimers by binding to a second multivalent polypeptide, such as an antibody. Antibodies suitable for use to multimerize LY6G6F, VSIG10, TMEM25 and/or LSR polypeptides, fusion proteins, or fragments thereof include, but are not limited to, IgM antibodies and cross-linked, multivalent IgG, IgA, IgD, or IgE complexes.

Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers. Fusion protein dimers as disclosed herein are of formula II: N-R1-R2-R3-C
N—R4-R5-R6-C or, alternatively, are of formula III: N—R1-R2-R3-C
C—R4-R5-R6-N wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "R1", "R2" and "R3" are as defined above with respect to formula I. With respect to both formula II and formula III, "R4" is a LY6G6F, VSIG10, TMEM25 and/or LSR polypeptide or a second polypeptide, "R5" is an optional peptide/polypeptide linker domain, and "R6" is a LY6G6F, VSIG10, TMEM25 and/or LSR polypeptide or a second polypeptide, wherein "R6" is a LY6G6F, VSIG10, TMEM25 and/or LSR polypeptide when "R4" is a second polypeptide, and "R6'" is a second polypeptide when "R4" is a LY6G6F, VSIG10, TMEM25 and/or LSR polypeptide. In one embodiment, "R1" is a LY6G6F, VSIG10, TMEM25 and/or LSR polypeptide, "R4" is also a LY6G6F, VSIG10, TMEM25 and/or LSR polypeptide, and "R3" and "R6" are both second polypeptides.

Fusion protein dimers of formula II are defined as homodimers when "R1"="R4", "R2"="R5" and "R3"="R6". Similarly, fusion protein dimers of formula III are defined as homodimers when "R1"="R6", "R2"="R5" and "R3"="R4". Fusion protein dimers are defined as heterodimers when these conditions are not met for any reason. For example, heterodimers may contain domain orientations that meet these conditions (i.e., for a dimer according to formula II, "R1" and "R4" are both LY6G6F, VSIG10, TMEM25 and/or LSR polypeptides, "R2" and "R5" are both peptide/polypeptide linker domains and "R3" and "R6" are both second polypeptides), however the species of one or more of these domains is not identical. For example, although "R3" and "R6" may both be LY6G6F, VSIG10, TMEM25 and/or LSR polypeptides, one polypeptide may contain a wild-type LY6G6F, VSIG10, TMEM25 and/or LSR amino acid sequence while the other polypeptide may be a variant LY6G6F, VSIG10, TMEM25 and/or LSR polypeptide. An exemplary variant LY6G6F, VSIG10, TMEM25 and/or LSR polypeptide is LY6G6F, VSIG10, TMEM25 and/or LSR polypeptide that has been modified to have increased or decreased binding to a target cell, increased activity on immune cells, increased or decreased half life or stability. Dimers of fusion proteins that contain either a CHI or CL region of an immunoglobulin as part of the polypeptide linker domain preferably form heterodimers wherein one fusion protein of the dimer contains a CHI region and the other fusion protein of the dimer contains a CL region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers. The fusion protein is optionally produced in dimeric form; more preferably, the fusion is performed at the genetic level as described below, by joining polynucleotide sequences corresponding to the two (or more) proteins, portions of proteins and/or peptides, such that a joined or fused protein is produced by a cell according to the joined polynucleotide sequence. A description of preparation for such fusion proteins is described with regard to U.S. Pat. No. 5,851,795 to Linsley et al, which is hereby incorporated by reference as if fully set forth herein as a non-limiting example only.

Targeting Domains

The LY6G6F, VSIG10, TMEM25 and/or LSR polypeptides and fusion proteins can contain a targeting domain to target the molecule to specific sites in the body. Optional targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-1 on the vascular epithelium. Additional targeting domains can be peptide aptamers specific for a proinflammatory molecule. In other embodiments, the LY6G6F, VSIG10, TMEM25 and/or LSR fusion protein can include a binding partner specific for a polypeptide displayed on the surface of an immune cell, for example a T cell. In still other embodiments, the targeting domain specifically targets activated immune cells. Optional immune cells that are targeted include Th0, Th1, Th 17, Th2 and Th22 T cells, other cells that secrete, or cause other cells to secrete inflammatory molecules including, but not limited to, IL-1 beta, TNF-alpha, TGF-beta, IFN-gamma, IL-17, IL-6, IL-23, IL-22, IL-21, and MMPs, and Tregs. For example, a targeting domain for Tregs may bind specifically to CD25. The above changes are intended as illustrations only of optional changes and are not meant to be limiting in any way. Furthermore, the above explanation is provided for descriptive purposes only, without wishing to be bound by a single hypothesis.

Addition of Groups

If a protein according to the present invention is a linear molecule, it is possible to place various functional groups at various points on the linear molecule which are susceptible to or suitable for chemical modification. Functional groups can be added to the termini of linear forms of the protein according to at least some embodiments of the invention. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions according to at least some embodiments of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are optionally independently an aliphatic, substituted aliphatic, benzyl, substituted benzyl, aryl or a substituted aryl group. In addition, taken together with the nitrogen atom, R$_2$ and R$_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687

(1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R, 3S)-methyl-phenylalanine and (2R,3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Protein Chemical Modifications

In the present invention any part of a protein according to at least some embodiments of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins according to at least some embodiments of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins according to at least some embodiments of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins according to at least some embodiments of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Use

As used herein "therapeutic agent" is any one of the LY6G6F, VSIG10, TMEM25 and/or LSR proteins and polypeptides according to at least some embodiments of the present invention, or orthologs, or fragments thereof, especially the ectodomain or secreted forms of LY6G6F, VSIG10, TMEM25 and/or LSR proteins, and/or fusion protein, and/or multimeric protein containing same, or nucleic acid sequence or fragments thereof of LY6G6F, VSIG10, TMEM25 and/or LSR, as well as drugs which specifically bind to the LY6G6F, VSIG10, TMEM25 and/or LSR proteins, and/or drugs which agonize or antagonize the binding of other moieties to the LY6G6F, VSIG10, TMEM25 and/or LSR proteins, and/or drugs which modulate (agonize or antagonize) at least one LY6G6F, VSIG10, TMEM25 and/or LSR related biological activity. Such drugs include monoclonal and/or polyclonal antibodies, and/or antigen binding fragments, and/or conjugates containing same, and/or alternative scaffolds, thereof comprising an antigen binding site that binds specifically to any one of the LY6G6F, VSIG10, TMEM25 and/or LSR polypeptides or an epitope thereof. Such drugs by way of example also include small molecules, peptides, ribozymes, aptamers, antisense molecules, siRNA's and the like.

Stimulation of activity of LY6G6F, VSIG10, TMEM25 and/or LSR is desirable in situations in which LY6G6F, VSIG10, TMEM25 and/or LSR is abnormally downregulated, and/or situations in which increased activity of LY6G6F, VSIG10, TMEM25 and/or LSR is likely to have a beneficial effect. Likewise, inhibition of activity of LY6G6F, VSIG10, TMEM25 and/or LSR is desirable in situations in which LY6G6F, VSIG10, TMEM25 and/or LSR is abnormally upregulated, and/or situations in which decreased activity of LY6G6F, VSIG10, TMEM25 and/or LSR is likely to have beneficial effect.

As mentioned herein above, the therapeutic agents can be used to treat immune related disorders as recited herein, and/or autoimmune disorders as recited herein, and/or infectious disorders as recited herein, and/or cancer as recited herein and/or for blocking and/or promoting immune costimulation mediated by any one of the LY6G6F, VSIG10, TMEM25 and/or LSR polypeptides.

According to an additional aspect of the present invention the therapeutic agents can be used to prevent pathologic inhibition of T cell activity, such as that directed against cancer cells or chronic infections; and/or prevent pathologic stimulation of T cell activity, such as that directed against autoantigens in autoimmune diseases. For example, these molecules can be administered to cells in culture, in vitro or ex vivo, or to human subjects, e.g., in vivo, to treat, prevent and to diagnose a variety of disorders. Preferred subjects include human patients, having disorders mediated by cells expressing the LY6G6F, VSIG10, TMEM25 and/or LSR protein, and cells that possess LY6G6F, VSIG10, TMEM25 and/or LSR activity.

According to an additional aspect of the present invention the therapeutic agents can be used to inhibit T cell activation, as can be manifested for example by T cell proliferation and cytokine secretion.

According to an additional aspect of the present invention the therapeutic agents can be used to elicit in vivo or in vitro one or more of the following biological activities: to inhibit the growth of and/or kill a cell expressing LY6G6F, VSIG10, TMEM25 and/or LSR; to mediate phagocytosis or ADCC of a cell expressing LY6G6F, VSIG10, TMEM25 and/or LSR in the presence of human effector cells, or to block LY6G6F, VSIG10, TMEM25 and/or LSR ligand binding to LY6G6F, VSIG10, TMEM25 and/or LSR, respectively.

Thus, according to an additional aspect of the present invention there is provided a method of treating immune related disorders as recited herein, and/or autoimmune disorders as recited herein, and/or infectious disorders as recited herein, and/or cancer as recited herein, and/or for blocking or promoting immune stimulation mediated by the LY6G6F, VSIG10, TMEM25 and/or LSR polypeptide in a subject by administering to a subject in need thereof an effective amount of any one of the therapeutic agents and/or a pharmaceutical composition comprising any of the therapeutic agents and further comprising a pharmaceutically acceptable diluent or carrier.

The subject according to the present invention is a mammal, preferably a human which is diagnosed with one of the disease, disorder or conditions described hereinabove, or alternatively is predisposed to at least one type of cancer and/or infectious disorders, and/or immune related disorder.

As used herein the term "treating" refers to preventing, delaying the onset of, curing, reversing, attenuating, alleviating, minimizing, suppressing or halting the deleterious effects of the above-described diseases, disorders or conditions. It also includes managing the disease as described above. By "manage" it is meant reducing the severity of the disease, reducing the frequency of episodes of the disease, reducing the duration of such episodes, reducing the severity of such episodes and the like.

Treating, according to the present invention, can be effected by specifically upregulating the expression of at least one of the polypeptides of the present invention in the subject.

It will be appreciated that treatment of the above-described diseases according to the present invention may be combined with other treatment methods known in the art (i.e., combination therapy). Thus the therapeutic agents and/or a pharmaceutical composition comprising same, as recited herein, according to at least some embodiments of the present invention can also be used in combination with one or more of the following agents to regulate an immune response: soluble gp39 (also known as CD40 ligand (CD40L), CD154, T-BAM, TRAP), soluble CD29, soluble CD40, soluble CD80 (e.g. ATCC 68627), soluble CD86, soluble CD28 (e.g. 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g. ATCC HB-10916, ATCC HB-12055 and ATCC HB-12056), antibodies reactive with CD40 (e.g. ATCC HB-9110), antibodies reactive with B7 (e.g. ATCC HB-253, ATCC CRL-2223, ATCC CRL-2226, ATCC HB-301, ATCC HB-11341, etc), antibodies reactive with CD28 (e.g. ATCC HB-11944 or mAb 9.3), antibodies reactive with LFA-1 (e.g. ATCC HB-9579 and ATCC TIB-213), antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-1 (ATCC CRL-2252), ICAM-2 and ICAM-3), antibodies reactive with CTLA4 (e.g. ATCC HB-304), antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44; L104EA29YIg, CD80 monoclonal antibodies (mAbs), CD86 mAbs, gp39 mAbs, CD40 mAbs, CD28 mAbs; anti-LFA1 mAbs, antibodies or other agents targeting mechanisms of the immune system such as CD52 (alemtuzumab), CD25 (daclizumab), VLA-4 (natalizumab), CD20 (rituximab), IL2R (daclizumab) and MS4A1 (ocrelizumab); novel oral immunomodulating agents have shown to prevent lymphocyte recirculation from lymphoid organs such as fingolimod (FTY720) or leading to lymphocyte depletion such as mylinax (oral cladribine) or teriflunomide; and agents that prevent immunoactivation such as panaclar (dimethyl fumarate BG-12) or laquinimod (ABR216062). Other combinations will be readily appreciated and understood by persons skilled in the art. In some embodiments, the therapeutic agents can be used to attenuate or reverse the activity of a pro-inflammatory drug, and/or limit the adverse effects of such drugs.

As persons skilled in the art will readily understand, the combination can include the therapeutic agents and/or a pharmaceutical composition comprising same, according to at least some embodiments of the invention and one other immunosuppressive agent; the therapeutic agents and/or a pharmaceutical composition comprising same, as recited herein, with two other immunosuppressive agents, the therapeutic agents and/or a pharmaceutical composition comprising same, as recited herein, with three other immunosuppressive agents, etc. The determination of the optimal combination and dosages can be determined and optimized using methods well known in the art.

The therapeutic agent according to the present invention and one or more other therapeutic agents can be administered in either order or simultaneously. The other therapeutic agents are for example, a cytotoxic agent, a radiotoxic agent or an immunosuppressive agent. The composition can be linked to the agent (as an immunocomplex) or can be administered separately from the agent. In the latter case (separate administration), the composition can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days.

Co-administration of the human anti-LY6G6F, anti-VSIG10, anti-TMEM25 and/or anti-LSR antibodies, or antigen binding fragments thereof, according to at least some embodiments of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody. Target-specific effector cells, e.g., effector cells linked to compositions (e.g., human antibodies, multispecific and bispecific molecules) according to at least some embodiments of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of 10-8 to 10-9 but will vary depending on the therapeutic purpose. In general, the amount will be sufficient to obtain localization at the target cell, e.g., a tumor cell expressing LY6G6F, VSIG10, TMEM25 and/or LSR proteins, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) according to at least some embodiments of the invention and/or effector cells armed with these compositions can be used in conjunction with chemotherapy. Additionally, combination immunotherapy may be used to direct two distinct cytotoxic effector populations toward tumor cell rejection. For example, anti-LY6G6F, anti-VSIG10, anti-TMEM25 and/or anti-LSR antibodies linked to anti-Fc-gamma RI or anti-CD3 may be used in conjunction with IgG- or IgA-receptor specific binding agents.

Bispecific and multispecific molecules according to at least some embodiments of the invention can also be used to modulate FcgammaR or FcgammaR levels on effector cells, such as by capping and elimination of receptors on the cell surface. Mixtures of anti-Fc receptors can also be used for this purpose.

The invention also encompasses the use of the compositions according to at least some embodiments of the invention in combination with other pharmaceutical agents to treat immune system diseases. For example, autoimmune disease may be treated with molecules according to at least some embodiments of the invention in conjunction with, but not limited to, immunosuppressants such as corticosteroids, cyclosporin, cyclophosphamide, prednisone, azathioprine, methotrexate, rapamycin, tacrolimus, biological agents such as TNF-alpha blockers or antagonists, or any other biological agent targeting any inflammatory cytokine, nonsteroidal anti-inflammatory drugs/Cox-2 inhibitors, hydroxychloroquine, sulphasalazopryine, gold salts, etanercept, infliximab, mycophenolate mofetil, basiliximab, atacicept, rituximab, cytoxan, interferon beta-1a, interferon beta-1b, glatiramer acetate, mitoxantrone hydrochloride, anakinra and/or other biologics and/or intravenous immunoglobulin (IVIG). Non-limiting examples of such known therapeutics include interferons, such as IFN-beta-1a (REBIF®, AVONEX® and CINNOVEX®) and IFN-beta-1b (BETASERON®, EXTAVIA®, BETAFERON®, ZIFERON®); glatiramer acetate (COPAXONE®), a polypeptide; natalizumab (TYSABRI®); and mitoxantrone (NOVANTRONE®), a cytotoxic agent.

Thus, treatment of multiple sclerosis using the agents according to at least some embodiments of the present invention may be combined with, for example, any known therapeutic agent or method for treating multiple sclerosis. Non-limiting examples of such known therapeutic agent or method for treating multiple sclerosis include interferon class, IFN-beta-1a (REBIF®, AVONEX® and CINNOVEX®) and IFN-beta-1b (BETASERON®, EXTAVIA®, BETAFERON®, ZIFERON®); glatiramer acetate (COPAXONE®), a polypeptide; natalizumab (TYSABRI®); and mitoxantrone (NOVANTRONE®), a cytotoxic agent, Fampridine (AMPYRA®). Other drugs include corticosteroids, methotrexate, cyclophosphamide, azathioprine, and intravenous immunoglobulin (IVIG), inosine, Ocrelizumab (R1594), Mylinax (Caldribine), alemtuzumab (Campath), daclizumab (Zenapax), Panaclar/dimethyl fumarate (BG-12), Teriflunomide (HMR1726), fingolimod (FTY720), laquinimod (ABR216062), as well as Haematopoietic stem cell transplantation, Neurovax, Rituximab (Rituxan) BCG vaccine, low dose naltrexone, helminthic therapy, angioplasty, venous stents, and alternative therapy, such as vitamin D, polyunsaturated fats, medical marijuana.

Thus, treatment of rheumatoid arthritis, using the agents according to at least some embodiments of the present invention may be combined with, for example, any known therapeutic agent or method for treating rheumatoid arthritis. Non-limiting examples of such known therapeutic agents or methods for treating rheumatoid arthritis include glucocorticoids, nonsteroidal anti-inflammatory drug (NSAID) such as salicylates, or cyclooxygenase-2 inhibitors, ibuprofen and naproxen, diclofenac, indomethacin, etodolac Disease-modifying antirheumatic drugs (DMARDs)-Oral DMARDs: Auranofin (Ridaura), Azathioprine (Imuran), Cyclosporine (Sandimmune, Gengraf, Neoral, generic), D-Penicillamine (Cuprimine), Hydroxychloroquine (Plaquenil), IM gold Gold sodium thiomalate (Myochrysine) Aurothioglucose (Solganal), Leflunomide (Arava), Methotrexate (Rheumatrex), Minocycline (Minocin), Staphylococcal protein A immunoadsorption (Prosorba column), Sulfasalazine (Azulfidine). Biologic DMARDs: TNF-α blockers including Adalimumab (Humira), Etanercept (Enbrel), Infliximab (Remicade), golimumab (Simponi), certolizumab pegol (Cimzia), and other Biological DMARDs, such as Anakinra (Kineret), Rituximab (Rituxan), Tocilizumab (Actemra), CD28 inhibitor including Abatacept (Orencia) and Belatacept.

Thus, treatment of IBD, using the agents according to at least some embodiments of the present invention may be combined with, for example, any known therapeutic agent or method for treating IBD. Non-limiting examples of such known therapeutic agents or methods for treating IBD include immunosuppression to control the symptom, such as prednisone, Mesalazine (including Asacol, Pentasa, Lialda, Aspiro), azathioprine (Imuran), methotrexate, or 6-mercaptopurine, steroids, Ondansetron, TNF-α blockers (including infliximab, adalimumab golimumab, certolizumab pegol), Orencia (abatacept), ustekinumab (Stelara®), Briakinumab (ABT-874), Certolizumab pegol (Cimzia®), ITF2357 (givinostat), Natalizumab (Tysabri), Firategrast (SB-683699), Remicade (infliximab), vedolizumab (MLN0002), other drugs including GSK1605786 CCX282-B (Traficet-EN), AJM300, Stelara (ustekinumab), Semapimod (CNI-1493) tasocitinib (CP-690550), LMW Heparin MMX, Budesonide MMX, Simponi (golimumab), MultiStem®, Gardasil HPV vaccine, Epaxal Berna (virosomal hepatitis A vaccine), surgery, such as bowel resection, strictureplasty or a temporary or permanent colostomy or ileostomy; antifungal drugs such as nystatin (a broad spectrum gut antifungal) and either itraconazole (Sporanox) or fluconazole (Diflucan); alternative medicine, prebiotics and probiotics, *cannabis*, Helminthic therapy or ova of the *Trichuris suis* helminth.

Thus, treatment of psoriasis, using the agents according to at least some embodiments of the present invention may be combined with, for example, any known therapeutic agent or method for treating psoriasis. Non-limiting examples of such known therapeutics for treating psoriasis include topical agents, typically used for mild disease, phototherapy for moderate disease, and systemic agents for severe disease. Non-limiting examples of topical agents: bath solutions and moisturizers, mineral oil, and petroleum jelly; ointment and creams containing coal tar, dithranol (anthralin), corticosteroids like desoximetasone (Topicort), Betamethasone, fluocinonide, vitamin D3 analogues (for example, calcipotriol), and retinoids. Non-limiting examples of phototherapy: sunlight; wavelengths of 311-313 nm, psoralen and ultraviolet A phototherapy (PUVA). Non-limiting examples of systemic agents: Biologics, such as interleukin antagonists, TNF-α blockers including antibodies such as infliximab (Remicade), adalimumab (Humira), golimumab, certolizumab pegol, and recombinant TNF-α decoy receptor, etanercept (Enbrel); drugs that target T cells, such as efalizumab (Xannelim/Raptiva), alefacept (Ameviv), dendritic cells such Efalizumab; monoclonal antibodies (MAbs) targeting cytokines, including anti-IL-12/IL-23 (ustekinumab (brand name Stelara)) and anti-Interleukin-17; Briakinumab (ABT-874); small molecules, including but not limited to ISA247; Immunosuppressants, such as methotrexate, cyclosporine; vitamin A and retinoids (synthetic forms of vitamin A); and alternative therapy, such as changes in diet and lifestyle, fasting periods, low energy diets and vegetarian diets, diets supplemented with fish oil rich in Vitamin A and Vitamin D (such as cod liver oil), Fish oils rich in the two omega-3 fatty acids eicosapentaenoic acid (EPA) and docosahexaenoic acid (DHA) and contain Vitamin E. Ichthyotherapy, Hypnotherapy, *cannabis*.

Thus, treatment of type 1 diabetes, using the agents according to at least some embodiments of the present invention may be combined with, for example, any known therapeutic agent or method for treating type 1 diabetes. Non-limiting examples of such known therapeutics for treating type 1 diabetes include insulin, insulin analogs, islet transplantation, stem cell therapy including PROCHYMAL®, non-insulin therapies such as il-1 beta inhibitors including Anakinra (Kineret®), Abatacept (Orencia®), Diamyd, alefacept (Ameviv®), Otelixizumab, DiaPep277 (Hsp60 derived peptide), Alpha 1-Antitrypsin, Prednisone, azathioprine, Ciclosporin, E1-INT (an injectable islet neogenesis therapy comprising an epidermal growth factor analog and a gastrin analog), statins including Zocor®, Simlup®, Simcard®, Simvacor®, Sitagliptin (dipeptidyl peptidase (DPP-4) inhibitor), Anti-CD3 mAb (e.g., Teplizumab); CTLA4-Ig (abatacept), Anti IL-1 Beta (Canakinumab), Anti-CD20 mAb (e.g, rituximab).

Thus, treatment of uveitis, using the agents according to at least some embodiments of the present invention may be combined with, for example, any known therapeutic agent or method for treating uveitis. Non-limiting examples of such known therapeutics for treating uveitis include corticosteroids, topical cycloplegics, such as atropine or homatropine, or injection of PSTTA (posterior subtenon triamcinolone acetate), antimetabolite medications, such as methotrexate, TNF-α blockers (including infliximab, adalimumab, etanercept, golimumab, certolizumab pegol).

Thus, treatment for Sjogren's syndrome, using the agents according to at least some embodiments of the present invention may be combined with, for example, any known therapeutic agent or method for treating for Sjogren's syndrome. Non-limiting examples of such known therapeutics for treating for Sjogren's syndrome include Cyclosporine, pilocarpine (Salagen) and cevimeline (Evoxac), Hydroxychloroquine (Plaquenil), cortisone (prednisone and others) and/or azathioprine (Imuran) or cyclophosphamide (Cytoxan), Dexamethasone, Thalidomide, Dehydroepiandrosterone, NGX267, Rebamipide, FID 114657, Etanercept, Raptiva, Belimumab, MabThera (rituximab); Anakinra, intravenous immune globulin (IVIG), Allogeneic Mesenchymal Stem Cells (AlloMSC), Automatic neuro-electrostimulation by "Saliwell Crown".

Thus, treatment for systemic lupus erythematosus, using the agents according to at least some embodiments of the present invention may be combined with, for example, any known therapeutic agent or method for treating for systemic lupus erythematosus. Non-limiting examples of such known therapeutics for treating for systemic lupus erythematosus include corticosteroids and Disease-modifying antirheumatic drugs (DMARDs), commonly anti-malarial drugs such as plaquenil and immunosuppressants (e.g. methotrexate and azathioprine) Hydroxychloroquine, cytotoxic drugs (e.g., cyclophosphamide and mycophenolate), Hydroxychloroquine (HCQ), Benlysta (belimumab), nonsteroidal anti-inflammatory drugs, Prednisone, Cellcept, Prograf, Atacicept, Lupuzor, Intravenous Immunoglobulins (IVIGs), CellCept (mycophenolate mofetil), Orencia, CTLA4-IgG4m (RG2077), rituximab, Ocrelizumab, Epratuzumab, CNTO 136, Sifalimumab (MEDI-545), A-623 (formerly AMG 623), AMG 557, Rontalizumab, paquinimod (ABR-215757), LY2127399, CEP-33457, Dehydroepiandrosterone, Levothyroxine, abetimus sodium (LIP 394), Memantine, Opiates, Rapamycin, Renal transplantation, stem cell transplantation.

The therapeutic agents and/or a pharmaceutical composition comprising same, as recited herein, according to at least some embodiments of the invention, may be administered as the sole active ingredient or together with other drugs in immunomodulating regimens or other anti-inflammatory agents e.g. for the treatment or prevention of alto- or xenograft acute or chronic rejection or inflammatory or autoimmune disorders, or to induce tolerance.

For example, it may be used in combination with a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g. CTLA4-Ig (abatacept, ORENCIA® or belatacept), CD28-Ig, B7-H4-Ig, or other costimulatory agents, or adhesion molecule inhibitors, e.g. mAbs or low molecular weight inhibitors including LFA-1 antagonists, Selectin antagonists and VLA-4 antagonists.

Where the therapeutic agents and/or a pharmaceutical composition comprising same, as recited herein, according to at least some embodiments of the invention are administered in conjunction with other immunosuppressive/immunomodulatory or anti-inflammatory therapy, e.g. as herein above specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth.

Treatment of malignancies using the agents of the present invention may be combined with other treatment methods known in the art, one or more of, for example, radiation therapy, antibody therapy, chemotherapy, photodynamic therapy, surgery or in combination therapy with conventional drugs, such as immunosuppressants or cytotoxic drugs.

A therapeutic agent or pharmaceutical composition according to at least some embodiments of the present invention may also be administered in conjunction with other compounds or immunotherapies. For example, the combination therapy can include a compound of the present invention combined with at least one other therapeutic or immune modulatory agent, or immunostimulatory strategy, including, but not limited to, tumor vaccines, adoptive T cell therapy, Treg depletion, antibodies (e.g. bevacizumab, erbitux), pep-tides, pepti-bodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immunostimulatory antibodies, growth hormones or other cytokines, folic acid, vitamins, minerals, aromatase inhibitors, RNAi, Histone Deacetylase Inhibitors, proteasome inhibitors, and so forth.

According to at least some embodiments of the present invention, there is provided use of a combination of the therapeutic agents and/or a pharmaceutical composition comprising same, as recited herein, and a known therapeutic agent effective for treating infection.

The therapeutic agents and/or a pharmaceutical composition comprising same, as recited herein, can be administered in combination with one or more additional therapeutic agents used for treatment of bacterial infections, including, but not limited to, antibiotics including Aminoglycosides, Carbapenems, Cephalosporins, Macrolides, Lincosamides, Nitrofurans, penicillins, Polypeptides, Quinolones, Sulfonamides, Tetracyclines, drugs against mycobacteria including but not limited to Clofazimine, Cycloserine, Cycloserine, Rifabutin, Rifapentine, Streptomycin and other antibacterial drugs such as Chloramphenicol, Fosfomycin, Metronidazole, Mupirocin, and Tinidazole.

The therapeutic agents and/or a pharmaceutical composition comprising same, as recited herein, can be administered in combination with one or more additional therapeutic agents used for treatment of viral infections, including, but not limited to, antiviral drugs such as oseltamivir (brand name Tamiflu) and zanamivir (brand name Relenza) Arbidol—adamantane derivatives (Amantadine, Rimantadine)—neuraminidase inhibitors (Oseltamivir, Laninamivir, Peramivir, Zanamivir) nucleotide analog reverse transcriptase inhibitor including Purine analogue guanine (Aciclovir#/Valacyclovir, Ganciclovir/Valganciclovir, Penciclovir/Famciclovir) and adenine (Vidarabine), Pyrimidine analogue, uridine (Idoxuridine, Trifluridine, Edoxudine), thymine (Brivudine), cytosine (Cytarabine); Foscarnet; Nucleoside analogues/NARTIs: Entecavir, Lamivudine, Telbivudine, Clevudine; Nucleotide analogues/NtRTIs: Adefovir, Tenofovir; Nucleic acid inhibitors such as Cidofovir; InterferonInterferon alfa-2b, Peginterferon alfa-2a; Ribavirin#/Taribavirin; antiretroviral drugs including zidovudine, lamivudine, abacavir, lopinavir, ritonavir, tenofovir/emtricitabine, efavirenz each of them alone or a various combinations, gp41 (Enfuvirtide), Raltegravir, protease inhibitors such as Fosamprenavir, Lopinavir and Atazanavir, Methisazone, Docosanol, Fomivirsen, Tromantadine.

The therapeutic agents and/or a pharmaceutical composition comprising same, as recited herein, can be administered in combination with one or more additional therapeutic agents used for treatment of fungal infections, including, but not limited to, antifungal drugs of the Polyene antifungals, Imidazole, triazole, and thiazole antifungals, Allylamines, Echinocandins or other anti fungal drugs.

Alternatively or additionally, an upregulating method may optionally be effected by specifically upregulating the amount (optionally expression) in the subject of at least one of the polypeptides of the present invention or active portions thereof.

As is mentioned hereinabove and in the Examples section which follows, the biomolecular sequences of this aspect of the present invention may be used as valuable therapeutic tools in the treatment of diseases, disorders or conditions in which altered activity or expression of the wild-type gene product (known protein) is known to contribute to disease, disorder or condition onset or progression. For example, in case a disease is caused by overexpression of a membrane bound-receptor, a soluble variant thereof may be used as an antagonist which competes with the receptor for binding the ligand, to thereby terminate signaling from the receptor.

According to at least some embodiments, immune cells, preferably T cells, can be contacted in vivo or ex vivo with the therapeutic agents to modulate immune responses. The T cells contacted with the therapeutic agents can be any cell which expresses the T cell receptor, including α/β and γ/δ T cell receptors. T-cells include all cells which express CD3, including T-cell subsets which also express CD4 and CD8. T-cells include both naive and memory cells and effector cells such as CTL. T-cells also include cells such as Th1, Tc1, Th2, Tc2, Th3, Th17, Th22, Treg, and Tr1 cells. T-cells also include NKT-cells and similar unique classes of the T-cell lineage.

Inhibition of Epitope Spreading

Epitope spreading refers to the ability of B and T cell immune response to diversify both at the level of specificity, from a single determinant to many sites on an auto antigen, and at the level of V gene usage (Monneaux, F. et al., Arthritis & amp; Rheumatism, 46(6): 1430-1438 (2002). Epitope spreading is not restricted to systemic autoimmune disease. It has been described in T cell dependent organ specific diseases such as Diabetes mellitus type 1 and multiple sclerosis in humans, and EAE induced experimental animals with a variety of myelin proteins.

Epitope spreading involves the acquired recognition of new epitopes in the same self molecule as well as epitopes residing in proteins that are associated in the same macromolecular complex. Epitope spreading can be assessed by measuring delayed-type hypersensitivity (DTH) responses, methods of which are known in the art.

One embodiment provides a method for inhibiting or reducing epitope spreading in a subject by administering to the subject an effective amount of the therapeutic agents. In a further embodiment any one of the therapeutic agents inhibits epitope spreading in individuals with multiple sclerosis. Preferably, the therapeutic agents inhibit or block multiple points of the inflammation pathway.

Yet another embodiment provides a method for inhibiting or reducing epitope spreading in subjects with multiple sclerosis by administering to a subject an effective amount of the therapeutic agents to inhibit or reduce differentiation of, proliferation of, activity of, and/or cytokine production and/or secretion by Th1, Th17, Th22, and/or other cells that secrete, or cause other cells to secrete, inflammatory molecules, including, but not limited to, IL-1 beta, TNF-alpha, TGF-beta, IFN-gamma, IL-17, IL-6, IL-23, IL-22, IL-21, and MMPs.

Use of the Therapeutic Agents According to at Least Some Embodiments of the Invention as Adjuvant for Cancer Vaccination:

Immunization against tumor-associated antigens (TAAs) is a promising approach for cancer therapy and prevention, but it faces several challenges and limitations, such as tolerance mechanisms associated with self-antigens expressed by the tumor cells. Costimulatory molecules such as B7.1 (CD80) and B7.2 (CD86) have improved the efficacy of gene-based and cell-based vaccines in animal models and are under investigation as adjuvant in clinical trials. This adjuvant activity can be achieved either by enhancing the costimulatory signal or by blocking inhibitory signal that is transmitted by negative costimulators expressed by tumor cells (Neighbors et al., 2008 J Immunother.; 31(7):644-55). According to at least some embodiments of the invention, any one of LY6G6F, VSIG10, TMEM25 and/or LSR secreted or soluble form or ECD and/or variants, and/or orthologs, and/or conjugates thereof, and/or a polyclonal or monoclonal antibody and/or antigen binding fragments and/or conjugates containing same, and/or alternative scaffolds, specific to any one of LY6G6F, VSIG10, TMEM25 and/or LSR proteins, can be used as adjuvant for cancer vaccination. According to at least some embodiments, the invention provides methods for improving immunization against TAAs, comprising administering to a patient an effective amount of any one of LY6G6F, VSIG10, TMEM25 and/or LSR secreted or soluble form or ECD and/or variants, and/or orthologs, and/or conjugates thereof, and/or a polyclonal or monoclonal antibody and/or antigen binding fragments and/or conjugates containing same, and/or alternative scaffolds, specific to any one of LY6G6F, VSIG10, TMEM25 and/or LSR proteins.

Use of the Therapeutic Agents According to at Least Some Embodiments of the Invention for Adoptive Immunotherapy:

One of the cardinal features of some models of tolerance is that once the tolerance state has been established, it can be perpetuated to naive recipients by the adoptive transfer of donor-specific regulatory cells. Such adoptive transfer studies have also addressed the capacity of T-cell subpopulations and non-T cells to transfer tolerance. Such tolerance can be induced by blocking costimulation or upon engagement of a co-inhibitory B7 with its counter receptor. This approach, that have been successfully applied in animals and is evaluated in clinical trials in humans, (Scalapino K J and Daikh D I. PLoS One. 2009; 4(6):e6031; Riley et al., Immunity. 2009; 30(5): 656-665) provides a promising treatment option for autoimmune disorders and transplantation. According to at least some embodiments of the invention, LY6G6F, VSIG10, TMEM25 and/or LSR secreted or soluble form or ECD and/or variants, and/or orthologs, and/or conjugates thereof, and/or a polyclonal or monoclonal antibody and/or antigen binding fragments and/or conjugates containing same, and/or alternative scaffolds, specific to any one of LY6G6F, VSIG10, TMEM25 and/or LSR proteins are used for adoptive immunotherapy. Thus, according to at least some embodiments, the invention provides methods for in vivo or ex vivo tolerance induction, comprising administering effective amount of LY6G6F, VSIG10, TMEM25 and/or LSR secreted or soluble form or ECD and/or variants, and/or orthologs, and/or conjugates thereof, and/or a polyclonal or monoclonal antibody or and/or antigen binding fragments and/or conjugates containing same, and/or alternative scaffolds, specific to any one of LY6G6F, VSIG10, TMEM25 and/or LSR proteins, to a patient or to leukocytes isolated from the patient, in order to induce differentiation of tolerogenic regulatory cells; followed by ex-vivo enrichment and expansion of said cells and reinfusion of the tolerogenic regulatory cells to said patient.

Alternatively, immune responses can be enhanced in a patient by removing immune cells from the patient, contacting immune cells in vitro with an agent that inhibits LY6G6F, VSIG10, TMEM25 and/or LSR activity, and/or which inhibits the interaction of LY6G6F, VSIG10, TMEM25 and/or LSR with their natural binding partners, and reintroducing the in vitro stimulated immune cells into the patient. In another embodiment, a method of modulating immune responses involves isolating immune cells from a patient, transfecting them with a nucleic acid molecule encoding a form of LY6G6F, VSIG10, TMEM25 and/or LSR, such that the cells express all or a portion of the LY6G6F, VSIG10, TMEM25 and/or LSR polypeptide according to various embodiments of the present invention on their surface, and reintroducing the transfected cells into the patient. The transfected cells have the capacity to modulate immune responses in the patient.

Use of the Therapeutic Agents According to at Least Some Embodiments of the Invention for Immunoenhancement 1. Treatment of Cancer The therapeutic agents provided herein are generally useful in vivo and ex vivo as immune response-stimulating therapeutics. In general, the disclosed therapeutic agent compositions are useful for treating a subject having or being predisposed to any disease or disorder to which the subject's immune system mounts an immune response. The ability of therapeutic agents to modulate LY6G6F, VSIG10, TMEM25 and/or LSR immune signals enable a more robust immune response to be possible. The therapeutic agents according to at least some embodiments of the invention are useful to stimulate or enhance immune responses involving immune cells, such as T cells.

The therapeutic agents according to at least some embodiments of the invention are useful for stimulating or enhancing an immune response in host for treating cancer by administering to a subject an amount of a therapeutic agent effective to stimulate T cells in the subject.

2. Use of the Therapeutic Agents in Vaccines

The therapeutic agents according to at least some embodiments of the invention, are administered alone or in combination with any other suitable treatment. In one embodiment the therapeutic agents can be administered in conjunction with, or as a component of a vaccine composition as described above. The therapeutic agents according to at least some embodiments of the invention can be administered prior to, concurrently with, or after the administration of a vaccine. In one embodiment the therapeutic agents is administered at the same time as administration of a vaccine.

Pharmaceutical Compositions

In another aspect, the present invention provides a composition, e.g., a pharmaceutical composition, containing one or a combination of the therapeutic agent, according to at least some embodiments of the invention.

Thus, the present invention features a pharmaceutical composition comprising a therapeutically effective amount of a therapeutic agent according to at least some embodiments of the present invention.

The pharmaceutical composition according to at least some embodiments of the present invention is further preferably used for the treatment of cancer, wherein the cancer may be non-metastatic, invasive or metastatic, treatment of immune related disorder and/or infectious disorder.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of agent according to the present invention that is effective to treat a disease or disorder in a mammal.

The therapeutic agents of the present invention can be provided to the subject alone, or as part of a pharmaceutical composition where they are mixed with a pharmaceutically acceptable carrier.

Pharmaceutical compositions according to at least some embodiments of the invention also can be administered in combination therapy, i.e., combined with other agents. For example, the combination therapy can include an anti-LY6G6F, anti-VSIG10, anti-TMEM25 and/or anti-LSR antibody or LY6G6F, VSIG10, TMEM25 and/or LSR modulating agent according to at least some embodiments of the present invention, such as a soluble polypeptide conjugate containing the ectodomain of the LY6G6F, VSIG10, TMEM25 and/or LSR antigen or a small molecule such as a peptide, ribozyme, aptamer, siRNA, or other drug that binds LY6G6F, VSIG10, TMEM25 and/or LSR, combined with at least one other therapeutic or immune modulatory agent.

A composition is said to be a "pharmaceutical acceptable carrier" if its administration can be tolerated by a recipient patient. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

Such compositions include sterile water, buffered saline (e.g., Tris-HCl, acetate, phosphate), pH and ionic strength and optionally additives such as detergents and solubulizing agents (e.g., Polysorbate 20, Polysorbate 80), antioxidants (e.g, ascorbic acid, sodium metabisulfite), preservatives (e.g., Thimersol, benzyl alcohol) and blulking substances (e.g., lactose, manitol). Non-aqueous solvents or vehicles may also be used as detailed below.

Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Depending on the route of administration, the active compound, i.e., soluble polypeptide conjugate containing the ectodomain of the LY6G6F, VSIG10, TMEM25 and/or LSR antigen, monoclonal or polyclonal antibodies and antigen binding fragments and conjugates containing same, and/or alternative scaffolds, that specifically bind any one of LY6G6F, VSIG10, TMEM25 and/or LSR proteins, or bispecific molecule, may be coated in a material to protect the compound from the action of acids and other natural conditions that may inactivate the compound. The pharmaceutical compounds according to at least some embodiments of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody according to at least some embodiments of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

For fusion proteins as described herein, optionally a similar dosage regimen is followed; alternatively, the fusion proteins may optionally be administered in an amount between 0.0001 to 100 mg/kg weight of the patient/day, preferably between 0.001 to 10.0 mg/kg/day, according to any suitable timing regimen. A therapeutic composition according to at least some embodiments of the invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 mug/ml and in some methods about 25-300 .mu.g/ml.

Alternatively, therapeutic agent can be administered as a sustained release formulation, in which case less frequent administration is required. Dosage and frequency vary depending on the half-life of the therapeutic agent in the patient. In general, human antibodies show the longest half life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of LY6G6F, VSIG10, TMEM25 and/or LSR soluble protein or LY6G6F, VSIG10, TMEM25 and/or LSR ectodomain or fusion protein containing same, or an anti-LY6G6F, anti-VSIG10, anti-TMEM25 and/or anti-LSR antibody according to at least some embodiments of the invention preferably results in a decrease in severity of disease symptoms, an increase in frequency and duration of disease symptom-free periods, an increase in lifepan, disease remission, or a prevention or reduction of impairment or disability due to the disease affliction. For example, for the treatment of LY6G6F, VSIG10, TMEM25 and/or LSR positive tumors, e.g., melanoma, cancers of liver, renal, brain, breast, colon, lung, ovary, pancreas, prostate, stomach, multiple myeloma and hematopoietic cancer, including but not limited to lymphoma (Hodgkin's and non Hodgkin's), acute and chronic lymphoblastic leukemia and acute and chronic myeloid leukemia.], a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject.

One of ordinary skill in the art would be able to determine a therapeutically effective amount based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intra-cerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In a specific embodiment, a protein, a therapeutic agent or a pharmaceutical composition according to at least some embodiments of the present invention can be administered intraperitoneally or intravenously.

Alternatively, an LY6G6F, VSIG10, TMEM25 and/or LSR specific antibody or other LY6G6F, VSIG10, TMEM25 and/or LSR drug or molecule and their conjugates and combinations thereof that modulates a LY6G6F, VSIG10, TMEM25 and/or LSR protein activity can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies, LY6G6F, VSIG10, TMEM25 and/or LSR soluble proteins, ectodomains, and/or fusion proteins, can be formulated to ensure proper distribution in vivo. For example, the blood-brain bather (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The anti-LY6G6F, anti-VSIG10, anti-TMEM25 and anti-LSR antibodies, according to at least some embodiments of the present invention, can be used as neutralizing antibodies. A Neutralizing antibody (Nabs), is an antibody that is capable of binding and neutralizing or inhibiting a specific antigen thereby inhibiting its biological effect, for example by blocking the receptors on the cell or the virus, inhibiting the binding of the virus to the host cell. NAbs will partially or completely abrogate the biological action of an agent by either blocking an important surface molecule needed for its activity or by interfering with the binding of the agent to its receptor on a target cell.

In yet another embodiment, immunoconjugates of the invention can be used to target compounds (e.g., therapeutic agents, labels, cytotoxins, radiotoxins immunosuppressants, etc.) to cells which have LY6G6F, VSIG10, TMEM25 and/or LSR cell surface receptors by linking such compounds to the antibody. Thus, the invention also provides methods for localizing ex vivo or in vivo cells expressing LY6G6F, VSIG10, TMEM25 and/or LSR (e.g., with a detectable label, such as a radioisotope, a fluorescent compound, an enzyme, or an enzyme co-factor). Alternatively, the immunoconjugates can be used to kill cells which have LY6G6F, VSIG10, TMEM25 and/or LSR cell surface receptors by targeting cytotoxins or radiotoxins to LY6G6F, VSIG10, TMEM25 and/or LSR antigen.

Diagnostic Uses of LY6G6f, VSIG10, TMEM25 and/or LSR Polypeptides and Corresponding Polynucleotides According to some embodiments, the sample taken from a subject (patient) to perform the diagnostic assay according to at least some embodiments of the present invention is selected from the group consisting of a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, synovial fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cells or tissues, wherein the cell or tissue can be obtained from an organ selected from, but not limited to lung, colon, ovarian and/or breast tissue; stool or a tissue sample, or any combination thereof. In some embodiments, the term encompasses samples of in vivo cell culture constituents. Prior to be subjected to the diagnostic assay, the sample can optionally be diluted with a suitable eluant.

In some embodiments, the phrase "marker" in the context of the present invention refers to a nucleic acid fragment, a peptide, or a polypeptide, which is differentially present in a sample taken from patients (subjects) having one of the herein-described diseases or conditions, as compared to a comparable sample taken from subjects who do not have one the above-described diseases or conditions.

In some embodiments, the phrase "differentially present" refers to differences in the quantity or quality of a marker present in a sample taken from patients having one of the herein-described diseases or conditions as compared to a comparable sample taken from patients who do not have one of the herein-described diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of each individual marker below.

In some embodiments, the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the term "diagnosis" refers to the process of identifying a medical condition or disease by its signs, symptoms, and in particular from the results of various diagnostic procedures, including e.g. detecting the expression of the nucleic acids or polypeptides according to at least some embodiments of the invention in a biological sample (e.g. in cells, tissue or serum, as defined below) obtained from an individual. Furthermore, as used herein the term "diagnosis" encompasses screening for a disease, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. The diagnostic procedure can be performed in vivo or in vitro.

In some embodiments, the phrase "qualitative" when in reference to differences in expression levels of a polynucleotide or polypeptide as described herein, refers to the presence versus absence of expression, or in some embodiments, the temporal regulation of expression, or in some embodiments, the timing of expression, or in some embodiments, any post-translational modifications to the expressed molecule, and others, as will be appreciated by one skilled in the art. In some embodiments, the phrase "quantitative" when in reference to differences in expression levels of a polynucleotide or polypeptide as described herein, refers to absolute differences in quantity of expression, as determined by any means, known in the art, or in other embodiments, relative differences, which may be statistically significant, or in some embodiments, when viewed as a whole or over a prolonged period of time, etc., indicate a trend in terms of differences in expression.

In some embodiments, the term "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

In some embodiments, the term "level" refers to expression levels of RNA and/or protein or to DNA copy number of a marker of the present invention.

Typically the level of the marker in a biological sample obtained from the subject is different (i.e., increased or decreased) from the level of the same marker in a similar sample obtained from a healthy individual (examples of biological samples are described herein).

Numerous well known tissue or fluid collection methods can be utilized to collect the biological sample from the subject in order to determine the level of DNA, RNA and/or polypeptide of the marker of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the marker can be determined and a diagnosis can thus be made.

Determining the level of the same marker in normal tissues of the same origin is preferably effected along-side to detect an elevated expression and/or amplification and/or a decreased expression, of the marker as opposed to the normal tissues.

In some embodiments, the term "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals).

In some embodiments, the term "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

In some embodiments, the term "detect" refers to identifying the presence, absence or amount of the object to be detected.

In some embodiments, the term "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxidase, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

In another embodiment, this invention provides a method for detecting the polypeptides of this invention in a biological sample, comprising: contacting a biological sample with an antibody specifically recognizing a polypeptide according to the present invention and detecting said interaction; wherein the presence of an interaction correlates with the presence of a polypeptide in the biological sample.

In some embodiments of the present invention, the polypeptides described herein are non-limiting examples of markers for diagnosing a disease and/or an indicative condition. Each marker of the present invention can be used alone or in combination, for various uses, including but not limited to, prognosis, prediction, screening, early diagnosis, determination of progression, therapy selection and treatment monitoring of a disease and/or an indicative condition.

In a related object the detected diseases will include cancers such as non-solid and solid tumors, sarcomas and hematological malignancies.

In another related object the detected diseases will include autoimmune disorders, rejection of any organ transplant and/or Graft versus host disease.

Each polypeptide/polynucleotide of the present invention can be used alone or in combination, for various uses, including but not limited to, prognosis, prediction, screening, early diagnosis, determination of progression, therapy selection and treatment monitoring of disease and/or an indicative condition, as detailed above.

Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

In some embodiments of the present invention, there are provided of methods, uses, devices and assays for the diagnosis of a disease or condition. Optionally a plurality of markers may be used with the present invention. The plurality of markers may optionally include a markers described herein, and/or one or more known markers. The plurality of markers is preferably then correlated with the disease or condition. For example, such correlating may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level.

Also alternatively, such correlating may optionally comprise determining a temporal change in at least one of the markers, and wherein the temporal change is used in the correlating step.

Also alternatively, such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Also alternatively, such correlating may optionally comprise determining whether a ratio of marker concentrations for two markers is outside a range and/or above or below a threshold. Optionally, if the ratio is above or below the threshold level and/or outside a range, the ratio correlates with the disease or condition.

Optionally, a combination of two or more these correlations may be used with a single panel and/or for correlating between a plurality of panels.

Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, etc., may be combined in a single assay or device. Markers may also be commonly used for multiple purposes by, for example, applying a different threshold or a different weighting factor to the marker for the different purposes.

In one embodiment, the panels comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those diseases that may feature one or more similar or identical symptoms.

In certain embodiments, one or more diagnostic or prognostic indicators are correlated to a condition or disease by merely the presence or absence of the indicators. In other embodiments, threshold levels of a diagnostic or prognostic indicators can be established, and the level of the indicators in a patient sample can simply be compared to the threshold levels. The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

According to at least some embodiments of the present invention, LY6G6F, VSIG10, TMEM25 and/or LSR protein, polynucleotide or a fragment thereof, may be featured as a biomarker for detecting disease and/or an indicative condition, as detailed above.

According to still other embodiments, the present invention optionally and preferably encompasses any amino acid sequence or fragment thereof encoded by a nucleic acid sequence corresponding to LY6G6F, VSIG10, TMEM25 and/or LSR as described herein. Any oligopeptide or peptide relating to such an amino acid sequence or fragment thereof may optionally also (additionally or alternatively) be used as a biomarker.

In still other embodiments, the present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described below.

The present invention also relates to kits based upon such diagnostic methods or assays. Also within the scope of the present invention are kits comprising the LY6G6F, VSIG10, TMEM25 and/or LSR protein or LY6G6F, VSIG10, TMEM25 and/or LSR conjugates or antibody compositions of the invention (e.g., human antibodies, bispecific or multi-specific molecules, or immunoconjugates) and instructions for use. The kit can further contain one or more additional reagents, such as an immunosuppressive reagent, a cytotoxic agent or a radiotoxic agent, or one or more additional human antibodies according to at least some embodiments of the invention (e.g., a human antibody having a complementary activity which binds to an epitope in the antigen distinct from the first human antibody).

Nucleic Acid Technology (Nat) Based Assays:

Detection of a nucleic acid of interest in a biological sample may also optionally be effected by NAT-based assays, which involve nucleic acid amplification technology, such as PCR for example (or variations thereof such as real-time PCR for example). As used herein, a "primer" defines an oligonucleotide which is capable of annealing to (hybridizing with) a target sequence, thereby creating a double stranded region which can serve as an initiation point for DNA synthesis under suitable conditions. Amplification of a selected, or target, nucleic acid sequence may be carried out by a number of suitable methods known in the art. Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Non-limiting examples of Nucleic Acid Technology-based assay is selected from the group consisting of a PCR, Real-Time PCR, LCR, Self-Sustained Synthetic Reaction, Q-Beta Replicase, Cycling probe reaction, Branched DNA, RFLP analysis, DGGE/TGGE, Single-Strand Conformation Polymorphism, Dideoxy fingerprinting, microarrays, Fluorescense In Situ Hybridization and Comparative Genomic Hybridization. The terminology "amplification pair" (or "primer pair") refers herein to a pair of oligonucleotides (oligos) of the present invention, which are selected to be used together in amplifying a selected nucleic acid sequence by one of a number of types of amplification processes, preferably a polymerase chain reaction. As commonly known in the art, the oligos are designed to bind to a complementary sequence under selected conditions. In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. It will be realized by a person skilled in the art that such methods could be adapted for the detection of differentially expressed proteins instead of differentially expressed nucleic acid sequences. The nucleic acid (i.e. DNA or RNA) for practicing the present invention may be obtained according to well known methods.

Oligonucleotide primers of the present invention may be of any suitable length, depending on the particular assay format and the particular needs and targeted genomes employed. Optionally, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning-A Laboratory Manual, 2nd Edition, CSH Laboratories; Ausubel et al., 1989, in Current Protocols in Molecular Biology, John Wiley & Sons Inc., N.Y.).

Immunoassays

In another embodiment of the present invention, an immunoassay can be used to qualitatively or quantitatively detect and analyze markers in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support.

After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

The immunoassay can be used to determine a test amount of a marker in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Radio-immunoassay (RIA): In one version, this method involves precipitation of the desired substrate and in the methods detailed herein below, with a specific antibody and radiolabeled antibody binding protein (e.g., protein A labeled with 1125) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-Imaging Methods

These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Theranostics:

The term theranostics describes the use of diagnostic testing to diagnose the disease, choose the correct treatment regime according to the results of diagnostic testing and/or monitor the patient response to therapy according to the results of diagnostic testing. Theranostic tests can be used to select patients for treatments that are particularly likely to benefit them and unlikely to produce side-effects. They can also provide an early and objective indication of treatment efficacy in individual patients, so that (if necessary) the treatment can be altered with a minimum of delay. For example: DAKO and Genentech together created HercepTest and Herceptin (trastuzumab) for the treatment of breast cancer, the first theranostic test approved simultaneously with a new therapeutic drug. In addition to HercepTest (which is an immunohistochemical test), other theranostic tests are in development which use traditional clinical chemistry, immunoassay, cell-based technologies and nucleic acid tests. PPGx's recently launched TPMT (thiopurine S-methyltransferase) test, which is enabling doctors to identify patients at risk for potentially fatal adverse reactions to 6-mercaptopurine, an agent used in the treatment of leukemia. Also, Nova Molecular pioneered SNP genotyping of the apolipoprotein E gene to predict Alzheimer's disease patients' responses to cholinomimetic therapies and it is now widely used in clinical trials of new drugs for this indication. Thus, the field of theranostics represents the intersection of diagnostic testing information that predicts the response of a patient to a treatment with the selection of the appropriate treatment for that particular patient.

Surrogate Markers:

A surrogate marker is a marker, that is detectable in a laboratory and/or according to a physical sign or symptom on the patient, and that is used in therapeutic trials as a substitute for a clinically meaningful endpoint. The surrogate marker is a direct measure of how a patient feels, functions, or survives which is expected to predict the effect of the therapy. The need for surrogate markers mainly arises when such markers can be measured earlier, more conveniently, or more frequently than the endpoints of interest in terms of the effect of a treatment on a patient, which are referred to as the clinical endpoints. Ideally, a surrogate marker should be biologically plausible, predictive of disease progression and measurable by standardized assays (including but not limited to traditional clinical chemistry, immunoassay, cell-based technologies, nucleic acid tests and imaging modalities).

The therapeutic compositions (e.g., human antibodies, multispecific and bispecific molecules and immunoconjugates) according to at least some embodiments of the invention which have complement binding sites, such as portions from IgG1, -2, or -3 or IgM which bind complement, can also be used in the presence of complement. In one embodiment, ex vivo treatment of a population of cells comprising target cells with a binding agent according to at least some embodiments of the invention and appropriate effector cells can be supplemented by the addition of complement or serum containing complement. Phagocytosis of target cells coated with a binding agent according to at least some embodiments of the invention can be improved by binding of complement proteins. In another embodiment target cells coated with the compositions (e.g., human antibodies, multispecific and bispecific molecules) according to at least some embodiments of the invention can also be lysed by complement. In yet another embodiment, the compositions according to at least some embodiments of the invention do not activate complement.

The therapeutic compositions (e.g., human antibodies, multispecific and bispecific molecules and immunoconjugates) according to at least some embodiments of the invention can also be administered together with complement. Thus, according to at least some embodiments of the invention there are compositions, comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules according to at least some embodiments of the invention and the complement or serum can be administered separately.

The present invention is further illustrated by the following examples. This information and examples is illustrative and should not be construed as further limiting. The contents of all figures and all references, patents and published patent applications cited throughout this application are expressly incorporated herein by reference.

EXAMPLES

Example 1

Expression Pattern of the Proteins According to at Least Some Embodiments of The Invention Using MED Discovery Engine MED is a proprietary software platform for collection of public gene-expression data, normalization, annotation and performance of various queries. Expression data from the most widely used Affymetrix microarrays is downloaded from the Gene Expression Omnibus (GEO—www.ncbi.nlm.nih.gov/GEO). Data is multiplicatively normalized by setting the 95 percentile to a constant value (normalized expression=1200), and noise is filtered by setting the lower 30% to 0. Experiments are annotated, first automatically, and then manually, to identify tissue and condition, and chips are grouped according to this annotation, and cross verification of this grouping by comparing the overall expression pattern of the genes of each chip to the overall average expression pattern of the genes in this group. Each probeset in each group is assigned an expression value which is the median of the expressions of that probeset in all chips included in the group. The vector of expression of all probesets within a certain group forms the virtual chip of that group, and the collection of all such virtual chips is a virtual panel. The panel (or sub-panels) can be queried to identify probesets with a required behavior (e.g. specific expression in a sub-set of tissues, or differential expression between disease and healthy tissues). These probesets are linked to LEADS contigs and to RefSeqs (http://www.ncbi.nlm.nih.gov/RefSeq/) by probe-level mapping, for further analysis.

The Affymetrix platforms that are downloaded are HG-U95A and the HG-U133 family (A,B, A2.0 and PLUS 2.0). Three virtual panels were created: U95 and U133 Plus 2.0, based on the corresponding Affymetrix platforms, and U133 which uses the set of common probesets for HG-U133A, HG-U133A2.0 and HG-U133 PLUS 2.0+.

The results of the MED discovery engine are presented in scatter plots. The scatter plot is a compact representation of a given panel (collection of groups). The y-axis is the (normalized) expression and the x-axis describes the groups in the panel. For each group, the median expression is represented by a solid marker, and the expression values of the different chips in the group are represented by small dashes ("-"). The groups are ordered and marked as follows—"Other" groups (e.g. benign, non-cancer diseases, etc.) with a triangle, Treated cells with a square, Normal with a circle, Matched with a cross, and Cancer with a diamond. The number of chips in each group is also written adjacent to its name.

Figure 3A:
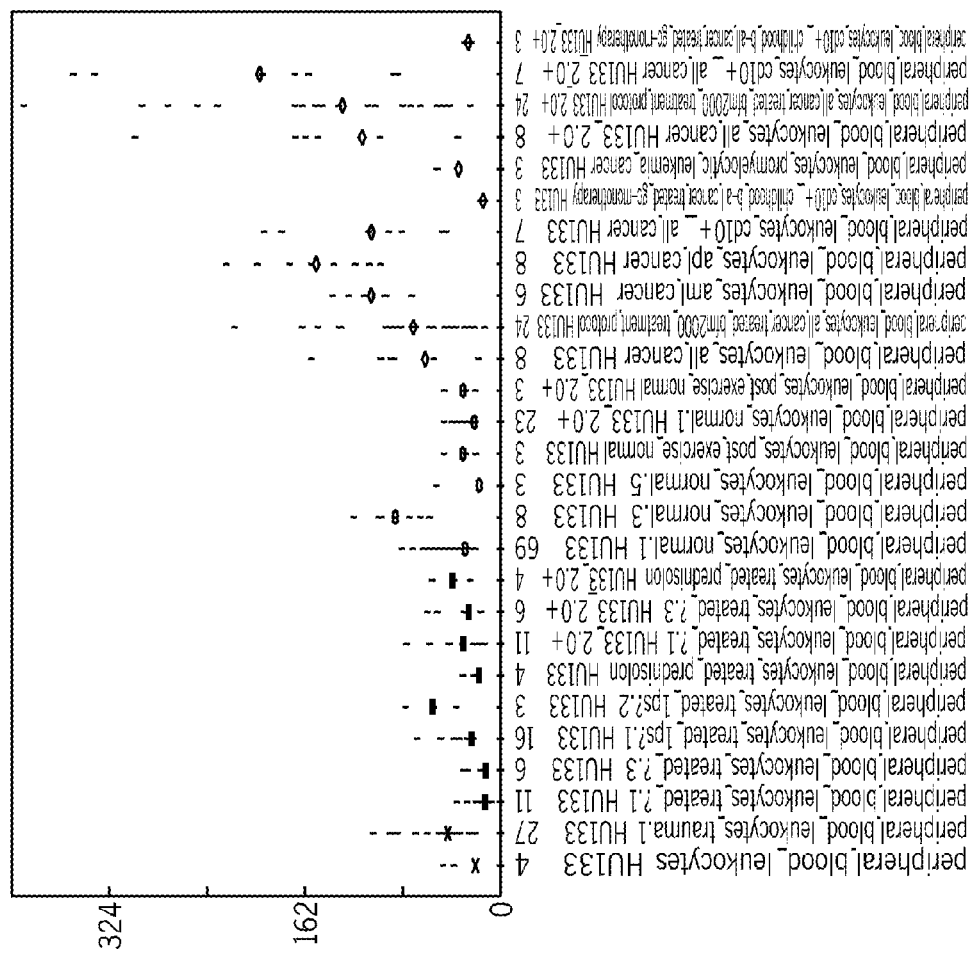
FIG. 3 shows a scatter plot, demonstrating the expression of VSIG10 transcripts, that encode the VSIG10 proteins, on a virtual panel of all tissues and conditions using MED discovery engine, demonstrating differential expression of VSIG10 transcripts in several groups of cells from the immune system, mainly in leukocytes, and in various cancer conditions, such as CD10+ leukocytes from ALL and BM-CD34+ cells from AML.
Figure 3B:
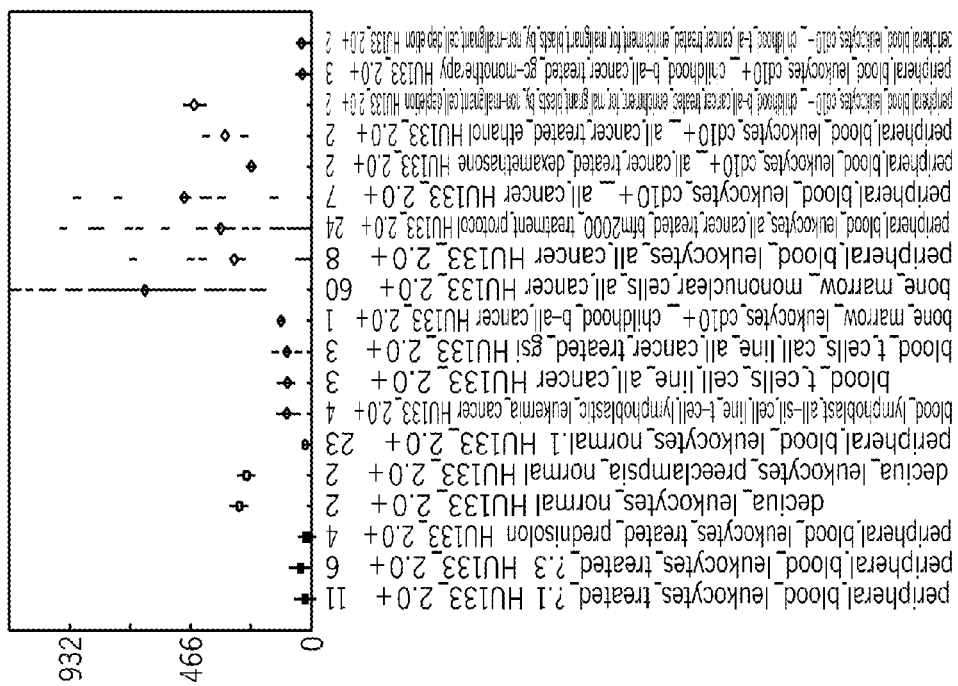

The MED discovery engine was used to assess the expression of VSIG10 transcripts. Expression data for Affymetrix probe sets 220137_at representing the VSIG10 gene data is shown in FIG. 3 (for all figures related to the MED discovery engine, a division was made into "A", "B", etc for reasons of space only, so as to be able to show all probe results). As evident from the scatter plot, presented in FIG. 3, the expression of VSIG10 transcripts detectable with the above probe sets was observed in several groups of cells from the immune system, mainly in leukocytes. In various cancer conditions, differential expression was observed, for example on CD10+ leukocytes from ALL (Acute Lymphoblastic Leukemia) and BM-CD34+ cells from AML (Acute Myeloid Leukemia) cells.

FIG. 3 shows a scatter plot, demonstrating the expression of VSIG10 transcripts that encode the VSIG10 proteins, on a virtual panel of all tissues and conditions using MED discovery engine.

MED discovery engine was used to assess the expression of LSR transcripts. Expression data for Affymetrix probe sets 208190_s_at representing the LSR gene data is shown in FIG. 4. As evident from the scatter plot, presented in FIG. 4, the expression of LSR transcripts detectable with the above probe sets was observed in several groups of cells from the immune system, mainly in bone marrow cells. High expression of LSR transcripts was also observed in various cancerous conditions of tissues, such as in breast, lung, ovary, pancreas, prostate and skin cancers.

FIG. 4 shows a scatter plot, demonstrating the expression of LSR transcripts that encode the LSR proteins, on a virtual panel of all tissues and conditions using MED discovery engine.

Example 2

Methods Used to Analyze the Expression of the RNA Encoding LY6G6F, VSIG10, TMEM25 and/or LSR Proteins The targets according to at least some embodiments of the present invention were tested with regard to their expression in various cancerous and non-cancerous tissue samples. A description of the samples used in the Ovary cancer testing panel is provided in Table 1 below. A description of the samples used in the Breast cancer testing panel is provided in Table 2 below. A description of the samples used in the Lung cancer testing panel is provided in Table 3. A description of the samples used in the Healthy testing panel is provided in Table 4. A description of the samples used in the Kidney cancer testing panel is provided in Table 5. A description of the samples used in the Liver cancer testing panel is provided in Table 6. Tests were then performed as described in the Materials and Methods section below.

Materials and Methods

RNA Preparation—

RNA was obtained from ABS (Wilmington, Del. 19801, USA, http://www.absbioreagents.com), BioChain Inst. Inc. (Hayward, Calif. 94545 USA, www.biochain.com), GOG for ovary samples—Pediatic Cooperative Human Tissue Network, Gynecologic Oncology Group Tissue Bank, Children Hospital of Columbus (Columbus Ohio 43205 USA), Ambion (Austin, Tex. 78744 USA, http://www.ambion-.com), Analytical Biological Services Inc. (Wilmington, Del. 19801 USA, www.absbioreagents.com), Asternad (Detroit, Mich. 48202-3420, USA, www.asterand.com), Genomics Collaborative Inc. a Division of Seracare (Cambridge, Mass. 02139, USA, www.genomicsinc.com), The Tel Aviv Sourasky Medical Center Ichilov Hospital (Tel-Aviv, ISRAEL, www.tasmc.org.il/e/) and from The Chaim Sheba Medical Center (Tel-Hashomer, ISRAEL, eng.sheba.co.il). RNA samples were obtained from patients or from postmortem. All total RNA samples were treated with DNaseI (Ambion).

RT-PCR for Ovary, Kidney and Healthy Panel—

10 ug of Purified RNA was mixed with Random Hexamer primers (Applied Biosystems, according to manufactures instructions), 4 mM dNTPs, 12.5 µl of 10× MultiScribe™ buffer (Applied Biosystems), 6 (50 U/µL) RNasin (Promega) and 6 µl (50 U/µL) of MultiScribe (Applied Biosystems) in a total volume of 125 µl. The reaction was incubated for 10 min at 25° C., followed by further incubation at 37° C. for 2 hours. Then, the mixture was inactivated at 85° C. for 5 sec. The resulting cDNA was diluted 1:10-1:40 (depend on the panel calibration) in TE buffer (10 mM Tris pH=8, 1 mM EDTA pH=8).

Real-Time RT-PCR analysis was carried out as described below—cDNA (5 µl), prepared as described above, was used as a template for Real-Time PCR reactions (final volume of 20 µl) using the SYBR Green I assay (PE Applied Biosystem) with specific primers and UNG Enzyme (Eurogentech or ABI or Roche). The amplification was effected as follows: 50° C. for 2 min, 95° C. for 10 min, and then 40 cycles of 95° C. for 15 sec, followed by 60° C. for 30 sec, following by dissociation step. Detection was performed using the PE Applied Biosystem SDS 7000. The cycle in which the reactions achieved a threshold level of fluorescence (Ct=Threshold Cycle, described in detail below) was registered and was used to calculate the relative transcript quantity in the RT reactions. The relative quantity was calculated using the equation Q=efficiency^-Ct. The efficiency of the PCR reaction was calculated from a standard curve, created by using different dilutions of several reverse transcription (RT) reactions. To minimize inherent differences in the RT reaction, the resulting relative quantities were normalized using a normalization factor calculated in the following way:

The expression of several housekeeping (HSKP) genes was checked in every panel. The relative quantity (Q) of each housekeeping gene in each sample, calculated as described above, was divided by the median quantity of this gene in all panel samples to obtain the "Relative Q rel to MED". Then, for each sample the median of the "relative Q rel to MED" of the selected housekeeping genes was calculated and served as normalization factor of this sample for further calculations.

For each RT sample, the expression of the specific amplicon was normalized to the normalization factor calculated from the expression of different housekeeping genes. Housekeeping genes (HSKG) used for Ovary, Kidney, Lung, Liver, Breast and Healthy panels are listed in Table 7.

The HSKGs that were used for Ovary and Healthy panels calibration are: HPRT1, SDHA and G6PD; The HSKP genes used for Kidney and Liver panel calibration are: G6PD, PBGD and SDHA; The HSKP genes used for Lung panel calibration are: UBC, PBGD, HPRT and SDHA; The HSKP genes used for Breast panel calibration are: G6PD, PBGD, RPL19 and SDHA;

TABLE 1

| Ovary RNA details: | | | | |
|---|---|---|---|---|
| sample name | Source | sample_id | DIAGNOSIS | CANCER_STAGE |
| 1-As-SI-SER | Asterand | 23074 | SEROUS ADENOCARCINOMA | STAGE I |
| 2-As-SI-SER | Asterand | 22653 | SEROUS ADENOCARCINOMA | STAGE I |
| 3-As-SIB-SER | Asterand | 18700 | SEROUS ADENOCARCINOMA | STAGE IB |
| 4-As-SIB-SER | Asterand | 17646 | SEROUS ADENOCARCINOMA | STAGE IB |
| 5-As-SIC-SER | Asterand | 15644 | SEROUS ADENOCARCINOMA | STAGE IC |
| 6-GC-SIIB-SER | GCI-1st_del | 7B3DP | SEROUS ADENOCARCINOMA | STAGE IIB |
| 7-As-SIIIC-SER | Asterand | 13268 | SEROUS ADENOCARCINOMA | STAGE IIIC |
| 8-GC-SIIIC-SER | GCI-1st_del | 3NTIS | SEROUS ADENOCARCINOMA | STAGE IIIC |
| 9-GC-SIIIC-SER | GCI-1st_del | CEJUS | SEROUS ADENOCARCINOMA | STAGE IIIC |
| 10-GC-SIIIC-SER | GCI-1st_del | 1HI5H | SEROUS ADENOCARCINOMA | STAGE IIIC |
| 11-GC-SIIIC-SER | GCI-1st_del | 7RMHZ | SEROUS ADENOCARCINOMA | STAGE IIIC |
| 12-GC-SIIIC-SER | GCI-1st_del | 4WAAB | SEROUS ADENOCARCINOMA | STAGE IIIC |
| 13-GC-SIIIC-SER | GCI-1st_del | 79Z67 | SEROUS ADENOCARCINOMA | STAGE IIIC |
| 14-GC-SIIIC-SER | GCI-1st_del | DDSNL | SEROUS ADENOCARCINOMA | STAGE IIIC |
| 15-GC-SIV-SER | GCI-1st_del | DH8PH | SEROUS ADENOCARCINOMA | STAGE IV |
| 16-GC-SIA-ENDO | GCI-1st_del | E2WKF | ENDOMETROID ADENOCARCINOMA | STAGE IA |
| 17-GC-SIA-ENDO | GCI-1st_del | HZ2EY | ENDOMETROID ADENOCARCINOMA | STAGE IA |
| 18-GC-SIA-ENDO | GCI-1st_del | RWOIV | ENDOMETROID ADENOCARCINOMA | STAGE IA |
| 19-GC-SIIA-ENDO | GCI-1st_del | 1U52X | ENDOMETROID ADENOCARCINOMA | STAGE IIA |
| 20-GC-SIIB-ENDO | GCI-1st_del | A17WS | ENDOMETROID ADENOCARCINOMA | STAGE IIB |
| 21-GC-SIIIC-ENDO | GCI-1st_del | 1VT3I | ENDOMETROID ADENOCARCINOMA | STAGE IIIC |
| 22-GC-SIIIC-ENDO | GCI-1st_del | PZQXH | ENDOMETROID ADENOCARCINOMA | STAGE IIIC |
| 23-GC-SIV-ENDO | GCI-1st_del | I8VHZ | ENDOMETROID ADENOCARCINOMA | STAGE IV |
| 24-GC-SIC-MUC | GCI-1st_del | IMDA1 | MUCINOUS ADENOCARCINOMA | STAGE IC |
| 25-As-SIC-MUC | Asterand | 12742 | MUCINOUS ADENOCARCINOMA | STAGE IC |
| 26-AB-SIC-MUC | ABS | A0139 | Mucinous cystadenocarcinoma | Stage IC |
| 27-AB-SIIIA-MUC | ABS | USA-00273 | Papillary mucinous cystadenocarcinoma | STAGE IIIA |
| 28-GC-SIIIA-MUC | GCI-2nd_del | RAFCW | MUCINOUS ADENOCARCINOMA | STAGE IIIA |
| 29-As-SIIIC-MUC | Asterand | 23177 | MUCINOUS ADENOCARCINOMA | STAGE IIIC |
| 30-As-SIIIC-MUC | Asterand | 16103 | MUCINOUS ADENOCARCINOMA | STAGE IIIC |
| 31-GC-SIA-BRD | GCI-3rd_del | SC656 | MUCINOUS BORDERLINE TUMOR | STAGE IA |
| 32-GC-SIA-BRD | GCI-3rd_del | 3D5FO | MUCINOUS BORDERLINE TUMOR | STAGE IA |
| 33-GC-SIA-BRD | GCI-3rd_del | 7JP3F | MUCINOUS BORDERLINE TUMOR | STAGE IA |
| 34-GC-Muc-BNG | GCI-1st_del | QLIKY | BENIGN MUCINOUS CYSTADENOMA | |
| 35-As-Muc-BNG | Asterand | 16870 | BENIGN MUCINOUS CYSTADENOMA | |
| 36-GC-Muc-BNG | GCI-1st_del | 943EC | BENIGN MUCINOUS CYSTADENOMA | |
| 37-GC-Muc-BNG | GCI-2nd_del | JO8W7 | BENIGN MUCINOUS CYSTADENOMA | |
| 38-As-Ser-BNG | Asterand | 17016 | BENIGN SEROUS CYSTADENOMA | IA |

TABLE 1-continued

Ovary RNA details:

| sample name | Source | sample_id | DIAGNOSIS | CANCER_STAGE |
|---|---|---|---|---|
| 39-GO-Ser-BNG | GOG | 99-06-G039 | BENIGN SEROUS CYSTADENOMA | |
| 40-GC-Ser-BNG | GCI-2nd_del | DQQ2F | BENIGN SEROUS CYSTADENOFIBROMA | |
| 41-As-BM-N | Asterand | 15690 | NORMAL OVARY-BM | |
| 42-As-BM-N | Asterand | 16850 | NORMAL OVARY-BM | |
| 43-As-BM-N | Asterand | 16848 | NORMAL OVARY-BM | |
| 44-GC-PS-N | GCI-4th_del | WPU1U | NORMAL OVARY-PS | |
| 45-GC-PS-N | GCI-4th_del | Y9VHI | NORMAL OVARY-PS | |
| 46-GC-PS-N | GCI-4th_del | 76VM9 | NORMAL OVARY-PS | |
| 47-GC-PS-N | GCI-1st_del | DWHTZ | NORMAL OVARY-PS | |
| 48-GC-PS-N | GCI-1st_del | SJ2R2 | NORMAL OVARY-PS | |
| 49-GC-PS-N | GCI-4th_del | 9RQMN | NORMAL OVARY-PS | |
| 50-GC-PS-N | GCI-1st_del | TOAE5 | NORMAL OVARY-PS | |
| 51-GC-PS-N | GCI-1st_del | TW9PM | NORMAL OVARY-PS | |
| 52-GC-PS-N | GCI-4th_del | 2VND2 | NORMAL OVARY-PS | |
| 53-GC-PS-N | GCI-1st_del | L629F | NORMAL OVARY-PS | |
| 54-GC-PS-N | GCI-1st_del | XLB23 | NORMAL OVARY-PS | |
| 55-GC-PS-N | GCI-1st_del | IDUVY | NORMAL OVARY-PS | |
| 56-GC-PS-N | GCI-4th_del | ZCXAD | NORMAL OVARY-PS | |
| 57-GC-PS-N | GCI-4th_del | PEQ6C | NORMAL OVARY-PS | |
| 58-GC-PS-N | GCI-1st_del | DD73B | NORMAL OVARY-PS | |
| 59-GC-PS-N | GCI-4th_del | E2UF7 | NORMAL OVARY-PS | |
| 60-GC-PS-N | GCI-4th_del | 4YG5P | NORMAL OVARY-PS | |
| 61-GC-PS-N | GCI-1st_del | FDPL9 | NORMAL OVARY-PS | |
| 62-Bc-PM-N | BioChain | A503274 | NORMAL OVARY-PM | |
| 63-Bc-PM-N | BioChain | A504086 | NORMAL OVARY-PM | |
| 64-Ic-PM-N | Ichilov | CG-188-7 | NORMAL OVARY-PM | |
| 65-GO-SIIIC-SER | GOG | 2001-12-G035 | Serous adenocarcinoma | Stage 3C |
| 66-AB-SIIIC-SER | ABS | N0021 | Papillary serous adenocarcinoma | Stage 3C |
| 67-BC-SER | BioChain | A503175 | Serous papillary cystadenocarcinoma | |
| 68-Bc-SER | Biochain | A406023 | Adenocarcinoma | |
| 69-Bc-SER | Biochain | A407068 | Adenocarcinoma | |
| 70-AB-SER | ABS | ILS-7286 | Papillary cystadenocarcinoma | UN |
| 71-AB-SER | ABS | A0106 | adenocarcinoma | UN |
| 72-AB-SER | ABS | ILS-1431 | Papillary adenocarcinoma | UN |
| 73-Bc-SER | BioChain | A503176 | Serous papillary cystadenocarcinoma | |
| 74-AB-SER | ABS | ILS-1408 | Papillary adenocarcinoma | UN |
| 75-Bc-SER | Biochain | A407069 | Adenocarcinoma | |
| 76-AB-SER | ABS | ILS-1406 | Papillary adenocarcinoma | UN |
| 77-GO-Ser Mix SIIIC-OTR | GOG | 2002-05-G509 | Mixed serous and endometrioid adenocarcinoma of mullerian | Stage3C |
| 78-Bc-MUC | BioChain | A504083 | Mucinous adenocarcinoma | |
| 79-Bc-MUC | BioChain | A504084 | Mucinous adenocarcinoma | |
| 80-Bc-Car-OTR | BioChain | A407065 | Carcinoma | |
| 81-GO-Clear cell SIIIA-OTR | GOG | 2001-10-G002 | Clear cell adenocarcinoma | Stage 3A |
| 82-AB-BRD | ABS | VNM-00187 | Mucinous cystadenocarcinoma with low malignant | |
| 83-GO-SIA-BRD | GOG | 98-08-G001 | Endometroid adenocarcinoma of borderline malignancy | Stage 1A |

TABLE 2

Breast RNA details:

| sample name | Source | sample_id | Sample DIAGNOSIS | CANCER_STAGE |
|---|---|---|---|---|
| 1-As-DCIS S0 | Asterand | 19723 | Ductal Carcinoma In Situ(DCIS) | STAGE 0 |
| 2-GC-IDC SI | GCI-1st_del | 5IRTK | INFILTRATING DUCTAL CARCINOMA | STAGE I |

TABLE 2-continued

Breast RNA details:

| sample name | Source | sample_id | Sample DIAGNOSIS | CANCER_STAGE |
|---|---|---|---|---|
| 3-(42)-AB-IDC SI | ABS | 6005020031T | INFILTRATING DUCTAL CARCINOMA | STAGE I |
| 4-(7)-AB-IDC SI | ABS | 7263T | INFILTRATING DUCTAL CARCINOMA | STAGE I |
| 5-GC-IDC SI | GCI-1st_del | DSI52 | INFILTRATING DUCTAL CARCINOMA | STAGE I |
| 6-GC-IDC SI | GCI-1st_del | S2GBY | INFILTRATING DUCTAL CARCINOMA | STAGE I |
| 7-GC-IDC SI | GCI-1st_del | POPHP | INFILTRATING DUCTAL CARCINOMA | STAGE I |
| 8-GC-IDC SI | GCI-1st_del | I2YLE | INFILTRATING DUCTAL CARCINOMA | STAGE I |
| 9-As-IDC SI | Asterand | 17959 | INFILTRATING DUCTAL CARCINOMA | STAGE I |
| 10-(12)-AB-IDC SIIA | ABS | 1432T | INFILTRATING DUCTAL CARCINOMA | STAGE IIA |
| 11-As-IDC SIIA | Asterand | 17138 | INFILTRATING DUCTAL CARCINOMA | STAGE IIA |
| 12-GC-IDC SIIA | GCI-1st_del | YSZ67 | INFILTRATING DUCTAL CARCINOMA | STAGE IIA |
| 13-(6)-AB-IDC SIIA | ABS | 7238T | INFILTRATING DUCTAL CARCINOMA | STAGE IIA |
| 14-(26)-AB-IDC SIIA | ABS | 7249T | INFILTRATING DUCTAL CARCINOMA | STAGE IIA |
| 15-GC-IDC SIIA | GCI-1st_del | UT3SE | INFILTRATING DUCTAL CARCINOMA | STAGE IIA |
| 16-GC-IDC SIIA | GCI-1st_del | PVSYX | INFILTRATING DUCTAL CARCINOMA | STAGE IIA |
| 17-GC-IDC SIIA | GCI-1st_del | GETCV | INFILTRATING DUCTAL CARCINOMA | STAGE IIA |
| 18-(27)-AB-IDC SIIA | ABS | 4907020072T | INFILTRATING DUCTAL CARCINOMA | STAGE IIA |
| 19-GC-IDC SIIB | GCI-1st_del | SE5BK | INFILTRATING DUCTAL CARCINOMA | STAGE IIB |
| 20-GC-IDC SIIB | GCI-1st_del | OLKL4 | INFILTRATING DUCTAL CARCINOMA | STAGE IIB |
| 21-GC-IDC SIIB | GCI-1st_del | VK1EJ | INFILTRATING DUCTAL CARCINOMA | STAGE IIB |
| 22-GC-IDC SIIB | GCI-1st_del | 3Z5Z4 | INFILTRATING DUCTAL CARCINOMA | STAGE IIB |
| 23-(13)-AB-IDC SIIB | ABS | A0133T | INFILTRATING DUCTAL CARCINOMA | STAGE IIB |
| 24-GC-IDC SIIB | GCI-1st_del | J5MPN | INFILTRATING DUCTAL CARCINOMA | STAGE IIB |
| 25-GC-IDC SIIB | GCI-1st_del | 54NTA | INFILTRATING DUCTAL CARCINOMA | STAGE IIB |
| 27-GC-IDC SIIIA | GCI-1st_del | RD3F9 | INFILTRATING DUCTAL CARCINOMA | STAGE IIIA |
| 28-(17)-AB-IDC SIIIA | ABS | 4904020036T | INFILTRATING DUCTAL CARCINOMA | STAGE IIIA |

TABLE 2-continued

Breast RNA details:

| sample name | Source | sample_id | Sample DIAGNOSIS | CANCER_STAGE |
| --- | --- | --- | --- | --- |
| 29-(16)-AB-IDC IIIA | ABS | 4904020032T | INFILTRATING DUCTAL CARCINOMA | STAGE IIIA |
| 30-(15)-AB-IDC SIIIA | ABS | 7259T | INFILTRATING DUCTAL CARCINOMA | STAGE IIIA |
| 31-GC-IDC SIIIA | GCI-1st_del | YOLOF | INFILTRATING DUCTAL CARCINOMA | STAGE IIIA |
| 32-GC-IDC SIIIB | GCI-1st_del | 4W2NY | INFILTRATING DUCTAL CARCINOMA | STAGE IIIB |
| 33-GC-IDC SIIIB | GCI-1st_del | YQ1WW | INFILTRATING DUCTAL CARCINOMA | STAGE IIIB |
| 34-GC-IDC SIIIB | GCI-1st_del | KIOE7 | INFILTRATING DUCTAL CARCINOMA | STAGE IIIB |
| 35-As-ILC SI | Asterand | 17090 | INFILTRATING LOBULAR CARCINOMA | STAGE I |
| 36-GC-ILC SIIA | GCI-1st_del | I35US | INFILTRATING LOBULAR CARCINOMA | STAGE IIA |
| 37-GC-ILC SIIB | GCI-1st_del | IS84Y | INFILTRATING LOBULAR CARCINOMA | STAGE IIB |
| 38-(52)-Bc-ILC | Biochain | A605360 | INFILTRATING LOBULAR CARCINOMA | |
| 39-As-BNG | Asterand | 11975 | FIBROADENOMA | |
| 40-GC-BNG | GCI-2nd_del | ZT15M | FIBROADENOMA | |
| 41-GC-BNG | GCI-2nd_del | NNP3Q | FIBROADENOMA | |
| 42-GC-BNG | GCI-2nd_del | QK8IY | FIBROADENOMA | |
| 43-GC-N PS | GCI-1st_del | 83LO7 | NORMAL BREAST-PS | |
| 45-GC-N PS | GCI-2nd_del | O6JBJ | NORMAL BREAST-PS | |
| 46-GC-N PS | GCI-2nd_del | E6UDD | NORMAL BREAST-PS | |
| 47-GC-N PS | GCI-1st_del | DHLR1 | NORMAL BREAST-PS | |
| 48-GC-N PS | GCI-2nd_del | JHQEH | NORMAL BREAST-PS | |
| 49-(63)-Am-N PS | Ambion | 26486 | NORMAL BREAST-PS | |
| 50-GC-N PS | GCI-2nd_del | ONBFK | NORMAL BREAST-PS | |
| 51-GC-N PS | GCI-1st_del | TG6J6 | NORMAL BREAST-PS | |
| 52-As-N PS | Asterand | 14398 | NORMAL BREAST-PS | |
| 54-GC-N PS | GCI-2nd_del | AJGXV | NORMAL BREAST-PS | |
| 56-GC-N PS | GCI-1st_del | HLCZX | NORMAL BREAST-PS | |
| 58-GC-N PS | GCI-1st_del | FGV8P | NORMAL BREAST-PS | |
| 59-As-N PS | Asterand | 9264 | NORMAL BREAST-PS | |
| 60-(57)-Bc-N PM | Biochain | A609233 | NORMAL BREAST-PM | |
| 61-(59)-Bc-N PM | Biochain | A607155 | NORMAL BREAST-PM | |
| 62-(60)-Bc-N PM | Biochain | A609234 | NORMAL BREAST-PM | |
| 63-(66)-Am-N PM | Ambion | 36678 | NORMAL BREAST-PM | |
| 64-(64)-Am-N PM | Ambion | 23036 | NORMAL BREAST-PM | |
| 66-(67)-Am-N PM | Ambion | 073P010602086A | NORMAL BREAST-PM | |

TABLE 2-continued

Breast RNA details:

| sample name | Source | sample_id | Sample DIAGNOSIS | CANCER_STAGE |
|---|---|---|---|---|
| 67-(58)-Bc-N PM | Biochain | A609232 | NORMAL BREAST-PM | |
| 68-As-N PM | Asterand | 8862 | NORMAL BREAST-PM | |
| 69-As-N PM | Asterand | 8457 | NORMAL BREAST-PM | |
| 70-(43)-Bc-IDC | Biochain | A609183 | INFILTRATING DUCTAL CARCINOMA | |
| 71-(54)-Bc-IDC | Biochain | A605353 | INFILTRATING DUCTAL CARCINOMA | |
| 72-(55)-Bc-IDC | ABS | A609179 | INFILTRATING DUCTAL CARCINOMA | |
| 73-(47)-Bc-IDC | Biochain | A609221 | INFILTRATING DUCTAL CARCINOMA | |
| 74-(48)-Bc-IDC | Biochain | A609222 | INFILTRATING DUCTAL CARCINOMA | |
| 75-(53)-Bc-IDC | Biochain | A605151 | INFILTRATING DUCTAL CARCINOMA | |
| 76-(61)-Bc-IDC | Biochain | A610029 | INFILTRATING DUCTAL CARCINOMA | |
| 77-(46)-Bc-Carci | Biochain | A609177 | Carcinoma | |
| 78-(62)-Bc-IDC | Biochain | A609194 | INFILTRATING DUCTAL CARCINOMA | |
| 79-(32)-AB-Muc Carci SIIA | Ambion | 7116T | Mucinous carcinoma | STAGE IIA |
| 80-(49)-Bc-IDC | Biochain | A609223 | INFILTRATING DUCTAL CARCINOMA | |
| 81-(45)-Bc-IDC | Biochain | A609181 | INFILTRATING DUCTAL CARCINOMA | |
| 82-(50)-Bc-IDC | Biochain | A609224 | INFILTRATING DUCTAL CARCINOMA | |
| 83-(44)-Bc-IDC | Biochain | A609198 | INFILTRATING DUCTAL CARCINOMA | |
| 84-(51)-Bc-IDC | Biochain | A605361 | INFILTRATING DUCTAL CARCINOMA | |
| 85-(31)-Ic-IDC | Ambion | CG-154 | INFILTRATING DUCTAL CARCINOMA | |

TABLE 3

Lung Panel RNA Details

| sample name | Source | sample_id | DIAGNOSIS | CANCER_STAGE |
|---|---|---|---|---|
| 1-GC-BAC-SIA | GCI-1st_del | 7Z9V4 | ADENOCARCINOMA | STAGE IA |
| 2-GC-BAC-SIB | GCI-1st_del | ZW2AQ | ADENOCARCINOMA | STAGE IB |
| 4-GC-Adeno-SIA | GCI-1st_del | 3MOPL | ADENOCARCINOMA | STAGE IA |
| 5-GC-Adeno-SIA | GCI-1st_del | KOJXD | ADENOCARCINOMA | STAGE IA |
| 6-GC-Adeno-SIA | GCI-1st_del | X2Q44 | ADENOCARCINOMA | STAGE IA |
| 8-GC-Adeno-SIA | GCI-1st_del | BS9AF | ADENOCARCINOMA | STAGE IA |
| 9-GC-Adeno-SIA | GCI-1st_del | UCLOA | ADENOCARCINOMA | STAGE IA |

TABLE 3-continued

| Lung Panel RNA Details | | | | |
|---|---|---|---|---|
| sample name | Source | sample_id | DIAGNOSIS | CANCER_STAGE |
| 10-GC-Adeno-SIA | GCI-1st_del | BVYK3 | ADENOCARCINOMA | STAGE IA |
| 11-GC-Adeno-SIB | GCI-1st_del | U4DM4 | ADENOCARCINOMA | STAGE IB |
| 12-GC-Adeno-SIB | GCI-1st_del | OWX5Y | ADENOCARCINOMA | STAGE IB |
| 13-GC-Adeno-SIIA | GCI-1st_del | XYY96 | ADENOCARCINOMA | STAGE IIA |
| 14-GC-Adeno-SIIA | GCI-1st_del | SO7B1 | ADENOCARCINOMA | STAGE IIA |
| 15-GC-Adeno-SIIIA | GCI-1st_del | QANSY | ADENOCARCINOMA | STAGE IIIA |
| 18-(76)-Bc-Adeno | Biochain | A609218 | ADENOCARCINOMA | |
| 19-As-Sq-S0 | Asterand | 9220 | Squamous Cell Carcinoma | Occult |
| 20-GC-Sq-SIA | GCI-1st_del | U2QHS | Squamous Cell Carcinoma | STAGE IA |
| 21-GC-Sq-SIB | GCI-2nd_del | TRQR7 | Squamous Cell Carcinoma | STAGE IB |
| 22-As-Sq-SIB | Asterand | 17581 | Squamous Cell Carcinoma | STAGE IB |
| 23-As-Sq-SIB | Asterand | 18309 | Squamous Cell Carcinoma | STAGE IB |
| 24-As-Sq-SIB | Asterand | 9217 | Squamous Cell Carcinoma | STAGE IB |
| 25-GC-Sq-SIIB | GCI-1st_del | RXQ1P | Squamous Cell Carcinoma | STAGE IIB |
| 26-GC-Sq-SIIB | GCI-1st_del | KB5KH | Squamous Cell Carcinoma | STAGE IIB |
| 27-GC-Sq-SIIIA | GCI-1st_del | LAYMB | Squamous Cell Carcinoma | STAGE IIIA |
| 30-(19)-Bc-Sq | Biochain | A408175 | Squamous Cell Carcinoma | |
| 31-(78)-Bc-Sq | Biochain | A607125 | Squamous Cell Carcinoma | |
| 33-(80)-Bc-Sq | Biochain | A609163 | Squamous Cell Carcinoma | |
| 34-(18)-Bc-Sq | Biochain | A503387 | Squamous Cell Carcinoma | |
| 35-(81)-Bc-Sq | Biochain | A609076 | Squamous Cell Carcinoma | |
| 36-GC-LCC-SIA | GCI-1st_del | AF8AL | LARGE CELL CARCINOMA | STAGE IA |
| 37-GC-LCC-SIB | GCI-1st_del | O62XU | LARGE CELL CARCINOMA | STAGE IB |
| 38-GC-LCC-SIB | GCI-2nd_del | OLOIM | LARGE CELL CARCINOMA | STAGE IB |
| 39-GC-LCC-SIIB | GCI-4th_del | 1ZWSV | LARGE CELL CARCINOMA | STAGE IIB |
| 41-GC-LCC-SIIB | GCI-1st_del | 38B4D | LARGE CELL CARCINOMA | STAGE IIB |
| 42-GC-SCC-SIB | GCI-1st_del | QPJQL | SMALL CELL CARCINOMA | STAGE IB |
| 43-(32)-Bc-SCC | Biochain | A501391 | SMALL CELL CARCINOMA | |
| 44-(30)-Bc-SCC | Biochain | A501389 | SMALL CELL CARCINOMA | |
| 45-(83)-Bc-SCC | Biochain | A609162 | SMALL CELL CARCINOMA | |
| 46-(86)-Bc-SCC | Biochain | A608032 | SMALL CELL CARCINOMA | |
| 47-(31)-Bc-SCC | Biochain | A501390 | SMALL CELL CARCINOMA | |
| 48-(84)-Bc-SCC | Biochain | A609167 | SMALL CELL CARCINOMA | |
| 49-(85)-Bc-SCC | Biochain | A609169 | SMALL CELL CARCINOMA | |
| 50-(33)-Bc-SCC | Biochain | A504115 | SMALL CELL CARCINOMA | |
| 51-As-N-PS | Asterand | 9078 | Normal lung | |
| 52-As-N-PM | Asterand | 8757 | Normal lung | |
| 53-As-N-PM | Asterand | 6692 | Normal lung | |
| 54-As-N-PM | Asterand | 7900 | Normal lung | |
| 55-As-N-PM | Asterand | 8771 | Normal lung | |
| 56-As-N-PM | Asterand | 13094 | Normal lung | |
| 57-As-N-PM | Asterand | 19174 | Normal lung | |
| 58-As-N-PM | Asterand | 13128 | Normal lung | |
| 59-As-N-PM | Asterand | 14374 | Normal lung | |
| 60-(99)-Am-N PM | Ambion | 36856 | Normal PM | |
| 61-(96)-Am-N PM | Ambion | 36853 | Normal PM | |
| 62-(97)-Am-N PM | Ambion | 36854 | Normal PM | |
| 63-(93)-Am-N PM | Ambion | 111P0103A | Normal PM | |
| 64-(98)-Am-N PM | Ambion | 36855 | Normal PM | |
| 69-(91)-Bc-N PM | Biochain | A607257 | Normal (Pool 2) PM | |
| 70-(90)-Bc-N PM | Biochain | A608152 | Normal (Pool 2) PM | |

TABLE 4

Healthy panel RNA Details:

| sample name | Source | Sample id |
|---|---|---|
| 1-Bc-Rectum | Biochain | A610297 |
| 2-Bc-Rectum | Biochain | A610298 |
| 3-GC-Colon | GCI | ZJ17R |
| 4-GC-Colon | GCI | YUZNR |
| 5-GC-Colon | GCI | 28QN6 |
| 6-Bc-Colon | Biochain | A501156 |
| 7-GC-Small bowel | GCI | V9L7D |
| 8-Bc-Esoph | Biochain | A603814 |
| 9-Bc-Esoph | Biochain | A603813 |
| 10-As-Panc | Asterand | 8918 |
| 11-As-Panc | Asterand | 10082 |
| 12-As-Liver | Asterand | 7916 |
| 13-GC-Kidney | GCI | N1EVZ |
| 14-GC-Kidney | GCI | BMI6W |
| 15-Bc-Adrenal | Biochain | A610374 |
| 16-Am-Lung | Ambion | 111P0103A |
| 17-Bc-Lung | Biochain | A503205 |
| 18-As-Lung | Asterand | 6692 |
| 19-As-Lung | Asterand | 7900 |
| 20-Am-Ovary | Asterand | 16848 |
| 21-GC-Ovary | GCI | Y9VHI |
| 22-GC-Ovary | GCI | DD73B |
| 23-GC-Ovary | GCI | FDPL9 |
| 24-GC-Cervix | GCI | E2P2N |
| 25-ABS-Bladder | ABS | 150300503 |
| 26-ABS-Bladder | ABS | 150700103 |
| 27-ABS-Bladder | ABS | 150700203 |
| 28-Am-Placen | Ambion | 021P33A |
| 29-Bc-Placen | Biochain | A411073 |
| 30-Am-Breast | Ambion | 26486 |
| 31-Am-Breast | Ambion | 23036 |
| 32-GC-Breast | GCI | E6UDD |
| 33-Bc-Breast | Biochain | A609234 |
| 34-Am-Prostate | Ambion | 25955 |
| 35-Bc-Prostate | Biochain | A609258 |
| 36-As-Testis | Asterand | 13071 |
| 37-As-Testis | Asterand | 19671 |
| 38-TH-Blood-PBMC | Tel-Hashomer | 52497 |
| 39-TH-Blood-PBMC | Tel-Hashomer | 31055 |
| 40-TH-Blood-PBMC | Tel-Hashomer | 31058 |
| 41-Ic-Spleen | Ichilov | CG-267 |
| 42-ABS-Spleen | ABS | 150800704 |
| 43-ABS-Spleen | ABS | 150800904 |
| 44-ABS-Spleen | ABS | 150801804 |
| 45-ABS-Thymus | ABS | 13066 |
| 46-ABS-Thymus | ABS | 13105 |
| 47-ABS-Thymus | ABS | 133968 |
| 48-Bc-Thyroid | Biochain | A610287 |
| 49-Ic-Thyroid | Ichilov | CG-119-2 |
| 50-GC-Sali gland | GCI | NNSMV |
| 51-Ic-Cerebellum | Ichilov | CG-183-5 |
| 52-Bc-Brain | Biochain | A411322 |
| 53-Bc-Brain | Biochain | A411079 |
| 54-ABS-Heart | ABS | 151101109 |
| 55-ABS-Heart | ABS | 352081026 |
| 56-ABS-Heart | ABS | 352JA02409 |
| 57-Ic-Heart (Fibrotic) | Ichilov | CG-255-9 |
| 58-GC-Skel Mus | GCI | T8YZS |
| 59-GC-Skel Mus | GCI | Q3WKA |
| 60-As-Skel Mus | Asterand | 8774 |
| 61-As-Skel Mus | Asterand | 10937 |
| 62-As-Skel Mus | Asterand | 6692 |
| 63-ABS-Skin | ABS | 151104009 |
| 64-ABS-Skin | ABS | 352MC01909 |
| 65-ABS-Skin | ABS | 150402309 |

TABLE 5

Kidney Panel RNA Details

| Sample Name | Source | Sample ID | Diagnosis | Cancer Stage |
|---|---|---|---|---|
| 1_AB_K_PM-N | ABS | ABS150303105 | Alzheimer's | |
| 2_AB_K_PM-N | ABS | ABS151200305 | Alzheimer's | |
| 3_AB_K_PM-N | ABS | ABS151201805 | Cardio Vascular Disease | |
| 4_AB_K_PM-N | ABS | ABS24724672102 | COPD | |
| 5_AB_K_RCC_ST2aN0MX | ABS | UH1003-29 | RCC | ST2aN0MX |
| 7_AS_K_RCC_ST3aN0M1 | Asterand | 52813 (1066748F-3152) | RCC | ST3aN0M1 |
| 8_AS_K_RCC_ST3NXM1 | Asterand | 52819 (1066176F-3152) | RCC | ST3NXM1 |
| 9_OR_K_RCC_ST4N1MX | Origene | CI0000011656 (1A26) | RCC | ST4N1MX |
| 10_OR_K_RCC_ST3aN0M1 | Origene | CU0000001623 (3714) | RCC | ST3aN0M1 |
| 11_OR_K_RCC_ST3N2M1 | Origene | CU0000009324 (1A1A) | RCC | ST3N2M1 |
| 12_OR_K_RCC_ST2NXMX | Origene | CX0000000190 (3D99) | RCC | ST2NXMX |
| 13_OR_K_RCC_ST2N0M1 | Origene | CU0000005834 (34DD) | RCC | ST2N0M1 |
| 14_OR_K_RCC_ST3bN0MX | Origene | CU0000000762 (374D) | RCC | ST3bN0MX |
| 15_OR_K_RCC_ST3NXMX | Origene | CI0000016503 (3743) | RCC | ST3NXMX |
| 16_OR_K_RCC_ST3aNXMX | Origene | CU0000001216 (3711) | RCC | ST3aNXMX |
| 17_AB_K_RCC_ST2N0MX | ABS | UH1002-14 | RCC | ST2N0MX |
| 18_AB_K_RCC_ST2bN0M1 | ABS | UH1007-18 | RCC | ST2bN0M1 |
| 19_AB_K_PM-N | ABS | ABS150400105 | ALS | |

TABLE 6

Liver Panel RNA Details

| Sample Name | Source | Sample ID | Diagnosis | Cancer Stage |
|---|---|---|---|---|
| 41_AB_L_PM-N | ABS | ABS151203707 | Alzheimer's | |
| 42_AB_L_PM-N | ABS | ABS151003509 | Dementia | |
| 43_AS_L_PM-N | Asterand | 49874 (1143071F-3152) | Respiratory arrest | |
| 44_AS_L_PM-N | Asterand | 50466 (1144029F-3152) | Unknown | |
| 45_AS_L_PM-N | Asterand | 50483 (1144465F-3152) | Cardiopulmonary arrest | |
| 46_AB_L_HCC_ST2N1MX | ABS | UH0603-43 | HCC | T2N1MX |
| 47_AB_L_HCC_ST3N0MX | ABS | UH0901-55 | HCC | T3N0MX |
| 48_AS_L_HCC_ST3N0M0 | Asterand | 51356 (1100251F-3152) | HCC | T3N0M0 |
| 49_AS_L_HCC_ST4NXMX | Asterand | 51365 (1100271F-3152) | HCC | T4NXMX |
| 50_AS_L_HCC_ST2N0M0 | Asterand | 52528 (1149074F-3152) | HCC | T2N0M0 |
| 51_OR_L_HCC_ST2N0MX | Origene | CI0000008358 (1A25) | HCC | T2N0MX |
| 52_OR_L_HCC_ST2NXMX | Origene | CI0000009200 (14B1) | HCC | T2NXMX |
| 53_OR_L_HCC_STXNXM1 | Origene | CI0000013002 (30B6) | HCC | TXNXM1 |
| 54_OR_L_HCC_ST3NXM1 | Origene | CI0000020838 (2445) | HCC | T3NXM1 |
| 55_OR_L_HCC_ST3NXMX | Origene | CU0000000996 (15F6) | HCC | T3NXMX |
| 56_OR_L_HCC_ST3NXMX | Origene | CU0000001197 (02DE) | HCC | T3NXMX |
| 57_OR_L_HCC_ST3NXMX | Origene | CI0000019267 (2441) | HCC | T3NXMX |
| 58_OR_L_HCC_ST2NXMX | Origene | CU0000005407 (0F2D) | HCC | T2NXMX |
| 59_OR_L_HCC_ST2NXMX | Origene | CU0000006675 (0F2E) | HCC | T2NXMX |

TABLE 7

Housekeeping Genes

| HSKG | Accession number | HSKG Seq ID | For primer seq ID | For primer sequence | Rev primer seq ID | Rev primer sequence | Amplicon seq id | Amplicon sequence |
|---|---|---|---|---|---|---|---|---|
| SDHA | NM_004168 | 103 | 104 | TGGGAACAAGAGGGCATCTG | 105 | CCACCACTGCATCAAATTCATG | 106 | TGGGAACAAGAGGGCATCTGCTAAAGTTTCAGATTCCATTTCTGCTCAGTATCCAGTAGTGGATCATGAATTTGATGCAGTGGTGG |
| HPRT1 | NM_000194 | 107 | 108 | TGACACTGGCAAAACAATGCA | 109 | GGTCCTTTTCACCAGCAAGCT | 110 | TGACACTGGCAAAACAATGCAGACTTTGCTTTCCTTGGTCAGGCAGTATAATCCAAAGATGGTCAAGGTCGCAAGCTTGCTGGTGAAAAGGACC |
| G6PD | NM_000402 | 111 | 112 | GAGGCCGTCACCAAGAACAT | 113 | GGACAGCCGGTCAGAGCTC | 114 | GAGGCCGTCACCAAGAACATTCACGAGTCCTGCATGAGCCAGATAGGCTGGAACCGCATCATCGTGGAGAAGCCCTTCGGGAGG |

TABLE 7 -continued

Housekeeping Genes

| HSKG | Accession number | HSKG Seq ID | For primer seq ID | For primer sequence | Rev primer seq ID | Rev primer sequence | Amplicon seq id | Amplicon sequence |
|---|---|---|---|---|---|---|---|---|
| | | | | | | | | GACCTGCAGAGC TCTGACCGGCTGT CC |
| UBC | BC000449 | 133 | 134 | ATTTGGG TCGCGGT TCTTG | 135 | TGCCTT GACATT CTCGAT GGT | 136 | ATTTGGGTCGCGG TTCTTGTTTGTGG ATCGCTGTGATCG TCACTTGACAATG CAGATCTTCGTGA AGACTCTGACTG GTAAGACCATCA CCCTCGAGGTTGA GCCCAGTGACAC CATCGAGAATGT CAAGGCA |
| RPL19 | NM_000981 | 119 | 120 | TGGCAAG AAGAAGG TCTGGTTA G | 121 | TGATCA GCCCAT CTTTGAT GAG | 122 | TGGCAAGAAGAA GGTCTGGTTAGAC CCCAATGAGACC AATGAAATCGCC AATGCCAACTCCC GTCAGCAGATCC GGAAGCTCATCA AAGATGGGCTGA TCA |
| PBGD | BC019323 | 115 | 116 | TGAGAGT GATTCGC GTGGG | 117 | CCAGGG TACGAG GCTTTC AAT | 118 | TGAGAGTGATTC GCGTGGGTACCC GCAAGAGCCAGC TTGCTCGCATACA GACGGACAGTGT GGTGGCAACATT GAAAGCCTCGTA CCCTGG |

Specific primers and amplicons used for expression analysis of LSR transcripts are provided in Table 8.

TABLE 8

LSR Primers and Amplicons

| Amplicon name | Amplicon SEQ ID NO | Amplicon sequence | Forward primer name | For primer SEQ ID NO | For primer sequence | Reverse primer name | Rev primer SEQ ID NO | Rev primer sequence |
|---|---|---|---|---|---|---|---|---|
| LSR_seg2 1-24_200- 307/308_ Amplicon | 137 | GTCACAAC CAGCTCAAT GCCCAGCTG GCAGCCGGG AACCCAGGC TACAACCCC TACGTC GAGTGCCAG GACAGCGTG CGCACCGTC AGGGTCGTG GCCACCAAG CAGGGCAAC GCTGTG ACCCTGGGA GATTACTAC CAGGGCCGG AGGATTACC ATCACCGGA AATGCTGAC CTGACC TT | LSR_seg 21F_ 200-307 | 138 | GTCGA CAACC AGCTC AATGC | LSR_seg2 4R_200- 308 | 139 | AAGGT CAGGT CAGCA TTTCC |

TABLE 8 -continued

LSR Primers and Amplicons

| Amplicon name | Amplicon SEQ ID NO | Amplicon sequence | Forward primer name | For primer SEQ ID NO | For primer sequence | Reverse primer name | Rev primer SEQ ID NO | Rev primer sequence |
|---|---|---|---|---|---|---|---|---|
| LSR_seg2 4-36_200- 309/310_ Amplicon | 140 | ATGCTGACC TGACCTTTGA CCAGACGGC GTGGGGGA CAGTGGTGT GTATTACTGC TCCG TGGTCTCAG CCCAGGACC TCCAGGGGA ACAATGAGG CCTACGCAG AGCTCATCG TCCTTG GGAGGACCT CAGGGGTGG CTGAGCTCTT ACCTGG | LSR_seg 24F_ 200-309 | 141 | ATGCT GACCT GACCT TTGAC | LSR_seg3 6R_200- 310 | 142 | CCAGG TAAGA GCTCA GCCAC |

Specific primers and amplicons used for expression analysis of TMEM25 transcript is provided in Table 9.

TABLE 9

TMEM25 primers and amplicons

| Amplicon name | Amplicon SEQ ID NO | Amplicon sequence | Forward primer name | For primer SEQ ID NO | For primer sequence | Reverse primer name | Rev primer SEQ ID NO | Rev primer sequence |
|---|---|---|---|---|---|---|---|---|
| TMEM25_ seg_21- 27_200- 344/346_ Amplicon | 123 | TTCACTGTCACT GCCCATCGGGCC CAGCATGAGCTC AACTGCTCTCTG CAGGACCCCAGA AGTGGCCGATCA GCCAACGCCTCT GTCATCCTTAAT GTGCAATTCAAG CCAGAGATTGCC CAAGTCGGCGCC AAGTACCAGGAA GCTCAGGGCCCA GGCCTCCTGGTT GTCCTGTTTGCC CTGGTG | TMEM25_ seg21F_ 200-344 | 124 | TTCA CTGT CACT GCCC ATCG G | TMEM25_ seg27R_ 200-346 | 125 | CACC AGGG CAAA CAGG ACAA C |

The expression data of LSR_seg24-36_200-309/310_Amplicon (SEQ ID:140) is described in Examples 3-9 below.

Example 3

Expression of LSR_ Transcripts which are Detectable by Amplicon as Depicted in Sequence Name LSR_Seg24-36_200-309/310 in Normal and Cancerous Ovary Tissues Expression of LSR transcripts detectable by or according to LSR_seg24-36_200-309/310_Amplicon (SEQ ID:140) and primers LSR_seg24F_200-309 (SEQ ID:141) and LSR_seg36R_200-310 (SEQ ID:142) was measured by real time PCR. Non-detected samples (sample(s) no. 28) were assigned Ct value of 41 and were calculated accordingly. In parallel the expression of several housekeeping genes—SDHA (SEQ ID:103) (GenBank Accession No. NM_004168; amplicon—SDHA_Amplicon (SEQ ID: 106)), HPRT1 (SEQ ID:107) (GenBank Accession No. NM_000194; HPRT1_Amplicon (SEQ ID:110)), and G6PD (SEQ ID:111) (GenBank Accession No. NM_000402; G6PD_Amplicon (SEQ ID:1114)) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the normal samples (sample numbers 41, 42, 43, 44, 45, 46, 47, 48, 49, 50, 51, 52, 53, 54, 55, 56, 57, 58, 59, 60, 61, 62, 63 and 64, Table 1 above), to obtain a value of fold up-regulation for each sample relative to median of the normal samples.

Figure 12A:
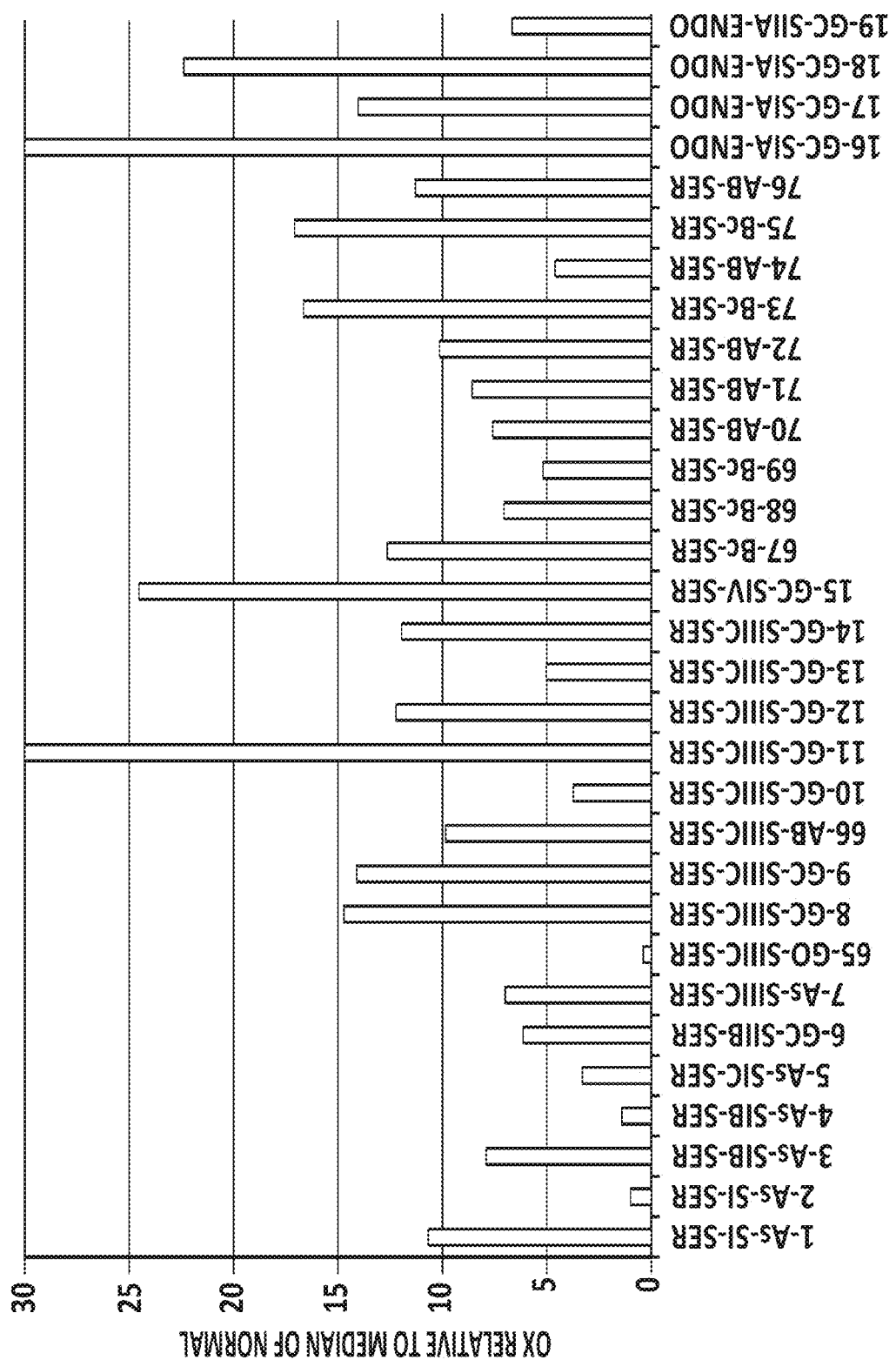
FIG. 12 is a histogram showing over expression of the LSR transcripts detectable by or according to LSR_seg24-36_200-309/310_Amplicon (SEQ ID:140) in cancerous ovary samples relative to the normal samples.
Figure 12B:
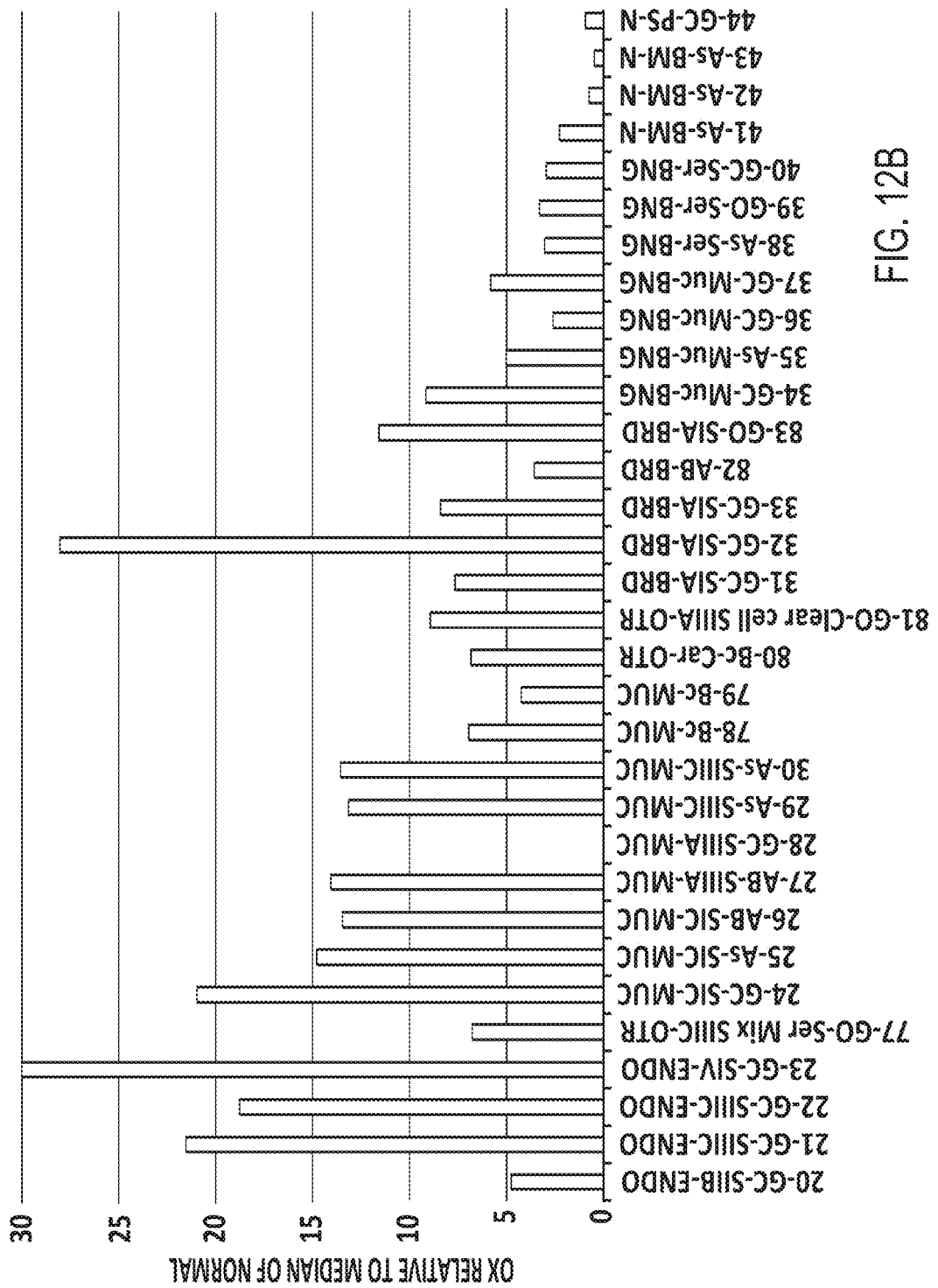
Figure 12C:
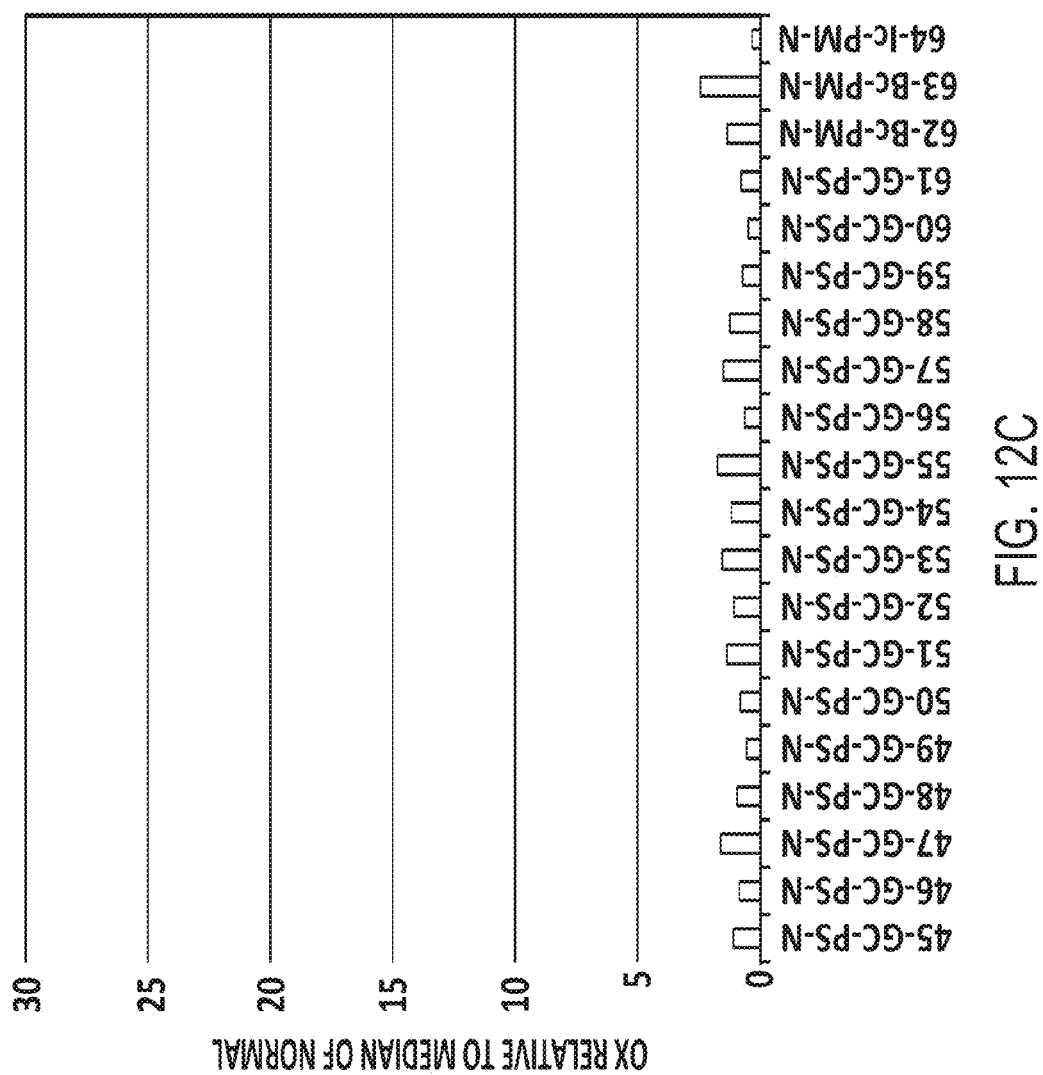

FIG. 12 is a histogram showing over expression of the above-indicated LSR transcripts in cancerous Ovary samples relative to the normal samples.

As is evident from FIG. 12, the expression of LSR transcripts detectable by the above amplicon in serous carcinoma, mucinous carcinoma and adenocarcinoma samples was significantly higher than in the non-cancerous samples (sample numbers 41, 42, 43, 44, 45, 46, 47, 48, 49, 50, 51, 52, 53, 54, 55, 56, 57, 58, 59, 60, 61, 62, 63 and 64, Table 1 above). Notably an over-expression of at least 5 fold was found in 21 out of 27 serous carcinoma samples, in 7 out of 9 mucinous carcinoma samples and in 7 out of 8 endometroid carcinoma samples.

Statistical analysis was applied to verify the significance of these results, as described below.

The P value for the difference in the expression levels of LSR transcripts detectable by the above amplicon in Ovary serous carcinoma samples versus the normal tissue samples was determined by T test as 2.22e-002. The P value for the difference in the expression levels of LSR transcripts detectable by the above amplicon in Ovary mucinous carcinoma samples versus the normal tissue samples was determined by T test as 6.84e-004. The P value for the difference in the expression levels of LSR transcripts detectable by the above amplicon in Ovary endometroid carcinoma samples versus the normal tissue samples was determined by T test as 4.61e-003. The P value for the difference in the expression levels of LSR transcripts detectable by the above amplicon in Ovary Adenocarcinoma samples versus the normal tissue samples was determined by T test as 5.68e-004.

Threshold of 5 fold over expression was found to differentiate between serous carcinoma and normal samples with P value of 2.59e-009 as checked by exact Fisher test. Threshold of 5 fold over expression was found to differentiate between mucinous carcinoma and normal samples with P value of 8.43e-006 as checked by exact Fisher test. Threshold of 5 fold over expression was found to differentiate between endometroid carcinoma and normal samples with P value of 2.38e-006 as checked by exact Fisher test. Threshold of 5 fold over expression was found to differentiate between Adenocarcinoma samples and normal samples with P value of 7.28e-012 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: LSR_seg24F_200-309 (SEQ ID:141); and LSR_seg36R_200-310 (SEQ ID:142).

The present invention also preferably encompasses any amplicon obtained through the use of any suitable primer pair; for example, for the above experiment, the following amplicon was obtained as a non-limiting illustrative example only of a suitable amplicon: LSR_seg24-36_200-309/310_Amplicon (SEQ ID:140).

Example 4

Expression of LSR_ Transcripts which are Detectable by Amplicon as Depicted in Sequence Name LSR_Seg24-36_200-309/310 in Normal and Cancerous Breast Tissues Expression of LSR transcripts detectable by or according to seg24-36FR—LSR_seg24-36_200-309/310_Amplicon (SEQ ID:140) and primers LSR_seg24F_200-309 (SEQ ID:141) and LSR_seg36R_200-310 (SEQ ID:142) was measured by real time PCR. Non-detected samples (sample(s) no. 81) were assigned Ct value of 41 and were calculated accordingly. In parallel the expression of several housekeeping genes—G6PD (SEQ ID:111) (GenBank Accession No. NM_000402; G6PD_Amplicon), PBGD (SEQ ID:115) (GenBank Accession No. BC019323; PBGD_Amplicon) RPL19 (SEQ ID:119) (GenBank Accession No. NM_000981RPL19_Amplicon) and SDHA (SEQ ID:103) (GenBank Accession No. NM_004168SDHA_Amplicon) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the normal samples (sample numbers 43, 45, 46, 47, 48, 49, 50, 51, 52, 54, 56, 58, 59, 60, 61, 62, 63, 64, 66, 67, 68 and 69, Table 2 above), to obtain a value of fold up-regulation for each sample relative to median of the normal samples.

Figure 13A:
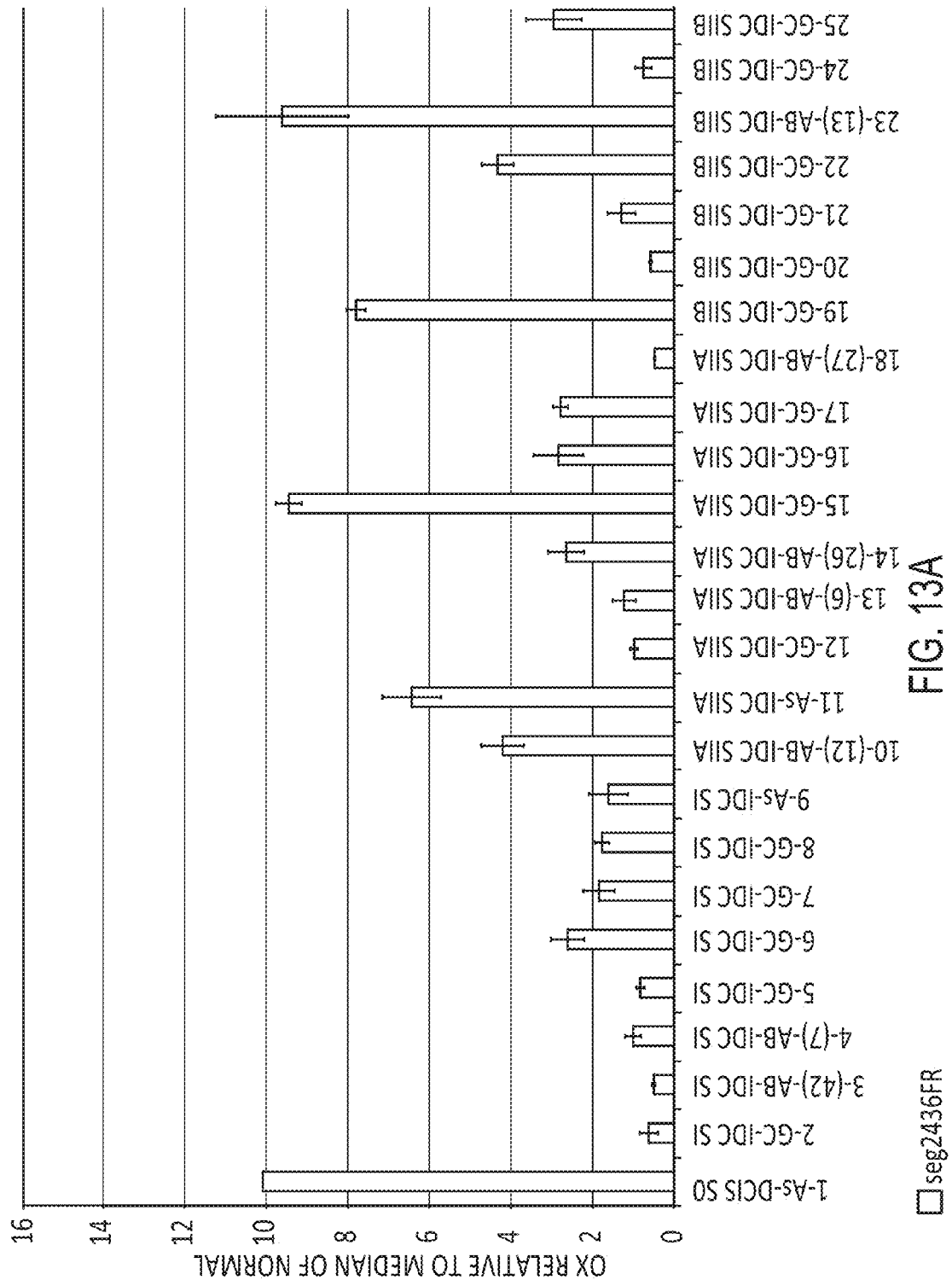
FIG. 13 is a histogram showing over expression of the LSR transcripts detectable by or according to LSR_seg24-36_200-309/310_Amplicon (SEQ ID:140) in cancerous breast samples relative to the normal samples.
Figure 13B:
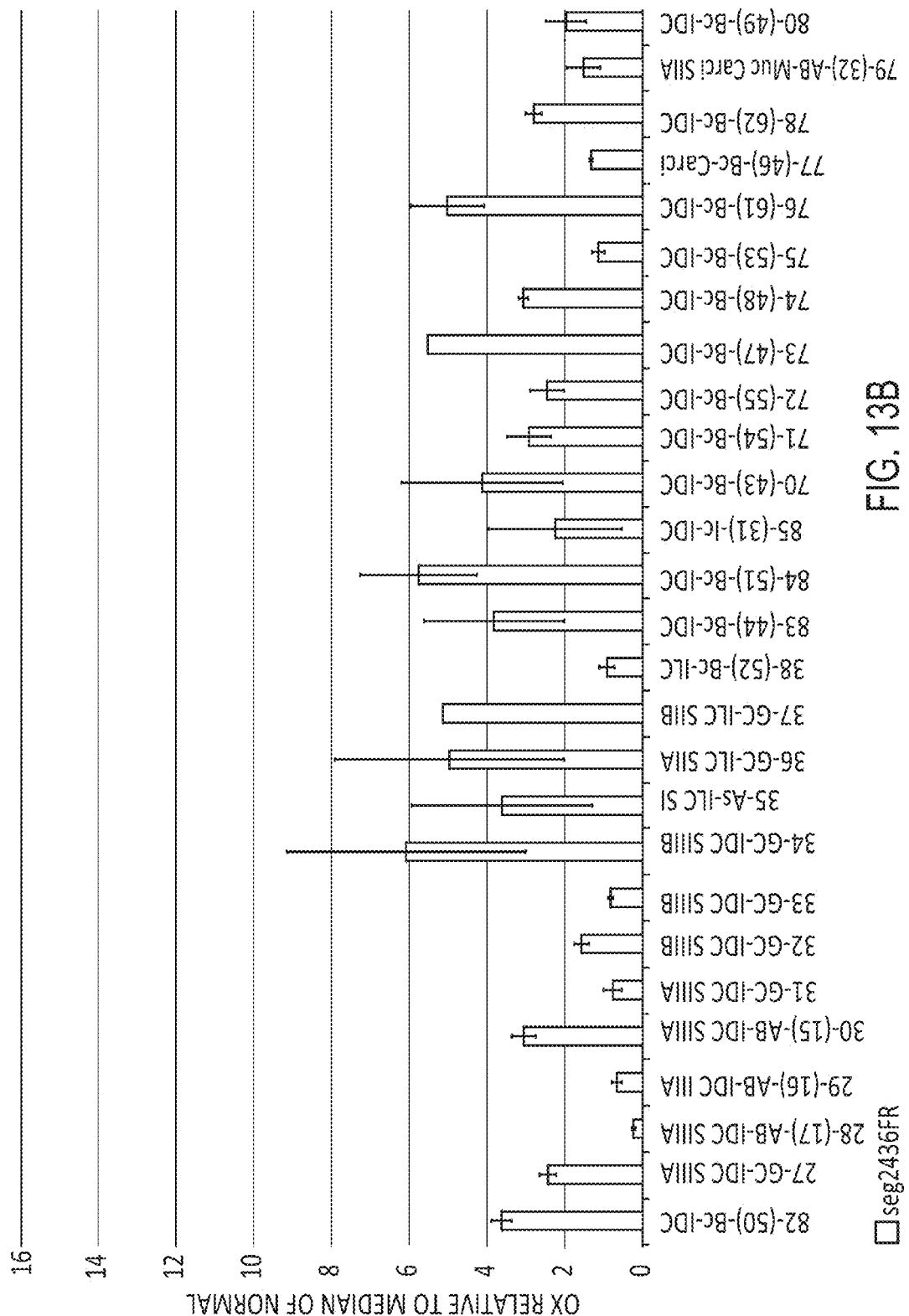
Figure 13C:
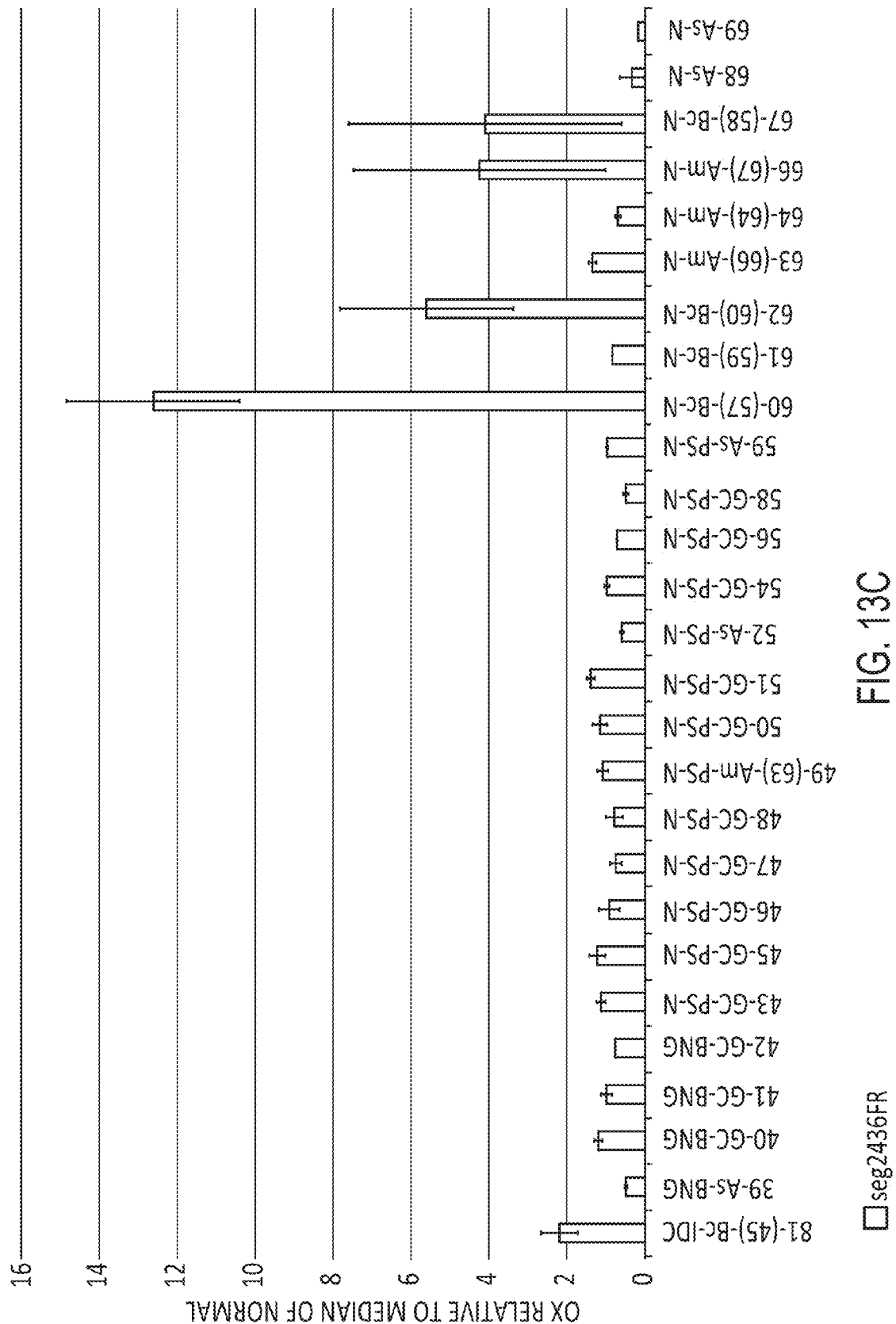

FIG. 13 is a histogram showing over expression of the above-indicated LSR transcripts in cancerous Breast samples relative to the normal samples.

As is evident from FIG. 13, the expression of LSR transcripts detectable by the above amplicon in cancer samples was higher than in the non-cancerous samples (sample numbers 43, 45, 46, 47, 48, 49, 50, 51, 52, 54, 56, 58, 59, 60, 61, 62, 63, 64, 66, 67, 68 and 69, Table 2 above). Notably an over-expression of at least 5 fold was found in 9 out of 53 adenocarcinoma samples.

Primer pairs are also optionally and preferably encompassed within the present invention; for example, for the above experiment, the following primer pair was used as a non-limiting illustrative example only of a suitable primer pair: LSR_seg24F_200-309 (SEQ ID: 141); and LSR_seg36R_200-310 (SEQ ID: 142).

The present invention also preferably encompasses any amplicon obtained through the use of any suitable primer pair; for example, for the above experiment, the following amplicon was obtained as a non-limiting illustrative example only of a suitable amplicon: LSR_seg24-36_200-309/310_Amplicon (SEQ ID: 140).

Example 5

Expression of LSR_ Transcripts which are Detectable by Amplicon as Depicted in Sequence Name LSR_Seg24-36_200-309/310 in Normal and Cancerous Lung Tissues Expression of LSR transcripts detectable by or according to seg24-36FR LSR_seg24-36_200-309/310_Amplicon (SEQ ID:140) and primers LSR_seg24F_200-309 (SEQ ID:141) and LSR_seg36R_200-310 (SEQ ID: 142) was measured by real time PCR. In parallel the expression of several housekeeping genes—HPRT1 (SEQ ID:107) (GenBank Accession No. NM_000194 HPRT1_Amplicon (SEQ ID:110)), PBGD (SEQ ID:115) (GenBank Accession No. BC019323; PBGD_Amplicon (SEQ ID:118)), SDHA (SEQ ID:103) (GenBank Accession No. NM_004168; SDHA_Amplicon (SEQ ID:106)) and Ubiquitin (SEQ ID:133) (GenBank Accession No. BC000449; Ubiquitin_Amplicon (SEQ ID:136)) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the normal samples (sample numbers 51, 52, 53, 54, 56, 57, 58, 59, 60, 61, 62, 63, 64, 69 and 70, Table 3 above), to obtain a value of fold up-regulation for each sample relative to median of the normal samples.

Figure 14A:
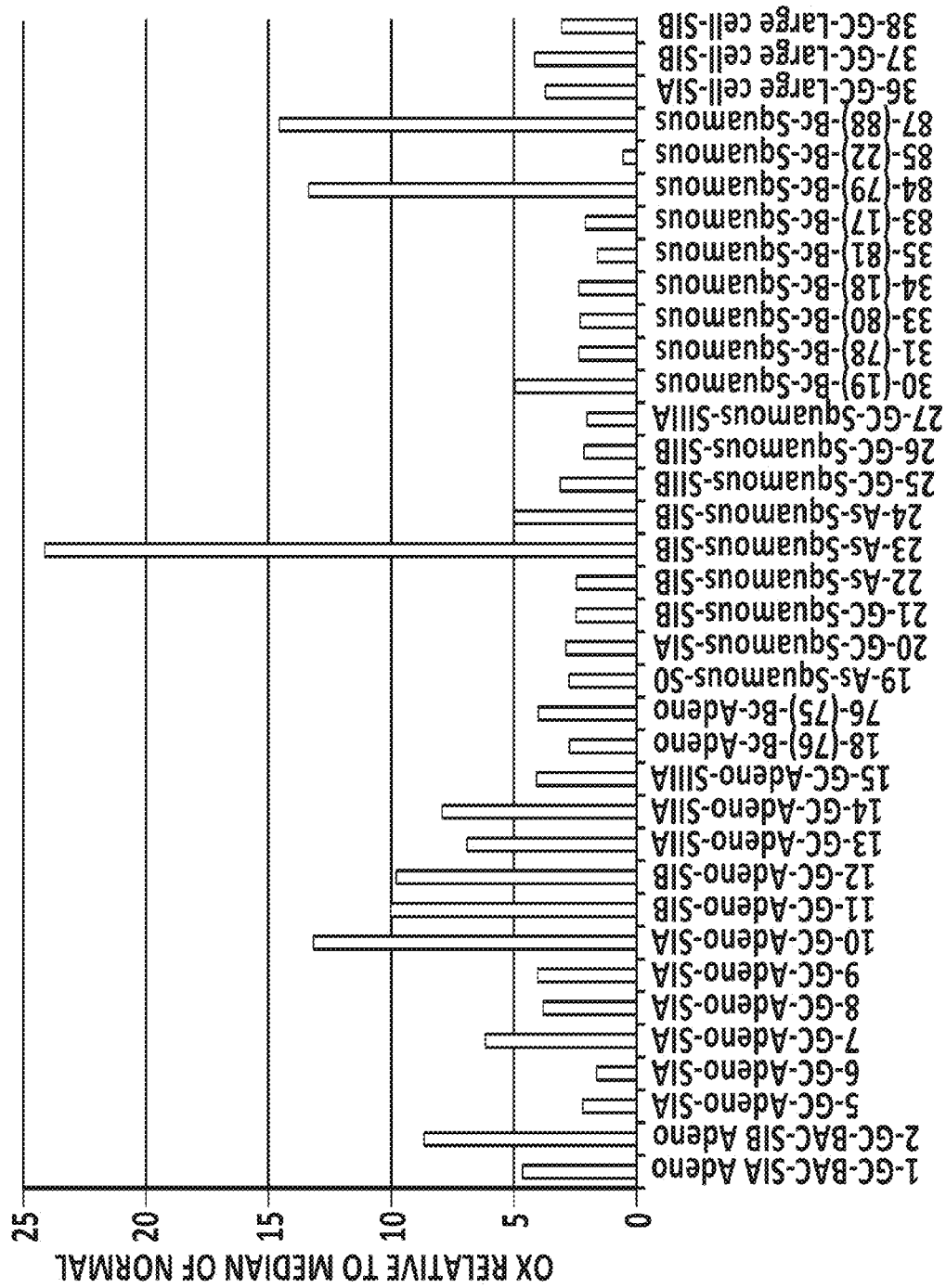
FIG. 14 is a histogram showing over expression of the LSR transcripts detectable by or according to LSR_seg24-36_200-309/310_Amplicon (SEQ ID:140) in cancerous lung samples relative to the normal samples.
Figure 14B:
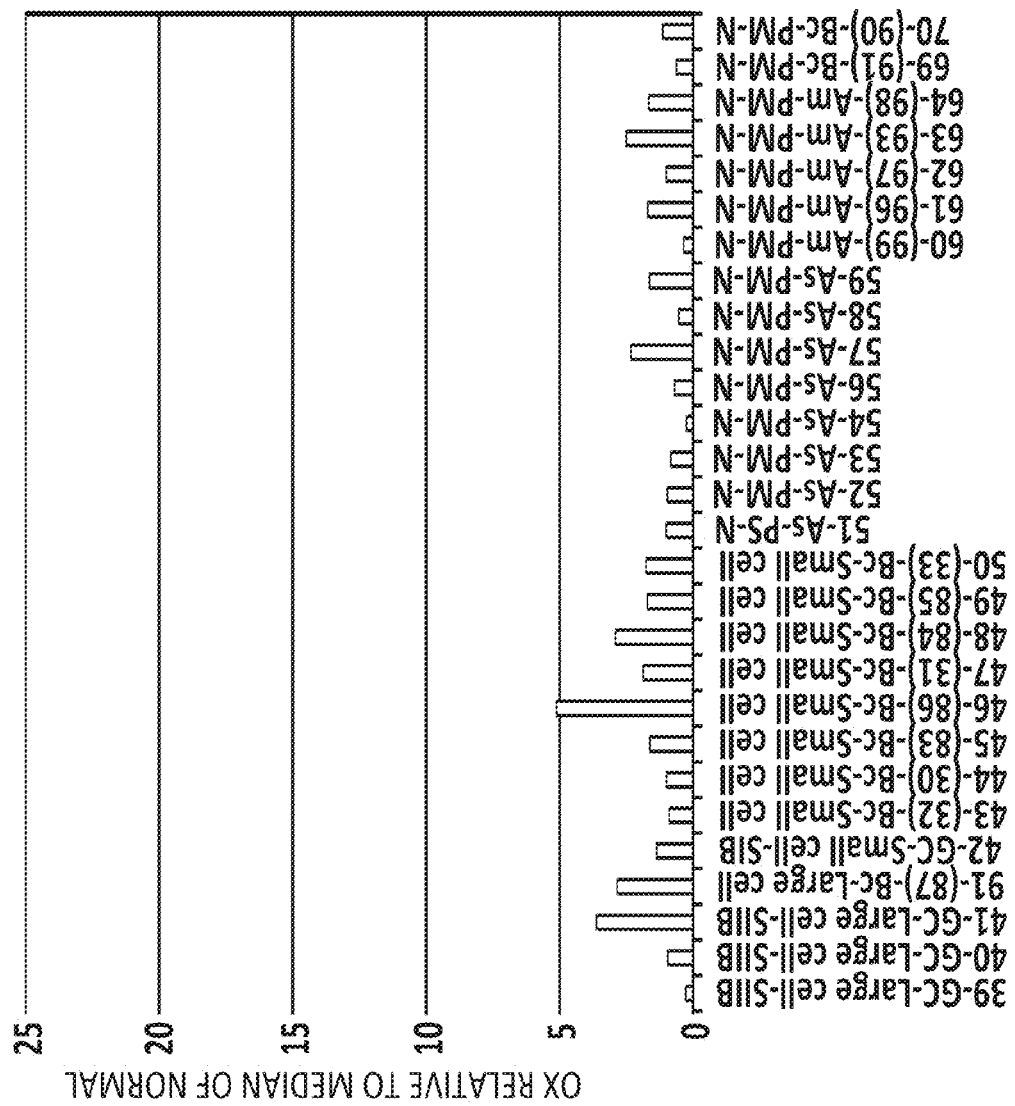

FIG. 14 is a histogram showing over expression of the above-indicated LSR transcripts in cancerous Lung samples relative to the normal samples.

As is evident from FIG. 14, the expression of LSR or transcripts detectable by the above amplicon in adenocarcinoma and non-small cell carcinoma samples was significantly higher than in the non-cancerous samples (sample numbers 51, 52, 53, 54, 56, 57, 58, 59, 60, 61, 62, 63, 64, 69 and 70, Table 3 above) and was higher in a few squamous cell carcinoma samples than in the non-cancerous samples. Notably an over-expression of at least 5 fold was found in 7 out of 15 adenocarcinoma samples, in 3 out of 18 squamous cell carcinoma samples and in 10 out of 40 non-small cell carcinoma samples.

Statistical analysis was applied to verify the significance of these results, as described below.

The P value for the difference in the expression levels of Homo sapiens lipolysis stimulated lipoprotein receptor transcripts detectable by the above amplicon in Lung adenocarcinoma samples versus the normal tissue samples was determined by T test as 2.98e-005. The P value for the difference in the expression levels of LSR transcripts detectable by the above amplicon in Lung squamous cell carcinoma samples versus the normal tissue samples was determined by T test as 7.42e-003. The P value for the difference in the expression levels of Homo sapiens lipolysis stimulated lipoprotein receptor transcripts detectable by the above amplicon in Lung large cell carcinoma samples versus the normal tissue samples was determined by T test as 1.76e-002. The P value for the difference in the expression levels of Homo sapiens lipolysis stimulated lipoprotein receptor transcripts detectable by the above amplicon in Lung small cell carcinoma samples versus the normal tissue samples was determined by T test as 4.35e-002. The P value for the difference in the expression levels of Homo sapiens lipolysis stimulated lipoprotein receptor transcripts detectable by the above amplicon in Lung non-small cell carcinoma samples versus the normal tissue samples was determined by T test as 4.31e-006.

Threshold of 5 fold over expression was found to differentiate between adenocarcinoma and normal samples with P value of 3.16e-003 as checked by exact Fisher test. Threshold of 5 fold over expression was found to differentiate between non-small cell carcinoma and normal samples with P value of 2.90e-002 as checked by exact Fisher test.

The above values demonstrate statistical significance of the results.

Primer pairs are also optionally and preferably encompassed within the present invention; for example, for the above experiment, the following primer pair was used as a non-limiting illustrative example only of a suitable primer pair: LSR_seg24F_200-309 (SEQ ID: 141).; and LSR_seg36R_200-310 (SEQ ID: 142).

The present invention also preferably encompasses any amplicon obtained through the use of any suitable primer pair; for example, for the above experiment, the following amplicon was obtained as a non-limiting illustrative example only of a suitable amplicon: LSR_seg24-36_200-309/310_Amplicon (SEQ ID: 140).

Example 6

Expression of LSR_ Transcripts which are Detectable by Amplicon as Depicted in Sequence Name LSR_Seg24-36_200-309/310 in Different Normal Tissues Expression of LSR transcripts detectable by or according to seg24-36FR LSR_seg24-36_200-309/310_Amplicon (SEQ ID: 140) and primers LSR_seg24F_200-309 (SEQ ID:141) and LSR_seg36R_200-310 (SEQ ID: 142) was measured by real time PCR. In parallel the expression of several housekeeping genes—SDHA (SEQ ID:103) (GenBank Accession No. NM_004168; SDHA_Amplicon (SEQ ID:106)), HPRT1 (SEQ ID:107) (GenBank Accession No. NM_000194; HPRT1_Amplicon (SEQ ID:110)), and G6PD (SEQ ID:111) (GenBank Accession No. NM_000402; G6PD_Amplicon (SEQ ID:114)) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the Ovary samples (sample numbers 20, 21, 22 and 23, Table 4 above), to obtain a value of relative expression of each sample relative to median of the Ovary samples.

Figure 15A:
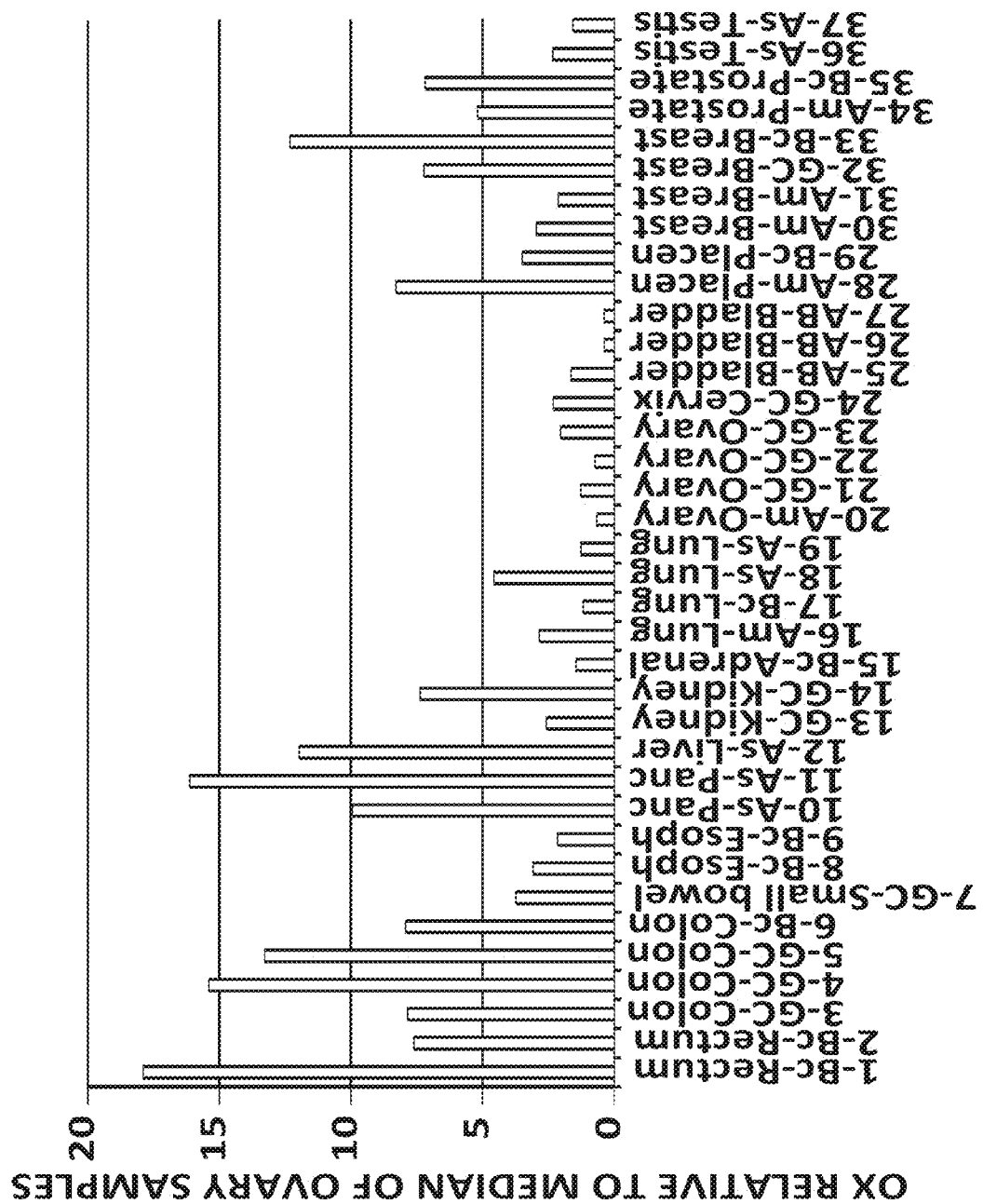
FIG. 15 is a histogram showing over expression of the LSR transcripts detectable by or according to LSR_seg24-36_200-309/310_Amplicon (SEQ ID:140) in normal tissue samples relative to the ovary samples.
Figure 15B:
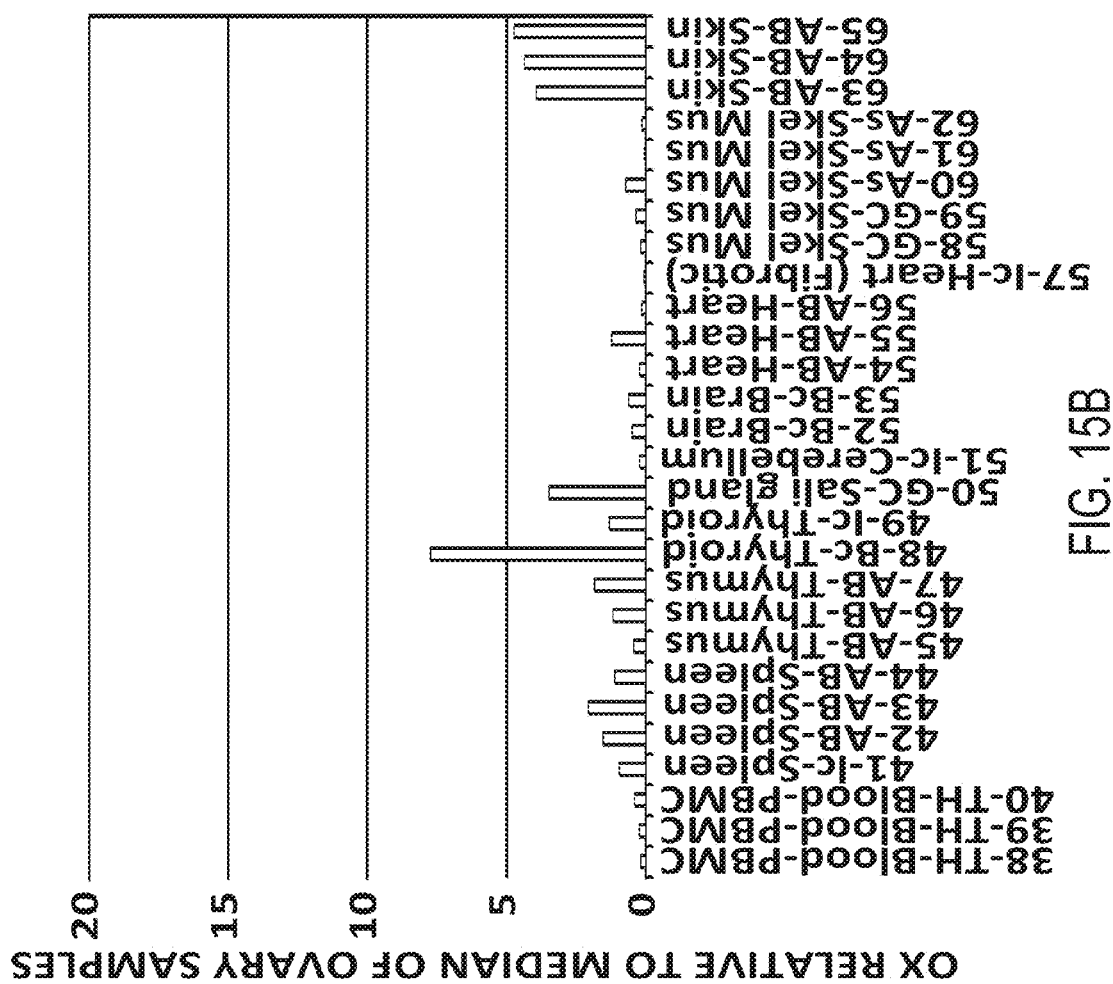

FIG. 15 is a histogram showing the expression of the above-indicated LSR transcripts in normal tissue samples relative to the ovary samples.

Example 7

Expression of LSR_ Transcripts which are Detectable by Amplicon as Depicted in Sequence Name LSR_Seg24-36_200-309/310 in Normal and Cancerous Kidney Tissues Expression of LSR transcripts detectable by or according to seg24-36FR—LSR_seg24-36_200-309/310_Amplicon (SEQ ID: 140) and primers LSR_seg24F_200-309 (SEQ ID: 141) and LSR_seg36R_200-310 (SEQ ID: 142) was measured by real time PCR. In parallel the expression of several housekeeping genes—SDHA (SEQ ID:103) (GenBank Accession No. NM_004168; SDHA_Amplicon (SEQ ID:106)), G6PD (SEQ ID:111) (GenBank Accession No. NM_000402; G6PD_Amplicon (SEQ ID:114)) and PBGD (SEQ ID:115) (GenBank Accession No. BC019323; PBGD_Amplicon (SEQ ID:118)) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the normal samples (sample numbers 1, 2, 3, 4 and 19, Table 5 above), to obtain a value of fold up-regulation for each sample relative to median of the normal samples.

FIG. 16 is a histogram showing down regulation of the above-indicated Homo sapiens lipolysis stimulated lipoprotein receptor transcripts in cancerous Kidney samples relative to the normal samples.

As is evident from FIG. 16, the expression of LSR transcripts detectable by the above amplicon in cancerous Kidney samples was significantly lower than in the non-cancerous samples (sample numbers 1, 2, 3, 4 and 19, Table 5 above).

Statistical analysis was applied to verify the significance of these results, as described below.

The P value for the difference in the expression levels of LSR transcripts detectable by the above amplicon in cancerous Kidney samples versus the normal tissue samples was determined by T test as 1.25e-01.

Primer pairs are also optionally and preferably encompassed within the present invention; for example, for the above experiment, the following primer pair was used as a non-limiting illustrative example only of a suitable primer pair: LSR_seg24F_200-309 (SEQ ID: 141); and LSR_seg36R_200-310 (SEQ ID: 142).

The present invention also preferably encompasses any amplicon obtained through the use of any suitable primer pair; for example, for the above experiment, the following amplicon was obtained as a non-limiting illustrative example only of a suitable_seg24-36_200-309/310_Amplicon (SEQ ID:140).

Example 8

Expression of LSR_ Transcripts which are Detectable by Amplicon as Depicted in Sequence Name LSR_Seg24-36_200-309/310 in Normal and Cancerous Liver Tissues Expression of LSR transcripts detectable by or according to seg24-36FR_seg24-36_200-309/310_Amplicon (SEQ ID: 140) and primers LSR_seg24F_200-309 (SEQ ID: 141) and LSR_seg36R_200-310 (SEQ ID: 142) was measured by real time PCR. In parallel the expression of several housekeeping genes—SDHA (SEQ ID:103) (GenBank Accession No. NM_004168; SDHA_Amplicon (SEQ ID: 106)), G6PD (SEQ ID:111) (GenBank Accession No. NM_000402; G6PD_Amplicon (SEQ ID:114)) and PBGD (SEQ ID: 115) (GenBank Accession No. BC019323; —PBGD_Amplicon (SEQ ID:118)) was measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the normal samples (sample numbers 41, 42, 43, 44 and 45, Table 6 above), to obtain a value of fold up-regulation for each sample relative to median of the normal samples.

FIG. 17 is a histogram showing the expression of the above-indicated LSR transcripts in cancerous Liver samples relative to the normal samples.

Primer pairs are also optionally and preferably encompassed within the present invention; for example, for the above experiment, the following primer pair was used as a non-limiting illustrative example only of a suitable primer pair: LSR_seg24F_200-309 (SEQ ID: 141); and LSR_seg36R_200-310 (SEQ ID: 142) reverse primer.

The present invention also preferably encompasses any amplicon obtained through the use of any suitable primer pair; for example, for the above experiment, the following amplicon was obtained as a non-limiting illustrative example only of a suitable amplicon: LSR_seg24-36_200-309/310_Amplicon (SEQ ID: 140).

Example 9

Cloning of LSR_T1_P5a ORF Fused to Flag Tag

Cloning of LSR_T1_P5a open reading frame (ORF) (SEQ ID NO 154) fused to FLAG (amino acid sequence: DYKDDDDK, SEQ ID NO: 153) to generated LSR_P5a protein (SEQ ID NO: 11) fused to flag, was performed by PCR as described below.

A 3-step PCR reaction was performed using PfuUltra II Fusion HS DNA Polymerase (Agilent, Catalog no. 600670) under the following conditions: on the first step, 1 µl of undiluted Ovary sample (ID PZQXH) from the Ovary panel (Table 1) served as a template for a PCR reaction with 0.5 µl of each of the primers 200_369_LSR_Kozak_NheI (SEQ ID NO: 147) and 200_379_LSR_Rev (SEQ ID NO: 148) in a total reaction volume of 25 µl. The reaction conditions were 5 minutes at 98° C.; 35 cycles of: 20 seconds at 98° C., 30 seconds at 55° C. and 1.5 minutes at 72° C.; then 5 minutes at 72° C. The PCR product was diluted 1:20 in DDW and 1 ul was used as a template for each of the PCR reactions on step 2.

For the second step the 5' part of LSR was amplified with 0.5 ul of each of the primers 200_369_LSR_Kozak_NheI (10 µM) (SEQ ID NO: 147) and 200_371_LSR_seg36R (10 uM) (SEQ ID NO: 149) in a total reaction volume of 25 µl. The 3' part of LSR was amplified with 0.5 ul of each of the primers 200_370_LSR_seg36F (10 µM) (SEQ ID NO: 150) and 200-373_LSR_Flag_BamHI_Rev (10 uM) (SEQ ID NO: 151) in a total reaction volume of 25 µl. The reaction conditions for both reactions were 5 minutes at 98° C.; 35 cycles of: 20 seconds at 98° C., 15 seconds at 60° C. and 1.5 minutes at 72° C.; then 5 minutes at 72° C. The products of each of the reactions were separated on 1% agarose gel and purified from the gel using Qiaquick™ Gel Extraction Kit (Qiagene, Catalog no. 28706). 100 ng of the 5' product and 100 ng of the 3' product were used as a template for the third step of the PCR reaction, in which the full LSR-Flag sequence was amplified. 0.5 µl of each of the primers 200_369_LSR_Kozak_NheI (SEQ ID NO: 147) and 200-373_LSR_Flag_BamHI_Rev (SEQ ID NO: 151) in a total reaction volume of 25 µl. The reaction conditions were 5 minutes at 98° C.; 35 cycles of: 20 seconds at 98° C., 30 seconds at 55° C. and 1.5 minutes at 72° C.; then 5 minutes at 72° C. All of the primers that were used include gene specific sequences, restriction enzyme sites, Kozak sequence and FLAG tag sequence. The PCR product of step 3 was separated on 1% agarose gel. After verification of the expected band size, the PCR product was purified using QIAquick™ Gel Extraction kit.

The purified full length PCR product was digested with NheI and BamHI restriction enzymes (New England Biolabs, Beverly, Mass., U.S.A.). After digestion, the DNA was separated on a 1% agarose gel. The expected band size was excised and extracted from the gel as described above. The digested DNA was then ligated into pIRESpuro3 vector that was digested with NheI and BamHI as described above, treated with Antarctic Phosphatase (New England Biolabs, Beverly, Mass., U.S.A., Catalog no. M0289L) for 30 minutes at 37° C. and purified from 1% agarose gel using QIAquick™ Gel Extraction kit as described above. The ligation reaction was performed with T4 DNA Ligase (Promega; Catalog no. M180A).

Example 10

Cloning of LSR_T1_P5a ORF

Cloning of LSR_T1_P5a open reading frame (ORF) (SEQ ID NO: 154) was performed by PCR to generate LSR_P5a protein (SEQ ID NO: 11), as described below.

A PCR reaction was performed using PfuUltra II Fusion HS DNA Polymerase (Agilent, Catalog no. 600670) under the following conditions: 50 ng of pIRES_puro3_LSR_T1_P5a_Flag construct described above served as a template for a PCR reaction with 0.5 microliter of each of the primers 200_369_LSR_Kozak_NheI (SEQ ID NO: 147) and 200-372_LSR_BamHI_Rev (SEQ ID NO: 152) in a total reaction volume of 25 µl. The reaction conditions were 5 minutes at 98° C.; 35 cycles of: 20 seconds at 98° C., 30 seconds at 55° C. and 1.5 minutes at 72° C.; then 10 minutes at 72° C. All of the primers that were used include gene specific sequences, restriction enzyme sites and Kozak sequence. The PCR product was separated on 1% agarose gel. After verification of the expected band size, the PCR product was purified using QIAquick™ Gel Extraction kit as described above.

The purified PCR product was digested with NheI and BamHI restriction enzymes (New England Biolabs, Beverly, Mass., U.S.A.). After digestion, the DNA was separated on a 1% agarose gel. The expected band size was excised and extracted from the gel as described above. The digested DNA was then ligated into pIRESpuro3 vector that was digested with NheI and BamHI as described above, incubated with Antarctic Phosphatase (New England Biolabs, Beverly, Mass., U.S.A., Catalog no. M0289L) for 30 minutes at 37° C. and purified from 1% agarose gel using QIAquick™ Gel Extraction kit as described above. The ligation reaction was performed with T4 DNA Ligase (Promega; Catalog no. M180A).

Sequence verification of both tagged and untagged constructs described above was performed (Hylabs, Rehovot, Israel). Two nucleotides mismatches were identified, as follows: G to A at nucleic acid position 119 of SEQ ID NO: 154, and A to G at nucleic acid position 626 from SEQ ID NO: 154, resulting in a nucleic sequence set forth in SEQ ID NO: 145 for the untagged construct, and SEQ ID NO: 146 for the tagged construct; yielding a polypeptide having an amino acid mismatch I to M in amino acid position 209 in SEQ ID NO:301, resulting in a protein having amino acid sequence set forth in SEQ ID NO: 143 for the untagged construct and SEQ ID NO: 144 for the tagged construct.

The above recombinant plasmids were processed for stable pool generation as described below.

Example 11

Establishment of a Stable Pool of Recombinant HEK293T Cells Expressing LSR_P5A_Flag_m Protein HEK-293T cells were stably transfected with LSR_T1_P5a_Flag_m (SEQ ID NO: 146) and pIRESpuro3 empty vector plasmids as follows:

HEK-293T (ATCC, CRL-11268) cells were plated in a sterile 6 well plate suitable for tissue culture, containing 2 ml pre-warmed of complete media, DMEM [Dulbecco's modified Eagle's Media, Biological Industries (Beit Ha'Emek, Israel, catalog number: 01-055-1A)+10% FBS [Fetal Bovine Serum, Biological Industries (Beit Ha'Emek, Israel, catalog number: 04-001-1A)+4 mM L-Glutamine (Biological Industries (Beit Ha'Emek, Israel), catalog number: 03-020-1A). 500,000 cells per well were transfected with 2 µg of DNA construct using 6 µl FuGENE 6 reagent (Roche, catalog number: 11-814-443-001) diluted into 94 ul DMEM. The mixture was incubated at room temperature for 15 minutes. The complex mixture was added dropwise to the cells. The cells were placed in an incubator maintained at 37° C. with 5% CO2 content. 48 hours after the transfection, the cells were transferred to a 75 cm2 tissue culture flask containing 15 ml of selection medium: complete medium supplemented with 5 µg\ml puromycin (Sigma, catalog number P8833). Cells were placed in an incubator, and the medium was replaced every 3-4 days, until clone formation was observed.

Example 12

Analysis of the ectopic expression of LSR_P5A_Flag_m in stably-Transfected HEK293T Cells The expression of LSR_P5a_Flag_m (SEQ ID NO 144) in stably-transfected HEK293T cells was determined by Western blot analysis of the cell lysates, using anti LSR Antibodies and anti flag antibody as indicated in Table 9.

Cells were dissociated from the plate using Cell Dissociation Buffer Enzyme-Free PBS-Based (Gibco; 13151-014), washed in Dulbecco's Phosphate Buffered Saline (PBS) (Biological Industries, 02*023-1A) and centrifuged at 1200 g for 5 minutes. Whole cell extraction was performed by resuspending the cells in 50 mM Tris-HCl pH7.4, 150 mM NaCl, 1 mM EDTA, 1% Triton X-100, supplemented with 25× complete EDTA free protease inhibitor cocktail (Roche, 11 873 580 001) and vortexing for 20 seconds. Cell extracts were collected following centrifugation at 20000 g for 20 minutes at 4° C. and protein concentration was determined with Bradford Biorad Protein Assay (Biorad cat#500-0006). Equal protein amounts were analyzed by SDS-PAGE (Invitrogen NuPAGE 4-12% NuPAGE Bis Tris, Cat#NP0335, NP0322) and transferred to Nitrocellulose membrane (BA83, 0.2 µm, Schleicher & Schuell, Cat#401385). The membrane was blocked with TTBS (Biolab, Cat#: 20892323)/10% skim milk (Difco, Cat#232100) and incubated with the indicated primary antibodies (FIG. 18) diluted in TTBS/5% BSA (Sigma-Aldrich, A4503) at the indicated concentrations (Table 9), for 16 hours at 4° C. After 3 washes with TTBS, The membrane was further incubated for 1 hour at Room Temperature with the secondary-conjugated antibodies as indicated, diluted in TTBS. Chemiluminescence reaction was performed with ECL Western Blotting Detection Reagents (GE Healthcare, Cat #RPN2209) and the membrane was exposed to Super RX Fuji X-Ray film (Catalog no. 4741008389).

Figure 18:
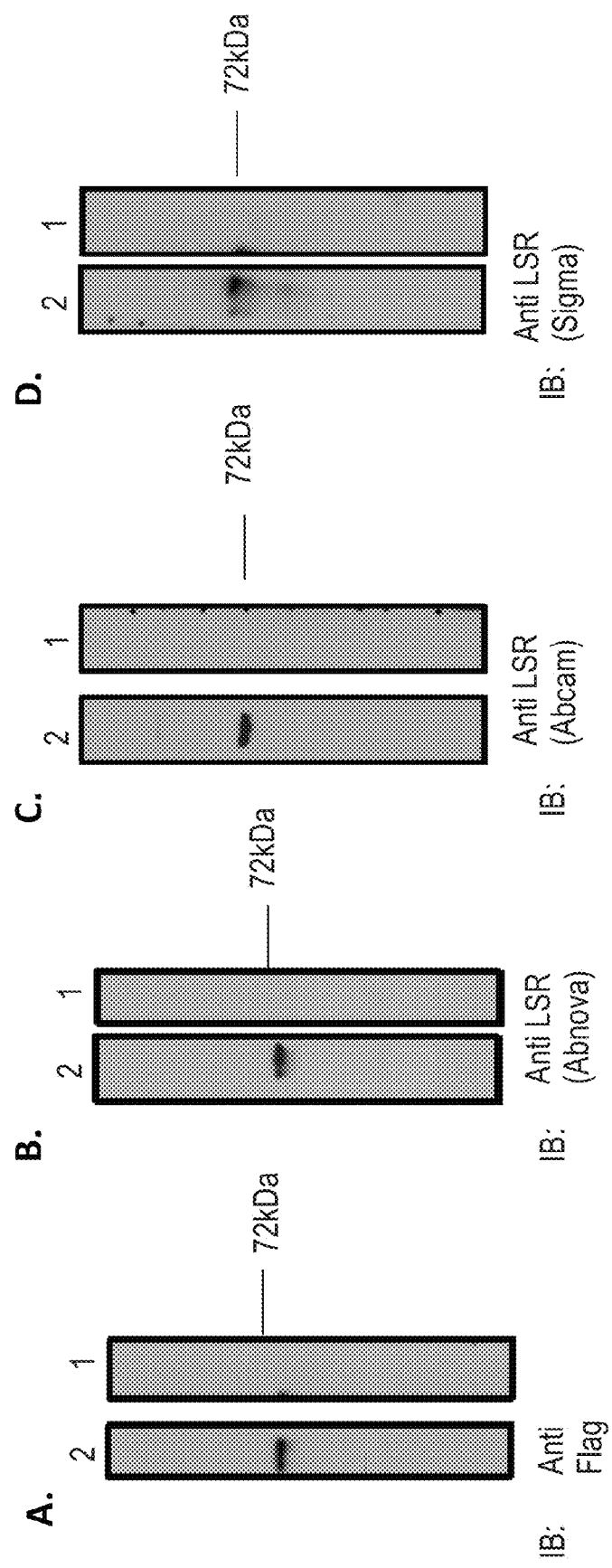
FIG. 18 demonstrates Western Blot analysis of the expression of LSR_P5a_Flag_m protein (SEQ ID: 144) in stably-transfected recombinant HEK293T cells, as detected with anti Flag (Sigma cat#A8592) (FIG. 18A) and anti LSR antibodies as follow: Abnova, cat#H00051599-B01P (FIG. 18B) Abcam, cat ab59646 (FIG. 18C) and Sigma cat#HPA007270 (FIG. 18D). Lane 1: HEK293T_pIRESpuro3; lane 2: HEK293T_pIRESpuro3_LSR_P5a_Flag.

FIG. 18 demonstrates the expression of LSR_P5a_Flag_m protein (SEQ ID: 144) in recombinant HEK293T cells at the expected band size ~70 kDa, as detected with anti Flag (Sigma cat#A8592) (FIG. 18A) and anti LSR antibodies as follow: Abnova, cat#H00051599-B01P (FIG. 18B) Abcam, cat ab59646 (FIG. 18C) and Sigma cat#HPA007270 (FIG. 18D).

Example 13

Determination of the Subcellular Localization of the Ectopic LSR_P5A_Flag_m in HEK293T Cells The subcellular localization of the LSR_P5a_Flag_m protein (SEQ ID NO: 144) was determined in stably-transfected cells by confocal microscopy.

Stably transfected recombinant HEK293T cells expressing a LSR_P5a_Flag_m (SEQ ID NO: 144) described above were plated on coverslips pre-coated with Poly-L-Lysine (Sigma; Catalogue no. P4832). After 24 hrs the cells were processed for immunostaining and analyzed by confocal microscopy. The cover slip was washed in phosphate buffered saline (PBS), then fixed for 15 minutes in a solution of PBS/3.7% paraformaldehyde (PFA) (EMS, catalog number: 15710)/3% glucose (Sigma, catalog number: G5767). The PFA was Quenched with PBS/3 mM Glycine (Sigma, catalog number: G7126) for 5 minutes. After two 5-minute washes in PBS, the cells were permeabilized with PBS/0.1% Triton-X100 for 5 minutes at Room Temperature and washed twice in PBS. Then, blocking of non-specific regions was performed with PBS/5% Bovine Serum Albumin (BSA) (Sigma, catalog number: A4503) for 20 minutes. The coverslip was then incubated in a humid chamber for 1 hour with each of the primary antibodies diluted in PBS/5% BSA as indicated, followed by three 5-minute washes in PBS. The coverslips were then incubated for 30 minutes with the corresponding secondary antibody diluted in PBS/2.5% BSA at the indicated dilution.

The antibodies and the dilutions that were used are specified in Table 9. After a prewash in Hank's Balanced Salt Solutions w/o phenol red (HBSS) (Biological Industries Catalog no. 02-016-1), the coverslip was incubated with WGA-Alexa 488 (Invitrogen, catalog number W11261) diluted 1:200 in HBSS for 10 min, washed in HBSS and incubated in BISBENZIMIDE H 33258 (Sigma, catalog number: 14530) diluted 1:1000 in HBSS. The coverslip was then mounted on a slide with Gel Mount Aqueous medium (Sigma, catalog number: G0918) and cells were observed for the presence of fluorescent product using confocal microscopy.

The subcellular localization of LSR_P5a_Flag_m is demonstrated in FIG. 19, LSR_P5a_Flag_m (SEQ ID NO: 144) is localized mainly to the cell cytoplasm, but can also be detected on the cell surface as detected with anti Flag (Sigma cat#A9594) (FIG. 19A) and anti LSR antibodies as follows: Abcam, cat ab59646 (FIG. 19B) Abnova, cat#H00051599-B01P (FIG. 19C) and Sigma cat#HPA007270 (FIG. 19D).

Example 14

Analysis of the Expression of Endogenous LSR Protein in Various Cell Lines

The expression of endogenous LSR protein in various cell lines was analyzed by Western Blotting as described below.

SK-OV3 (ATCC no. HTB-77) Caov3 (ATCC no. HTB-75), OVCAR3 (ATCC no. HTB-161), ES-2 (ATCC no. CRL-1978), OV-90 (ATCC no. CRL-11732) TOV112D (ATCC no. CRL-11731) and Hep G2 (ATCC no. HB-8065) cell extracts were prepared as described above.

HeLa (catalog no. sc-2200), MCF-7 (catalog no. sc-2206), CaCo2 (catalog no. sc-2262) and SkBR3 (catalog no. sc-2218) cell extracts were purchased from SantaCruz Biotechnology.

Equal protein amounts were analyzed by SDS-PAGE and transferred to Nitrocellulose membrane as described above. The membrane was blocked with TTBS (Biolab, Cat#: 20892323)/10% skim milk (Difco, Cat#232100) and incubated with anti LSR antibodies (Abcam, cat#ab59646) diluted in TTBS/5% BSA (Sigma-Aldrich, A4503) at the indicated concentrations (Table 9), for 16 hours at 4° C. After 3 washes with in TTBS, The membrane was further incubated for 1 hour at Room Temperature with the secondary-conjugated antibodies as indicated (Table 9), diluted in TTBS. Chemiluminescence reaction was performed with ECL Western Blotting Detection Reagents (GE Healthcare, Cat #RPN2209) and the membrane was exposed to Super RX Fuji X-Ray film (Catalog no. 4741008389).

FIG. 20 demonstrates the endogenous expression of LSR in various cell lines. A band at 72 kDa corresponding to LSR was detected with anti LSR antibody in extracts of SK-OV3, Caov3, OVCAR3, OV-90, Hep G2, HeLa, CaCo2, and SkBR3 (FIG. 20A). Anti GAPDH (Abcam cat#ab9484) served as a loading control (FIG. 20B).

TABLE 9

Primary and secondary antibodies

| Antibody | Application | Dilution |
|---|---|---|
| Mouse Anti FLAG-Cy3 (Sigma catalog number: A9594) | IF | 1:200 |
| Mouse Anti FLAG-HRP (Sigma Catalog no. A8592) | WB | 1:2000 |
| Rabbit Anti LSR (Abcam catalog number: ab59646) | IF | 1:500 |
| | WB | 1:4000 |

TABLE 9-continued

Primary and secondary antibodies

| Antibody | Application | Dilution |
|---|---|---|
| Rabbit Anti LSR (Sigma catalog number: HPA007270) | IF | 1:100 |
| | WB | 1:2500 |
| Mouse Anti LSR (Abnova catalog number: H00051599-B01P) | IF | 1:500 |
| | WB | 1:1000 |
| Mouse Anti GAPDH (Abcam catalog number: ab9484) | WB | 1:1000 |
| Donkey Anti Rabbit Cy3 (Jackson ImmunoResearch Laboratories Inc. catalog no. 711-165-152) | IF | 1:200 |
| Donkey Anti Mouse Dylight 549 (Jackson ImmunoResearch Laboratories Inc. catalog no. 715-506-150) | IF | 1:100 |
| Peroxidase conjugated affinity purified Goat Anti Rabbit IgG (Jackson ImmunoResearch Laboratories Inc. catalog no. 111-035-003) | WB | 1:10000 |
| Peroxidase conjugated affinity purified Goat Anti-Mouse IgG (Jackson ImmunoResearch Laboratories Inc. catalog no. 115-035-146) | WB | 1:10000 |

Example 15

Expression of TMEM25_ Transcripts which are Detectable by Amplicon as Depicted in Sequence Name TMEM25_Seg21-27 in Normal and Cancerous Breast Tissues Expression of TMEM25 transcripts detectable by or according to seg21-27-TMEM25_seg_21-27_200-344/346_Amplicon (SEQ ID NO: 123) and primers TMEM25_seg21F_200-344 (SEQ ID NO.124) and TMEM25_seg27R_200-346 (SEQ ID NO.125) was measured by real time PCR. In parallel the expression of several housekeeping genes—G6PD (GenBank Accession No. NM_000402; (SEQ ID NO.111) G6PD_Amplicon (SEQ ID NO.114)), RPL19 (GenBank Accession No. NM_000981; (SEQ ID NO.119)—RPL19_Amplicon (SEQ ID NO.122)), PBGD (GenBank Accession No. BC019323; (SEQ ID NO.115) PBGD_Amplicon (SEQ ID NO.118)) and SDHA (GenBank Accession No. NM_004168; (SEQ ID NO.103) SDHA_Amplicon (SEQ ID NO.106)) was measured similarly. For each RT sample, the expression of the above amplicon was normalized to the normalization factor calculated from the expression of these house keeping genes as described in "materials and methods" section. The normalized quantity of each RT sample was then divided by the median of the quantities of the normal samples (sample numbers 43, 45, 46, 47, 48, 49, 50, 51, 52, 54, 56, 58, 59, 60, 61, 62, 63, 64, 66, 67, 68 and 69, Table 1 above), to obtain a value of fold differential expression for each sample relative to median of the normal samples.

In two experiments that were carried out no differential expression in the cancerous samples relative to the normal samples was observed (FIG. 21).

Primer pairs are also optionally and preferably encompassed within the present invention; for example, for the above experiment, the following primer pair was used as a non-limiting illustrative example only of a suitable primer pair: TMEM25_seg21F_200-344 (SEQ ID NO.124) forward primer; and TMEM25_seg27R_200-346 (SEQ ID NO.125) reverse primer.

The present invention also preferably encompasses any amplicon obtained through the use of any suitable primer pair; for example, for the above experiment, the following amplicon was obtained as a non-limiting illustrative example only of a suitable amplicon: TMEM25_seg_21-27_200-344/346_Amplicon (SEQ ID NO: 123).

Example 16

Expression of TMEM25_ Transcripts which are Detectable by Amplicon as Depicted in Sequence Name TMEM25 Seg21-27 in Different Normal Tissues Expression of TMEM25 transcripts detectable by or according to seg21-27-TMEM25_seg_21-27_200-344/346_Amplicon (SEQ ID NO: 123) and primers TMEM25_seg21F_200-344 (SEQ ID NO.124) and TMEM25_seg27R_200-346 (SEQ ID NO.125) was measured by real time PCR. In parallel the expression of several housekeeping genes—SDHA (GenBank Accession No. NM_004168; (SEQ ID NO.103) SDHA_Amplicon (SEQ ID NO.106)), G6PD (GenBank Accession No. NM_000402; (SEQ ID NO.111) G6PD_Amplicon (SEQ ID NO.114)) and HPRT1 (GenBank Accession No. NM_000194; (SEQ ID NO.107) HPRT1_Amplicon (SEQ ID NO.110)) were measured similarly. For each RT sample, the expression of the above amplicon was normalized to the normalization factor calculated from the expression of these house keeping genes as described in normalization method 2 in the "materials and methods" section. The normalized quantity of each RT sample was then divided by the median of the quantities of the Breast samples (sample numbers 30, 31, 32 and 33, Table 2 above), to obtain a value of relative expression of each sample relative to median of the Breast samples (FIG. 22).

Example 17

Cloning of TMEM25 Proteins

Cloning of TMEM25_T0_P5 ORF Fused to Flag Tag
Cloning of TMEM25_T0_P5 open reading frame (ORF) (SEQ ID NO: 130) fused to FLAG (SEQ ID NO: 153) was carried out by RT PCR as described below.
1 μl of undiluted Colon cancer pool DNA served as a template for a PCR reaction. The PCR was done using KAPA Hifi DNA polymerase (KAPABIOSYSTEM, Catalog no. KK2101) under the following conditions: 1 μl—cDNA described above; 1 μl (25 μM)—of each primer 200-374_TMEM25_NheI_Kozak_seg5F (SEQ ID NO: 127) and 200-375_TMEM25_Flag_STOP_EcoRI_seg43R (SEQ ID NO: 128) in a total reaction volume of 50 μl; with a reaction program of 5 minutes in 95° C.; 40 cycles of: 20 seconds at 98° C., 15 seconds at 55° C., 1 minute at 72° C.; then 5 minutes at 72° C. Primers which were used include gene specific sequences; restriction enzyme sites; Kozak sequence and FLAG tag.
25 μl of PCR product were loaded onto a 1.5% agarose gel stained with ethidium bromide, electrophoresed in 1×TAE solution at 100V, and visualized with UV light. After verification of expected band size. 1 μl of the PCR product above template were served as a template for reamplification. The PCR was done using KAPA Hifi DNA polymerase (KAPA-BIOSYSTEM, Catalog no. KK2101) under the same conditions described above.
PCR product was purified from gel using QIAquick™ Gel Extraction kit (Qiagen, catalog number: 28707).
The purified PCR product was digested with NheI and EcoRI restriction enzymes (New England Biolabs, Beverly, Mass., U.S.A.). The digested DNA was then ligated into pIRESpuro3 (pRp) vector (Clontech, cat No: 631619) previously digested with the above restriction enzymes, using T4 DNA ligase (Promega, catalog number: M1801). The resulting DNA was transformed into competent E. Coli bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C. The following day, positive colonies were screened by PCR using pIRE-Spuro3 vector specific primer and gene specific primer (data not shown). The PCR product was analyzed using 2% agarose gel as described above. After verification of expected band size, positive colonies were grown in 5 ml Terrific Broth supplemented with 100 μg/ml ampicillin, with shaking overnight at 37° C. Plasmid DNA was isolated from bacterial cultures using Qiaprep™ Spin Miniprep Kit (Qiagen, catalog number: 27106). Accurate cloning was verified by sequencing the inserts (Hylabs, Rehovot, Israel). Upon verification of an error-free colony (i.e. no mutations within the ORF), recombinant plasmids were processed for further analyses.
Cloning of TMEM25_T0_P5 ORF Non Tagged
Cloning of TMEM25_T0_P5 open reading frame (ORF) non tagged (SEQ ID NO: 130) was carried out by RT PCR as described below.
1 μl of undiluted Colon cancer pool DNA served as a template for a PCR reaction. The PCR was done using KAPA Hifi DNA polymerase (KAPABIOSYSTEM, Catalog no. KK2101) under the following conditions: 1 μl—cDNA described above; 1 μl (25 μM)—of each primer 200-374_TMEM25_NheI_Kozak_seg5F (SEQ ID NO: 127) and 200-377_TMEM25_STOP_EcoRI_seg43R (SEQ ID NO: 131) in a total reaction volume of 50 μl; with a reaction program of 5 minutes in 95° C.; 40 cycles of: 20 seconds at 98° C., 15 seconds at 55° C., 1 minute at 72° C.; then 5 minutes at 72° C. Primers which were used include gene specific sequences; restriction enzyme sites and Kozak sequence.
25 μl of PCR product were loaded onto a 1.5% agarose gel stained with ethidium bromide, electrophoresed in 1×TAE solution at 100V, and visualized with UV light. After verification of expected band size. 5 μl of the PCR product above template were served as a template for reamplification. The PCR was done using KAPA Hifi DNA polymerase (KAPA-BIOSYSTEM, Catalog no. KK2101) under the same conditions described above.
PCR product was purified from gel using QIAquick™ Gel Extraction kit (Qiagen, catalog number: 28707).
The purified PCR product was digested with NheI and EcoRI restriction enzymes (New England Biolabs, Beverly, Mass., U.S.A.). The digested DNA was then ligated into pIRESpuro3 (pRp) vector (Clontech, cat No: 631619) previously digested with the above restriction enzymes, using T4 DNA ligase (Promega, catalog number: M1801). The resulting DNA was transformed into competent E. Coli bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C. The following day, positive colonies were screened by PCR using pIRE-Spuro3 vector specific primer and gene specific primer (data not shown). The PCR product was analyzed using 2% agarose gel as described above. After verification of expected band size, positive colonies were grown in 5 ml Terrific Broth supplemented with 100 μg/ml ampicillin, with shaking overnight at 37° C. Plasmid DNA was isolated from bacterial cultures using Qiaprep™ Spin Miniprep Kit (Qiagen, catalog number: 27106). Accurate cloning was verified by sequencing the inserts (Hylabs, Rehovot, Israel). Upon verification of an error-free colony (i.e. no mutations within the ORF), recombinant plasmids were processed for further analyses.

Example 18

Generation of Stable Pool Expressing TMEM25_P5 and TMEM25_P5_FLAG PROTEINS

The TMEM25_T0_P5 (SEQ ID NO: 130) and TMEM25_T0_P5_FLAG (SEQ ID NO: 126) pIRESpuro3 constructs or pIRESpuro3 empty vector were stably transfected into HEK-293T cells as follows:

HEK-293T (ATCC, CRL-11268) cells were plated in a sterile 6 well plate suitable for tissue culture, using 2 ml pre-warmed of complete media, DMEM [Dulbecco's modified Eagle's Media, Biological Industries (Beit Ha'Emek, Israel, catalog number: 01-055-1A)+10% FBS [Fetal Bovine Serum, Biological Industries (Beit Ha'Emek, Israel, catalog number: 04-001-1A)+4 mM L-Glutamine (Biological Industries (Beit Ha'Emek, Israel), catalog number: 03-020-1A). 350,000 cells per well were transfected with 2 µg of DNA construct using 6 µl FuGENE 6 reagent (Roche, catalog number: 11-814-443-001) diluted into 94 ul DMEM. The mixture was incubated at room temperature for 15 minutes. The complex mixture was added dropwise to the cells and swirled. Cells were placed in incubator maintained at 37° C. with 5% CO2 content. 48 hours following transfection, transfected cells were transferred to a 75 cm2 tissue culture flask containing 15 ml of selection media: complete media supplemented with 5 µg\ml puromycin (Sigma, catalog number P8833). Cells were placed in incubator, and media was changed every 3-4 days, until clone formation observed.

Upon sufficient quantities of cells passing through selection, 3-5 million cells were harvested. Cells were lysed in 300 µl RIPA buffer (50 mM Tris HCl pH 8, 150 mM NaCl, 1% NP-40, 0.5% sodium Deoxycholate, 0.1% SDS) supplemented with protease inhibitors (Roche, catalog number: 11873580001), for 20 min at 4° C. Following centrifugation at 4° C. for 10 minutes at 14,000×rpm, the clear supernatants were transferred to clean tubes, and were used for WB procedure: 30 ug of lysate was mixed with DTT 1,4-Dithiothreitol (DTT; a reducing agent) to a final concentration of 100 mM.

In addition, the samples were then incubated at 100° C. for 10 minutes, followed by a 1 minute spin at 14,000×rpm. SDS-PAGE (Laemmli, U.K., Nature 1970; 227; 680-685) was performed upon loading of 30 µl of sample per lane into a 4-12% NuPAGE® Bis-Tris gels (Invitrogen, catalog number: NP0321), and gels were run in 1×MES SDS running buffer (Invitrogen, catalog number: NP0060), using the XCell SureLock™ Mini-Cell (Invitrogen, catalog number: E1 0001), according to manufacturer's instructions. The separated proteins were transferred to a nitrocellulose membrane (Schleicher & Schuell, catalog number: 401385) using the XCell™ II blotting apparatus (Invitrogen, catalog number E19051), according to manufacturer's instructions.

The membrane containing blotted proteins was processed for antibody detection as follows:

Non-specific regions of the membrane were blocked by incubation in 5% skim-milk diluted in Phosphate buffered saline (PBS) supplemented with 0.05% Tween-20 (PBST) for 1 hour at room temperature (all subsequent incubations occur for 1 hour at room temperature). Blocking solution was then replaced with primary Rabbit Anti TMEM25 antibody (Cat no. HPA012163, Sigma) diluted 1:500 in 5% bovine serum albumin (BSA) (Sigma, catalog number: A4503) (diluted in PBS). After 1 hour incubation, Three 5 minute washes, secondary antibody was applied: goat anti-rabbit conjugated to Peroxidase conjugated Affipure Goat anti Rabbit IgG (Jackson, catalog number: 111-035-003) diluted 1:20,000 in blocking solution. Proteins were also detected by Mouse anti Flag M2-Peroxidase (Sigma, catalog number: A8592) diluted 1:1000 in blocking solution. After 1 hour incubation, 3×5 minute washes, ECL substrate (PIERCE, catalog number: PIR-34080) was applied for 1 minute, followed by exposure to X-ray film (Fuji, catalog number: 100NIF). The results are presented in FIG. 23.

Figure 23A:
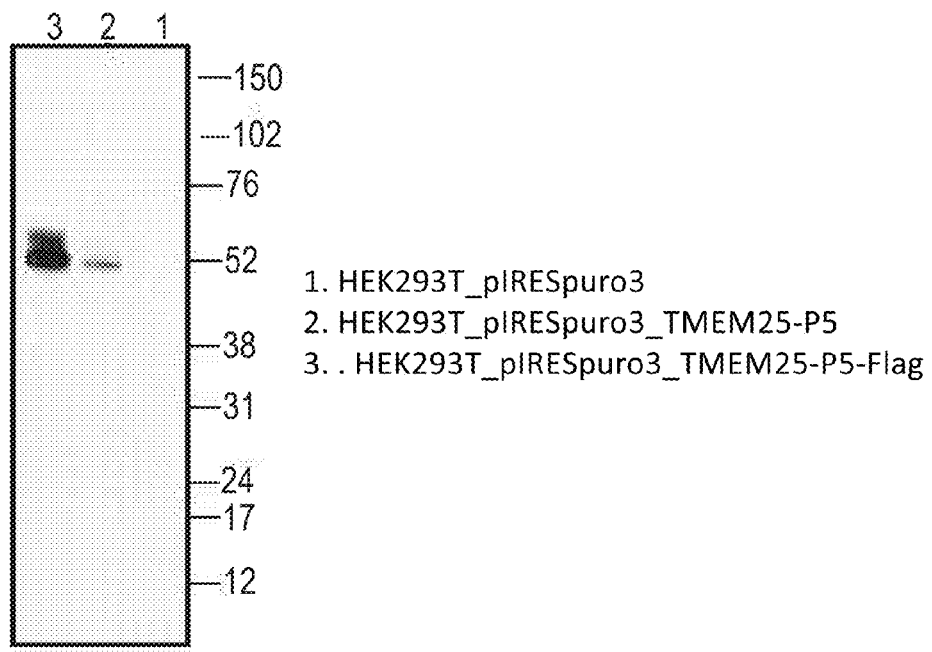

FIG. 23A demonstrate that Rabbit anti TMEM25 described above recognized specifically TMEM25_P5 protein (SEQ ID NO: 7) and TMEM25_P5_Flag (SEQ ID NO: 129) at the expected band size~40.2 kDa, but not HEK_293T_pRp3.

Figure 23B:
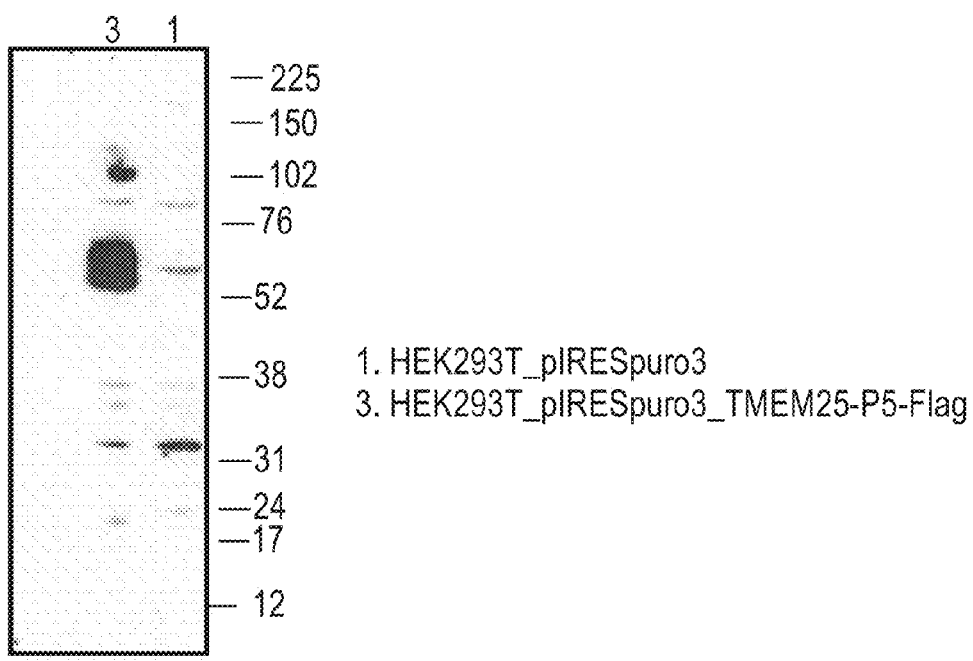

FIG. 23B demonstrate that TMEM25_P5_Flag proteins (SEQ ID NO: 129) were specifically recognized by anti-Flag at the expected band size~40.2 kDa.

Example 19

Determination of the Subcellular Localization of the Ectopic TMEM25_P5 and TMEM25_P5_Flag in HEK293T Cells by Immunofluorescence Protein localization of TMEM25_P5 (SEQ ID NO: 7) and of TMEM25_P5_FLAG (SEQ ID NO: 129) were observed upon Stable transfection as described above using confocal microscopy.

Stably transfected recombinant HEK293T cells expressing TMEM25_P5 (SEQ ID NO: 7) and TMEM25_P5_FLAG (SEQ ID NO: 129) were plated on coverslips pre-coated with Poly-L-Lysine (Sigma; Catalogue no. P4832). After 24 hrs the cells were processed for immunostaining and analyzed by confocal microscopy.

The cover slip was washed in phosphate buffered saline (PBS), then fixed for 15 minutes with a solution of 3.7% paraformaldehyde (PFA) (Sigma, catalog number: P-6148) 13% glucose (Sigma, catalog number: G5767) (diluted in PBS). Quenching of PFA was done by a 5 minute incubation in 3 mM glycine (Sigma, catalog number: G7126) (diluted in PBS). After two 5-minute washes in PBS, blocking of nonspecific regions was done with 5% bovine serum albumin (BSA) (Sigma, catalog number: A4503) (diluted in PBS) for 20 minutes.

The coverslip was then incubated, in a humid chamber for 1 hour, with mouse anti FLAG-Cy3 antibodies (Sigma, catalog number: A9594), diluted 1:200 in 5% BSA in PBS, OR with Rabbit Anti TMEM25 (Cat no. HPA012163, Sigma), diluted 1:50 in 5% BSA in PBS followed by three 5-minute washes in PBS. For the anti TMEM25 Ab only, a secondary Ab was needed: Donkey anti Rabbit cy3 (cat#711-165-152, Jackson) diluted 1:200 in 5% BSA in PBS, incubated in a humid chamber for 1 hour, followed by three 5-minute washes in PBS. After a prewash with BISBENZIMIDE H 33258 (HBSS) (Sigma, catalog number: 14530), the coverslip was incubated with WGA-Alexa 488 (Invitrogen, catalog number W11261) diluted 1:200 in HBSS for 10 min, followed by two washes in HBSS and incubated in BISBENZIMIDE H 33258 (Sigma, catalog number: 14530) diluted 1:1000 in HBSS. The coverslip was then mounted on a slide with Gel Mount Aqueous medium (Sigma, catalog number: G0918) and cells were observed for the presence of fluorescent product using confocal microscopy.

The subcellular localization of TMEM25_P5 (SEQ ID NO:132) and TMEM25_P5_Flag (SEQ ID NO: 129) using anti TMEM25 Abs, is demonstrated in FIGS. 24A and 24B respectively. FIG. 24C demonstrates TMEM25_P5_Flag (SEQ ID NO: 129) localization using anti-FLAG Abs (Sigma, catalog number: A9594). TMEM25_P5 protein is localized to the cell surface.

Example 20

Determining Cell Localization of TMEM25_P5_Flag by FACS

Membrane localization of TMEM25_P5_Flag protein (SEQ ID NO: 129) was observed upon stable transfection described above, by Flow cytometry analysis, using anti TMEM25 antibodies (Ab1628, Yomics) and by Normal mouse serum as negative control (015-000-120, Jackson). Recombinant HEK293T cells expressing TMEM25_P5_Flag were stained with anti TMEM25 antibodies (A) or by Normal mouse serum (B) followed by Donkey Anti Mouse-DyLight 549 conjugated secondary Ab (Jackson 715-506-150), and were observed for the presence of fluorescent signal.

Recombinant HEK293T-TMEM25_P5_Flag cells were dissociated from the plate using Cell dissociation buffer Enzyme-Free PBS-Based (Gibco; 13151-014), washed in FACS buffer [Dulbecco's Phosphate Buffered Saline (PBS) (Biological Industries, 02*023-1A)/1% Bovine Albumin (Sigma, A7030)]1 and counted. $0.5 \times 10^6$ cells were re-suspended in 100 µl of antibody solution, at a dilution 1:2250 ul, and incubated for 1 hour on ice. The cells were washed with ice-cold FACS buffer and incubated with secondary antibody as indicated for 1 hour on ice. The cells were washed with ice-cold FACS buffer and re-suspended in 500 µl FACS buffer, then analyzed on the FACS machine (FACSCalibur, BD). The data was acquired and analyzed using Cellquest Pro VER. 5.2.

The results presented in FIG. 25 demonstrate that anti TMEM25 antibodies (A) bind to the full length TMEM25 protein, in HEK293T recombinant cells expressing TMEM25_P5_Flag protein, as compare to mouse serum (B) used as a negative control, indicating membrane localization of TMEM25 protein.

Example 21

Analysis of the Expression of Endogenous TMEM25 Protein in Various Cell Lines

The expression of endogenous TMEM25 protein in various cell lines was analyzed by Western Blotting as described below.

JURKAT (ATCC no. TIB-152), Daudi (ATCC no. CCL-213), RPMI8226 (ATCC no. CCL-155), G-361 (ATCC no. CRL-1424), KARPAS (ATCC no. VR-702) cell extracts were prepared as described above (Lanes 3-7 in FIG. 26—see figure legend for the corresponding lane/material assignments).

Whole cell lysates were prepared and analyzed by western blot as described above. Equal protein amounts were analyzed by SDS-PAGE and transferred to Nitrocellulose membrane as described above.

The membrane was blocked by 5% skim-milk diluted in Phosphate buffered saline (PBS) supplemented with 0.05% Tween-20 (PBST) for 1 hour incubation at room temperature (all subsequent incubations occur for 1 hour at room temperature). Blocking solution was then replaced with primary Rabbit Anti TMEM25 antibody (Cat no. HPA012163, Sigma) diluted 1:500 in 5% bovine serum albumin (BSA) (Sigma, catalog number: A4503) (diluted in PBS). After 1 hour incubation, Three 5 minute washes, secondary antibody was applied: goat anti-rabbit conjugated to Peroxidase conjugated Affipure Goat anti Rabbit IgG (Jackson, catalog number: 111-035-003) diluted 1:20,000 in blocking solution. Proteins were also detected by Mouse anti Flag M2-Peroxidase (Sigma, catalog number: A8592) diluted 1:1000 in blocking solution. After 1 hour incubation, 3×5 minute washes, ECL substrate (PIERCE, catalog number: PIR-34080) was applied for 1 minute, followed by exposure to X-ray film (Fuji, catalog number: 100NIF).

FIG. 26 demonstrates the endogenous expression of TMEM25 in various cell lines. A protein at 40.2 kDa corresponding to TMEM25 as observed in HEK293T cells expressing TMEM25_P5_Flag (lane 2; lane 1 shows a control without Flag), detected with anti TMEM25 antibody in extracts of RPMI8226 (lane 5), Daudi (lane 6) and JURKAT (lane 7).

Example 22

Transfection of Stable HEK293T_TMEM25 with siRNA to TMEM25

Specific knockdown of TMEM25_P5_Flag protein (SEQ ID NO:129) expression was observed in HEK293T cells stably expressing TMEM25_P5_Flag (SEQ ID NO 129) previously described upon transfection with TMEM25_P5_SiRNAs.

siRNA was purchased from Dharmacon as follows: TMEM25 (L-018183-00-0005, Dharmacon, ON TARGET plus SMART pool, Human TMEM25 (84866), 5 nmol) and scrambled SiRNA as a negative control (Dharmacon, D-001810-10-05).

Cells were plated at 50-70% confluence 24 hr prior to transfection. siRNA complexes at 250 pmol were added to 250 ul reduced serum Opti-MEM (cat 31985, GIBCO). In parallel, Lipofectamine 2000 reagent (cat#11668019, Invitrogen) was mixed; 5 ul was added to 250 ul reduced serum Opti-MEM (cat 31985, GIBCO). Tubes were combined and incubated for 15-30 min at RT for sufficient complexes to form; the material was then distributed over the cells and incubated for 48 hr. Cells were harvested and cell lysates prepared as described above and detected by anti TMEM25 (Cat no. HPA012163, Sigma), following by secondary Donkey anti Rabbit conjugated to Peroxidase.

FIG. 27 demonstrates specific knockdown of TMEM25_P5_Flag protein (SEQ ID NO: 129) in HEK293T cells stably expressing TMEM25_P5_Flag (SEQ ID NO 129) transfected with TMEM25_P5 siRNA (L-018183-00-0005, Dharmacon) (Lane 2) compared to HEK293T cells stably expressing TMEM25_P5_FLAG transfected with Scrambled-SiRNA (Lane 1) (Dharmacon, D-001810-10-05), using anti TMEM25 antibodies (Sigma, cat#HPA012163).

Example 23

Immunohistochemistry (IHC) Using Anti LSR and Anti TMEM25 Poly Clonal Antibodies To assess the tissue binding profiles, anti-LSR (Abcam catalog number: ab59646) and Anti TMEM25 (Cat no. HPA012163, Sigma), were applied on a panel of tumor tissues microarray (TMA), as detailed in Table 10.

HEK-293 cells expressing LSR_P5a_Flag_m (SEQ ID NO 144) or TMEM25_P5_Flag (SEQ ID NO:129) were used as a positive control for calibration of the pAb for staining.

HEK293T cells transfected with empty vector were used as a negative controls as well as rabbit serum IgG antibodies.

The immunohistochemical detection of LSR_P5a_Flag_m (SEQ ID NO:144) or with TMEM25_P5_Flag (SEQ ID NO:129) by the antibodies anti-LSR and Anti TMEM25 accordingly, were calibrated in formalin-Fixed paraffin-embedded (FFPE) sections. Two antigen retrieval methods were used: pH6.1 and pH9.0 in three Abs concentrations (3.1, 0.3 ug/ml).

The antigen retrieval methods were performed as follows. The above described FFPE sections were deparaffinized, antigen retrieved and rehydrated using pH6.1 or pH9.0 Flex+ 3-in-1 antigen retrieval buffers and a PT Link automated antigen retrieval system, at 95° C. for 20 min with automatic heating and cooling.

Following antigen retrieval, sections were washed in distilled water for 2×5 min then loaded into a DAKO Autostainer Plus. The sections were then incubated for 10 min with Flex+ Peroxidase Blocking reagent, rinsed twice in 50 mM Tris.HCl, 300 mM NaCl, 0.1% Tween-20, pH 7.6 (TBST), followed by a 10 min incubation with Protein Block reagent (DAKO X0909).

The sections were incubated for 30 min with primary antibody diluted in DAKO Envision Flex antibody diluent (DAKO Cytomation, Cat #K8006). Following incubation with primary antibodies, the sections were then rinsed twice in FLEX buffer, incubated with anti-mouse/rabbit Flex+ HRP for 20 min, rinsed twice in FLEX buffer and then incubated with diaminobenzidine (DAB) substrate for 10 min. The chromagenic reaction was stopped by rinsing the slides with distilled water.

Following chromagenesis, the sections were counterstained with haematoxylin, dehydrated in an ascending series of ethanols (90-99-100%), cleared in three changes of xylene and coverslipped under DePeX. Stained sections were analysed by using an Olympus BX51 microscope with a Leica DFC290 camera.

FIG. 28 demonstrates that anti LSR antibody (Cat no. ab59646, Abcam) in sections of positive control cell line (panels A, C and E) showed specific immunoreactivity in a dose dependent concentrations of 3.1 and 0.3 ug/ml respectively, as compared to the negative control cell line (panels B, D and F), in pH 9, according to the antigen retrieval method previously described.

FIG. 29 demonstrates that anti TMEM25 (Cat no. HPA012163, Sigma) in sections of positive control cell line (panels A, C and E) shows specific immunoreactivity in a dose dependent concentrations of 3.1 and 0.3 ug/ml respectively, as compared to the negative control cell line (panels B, D and F), in pH 9, according to the antigen retrieval method previously described.

TABLE 10

Summary of the tissue samples included in the tissue microarray (TMA).

| TMA Map ID | (X, Y) position | Donor ID | Tissue | Path report | Age | Sex |
|---|---|---|---|---|---|---|
| 1 | (1, 1) | 15766 | tumour:breast:lobular carcinoma | Infiltrating lobular carcinoma. Grade2/3 | 42 | Female |
| 2 | (2, 1) | 5252 | tumour:breast:ductal-adenocarcinoma | This slide contains a sample of an in situ and infiltrating ductal carcinoma (modified Bloom and Richardson grade III). Breast - in situ and infiltrating ductal carcinoma. | 57 | Female |
| 3 | (3, 1) | 8723 | tumour:breast:ductal-adenocarcinoma | Primary breast cancer (invasive ductal pattern) | 74 | Female |
| 4 | (4, 1) | 15778 | tumour:breast:lobular carcinoma | Sections of skin with dermis and subcutis infiltrated by poorly differentiated, slightly discohesive carcinoma. Individual cells have rather pleomorphic nuclei. Appearances are consistent with a pleomorphic lobular carcinoma. | 52 | Female |
| 5 | (5, 1) | 3724 | tumour:breast:ductal-adenocarcinoma | Invasive and in situ ductal carcinoma of breast. | 82 | Female |
| 6 | (6, 1) | 2953 | tumour:breast:ductal-adenocarcinoma | The specimen consists of breast tissue including DCIS (ductal carcinoma in situ) and widespread invasive poorly differentiated adenocarcinoma. | 67 | Female |
| 7 | (7, 1) | 9533 | tumour:breast:ductal-adenocarcinoma | This slide contains breast tissues infiltrated by a poorly differentiated ductal carcinoma. Breast tumour - ductal carcinoma. | 50 | Female |
| 8 | (8, 1) | 3346 | tumour:breast:ductal-adenocarcinoma | The specimen consists of connective tissue elements widely infiltrated by a poorly differentiated ductal adenocarcinoma. | 63 | Female |
| 9 | (9, 1) | 5704 | breast | This section contains a good sample of normal breast tissue | 46 | Female |
| 10 | (10, 1) | 5347 | breast | Normal breast | 64 | Female |
| 11 | (11, 1) | 3550 | tumour:colon:adenocarcinoma | The large bowel is widely infiltrated by a moderately well differentiated adenocarcinoma consistent with a derivation from the colon. | 61 | Male |

TABLE 10-continued

Summary of the tissue samples included in the tissue microarray (TMA).

| TMA Map ID | (X, Y) position | Donor ID | Tissue | Path report | Age | Sex |
|---|---|---|---|---|---|---|
| 12 | (12, 1) | 3269 | tumour:colon:adenocarcinoma | Primary colonic pattern adenocarcinoma (moderately differentiated). | 58 | Male |
| 13 | (1, 2) | 15767 | tumour:colon:adenocarcinoma | Moderately differentiated adenocarcinoma. | 58 | Female |
| 14 | (2, 2) | 3751 | tumour:colon:adenocarcinoma | Moderately differentiated adenocarcinoma. | 79 | Female |
| 15 | (3, 2) | 3881 | tumour:colon:adenocarcinoma | Moderately differentiated adenocarcinoma. | 71 | Male |
| 16 | (4, 2) | 2889 | tumour:colon:adenocarcinoma | The specimen consists of large bowel showing surface ulceration associated with a moderately well differentiated primary adenocarcinoma. | 73 | Female |
| 17 | (5, 2) | 15764 | tumour:colon:adenocarcinoma | Moderately differentiated adenocarcinoma. | 75 | Female |
| 18 | (6, 2) | 15763 | tumour:colon:adenocarcinoma | Moderately differentiated adenocarcinoma. | 69 | Female |
| 19 | (7, 2) | 2681 | colon | Normal colon: full thickness. | 54 | Female |
| 20 | (8, 2) | 3121 | colon | Full thickness normal colon. Colon - normal. | 34 | Male |
| 21 | (9, 2) | 5638 | tumour:prostate | Prostate tumour - adenocarcinoma consistent with an origin in prostate. Gleason score 5 + 5 = 10. | 87 | Male |
| 22 | (10, 2) | 15295 | tumour:prostate:adenocarcinoma | Adenocarcinoma. Gleason Score 3 + 3 = 6 | 71 | Male |
| 23 | (11, 2) | 15301 | tumour:prostate:adenocarcinoma | Adenocarcinoma. Gleason Score 3 + 4 = 7 | 51 | Male |
| 24 | (12, 2) | 15758 | tumour:prostate:adenocarcinoma | Adenocarcinoma. Gleason Score 3 + 4 = 7 | 74 | Male |
| 25 | (1, 3) | 15745 | tumour:prostate:adenocarcinoma | Adenocarcinoma. Gleason Score 4 + 5 = 9 | 52 | Male |
| 26 | (2, 3) | 15777 | tumour:prostate:adenocarcinoma | Adenocarcinoma. Gleason Score 4 + 4 = 8 | 68 | Male |
| 27 | (3, 3) | 15755 | tumour:prostate:adenocarcinoma | Adenocarcinoma. Gleason Score 3 + 4 = 7 | 55 | Male |
| 28 | (4, 3) | 15756 | tumour:prostate:adenocarcinoma | Adenocarcinoma. Gleason Score 4 + 5 = 9 | 68 | Male |
| 29 | (5, 3) | 1317 | prostate | Normal prostate | 55 | Male |
| 30 | (6, 3) | 13951 | prostate | Normal prostate | 37 | Male |
| 31 | (7, 3) | 15052 | Lymphoma | Lymph node infiltrated by large cell lymphoma | 45 | Female |
| 32 | (8, 3) | 15760 | Lymphoma | Low Grade Non-Hodgkin's Lymphoma | 72 | Female |
| 33 | (9, 3) | 15754 | Lymphoma | High Grade Non-Hodgkin's Lymphoma | 77 | Male |
| 34 | (10, 3) | 15039 | Lymphoma | Infiltrate of medium to large size lymphocytes with high mitotic rates. High grade Non-Hodgkin's Lymphoma. | 47 | Male |
| 35 | (11, 3) | 15034 | Lymphoma | Diffuse infiltrate of monotamous lymphoid cells consistent with Non-Hodgkin's Lymphoma. | 71 | Male |
| 36 | (12, 3) | 15037 | Lymphoma | Diffuse infiltrate of monotamous lymphoid cells consistent with Non-Hodgkin's Lymphoma. Thyroid tissue seen on edge of section. | 53 | Female |
| 37 | (1, 4) | 15032 | Lymphoma | Diffuse infiltrate of small lymphocytes consistent with Non-Hodgkin's Lymphoma. | 50 | Female |
| 38 | (2, 4) | 15775 | Lymphoma | Hodgkin's Lymphoma | 75 | Female |
| 39 | (3, 4) | 4655 | lymph-node | Lymph node within normal limits. | 1 | Female |
| 40 | (4, 4) | 10789 | lymph-node | Normal lymph node. | 58 | Male |
| 41 | (5, 4) | 12053 | tumour:lung | Poorly differentiated non-small cell carcinoma with some squamoid features. NON SMALL CELL CARCINOMA | 72 | Male |
| 42 | (6, 4) | 15772 | tumour:lung:non-small cell carcinoma | Poorly differentiated non-small cell carcinoma | 44 | Male |
| 43 | (7, 4) | 13586 | tumour:lung | Moderately to poorly differentiated squamous carcinoma. | 67 | Female |

TABLE 10-continued

Summary of the tissue samples included in the tissue microarray (TMA).

| TMA Map ID | (X, Y) position | Donor ID | Tissue | Path report | Age | Sex |
|---|---|---|---|---|---|---|
| 44 | (8, 4) | 2760 | tumour:lung:squamous-cell-carcinoma | The specimen includes normal bronchus, a large vessel presumed to be an artery showing extensive intimal fibrosis/organisation as well as lung parenchyma widely infiltrated by a moderately well differentiated keratinising squamous cell carcinoma. | 64 | Male |
| 45 | (9, 4) | 9354 | tumour:lung:adenocarcinoma | Section of lung tissue containing a tumour growing along the alveolar spaces. The tumour is of large cell type showing features of an adenocarcinoma. | 63 | Male |
| 46 | (10, 4) | 3473 | tumour:lung:adenocarcinoma | Lung tumour - poorly differentiated adenocarcinoma consistent with a primary origin in lung if an origin elsewhere can be excluded. | 72 | Male |
| 47 | (11, 4) | 5757 | tumour:lung:adenocarcinoma | Lung tumour - adenocarcinoma of broncho-alveolar pattern. | 72 | Male |
| 48 | (12, 4) | 4852 | tumour:lung:adenocarcinoma | Lung tumour - adenocarcinoma with prominent broncho-alveolar pattern. | 56 | Female |
| 49 | (1, 5) | 10414 | small cell | Sections of lung showing a poorly differentiated, small cell carcinoma. DIAGNOSIS: Lung; small cell carcinoma. | 74 | Male |
| 50 | (2, 5) | 15055 | small cell | Fibrous tissue infiltrated by small cell carcinoma | 52 | Male |
| 51 | (3, 5) | 15054 | small cell | Sections of lung infiltrated by small cell carcinoma | 65 | Male |
| 52 | (4, 5) | 15053 | small cell | Sections of lung infiltrated by small cell carcinoma | 52 | Male |
| 53 | (5, 5) | 1311 | lung:parenchyma | Lung within normal limits. | 36 | Female |
| 54 | (6, 5) | 14 | lung:parenchyma | Normal lung and bronchus. | 39 | Female |
| 55 | (7, 5) | 5767 | lung:parenchyma | Lung parenchyma (including pleural surface) - normal limits. | 45 | Male |
| 56 | (8, 5) | 2649 | lung:parenchyma | Normal lung | 37 | Male |
| 57 | (9, 5) | 3588 | tumour:stomach | Biopsy shows poorly differentiated mucinous carcinoma. | 69 | Female |
| 58 | (10, 5) | 5065 | tumour:stomach | Sections show a well differentiated adenocarcinoma of the stomach. | 64 | Male |
| 59 | (11, 5) | 9275 | tumour:stomach | Sections of stomach antrum showing a moderately differentiated, infiltrating adenocarcinoma. The carcinoma is seen in both the mucosa and infiltrating the submucosa. DIAGNOSIS: gastric carcinoma. | 78 | Female |
| 60 | (12, 5) | 2295 | stomach | Section shows a moderately differentiated adenocarcinoma of the stomach. | 66 | Female |
| 61 | (1, 6) | 13665 | stomach:body | Full thickness section of normal stomach compatible with body. | 57 | Female |
| 62 | (2, 6) | 2874 | stomach:body | Stomach - full thickness wall with normal body type mucosa. | 53 | Male |
| 63 | (3, 6) | 12998 | tumour:ovary | A serous papillary cystic carcinoma. | 78 | Female |
| 64 | (4, 6) | 13003 | tumour:ovary | Invasive serous papillary carcinoma. | 74 | Female |
| 65 | (5, 6) | 5739 | tumour:ovary | Sections of ovary showing infiltrating islands of cohesive cells in which there are nuclei showing nuclear grooving. The appearances are consistent with a granulosa cell tumour. ovary; granulosa cell tumour. | 48 | Female |
| 66 | (6, 6) | 9407 | tumour:ovary | This slide contains a portion from the wall of a multi loculated ovarian tumour with a pattern best classified as serous cystadenocarcinoma. Ovary tumour - serous cystadenocarcinoma. | 75 | Female |

TABLE 10-continued

Summary of the tissue samples included in the tissue microarray (TMA).

| TMA Map ID | (X, Y) position | Donor ID | Tissue | Path report | Age | Sex |
|---|---|---|---|---|---|---|
| 67 | (7, 6) | 4739 | ovary | This is normal ovarian tissue showing follicular structures (primordial follicles and a cystic follicle) and an involuting corpus luteum. | 42 | Female |
| 68 | (8, 6) | 4781 | ovary | Normal ovarian cortex with follicles. | 34 | Female |
| 69 | (9, 6) | 15759 | melanoma | Malignant melanoma | 65 | Male |
| 70 | (10, 6) | 15753 | melanoma | High grade malignant melanoma | 46 | Female |
| 71 | (11, 6) | 15038 | melanoma | Sections of skin with ulcerated surface with a large dermal deposit of malignant melanoma | 41 | Male |
| 72 | (12, 6) | 15343 | melanoma | Malignant melanoma | 24 | Male |
| 73 | (1, 7) | 13779 | skin | This slide contains a well orientated section of normal skin including some subcutis. Hair follicles are few in number, sebaceous glands are few and sweat glands are moderately abundant. Skin, breast - normal. | 44 | Female |
| 74 | (2, 7) | 13280 | skin | Normal skin including dermis and epidermis. | 50 | Female |
| 75 | (3, 7) | 15342 | tumour:brain:glioblastoma multiforme | Sections of brain of a very cellular tumour composed of glial cells demonstrating nuclear pleiomorphism and focal necrosis | 56 | Male |
| 76 | (4, 7) | 9514 | tumour:brain | Sections shows brain tissue infiltrated by an Astrocytoma; grade 2. | 17 | Male |
| 77 | (5, 7) | 3306 | tumour:brain | Sections show a spindle cell meningioma. | 82 | Male |
| 78 | (6, 7) | 9516 | tumour:brain | Sections shows brain tissue infiltrated by an Astrocytoma; grade 4. | 25 | Female |
| 79 | (7, 7) | 2007 | brain:cortex:frontal | Normal brain | 40 | Male |
| 80 | (8, 7) | 4585 | brain:cortex:frontal | Sections show normal grey matter of the cortex containing unremarkable neurones and this overlies normal white matter. normal brain cortex. | 85 | Male |
| 81 | (9, 7) | 3737 | tumour:kidney | The specimen shows the features of a primary renal cell adenocarcinoma. | 54 | Female |
| 82 | (10, 7) | 13262 | tumour:kidney | Grade 1 papillary transitional cell carcinoma | 59 | Male |
| 83 | (11, 7) | 4764 | tumour:kidney | Renal cell (clear cell) carcinoma | 66 | Male |
| 84 | (12, 7) | 9043 | tumour:kidney | Clear cell renal cell carcinoma of kidney. | 45 | Male |
| 85 | (1, 8) | 2874 | kidney:cortex | Normal renal cortex | 53 | Male |
| 86 | (2, 8) | 4818 | kidney:cortex | Normal renal cortex. | 52 | Female |
| 87 | (3, 8) | 14022 | tumour:liver | Poorly differentiated cholangiocarcinoma | 45 | Male |
| 88 | (4, 8) | 15757 | tumour:liver | Fibrolamellar hepatocellular carcinoma | 25 | Male |
| 89 | (5, 8) | 14826 | tumour:liver | Low Grade hepatocellular carcinoma | 66 | Female |
| 90 | (6, 8) | 15750 | tumour:liver | Cholangiocarcinoma | 70 | Female |
| 91 | (7, 8) | 1991 | liver:parenchyma | Normal liver | 79 | Female |
| 92 | (8, 8) | 3123 | liver:parenchyma | Liver - normal limits. | 31 | Male |

Example 24

Full Length Validation of Encoding LY6G6F Transcript

A full Length transcript encoding LY6G6F (SEQ ID NO: 1) was validated as described below:

1. A reverse transcription reaction was carried out as follows: 10 µg of purified RNA (lung normal) was mixed with 150 ng Random Hexamer primers (Invitrogen, Carlsbad, Calif., USA, catalog number: 48190-011) and 500 µM dNTPs in a total volume of 156 µl. The mixture was incubated for 5 min at 65° C. and then quickly chilled on ice. Thereafter, 50 µl of 5× SuperscriptII first strand buffer (Invitrogen, catalog number: 18064-014, part number: Y00146), 24 µl 0.1M DTT and 400 units RNasin (Promega, Milwaukee, Wis., U.S.A., catalog number: N2511) were added, and the mixture was incubated for 10 min at 25° C., followed by further incubation at 42° C. for 2 min. Then, 10 µl (2000 units) of SuperscriptII (Invitrogen, catalog number: 18064-014) was added and the reaction (final volume of 250 µl) was incubated for 50 min at 42° C. and then inactivated at 70° C. for 15 min. The resulting cDNA was diluted 1:20 in TE buffer (10 mM Tris, 1 mM EDTA pH 8).

2. PCR was done using 2×GoTaq ReadyMix (Promega, catalog number: M7122.) under the following conditions: 12.5 ul GoTaq ready mix; 5 ul cDNA from the above; 1 ul of 10 uM forward primer 100-690 (SEQ ID NO:51); 1 ul of 10 uM reverse primer 100-691 (SEQ ID NO:52) and 5.5 ul H2O in a total reaction volume of 25 µl; with a reaction program of 5 minutes in 95° C.; 35 cycles of: 30 seconds at 94° C., 30 seconds at 53° C., 50 seconds at 72° C.; then 10 minutes at 72° C. The details regarding the primers are presented in Table 11 below.

The PCR product above was loaded on 1.2% agarose gel stained with ethidium bromide, electrophoresed in 1×TAE solution at 100V, and visualized with UV light. The expected band size was excised and extracted from the gel using QiaQuick™ Gel Extraction kit (Qiagen, catalog number: 28707). The purified DNA was then sequenced (Tel-Aviv University, Israel) using the above primers and was verified for the full length LY6G6F encoding transcript (SEQ ID NO:1).

Example 25

Cloning of Full Length Transcript Encoding LY6G6F Fused to EGFP

Cloning of Full Length transcript encoding LY6G6F fused to EGFP (Enhanced Green Fluorescent Protein) was performed as described below.

First, an EGFP expression vector was constructed and then the LY6G6F open reading frame (SEQ ID NO:57), encoding the amino acid sequence set forth in SEQ ID NO:58, was cloned. EGFP was subcloned into pIRESpuro3 (Clontech catalog number: 631619) as follows: EGFP-N1 vector (Clontech cataloge number: 6085-1) was digested with NheI and NotI to excise the EGFP gene. The EGFP insert was then ligated into pIRESpuro3 (Clontech cataloge number: 631619), which was previously digested with the same enzymes, in order to obtain the EGFP-pIRESpuro3 vector.

PCR was done using Platinum PFX™ (Invitrogen., Carlsbad, Calif., USA, catalog number: 1178-021) under the following conditions: 5 µl Platinum PFX 10× buffer; 2 µl—purified validated DNA from the above; 1 µl—10 mM dNTPs (2.5 mM of each nucleotide); 1 µl—Platinum PFX enzyme; 37 µl—H2O; 1 µl of 10 uM forward primer 100-729 (SEQ ID NO:53); 1 ul of 10 uM reverse primer 100-730 (SEQ ID NO:54) (10 µM each) in a total reaction volume of 50 µl; with a reaction program of 5 minutes in 95° C.; 35 cycles of: 30 seconds at 94° C., 30 seconds at 55° C., 60 seconds at 68° C.; then 10 minutes at 68° C. Primers which were used included gene specific sequences corresponding to the desired coordinates of the protein and restriction enzyme sites and Kozak sequence, as listed in Table 11, below and in FIG. 6. Bold letters in Table 11 represent the specific gene sequence while the restriction site extensions utilized for cloning purposes are in Italic and Kozak sequence are underlined.

5 µl of the PCR product above, were loaded on 1.2% agarose gel stained with ethidium bromide, electrophoresed in 1×TAE solution at 100V, and visualized with UV light. After verification of expected size band, remaining PCR product was processed for DNA purification using Qiaquick PCR purification kit (Qiagen™, Valencia, Calif., U.S.A., catalog number 28106). The extracted PCR product were digested with NheI and EcoRI restriction enzymes (New England Biolabs, Beverly, Mass., U.S.A.), as listed in Table 11. After digestion, DNAs were loaded onto a 1.2% agarose gel as described above. The expected band size was excised and extracted from the gel using QiaQuick™ Gel Extraction kit (Qiagen, catalog number: 28707).

The digested DNA was ligated to EGFP_pIRESpuro3 vector previously digested with NheI and EcoRI restriction enzymes, using the LigaFast™ Rapid DNA Ligation System (Promega, catalog number: M8221). The resulting DNA was transformed into competent *E. Coli* bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C.

Screening positive clones was performed by PCR using GoTaq Ready Mix (Promega, catalog number: M7122). Positive colonies were grown in 5 ml Terrific Broth supplemented with 100 µg/ml ampicillin, with shaking overnight at 37° C. Plasmid DNA was isolated from bacterial cultures using Qiaprep™ Spin Miniprep Kit (Qiagen, catalog number: 27106). Accurate cloning was verified by sequencing the inserts (Tel Aviv University, Israel). Upon verification of an error-free colony (i.e. no mutations within the ORF), recombinant plasmids were processed for further analysis.

The DNA sequence of the resulting LY6G6F full length_fused to EGFP (SEQ ID NO:55) is shown in FIG. 7. In FIG. 7 gene specific sequence corresponding to the LY6G6F full length sequence is marked in bold faced type, while the EGFP sequence is marked in Italics and underlining. The amino acid sequence of the resulting LY6G6F full length fused to EGFP (SEQ ID NO:56) is shown in FIG. 8; gene specific sequence corresponding to the full length sequence of LY6G6F is marked in bold faced type, while the EGFP sequence is marked in Italics and underlining.

TABLE 11 primer details

| SEQ ID NO: | Primer ID | Primer sequence | Restriction site |
|---|---|---|---|
| 51 | 100-690 | GAGAACTTGGCAGGCTCTCC | — |
| 52 | 100-691 | CACACTTCCCAGCAGATGTC | — |
| 53 | 100-729 | CTA*GCTAGCCACC*ATGGCAGTCTTATTCCTCCTC | NheI |
| 54 | 100-730 | CG*CGAATTC*GCCTGGGCTTGTGGGCAGGTG | EcoRI |

Example 26

Determining Cell Localization of LY6G6F

In order to determine the cellular localization of the LY6G6F protein, LY6G6F-EGFP fusion protein (SEQ ID NO:56) was used. LY6G6F protein localization was observed upon transient transfection (Chen et al., Molecular vision 2002; 8; 372-388) using the confocal microscope. The cells were observed for the presence of fluorescent products 48 hours following transfection.

The LY6G6F-EGFP pIRESpuro3 construct, described above, was transiently transfected into HEK-293T cells as follows:

HEK-293T (ATCC, CRL-11268) cells were plated on sterile glass coverslips, 13 mm diameter (Marienfeld, catalog number: 01 115 30), which were placed in a 6 well plate, using 2 ml pre-warmed DMEM [Dulbecco's modified Eagle's Media, Biological Industries (Beit Ha'Emek, Israel), cataloge number: 01-055-1A]+10% FBS (Fetal Bovine Serum)+4 mM L-Glutamine. 500,000 cells per well were transfected with 2 µg of the DNA construct using 6 µl FuGENE 6 reagent (Roche, catalog number: 11-814-443-001) diluted into 94 ul DMEM. The mixture was incubated at room temperature for 15 minutes. The complex mixture was added dropwise to the cells and swirled. Cells were placed in an incubator maintained at 37° C. with 5% CO2 content.

48 hours post transient transfection the cells were further processed for analysis in confocal microscopy. The cover slips were washed 3 times in phosphate buffered saline (PBS) and fixed for 15 minutes with 3.7% paraformaldehyde (PFA) (Sigma, catalog number: P-6148). After 2 washes in PBS, the fixed coverslips were glued to a slide using mounting solution (Sigma, catalog number: G0918) and cells were observed for the presence of fluorescent product using confocal microscope. The results are presented in FIG. 9.

Figure 9:
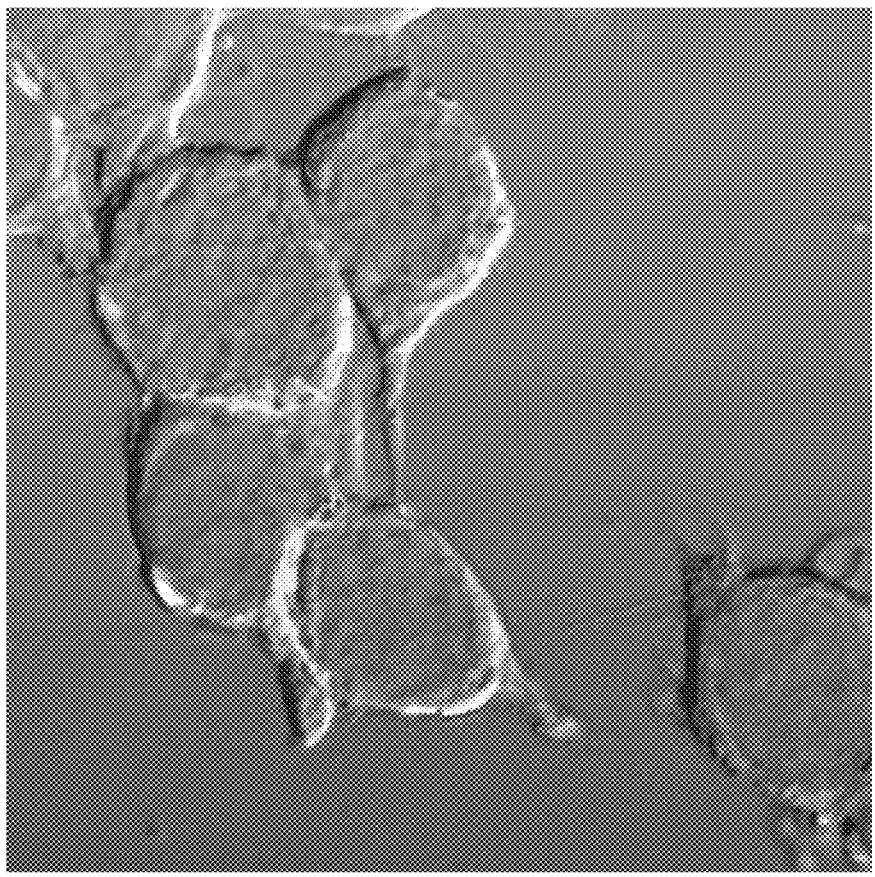
FIG. 9 presents cell localization of G6F_EGFP fusion protein transiently expressed in HEK293T cells. The image was obtained using the 40× objective of the confocal microscope.

FIG. 9 demonstrates that the LY6G6F_EGFP (SEQ ID NO:56) fused protein localizes to cell membrane upon expression in HEK 293T cells. The image was obtained using the 40× objective of the confocal microscope.

Example 27

Cloning and Expression of the LY6G6F, VSIG10, TMEM25 and LSR ECD-Mouse IGg2A-FC Fused Proteins Mouse orthologs of human LY6G6F, VSIG10, TMEM25, and LSR proteins were identified using BlastP software of the National Center of Biotechnology Information (NCBI) using default parameters and used to gain experimental proof of concept related to the functionality of the LY6G6F, VSIG10, TMEM25 and/or LSR Ig fusion proteins in animal model. The mouse orthologs corresponding to human LY6G6F, VSIG10, TMEM25 and LSR proteins are shown in SEQ ID NOs: 20, 19, 9 and 21, respectively. The amino acid alignment and comparison of the human LY6G6F, VSIG10, LSR and TMEM25 proteins to the respective mouse orthologs is shown in FIGS. 5A, 5B, 5C and 5D respectively.

cDNA sequence mouse TMEM25 (SEQ ID NO:9), LY6G6F (SEQ ID NO:20), VSIG10 (SEQ ID NO:19), and LSR (SEQ ID NO: 21) proteins were each fused to the Fc domain of mouse IgG2aFc (SEQ ID NO: 27). In all cases the natural corresponding signal peptide was used for each ECD. The resulted LY6G6F, VSIG10, TMEM25 or LSR ECD-mIgG2aFc Ig fused proteins (SEQ ID NOs: 23, 24, 25, or 26, respectively) are shown in FIGS. 10A-D, respectively.

The LY6G6F, VSIG10, TMEM25 or LSR ECD-mIgG2aFc fused proteins (SEQ ID NOs: 23, 24, 25, or 26, respectively), were cloned into GPEx® retrovectors, followed by retrovector transduction into Catalent's "in-house" CHO-S cell line. A pooled population was produced and the productivity was validated. The pool was then expanded and relative productivity and relative copy number of the pool was determined Cell culture supernatants were analyzed by Catalent's Fc ELISA assay to confirm production of LY6G6F, VSIG10, TMEM25 or LSR ECD-mIgG2aFc fused proteins.

Protein solutions were tested for bioburden and endotoxin. Human fusion proteins composed of the human ECD of either of LY6G6F, VSIG10, TMEM25 or LSR ECD fused to human IgG1 (as depicted on FIG. 11) were also expressed using a similar system.

Assessment of the effect of LY6G6f, VSIG10, TMEM25 or LSR ECD-Ig Fusion Proteins on Mouse and Human T Cell Activation In Vitro:

Example 28

Effect of LY6G6f, VSIG10, TMEM25 or LSR ECD-Ig fusion proteins on Activation of DO11.10 Naïve Cd4+ T Cells with Ova Peptide Naive CD4$^+$ T cells were isolated from spleens of five DO11.10 mice (Jackson) via automax sort: CD4-negative sort (Miltenyi Cat#130-095-248), including anti-CD25 (Miltenyi Cat#130-091-072) in the negative sort cocktail, followed by CD62L-positive sort (Miltenyi Cat #130-049-701). Balb/c total splenocytes were also collected from one mouse, and irradiated with 3000 rads to serve as antigen presenting cells (APCs) for the DO11.10 CD4$^+$ T cells. Naive CD4$^+$ T cells were cultured at 5×10$^5$ cells per well in flat-bottom 96-well plates with irradiated APCs at a ratio of 1:1 (APCs to T cells) in 200 ul of HL-1 medium, and activated with 20 ug/ml or 2 ug/ml OVA323-339 in the presence of either TMEM25-ECD-Ig (SEQ ID NO:25), LSR-ECD-Ig (SEQ ID NO:26), LY6G6F-ECD-Ig (SEQ ID NO:23) at the indicated concentrations. As positive controls, B7-H4-Ig (R&D Systems) or CTA4-Ig (mouse ECD fused to mIgG2a Fc) were used. Isotype control Ig (mIgG2a, BioXCell Cat. #BE0085) was used as a negative control. The cells were pulsed with 1 uCi of tritiated-thymidine at 24 hours, and harvested at 72 hours.

As shown in FIG. 30, TMEM25-ECD-Ig, LSR-ECD-Ig and LY6G6F-ECD-Ig elicit dose dependent inhibition of T cell activation. This was demonstrated as inhibition of T cell proliferation which was induced by OVA323-339 at 20 ug/ml (FIGS. 30 A-C, E) or 2 ug/ml (FIG. 30 D).

VSIG10-ECD-Ig fusion protein (SEQ ID NO:24) did not show activity in three experiments carried out in similar assay.

Example 29

Effect of LY6G6f, VSIG10, TMEM25 or LSR ECD-Ig Fusion Proteins on Activation of Naïve Cd4$^+$ T Cells with anti-Cd3/anti-Cd28 Coated Beads Naive CD4$^+$ T cells were isolated from 5 SJL (Harlan) mice via automax sort as described in the previous section. Beads were coated with anti-CD3 (0.5 ug/ml; clone 2C11) and anti-CD28 (2 ug/ml; clone 37.51 eBioscience) following manufacturer's protocol (Dynabeads M-450 Epoxy Cat. 140.11, Invitrogen), and with increasing concentrations of LSR-ECD-Ig or mIgG2a isotype control (mIgG2a, BioXCell Cat. #BE0085) (0.1-10 ug/ml). The total amount of protein used for beads coating with LSR-ECD-Ig was completed to 10 ug/ml with Control Ig. Naive CD4$^+$ T cells (0.5×10$^6$/well) were activated with the coated beads at a ratio of 1:2 (beads to T cells). The cells were pulsed with 1 uCi of tritiated-thymidine after 24 hours, and harvested after 72.

LSR-ECD-Ig (SEQ ID NO:26) pronouncedly inhibited proliferation of T cell proliferation and elicit its effect in a dose dependent manner (FIG. 31).

Figure 10:
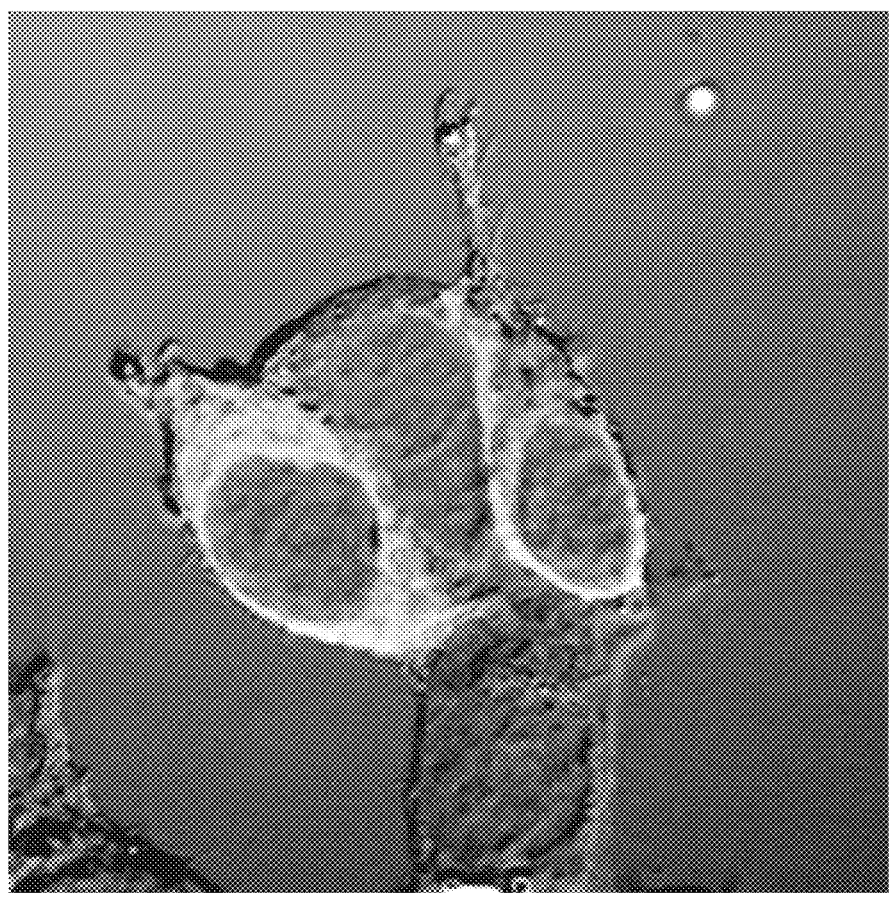
FIG. 10 presents mouse ECDs fused to mouse IgG2a Fc as follows: mouse LY6G6F (also referred to herein as LY6G6F-Ig, FIG. 10A), mouse VSIG10 (FIG. 10B), mouse TMEM25 (also referred to herein as TMEM25-Ig, FIG. 10C) or mouse LSR (also referred to herein as LSR-Ig, FIG. 10D) ECD-mIgG2aFc fused proteins (SEQ ID NOs: 23, 24, 25, or 26, respectively) Amino acid residues corresponding to signal peptide (SP) are shown in Italics. Amino acid residues corresponding to ECD sequence are underlined. Amino acid residues corresponding to mouse IgG2a Fc are shown in bold face (SEQ ID NO:27).

TMEM25, LY6G6F and VSIG10 ECD Ig fusion proteins shown in FIGS. 10 and 11 are tested in a similar assay with similar results.

Example 30

Dose Response Effect of LY6G6f, VSIG10, TMEM25 or LSR ECD-Ig Fusion Proteins on Mouse Cd4+ T Cell Activation with Plate Bound Anti-CD3, as Manifested in Cytokine Production and Expression of the Activation Marker CD69

Untouched CD4+CD25- T cells were isolated from pools of spleen and lymph node cells of BALB/C mice by negative selection using CD4+CD62L+ T cell isolation Kit (Miltenyi Cat#130-093-227) according to the manufacturer's instructions. The purity obtained was >95%.

Tissue culture 96-well plates were coated overnight at 4° C. with 2 ug/ml anti-CD3 mAb (clone 145-2C11) in the presence of LY6G6F, VSIG10, TMEM25 and LSR ECD-Ig fusion proteins (SEQ ID NOs: 23, 24, 25 and 26, respectively) at 1, 5 and 10 µg/ml. Control mIgG2a (Clone C1.18.4 from BioXCell; Cat#BE0085) was added to each well in order to complete a total protein concentration of 12 µg/ml per well. Wells were plated with $1 \times 10^5$ CD4+CD25- T cells per well. At 48 hrs post stimulation, culture supernatants were collected and analyzed using mouse IFNγ ELISA kit, and cells were analyzed for expression of the activation marker CD69 by flow cytometry.

The results shown in FIG. 32 demonstrate inhibitory effects of LY6G6F, VSIG10, TMEM25 and LSR ECD-Ig fusion proteins on CD4 T cell activation, manifested by reduced IFNγ secretion (FIG. 32A) and reduced expression of CD69 (FIG. 324B) upon TCR stimulation, compared to control mIgG2a and CTLA4-Ig.

Example 31

The Effect of LY6G6f, VSIG10, TMEM25 or LSR ECD-Ig Fusion Proteins On CD4+ T Cell Differentiation In Vitro To test the ability of LY6G6F, VSIG10, TMEM25 and LSR Ig fusion proteins to inhibit CD4+ T cell differentiation, naïve CD4+ T cells are isolated from D011.10 mice, which are transgenic for a T cell receptor (TCR) that is specific for OVA323-339 peptide. Using D011.10 T cells enables studying both polyclonal (anti-CD3/anti-CD28 mAbs) and peptide-specific responses on the same population of CD4+ T cells. Naïve CD4+ T cells are isolated from D011.10 mice and activated in culture in the presence of anti-CD3/anti-CD28 coated beads or OVA323-339 peptide plus irradiated BALB/c splenocytes, in the presence of LY6G6F, VSIG10, TMEM25 or LSR ECD-Ig fusion proteins, control Ig, or B7-H4 Ig. The cells are activated in the presence of Th driving conditions as follows: Th0 cell-(IL-2), Th1 cell-(IL-2+IL-12), Th2 cell-(IL-2+IL-4), or Th17 cell-(TGF-β+IL-6+IL-23+anti-IL-2). The effects on T cell differentiation and Th-specific responses are assessed by measuring cell proliferation and subtype specific cytokine production: IL-4, IL-5, IL-10, IL-17, IFN-γ.

Example 32

Assessment of the Effect of LY6G6f, VSIG10, TMEM25 or LSR ECD Ig Fusion Proteins on Human T Cells Activation The effect of LY6G6F, VSIG10, TMEM25 or LSR ECD Ig fusion proteins on human T cell response is tested by two different in vitro assays using purified human T cells. In the first assay, human T cells are activated by anti-CD3 and anti-CD28 coated beads, and in the other assay, activation is carried out using anti-CD3 and anti-CD28 antibodies in the presence of autologous, irradiated PBMCs. The regulatory activity of LY6G6F, VSIG10, TMEM25 or LSR ECD Ig fusion proteins on human T cell activation, is evaluated by measuring cell proliferation and cytokine release.

Study I—Activation of Human T Cells with Anti-CD3 and Anti-CD28-Coated Beads is Inhibited by Fusion Proteins Naïve CD4+ T cells are isolated from 4 healthy human donors and activated with anti-CD3 mAb/anti-CD28 mAb coated beads in the presence of control mIgG2a, or any one of the LY6G6F, VSIG10, TMEM25 or LSR ECD Ig fusion proteins. Two side-by-side culture sets are set up; one culture being pulsed at 24 hours with tritiated-thymidine and harvested at 72 hours while the second plate is harvested at 96 hours for cytokine production via LiquiChip.

Study II—Activation of Human T Cells with Irradiated Autologous PBMCs is Inhibited by Fusion Proteins Total PBMCs are isolated from fresh blood of healthy human donors using ficoll gradient. $10 \times 10^6$ total PBMCs are resuspended in Ex-Vivo 20 medium, and irradiated at 3000 rad. These cells are used to activate the isolated T cells in vitro, by presenting the anti-CD3, anti-CD28 and either of the test proteins. The rest of PBMCs are used for isolation of T cells using CD4+ T cell Isolation Kit II from Miltenyi.

For activation, $5 \times 10^5$ isolated T cells are cultured in the presence of $5 \times 10^5$ autologous irradiate PBMCs. Anti-CD3 (0.5 µg/ml), anti-CD28 (2 µg/ml) and either of LY6G6F, VSIG10, TMEM25 or LSR ECD Ig fusion proteins or control Ig (mIgG2a) are added in a soluble form. The cultures are pulsed with 1 uCi of triated thymidine at 24 hrs, and proliferation is measured at 72 hours.

Example 33

The Effect of LY6G6F, TMEM25 and LSR Proteins Upon Ectopic Expression in APC-Like Cells, on Human T Cell Responses The effects of LY6G6F, TMEM25 and LSR on human T cell responses were evaluated following their ectopic expression in 'T cell stimulator' cells: a murine thymoma cell line, Bw5147, which were engineered to express membrane-bound anti-human CD3 antibody fragments, that can trigger the TCR-complex on human T cells, with or without co-expression of putative costimulatory or coinhibitory ligands.

Codon-optimized cDNAs encoding LY6G6F (SEQ ID NO: 1), TMEM25 (SEQ ID NO: 7) and LSR (SEQ ID NO: 11) were gene-synthesized and directionally cloned into a retroviral vector pCJK2 via Sfi-I sites. Monocistronic expression constructs were generated. The constructs were validated by agarose gel electrophoresis and were expressed in Bw5147 cells displaying high levels of membrane bound anti-CD3 antibody (Bw-3/2) (Leitner et al., 2010). As negative control Bw5147 cells transduced with "empty" vector (pCJK2) were used. In addition, Bw-3/2 cells expressing costimulatory molecules (ICOSL and CD70) and Bw-3/2-cells expressing coinhibitory molecules (B7-H3 and B7-H1/PD-L1) were also used as controls. Homogenously high expression of the stimulating membrane-bound anti-CD3 antibody was confirmed by FACS using a DyLight-649 anti-mouse IgG (H+L) antibody that reacts with the murine single chain antibody expressed on the stimulator cells. Presence and high level transcription of expression monocistronic constructs in the respective stimulator cells was confirmed by qPCR.

T cells were purified from buffy coats or heparinised blood derived from healthy volunteer donors and the mononuclear fraction was obtained by standard density centrifugation using Ficoll-Paque (GE-Healthcare). Untouched bulk human T cells were obtained through MACS-depletion of CD11b, CD14, CD16, CD19, CD33 and MHC-class II-bearing cells with the respective biotinylated mAb in conjunction with paramagnetic streptavidin beads (Leitner et al., 2009). Purified CD8 T cells and CD4 T cells were obtained by adding biotinylated CD4 and CD8 mAb to the pools. Naïve CD4 T cells were isolated using the Naïve CD4+ T cell Isolation Kit II (Miltenyi Biotec). Following isolation, cells were analyzed for purity by FACS, and samples with sufficient purity (>90%) were used for the experiments.

The stimulator cells were harvested, counted, irradiated (2×3000 rad) and seeded in flat-bottom 96-well plates (20000 cells/well). Liquid nitrogen stored MACS-purified T cells were thawed, counted and added to the wells at 100.000 cells per well; total volume was 200 µl/well. Triplicate wells were set up for each condition. Following 48 hours of co-culture, $^3$H-thymidine (final concentration of 0.025 mCi; PerkinElmer/NewEngland Nuclear Corporation, Wellesley, Mass.) was added to the wells. Following further culturing for 18 hours, the plates were harvested on filter-plates and incorporation of $^3$H-Thymidine was determined as described in Pfistershammer et al., 2004. In addition, a series of experiments with MACS-purified T cell subsets (CD8 T cells, CD4 T cells, and naïve CD45RA-positive CD4 T cells) were performed. Additional controls in all experiments included wells with stimulator cells alone to assess the cells microscopically and also to determine basal $^3$H-Thymidine incorporation of the stimulator cell w/o T cells. Results with stimulator cells that quickly disintegrated following irradiation were excluded from the analysis.

Results shown in FIG. 33 are an average of several experiments, and show the effect of stimulator cells expressing LY6G6F, TMEM25 or LSR on the proliferation of human bulk T cells (FIG. 33A), CD4+ T cells (FIG. 33B), CD8+ T cells (FIG. 33C), or naïve CD4 CD45RA+ T cells (FIG. 33D). Expression of control costimulatory molecules (ICOSL and CD70) resulted in a consistent and pronounced stimulation of proliferation of all cell subtypes. Similarly to expression of control coinhibitory molecules (B7-H3 and B7-H1/PD-L1), which resulted in a mild inhibition of proliferation of different T cell subtypes, expression of LY6G6F, TMEM25 and LSR also resulted in a mild inhibition of T cell proliferation, with the most pronounced inhibitory effects exhibited on CD8+ T cells.

Example 34

Characterizing the Target Cells for LY6G6F, VSIG10, TMEM25 And/or LSR Proteins by Determining their Binding Profile to Immune Cells Splenocytes from DO11.10 mice (transgenic mice in which all of the CD4+ T cells express a T cell receptor that is specific for OVA323-339 peptide) are activated in the presence of OVA323-339 peptide, and cells are collected at t=0, 6, 12, 24, and 48 hours following initial activation to determine which cell type is expressing a receptor for LY6G6F, VSIG10, TMEM25 and/or LSR over time. Cells are then co-stained for CD3, CD4, CD8, B220, CD19, CD11b, and CD11c.

Example 35

Assessment of the Effect of LY6G6f, VSIG10, TMEM25 or LSR ECD Ig Fusion Proteins on the Ability of B Cells to Class-Switch and Secrete Antibody Resting B cells are isolated from unprimed C57BL/6 mice and activated in vitro in the presence of anti-CD40 plus (i) no exogenous cytokine, (ii) IL-4, or (iii) IFN-γ. The cell cultures receive control Ig (mIgG2a), anti-CD86 mAb (as a positive control for increased Ig production), or any one of LY6G6F, VSIG10, TMEM25 and LSR ECD fusion proteins described in Example 5 herein, at the time of culture set up, and are cultured for 5 days. The LY6G6F, VSIG10, TMEM25 and LSR ECD fusion proteins are tested at three concentrations each. At the end of culture, supernatants are tested for the presence of IgM, IgG1, and IgG2a via ELISA. If there appears to be an alteration in the ability of the B cells to class-switch to one isotype of antibody versus another, then the number of B cells that have class switched is determined via ELISPOT. If there is an alteration in the number of antibody producing cells, then it is determined if there is an alteration in the level of γ1- and γ2a-sterile transcripts versus the mature transcripts for IgG1 and IgG2a.
Assessment of the therapeutic effect of LY6G6f, VSIG10, TMEM25 or LSR ECD Ig Fusion Proteins for Treatment of Autoimmune Diseases Example 36

Efficacy of LY6G6f, VSIG10, TMEM25 or LSR ECD Ig Fusion Proteins in Mouse R-EAE Model of Multiple Sclerosis The therapeutic effect of TMEM25-ECD-Ig, LSR-ECD-Ig and VSIG10-ECD-Ig fusion proteins (SEQ ID NOs: 25, 26 and 24, respectively) for treatment of autoimmune diseases was tested in a mouse model of Multiple Sclerosis; Relapsing Remitting Experimental Autoimmune Encephalomyelitis (R-EAE):
Female SJL mice 6 weeks old were purchased from Harlan and maintained in the CCM facility for 1 week prior to beginning the experiment. Mice were randomly assigned into groups of 10 animals and primed with 50 µg PLP139-151/CFA on day 0. Mice received 6 i.p. injections of 100 ug/dose of TMEM25-ECD-Ig (SEQ ID NO: 25), LSR-ECD-Ig (SEQ ID NO: 26), mIgG2a isotype control, or CTLA4-Ig (mouse ECD fused to mouse IgG2a Fc) as positive control. Treatments began at the time of onset of disease remission and were given 3 times per week for 2 weeks. Mice were followed for disease symptoms. On day 35, (during the peak of disease relapse) 5 mice of each group were assayed for DTH (delayed type hypersensitivity) response to disease inducing epitope (PLP139-151) and to relapse-associated myelin epitope (PLP178-191) via injection of 10 µg of PLP139-151 in one ear and PLP178-191 into the opposite ear. The level of ear swelling was assayed at 24 hours post challenge.

The present Example shows a pronounced decrease in disease severity of R-EAE-induced mice upon treatment with TMEM25-ECD-Ig (SEQ ID NO: 25) or LSR-ECD-Ig (SEQ ID NO: 26), in a therapeutic mode with 100 ug/dose at 3 times per week, as shown in FIG. 34A. The level of inhibition was similar to that of CTLA4-Ig.

In addition, treatment of R-EAE mice with TMEM25-ECD-Ig (SEQ ID NO: 25) or LSR-ECD-Ig (SEQ ID NO: 26) dramatically inhibited DTH responses to the disease inducing epitope (PLP139-151) and to relapse-associated epitope (PLP178-191) at day 35 (FIG. 34B).

Figure 35A:
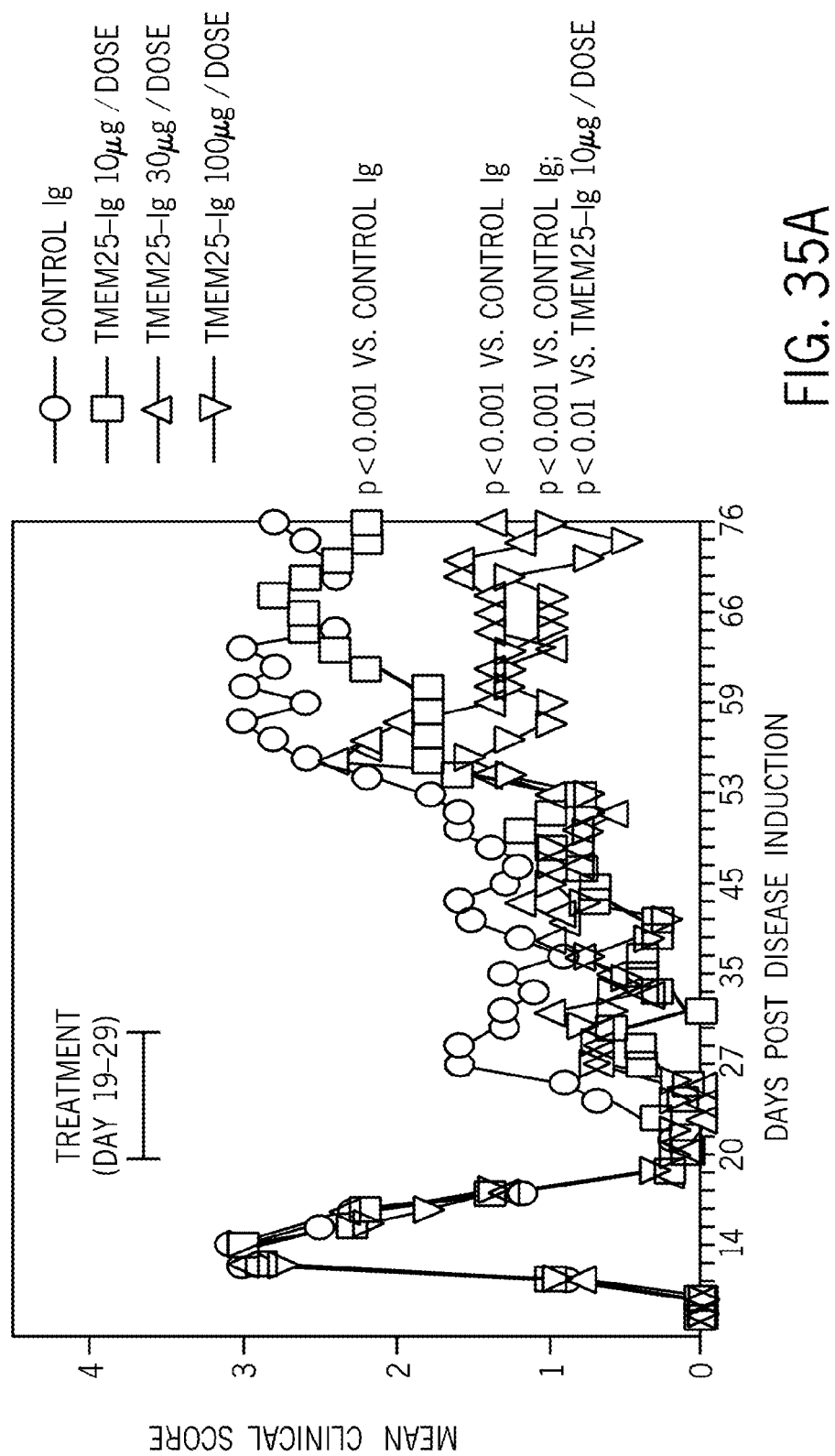
Figure 35B:
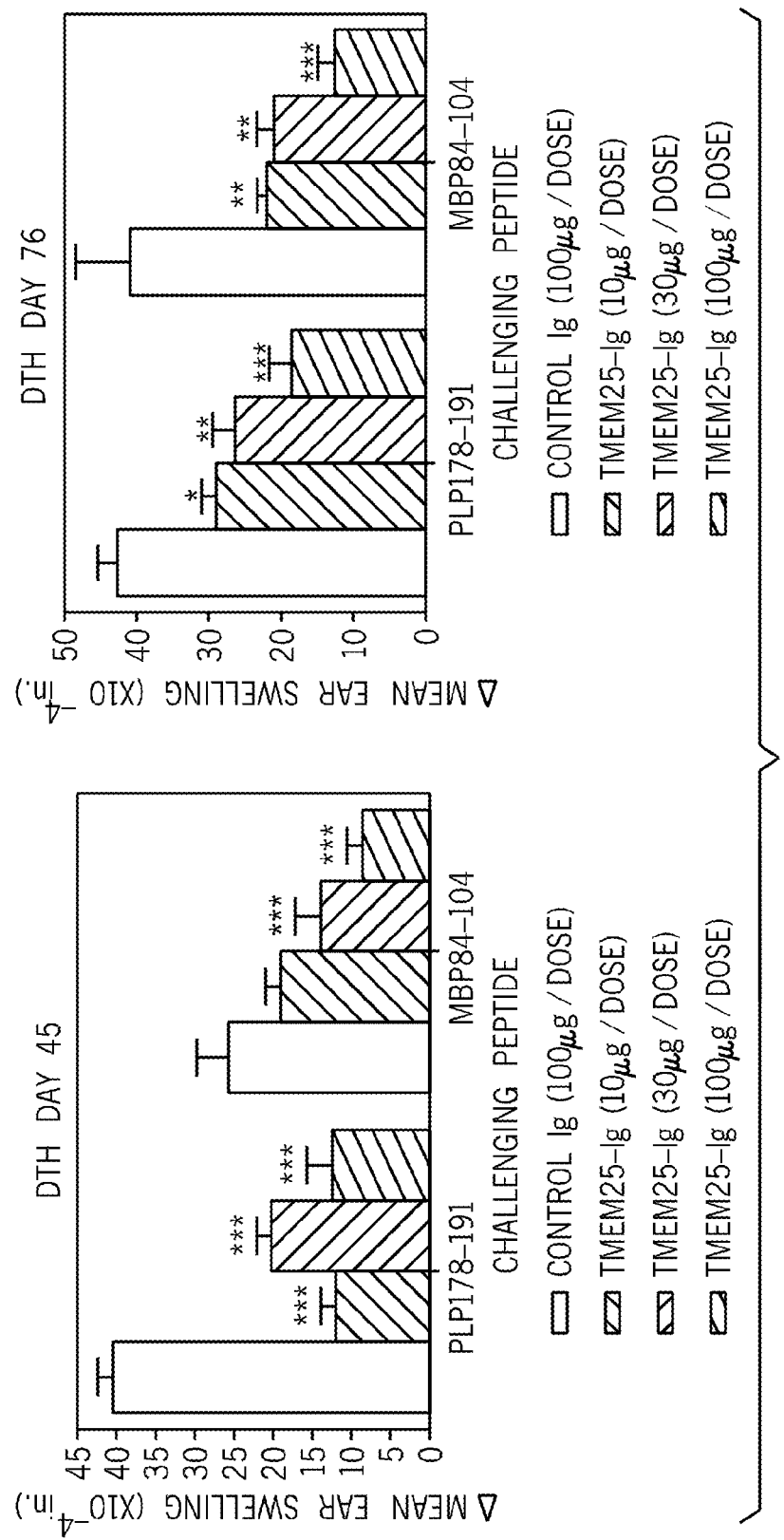
Figure 35C:
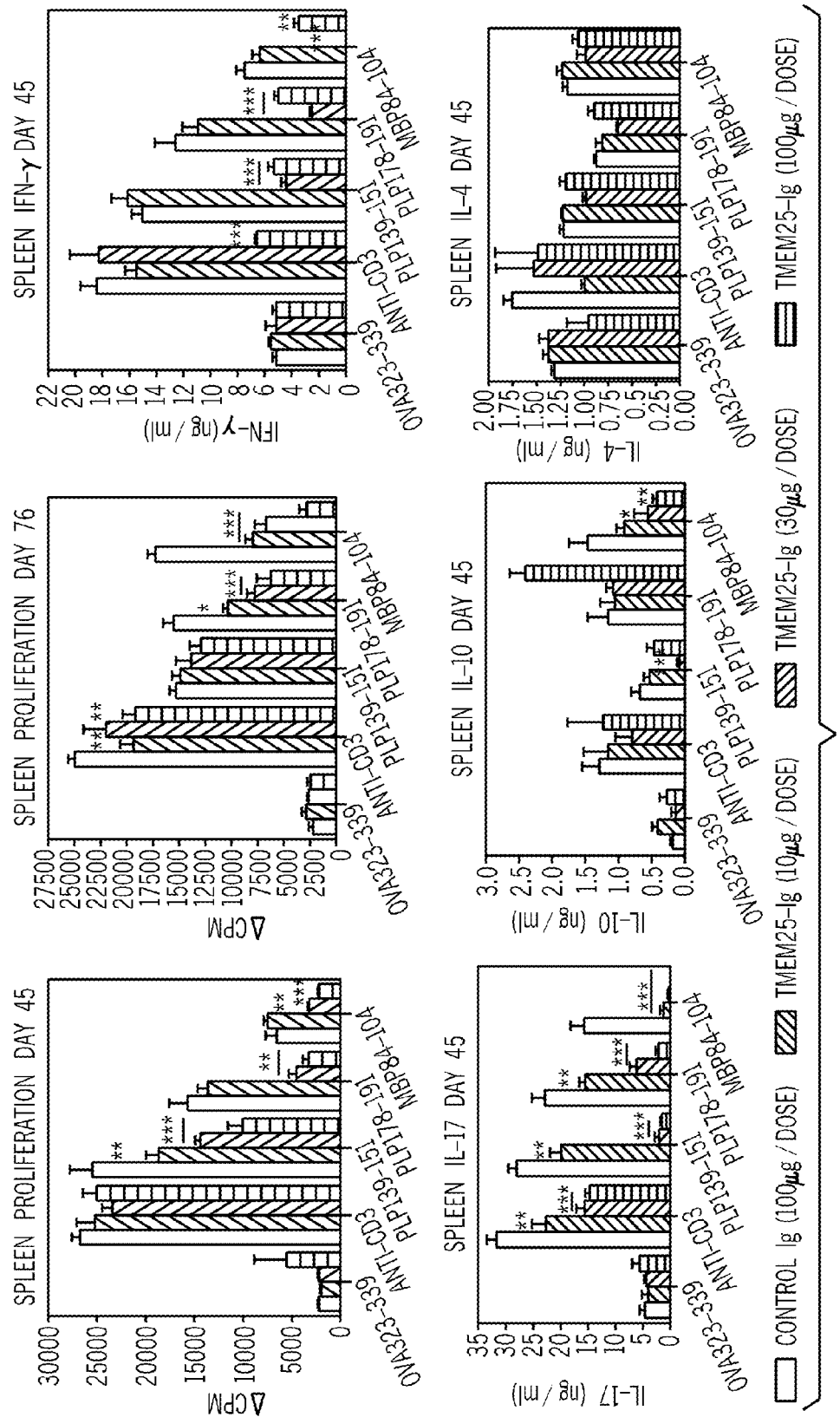
Figure 35D:
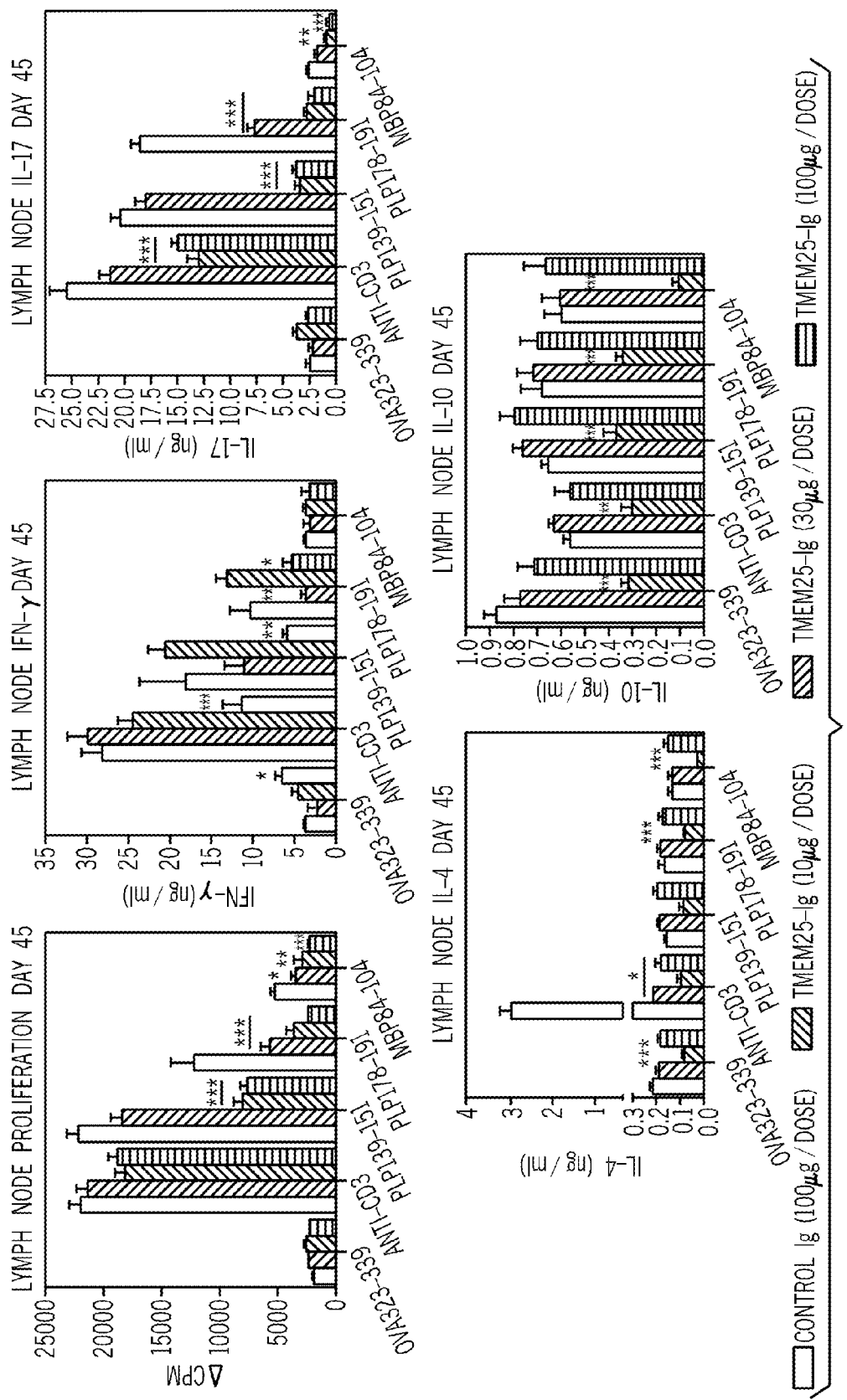

To test the dose dependency of the efficacy of TMEM25-ECD-Ig (SEQ ID NO: 25) as well as its mode of action in the PLP-induced R-EAE model, disease was induced as described above and mice were treated from onset of disease remission with 100, 30 or 10 ug/dose TMEM25-ECD-Ig, 3 times per week over two weeks. TMEM25-ECD-Ig decreased the level of disease severity in a dose dependent manner as shown by the milder effect observed by the lowest dose tested (10 ug/dose), which is significantly different from the effect of the high dose (100 ug/dose) (FIG. 35A). TMEM25-ECD-Ig also inhibited DTH responses to spread epitopes PLP178-191 and MBP84-104 on days 45 and 76 (FIG. 35B). Furthermore, TMEM25-ECD-Ig inhibited recall responses of day 45 and day 76 splenocytes and day 45 cervical lymph node cells, to PLP139-151, PLP178-191 and MBP84-104 (FIGS. 35C and 35D). This was manifested mainly in inhibition of proliferation as well as reduction in IFNγ and IL-17 release. TMEM25-ECD-Ig also inhibits IL-4 and IL-10 release from cervical lymph node cells of mice treated at 30 ug/dose TMEM25-ECD-Ig. There was no consistent effect on IL-4 and IL-10 release from splenocytes under these conditions.

Figure 35E:
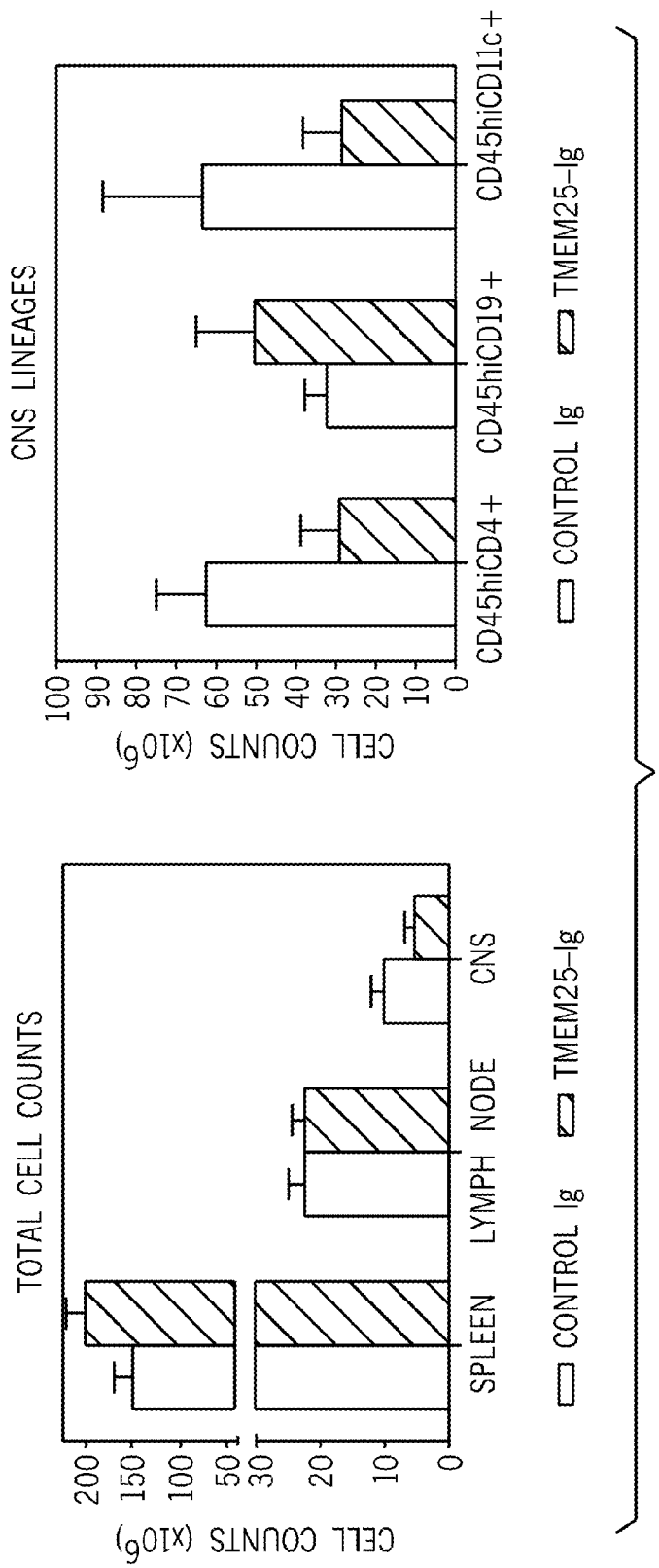

The beneficial effect of TMEM25-ECD-Ig (SEQ ID NO: 25) in the R-EAE model was also accompanied by a significant reduction in the infiltration of immune cells to the CNS (FIG. 35E). Although none of the lineages tested in the CNS was significantly changed, there was a clear trend for reduction in CD4+ T cells and Dc (CDL11C+) and some increase in the B cell (CD19+) population, although this did not reach statistical significance (FIG. 35E)

Figure 36A:
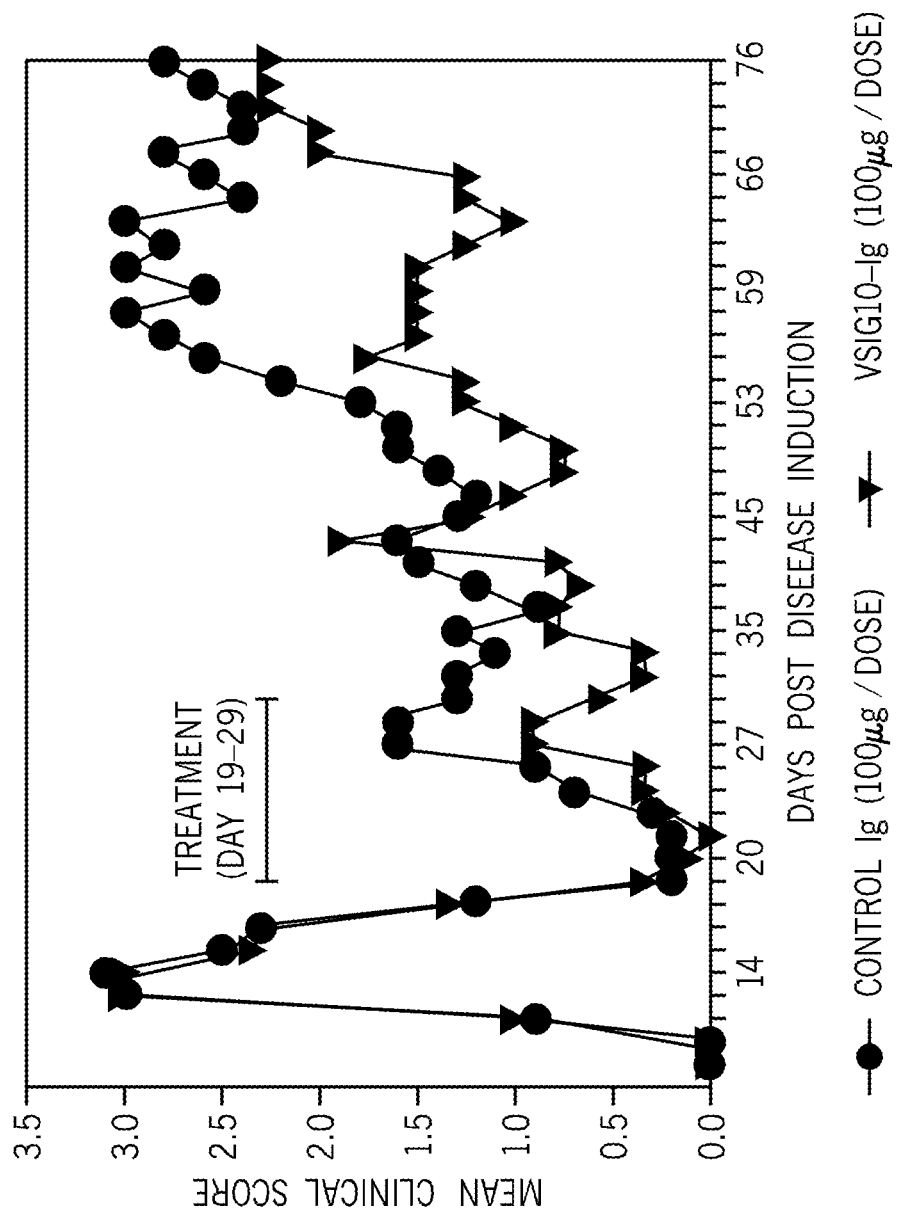

VSIG10-ECD-Ig (SEQ ID NO: 24) was also tested in the PLP-induced R-EAE model described above. Treatments began on the day of onset of remission and given at 100 ug/dose 3x/week over 2 weeks. VSIG10-ECD-Ig significantly reduced disease severity as manifested in reduction in disease score (FIG. 36A). The beneficial effect of VSIG10-ECD-Ig in this model was also accompanied by inhibition of day 45 and day 76

Figure 36B:
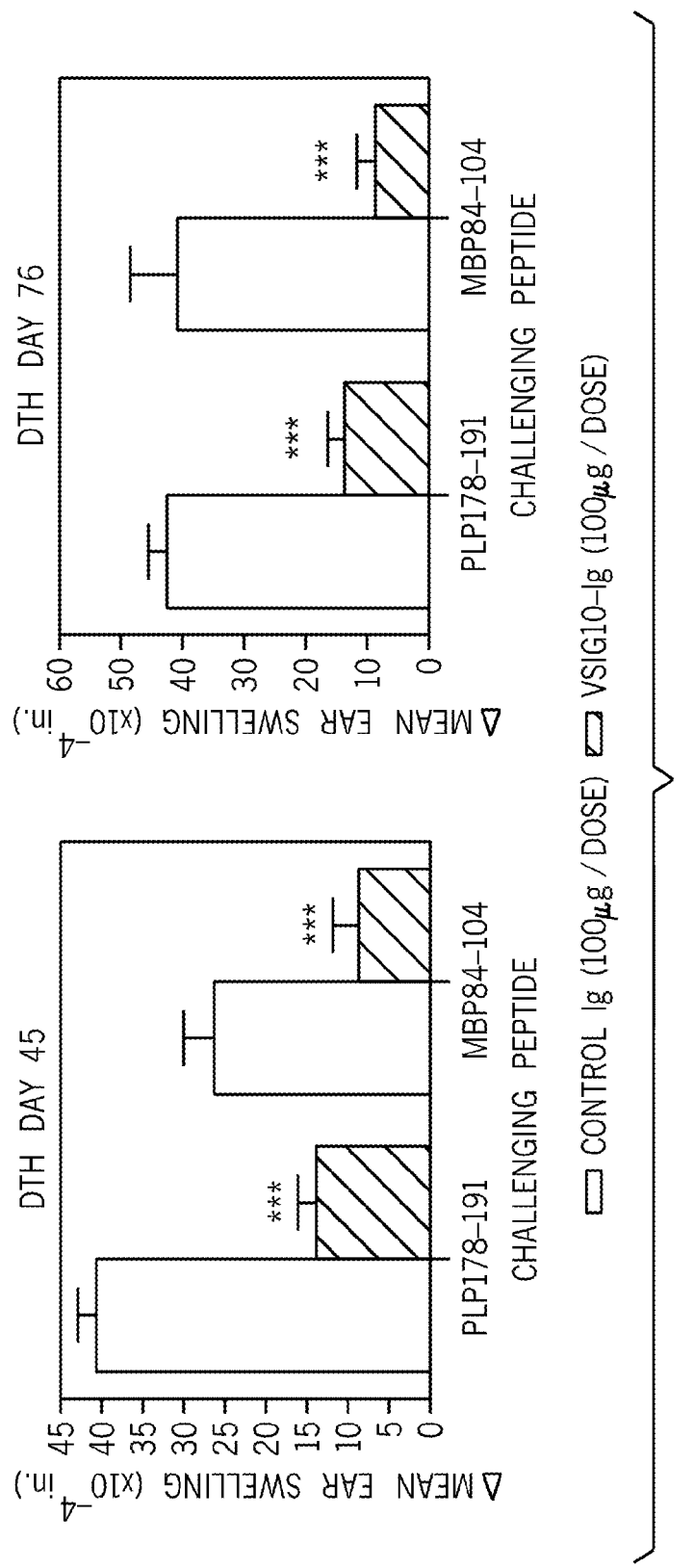
Figure 36C:
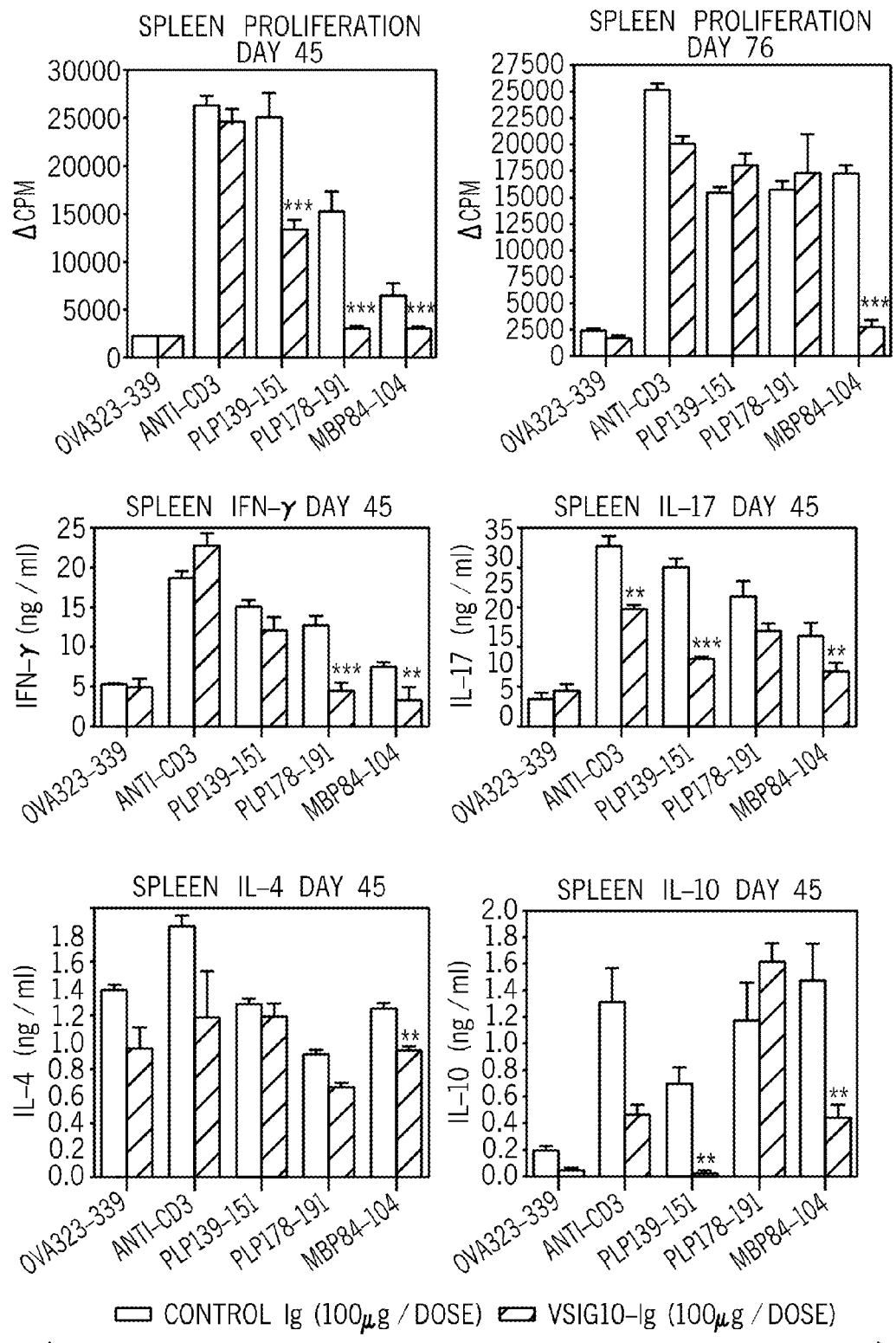
Figure 36D:
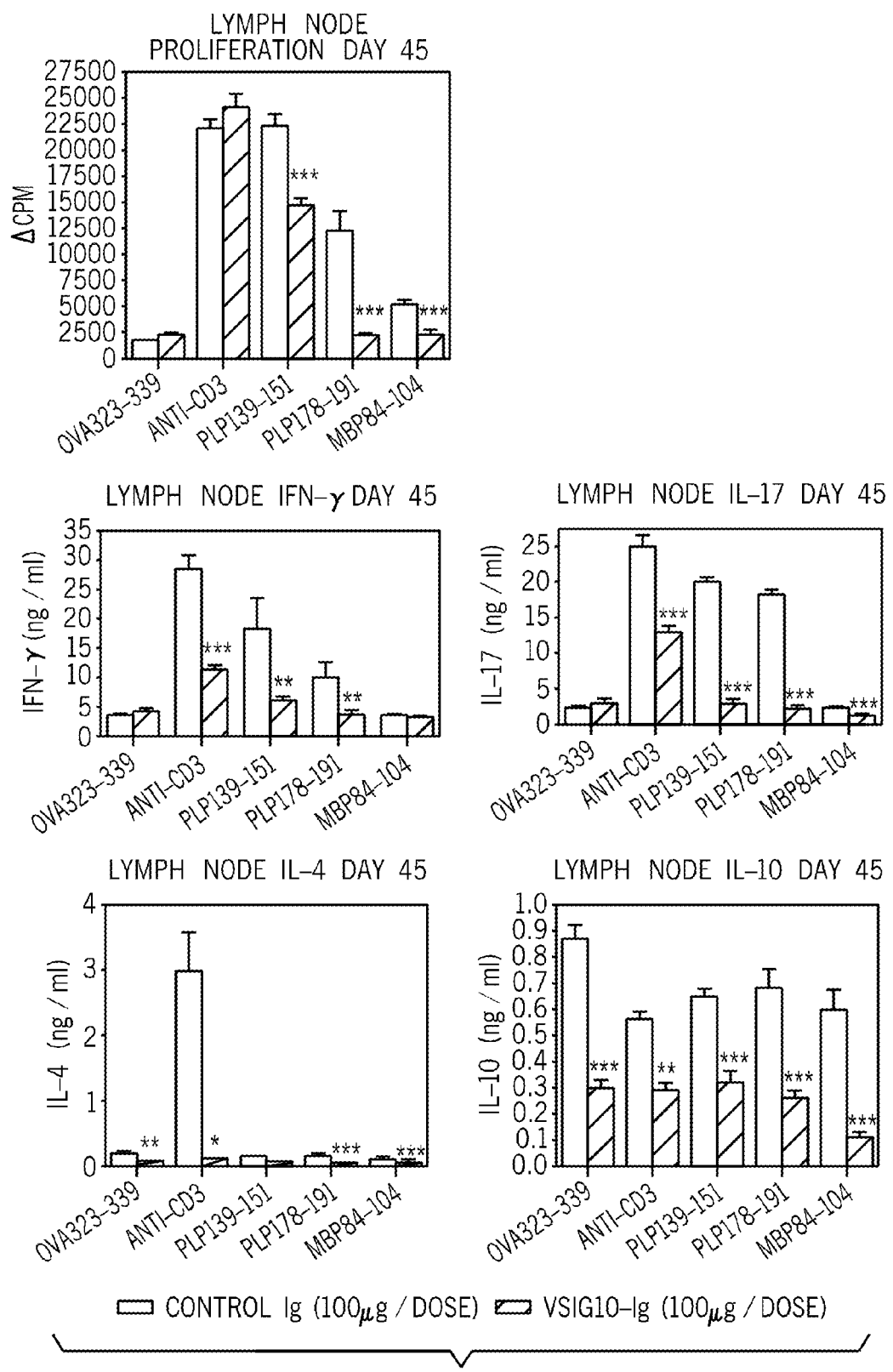

DTH responses to spread epitopes PLP178-191 and to MBP84-104 (FIG. 36B). In addition, VSIG10-ECD-Ig (SEQ ID NO: 24) inhibited recall responses of splenocytes and draining (cervical) lymph node cells taken on day 45, in response to activation with inducing epitope PLP139-151, or spread epitopes PLP178-191 and MBP84-104 (FIGS. 36C and 36D). This was manifested in inhibition of cell proliferation as well as secretion of IFNg, IL-17, IL-4 and IL-10.

Figure 36E:
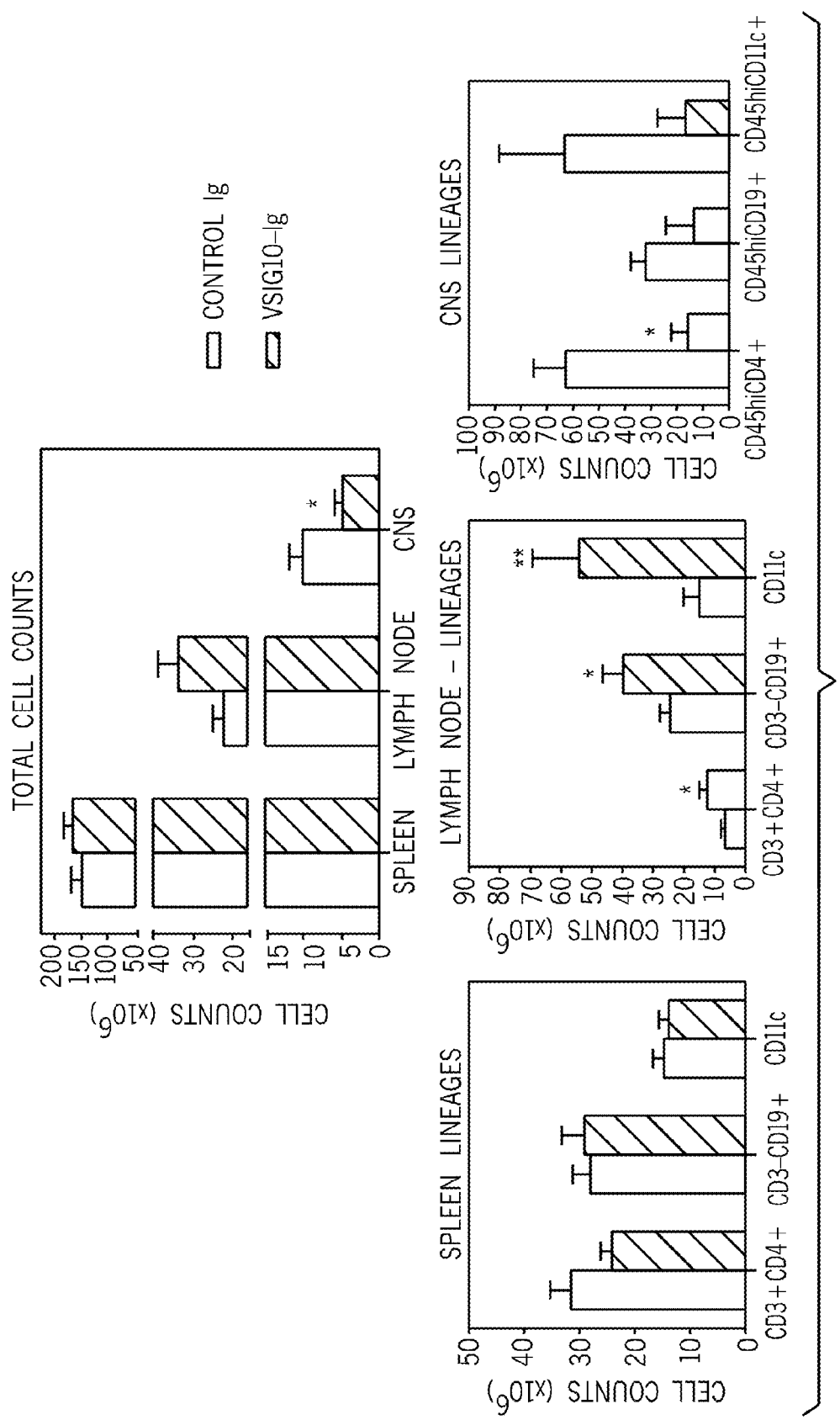

Interestingly, on day 76 VSIG10-ECD-Ig (SEQ ID NO: 24) inhibited only MBP84-104 induced splenocytes proliferation, but not proliferation induced by the earlier myelin epitopes, (FIG. 36C). VSIG10-ECD-Ig treatment in the R-EAE model also significantly reduced the infiltration of immune cells to the CNS which was accompanied by evident but not significant elevation in the number of cells in the lymph nodes, (FIG. 36E). The major cell subtype that was reduced in the CNS was CD4+ T cells, however, there was also a clear trend of reduction of CD19+ B cells and CD11c+ Dcs in the CNS. All these immune cell subtypes were significantly elevated in the lymph nodes, suggesting that VSIG10-ECD-Ig may inhibit trafficking of immune cells from the lymph nodes to the CNS.

LY6G6F-ECD-Ig fusion protein is studied in a similar model of Multiple Sclerosis.

Example 37

Efficacy of LY6G6f, VSIG10, TMEM25 or LSR ECD Ig Fusion Proteins in Mouse CIA Models of Rheumatoid Arthritis Study I:
LSR-ECD-Ig (SEQ ID NO: 26) was tested in mouse model of collagen-induced arthritis (CIA) which is a model of rheumatoid arthritis. Male DBA/1 mice were housed in groups of 8-10, and maintained at 21° C.±2° C. on a 12 h light/dark cycle with food and water ad libitum. Arthritis was induced by immunisation with type II collagen emulsified in complete Freund's adjuvant. Mice were monitored on a daily basis for signs of arthritis. On the appearance of arthritis (day 1) treatment with LSR-ECD-Ig (SEQ ID NO: 26), mIgG2a isotype control or CTLA4-Ig (mouse ECD fused to mouse IgG2a Fc) as positive control (100 ug/dose, each) was initiated and given 3 times per week for 10 days. Hind footpad swelling was measured (using microcalipers), as well as the number and degree of joint involvement in all four limbs. This yielded two measurements, clinical score and footpad thickness that can be used for statistical assessment.

At the end of the treatment period mice were bled and sacrificed. For histological analysis, paws were removed at post mortem, fixed in buffered formalin (10% v/v), then decalcified in EDTA in buffered formalin (5.5% w/v). The tissues are then embedded in paraffin, sectioned and stained with haematoxylin and eosin. The scoring system is as follows:
0=normal; 1=synovitis but cartilage loss and bone erosions absent or limited to discrete foci; 2=synovitis and significant erosions present but normal joint architecture intact; 3=synovitis, extensive erosions, joint architecture disrupted.

Figure 37C:
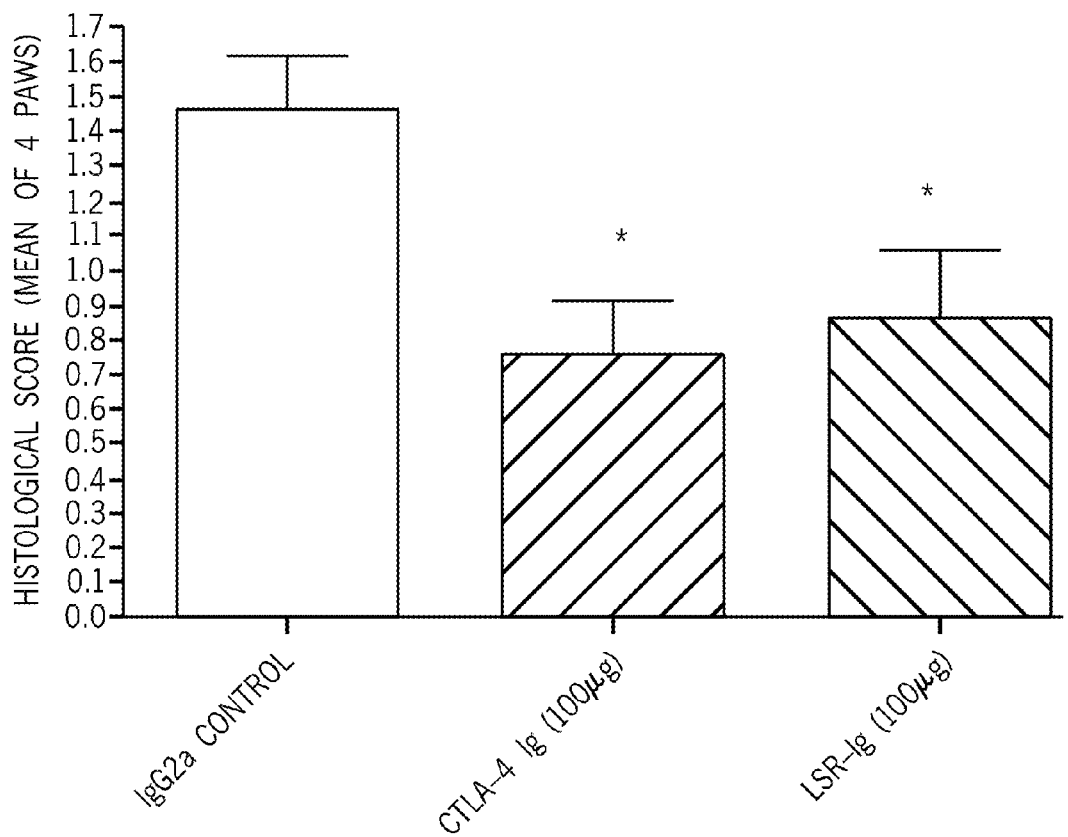

The present Example shows that treatment of mice with established CIA with LSR-ECD-Ig at 100 ug/dose 3 times/week for 10 days resulted in potent reduction of clinical score (FIG. 37A) and paw swelling (FIG. 37B) and histological damage (FIG. 37C). The efficacy of LSR-ECD-Ig (SEQ ID NO: 26) was similar to that obtained with CTLA4-Ig.

The efficacy of TMEM25-ECD-Ig, VSIG10-ECD-Ig and LY6G6F-ECD-Ig is evaluated in this CIA model.

Treatment with TMEM25-ECD-Ig (SEQ ID NO: 25) or with LSR-ECD-Ig (SEQ ID NO: 26) did not show efficacy in a more severe CIA model in which a boost with type II collagen emulsified in complete Freund's adjuvant is given on day 21. In this severe CIA Enbrel, a positive control, given at the same regimen and dosage, had very weak efficacy. Treatment with TMEM25-ECD-Ig also did not show a therapeutic effect in a CIA model with a collagen type II boost without the adjuvant given on day 21.

Study II: The Efficacy of LY6G6F ECD Ig Fusion Protein in the CIA Model was Studied Using a Modified CIA Model as Follows:
female DBA/1 mice (Taconic Farms, 9-11 weeks old) were acclimated for 7 days. On day 0, mice were immunized with chicken collagen/CFA, 0.05 mL EK-0210 emulsion/mouse (Hooke Laboratories, Inc.) and on day 20 a booster with chicken collagen/IFA, 0.05 mL EK-0211 emulsion/mouse (Hooke Laboratories, Inc.) was injected. Mice were scored daily and enrolled into one of the following treatment groups on the day of onset of arthritis:
Group 1: LY6G6F-ECD-Ig (SEQ ID NO: 23), i.p., Q2D, 30 mg/kg for 2 wks, 10 mL/kg.
Group 2: Vehicle (PBS) Q2D, for 2 wks, 10 mL/kg (negative control).

From the time of enrolment, mice were scored every other day for clinical signs and ankylosis according to the following scoring system:
Clinical score:

| | |
|---|---|
| 0 | Normal paw. |
| 1 | One toe inflamed and swollen. |
| 2 | More than one toe, but not entire paw, inflamed and swollen, OR Mild swelling of entire paw. |
| 3 | Entire paw inflamed and swollen. |
| 4 | Very inflamed and swollen paw or ankylosed paw. If the paw is ankylosed, the mouse cannot grip the wire top of the cage. |

Ankylosis score:

| Paw Score | Clinical Observations |
|---|---|
| 0 | No ankylosis |
| 1 | Mild ankylosis |
| 2 | Moderate ankylosis |
| 3 | Severe ankylosis |

The present Example shows that treatment of mice with established CIA with 30 mg/kg LY6G6F-ECD-Ig Q2D over 2 weeks from onset of arthritis resulted in alleviation of disease manifested in reduction of disease score (FIG. 38).

The efficacy of VSIG10-ECD-Ig (SEQ ID NO: 24) and TMEM25-ECD-Ig (SEQ ID NO: 25) is evaluated in a similar model.

Study III: Effect of LY6G6F, VSIG10, TMEM25 and LSR ECD-Ig Fusion Proteins on Tolerance Induction in Transfer Model of CIA To further understand the effect of LY6G6F, VSIG10, TMEM25 and LSR ECD-Ig fusion proteins on immune regulation, the ability of these proteins to induce tolerance in a transfer model of arthritis is analysed.

In brief, spleen and LN cells from arthritic DBA/1 mice treated for 10 days with LY6G6F, VSIG10, TMEM25 and LSR ECD Ig fusion proteins (SEQ ID NOs: 23, 24, 25 and 26, respectively) or control Ig2a are removed and injected i.p into T-cell deficient C.B-17 SCID recipients. The mice then receive an injection of 100 µg type II collagen (without CFA), necessary for successful transfer of arthritis. Arthritis is then monitored in the SCID mice. Histology is performed and anti-collagen antibody levels are measured to determine that the LY6G6F, VSIG10, TMEM25 and LSR ECD Ig fusion proteins treatment confers long-term disease protection.

Example 38

Assessment of the Effect of LY6G6F, VSIG10, TMEM25 and LSR ECD-Ig Fusion Proteins in a Viral Infection Model of TMEV Theiler's murine encephalomyelitis virus (TMEV) is a natural endemic pathogen of mice that causes an induced demyelinating disease (TMEV-IDD) in susceptible strains of mice (SJL/J, H-2KS) that resembles the primary progressive form of MS (Munz et al., Nat Rev Immunol 2009; 9:246-58). TMEV infection results in a life-long persistent virus infection of the CNS leading to development of a chronic T cell-mediated autoimmune demyelinating disease triggered via de novo activation of CD4 T cell responses to endogenous myelin epitopes in the inflamed CNS (i.e. epitope spreading) (Miller et al., Nat Med 1997; 3:1133-6; Katz-Levy et al., J Clin Invest 1999; 104:599-610).

SJL mice clear the majority of the virus within 21 days post infection, however a latent viral infection is maintained and infect microglia, astrocytes, and neurons. Disease symptoms are manifested around day 25-30 post infection.

The effect of treatment with LY6G6F, VSIG10, TMEM25 or LSR Ig fusion proteins (SEQ ID NOs: 23, 24, 25 and 26, respectively) on acute and chronic phases of viral infection is studied in the TMEV-IDD model by assessment of viral clearance and disease severity.

Method:

Female SJL/J mice (5-6 weeks) are infected with TMEV by intracranial inoculation in the right cerebral hemisphere of $3\times10^7$ plaque forming units (PFU) of the BeAn strain 8386 of TMEV in 30 ul serum-free medium. From day 2 post infection mice are treated with Control Ig, LY6G6F, VSIG10, TMEM25 or LSR ECD-Ig fusion proteins, at 100 ug/dose each; 3 doses/week for 2 weeks.

Mice are followed for clinical scoring. On day 7 and day 14 post infection (after 3 and 6 treatments respectively) brains and spinal cords are collected from 5 mice in each treatment group for plaque assays. The tissues are weighted so that the ratio of PFU/mg of CNS tissue could be calculated after the plaque assay is completed.

TMEV Plaque Assay:

Brains and spinal cords of mice treated with Control Ig (mouse IgG2a), or with each of LY6G6F, VSIG10, TMEM25 or LSR ECD-Ig fusion proteins (SEQ ID NOs: 23, 24, 25 and 26, respectively) are collected at days 7 and 14 post-infection from non-perfused anesthetized mice. The Brains and spinal cords are weighed, and homogenized. CNS homogenates are serially diluted in DMEM and added to tissue culture-treated plates of confluent BHK-21 cells for 1 h incubation at room temperature, with periodic gentle rocking.

A media/agar solution is mixed 1:1 (volume:volume), added to cells and allowed to solidify at room temperature. The plates are then cultured at 34 deg C. for 5 days. At the end of culture, 1 ml of formalin is added and incubated at room temperature for 1 h to fix the BHK monolayer. The formalin is poured off into a waste container, and the agar is removed from the plates. Plaques are visualized by staining with crystal violet for 5 min, and plates are gently rinsed with diH2O. To determine PFU/ml homogenate, the number of plaques on each plate is multiplied by the dilution factor of the homogenate and divided by the amount of homogenate added per plate. The PFU/ml is divided by the weight of the tissue to calculate PFU/mg tissue.

Example 39

Assessment of the Effect of LY6G6F, VSIG10, TMEM25 and LSR ECD-Ig Fusion Proteins on Primary and Secondary Immune Response to Viral Infection in a Mouse Model of Influenza To test the effect of LY6G6F, VSIG10, TMEM25 or LSR ECD-Ig fusion proteins (SEQ ID NOs: 23, 24, 25 and 26, respectively) on primary and secondary immune responses to viral infection, BALB/c naïve mice (for primary immune responses) and 'HA-memory mice', is used, as well as 'polyclonal flu-memory mice' (to assess secondary responses mediated by memory CD4 T cells), which are generated as detailed in Teijaro et al., J Immunol. 2009: 182; 5430-5438, and described below.

To obtain 'HA-memory mice', first HA-specific memory CD4 T cells are generated, naive CD4 T cells are purified from spleens of HA-TCR mice [BALB/c-HA mice which express transgenic T cell receptor (TCR) specific for influenza hemagglutinin (HA) peptide (110-119)] and primed in vitro by culture with 5.0 microg/ml HA peptide and mitomycin C-treated, T-depleted BALB/c splenocytes as APCs for 3 days at 37° C. The resultant activated HA-specific effector cells are transferred into congenic BALB/c (Thy1.1) hosts ($5\times10^6$ cells/mouse) to yield "HA-memory mice" with a stable population of HA-specific memory CD4 T cells.

To obtain 'polyclonal-memory mice', first polyclonal influenza-specific memory CD4 T cells are generated, by infecting BALB/c mice intranasally with a sublethal dose of PR8 influenza, CD4 T cells are isolated 2-4 months postinfection, and the frequency of influenza-specific memory CD4 T cells is determined by ELISPOT. CD4 T cells from previously primed mice are transferred into BALB/c hosts to generate "polyclonal flu-memory" mice with a full complement of endogenous T cells.

Primary and secondary responses to influenza virus are tested by infecting naïve BALB/c mice or BALB/c-HA memory mice and BALB/c 'polyclonal flu-memory mice' with sublethal or lethal doses of PR8 influenza virus by intranasal administration.

Mice are treated with LY6G6F, VSIG10, TMEM25 or LSR ECD-Ig fusion proteins or with mIgG2a control before and following influenza challenge. Weight loss and mortality will be monitored daily. Six days after the challenge, viral content in the bronchoalveolar lavage (BAL) is analyzed by collecting lavage liquid and testing the supernatant for viral content by determining the tissue culture infectious dose 50% (TCID50) in MDCK cells. In addition, lung tissue histopathology is performed.

To test the effect LY6G6F, VSIG10, TMEM25 and LSR ECD-Ig fusion proteins on T cell expansion BALB/c or BALB/c-HA memory mice or BALB/c 'polyclonal flu-memory mice' are infected as above and administered with BrdU (1 mg/dose) on days 3, 4 and 5 post infection. On day 6, spleen and lung are harvested and BrdU incorporation is estimated. Cytokine production by lung memory CD4 T cells during influenza challenge is also studied in HA-specific memory CD4 T cells stimulated in vitro with HA peptide in the presence LY6G6F, VSIG10, TMEM25 or LSR ECD-Ig fusion proteins or with IgG2a for 18 hours.

Example 40

Assessment of the Effect of LY6G6F, VSIG10, TMEM25 and LSR ECD—Ig Fusion Proteins on Primary and Secondary Cd8 T Cell Response to Viral Infection in a Mouse Model of Influenza The effect of LY6G6F, VSIG10, TMEM25 and LSR ECD Ig fusion proteins (SEQ ID NOs: 23, 24, 25 and 26, respectively) on primary CD8 T cell responses to influenza virus is studied according to methods as described in the literature (Hendriks et al., J Immunol 2005; 175; 1665-1676; Bertram et al., J Immunol. 2004; 172:981-8) using C57BL/6 mice infected with influenza A HKx31 by intranasal or intraperitoneal administration. LY6G6F, VSIG10, TMEM25 or LSR ECD Ig fusion proteins or mIgG2a control are administered during priming Animal weight loss and mortality is monitored daily. To follow virus-specific CD8+ T cells, MHC H-2 Db tetramers loaded with the major CD8 T cell epitope, the $NP_{366-374}$ peptide are used. Virus-specific H-$2D^b$/NP366-374+ CD8+ T cells in the lung, draining lymph nodes, and spleen are expected to reach a peak around day 8-10 post infection and decline thereafter to only 1.5% virus-specific CD8 T cells (Hendriks et al J Immunol 2005; 175; 1665-1676; Bertram et al., J Immunol. 2002; 168:3777-85; Bertram et al., J Immunol. 2004; 172:981-8). Thus, mice are sacrificed at days 8 and 21 post infection, and virus-specific CD8 T cell numbers is evaluated in the lung, draining lymph nodes and spleen. Viral clearance is assessed. CD8 T cell responses are evaluated in spleen cell suspensions, and include intracellular IFN-γ staining and CTL activity, as previously described (Bertram et al., J Immunol. 2004; 172:981-8) and detailed below.

Cells are surface-stained with FITC-conjugated anti-mouse CD62L, PE-conjugated anti-mouse CD8 to measure CD8+ activated T cells (or anti-mouse CD4 to follow CD4+ cells). In addition to these Abs, allophycocyanin-labeled tetramers consisting of murine class I MHC molecule H-$2D^b$, $\beta_2$-microglobulin, and influenza NP peptide, $NP_{366-374}$ are used to measure influenza-specific CD8 T cells. For intracellular IFN-γ staining, cell suspensions are restimulated in culture medium for 6 h at 37° C. with 1 µM $NP_{366-374}$ peptide and GolgiStop (BD PharMingen, San Diego, Calif.). Cells are then harvested, resuspended in PBS/2% FCS/azide, and surface stained with PE-anti-CD8 and FITC-anti-CD62L as described above. After surface staining, cells will be fixed in Cytofix/Cytoperm solution (BD PharMingen) and then stained with allophycocyanin-conjugated antimouse IFN-γ diluted in 1× perm/wash solution (BD PharMingen). Samples are analyzed by Flow Cytometry.

For cytotoxicity assays (CTL responses) splenocytes from influenza-infected mice are incubated for 2 h at 37° C. to remove adherent cells. Serial 3-fold dilutions of effectors are assayed for anti-influenza $NP_{366-374}$-specific CTL activity against $^{51}$Cr-labeled EL4 cells pulsed with 50 µM $NP_{366-374}$ peptide for 6 h as described by Bertram et al 2002 and Bertram et al 2004.

At 3 weeks postinfection, some mice are rechallenged with the serologically distinct influenza A/PR8/34 (PR8), which shares the NP gene with influenza A HKx31, but differs in hemagglutinin and neuraminidase, so that neutralizing Abs do not limit the secondary CTL response. Mice are sacrificed at days 5 & 7 following virus rechallenge, and virus-specific CD8 T cell numbers is evaluated in the lung, draining lymph nodes and spleen as described by Hendriks et al and Bertram et al (Hendriks et al., J Immunol 2005; 175; 1665-1676; Bertram et al., J Immunol. 2004; 172:981-8) and detailed above. Secondary CD8 T cell responses, including intracellular IFN-γ staining and CTL activity, are evaluated in spleen cell suspensions of mice at days 5 & 7 following virus rechallenge, as described above.

To determine the effect of LY6G6F, VSIG10, TMEM25 and LSR ECD-Ig fusion proteins on expansion and accumulation of memory CD8+ T cells during the secondary response, adoptive transfer experiments are performed, according to methods previously described (Hendriks et al., J Immunol 2005; 175; 1665-1676; Bertram et al., J Immunol. 2004; 172:981-8): mice are immunized with influenza A HKx31. Twenty-one days later, T cells are purified from spleens on mouse T cell enrichment immunocolumns (Cedarlane Laboratories, Hornsby, Ontario, Canada) and labeled with CFSE (alternatively Thy1.1 congenic mice are used as recipients). Equal numbers of tetramer-positive T cells are injected through the tail vein of recipient mice. Mice are rechallenged with influenza virus as described above, and 7 days later splenocytes are evaluated for donor virus-specific CD8 T cells, as detailed above.

Example 41

Assessment of Protein Expression in Exhausted T Cells, and the Binding and Effect of the LY6G6F, VSIG10, TMEM25 and LSR ECD-Ig Fusion Proteins on Reversing Exhausted T Cell Phenotype Memory CD8 T-cell differentiation proceeds along distinct pathways after an acute versus a chronic viral infection (Klenerman and HillNat Immunol 6, 873-879, 2005). Memory CD8 T cells generated after an acute viral infection are highly functional and constitute an important component of protective immunity. In contrast, chronic infections are often characterized by varying degrees of functional impairment of virus-specific T-cell responses, and this defect is a principal reason for the inability of the host to eliminate the persisting pathogen. Although functional effector T cells are initially generated during the early stages of infection, they gradually lose function during the course of the chronic infection leading to exhausted phenotype characterized by impaired T cell functionality.

Study I. The Effect of LY6G6F, VSIG10, TMEM25 and LSR ECD Ig Fusion Proteins on Clearance of Viral Infection and on T Cell Functions During Acute and Chronic Viral Infection.

The effect of LY6G6F, VSIG10, TMEM25 and LSR ECD Ig fusion proteins (SEQ ID NOs: 23, 24, 25 and 26, respectively) on acute and chronic viral infection is evaluated in a mouse model of infection with LCMV (lymphocytic chroriomeningitis virus) according to methodology described by Wherry et al J. Virol. 77: 4911-4927, 2003 and Barber et al Nature, 2006, and detailed below.

Two LCMV strains that can cause either acute or chronic infections in adult mice are used; the Armstrong strain which is cleared within a week, and the clone 13 strain which establishes a persistent infection that can last for months. As these two strains differ in only two amino acids, preserving all known T cell epitopes, it is possible to track the same CD8 T cell responses after an acute or chronic viral infection. In contrast to the highly robust memory CD8 T cells generated after an acute Armstrong infection, LCMV-specific CD8 T cells become exhausted during a persistent clone 13 infection (Wherry et al J. Virol. 77: 4911-4927, 2003; Barber et al., Nature. 2006; 439:682-7).

Mice are infected with $2 \times 10^5$ PFU of Armstrong strain of LCMV intraperitoneally to initiate acute infection or $2 \times 10^6$ PFU of Cl-13 intravenously to initiate chronic infection. Mice are treated i.p. with LY6G6F, VSIG10, TMEM25 or LSR ECD Ig fusion proteins or with mIgG2a control, and with specific anti-LY6G6F, anti-VSIG10, anti-TMEM25, anti LSR—antibody or an isotype control.

The mice are monitored for numbers of virus specific CD8 T cells in the spleen, using virus-specific MHC tetramer epitopes, such as $D^bNP_{396-404}$ and $D^bGP_{33-41}$ which differ in acute or chronic infections. CD8 T cell functional assays, such as intracellular cytokines levels and CTL activity, are carried out as described by Wherry et al J. Virol. 77: 4911-4927, 2003, and similarly to those described in Example 40. Additional assays include production by splenocytes after stimulation with virus specific epitopes; and assessment of viral titers in the serum and in the spleen, liver, lung and kidney (Wherry et al J. Virol. 77: 4911-4927, 2003; Barber et al., Nature. 2006; 439:682-7).

Study II.

Assessment of LY6G6F, VSIG10, TMEM25 and LSR expression on exhausted T cells and binding of LY6G6F, VSIG10, TMEM25 and LSR ECD Ig fusion proteins to exhausted T cells in order to evaluate regulation of these proteins or their counterpart receptors during exhaustion of T cells:

T cells are isolated from mice with chronic LCMV infection induced with Cl-13 strain. The cells are co-stained with fluorescently labeled anti-PD-1 Ab as positive control (PD-1 is highly expressed by exhausted T cells) and biotinylated LY6G6F, VSIG10, TMEM25 and LSR ECD Ig fusion proteins or biotinylated anti-LY6G6F, anti-VSIG10, anti-TMEM25 and anti-LSR fusion proteins antibodies, and respective isotype control. Binding is detected by FACS analysis using fluorescently labeled streptavidin.

Example 42

Assessment of LY6G6f, VSIG10, TMEM25 and/or LSR Protein Expression In Follicular Helper T (Tfh) Cells and the Binding of Ig Fusion Proteins to Tfh Cells Follicular helper T (Tfh) cells are a subset of CD4+ T cells specialized in B cell help (reviewed by Crotty, Annu. Rev. Immunol. 29: 621-663, 2011). Tfh cells migrate into B cell follicles within lymph nodes, and interact with cognate B cells at the T cell-B cell border and subsequently induce germinal center B cell differentiation and germinal center formation within the follicle (Reviewed by Crotty, Annu. Rev. Immunol. 29: 621-663, 2011). The requirement of Tfh cells for B cell help and T cell-dependent antibody responses, indicates that this cell type is of great importance for protective immunity against various types of infectious agents, as well as for rational vaccine design.

Tfh cells are readily identifiable at the peak of the CD4+ T cell response to an acute lymphocytic choriomeningitis virus (LCMV) infection as $CXCR5^{hi}SLAM^{lo}BTLA^{hi}PD1^{hi}Bcl6^+$ virus-specific CD4+ T cells (Choi et al 2011, Immunity 34: 932-946). T cells are isolated from mice with acute LCMV infection induced with $2 \times 10^5$ PFU of Armstrong strain of LCMV administered intraperitoneally. The cells are co-stained with fluorescently labeled antibodies for markers of Tfh (CXCR5, PD1, BTLA, Bcl6) which are highly expressed by Tfh cells, and biotinylated LY6G6F, VSIG10, TMEM25 and LSR ECD-Ig fusion proteins or biotinylated antibodies specific for LY6G6F, VSIG10, TMEM25 and LSR, and respective isotype controls. Binding of Fc fused protein or antibody is detected by FACS analysis using fluorescently labeled streptavidin.

Example 43

Assessment of the Effect of LY6G6f, VSIG10, TMEM25 and LSR Ig Fusion Proteins on Follicular Helper T (Tfh) Cells Generation and Activity In order to investigate the effect of LY6G6F, VSIG10, TMEM25 and LSR ECD Ig fusion proteins on Tfh differentiation and development of B cell immunity in vivo, C57BL/6 are treated with LY6G6F, VSIG10, TMEM25 and LSR ECD Ig fusion proteins and an isotype control throughout the course of an acute viral infection with Armstrong strain of LCMV (lymphocytic choriomeningitis virus). Tfh differentiation and Bcl6 protein expression is assessed by FACS analysis as described by Eto et al 2011 (PLoS One 6: e17739). Splenocytes are analyzed 8 days following LCMV infection, Tfh generation) ($CD44^{hi}CXCR5^{hi}SLAM^{lo}$) and Bcl6 expression is evaluated by FACS analysis. In addition, the effect of LY6G6F, VSIG10, TMEM25 and LSR ECD Ig fusion proteins (SEQ ID NOs: 23, 24, 25 and 26, respectively) on antigen-specific B cell responses is evaluated as described by Eto et al 2011 (PLoS One 6: e17739), including titers of anti-LCMV IgG in the serum at 8 days following LCMV infection, and quantitation by FACS analysis of plasma cell (CD138$^+$IgD$^-$) development at 8 days post-infection, gated on CD19+ splenocytes.

Example 44

The Effect of LY6G6f, VSIG10, TMEM25 and LSR ECD Ig Fusion Proteins In Modulation of Type 1 Diabetes in Nod Mice, Cd28-KO Nod, and B7-2-KO NOD The effect of LY6G6F, VSIG10, TMEM25 and LSR ECD Ig fusion proteins are studied in a widely used mouse model of type 1 diabetes: nonobese diabetic (NOD) mice which develop spontaneous In NOD mice, spontaneous insulitis, the hallmark pathologic lesion, evolves through several characteristic stages that begin with peri-insulitis and end with invading and destructive insulitis and overt diabetes. Peri-insulitis is first observed at 3-4 wk of age, invading insulitis at 8-10 wk, and destructive insulitis appears just before the onset of clinical diabetes, with the earliest cases at 10-12 wk. At 20 wk of age, 70-80% of female NOD mice become diabetic (Ansari et al 2003 J. Exp. Med. 198: 63-69).

Two KO mice: CD-28-KO NOD mice and B7-1/B7-2 double KO NOD mice, —which develop accelerated diabetes (Lenschow et al 1996 Immunity 5: 285-293; Salomon et al 2000 Immunity 12: 431-440), are also used.

Study I:
NOD mice are treated with LY6G6F, VSIG10, TMEM25 or LSR ECD-Ig fusion proteins (SEQ ID NOs: 23, 24, 25 and 26, respectively) early and late phases during the evolution of diabetes, before or after disease onset, to examine the effects of these compounds on disease pathogenesis and to demonstrate that such treatment reduces disease onset and ameliorates pathogenesis. To study the effect on insulitis, blood glucose levels are measured 3 times/week, for up to 25 weeks (Ansari et al 2003 J. Exp. Med. 198: 63-69).

Mechanism of disease modification and mode of action is studied by experimental evaluation of individual immune cell types: pancreas, pancreatic LNs and spleen will be harvested to obtain Tregs, Th subtypes and CD8 T cells, DCs and B cells. Effect on cytokines secretion from cells isolated from pancreas, pancreatic LN and spleen is analysed, focused on IFNg, IL-17, IL-4, IL-10 and TGFb. Upon effect of the tested compounds, the mechanism of disease modification is studied by examination of individual immune cell types (including Tregs, Th subtypes and CD8 T cells, DCs and B cells); cytokines (IFNg, IL-17, IL-4, IL-10 and TGFb) and histology. Histologycal analysis of the pancreas is carried out to compare the onset of insulitis, and the lymphocyte infiltration.

Study II—the effect of LY6G6F Ig Fusion Proteins in Modulation of Type 1 Diabetes in Adoptive Transfer Model To further investigate the mode of action of the Ig fusion proteins, an adoptive transfer model of diabetes is used. T cells from diabetic or prediabetic NOD donors are transferred to NOD SCID recipient mice. These mice are monitored for development of diabetes. The urine glucose and blood glucose, and assess histology of the pancreas, and T cell responses are monitored as described in the previous example.

Study III:
Diabetes is also Induced by the transfer of activated CD4+ CD62L+CD25−BDC2.5 T cells (transgenic for TCR recognizing islet specific peptide 1040-p31 activated by incubation with 1040-p31) to NOD recipients. Mice are treated with LY6G6F, VSIG10, TMEM25 or LSR ECD Ig fusion proteins, control mIgG2a or positive control. Treatments begin 1 day following transfer. Mice are followed for glucose levels 10-28 days post transfer (Bour-Jordan et al., J Clin Invest. 2004; 114(7):979-87).

Seven days post treatment pancreas, spleen, pancreatic LN and peripheral lymph node cells are extracted and examined for different immune cell populations. In addition, recall responses are measured by testing ex-vivo proliferation and cytokine secretion in response to p31 peptide.

LY6G6F, VSIG10, TMEM25 and LSR ECD Ig fusion proteins prevent or reduce disease onset or the severity thereof in the above studies.

Example 45

The Effect of LY6G6f, VSIG10, TMEM25 and LSR ECD Ig Fusion Proteins in Lupus Mouse Models Study I:
The lupus-prone mouse model, (NZB×NZW)F1 (B/W) is used. Cyclophosphamide (CTX) is the primary drug used for diffuse proliferative glomerulonephritis in patients with renal lupus, Daikh and Wofsy reported that combination treatment with CTX and CTLA4-Ig was more effective than either agent alone in reducing renal disease and prolonging survival of NZB/NZW Fl lupus mice with advanced nephritis (Daikh and Wofsy, J Immunol, 166(5):2913-6 (2001)). In the proof-of-concept study, treatments with LY6G6F, VSIG10, TMEM25 or LSR ECD Ig fusion proteins and CTX either alone or in combination are tested.

Blood samples are collected 3 days before the protein treatment and then every other week during and after treatments for plasma anti-dsDNA autoantibody analysis by ELISA. Glomerulonephritis is evaluated by histological analysis of kidneys. Proteinuria is measured by testing fresh urine samples using urinalysis dipsticks.

LY6G6F, VSIG10, TMEM25 and LSR ECD Ig fusion proteins (SEQ ID NOs: 23, 24, 25 and 26, respectively) have a beneficial effect in at least ameliorating lupus nephtiris.

Study II:
The NZM2410-derived B6.Sle1.Sle2.S1e3 mouse model of SLE is used. NZM2410 is a recombinant inbred strain produced from NZB and NZW that develops a highly penetrant lupus-like disease with an earlier onset of disease (Blenman et al 2006 Lab. Invest. 86: 1136-1148). The effect of LY6G6F, VSIG10, TMEM25 and LSR ECD Ig fusion proteins is studied in this model by assessment of proteinuria and autoantibodies as described above.

Study III:
An induced lupus model is used. This model is based on chronic graft-vs-host (cGVH) disease induced by the transfer of Ia-incompatible spleen cells from one normal mouse strain (such as B6.C-H2(bm12)/KhEg (bm12)) to another (such as C57BL/6), which causes an autoimmune syndrome resembling systemic lupus erythematosus (SLE), including anti-double-stranded DNA (anti-dsDNA) autoantibodies and immune complex-type proliferative glomerulonephritis (Appleby et al Clin. Exp. Immunol. 1989 78: 449-453); Eisenberg and Choudhury 2004 Methods Mol. Med. 102: 273-284).

Lupus is induced in this model following injection of spleen cells from bm12 mice into C57BL/6 recipients. The effect of LY6G6F, VSIG10, TMEM25 and LSR ECD Ig fusion proteins is studied in this model by assessment of proteinuria and autoantibodies as described above. T cell and responses B cell responses will also be evaluated.

Study IV:

The MRL/lpr lupus prone mouse model is used. The effect of LY6G6F, VSIG10, TMEM25 and LSR ECD Ig fusion proteins is studied in this model by assessment of proteinuria and autoantibodies as described above.

Example 46

The Effect of LY6G6f, VSIG10, TMEM25 and LSR ECD Ig Fusion Proteins in the Control of Intestinal Inflammation An adoptive transfer mouse model of colitis in mice is used, whereby Transfer of CD45RB$^{high}$-CD4+ naïve T cells from BALB/c mice to syngeneic SCID mice leads to the development of an IBD-like syndrome by 6-10 wks after T cell reconstitution, similar to human Crohn's disease.

SCID mice are reconstituted by i.p. injection of syngeneic CD45RB$^{high}$-CD4$^+$ T cells either alone or cotransferred with syngeneic CD45RB$^{low}$-CD4$^+$ or CD25$^+$CD4$^+$ cells (4×10$^5$/ mouse of each cell population) (Liu et al., J Immunol. 2001; 167(3): 1830-8). Colitic SCID mice, reconstituted with syngeneic CD45RB$^{high}$CD4$^+$ T cells from spleen of normal mice, are treated i.p. with LY6G6F, VSIG10, TMEM25 or LSR ECD Ig fusion proteins or Ig isotype control, twice a week starting at the beginning of T cell transfer up to 8 wk. All mice are monitored weekly for weight, soft stool or diarrhea, and rectal prolapse. All mice are sacrificed 8 wk after T cell transfer or when they exhibit a loss of. 20% of original body weight. Colonic tissues are collected for histologic and cytologic examinations. LY6G6F, VSIG10, TMEM25 and LSR ECD Ig fusion proteins have a beneficial effect in at least ameliorating inflammatory bowel disease.

Example 47

The Effect of LY6G6F, VSIG10, TMEM25 and LSR ECD Ig Fusion Proteins in Mouse Model of Psoriasis Study I: Establishment of Psoriasis SCID Xenograft Model.

Human psoriasis plaques are transplanted on to the SCID mice. Shave biopsies (2.5_2.5 cm) are taken from patients with generalized plaque psoriasis involving 5-10% of the total skin that did not receive any systemic treatment for psoriasis or phototherapy for 6 months and did not receive any topical preparations other than emollients for 6 weeks. The biopsies are obtained from active plaques located on the thigh or arm. Each piece of biopsy is divided into four equal parts of approximately 1 cm2 size. Each piece is transplanted to a separate mouse.

Under general anesthesia, a graft bed of approximately 1 cm2 is created on the shaved area of the back of a 7- to 8-week-old CB 17 SCID mouse by removing a full-thickness skin sample, keeping the vessel plexus intact on the fascia covering the underlying back muscles. The partial thickness human skin obtained by shave biopsy is then orthotopically transferred onto the graft bed. Nexaband, a liquid veterinary bandage (Veterinary Products Laboratories, Phoenix, Ariz.) is used to attach the human skin to the mouse skin and an antibiotic ointment (bacitracin) is applied. Mice are treated intraperitoneally three times per week for 4 weeks with LY6G6F, VSIG10, TMEM25 or LSR ECD Ig fusion proteins, isotype control or CTLA4-Ig (positive control).

Punch biopsies (2 mm) are obtained on day 0 (before treatment) and day 28 (after treatment) of the study period. Biopsies are snap frozen and cryosections for histopathological and immunohistochemical studies. Therapeutic efficacy is determined by comparing pre- and post treatment data: (i) rete peg lengths to determine the effect on epidermal thickness and (ii) the level of lymphomononuclear cell infiltrates to determine the effect on inflammatory cellular infiltrates. (Raychaudhuri et al. 2008, J Invest Dermatol.;128(8):1969-76; Boehncke et al., 1999 Arch Dermatol Res 291:104-6).

LY6G6F, VSIG10, TMEM25 and LSR ECD Ig fusion proteins (SEQ ID NOs: 23, 24, 25 and 26, respectively) have a beneficial effect in at least ameliorating psoriasis.

Study II: The Effect of LY6G6f, VSIG10, TMEM25 and LSR in Psoriasis and Colitis Model by Adoptive Transfer of Cd45RBhi Cd4+ T Cells in SCID Mice Immunocompromised mice are injected intraveneously (i.v.) with 0.3_10$^6$ CD4+ CD45RBhi cells. On the day following the adoptive transfer of cells, mice are injected intraperitoneally (i.p.) with 10 microg of staphylococcal enterotoxin B (Davenport et al., Int Immunopharmacol. 2002 April; 2(5):653-72). Recipient mice are treated with LY6G6F, VSIG10, TMEM25 or LSR ECD-Ig fusion proteins (SEQ ID NOs: 23, 24, 25 and 26, respectively), isotype control or CTLA4-Ig (positive control). Mice are evaluated once a week for 8 weeks for weight loss and presence of skin lesions.

Obtained results are similar to those described above.

Example 48

The Effect of LY6G6f, VSIG10, TMEM25 and LSR ECD Ig Fusion Proteins in Modulating Transplant Rejection Study I: The Effect of LY6G6F, VSIG10, TMEM25 and LSR in a Model of Allogeneic Islet Transplantation in Diabetic Mice.

To test the effect of LY6G6F, VSIG10, TMEM25 and LSR ECD Ig fusion proteins (SEQ ID NOs: 23, 24, 25 and 26, respectively) on transplant rejection, a model of allogeneic islet transplantation is used. Diabetes is induced in C57BL/6 mice by treatment with streptozotocin. Seven days later, the mice are transplanted under the kidney capsule with pancreatic islets which are isolated from BALB/c donor mice. Recipient mice are treated with LY6G6F, VSIG10, TMEM25 or LSR ECD Ig fusion proteins or with mIgG2a as a negative control. Tolerance with ECDI-fixed donor splenocytes is used as the positive control for successful modulation islet graft rejection. Recipient mice are monitored for blood glucose levels as a measure of graft acceptance/rejection (Luo et al., PNAS, Sep. 23, 2008_vol. 105_no. 38_14527-14532).

Study II: The Effect of LY6G6f, VSIG10, TMEM25 and LSR in the Hya-Model of Skin Graft Rejection.

In humans and certain strains of laboratory mice, male tissue is recognized as non-self and destroyed by the female immune system via recognition of histocompatibility-Y chromosome encoded antigens (Hya). Male tissue destruction is thought to be accomplished by cytotoxic T lymphocytes in a helper-dependent manner.

To test the effect of LY6G6F, VSIG10, TMEM25 and LSR ECD Ig fused proteins (SEQ ID NOs: 23, 24, 25 and 26, respectively) on transplanatation, the Hya model system is used, in which female C57BL/6 mice receive tail skin grafts from male C57BL/6 donors.

In this study, female C57BL/6 mice are engrafted with orthotopic split-thickness tail skin from age matched male C57BL/6 mice. The mice are treated with LY6G6F, VSIG10, TMEM25 or LSR ECD Ig fusion proteins, isotype control mIgG2a. Immunodominant Hya-encoded CD4 epitope (Dby) attached to female splenic leukocytes (Dby-SP) serve as positive control for successful modulation of graft rejection (Martin et al., J Immunol. 2010 Sep. 15; 185(6): 3326-3336). Skin grafts are scored daily for edema, pigment loss and hair loss. Rejection is defined as complete hair loss and more than 80% pigment loss.

In addition, T cell recall responses of cells isolated from spleens and draining lymph nodes at different time points are studied in response to CD4 specific epitope (Dby), CD8 epitopes (Uty and Smcy) or irrelevant peptide (OVA 323-339) while anti CD3 stimulation is used as positive control for prolifereation and cytokine secretion.

Study III:

The effect of LY6G6F, VSIG10, TMEM25 and LSR ECD Ig fusion proteins on graft rejection is studied in a murine model of syngeneic bone marrow cells transplantation using the Hya model system described above. Male hematopoietic cells expressing the CD45.1 marker are transplanted to female host mice which express the CD45.2 congenic marker. Female hosts are treated with LY6G6F, VSIG10, TMEM25 or LSR ECD Ig fusion proteins or with isotype control mIgG2a. The female hosts are followed over time and the presence of CD45.1+ cells is monitored.

Example 49

Establishment of the Role of LY6G6F, VSIG10, TMEM25 and/or LSR Proteins According to at Least Some Embodiments of the Invention as Modulators of Cancer Immune Surveillance 1) In Vivo Proof of Concept
a) Mouse Cancer Syngeneic Model:
(i) Tumor cells, over expressing any one of LY6G6F, VSIG10, TMEM25 and/or LSR proteins or a non-relevant control protein are transplanted to genetically matched mice. Tumor volume (and tumor weight after sacrificing the animals) and ex vivo analysis of immune cells from tumor draining lymph nodes or spleens are then examined to demonstrate the rejection of the tumor to be delayed (i.e. tumor over expressing LY6G6F, VSIG10, TMEM25 and/or LSR grow faster than tumors over expressing the non-relevant control protein). Ex vivo analysis of immune cells from tumor draining lymph nodes is expected to reveal an increase in the frequency of regulatory T cells and a decrease in the responsiveness of effector T cells to stimulation. (J. Exp. Med. 2011 Vol. 208 No. 3 577-592).

(ii) In vivo syngeneic model using the extra cellular domain of the mouse orthologs of any one of LY6G6F, VSIG10, TMEM25 and/or LSR protein fused to an antibody Fc fragment (mouse ECD-Fc) (SEQ ID NO: 23, 24, 25 and 26, respectively) is tested as follows. The mouse ECD-FC is injected IV to C57BL/6 mice at 3-4 day intervals, after tumor establishment, as described in J immunol 2010; 185; 2747-2753. Tumor volume (and tumor weight after sacrificing the animals) and ex vivo analysis of immune cells from tumor draining lymph nodes or spleens are then examined. As a result of IV treatment with Mouse ECD-FC of LY6G6F, VSIG10, TMEM25 and/or LSR the rejection of the tumor is delayed (i.e. in mice treated with the Mouse ECD-FC of LY6G6F, VSIG10, TMEM25 and/or LSR tumors grow faster than tumors in mice treated with non-relevant control protein). Ex vivo analysis of immune cells from tumor draining lymph nodes reveal an increase in the frequency of regulatory T cells and a decrease in the responsiveness of effector T cells to stimulation.

(iii) Establishment of a syngeneic tumor and treat with neutralizing antibodies directed against any one of LY6G6F, VSIG10, TMEM25 and/or LSR protein (1, 3, 5, 7, 11, 143, 13, 15-17, 18, 28, 29-32). Tumor cells are transplanted to genetically identical mice. After the establishment of tumors, mice are injected IV with different doses of neutralizing antibodies aimed against any one of LY6G6F, VSIG10, TMEM25 and/or LSR protein. As a result of IV treatment with neutralizing antibodies specific for any one of LY6G6F, VSIG10, TMEM25 and/or LSR protein the rejection of the tumor is increased (i.e. in mice treated with neutralizing antibodies against any one of LY6G6F, VSIG10, TMEM25 and/or LSR protein tumors grow slower than tumors in mice treated with non-relevant antibody). Ex vivo analysis of immune cells from tumor draining lymph nodes reveal a decrease in the frequency of regulatory T cells and an increase in the responsiveness of effector T cells to stimulation.

b) Human Cancer Xenograft Model:
(i) Reconstitution of the tumor immune response in a model of immune compromised NOD.Cg-Prkdcscid Il2rgtm1Wjl/SzJ mice (Jackson lab), "NSG" mice. Human tumor is established in NSG model, and APCs pre-loaded with Tumor antigens, or/and T cells (CD8 T cells pre-activated with cancer target cells are transferred into tumor bearing NSG mice (all cells transplanted/injected originate from cancer patients). This model consists of four arms: 1. APC's over expressing any one of LY6G6F, VSIG10, TMEM25 and/or LSR proteins, 2. silencing of any one of LY6G6F, VSIG10, TMEM25 and/or LSR proteins (either siRNA or ShRNA) on APC's, 3. Cancer cells over expressing any one of LY6G6F, VSIG10, TMEM25 and/or LSR proteins and 4. Silencing of any one of LY6G6F, VSIG10, TMEM25 and/or LSR proteins (either siRNA or ShRNA) on cancer cells. Positive (e.g. B7-H1, PD-L1) and negative (e.g. Vector and cells alone) controls are included. Tumor volume or tumor metastasis and mouse survival are then examined (J. Exp. Med.; 2006; Vol. 203; p. 871-881). Over expression of any one of LY6G6F, VSIG10, TMEM25 and/or LSR proteins either on APC's or on Tumor cells, lead to delayed rejection of the tumor (i.e. in mice treated with the APC's or tumor cells over expressing any of LY6G6F, VSIG10, TMEM25 and/or LSR tumors grow faster than tumors in mice treated with non-relevant control protein). Silencing (with SiRNA or SHRNA) of any of LY6G6F, VSIG10, TMEM25 and/or LSR either on APC's or on tumor cells lead to enhanced rejection of the tumor.

(ii) Establishment of the NSG cancer Xenograft as described above (without genetic manipulation of APC's and/or cancer cells) and treatment with neutralizing antibodies directed against the any one of LY6G6F, VSIG10, TMEM25 and/or LSR proteins. Treatment of the NSG Xenograft model with neutralizing antibodies directed against any of LY6G6F, VSIG10, TMEM25 and/or LSR is gives rise to enhanced rejection of the tumor.

2) In Vitro Validation of Natural Killer (NK) Cell Activity
a) Binding Assay:
(i) Binding assay with human LY6G6F, VSIG10, TMEM25 and/or LSR ECD-FC proteins on activated primary-culture NK cells is performed as described in J Immunol 2005; 174; 6692-6701. If the counter receptor of LY6G6F, VSIG10, TMEM25 and/or LSR is expressed on NK cells, binding of LY6G6F, VSIG10, TMEM25 and/or LSR ECD-Fc is observed.

(ii) Binding assay with a specific antibody directed against the any one of LY6G6F, VSIG10, TMEM25 and/or LSR proteins on activated primary-culture NK cells is performed as described in PNAS, 2009, vol. 109; 17858-17863. If any one of LY6G6F, VSIG10, TMEM25 and/or LSR is expressed on NK cells, binding of LY6G6F, VSIG10, TMEM25 and/or LSR specific antibody, respectively, is observed.

(iii) Binding assay with human LY6G6F, VSIG10, TMEM25 and/or LSR ECD-FC proteins on various human cancer cell lines that may serve as target cells for NK killing is performed as described in J Immunol 2006; 176; 6762-6769. If the counter receptor of any one of LY6G6F, VSIG10, TMEM25 and/or LSR is expressed on the cancer target cells, binding of LY6G6F, VSIG10, TMEM25 and/or LSR ECD-Fc, respectively is observed.

b) Functional Killing Assay:

(i) Killing assays are performed using an over expression system (either NK cells or cancer target cells, over expressing any one of LY6G6F, VSIG10, TMEM25 and/or LSR proteins). The NK cells (effector; e) are co-incubated with radioactive (S35) labeled cancer target cells (target; t) in various e:t ratios, as described in PNAS, 2009, vol. 109; 17858-17863. Lysis of target cells by NK killing activity is then evaluated by measurement of radioactive emission. Over expression of any one of LY6G6F, VSIG10, TMEM25 and/or LSR proteins on the target cancer cells and/or the NK cell lines lead to down regulation of the NK mediated killing activity.

(ii) Killing assays are performed in the presence of the human LY6G6F, VSIG10, TMEM25 and/or LSR ECD-FC proteins, as described in PLoS ONE; 2010; Vol. 5; p. 1-10. Treatment with the ECD-Fc of any of LY6G6F, VSIG10, TMEM25 and/or LSR interfere with the interaction of LY6G6F, VSIG10, TMEM25 and/or LSR with their counter receptors and thus decrease their inhibitory activity, giving rise to enhanced killing activity.

(iii) Killing assays are performed in the presence of a neutralizing antibody directed against any one of LY6G6F, VSIG10, TMEM25 and/or LSR proteins, as described in PNAS, 2009, vol. 109; 17858-17863. Treatment with neutralizing antibodies directed towards any of LY6G6F, VSIG10, TMEM25 and/or LSR, give rise to enhanced NK killing activity.

(iv) "Re-directed killing assay" is performed as follows: cancer target cells expressing high density Fc receptors are coated with activating antibodies directed against any one of LY6G6F, VSIG10, TMEM25 and/or LSR proteins and exposed to NK cells (expressing the designated LY6G6F, VSIG10, TMEM25 and/or LSR protein), as described in PNAS, 2009, vol. 109; 17858-17863. Cross linking of any one of LY6G6F, VSIG10, TMEM25 and/or LSR with activating antibodies give rise to reduced NK mediated killing activity.

3) Expression Analysis a) Expression of LY6G6F, VSIG10, TMEM25 and/or LSR Proteins on Cells Isolated from Human Tumor Biopsies i) Expression validation of any one of LY6G6F, VSIG10, TMEM25 and/or LSR proteins using specific antibodies directed against the any one of LY6G6F, VSIG10, TMEM25 and/or LSR proteins, respectively, is carried out on separated cell populations from the tumor. Various cell populations are freshly isolated from tumor biopsies (e.g. Tumor cells, endothelia, tumor associated macrophages (TAMs) and DCs, B cells and different T cells (CD4, CD8 and Tregs) as described in J. Exp. Med.; 2006; Vol. 203; p. 871-881 and Cancer res. 2007; 67; 8900-8905, to demonstrate expression of any of LY6G6F, VSIG10, TMEM25 and/or LSR in tumor cells and on tumor stroma and immune infiltrate.

ii) Binding assay is performed with the human LY6G6F, VSIG10, TMEM25 and/or LSR ECD-FC proteins on separated cell populations from the tumor. Isolate various cell populations from tumor biopsies (e.g. Tumor cells, endothelia, tumor associated macrophages (TAMs) and DCs, B cells and different T cells (CD4, CD8 and Tregs) freshly isolated from tumors as described in J. Exp. Med.; 2006; Vol. 203; p. 871-881 and Cancer res. 2007; 67; 8900-8905, to show expression of the counter receptor for any of LY6G6F, VSIG10, TMEM25 and/or LSR in tumor cells and on tumor stroma and immune cells.

b) Expression of LY6G6F, VSIG10, TMEM25 and/or LSR Proteins on Cells Isolated from Draining Lymph Nodes and Spleens of Tumor Bearing Mice (i) Expression validation of LY6G6F, VSIG10, TMEM25 and/or LSR proteins using specific antibodies directed against LY6G6F, VSIG10, TMEM25 and/or LSR proteins, respectively, is done on epithelial cancer cells as well as on immune cells from tumor draining lymph nodes vs. spleen of tumor bearing C57 mice, as described in Clinical Cancer Research 1996 Vol. 2, 811-820. Three different cancer types are being tested: B 16 (melanoma), ID8 (ovarian) and MC38 (colon)), to show expression of any of LY6G6F, VSIG10, TMEM25 and/or LSR in tumor cells and in immune cells in the tumor draining lymph node.

ii) Binding assay with mouse LY6G6F, VSIG10, TMEM25 and/or LSR ECD-FC proteins on cells isolated from epithelial cancer as well as on immune cells from tumor draining lymph nodes versus spleen of tumor bearing C57 mice, is carried out as described above, to show expression of the counter receptor for any of LY6G6F, VSIG10, TMEM25 and/or LSR in tumor cells and in immune cells in the tumor draining lymph node.

c) Expression of LY6G6F, VSIG10, TMEM25 and/or LSR Proteins on M2 Polarized Macrophages (i) Expression validation of LY6G6F, VSIG10, TMEM25 and/or LSR proteins using specific antibodies directed against LY6G6F, VSIG10, TMEM25 and/or LSR proteins, respectively, is done on primary monocytes isolated from peripheral blood, differentiated into macrophages and exposed to "M2 driving stimuli" (e.g. IL4, IL10, Glucocorticoids, TGF beta), as described in Nat. Immunol. 2010; Vol. 11; p. 889-896, to show expression of any of LY6G6F, VSIG10, TMEM25 and/or LSR in M2 differentiated Macrophages.

ii) Binding assay with LY6G6F, VSIG10, TMEM25 and/or LSR human ECD-FC proteins on primary monocytes isolated from peripheral blood, differentiated into macrophages and exposed to "M2 driving stimuli" (e.g. IL4, IL10, Glucocorticoids, TGF beta) is carried out as described above, to show expression of the counter receptor for any of LY6G6F, VSIG10, TMEM25 and/or LSR in M2 differentiated Macrophages.

Example 50

Development Of Fully Human Anti-LY6G6f, Anti-VSIG10, Anti-TMEM25 and/or Anti-LSR Antibodies Generation Of Human Monoclonal Antibodies Against LY6G6F, VSIG10, TMEM25 and/or LSR Antigen Fusion proteins composed of the extracellular domain of the LY6G6F, VSIG10, TMEM25 and/or LSR linked to a mouse IgG2 Fc polypeptide are generated by standard recombinant methods and used as antigen for immunization.

Transgenic HuMab Mouse.

Fully human monoclonal antibodies to LY6G6F, VSIG10, TMEM25 and/or LSR are prepared using mice from the HCo7 strain of the transgenic HuMab Mouse®, which expresses human antibody genes. In this mouse strain, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al. (1996) Nature Biotechnology 14:845-851, and a human heavy chain transgene, HCo7, as described in U.S. Pat. Nos. 5,545,806; 5,625,825; and 5,545,807.

HuMab Immunizations:

To generate fully human monoclonal antibodies to LY6G6F, VSIG10, TMEM25 and/or LSR, mice of the HCo7 HuMab Mouse strain can be immunized with purified recombinant LY6G6F, VSIG10, TMEM25 and/or LSR fusion protein derived from mammalian cells that are transfected with an expression vector containing the gene encoding the fusion protein. General immunization schemes for the HuMab Mouse are described in Lonberg, N. et al (1994) Nature 368(6474): 856-859; Fishwild, D. et al. (1996) Nature Biotechnology 14: 845-851 and PCT Publication WO 98/24884. The mice are 6-16 weeks of age upon the first infusion of antigen. A purified recombinant LY6G6F, VSIG10, TMEM25 and/or LSR antigen preparation (5-50 .mu.g, purified from transfected mammalian cells expressing LY6G6F, VSIG10, TMEM25 and/or LSR fusion protein) is used to immunize the HuMab mice intraperitoneally.

Transgenic mice are immunized twice with antigen in complete Freund's adjuvant or Ribi adjuvant IP, followed by 3-21 days IP (up to a total of 11 immunizations) with the antigen in incomplete Freund's or Ribi adjuvant. The immune response is monitored by retroorbital bleeds. The plasma is screened by ELISA (as described below), and mice with sufficient titers of anti-LY6G6F, VSIG10, TMEM25 and/or LSR human immunoglobulin are used for fusions. Mice are boosted intravenously with antigen 3 days before sacrifice and removal of the spleen.

Selection of HuMab mice producing anti-LY6G6F, anti-VSIG10, anti-TMEM25 and/or anti-LSRAntibodies:

To select HuMab mice producing antibodies that bind LY6G6F, VSIG10, TMEM25 and/or LSR sera from immunized mice is tested by a modified ELISA as originally described by Fishwild, D. et al. (1996). Briefly, microtiter plates are coated with purified recombinant LY6G6F, VSIG10, TMEM25 and/or LSR fusion protein at 1-2 .mu.g/ml in PBS, 50 .mu.l/wells incubated 4 degrees C. overnight then blocked with 200 .mu.l/well of 5% BSA in PBS. Dilutions of plasma from LY6G6F, VSIG10, TMEM25 and/or LSR-immunized mice are added to each well and incubated for 1-2 hours at ambient temperature. The plates are washed with PBS/Tween and then incubated with a goat-anti-human kappa light chain polyclonal antibody conjugated with alkaline phosphatase for 1 hour at room temperature. After washing, the plates are developed with pNPP substrate and analyzed by spectrophotometer at OD 415-650. Mice that developed the highest titers of anti-LY6G6F, anti-VSIG10, anti-TMEM25 and/or anti-LSR antibodies are used for fusions. Fusions are performed as described below and hybridoma supernatants are tested for anti-LY6G6F, anti-VSIG10, anti-TMEM25 and/or anti-LSR activity by ELISA.

Generation of Hybridomas Producing Human Monoclonal Antibodies to LY6G6F, VSIG10, TMEM25 and/or LSR.

The mouse splenocytes, isolated from the HuMab mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of P3X63 Ag8.6.53 (ATCC CRL 1580) nonsecreting mouse myeloma cells with 50% PEG (Sigma). Cells are plated at approximately 1×10-5/well in flat bottom microtiter plate, followed by about two week incubation in selective medium containing 10% fetal calf serum, supplemented with origen (IGEN) in RPMI, L-glutamine, sodium pyruvate, HEPES, penicillin, streptamycin, gentamycin, 1×HAT, and beta-mercaptoethanol. After 1-2 weeks, cells are cultured in medium in which the HAT is replaced with HT. Individual wells are then screened by ELISA (described above) for human anti-LY6G6F, anti-VSIG10, anti-TMEM25 and/or anti-LSR-monoclonal IgG antibodies. Once extensive hybridoma growth occurred, medium is monitored usually after 10-14 days. The antibody secreting hybridomas are replated, screened again and, if still positive for human IgG, anti-LY6G6F, anti-VSIG10, anti-TMEM25 and/or anti-LSR monoclonal antibodies are subcloned at least twice by limiting dilution. The stable subclones are then cultured in vitro to generate small amounts of antibody in tissue culture medium for further characterization.

Hybridoma clones are selected for further analysis.

Structural Characterization Of Desired Anti-LY6G6F, anti-VSIG10, anti-TMEM25 and/or anti-LSR Human Monoclonal Antibodies The cDNA sequences encoding the heavy and light chain variable regions of the obtained anti-LY6G6F, anti-VSIG10, anti-TMEM25 and/or anti-LSRmonoclonal antibodies are obtained from the resultant hybridomas, respectively, using standard PCR techniques and are sequenced using standard DNA sequencing techniques.

The nucleotide and amino acid sequences of the heavy chain variable region and of the light chain variable region are identified. These sequences may be compared to known human germline immunoglobulin light and heavy chain sequences and the CDRs of each heavy and light of the obtained anti-LY6G6F, anti-VSIG10, anti-TMEM25 and/or anti-LSR sequences identified.

Characterization Of Binding Specificity And Binding Kinetics Of Anti-LY6G6F, anti-VSIG10, anti-TMEM25 and/or anti-LSR Human Monoclonal Antibodies The binding affinity, binding kinetics, binding specificity, and cross-competition of anti-LY6G6F, anti-VSIG10, anti-TMEM25 and/or anti-LSR antibodies are examined by Biacore analysis. Also, binding specificity is examined by flow cytometry.

Binding Affinity and Kinetics

Anti-LY6G6F, anti-VSIG10, anti-TMEM25 and/or anti-LSR antibodies produced according to the invention are characterized for affinities and binding kinetics by Biacore analysis (Biacore AB, Uppsala, Sweden). Purified recombinant human LY6G6F, VSIG10, TMEM25 and/or LSR fusion protein is covalently linked to a CM5 chip (carboxy methyl dextran coated chip) via primary amines, using standard amine coupling chemistry and kit provided by Biacore. Binding is measured by flowing the antibodies in HBS EP buffer (provided by BIAcore AB) at a concentration of 267 nM at a flow rate of 50 .mu.l/min. The antigen-association antibodies association kinetics is followed for 3 minutes and the dissociation kinetics is followed for 7 minutes. The association and dissociation curves are fit to a 1:1 Langmuir binding model using BIAevaluation software (Biacore AB). To minimize the effects of avidity in the estimation of the binding constants, only the initial segment of data corresponding to association and dissociation phases are used for fitting.

Epitope Mapping of Obtained anti-LY6G6F, anti-VSIG10, anti-TMEM25 and/or anti-LSR Antibodies Biacore is used to determine epitope grouping of anti-LY6G6F, anti-VSIG10, anti-TMEM25 and/or anti-LSR HuMAbs. Obtained anti-LY6G6F, anti-VSIG10, anti-TMEM25 and/or anti-LSR antibodies are used to map their epitopes on the LY6G6F, VSIG10, TMEM25 and/or LSR antigen, respectively. These different antibodies are coated on three different surfaces of the same chip to 8000 RUs each. Dilutions of each of the mAbs are made, starting at 10 mu.g/mL and is incubated with Fc fused LY6G6F, VSIG10, TMEM25 and/or LSR (50 nM) for one hour. The incubated complex is injected over all the three surfaces (and a blank surface) at the same time for 1.5 minutes at a flow rate of 20 .mu.L/min. Signal from each surface at end of 1.5 minutes, after subtraction of appropriate blanks, has been plotted against concentration of mAb in the complex. Upon analysis of the data, the anti-LY6G6F, anti-VSIG10, anti-TMEM25 and/or anti-LSR antibodies are categorized into different epitope groups depending on the epitope mapping results. The functional properties thereof are also compared.

Chinese hamster ovary (CHO) cell lines that express LY6G6F, VSIG10, TMEM25 and/or LSR protein at the cell surface are developed and used to determine the specificity of the LY6G6F, VSIG10, TMEM25 and/or LSR HuMAbs by flow cytometry. CHO cells are transfected with expression plasmids containing full length cDNA encoding a transmembrane forms of LY6G6F, VSIG10, TMEM25 and/or LSR antigen or a variant thereof. The transfected proteins contained an epitope tag at the N-terminus are used for detection by an antibody specific for the epitope. Binding of a anti-LY6G6F, anti-VSIG10, anti-TMEM25 and/or anti-LSR MAb is assessed by incubating the transfected cells with each of the LY6G6F, VSIG10, TMEM25 and/or LSR Abs at a concentration of 10 mu.g/ml. The cells are washed and binding is detected with a FITC-labeled anti-human IgG Ab. A murine anti-epitope tag Ab, followed by labeled anti-murine IgG, is used as the positive control. Non-specific human and murine Abs are used as negative controls. The obtained data is used to assess the specificity of the HuMAbs for the LY6G6F, VSIG10, TMEM25 and/or LSR antigen target.

These antibodies and other antibodies specific to LY6G6F, VSIG10, TMEM25 and/or LSR may be used in the aforedescribed anti-LY6G6F, anti-VSIG10, anti-TMEM25 and/or anti-LSR related therapies such as treatment of cancers wherein LY6G6F, VSIG10, TMEM25 and/or LSR antigen is differentially expressed and/or for modulating (enhancing or inhibiting) B7 immune co-stimulation involving the LY6G6F, VSIG10, TMEM25 and/or LSR antigen such as in the treatment of cancers and autoimmune diseases wherein such antibodies will e.g., prevent negative stimulation of T cell activity against desired target cancer cells or prevent the positive stimulation of T cell activity thereby eliciting a desired anti-autoimmune effect.

The invention has been described and various embodiments provided relating to manufacture and selection of desired anti-LY6G6F, anti-VSIG10, anti-TMEM25 and/or anti-LSR antibodies for use as therapeutics and diagnostic methods wherein the disease or condition is associated with LY6G6F, VSIG10, TMEM25 and/or LSR antigen. Different embodiments may optionally be combined herein in any suitable manner, beyond those explicit combinations and subcombinations shown herein. The invention is now further described by the claims which follow.

What is claimed is:

1. A method of treatment of cancer, comprising administering a pharmaceutically active amount of a monoclonal or polyclonal antibody or an antigen binding fragment thereof comprising an antigen binding site that binds specifically to an extracellular domain of a polypeptide, consisting essentially of 108, 145, or 170 amino acids of an amino acid sequence selected from the group consisting of SEQ ID NOs: 11, 13, 15-18, 67, 143, or comprising an antigen binding site that binds specifically to a polypeptide consisting of an amino acid sequence set forth in any one of SEQ ID NOs: 10, 12, 14, 22, 47-50 and 102, to the subject in need of treatment thereof.

2. The method of claim 1, wherein the antibody is selected from the group consisting of a fully human antibody, chimeric antibody, humanized antibody, primatized antibody, Fab, Fab', F(ab')2, F(ab'), F(ab), Fv, scFv fragment and minimal recognition unit.

3. The method of claim 2, wherein the antibody is coupled to a moiety selected from the group consisting of a drug, a radionuclide, an enzyme, a toxin, a therapeutic agent, and a chemotherapeutic agent.

4. The method of claim 1, wherein the treatment is combined with administering to the subject another moiety or therapy useful for treating cancer.

5. The method of claim 4, wherein the therapy is radiation therapy, antibody therapy, chemotherapy, photodynamic therapy, adoptive T cell therapy, Treg depletion, surgery or a combination therapy with conventional drugs.

6. The method of claim 4, wherein the moiety is selected from the group consisting of a cytotoxic drug, a tumor vaccine, an antibody selected from the group consisting of bevacizumab, erbitux and immunostimulatory antibodies; peptides, pepti-bodies, small molecules, a chemotherapeutic agent, interferons, interleukins, growth hormones, folic acid, vitamins, minerals, aromatase inhibitors, RNAi, histone deacetylase inhibitors, and proteasome inhibitors.

7. The method of claim 1, wherein the cancer is selected from the group consisting of breast cancer, cervical cancer, ovary cancer, endometrial cancer, melanoma, bladder cancer, lung cancer, pancreatic cancer, colon cancer, prostate cancer, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma, benign tumor of the skin, keratoacanthomas, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, and gastrointestinal stromal tumor (GIST), and wherein the cancer is non-metastatic, invasive or metastatic.

8. The method of claim 1, wherein the cancer is selected from the group consisting of liver cancer, prostate cancer, lung cancer, ovarian cancer, colon cancer, breast cancer, stomach cancer and renal cancer.

9. A method of using a monoclonal or polyclonal antibody or an antigen binding fragment thereof comprising an antigen binding site that binds specifically to an extracellular domain of a polypeptide, consisting essentially of 108, 145, or 170 amino acids of an amino acid sequence selected from the group consisting of SEQ ID NOs: 11, 13, 15-18, 67, 143, or comprising an antigen binding site that binds specifically to a polypeptide consisting of an amino acid sequence set forth in any one of 12, 14, 47-50, 10, 22 or 102, as a cancer vaccine adjuvant, comprising administration to a patient an immunogenic amount of a tumor associated antigen preparation of interest; and the cancer vaccine adjuvant in a formulation suitable for immunization, wherein the immune response against the tumor associated antigen in the presence of the cancer vaccine adjuvant is stronger than in the absence of the cancer vaccine adjuvant.

10. The method of claim 6, wherein the antibody is selected from the group consisting of bevacizumab and erbitux.

11. The method of claim 6, wherein the chemotherapeutic agent is selected from the group consisting of a cytotoxic agent and a cytostatic agent.

12. The method of claim 6, wherein the chemotherapeutic agent is selected from the group consisting of paclitaxel, cisplatin, vinorelbine, docetaxel, gemcitabine, temozolomide, irinotecan, 5FU and carboplatin.

* * * * *